United States Patent
Osterhout et al.

(10) Patent No.: US 10,808,262 B2
(45) Date of Patent: *Oct. 20, 2020

(54) MICROORGANISMS AND METHODS FOR IMPROVING PRODUCT YIELDS ON METHANOL USING ACETYL-COA SYNTHESIS

(71) Applicant: GENOMATICA, INC., San Diego, CA (US)

(72) Inventors: Robin E. Osterhout, San Diego, CA (US); Anthony P. Burgard, Bellefonte, PA (US); Priti Pharkya, San Diego, CA (US); Stefan Andrae, San Diego, CA (US)

(73) Assignee: Genomatica, Inc., San Diego, CA (US)

(*) Notice: Subject to any disclaimer, the term of this patent is extended or adjusted under 35 U.S.C. 154(b) by 548 days.

This patent is subject to a terminal disclaimer.

(21) Appl. No.: 15/039,221

(22) PCT Filed: Nov. 25, 2014

(86) PCT No.: PCT/US2014/067287
§ 371 (c)(1),
(2) Date: May 25, 2016

(87) PCT Pub. No.: WO2015/084633
PCT Pub. Date: Jun. 11, 2015

(65) Prior Publication Data
US 2017/0159075 A1  Jun. 8, 2017

Related U.S. Application Data

(60) Provisional application No. 61/945,056, filed on Feb. 26, 2014, provisional application No. 61/911,414, filed on Dec. 3, 2013.

(51) Int. Cl.
| | | |
|---|---|---|
| *C12N 1/16* | (2006.01) | |
| *C12N 1/20* | (2006.01) | |
| *C12P 7/02* | (2006.01) | |
| *C12P 5/02* | (2006.01) | |
| *C12P 7/18* | (2006.01) | |
| *C12N 1/14* | (2006.01) | |
| *C12P 7/42* | (2006.01) | |
| *C12P 7/40* | (2006.01) | |
| *C12N 15/70* | (2006.01) | |
| *C12N 15/81* | (2006.01) | |
| *C12P 7/04* | (2006.01) | |
| *C12P 7/44* | (2006.01) | |
| *C12P 13/00* | (2006.01) | |
| *C12P 17/10* | (2006.01) | |

(52) U.S. Cl.
CPC .............. *C12P 5/026* (2013.01); *C12N 1/14* (2013.01); *C12N 1/20* (2013.01); *C12N 15/70* (2013.01); *C12N 15/81* (2013.01); *C12P 7/02* (2013.01); *C12P 7/04* (2013.01); *C12P 7/18* (2013.01); *C12P 7/40* (2013.01); *C12P 7/42* (2013.01); *C12P 7/44* (2013.01); *C12P 13/001* (2013.01); *C12P 13/005* (2013.01); *C12P 17/10* (2013.01); *Y02E 50/343* (2013.01)

(58) Field of Classification Search
None
See application file for complete search history.

(56) References Cited

U.S. PATENT DOCUMENTS

| | | | |
|---|---|---|---|
| 3,090,815 A | 5/1963 | Denton | |
| 3,090,816 A | 5/1963 | Denton | |

(Continued)

FOREIGN PATENT DOCUMENTS

| | | |
|---|---|---|
| EP | 2062967 A1 | 11/2007 |
| EP | 2947143 A1 | 1/2014 |

(Continued)

OTHER PUBLICATIONS

Leßmeier et al. (2015) Identification of two mutations increasing the methanol tolerance of Corynebacterium glutamicum, BMC Microbiol., vol. 15, No. 216, pp. 1-11.*
Vorholt et al. (2000) Novel Formaldehyde-Activating Enzyme in Methylobacterium extorquens AM1 Required for Growth on Methanol, J. Bacteriol., vol. 182, pp. 6645-6650.*
Distel et al. (1987) Import of alcohol oxidase into peroxisomes of *Saccharomyces cerevislae*, EMBO J.,vol. 6, No. 1, pp. 3111-3116.*
Adams et al., "Oxidoreductase-type enzymes and redox proteins involved in fermentative metabolisms of hyperthermophilic Archaea," *Adv. Protein Chem.*, 48:101-180 (1996).

(Continued)

*Primary Examiner* — Manjunath N Rao
*Assistant Examiner* — Samuel W Liu
(74) *Attorney, Agent, or Firm* — Jones Day

(57) ABSTRACT

The invention provides non-naturally occurring microbial organisms containing enzymatic pathways and/or metabolic modifications for enhancing carbon flux through acetyl-CoA. In some embodiments, the microbial organisms having such pathways also include pathways for generating reducing equivalents, formaldehyde fixation and/or formate assimilation. The enhanced carbon flux through acetyl-CoA, in combination with pathways for generating reducing equivalents, formaldehyde fixation and/or formate assimilation can, in some embodiments, be used for production of a bioderived compound. Accordingly, in some embodiments, the microbial organisms of the invention can include a pathway capable of producing a bioderived compound of the invention. The invention still further provides a bioderived compound produced by a microbial organism of the invention, culture medium having the bioderived compound of the invention, compositions having the bioderived compound of the invention, a biobased product comprising the bioderived compound of the invention, and a process for producing a bioderived compound of the invention.

21 Claims, 10 Drawing Sheets

(56) References Cited

U.S. PATENT DOCUMENTS

| | | | |
|---|---|---|---|
| 3,542,883 | A | 11/1970 | Nenitescu et al. |
| 5,352,590 | A | 10/1994 | Kato et al. |
| 6,280,972 | B1 | 8/2001 | Yasueda |
| 6,331,428 | B1 | 12/2001 | Kato |
| 6,630,341 | B2 | 10/2003 | Kato et al. |
| 6,911,332 | B2 | 6/2005 | Usuda et al. |
| 7,127,379 | B2 | 10/2006 | Palsson et al. |
| 7,160,704 | B2 | 1/2007 | Takeshita et al. |
| 7,163,810 | B2 | 1/2007 | Yasueda et al. |
| 7,186,856 | B2 | 3/2007 | Meng et al. |
| 7,192,748 | B2 | 3/2007 | Usuda et al. |
| 7,211,416 | B2 | 5/2007 | Asahara et al. |
| 7,858,350 | B2 | 12/2010 | Burk et al. |
| 7,947,483 | B2 | 5/2011 | Burgard et al. |
| 7,977,084 | B2 | 7/2011 | Sun et al. |
| 8,026,386 | B2 | 9/2011 | Burk et al. |
| 8,062,871 | B2 | 11/2011 | Burgard et al. |
| 8,067,214 | B2 | 11/2011 | Burk et al. |
| 8,129,154 | B2 | 3/2012 | Burk et al. |
| 8,129,155 | B2 | 3/2012 | Trawick et al. |
| 8,129,169 | B2 | 3/2012 | Van Dien et al. |
| 8,241,877 | B2 | 8/2012 | Burgard et al. |
| 8,268,607 | B2 | 9/2012 | Burgard et al. |
| 8,323,950 | B2 | 12/2012 | Burk et al. |
| 8,377,666 | B2 | 2/2013 | Haselbeck et al. |
| 8,377,680 | B2 | 2/2013 | Burk et al. |
| 8,420,375 | B2 | 4/2013 | Osterhout et al. |
| 2002/0012939 | A1 | 1/2002 | Palsson |
| 2002/0168654 | A1 | 11/2002 | Maranas et al. |
| 2003/0059792 | A1 | 3/2003 | Palsson et al. |
| 2003/0224363 | A1 | 12/2003 | Park et al. |
| 2003/0233218 | A1 | 12/2003 | Schilling |
| 2004/0009466 | A1 | 1/2004 | Maranas et al. |
| 2004/0029149 | A1 | 2/2004 | Palsson et al. |
| 2004/0072723 | A1 | 4/2004 | Palsson et al. |
| 2006/0040365 | A1 | 2/2006 | Kozlov et al. |
| 2007/0111294 | A1 | 5/2007 | Burgard et al. |
| 2008/0199926 | A1 | 8/2008 | Burgard et al. |
| 2009/0047719 | A1 | 2/2009 | Burgard et al. |
| 2010/0003716 | A1 | 1/2010 | Cervin et al. |
| 2010/0021978 | A1 | 1/2010 | Burk et al. |
| 2010/0184173 | A1 | 7/2010 | Burk et al. |
| 2010/0323418 | A1 | 12/2010 | Burgard |
| 2010/0330635 | A1 | 12/2010 | Burgard et al. |
| 2011/0003355 | A1 | 1/2011 | Clark et al. |
| 2011/0014668 | A1 | 1/2011 | Osterhout et al. |
| 2011/0091374 | A1 | 4/2011 | Robinson et al. |
| 2011/0097767 | A1 | 4/2011 | Pharkya |
| 2011/0124911 | A1 | 5/2011 | Burk et al. |
| 2011/0195461 | A1 | 8/2011 | Burk et al. |
| 2011/0196180 | A1 | 8/2011 | Alibhai et al. |
| 2011/0201068 | A1 | 8/2011 | Pharkya et al. |
| 2011/0207185 | A1 | 8/2011 | Osterhout et al. |
| 2011/0217742 | A1 | 9/2011 | Sun et al. |
| 2011/0269204 | A1 | 11/2011 | Burk et al. |
| 2011/0300597 | A1 | 12/2011 | Burk et al. |
| 2011/0306107 | A1* | 12/2011 | Kalisz ............... C12N 1/14 435/173.1 |
| 2011/0312049 | A1 | 12/2011 | Osterhout et al. |
| 2012/0003652 | A1 | 1/2012 | Reeves et al. |
| 2012/0021478 | A1 | 1/2012 | Osterhout et al. |
| 2012/0064622 | A1 | 3/2012 | Fischer et al. |
| 2012/0156740 | A1 | 6/2012 | Pharkya et al. |
| 2012/0225466 | A1 | 9/2012 | Burk et al. |
| 2012/0276587 | A1 | 11/2012 | Beck et al. |
| 2012/0302800 | A1 | 11/2012 | Hassan et al. |
| 2012/0322078 | A1* | 12/2012 | Mcbride ............... C12P 7/04 435/6.18 |
| 2012/0329119 | A1 | 12/2012 | Burgard et al. |
| 2013/0011891 | A1 | 1/2013 | Burk et al. |
| 2013/0034884 | A1 | 2/2013 | Burgard et al. |
| 2013/0065279 | A1 | 3/2013 | Burk et al. |
| 2013/0066035 | A1 | 3/2013 | Burgard et al. |
| 2013/0071886 | A1 | 3/2013 | Burk et al. |
| 2013/0109064 | A1 | 5/2013 | Osterhout et al. |
| 2013/0122563 | A1 | 5/2013 | Burk et al. |
| 2013/0144029 | A1 | 6/2013 | Burgard et al. |
| 2013/0157321 | A1* | 6/2013 | Kozlov ............... C12N 9/88 435/107 |
| 2013/0295616 | A1 | 11/2013 | Muramatsu et al. |
| 2013/0295621 | A1 | 11/2013 | Nishio et al. |
| 2017/0273924 | A1* | 9/2017 | Greenberg ............ A61K 31/19 |

FOREIGN PATENT DOCUMENTS

| | | |
|---|---|---|
| JP | S5513230 A | 1/1980 |
| WO | WO 2002/055995 A2 | 7/2002 |
| WO | WO 2003/078643 A1 | 9/2003 |
| WO | WO 2003/106998 A1 | 12/2003 |
| WO | WO 2006/016705 A1 | 2/2006 |
| WO | WO 2007/030830 A2 | 3/2007 |
| WO | WO 2007/136762 A2 | 11/2007 |
| WO | WO 2008/027742 A1 | 3/2008 |
| WO | WO 2008/091627 A1 | 7/2008 |
| WO | WO 2008/115840 A2 | 9/2008 |
| WO | WO 2008/144791 A2 | 12/2008 |
| WO | WO 2009/023493 A1 | 2/2009 |
| WO | WO 2009/045637 A2 | 4/2009 |
| WO | WO 2009/094485 A1 | 7/2009 |
| WO | WO 2009/111672 A1 | 9/2009 |
| WO | WO 2009/135074 A2 | 11/2009 |
| WO | WO 2009/151728 A2 | 12/2009 |
| WO | WO 2009/155382 A1 | 12/2009 |
| WO | WO 2010/030711 A2 | 3/2010 |
| WO | WO 2010/031079 A1 | 3/2010 |
| WO | WO 2010/104938 A1 | 3/2010 |
| WO | WO 2010/057022 A1 | 5/2010 |
| WO | WO 2010/071697 A1 | 6/2010 |
| WO | WO 2010/127303 A1 | 11/2010 |
| WO | WO 2010/127319 A2 | 11/2010 |
| WO | WO 2010/129936 A1 | 11/2010 |
| WO | WO 2010/132845 A1 | 11/2010 |
| WO | WO 2010/141780 A1 | 12/2010 |
| WO | WO 2010/141920 A2 | 12/2010 |
| WO | WO 2010/144746 A2 | 12/2010 |
| WO | WO 2011/017560 A1 | 2/2011 |
| WO | WO 2011/031897 A1 | 3/2011 |
| WO | WO 2011/047101 A1 | 4/2011 |
| WO | WO 2011/050326 A1 | 4/2011 |
| WO | WO 2011/066076 A1 | 6/2011 |
| WO | WO 2011/071682 A1 | 6/2011 |
| WO | WO 2011/094131 A1 | 8/2011 |
| WO | WO 2011/130378 A1 | 10/2011 |
| WO | WO 2011/137198 A1 | 11/2011 |
| WO | WO 2011/140171 A2 | 11/2011 |
| WO | WO 2011/159853 A1 | 12/2011 |
| WO | WO 2012/018624 A2 | 2/2012 |
| WO | WO 2012/082978 A1 | 6/2012 |
| WO | WO 2012/098662 A1 | 7/2012 |
| WO | WO 2012/099621 A1 | 7/2012 |
| WO | WO 2012/106516 A1 | 8/2012 |
| WO | WO 2012/109176 A2 | 8/2012 |
| WO | WO 2012/129555 A2 | 9/2012 |
| WO | WO 2012/135789 A2 | 10/2012 |
| WO | WO 2012/177599 A2 | 12/2012 |
| WO | WO 2012/177619 A2 | 12/2012 |
| WO | WO 2012/177710 A1 | 12/2012 |
| WO | WO 2012/177721 A1 | 12/2012 |
| WO | WO 2012/177726 A1 | 12/2012 |
| WO | WO 2012/177943 A1 | 12/2012 |
| WO | WO 2012/177983 A2 | 12/2012 |
| WO | WO 2013/003432 A1 | 1/2013 |
| WO | WO 2013/007786 A1 | 1/2013 |
| WO | WO 2013/012975 A1 | 1/2013 |
| WO | WO 2013/028519 A1 | 2/2013 |
| WO | WO 2013/036764 A1 | 3/2013 |
| WO | WO 2013/040383 A1 | 3/2013 |
| WO | WO 2013/066568 A1 | 5/2013 |
| WO | WO 2013/067432 A1 | 5/2013 |
| WO | WO 2013/069634 A1 | 5/2013 |
| WO | WO 2013/071172 A1 | 5/2013 |
| WO | WO 2013/071226 A1 | 5/2013 |
| WO | WO 2013/110797 A1 | 8/2013 |
| WO | WO 2013/181647 A2 | 12/2013 |

(56) References Cited

FOREIGN PATENT DOCUMENTS

| WO | WO 2014/081803 A1 | 5/2014 |
|---|---|---|
| WO | WO 2014/144135 A2 | 9/2014 |
| WO | WO 2014/153036 A1 | 9/2014 |
| WO | WO 2014/153207 A2 | 9/2014 |

OTHER PUBLICATIONS

Afolabi et al., "Site-directed mutagenesis and X-ray crystallography of the PQQ-containing quinoprotein methanol dehydrogenase and its electron acceptor, cytochrome c(L)," *Biochem.*, 40(33):9799-9809 (2001).
Alber et al., "Malonyl-Coenzyme A Reductase in the Modified 3-Hydroxypropionate Cycle for Autotrophic Carbon Fixation in *Archaeal Metallosphaera* and *Sulfolobus* spp.," *J. Bacteriol.*, 188(24):8551-8559 (2006).
Alhapel et al., "Molecular and functional analysis of nicotinate catabolism in Eubacterium barkeri," *Proc. Natl. Acad. Sci. USA*, 103:12341-12346 (2006).
Andreassi et al., "Crystal structure of the *Streptococcus pneumonia* mevalonate kinase in complex with diphosphomevalonate," *Protein Sci.*, 16:983-989 (2007).
Angov et al., "Codon usage: nature's roadmap to expression and folding of proteins," *Biotechnol. J.*, 6(6):650-659 (2011).
Anthony, "How half a century of research was required to understand bacterial growth on C1 and C2 compounds; the story of the serine cycle and the ethylmalonyl-CoA pathway," *Sci. Prog.*, 94:109-137 (2011).
Araujo et al., "Before It Gets Started: Regulating Translation at the 5' UTR," *Comp. Funct. Genomics*, 475731 (2012).
Arfman et al., "Purification and characterization of an activator protein for methanol dehydrogenase from thermotolerant *Bacillus* spp," *J. Biol. Chem.*, 266(6):3955-3960 (1991).
Arraiano et al., "The critical role of RNA processing and degradation in the control of gene expression," *FEMS Microbiol. Rev.*, 34(5):883-923 (2010).
Atsumi et al., "Metabolic engineering of *Escherichia coli* for 1-butanol production," *Metabolic Engineering*, 10:305-311 (2008).
Berg et al., "A 3-Hydroxypropionate/4-Hydroxybutyrate Autotrophic Carbon Dioxide Assimilation Pathway in Archaea," *Science*, 318:1782-1786 (2007).
Bergquist et al., "Degenerate oligonucleotide gene shuffling (DOGS) and random drift mutagenesis (RNDM): Two complementary techniques for enzyme evolution," *Biomol. Eng.*, 22:63-72 (2005).
Bergquist et al., "Degenerate Oligonucleotide Gene Shuffling," *Methods Mol. Biol.*, 352:191-204 (2007).
Bernhard et al., "Functional and structural role of the cytochrome b subunit of the membrane-bound hydrogenase complex of Alcaligenes eutrophus H16," *Eur. J. Biochem.*, 248:179-186 (1997).
Binstock et al., "Fatty Acid Oxidation Complex from *Escherichia coli*," *Methods Enzymol.*, 71:403-411 (1981).
Blaschkowski et al., "Routes of flavodoxin and ferredoxin reduction in *Escherichia coli*: CoA-acylating pyruvate: flavodoxin and NADPH: flavodoxin oxidoreductases participating in the activation of pyruvate formate-lyase," *Eur. J. Biochem.*, 123:563-569 (1982).
Bleykasten-Grosshan et al., "Transposable elements in yeasts," *C.R. Biol.*, 33(8-9):679-686 (2011).
Bobik et al., "HPLC assay for methylmalonyl-CoA epimerase," *Anal. Bioanal. Chem.*, 375:344-349 (2003).
Bock et al., "Purification and Characterization of Two Extremely Thermostable Enzymes, Phosphate Acetyltransferase and Acetate Kinase, from the Hyperthermophilic Eubacterium Thermotoga maritima," *J. Bacteriol.*, 181(6):1861-1867 (1999).
Bogorad et al., "Synthetic non-oxidative glycolysis enables complete carbon conservation," *Nature*, 502:693-697 (2013).
Boles et al., "Characterization of a Glucose-Repressed Pyruvate Kinase (Pyk2p) in *Saccharomyces cerevisiae* That Is Catalytically Insensitive to Fructose-1,6-Bisphosphate," *J. Bacteriol.*, 179(9):2987-2993 (1997).
Bower et al., "Cloning, Sequencing, and Characterization of the Bacillus subtilis Biotin Biosynthetic Operon," *J. Bacteriol.*, 178(14):4122-4130 (1996).
Boynton et al., "Cloning, Sequencing, and Expression of Clustered Genes Encoding b-Hydroxybutyryl-Coenzyme A (CoA) Dehydrogenase, Crotonase, and Butyryl-CoA Dehydrogenase from Clostridium acetobutylicum ATCC 824," *J. Bacteriol.*, 178(11):3015-3024 (1996).
Branlant et al., "Nucleotide sequence of the *Escherichia coli* gap gene. Different evolutionary behavior of the NAD+-binding domain and of the catalytic domain of D-glyceraldehyde-3-phosphate dehydrogenase," *Eur. J. Biochem.*, 150:61-66 (1985).
Brasen et al., "Unusual ADP-forming acetyl-coenzyme A synthetases from the mesophilic halophilic euryarchaeon Haloarcula marismortui and from the hyperthermophilic crenarchaeon Pyrobaculum aerophilum," *Arch. Microbiol.*, 182:277-287 (2004).
Bravo et al., "Reliable, Sensitive, Rapid and Quantitative Enzyme-Based Assay for Gamma-Hydroxybutyric Acid (GHB)," *J. Forensic Sci.*, 49(2):379-387 (2004).
Breitkreuz et al., "A Novel gamma-Hydroxybutyrate Dehydrogenase: identification and expression of an *Arabidopsis* cDNA and potential role under oxygen deficiency," *J. Biol. Chem.*, 278(42):41552-41556 (2003).
Brizio et al., "Over-expression in *Escherichia coli*, functional characterization and refolding of rat dimethylglycine dehydrogenase," *Protein Expr. Purif.*, 37(2):434-442 (2004).
Brodkorb et al., "Linalool dehydratase-isomerase, a bifunctional enzyme in the anaerobic degradation of monoterpenes," *J. Biol. Chem.*, 285:30436-30442 (2010).
Buchanan et al., "Photoreduction of ferredoxin and its use in NAD(P)+ reduction by a subcellular preparation from the photosynthetic bacterium, Chlorobium thiosulfatophilum," *Biochim Biophys Acta*, 180(1):123-129 (1969).
Buck et al., "Primary Structure of the Succinyl-CoA Synthetase of *Escherichia coli*," *Biochem.*, 24:6245-6252 (1985).
Buckel et al., "ATP-driven electron transfer in enzymatic radical reactions," *Curr. Opin. Chem. Biol.*, 8:462-467 (2004).
Buckel et al., "Glutaconate CoA-transferase from Acidaminococcus fermentans," *Eur. J. Biochem.*, 118:315-321 (1981).
Buckel et al., "Radical Enzymes in Anaerobes," *Annu. Rev. Microbiol.*, 60:27-49 (2006).
Buckel et al., "Radical-mediated dehydration reactions in anaerobic bacteria," *Biol. Chem.*, 386:951-959 (2005).
Buckel et al., "Two pathways of glutamate fermentation by anaerobic bacteria," *J. Bacteriol.*, 117(3):1248-1260 (1974).
Burgard et al., "Minimal reaction sets for *Escherichia coli* metabolism under different growth requirements and uptake environments," *Biotechnol. Prog.*, 17:791-797 (2001).
Burgard et al., "OptKnock: A Bilevel Programming Framework for Identifying Gene Knockout Strategies for Microbial Strain Optimization," *Biotechnol. Bioeng.*, 84:647-657 (2003).
Burgdorf et al., "The Soluble $NAD^+$-Reducing [NiFe]-Hydrogenase from Ralstonia eutropha H16 Consists of Six Subunits and Can Be Specifically Activated by NADPH," *J. Bacteriol.*, 187(9):3122-3132 (2005).
Burke et al., "The isolation, characterization, and sequence of the pyruvate kinase gene of *Saccharomyces cerevisiae*," *J. Biol. Chem.*, 258(4):2193-2201 (1983).
Campbell et al., "A new *Escherichia coli* metabolic competency: growth on fatty acids by a novel anaerobic beta-oxidation pathway," *Mol. Microbiol.*, 47(3):793-805 (2003).
Campbell et al., "The Enigmatic *Escherichia coli* fadE Gene Is yafH," *J. Bacteriol.*, 184(13):3759-3764 (2002).
Castel et al., "RNA interference in the nucleus: roles for small RNAs in transcription, epigenetics and beyond," *Nat. Rev. Genet.*, 14(2):100-112 (2013).
Clark et al., "Purification and properties of 5,10-methylenetetrahydrofolate reductase, an iron-sulfur flavoprotein from Clostridium formicoaceticum," *J. Biol. Chem.*, 259(17):10845-10849 (1984).
Coco et al., "DNA shuffling method for generating highly recombined genes and evolved enzymes," *Nat. Biotechnol.*, 19:354-359 (2001).

(56) References Cited

OTHER PUBLICATIONS

Colonna et al., "Synthesis and radiocarbon evidence of terephthalate polyesters completely prepared from renewable resources," *Green Chem.*, 13:2543 (2011).
Coppi, "The hydrogenases of Geobacter sulfurreducens: a comparative genomic perspective," *Microbiol.*, 151:1239-1254 (2005).
Corthesy-Theulaz et al., "Cloning and Characterization of Helicobacter pylori Succinyl CoA:Acetoacetate CoA-transferase, a Novel Prokaryotic Member of the CoA-transferase Family," *J. Biol. Chem.*, 272:25659-25667 (1997).
Cracknell et al., "A kinetic and thermodynamic understanding of O2 tolerance in [NiFe]-hydrogenases," *Proc. Natl. Acad. Sci. USA*, 106(49):20681-20686 (2009).
Crans et al., "Glycerol Kinase:Substrate Specificity," *J. Am. Chem. Soc.*, 107:7008-7018 (1985).
Currie et al., "Authentication and dating of biomass components of industrial materials; links to sustainable technology," *Nucl. Instr. Methods Phys. Res.*, 172:281-287 (2000).
D'Ari et al., "Purification, characterization, cloning, and amino acid sequence of the bifunctional enzyme 5,10-methylenetetrahydrofolate dehydrogenase/5,10-methenyltetrahydrofolate cyclohydrolase from *Escherichia coli*," *J. Biol. Chem.*, 266(35):23953-23958 (1991).
Daigaku et al., "Loss of heterozygosity in yeast can occur by ultraviolet irradiation during the S phase of the cell cycle," *Mutation Res.*, 600:177-183 (2006).
Das et al., "Characterization of a Corrinoid Protein Involved in the C1 Metabolism of Strict Anaerobic Bacterium Moorella thermoacetica," *Proteins*, 67:167-176 (2007).
Datsenko et al., "One-step inactivation of chromosomal genes in *Escherichia coli* K-12 using PCR products," *Proc. Natl. Acad. Sci. USA*, 97(12):6640-6645 (2000).
De Bok et al., "Two W-containing formate dehydrogenases (CO2-reductases) involved in syntrophic propionate oxidation by Syntrophobacter fumaroxidans," *Eur. J. Biochem.*, 270:2476-2485 (2003).
Deana, "Substrate specificity of a dicarboxyl-CoA: dicarboxylic acid coenzyme A transferase from rat liver mitochondria," *Biochem. Int.*, 26(4):767-773 (1992).
Di Gennaro et al., "Styrene lower catabolic pathway in Pseudomonas Xuorescens ST: identification and characterization of genes for phenylacetic acid degradation," *Arch. Microbiol.*, 188:117-125 (2007).
Dietrich et al., "High-throughput metabolic engineering: advances in small-molecule screening and selection," *Annu. Rev. Biochem.*, 79:563-590 (2010).
Donovan et al., "Review: optimizing inducer and culture conditions for expression of foreign proteins under the control of the lac promoter," *J. Ind. Microbiol.*, 16(3):145-154 (1996).
Drake et al., "Demonstration of hydrogenase in extracts of the homoacetate-fermenting bacterium Clostridium thermoaceticum," *J. Bacteriol.*, 150(2):702-709 (1982).
Drake et al., "Physiology of the thermophilic acetogen Moorella thermoacetica," *Res. Microbiol.*, 155:869-883 (2004).
Drevland et al., "Enzymology and Evolution of the Pyruvate Pathway to 2-Oxobutyrate in Methanocaldococcus jannaschii," *J. Bacteriol.*, 189:4391-4400 (2007).
Duncombe et al., "Molecular and catalytic properties of the acetoacetyl-coenzyme A thiolase of *Escherichia coli*," *Arch. Biochem. Biophys.*, 176:159-170 (1976).
Evans et al., "A new ferredoxin-dependent carbon reduction cycle in a photosynthetic bacterium," *Proc. Natl. Acad. Sci. USA*, 55:928-934 (1966).
Fernandez-Valverde et al., "Purification of Pseudomonas putida acyl coenzyme A ligase active with a range of aliphatic and aromatic substrates," *Appl. Environ. Microbiol.*, 59(4):1149-1154 (1993).
Fonknechten et al., "A Conserved Gene Cluster Rules Anaerobic Oxidative Degradation of L-Ornithine," *J. Bacteriol.*, 191(9):3162-3167 (2009).
Fontaine et al., "Molecular Characterization and Transcriptional Analysis of adhE2, the Gene Encoding the NADH-Dependent Aldehyde/Alcohol Dehydrogenase Responsible for Butanol Production in Alcohologenic Cultures of Clostridium acetobutylicum ATCC 824," *J. Bacteriol.*, 184(3):821-830 (2002).
Fox et al., "Characterization of the Region Encoding the CO-Induced Hydrogenase of Rhodospirillum rubrum," *J. Bacteriol.*, 178(21):6200-6208 (1996).
Fox et al., "Isolation and characterization of homogeneous acetate kinase from *Salmonella typhimurium* and *Escherichia coli*," *J. Biol. Chem.*, 261(29):13487-13497 (1986).
Francois et al., "Structure of a NADH-insensitive hexameric citrate synthase that resists acid inactivation," *Biochem.*, 45:13487-13499 (2006).
Frerman et al., "Studies on the subunits of *Escherichia coli* coenzyme A transferase. Reconstitution of an active enzyme," *Biochem. Biophys. Acta*, 580:289-297 (1979).
Fuchs et al., "Alternative pathways of carbon dioxide fixation: insights into the early evolution of life?," *Annu. Rev. Microbiol.*, 65:631-658 (2011).
Fujii et al., "Error-prone rolling circle amplification: the simplest random mutagenesis protocol," *Nat. Protoc.*, 1(5):2493-2497 (2006).
Fujii et al., "One-step random mutagenesis by error-prone rolling circle amplification," *Nucl. Acids Res.*, 32(19):e145 (2004).
Fujinaga et al., "Cloning and expression in *Escherichia coli* of the gene encoding the [2Fe—2S] ferredoxin from Clostridium pasteurianum," *Biochem. Biophys. Res. Commun.*, 192(3):1115-1122 (1993).
Furdui et al., "The Role of Pyruvate Ferredoxin Oxidoreductase in Pyruvate Synthesis during Autotrophic Growth by the Wood-Ljungdahl Pathway," *J. Biol. Chem.*, 275(37):28494-28499 (2000).
Galagan et al., "The Genome of M. acetivorans Reveals Extensive Metabolic and Physiological Diversity," *Genome Res.*, 12:532-542 (2002).
Germer et al., "Overexpression, Isolation, and Spectroscopic Characterization of the Bidirectional [NiFe] Hydrogenase from *Synechocystis* sp. PCC 6803," *J. Biol. Chem.*, 284(52):36462-36472 (2009).
Gibbs et al., "Degenerate oligonucleotide gene shufing (DOGS): a method for enhancing the frequency of recombination with family shuffling," *Gene*, 271:13-20 (2001).
Goenrich et al., "A glutathione-dependent formaldehyde-activating enzyme (Gfa) from Paracoccus denitrificans detected and purified via two-dimensional proton exchange NMR spectroscopy," *J. Biol. Chem.*, 277(5):3069-3072 (2002).
Grill et al., "Characterization of Fructose 6 Phosphate Phosphoketolases Purified from *Bifidobacterium* Species," *Curr. Microbiol.*, 31:49-54 (1995).
Guest et al., "The fumarase genes of *Escherichia coli*: location of the fumB gene and discovery of a new gene (fumC)," *J. Gen. Microbiol.*, 131:2971-2984 (1985).
Gutierrez et al., "Structure-guided redesign of D-fructose-6-phosphate aldolase from *E. coli*: remarkable activity and selectivity towards acceptor substrates by two-point mutation," *Chem. Commun.*, 47(20):5762-5764 (2011).
Haller et al., "Discovering New Enzymes and Metabolic Pathways: Conversion of Succinate to Propionate by *Escherichia coli*," *Biochem.*, 39:4622-4629 (2000).
Hansen et al., "De Novo Biosynthesis of Vanillin in Fission Yeast (*Schizosaccharomyces pombe*) and Baker's Yeast (*Saccharomyces cerevisiae*)," *Appl. Environ. Microbiol.*, 75(9):2765-2774 (2009).
Hansen et al., "The effect of the lacY gene on the induction of IPTG inducible promoters, studied in *Escherichia coli* and Pseudomonas fluorescens," *Curr. Microbiol.*, 36(6):341-347 (1998).
Hansford et al., "Control of Mitochondrial Substrate Oxidation," *Cur. Topics Bioeng.*, 10:217-278 (1980).
Hanson et al., "Methanotrophic bacteria," *Microbiol. Rev.*, 60(2):439-471 (1996).
Harms et al., "Methylcobalamin: coenzyme M methyltransferase isoenzymes MtaA and MtbA from Methanosarcina barkeri. Cloning, sequencing and differential transcription of the encoding genes, and functional overexpression of the mtaA gene in *Escherichia coli*," *Eur. J. Biochem.*, 235:653-659 (1996).
Hartmanis et al., "Butyrate kinase from Clostridium acetobutylicum," *J. Biol. Chem.*, 262:617-621 (1987).

(56) References Cited

OTHER PUBLICATIONS

Hashimoto et al., "Activation of L-lysine epsilon-dehydrogenase from Agrobacterium tumefaciens by several amino acids and monocarboxylates," *J. Biochem.*, 106:76-80 (1989).
Hawes et al., "Mammalian 3-Hydroxyisobutyrate Dehydrogenase,"*Methods Enzymol.*, 324:218-228 (2000).
Hawes et al., "Primary Structure and Tissue-specific Expression of Human b-Hydroxyisobutyryl-coenzyme A Hydrolase," *J. Biol. Chem.*, 271(42):26430-26434 (1996).
Hayes et al., "Combining computational and experimental screening for rapid optimization of protein properties," *Proc. Natl. Acad. Sci. USA*, 99:15926-15931 (2002).
Hayes, "Transposon-based strategies for microbial functional genomics and proteomics," *Annu. Rev. Genet.*, 37:3-29 (2003).
Heggeset et al., "Genome Sequence of Thermotolerant Bacillus methanolicus: Features and Regulation Related to Methylotrophy and Production of L-Lysine and L-Glutamate from Methanol," *Appl. Environ. Microbiol.*, 78(15):5170-5181 (2012).
Heil et al., "Glycine binds the transcriptional accessory protein GcvR to disrupt a GcvA/GcvR interaction and allow GcvA-mediated activation of the *Escherichia coli* gcvTHP operon," *Microbiol.*, 148:2203-2214 (2002).
Hektor et al., "Identification of a Magnesium-dependent NAD(P)(H)-binding Domain in the Nicotinoprotein Methanol Dehydrogenase from Bacillus methanolicus," *J. Biol. Chem.*, 277(49):46966-46973 (2002).
Herrmann et al., "Energy Conservation via Electron-Transferring Flavoprotein in Anaerobic Bacteria," *J. Bacteriol.*, 190(3):784-791 (2008).
Hesslinger et al., "Novel keto acid formate-lyase and propionate kinase enzymes are components of an anaerobic pathway in *Escherichia coli* that degrades L-threonine to propionate," *Mol. Microbiol.*, 27(2):477-492 (1998).
Heydari et al., "Highly Stable L-Lysine 6-Dehydrogenase from the Thermophile Geobacillus stearothermophilus Isolated from a Japanese Hot Spring: Characterization, Gene Cloning and Sequencing, and Expression," *Appl. Environ. Microbiol.*, 70(2):937-942 (2004).
Hibbert et al., "Directed evolution of biocatalytic processes," *Biomol. Eng.*, 22:11-19 (2005).
Hillmer et al., "Particulate nature of enzymes involved in the fermentation of ethanol and acetate by Clostridium kluyveri," *FEBS Lett.*, 21(3):351-354 (1972).
Hochstrasser, "Ubiquitin-Dependent Protein Degradation," *Annu. Rev. Genet.*, 30:405-439 (1996).
Hoffmeister et al., "Mitochondrial trans-2-Enoyl-CoA Reductase of Wax Ester Fermentation from Euglena gracilis Defines a New Family of Enzymes Involved in Lipid Synthesis," *J. Biol. Chem.*, 280(6):4329-4338 (2005).
Horiguchi et al., "Peroxisomal Catalase in the Methylotrophic Yeast Candida boidinii: Transport Efficiency and Metabolic Significance," *J. Bacteriol.*, 183(21):6372-6383 (2001).
Houseley et al., "The Many Pathways of RNA Degradation," *Cell*, 136:763-776 (2009).
Huang et al., "Identification and Characterization of a Second Butyrate Kinase from Clostridium acetobutylicum ATCC 824," *J. Mol. Microbiol. Biotechnol.*, 2(1):33-38 (2000).
Hugler et al., "Malonyl-Coenzyme A Reductase from Chloroflexus aurantiacus, a Key Enzyme of the 3-Hydroxypropionate Cycle for Autotrophic CO2 Fixation," *J. Bacteriol.*, 184(9):2404-2410 (2002).
Huisman et al., *Biocatalysis in the Pharmaceutical and Biotechnology Industries*, ed. Patel, CRC Press, Boca Raton, FL, pp. 717-742 (2007).
Ichikawa et al., "Catalytic reaction of 1,3-butanediol over solid acids," *J. Mol. Catalys. A. Chem.*, 256:106-112 (2006).
Ichikawa et al., "PIO study on 1,3-butanediol dehydration over CeO2 (1 1 1) surface," *J. Mol. Catalys. A. Chem.*, 231:181-189 (2006).
Ingoldsby et al., "The discovery of four distinct glutamate dehydrogenase genes in a strain of Halobacterium salinarum," *Gene*, 349:237-244 (2005).

Ingram-Smith et al., "Characterization of the Acetate Binding Pocket in the Methanosarcina thermophila Acetate Kinase," *J. Bacteriol.*, 187(7):2386-2394 (2005).
Ishige et al., "Wax Ester Production from n-Alkanes by *Acinetobacter* sp. Strain M-1: Ultrastructure of Cellular Inclusions and Role of Acyl Coenzyme A Reductase," *Appl. Environ. Microbiol.*, 68(3):1192-1195 (2002).
Ismail et al., "Functional genomics by NMR spectroscopy: Phenylacetate catabolism in *Escherichia coli*," *Eur. J. Biochem.*, 370:3047-3054 (2003).
Ito et al., "Cloning and high-level expression of the glutathione-independent formaldehyde dehydrogenase gene from Pseudomonas putida," *J. Bacteriol.*, 176(9):2483-2491 (1994).
Itoh et al., "Continuous production of chiral 1,3-butanediol using immobilized biocatalysts in a packed bed reactor: promising biocatalysis method with an asymmetric hydrogen-transfer bioreduction," *Appl. Microbiol. Biotechnol.*, 75:1249-1256 (2007).
Iverson et al., "Structure of the *Escherichia coli* Fumarate Reductase Respiratory Complex," *Science*, 284:1961-1966 (1999).
Jacobi et al., "The hyp operon gene products are required for the maturation of catalytically active hydrogenase isoenzymes in *Escherichia coli*," *Arch. Microbiol.*, 158(6):444-451 (1992).
Jeng et al., "Ornithine degradation in Clostridium sticklandii; pyridoxal phosphate and coenzyme A dependent thiolytic cleavage of 2-amino-4-ketopentanoate to alanine and acetyl coenzyme A," *Biochem.*, 13:2898-2903 (1974).
Jeong et al., "Cloning and Characterization of a Gene Encoding Phosphoketolase in a Lactobacillus paraplantarum Isolated from Kimchi," *J. Microbiol. Biotechnol.*, 17(5):822-829 (2007).
Jerome et al., "Development of a fed-batch process for the production of a dye-linked formaldehyde dehydrogenase in Hyphomicrobium zavarzinii ZV 580," *Appl. Microbiol. Biotechnol.*, 77:779-788 (2007).
Jones et al., "Acetone-Butanol Fermentation Revisited," *Microbiol. Rev.*, 50(4):484-524 (1986).
Karlen et al., "Absolute determination of the activity of two $C^{14}$ dating standards," *Arkiv Geofysik*, 4:465-471 (1964).
Kaschabek et al., "Degradation of chloroaromatics: purification and characterization of maleylacetate reductase from *Pseudomonas* sp. strain B13," *J. Bacteriol.*, 175:6075-6081 (1993).
Kaschabek et al., "Maleylacetate Reductase of *Pseudomonas* sp. Strain B13: Specificity of Substrate Conversion and Halide Elimination," *J. Bacteriol.*, 177(2):320-325 (1995).
Kato et al., "3-Methylaspartate ammonia-lyase as a marker enzyme of the mesaconate pathway for (S)-glutamate fermentation in Enterobacteriaceae," *Arch. Microbiol.*, 168:457-463 (1997).
Kawasaki et al., "Transcriptional gene silencing by short interfering RNAs," *Curr. Opin. Mol. Ther.*, 7(2):125-131 (2005).
Kellum et al., "Effects of cultivation gas phase on hydrogenase of the acetogen Clostridium thermoaceticum," *J. Bacteriol.*, 160(1):466-469 (1984).
Kenklies et al., "Proline biosynthesis from L-ornithine in Clostridium sticklandii: purification of deltal-pyrroline-5-carboxylate reductase, and sequence and expression of the encoding gene, proC," *Microbiol.*, 145:819-826 (1999).
Kessler et al., "Pyruvate-formate-lyase-deactivase and acetyl-CoA reductase activities of *Escherichia coli* reside on a polymeric protein particle encoded by adhE," *FEBS Lett.*, 281(1-2):59-63 (1991).
Kikuchi et al., "Glycine cleavage system: reaction mechanism, physiological significance, and hyperglycinemia," *Proc. Jpn. Acad. Ser. B.*, 84:246-263 (2008).
Kim et al., "2-Hydroxyisocaproyl-CoA dehydratase and its activator from Clostridium difficile," *FEBS J.*, 272:550-561 (2005).
Kim et al., "Construction of an *Escherichia coli* K-12 Mutant for Homoethanologenic Fermentation of Glucose or Xylose without Foreign Genes," *Appl. Environ. Microbiol.*, 73(6):1766-1771 (2007).
Kim et al., "Dehydration of (R)-2-hydroxyacyl-CoA to enoyl-CoA in the fermentation of a-amino acids by anaerobic bacteria," *FEMS Microbiol. Rev.*, 28:455-468 (2004).
Kim et al., "Dihydrolipoamide Dehydrogenase Mutation Alters the NADH Sensitivity of Pyruvate Dehydrogenase Complex of *Escherichia coli* K-12," *J. Bacteriol.*, 190(11):3851-3858 (2008).

(56) References Cited

OTHER PUBLICATIONS

Kim et al., "Effect of Overexpression of Actinobacillus succinogenes Phosphoenolpyruvate Carboxykinase on Succinate Production in *Escherichia coli*," *Appl. Environ. Microbiol.*, 70(2):1238-1241 (2004).
Kim, "Purification and properties of a diamine alpha-ketoglutarate transaminase from *Escherichia coli*," *J. Biol. Chem.*, 239:783-786 (1964).
Kloosterman et al., "Molecular, Biochemical, and Functional Characterization of a Nudix Hydrolase Protein That Stimulates the Activity of a Nicotinoprotein Alcohol Dehydrogenase," *J. Biol. Chem.*, 277(38):34785-34792 (2002).
Kocharin et al., "Improved polyhydroxybutyrate production by *Saccharomyces cerevisiae* through the use of the phosphoketolase pathway," *Biotech. Bioeng.*, 110(8):2216-2224 (2013).
Koksal et al., "Structure of isoprene synthase illuminates the chemical mechanism of teragram atmospheric carbon emission," *J. Mol. Biol.*, 402(2):363-373 (2010).
Koland et al., "Proximity of reactive cysteine residue and flavin in *Escherichia coli* pyruvate oxidase as estimated by fluorescence energy transfer," *Biochem.*, 21:4438-4442 (1982).
Kollmann-Koch et al., "Nicotinic Acid Metabolism," *Hoppe Seylers Z. Physiol. Chem.*, 365:847-857 (1984).
Korber et al., "Crystallization of the NADP(+)-dependent glutamate dehydrogenase from *Escherichia coli*," *J. Mol. Biol.*, 234:1270-1273 (1993).
Korolev et al., "Autotracing of *Escherichia coli* acetate CoA-transferase alpha-subunit structure using 3.4 A MAD and 1.9 A native data," *Acta Crystallogr. D. Biol. Crystallogr.*, 58:2116-2121 (2002).
Korotkova et al., "MeaB Is a Component of the Methylmalonyl-CoA Mutase Complex Required for Protection of the Enzyme from Inactivation," *J. Biol. Chem.*, 279(14):13652-13658 (2004).
Kort et al., "Glutamate dehydrogenase from the hyperthermophilic bacterium Thermotoga maritima: molecular characterization and phylogenetic implications," *Extremophiles*, 1:52-60 (1997).
Koutz et al., "Structural comparison of the Pichia pastoris alcohol oxidase genes," *Yeast*, 5:167-177 (1989).
Kowalchuk et al., "Contrasting patterns of evolutionary divergence within the Acinetobacter calcoaceticus pca operon," *Gene*, 146:23-30 (1994).
Kretz et al., "Gene Site Saturation Mutagenesis: A Comprehensive Mutagenesis Approach," *Methods Enzymol.*, 388:3-11 (2004).
Kumari et al., "Cloning, Characterization, and Functional Expression of acs, the Gene Which Encodes Acetyl Coenzyme A Synthetase in *Escherichia coli*," *J. Bacteriol.*, 177(10):2878-2886 (1995).
Kurdistani et al., "Histone acetylation and deacetylation in yeast," *Nat. Rev. Mol. Cell Biol.*, 4(4):276-284 (2003).
Kwon et al., "Influence of Gluconeogenic Phosphoenolpyruvate Carboxykinase (PCK) Expression on Succinic Acid Fermentation in *Escherichia coli* Under High Bicarbonate Condition," *J. Microbiol. Biotechnol.*, 16(9):1448-1452 (2006).
Lamas-Maceiras et al., "Amplification and disruption of the phenylacetyl-CoA ligase gene of Penicillium chrysogenum encoding an aryl-capping enzyme that supplies phenylacetic acid to the isopenicillin N-acyltransferase," *Biochem. J.*, 395:147-155 (2006).
Lametschwandtner et al., "The Difference in Recognition of Terminal Tripeptides as Peroxisomal Targeting Signal 1 between Yeast and Human Is Due to Different Affinities of Their Receptor Pex5p to the Cognate Signal and to Residues Adjacent to It," *J. Biol. Chem.*, 273(50):33635-33643 (1998).
Lawrence et al., "Evolution of coenzyme B12 synthesis among enteric bacteria: evidence for loss and reacquisition of a multigene complex," *Genetics*, 142(1):11-24 (1996).
Lawrence et al., "The Cobalamin (Coenzyme B12) Biosynthetic Genes of *Escherichia coli*," *J. Bacteriol.*, 177(22):6371-6380 (1995).
Lebbink et al., "Engineering activity and stability of Thermotoga maritima Glutamate Dehydrogenase. I. Introduction of a Six-residue Ion-pair Network in the Hinge Region," *J. Mol. Biol.*, 280:287-296 (1998).
Lebbink et al., "Engineering Activity and Stability of Thermotoga maritima Glutamate Dehydrogenase. II: Construction of a 16-Residue Ion-pair Network at the Subunit Interface," *J. Mol. Biol.*, 289:357-369 (1999).
Ledeboer et al., "Molecular cloning and characterization of a gene coding for methanol oxidase in Hansenula polymorpha," *Nucl. Acids Res.*, 13(9):3063-3082 (1985).
Lee et al., "A new approach to directed gene evolution by recombined extension on truncated templates (RETT)," *J. Molec. Catalysis*, 26:119-129 (2003).
Lee et al., "Antisense technology in molecular and cellular bioengineering," *Curr. Opin. Biotechnol.*, 14:505-511 (2003).
Lee et al., "Cloning and characterization of the gene encoding phosphoketolase in Leuconostoc mesenteroides isolated from kimchi," *Biotechnol. Lett.*, 27:853-858 (2005).
Lessner et al., "An unconventional pathway for reduction of CO2 to methane in CO-grown Methanosarcina acetivorans revealed by proteomics," *Proc. Natl. Acad. Sci. USA*, 103:17921-17926 (2006).
Leys et al., "Channelling and formation of 'active' formaldehyde in dimethylglycine oxidase," *EMBO J.*, 22(16):4038-4048 (2003).
Li et al., "Integrated electromicrobial conversion of CO2 to higher alcohols," *Science*, 335:1596 (2012).
Lin et al., "Fed-Batch Culture of a Metabolically Engineered *Escherichia coli* Strain Designed for High-Level Succinate Production and Yield Under Aerobic Conditions," *Biotechnol. Bioeng.*, 90:775-779 (2005).
Lindberg et al., "Engineering a platform for photosynthetic isoprene production in cyanobacteria, using Synechocystis as the model organism," *Metabolic Eng.*, 12:70-79 (2010).
Louie et al., "Cloning and characterization of the gamma-glutamyl phosphate reductase gene of Campylobacter jejuni," *Mol. Gen. Genet.*, 240:29-35 (1993).
Louis et al., "Restricted Distribution of the Butyrate Kinase Pathway among Butyrate-Producing Bacteria from the Human Colon," *J. Bacteriol.*, 186(7):2099-2106 (2004).
Low et al., "Mimicking Somatic Hypermutation: Affinity Maturation of Antibodies Displayed on Bacteriophage Using a Bacterial Mutator Strain," *J. Mol. Biol.*, 260:359-368 (1996).
Lu et al., "Functional Analysis and Regulation of the Divergent spuABCDEFGH-spuI Operons for Polyamine Uptake and Utilization in Pseudomonas aeruginosa PAO1," *J. Bacteriol.*, 184:3765-3773 (2002).
Lu et al., "Sequence and expression of the gene encoding the corrinoid/iron-sulfur protein from Clostridium thermoaceticum and reconstitution of the recombinant protein to full activity," *J. boil. Chem.*, 268:5605-5614 (1993).
Luers et al., "The Pichia pastoris dihydroxyacetone kinase is a PTS1-containing, but cytosolic, protein that is essential for growth on methanol," *Yeast*, 14:759-771 (1998).
Lutz et al., "Creating multiple-crossover DNA libraries independent of sequence identity," *Proc. Natl. Acad. Sci. USA*, 98:11248-11253 (2001).
Lutz et al., "Rapid generation of incremental truncation libraries for protein engineering using α-phosphothioate nucleotides," *Nucl. Acids Res.*, 29(4):e16 (2001).
Maaheimo et al., "Central carbon metabolism of *Saccharomyces cerevisiae* explored by biosynthetic fractional 13C labeling of common amino acids," *Eur. J. Biochem.*, 268:2464-2479 (2001).
Macheroux et al., "A unique reaction in a common pathway: mechanism and function of chorismate synthase in the shikimate pathway," *Planta*, 207:325-334 (1999).
Mack et al., "Conversion of glutaconate CoA-transferase from Acidaminococcus fermentans into an acyl-CoA hydrolase by site-directed mutagenesis," *FEBS Lett.*, 405:209-212 (1997).
Mack et al., "Location of the two genes encoding glutaconate coenzyme A-transferase at the beginning of the hydroxyglutarate operon in Acidaminococcus fermentans," *Eur. J. Biochem.*, 226:41-51 (1994).
Maeda et al., "Enhanced hydrogen production from glucose by metabolically engineered *Escherichia coli*," *Appl. Microbiol. Biotechnol.*, 77:879-890 (2007).
Maeder et al., "The Methanosarcina barkeri Genome: Comparative Analysis with Methanosarcina acetivorans and Methanosarcina

(56) References Cited

OTHER PUBLICATIONS mazei Reveals Extensive Rearrangement within Methanosarcinal Genomes," *J. Bacteriol.*, 188:7922-7931 (2006).
Mahan et al., "Genetic analysis of the proBA genes of *Salmonella typhimurium*: physical and genetic analyses of the cloned proB+ A+ genes of *Escherichia coli* and of a mutant allele that confers proline overproduction and enhanced osmotolerance," *J. Bacteriol.*, 156(3):1249-1262 (1983).
Malone et al., "Characterization of a Pseudomonas putida allylic alcohol dehydrogenase induced by growth on 2-methyl-3-buten-2-ol," *Appl. Environ. Microbiol.*, 65(6):2622-2630 (1999).
Mann et al., "An international reference material for radiocarbon dating," *Radiocarbon*, 25(2): 519-527 (1983).
Mann et al., "Proteomic analysis of post-translational modifications," *Nature Biotech.*, 21:255-261 (2003).
Marolewski et al., "Cloning and characterization of a new purine biosynthetic enzyme: a non-folate glycinamide ribonucleotide transformylase from *E. coli*," *Biochem.*, 33:2531-2537 (1994).
Martinez-Blanco et al., "Purification and biochemical characterization of phenylacetyl-• CoA ligase from Pseudomonas putida. A specific enzyme for the catabolism of phenylacetic acid," *J. Biol. Chem.*, 265(12):7084-7090 (1990).
Martins et al., "Crystal structure of 4-hydroxybutyryl-CoA dehydratase: Radical catalysis involving a [4Fe—4S] cluster and Flavin," *Proc. Natl. Acad. Sci. USA*, 101:15645-15649 (2004).
Matsumoto et al., "A new pathway for poly(3-hydroxybutyrate) production in *Escherichia coli* and Corynebacterium glutamicum by functional expression of a new acetoacetyl-coenzyme A synthase," *Biosci. Biotechnol. Biochem.*, 75(2):364-366 (2011).
Matsuyama et al., "Industrial production of ®-1,3-butanediol by new biocatalysts," *J. Mol. Cat. B. Enzym.*, 11:513-521 (2001).
Matthies et al., "Reciprocal isomerization of butyrate and isobutyrate by the strictly anaerobic bacterium strain WoG13 and methanogenic isobutyrate degradation by a defined triculture," *Appl. Environ. Microbiol.*, 58(5):1435-1439 (1992).
McCue et al., "Gene expression and stress response mediated by the epigenetic regulation of a transposable element small RNA," *PLoS Genet.*, 8(2):e1002474 (2012).
McPherson et al., "Complete nucleotide sequence of the *Escherichia coli* gdhA gene," *Nucleic Acids Res.*, 11:5257-5266 (1983).
Meile et al., "Characterization of the D-Xylulose 5-Phosphate/D-Fructose 6-Phosphate Phosphoketolase Gene (xfp) from Bifidobacterium lactis," *J. Bacteriol.*, 183(9):2929-2936 (2001).
Menon et al., "Mechanism of the Clostridium thermoaceticum Pyruvate:Ferredoxin Oxidoreductase: Evidence for the Common Catalytic Intermediacy of the Hydroxyethylthiamine Pyropyrosphate Radical," *Biochem.*, 36:8484-8494 (1997).
Menzel et al., "Enzymatic evidence for an involvement of pyruvate dehydrogenase in the anaerobic glycerol metabolism of Klebsiella pneumonia," *J. Biotechnol.*, 56(2):135-142 (1997).
Miko, "Phenotype Variability: Penetrance and Expressivity," *Nature Education*, 1(1):137 (2008).
Miller et al., "First isolation of an isoprene synthase gene from poplar and successful expression of the gene in *Escherichia coli*," *Planta*, 213:483-487 (2001).
Misono et al., "Occurrence of L-lysine epsilon-dehydrogenase in Agrobacterium tumefaciens," *J. Bacteriol.*, 150:398-401 (1982).
Mizugaki et al, "Studies on the metabolism of unsaturated fatty acids. IX. Stereochemical studies of the reaction catalyzed by trans-2-enoyl-coenzyme A reductase of *Escherichia coli*," *J. Biochem.*, 92:1649-1654 (1982).
Molin et al., "Dihydroxyacetone Kinases in *Saccharomyces cerevisiae* Are Involved in Detoxification of Dihydroxyacetone," *J. Biol. Chem.*, 278(3):1415-1423 (2003).
Morita et al., "Bacterial Distribution of Glycolaldehyde Dehydrogenase in Relation to Vitamin B6 Biosynthesis," *Agric. Biol. Chem.*, 43(1):185-186 (1979).
Morton et al., "The primary structure of the subunits of carbon monoxide dehydrogenase/acetyl-CoA synthase from Clostridium thermoaceticum," *J. Biol. Chem.*, 266(35):23824-23828 (1991).

Mukhopadhyay et al., "The fdxA Ferredoxin Gene Can Down-Regulate frxA Nitroreductase Gene Expression and Is Essential in Many Strains of Helicobacter pylori," *J. Bacteriol.*, 185(9):2927-2935 (2003).
Muller et al., "Nucleotide exchange and excision technology (NExT) DNA shuffling: a robust method for DNA fragmentation and directed evolution," *Nucl. Acids Res.*, 33(13):e117 (2005).
Musfeldt et al., "Novel Type of ADP-Forming Acetyl Coenzyme A Synthetase in Hyperthermophilic Archaea: Heterologous Expression and Characterization of Isoenzymes from the Sulfate Reducer Archaeoglobus fulgidus and the Methanogen Methanococcus jannaschii," *J. Bacteriol.*, 184(3):636-644 (2002).
Myronova et al., "Three-Dimensional Structure Determination of a Protein Supercomplex That Oxidizes Methane to Formaldehyde in Methylococcus capsulatus (Bath)," *Biochem.*, 45:11905-11914 (2006).
Naggert et al., "Cloning, sequencing, and characterization of *Escherichia coli* thioesterase II," *J. Biol. Chem.*, 266:11044-11050 (1991).
Nagy et al., "Formyltetrahydrofolate Hydrolase, a Regulatory Enzyme That Functions to Balance Pools of Tetrahydrofolate and One-Carbon Tetrahydrofolate Adducts in *Escherichia coli*," *J. Bacteriol.*, 177(5):1292-1298 (1995).
Nakagawa et al., "Alcohol Oxidase Hybrid Oligomers Formed In Vivo and In Vitro," *Yeast*, 15:1223-1230 (1999).
Nakahigashi et al., "Nucleotide sequence of the fadA and fadB genes from *Escherichia coli*," *Nucl. Acids Res.*, 18(16):4937 (1990).
Nakai et al., "A knowledge base for predicting protein localization sites in eukaryotic cells," *Genomics*, 14(4):897-911 (1992).
Nakano et al., "Characterization of Anaerobic Fermentative Growth of Bacillus subtilis: Identification of Fermentation End Products and Genes Required for Growth," *J. Bacteriol.*, 179(21):6749-6755 (1997).
Nakazawa et al., "Pyruvate:NADP+ oxidoreductase is stabilized by its cofactor, thiamin pyrophosphate, in mitochondria of Euglena gracilis," *Arch. Biochem. Biophys.*, 411:183-188 (2003).
Nashizawa et al., "Regulation of inducible gene expression by natural antisense transcripts," *Front Biosci.*, 17:938-958 (2012).
Ness et al., "Synthetic shuffling expands functional protein diversity by allowing amino acids to recombine independently," *Nat. Biotechnol.*, 20:1251-1255 (2002).
Neuberger et al., "Prediction of Peroxisomal Targeting Signal 1 Containing Proteins from Amino Acid Sequence," *J. Mol. Biol.*, 328:581-592 (2003).
Nishimaki et al., "Studies on the metabolism of unsaturated fatty acids. XIV. Purification and properties of NADPH-dependent trans-2-enoyl-CoA reductase of *Escherichia coli* K-12," *J. Biochem.*, 95:1315-1321 (1984).
Nogales et al., "Characterization of the last step of the aerobic phenylacetic acid degradation pathway," *Microbiol.*, 153:357-365 (2007).
Nunn et al., "The nucleotide sequence and deduced amino acid sequence of the genes for cytochrome cL and a hypothetical second subunit of the methanol dehydrogenase of Methylobacterium AM1," *Nucl. Acids Res.*, 16(15):7722 (1988).
O'Brien et al., "Regulation by lipids of cofactor binding to a peripheral membrane enzyme: binding of thiamin pyrophosphate to pyruvate oxidase," *Biochem.*, 16(14):3105-3109 (1977).
O'Brien et al., "Studies of the thiamin pyrophosphate binding site of *Escherichia coli* pyruvate oxidase. Evidence for an essential tryptophan residue," *J. Biol. Chem.*, 255:3302-3307 (1980).
O'Reilly et al., "Sequence and analysis of the citrulline biosynthetic operon argC-F from Bacillus subtilis," *Microbiol.*, 140:1023-1025 (1994).
O'Sullivan, "Aptasensors—the future of biosensing?," *Anal. Bioanal. Chem.*, 372:44-48 (2002).
Ohsugi et al., "Metabolism of L-beta-lysine by a Pseudomonas," *J. Biol. Chem.*, 256(14):7642-7651 (1981).
Okamura-Ikeda et al., "Cloning and nucleotide sequence of the gev operon encoding the *Escherichia coli* glycine-cleavage system," *Eur. J. Biochem.*, 216:539-548 (1993).
Olivera et al., "Molecular characterization of the phenylacetic acid catabolic pathway in Pseudomonas putida U: The phenylacetyl-CoA catabolon," *Proc. Natl. Acad. Sci. USA*, 95:6419-6424 (1998).

(56) References Cited

OTHER PUBLICATIONS

Orita et al., "Bifunctional enzyme fusion of 3-hexulose-6-phosphate synthase and 6-phospho-3-hexuloisomerase," *Appl. Microbiol. Biotechnol.*, 76:439-445 (2007).
Ostermeier et al., "A combinatorial approach to hybrid enzymes independent of DNA homology," *Nat. Biotechnol.*, 17:1205-1209 (1999).
Ostermeier et al., "Combinatorial protein engineering by incremental truncation," *Proc. Natl. Acad. Sci. USA*, 96:3562-3567 (1999).
Otten et al., "Directed evolution: selecting today's biocatalysts," *Biomol. Eng.*, 22:1-9 (2005).
Padovani et al., "Assembly and Protection of the Radical Enzyme, Methylmalonyl-CoA Mutase, by Its Chaperone," *Biochem.*, 45:9300-9306 (2006).
Papini et al., "Physiological characterization of recombinant *Saccharomyces cerevisiae* expressing the *Aspergillus nidulans* phosphoketolase pathway: validation of activity through 13C-based metabolic flux analysis," *Appl. Microbiol. Biotechnol.*, 95:1001-1010 (2012).
Park et al., "Biosynthesis of Poly(3-hydroxybutyrateco-3-hydroxyalkanoates) by Metabolically Engineered *Escherichia coli* Strains," *Appl. Biochem. Biotechnol.*, 113-116:335-346 (2004).
Park et al., "Identification and Characterization of a New Enoyl Coenzyme A Hydratase Involved in Biosynthesis of Medium-Chain-Length Polyhydroxyalkanoates in Recombinant *Escherichia coli*," *J. Bacteriol.*, 185(18):5391-5397 (2003).
Park et al., "New FadB Homologous Enzymes and Their Use in Enhanced Biosynthesis of Medium-Chain-Length Polyhydroxyalkanoates in fadB Mutant *Escherichia coli*," *Biotechnol. Bioeng.*, 86:681-686 (2004).
Park et al., "Purifications and Characterizations of a Ferredoxin and Its Related 2-Oxoacid:Ferredoxin Oxidoreductase from the Hyperthermophilic Archaeon, *Sulfolobus solfataricus* P1," *J. Biochem. Mol. Boil.*, 39(1):46-54 (2006).
Parkin et al., "Rapid and Efficient Electrocatalytic CO2/CO Interconversions by *Carboxydothermus hydrogenoformans* CO Dehydrogenase I on an Electrode," *J. Am. Chem. Soc.*, 129:10328-10329 (2007).
Parsot et al., "Nucleotide sequence of *Escherichia coli* argB and argC genes: comparison of N-acetylglutamate kinase and N-acetylglutamate-gamma-semialdehyde dehydrogenase with homologous and analogous enzymes," *Gene*, 68:275-283 (1988).
Pasquinelli, "MicroRNAs and their targets: recognition, regulation and an emerging reciprocal relationship," *Nat. Rev. Genet.*, 13(4):271-282 (2012).
Pauwels et al., "The N-acetylglutamate synthase/N-acetylglutamate kinase metabolon of *Saccharomyces cerevisiae* allows co-ordinated feedback regulation of the first two steps in arginine biosynthesis," *Eur. J. Biochem.*, 270:1014-1024 (2003).
Paxton et al., "Role of branched-chain 2-oxo acid dehydrogenase and pyruvate dehydrogenase in 2-oxobutyrate metabolism," *Biochem. J.*, 234:295-303 (1986).
Peoples et al., "Fine structural analysis of the *Zoogloea ramigera* phbA'-phbB locus encoding beta-ketothiolase and acetoacetyl-CoA reductase: nucleotide sequence of phbB," *Mol. Microbiol.*, 3(3):349-357 (1989).
Peplinski et al., "Investigations on the microbial catabolism of the organic sulfur compounds TDP and DTDP in *Ralstonia eutropha* H16 employing DNA microarrays," *Appl. Microbiol. Biotechnol.*, 88:1145-1159 (2010).
Pereira et al., "Active site mutants of *Escherichia coli* citrate synthase: Effects of mutations on catalytic and allosteric properties," *J. Biol. Chem.*, 269(1):412-417 (1994).
Pierce et al., "The complete genome sequence of *Moorella thermoacetica* (f. *Clostridium thermoaceticum*)," *Environ. Microbiol.*, 10(10):2550-2573 (2008).
Pieulle et al., "Isolation and Analysis of the Gene Encoding the Pyruvate-Ferredoxin Oxidoreductase of *Desulfovibrio africanus*, Production of the Recombinant Enzyme in *Escherichia coli*, and Effect of Carboxy-Terminal Deletions on Its Stability," *J. Bacteriol.*, 179(18):5684-5692 (1997).
Ploux et al., "The NADPH-linked acetoacetyl-CoA reductase from *Zoogloea ramigera*: Characterization and mechanistic studies of the cloned enzyme over-produced in *Escherichia coli*," *Eur. J. Biochem.*, 174:177-182 (1988).
Poehlein et al., "An Ancient Pathway Combining Carbon Dioxide Fixation with the Generation and Utilization of a Sodium Ion Gradient for ATP Synthesis," *PLoS One*, 7:e33439 (2012).
Pohl et al., "Remarkably Broad Substrate Tolerance of Malonyl-CoA Synthetase, an Enzyme Capable of Intracellular Synthesis of Polyketide Precursors," *J. Am. Chem. Soc.*, 123:5822-5823 (2001).
Porter et al., "Enzymatic properties of dimethylglycine dehydrogenase and sarcosine dehydrogenase from rat liver," *Arch. Biochem. Biophys.*, 243(2):396-407 (1985).
Postma et al., "Phosphoenolpyruvate:carbohydrate phosphotransferase systems of bacteria," *Microbiol. Rev.*, 57(3):543-594 (1993).
Powlowski et al., "Purification and properties of the physically associated meta-cleavage pathway enzymes 4-hydroxy-2-ketovalerate aldolase and aldehyde dehydrogenase (acylating) from *Pseudomonas* sp. strain CF600," *J. Bacteriol.*, 175:377-385 (1993).
Primak et al., "Characterization of a Feedback-Resistant Mevalonate Kinase from the Archaeon *Methanosarcina mazei*," *Appl. Environ. Microbiol.*, 77(21):7772-7778 (2011).
Pritchard et al., "A general model of error-prone PCR," *J. Theor. Biol.*, 234:497-509 (2005).
Pronk et al., "Pyruvate metabolism in *Saccharomyces cerevisiae*," *Yeast*, 12:1607-1633 (1996).
Rado et al., "Phosphotransacetylase from *Bacillus subtilis*: purification and physiological studies," *Biochim. Biophys. Acta*, 321:114-1258 (1973).
Ragsdale et al., "Enzymology of the Wood—Ljungdahl Pathway of Acetogenesis," *Ann. N.Y. Acad. Sci.*, 1125:129-136 (2008).
Ragsdale et al., "Life with Carbon Monoxide," *Crit. Rev. Biochem. Mol. Biol.*, 39:165-195 (2004).
Ragsdale, "Pyruvate Ferredoxin Oxidoreductase and Its Radical Intermediate," *Chem. Rev.*, 103:2333-2346 (2003).
Rajpal et al., "A general method for greatly improving the affinity of antibodies by using combinatorial libraries," *Proc. Natl. Acad. Sci. USA*, 102:8466-8471 (2005).
Rakhely et al., "Cyanobacterial-Type, Heteropentameric, $NAD^+$-Reducing NiFe Hydrogenase in the Purple Sulfur Photosynthetic Bacterium *Thiocapsa roseopersicina*," *Appl. Environ. Microbiol.*, 70(2):722-728 (2004).
Ramos-Vera et al., "Autotrophic Carbon Dioxide Assimilation in Thermoproteales Revisited," *J. Bacteriol.*, 191(13):4286-4297 (2009).
Rangarajan et al., "Structure of [NiFe] Hydrogenase Maturation Protein HypE from *Escherichia coli* and Its Interaction with HypF," *J. Bacteiol.*, 190(4):1447-1458 (2008).
Ratnatilleke et al., "Cloning and Sequencing of the Coenzyme B12-binding Domain of Isobutyryl-CoA Mutase from *Streptomyces cinnamonensis*, Reconstitution of Mutase Activity, and Characterization of the Recombinant Enzyme Produced in *Escherichia coli*," *J. Biologi. Chem.*, 274(44):31679-31685 (1995).
Raux et al., "*Salmonella typhimurium* Cobalamin (Vitamin B12) Biosynthetic Genes: Functional Studies in *S. typhimurium* and *Escherichia coli*," *J. Bacteriol.*, 178(3):753-767 (1996).
Reda et al., "Reversible interconversion of carbon dioxide and formate by an electroactive enzyme," *Proc. Natl. Acad. Sci. USA*, 105(31):10654-10658 (2008).
Reetz et al., "Directed Evolution of an Enantioselective Enzyme through Combinatorial Multiple-Cassette Mutagenesis," *Angew. Chem. Int. Ed.*, 40(19):3589-3591 (2001).
Reetz et al., "Iterative saturation mutagenesis (ISM) for rapid directed evolution of functional enzymes," *Nat. Protoc.*, 2(4):891-903 (2007).
Reetz et al., "Iterative Saturation Mutagenesis on the Basis of B Factors as a Strategy for Increasing Protein Thermostability," *Angew. Chem. Int. Ed. Eng.*, 45:7745-7751 (2006).
Reidhaar-Olson et al., "Combinatorial Cassette Mutagenesis as a Probe of the Informational Content of Protein Sequences," *Science*, 241:53-57 (1988).
Reidhaar-Olson et al., "Random Mutagenesis of Protein Sequences Using Oligonucleotiede Cassettes," *Methods Enzymol.*, 208:564-586 (1991).

(56) References Cited

OTHER PUBLICATIONS

Reiser et al., "Isolation of Mutants of Acinetobacter calcoaceticus Deficient in Wax Ester Synthesis and Complementation of One Mutation with a Gene Encoding a Fatty Acyl Coenzyme A Reductase," *J. Bacteriol.*, 179(9):2969-2975 (1997).
Ringner et al., "Folding free energies of 5'-UTRs impact post-transcriptional regulation on a genomic scale in yeast," *PLoS Comput. Biol.*, 1(7):e72 (2005).
Riviere et al., "Acetyl:Succinate CoA-transferase in Procyclic Trypanosoma brucei," *J. Biol. Chem.*, 279(44):45337-45346 (2004).
Roberts et al., "Cloning and expression of the gene cluster encoding key proteins involved in acetyl-CoA synthesis in Clostridium thermoaceticum: CO dehydrogenase, the corrinoid/Fe—S protein, and methyltransferase," *Proc. Natl. Acad. Sci. USA*, 86:32-36 (1989).
Roberts et al., "The role of enoyl-coa hydratase in the metabolism of isoleucine by Pseudomonas putida," *Arch. Microbiol.*, 177:99-108 (1978).
Robinson et al., "Studies on rat brain acyl-coenzyme A hydrolase (short chain)," *Biochem. Biophys. Res. Commun.*, 71:959-965 (1976).
Rohwerder et al., "The Alkyl tert-Butyl Ether Intermediate 2-Hydroxyisobutyrate Is Degraded via a Novel Cobalamin-Dependent Mutase Pathway," *Appl. Environ. Microbiol.*, 72(6):4128-4135 (2006).
Rother et al., "Anaerobic growth of Methanosarcina acetivorans C2A on carbon monoxide: An unusual way of life for a methanogenic archaeon," *Proc. Natl. Acad. Sci. USA*, 101(48):16929-16934 (2004).
Rother et al., "Genetic and proteomic analyses of CO utilization by Methanosarcina acetivorans," *Arch. Microbiol.*, 188:463-472 (2007).
Ruldeekulthamrong et al., "Molecular characterization of lysine 6-dehydrogenase from Achromobacter denitrificans," *BMB Rep.*, 41:790-795 (2008).
Russell et al., "Peptide Signals Encode Protein Localization," *J. Bacteriol.*, 189(21):7581-7585 (2007).
Sakai et al., "Cloning and sequencing of the alcohol oxidase-encoding gene (AOD1) from the formaldehyde-producing asporogeneous methylotrophic yeast, Candida boidinii S2," *Gene*, 114:67-73 (1992).
Samsonova et al., "Molecular cloning and characterization of Escherichia coli K12 ygjG gene," *BMC Microbiol.*, 3:1-10 (2003).
Sasaki et al., "Gene expression and characterization of isoprene synthase from Populus alba," *FEBS Lett.*, 579:2514-2518 (2005).
Sato et al., "Poly[(R)-3-Hydroxybutyrate] Formation in *Escherichia coli* from Glucose through an Enoyl-CoA Hydratase-Mediated Pathway," *J. Biosci. Bioeng.*, 103:38-44 (2007).
Sawers et al., "Characterization and physiological roles of membrane-bound hydrogenase isoenzymes from Salmonella typhimurium," *J. Bacteriol.*, 168(1):398-404 (1986).
Sawers et al., "Differential expression of hydrogenase isoenzymes in *Escherichia coli* K-12: evidence for a third isoenzyme," *J. Bacteriol.*, 164(3):1324-1331 (1985).
Sawers et al., "Purification and properties of membrane-bound hydrogenase isoenzyme 1 from anaerobically grown *Escherichia coli* K12," *Eur. J. Biochem.*, 156:265-275 (1986).
Sawers et al., "The hydrogenases and formate dehydrogenases of *Escherichia coli*," *Antonie Van Leeuwenhoek*, 66:57-88 (1994).
Schink et al., "The membrane-bound hydrogenase of alcaligenes eutrophus," *Biochim. Biophys. Acta*, 567:315-324 (1979).
Schneider et al., "Purification and properties of soluble hydrogenase from Alcaligenes eutrophus H 16.," *Biochim. Biophys. Acta*, 452:66-80 (1976).
Schwarzer et al., "Nonribosomal peptides: from genes to products," *Nat. Prod. Rep.*, 20:275-287 (2003).
Seedorf et al., "The genome of Clostridium kluyveri, a strict anaerobe with unique metabolic features," *Proc. Natl. Acad. Sci. USA*, 105:2128-2133 (2008).
Selifonova et al., "Rapid Evolution of Novel Traits in Microorganisms," *Appl. Environ. Microbiol.*, 67(8):3645-3649 (2001).
Sen et al., "Developments in Directed Evolution for Improving Enzyme Functions," *Appl. Biochem. Biotechnol.*, 143:212-223 (2007).
Servinsky et al., "Arabinose is metabolized via a phosphoketolase pathway in Clostridium acetobutylicum ATCC 824," *J. Ind. Microbiol. Biotechnol.*, 39:1859-1867 (2012).
Sgorbati et al., "Purification and properties of two fructose-6-phosphate phosphoketolases in Bifidobacterium," *Antoine van Leeuwenhoek*, 42:49-57 (1976).
Shames et al., "Interaction of aspartate and aspartate-derived antimetabolites with the enzymes of the threonine biosynthetic pathway of *Escherichia coli,*" *J. Biol. Chem.*, 259(24):15331-15339 (1984).
Shao et al., "Random-priming in vitro recombination: an effective tool for directed evolution," *Nucl. Acids Res.*, 26(2):681-683 (1998).
Sharkey et al., "Evolution of the Isoprene Biosynthetic Pathway in Kudzu," *Plant Physiol.*, 137(2):700-712 (2005).
Sheppard et al., "Purification and Properties of NADH-Dependent 5,10-Methylenetetrahydrofolate Reductase (MetF) from *Escherichia coli,*" *J. Bacteriol.*, 181(3):718-725 (1999).
Shiba et al., "The CO2 assimilation via the reductive tricarboxylic acid cycle in an obligatory autotrophic, aerobic hydrogen-oxidizing bacterium, Hydrogenobacter thermophiles," *Arch. Microbiol.*, 141:198-203 (1985).
Shimomura et al., "Purification and partial characterization of 3-hydroxyisobutyryl-coenzyme A hydrolase of rat liver," *J. Biol. Chem.*, 269(19):14248-14253 (1994).
Sieber et al., "Libraries of hybrid proteins from distantly related sequences," *Nat. Biotechnol.*, 19:456-460 (2001).
Simicevic et al.,"DNA-centered approaches to characterize regulatory protein-DNA interaction complexes," *Mol. Biosyst.*, 6(3):462-468 (2010).
Skarstedt et al., "*Escherichia coli* acetate kinase mechanism studied by net initial rate, equilibrium, and independent isotopic exchange kinetics," *J. Biol. Chem.*, 251:6775-6783 (1976).
Slater et al., "Multiple beta-ketothiolases mediate poly(beta-hydroxyalkanoate) copolymer synthesis in Ralstonia eutropha," *J. Bacteriol.*, 180(8):1979-1987 (1998).
Smith et al., "Purification and characteristics of a gamma-glutamyl kinase involved in *Escherichia coli* proline biosynthesis," *J. Bacteriol.*, 157(2):545-551 (1984).
Sohling et al., "Molecular Analysis of the Anaerobic Succinate Degradation Pathway in Clostridium kluyveri," *J. Bacteriol.*, 178(3):871-880 (1996).
Sohling et al., "Purification and characterization of a coenzyme-A-dependent succinate-semialdehyde dehydrogenase from Clostridium kluyveri," *Eur. J. Biochem.*, 212:121-127 (1993).
Soini et al., "High cell density media for *Escherichia coli* are generally designed for aerobic cultivations—consequences for large-scale bioprocesses and shake flask cultures," *Microb. Cell. Fact.*, 7:26 (2008).
Speer et al., "Sequence of the gene for a NAD( P)-dependent formaldehyde dehydrogenase (class III alcohol dehydrogenase) from a marine methanotroph Methylobacter marinus A45," *FEMS Microbiol. Lett.*, 121:349-356 (1994).
St. Maurice et al., "Flavodoxin:Quinone Reductase (FqrB): a Redox Partner of Pyruvate: Ferredoxin Oxidoreductase That Reversibly Couples Pyruvate Oxidation to NADPH Production in Helicobacter pylori and Campylobacter jejuni," *J. Bacteriol.*, 189(13):4764-4773 (2007).
Stadtman et al., "Phosphotransacetylase from Clostridium kluyveri," *Methods Enzymol.*, 596-599 (1955).
Starai et al., "Acetate excretion during growth of *Salmonella enterica* on ethanolamine requires phosphotransacetylase (EutD) activity, and acetate recapture requires acetyl-CoA synthetase (Acs) and phosphotransacetylase (Pta) activities," *Microbiol.*, 151:3793-3801 (2005).
Starai et al., "Residue Leu-641 of Acetyl-CoA synthetase is critical for the acetylation of residue Lys-609 by the Protein acetyltransferase enzyme of *Salmonella enterica,*" *J. Biol. Chem.*, 280:26200-26205 (2005).
Stemmer, "DNA shuffling by random fragmentation and reassembly: In vitro recombincation for molecular evolution," *Proc. Natl. Acad. Sci. USA*, 91:10747-10751 (1994).
Stemmer, "Rapid evolution of a protein in vitro by DNA shuffling," *Nature*, 370:389-391 (1994).

(56) References Cited

OTHER PUBLICATIONS

Stokell et al., "Probing the Roles of Key Residues in the Unique Regulatory NADH Binding Site of Type II Citrate Synthase of *Escherichia coli,*" *J. Biol. Chem.*, 278(37):35435-35443 (2003).
Stols et al., "New vectors for co-expression of proteins: Structure of Bacillus subtilis ScoAB obtained by high-throughput protocols," *Protein. Expr. Purif.*, 53:396-403 (2007).
Sunga et al., "The Pichia pastoris formaldehyde dehydrogenase gene (FLD1) as a marker for selection of multicopy expression strains of P. pastoris," *Gene*, 330:39-47 (2004).
Sunohara et al., "Nascent-peptide-mediated ribosome stalling at a stop codon induces mRNA cleavage resulting in nonstop mRNA that is recognized by tmRNA," *RNA*, 10(3):378-386 (2004).
Sunohara et al., "Ribosome stalling during translation elongation induces cleavage of mRNA being translated in *Escherichia coli,*" *J. Biol. Chem.*, 179(15):15968-15975 (2004).
Suzuki et al., "Overexpression, crystallization and preliminary X-ray analysis of xylulose-5-phosphate/ fructose-6-phosphate phosphoketolase from Bifidobacterium breve," *Acta Crystallogr. Sect. F. Stuct. Biol. Cryst. Commun.*, 66:941-943 (2010).
Suzuki, "Phosphotransacetylase of *Escherichia coli* B, activation by pyruvate and inhibition by NADH and certain nucleotides," *Biochem. Biophys. Acta*, 191:559-569 (1969).
Svetlitchnyi et al., "A functional Ni—Ni—[4Fe—4S] cluster in the monomeric acetyl-CoA synthase from Carboxydothermus hydrogenoformans," *Proc. Natl. Acad. Sci. USA*, 101(2):446-451 (2004).
Takács et al., "Formate hydrogenlyase in the hyperthermophilic archaeon, Thermococcus litoralis," *BMC Microbiol.*, 8:88 (2008).
Takahashi et al., "Functional assignment of the ORF2-iscS-iscU-iscA-hscB-hscA-fdx-ORF3 gene cluster involved in the assembly of Fe—S clusters in *Escherichia coli,*" *J. Biochem.*, 126:917-926 (1999).
Takahashi et al., "Metabolic Pathways for Cytotoxic End Product Formation from Glutamate- and Aspartate-Containing Peptides by Porphyromonas gingivalis," *J. Bacteriol.*, 182(17):4704-4710 (2000).
Takeo et al., "Existence and properties of two malic enzymes in *Escherichia coli* especially of NAD-linked enzyme," *J. Biochem.*, 66(3):379-387 (1969).
Tani et al., "Glycolaldehyde Dehydrogenase, Its Involvement in Vitamin B6 Biosynthetic Pathway of *Escherichia coli* B," *Agric. Biol. Chem.*, 38:2057-2058 (1974).
Tani et al., "Separation and Characterization of Glycolaldehyde Dehydrogenase Isozymes in *Escherichia coli* B," *Agric. Biol. Chem.*, 42(1):63-68 (1978).
Thai et al., "Farnesol is utilized for isoprenoid biosynthesis in plant cells via farnesyl pyrophosphate formed by successive monophosphorylation reactions," *Proc. Natl. Acad. Sci. USA*, 96(23):13080-13085 (1999).
Thauer et al., "A Fifth Pathway of Carbon Fixation," *Science*, 318:1732-1733 (2007).
Tseng et al., "Oxygen- and Growth Rate-Dependent Regulation of *Escherichia coli* Fumarase (FumA, FumB, and FumC) Activity," *J. Bacteriol.*, 183(2):461-467 (2001).
Tucci et al., "A novel prokaryotic trans-2-enoyl-CoA reductase from the spirochete Treponema denticola," *FEBS Lett.*, 581:1561-1566 (2007).
Twarog et al., "Role of Butyryl Phosphate in the Energy Metabolism of Clostridium Tetanomorphum," *J. Bacteriol.*, 86:112-117 (1963).
Valdes-Hevia et al., "Isolation and characterization of the gene encoding phosphoenolpyruvate carboxykinase from *Saccharomyces cerevisiae,*" *FEBS Lett.*, 258:313-316 (1989).
Vamecq et al., "The microsomal dicarboxylyl-CoA synthetase," *Biochem. J.*, 230:683-693 (1985).
Van Der Klei et al., "The Hansenula polymorpha per6 mutant is affected in two adjacent genes which encode dihydroxyacetone kinase and a novel protein, Pak1p, involved in peroxisome integrity," *Curr. Genet.*, 34:1-11 (1998).

Van Grinsven et al., "Acetate:Succinate CoA-transferase in the Hydrogenosomes of Trichomonas vaginalis," *J. Biol. Chem.*, 283(3):1411-1418 (2008).
Van Vliet et al., "The iron-induced ferredoxin FdxA of Campylobacter jejuni is involved in aerotolerance," *FEMS Microbiol. Lett.*, 196:189-193 (2001).
Vanderwinkel et al., "Growth of *Escherichia coli* on fatty acids: requirement for coenzyme A transferase activity," *Biochem. Biophys. Res. Commun.*, 33:902-908 (1968).
Vardar-Schara et al., "Metabolically engineered bacteria for producing hydrogen via fermentation," *Microbiol. Biotechnol.*, 1(2):107-125 (2008).
Vazquez et al., "Phosphotransbutyrylase Expression in Bacillus megaterium," *Curr. Microbiol.*, 42:345-349 (2001).
Vita et al., "Disulfide Bond-Dependent Mechanism of Protection against Oxidative Stress in Pyruvate-Ferredoxin Oxidoreductase of Anaerobic DesulfoVibrio Bacteria," *Biochem.*, 47:957-964 (2008).
Volkov et al., "Random Chimeragenesis by Heteroduplex Recombination," *Methods Enzym.*, 328:456-463 (2000).
Volkov et al., "Recombination and chimeragenesis by in vitro heteroduplex formation and in vivo repair," *Nucl. Acids Res.*, 27(18):e18 (1999).
Vonck et al., "Electron microscopic analysis and biochemical characterization of a novel methanol dehydrogenase from the thermotolerant Bacillus sp. C1," *J. Biol. Chem.*, 266(6):3949-3954 (1991).
Vorholt et al., "Novel Formaldehyde-Activating Enzyme in Methylobacterium extorquens AMI Required for Growth on Methanol," *J. Bacteriol.*, 182(23):6645-6650 (2000).
Walter et al., "Sequence and arrangement of two genes of the butyrate-synthesis pathway of Clostridium acetobutylicum ATCC 824," *Gene*, 134:107-111 (1993).
Wang et al., "Activation of silent genes by transposons Tn5 and Tn10," *Genetics*, 120(4):875-885 (1988).
Wang et al., "Molecular cloning and functional identification of a novel phenylacetyl-CoA ligase gene from Penicillium chrysogenum," *Biochem. Biophys. Res. Commun.*, 360(2):453-458 (2007).
Wang et al., "Overview of Regulatory Strategies and Molecular Elements in Metabolic Engineering of Bacteria," *Mol. Biotechnol.*, 52(2):300-308 (2012).
Weaver, "Structure of free fumarase C from *Escherichia coli,*" *Acta Crystallogr. D. Biol. Crystallogr.*, 61:1395-1401 (2005).
Westin et al., "The Identification of a Succinyl-CoA Thioesterase Suggests a Novel Pathway for Succinate Production in Peroxisomes," *J. Biol. Chem.*, 280(46):38125-38132 (2005).
Wieland et al., "Engineering of ribozyme-based riboswitches for mammalian cells," *Methods*, 56(3):351-357 (2012).
Wiesenborn et al., "Phosphotransbutyrylase from Clostridium acetobutylicum ATCC 824 and its role in acidogenesis," *Appl. Environ. Microbiol.*, 55(2):317-322 (1989).
Winzer et al., "Acetate kinase from Clostridium acetobutylicum: a highly specific enzyme that is actively transcribed during acidogenesis and solventogenesis," *Microbiol.*, 143:3279-3286 (1997).
Wolff et al., "Purification and characterization of the oxygen-sensitive 4-hydroxybutanoate dehydrogenase from Clostridium kluyveri," *Protein Expir. Purif.*, 6:206-212 (1995).
Wong et al., "Sequence saturation mutagenesis (SeSaM): a novel method for directed evolution," *Nucl. Acids Res.*, 33:e26 (2004).
Wong et al., "Sequence saturation mutagenesis with tunable mutation frequencies," *Anal. Biochem.*, 341:187-189 (2005).
Wong et al., "Transversion-enriched sequence saturation mutagenesis (SeSaM-Tv+): A random mutagenesis method with consecutive nucleotide exchanges that complements the bias of error-prone PCR," *Biotechnol. J.*, 3:74-82 (2008).
Woods et al., "Two biochemically distinct classes of fumarase in *Escherichia coli,*" *Biochim. Biophys. Acta*, 954:14-26 (1988).
Wu et al., "Life in Hot Carbon Monoxide: The Complete Genome Sequence of Carboxydothermus hydrogenoformans Z-2901," *PLoS Genet.*, 1:e65 (2005).
Yamamoto et al., "Carboxylation reaction catalyzed by 2-oxoglutarate:ferredoxin oxidoreductases from Hydrogenobacter thermophiles," *Extremophiles*, 14:79-85 (2010).

(56) References Cited

OTHER PUBLICATIONS

Yang et al., "Collaborative spirit of histone deacetylases in regulating chromatin structure and gene expression," *Curr. Opin. Genet. Dev.*, 13(2):143-153 (2003).

Yang et al., "Nucleotide Sequence of the fadA Gene," *J. Biol. Chem.*, 265(18):10424-10429 (1990).

Yang et al., "Nucleotide Sequence of the fadA Gene," *J. Biol. Chem.*, 266:16255 (1991).

Yang et al., "Nucleotide sequence of the promoter and fadB gene of the fadBA operon and primary structure of the multifunctional fatty acid oxidation protein from *Escherichia coli*," *Biochem.*, 30:6788-6795 (1991).

Yin et al., "The gene encoding xylulose-5-phosphate/fructose-6-phosphate phosphoketolase (xfp) is conserved among *Bifidobacterium* species within a more variable region of the genome and both are useful for strain identification," *FEMS Microbiol. Lett.*, 246:251-257 (2005).

Yim et al., "Metabolic engineering of *Escherichia coli* for direct production of 1,4-butanediol," *Nature Chem. Biol.*, 7(7):445-452 (2011).

Youngleson et al., "Homology between Hydroxybutyryl and Hydroxyacyl Coenzyme A Dehydrogenase Enzymes from Clostridium acetobutylicum Fermentation and Vertebrate Fatty Acid β-Oxidation Pathways," *J. Bacteriol.*, 171(12):6800-6807 (1989).

Yuan et al., "Prokaryotic ubiquitin-like ThiS fusion enhances the heterologous protein overexpression and aggregation in *Escherichia coli*," *PLoS One*, 8(4):e62529 (2013).

Yurimoto et al., "Yeast methylotrophy: metabolism, gene regulation and peroxisome homeostasis," *Int. J. Microbiol.*, 2011:101298 (2011).

Zhang et al., "Genes encoding acyl-CoA dehydrogenase (AcdH) homologues from Streptomyces coelicolor and Streptomyces avermitilis provide insights into the metabolism of small branched-chain fatty acids and macrolide antibiotic production," *Microbiol.*, 145:2323-2334 (1999).

Zhao et al., "Molecular evolution by staggered extension process (StEP) in vitro recombination," *Nat. Biotechnol.*, 16(3):258-261 (1998).

Zhou et al., "Engineering a native homoethanol pathway in *Escherichia coli* B for ethanol production," *Biotechnol. Lett.*, 30:335-342 (2008).

Chinen et al., "Innovative metabolic pathway design for efficient 1-glutamate production by suppressing CO2 emission," *J Biosci. Bioeng.*, 103(3):262-269 (2007).

Jakobsen et al., "Upregulated Transcription of Plasmid and Chromosomal Ribulose Monophosphate Pathway Genes Is Critical for Methanol Assimilation Rate and Methanol Tolerance in the Methylotrophic Bacterium Bacillus methanolicus," *J Bacteriol.*, 188(8):3063-3072 (2006).

Kern et al., "Engineering primary metabolic pathways of industrial micro-organisms," *J. Bacteriol.*, 129:6-29 (2007).

Sonderegger et al., "Metabolic Engineering of a Phosphoketolase Pathway for Pentose Catabolism in Saccharomyces cerevisiae," *Appl. Environ. Microbiol.*, 70(5):2892-2897 (2004).

\* cited by examiner

MICROORGANISMS AND METHODS FOR IMPROVING PRODUCT YIELDS ON METHANOL USING ACETYL-COA SYNTHESIS

CROSS-REFERENCE TO RELAYED APPLICATIONS

This application is a United States National Stage Application under 35 U.S.C. § 371 of International Patent Application No. PCT/US2014/067287, filed Nov. 25, 2014, which claims the benefit of priority of U.S. Provisional Application Ser. No. 61/945,056, filed Feb. 26, 2014, and 61/911,414, filed Dec. 3, 2013, the entire contents of which are each incorporated herein by reference.

BACKGROUND OF THE INVENTION

The present invention relates generally to biosynthetic processes, and more specifically to organisms having pathways for enhanced carbon flux through acetyl-CoA.

1,3-butanediol (1,3-BDO) is a four carbon diol traditionally produced from acetylene via its hydration. The resulting acetaldehyde is then converted to 3-hydroxybutyraldehdye which is subsequently reduced to form 1,3-BDO. More recently, acetylene has been replaced by the less expensive ethylene as a source of acetaldehyde. 1,3-BDO is commonly used as an organic solvent for food flavoring agents. It is also used as a co-monomer for polyurethane and polyester resins and is widely employed as a hypoglycemic agent. Optically active 1,3-BDO is a useful starting material for the synthesis of biologically active compounds and liquid crystals. Another use of 1,3-butanediol is that its dehydration affords 1,3-butadiene (Ichikawa et al. *Journal of Molecular Catalysis A-Chemical* 256:106-112 (2006); Ichikawa et al. *Journal of Molecular Catalysis A-Chemical* 231:181-189 (2005), which is useful in the manufacture synthetic rubbers (e.g., tires), latex, and resins. The reliance on petroleum based feedstocks for either acetylene or ethylene warrants the development of a renewable feedstock based route to 1,3-butanediol and to butadiene.

1,4-butanediol (1,4-BDO) is a valuable chemical for the production of high performance polymers, solvents, and fine chemicals. It is the basis for producing other high value chemicals such as tetrahydrofuran (THF) and gamma-butyrolactone (GBL). The value chain is comprised of three main segments including: (1) polymers, (2) THF derivatives, and (3) GBL derivatives. In the case of polymers, 1,4-BDO is a comonomer for polybutylene terephthalate (PBT) production. PBT is a medium performance engineering thermoplastic used in automotive, electrical, water systems, and small appliance applications. Conversion to THF, and subsequently to polytetramethylene ether glycol (PTMEG), provides an intermediate used to manufacture spandex products such as LYCRA® fibers. PTMEG is also combined with 1,4-BDO in the production of specialty polyester ethers (COPE). COPEs are high modulus elastomers with excellent mechanical properties and oil/environmental resistance, allowing them to operate at high and low temperature extremes. PTMEG and 1,4-BDO also make thermoplastic polyurethanes processed on standard thermoplastic extrusion, calendaring, and molding equipment, and are characterized by their outstanding toughness and abrasion resistance. The GBL produced from 1,4-BDO provides the feedstock for making pyrrolidones, as well as serving the agrochemical market. The pyrrolidones are used as high performance solvents for extraction processes of increasing use, including for example, in the electronics industry and in pharmaceutical production.

1,4-BDO is produced by two main petrochemical routes with a few additional routes also in commercial operation. One route involves reacting acetylene with formaldehyde, followed by hydrogenation. More recently 1,4-BDO processes involving butane or butadiene oxidation to maleic anhydride, followed by hydrogenation have been introduced. 1,4-BDO is used almost exclusively as an intermediate to synthesize other chemicals and polymers.

Over 25 billion pounds of butadiene (1,3-butadiene, BD) are produced annually and is applied in the manufacture of polymers such as synthetic rubbers and ABS resins, and chemicals such as hexamethylenediamine and 1,4-butanediol. For example, butadiene can be reacted with numerous other chemicals, such as other alkenes, e.g. styrene, to manufacture numerous copolymers, e.g. acrylonitrile 1,3-butadiene styrene (ABS), styrene-1,3-butadiene (SBR) rubber, styrene-1,3-butadiene latex. These materials are used in rubber, plastic, insulation, fiberglass, pipes, automobile and boat parts, food containers, and carpet backing. Butadiene is typically produced as a by-product of the steam cracking process for conversion of petroleum feedstocks such as naphtha, liquefied petroleum gas, ethane or natural gas to ethylene and other olefins. The ability to manufacture butadiene from alternative and/or renewable feedstocks would represent a major advance in the quest for more sustainable chemical production processes.

Crotyl alcohol, also referred to as 2-buten-1-ol, is a valuable chemical intermediate. It serves as a precursor to crotyl halides, esters, and ethers, which in turn are chemical intermediates in the production of monomers, fine chemicals, agricultural chemicals, and pharmaceuticals. Exemplary fine chemical products include sorbic acid, trimethylhydroquinone, crotonic acid and 3-methoxybutanol. Crotyl alcohol is also a precursor to 1,3-butadiene. Crotyl alcohol is currently produced exclusively from petroleum feedstocks. For example Japanese Patent 47-013009 and U.S. Pat. Nos. 3,090,815, 3,090,816, and 3,542,883 describe a method of producing crotyl alcohol by isomerization of 1,2-epoxybutane. The ability to manufacture crotyl alcohol from alternative and/or renewable feedstocks would represent a major advance in the quest for more sustainable chemical production processes.

3-Buten-2-ol (also referenced to as methyl vinyl carbinol (MVC)) is an intermediate that can be used to produce butadiene. There are significant advantages to use of 3-buten-2-ol over 1,3-BDO because there are fewer separation steps and only one dehydration step. 3-Buten-2-ol can also be used as a solvent, a monomer for polymer production, or a precursor to fine chemicals. Accordingly, the ability to manufacture 3-buten-2-ol from alternative and/or renewable feedstock would again present a significant advantage for sustainable chemical production processes.

Adipic acid, a dicarboxylic acid, has a molecular weight of 146.14. It can be used is to produce nylon 6,6, a linear polyamide made by condensing adipic acid with hexamethylenediamine. This is employed for manufacturing different kinds of fibers. Other uses of adipic acid include its use in plasticizers, unsaturated polyesters, and polyester polyols. Additional uses include for production of polyurethane, lubricant components, and as a food ingredient as a flavorant and gelling aid.

Historically, adipic acid was prepared from various fats using oxidation. Some current processes for adipic acid synthesis rely on the oxidation of KA oil, a mixture of cyclohexanone, the ketone or K component, and cyclohexanol, the alcohol or A component, or of pure cyclohexanol using an excess of strong nitric acid. There are several variations of this theme which differ in the routes for production of KA or cyclohexanol. For example, phenol is an alternative raw material in KA oil production, and the process for the synthesis of adipic acid from phenol has been described. The other versions of this process tend to use oxidizing agents other than nitric acid, such as hydrogen peroxide, air or oxygen.

In addition to hexamethylenediamine (HMDA) being used in the production of nylon-6,6 as described above, it is also utilized to make hexamethylene diisocyanate, a monomer feedstock used in the production of polyurethane. The diamine also serves as a cross-linking agent in epoxy resins. HMDA is presently produced by the hydrogenation of adiponitrile.

Caprolactam is an organic compound which is a lactam of 6-aminohexanoic acid (ε-aminohexanoic acid, 6-aminocaproic acid). It can alternatively be considered cyclic amide of caproic acid. One use of caprolactam is as a monomer in the production of nylon-6. Caprolactam can be synthesized from cyclohexanone via an oximation process using hydroxylammonium sulfate followed by catalytic rearrangement using the Beckmann rearrangement process step.

Methylacrylic acid (MAA) is a key precursor of methyl methacrylate (MMA), a chemical intermediate with a global demand in excess of 4.5 billion pounds per year, much of which is converted to polyacrylates. The conventional process for synthesizing methyl methacrylate (i.e., the acetone cyanohydrin route) involves the conversion of hydrogen cyanide (HCN) and acetone to acetone cyanohydrin which then undergoes acid assisted hydrolysis and esterification with methanol to give MAA. Difficulties in handling potentially deadly HCN along with the high costs of byproduct disposal (1.2 tons of ammonium bisulfate are formed per ton of MAA) have sparked a great deal of research aimed at cleaner and more economical processes. As a starting material, MAA can easily be converted into MAA via esterification with methanol.

Thus, there exists a need for the development of methods for effectively producing commercial quantities of compounds such as fatty alcohols, 1,3-butanediol, 1,4-butanediol, butadiene, crotyl alcohol, 3-buten-2-ol, adipate, 6-aminocaproate, caprolactam, hexamethylenediamine and methacylic acid. The present invention satisfies this need and provides related advantages as well.

SUMMARY OF INVENTION

The invention provides non-naturally occurring microbial organisms containing enzymatic pathways for enhancing carbon flux through acetyl-CoA. In some embodiments, the microbial organisms of the invention having such pathways also include pathways for generating reducing equivalents, formaldehyde fixation and/or formate assimilation. The enhanced carbon flux through acetyl-CoA, in combination with pathways for generating reducing equivalents, formaldehyde fixation and/or formate assimilation can, in some embodiments, be used for production of a bioderived compound of the invention. Accordingly, in some embodiments, the microbial organisms of the invention can include a pathway capable of producing a bioderived compound of the invention. Bioderived compounds of the invention include alcohols, glycols, organic acids, alkenes, dienes, organic amines, organic aldehydes, vitamins, nutraceuticals and pharmaceuticals. In some embodiments, the bioderived compound is 1,3-butanediol, crotyl alcohol, butadiene, 3-buten-2-ol, 1,4-butanediol, adipate, 6-aminocaproate, caprolactam, hexamethylenediamine, methacrylic acid, 2-hydroxyisobutyric acid, or an intermediate thereto.

In some embodiments, a non-naturally occurring microbial organism of the invention includes a methanol metabolic pathway as depicted in FIG. 2 and an acetyl-CoA pathway as depicted in FIG. 1 or 3. In some aspects the microbial organism can further includes a formaldehyde fixation pathway and/or formate assimilation pathway as depicted in FIG. 1. Alternatively, in some embodiments, the non-naturally occurring microbial organism of the invention includes a formaldehyde fixation pathway as depicted in FIG. 1, a formate assimilation pathway as depicted in FIG. 1, and/or an acetyl-CoA pathway as depicted in FIG. 1 or 3.

In one aspect, the formaldehyde fixation pathway, formate assimilation pathway, and/or a methanol metabolic pathway present in the microbial organisms of the invention enhances the availability of substrates and/or pathway intermediates, such as acetyl-CoA, and/or reducing equivalents, which can be utilized for bioderived compound production through one or more bioderived compound pathways of the invention. For example, in some embodiments, a non-naturally occurring microbial organism of the invention that includes a methanol metabolic pathway can enhance the availability of reducing equivalents in the presence of methanol and/or convert methanol to formaldehyde, a substrate for the formaldehyde fixation pathway. Likewise, a non-naturally occurring microbial organism of the invention having a formate assimilation pathway can reutilize formate to generate substrates and pathway intermediates such as formaldehyde, pyruvate and/or acetyl-CoA. In another embodiment, a non-naturally occurring microbial organism of the invention can include a pathway for producing acetyl-CoA and/or succinyl-CoA by a pathway depicted in FIG. 4. Such substrates, intermediates and reducing equivalents can be used to increase the yield of a bioderived compound produced by the microbial organism.

In some embodiments, the invention provides a non-naturally occurring microbial organism containing an acetyl-CoA pathway, a methanol oxidation pathway, a hydrogenase and/or a carbon monoxide dehydrogenase.

Accordingly, in some embodiments, the invention provides a non-naturally occurring microbial organism having an acetyl-CoA pathway and at least one exogenous nucleic acid encoding an acetyl-CoA pathway enzyme expressed in a sufficient amount to produce or enhance carbon flux through acetyl-CoA, wherein the acetyl-CoA pathway includes a pathway shown in FIG. 3. In some embodiments, the invention provides a non-naturally occurring microbial organism having a methanol oxidation pathway enzyme expressed in a sufficient amount to produce formaldehyde in the presence of methanol. An exemplary methanol oxidation pathway enzyme is a methanol dehydrogenase as depicted in FIG. 1, Step A. In some embodiments, the invention provides a non-naturally occurring microbial organism having a hydrogenase and/or a carbon monoxide dehydrogenase for generating reducing equivalents as depicted in FIGS. 2 and 3.

The invention further provides non-naturally occurring microbial organisms that have elevated or enhanced synthesis or yield of acetyl-CoA (e.g. intracellular) or bioderived compound including alcohols, diols, fatty acids, glycols, organic acids, alkenes, dienes, organic amines, organic aldehydes, vitamins, nutraceuticals and pharmaceuticals and methods of using those non-naturally occurring organisms to produce such biosynthetic products. The enhanced synthesis of intracellular acetyl-CoA enables enhanced production of bioderived compounds for which acetyl-CoA is an intermediate and further, may have been rate-limiting.

In some embodiments, the invention provides a non-naturally occurring microbial organism having attenuation of one or more endogenous enzymes, which enhances carbon flux through acetyl-CoA, or a gene disruption of one or more endogenous nucleic acids encoding such enzymes. For example, in some aspects, the endogenous enzyme can be selected from dihydroxyacetone (DHA) kinase, methanol oxidase, pyrroloquinoline quinone (PQQ)-dependent methanol dehydrogenase, DHA synthase or any combination thereof.

In some embodiments, the invention provides a non-naturally occurring microbial organism having attenuation of one or more endogenous enzymes of a competing formaldehyde assimilation or dissimilation pathway or a gene disruption of one or more endogenous nucleic acids encoding enzymes of a competing formaldehyde assimilation or dissimilation pathway. Examples of these endogenous enzymes are described herein.

The invention still further provides a bioderived compound produced by a microbial organism of the invention, culture medium having the bioderived compound of the invention, compositions having the bioderived compound of the invention, a biobased product comprising the bioderived compound of the invention, and a process for producing a bioderived compound of the invention.

DETAILED DESCRIPTION OF THE INVENTION

Figure 1:
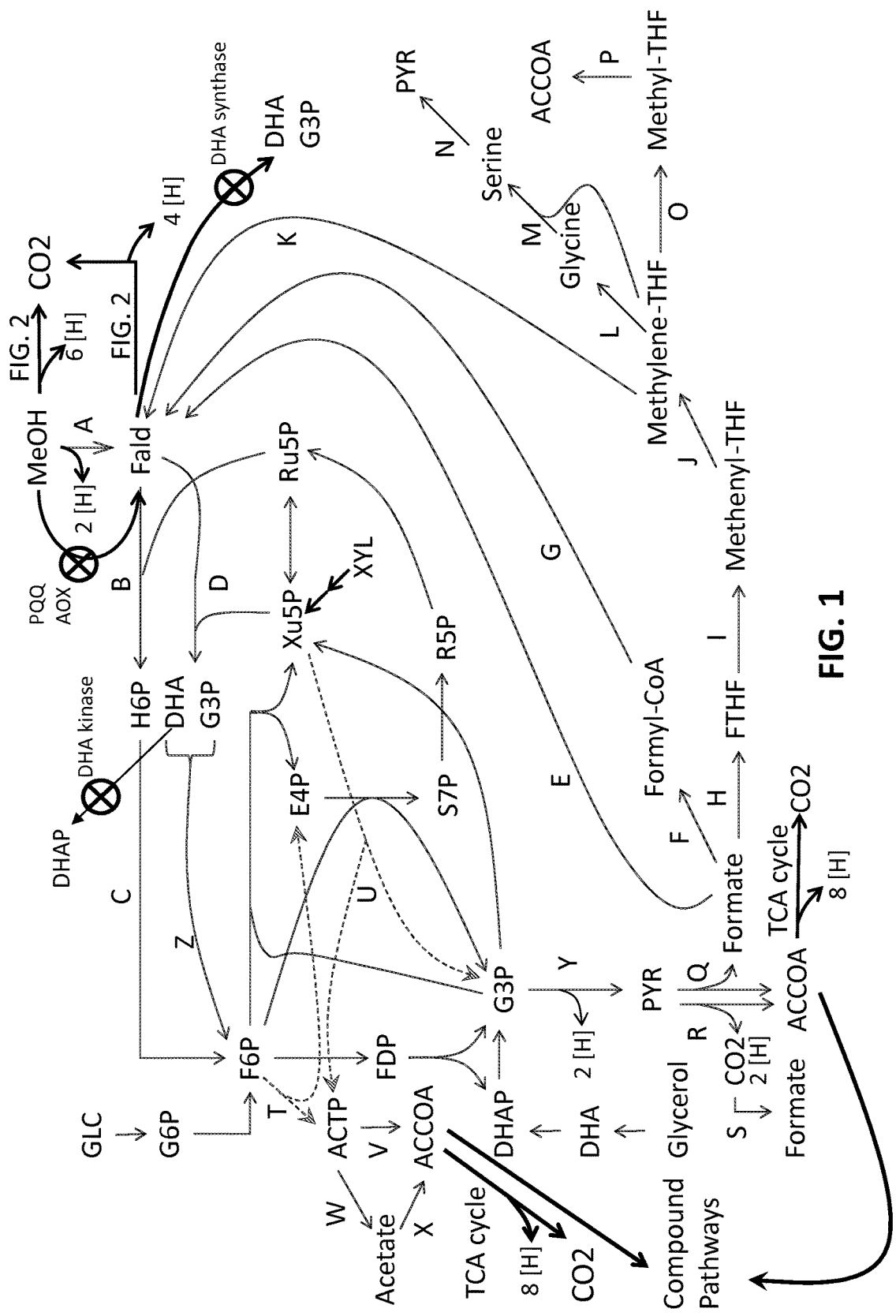
FIG. 1 shows exemplary metabolic pathways enabling the conversion of CO2, formate, formaldehyde (Fald), methanol (MeOH), glycerol, xylose (XYL) and glucose (GLC) to acetyl-CoA (ACCOA) and exemplary endogenous enzyme targets for optional attenuation or disruption. The exemplary pathways can be combined with bioderived compound pathways, including the pathways depicted herein that utilize ACCOA, such as those depicted in FIGS. 4-10. The enzyme targets are indicated by arrows having "X" markings. The endogenous enzyme targets include DHA kinase, methanol oxidase (AOX), PQQ-dependent methanol dehydrogenase (PQQ) and/or DHA synthase. The enzymatic transformations shown are carried out by the following enzymes: A) methanol dehydrogenase, B) 3-hexulose-6-phosphate synthase, C) 6-phospho-3-hexuloisomerase, D) dihydroxyacetone synthase, E) formate reductase, F) formate ligase, formate transferase, or formate synthetase, G) formyl-CoA reductase, H) formyltetrahydrofolate synthetase, I) methenyltetrahydrofolate cyclohydrolase, J) methylenetetrahydrofolate dehydrogenase, K) spontaneous or formaldehyde-forming enzyme, L) glycine cleavage system, M) serine hydroxymethyltransferase, N) serine deaminase, O) methylenetetrahydrofolate reductase, P) acetyl-CoA synthase, Q) pyruvate formate lyase, R) pyruvate dehydrogenase, pyruvate ferredoxin oxidoreductase, or pyruvate:NADP+ oxidoreductase, S) formate dehydrogenase, T) fructose-6-phosphate phosphoketolase, U) xylulose-5-phosphate phosphoketolase, V) phosphotransacetylase, W) acetate kinase, X) acetyl-CoA transferase, synthetase, or ligase, Y) lower glycolysis including glyceraldehyde-3-phosphate dehydrogenase, Z) fructose-6-phosphate aldolase. See abbreviation list below for compound names.

The present invention is directed to metabolic and biosynthetic processes and microbial organisms capable of enhancing carbon flux through acetyl-CoA. The invention disclosed herein is based, at least in part, on non-naturally occurring microbial organisms capable of synthesizing a bioderived compound using an acetyl-CoA pathway, methanol metabolic pathway, a formaldehyde fixation pathway, and/or a formate assimilation pathway in combination with a bioderived compound pathway. Additionally, in some embodiments, the non-naturally occurring microbial organisms can further include a methanol oxidation pathway, a hydrogenase and/or a carbon monoxide dehydrogenase.

The following is a list of abbreviations and their corresponding compound or composition names. These abbreviations, which are used throughout the disclosure and the figures. It is understood that one of ordinary skill in the art can readily identify these compounds/compositions by such nomenclature: MeOH or MEOH=methanol; Fald=formaldehyde; GLC=glucose; G6P=glucose-6-phosphate; H6P=hexulose-6-phosphate; F6P=fructose-6-phosphate; FDP=fructose diphosphate or fructose-1,6-diphosphate; DHA=dihydroxyacetone; DHAP=dihydroxyacetone phosphate; G3P=glyceraldehyde-3-phosphate; PYR=pyruvate; ACTP=acetyl-phosphate; ACCOA=acetyl-CoA; AACOA=acetoacetyl-CoA; MALCOA=malonyl-CoA; FTHF=formyltetrahydrofolate; THF=tetrahydrofolate; E4P=erythrose-4-phosphate: Xu5P=xyulose-5-phosphate; Ru5P=ribulose-5-phosphate; S7P=sedoheptulose-7-phosphate: R5P=ribose-5-phosphate; XYL=xylose; TCA=tricarboxylic acid; PEP=Phosphoenolpyruvate; OAA=Oxaloacetate; MAL=malate; CIT=citrate; ICIT=isocitrate; AKG=alpha-ketoglutarate; FUM=Fumarate; SUCC=Succinate; SUCCOA=Succinyl-CoA; 3HBCOA=3-hydroxybutyryl-CoA; 3-HB=3-hydroxybutyrate; 3HBALD=3-hydroxybutyraldehyde; 13BDO=1,3-butanediol; CROTCOA=crotonyl-CoA; CROT=crotonate; CROTALD=crotonaldehyde; CROTALC=crotyl alcohol; CROT-Pi=crotyl phosphate; CROT-PPi=crotyl diphosphate or 2-butenyl-4-diphosphate.

It is also understood that association of multiple steps in a pathway can be indicated by linking their step identifiers with or without spaces or punctuation; for example, the following are equivalent to describe the 4-step pathway comprising Step W, Step X, Step Y and Step Z: steps WXYZ or W,X,Y,Z or W;X;Y;Z or W-X-Y-Z. One of ordinary skill can readily distinguish a single step designator of "AA" or "AB" or "AD" from a multiple step pathway description based on context and use in the description and figures herein.

As used herein, the term "non-naturally occurring" when used in reference to a microbial organism or microorganism of the invention is intended to mean that the microbial organism has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial organism's genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Exemplary metabolic polypeptides include enzymes or proteins within an acetyl-CoA or bioderived compound biosynthetic pathway.

A metabolic modification refers to a biochemical reaction that is altered from its naturally occurring state. Therefore, non-naturally occurring microorganisms can have genetic modifications to nucleic acids encoding metabolic polypeptides, or functional fragments thereof. Exemplary metabolic modifications are disclosed herein.

As used herein, the term "isolated" when used in reference to a microbial organism is intended to mean an organism that is substantially free of at least one component as the referenced microbial organism is found in nature. The term includes a microbial organism that is removed from some or all components as it is found in its natural environment. The term also includes a microbial organism that is removed from some or all components as the microbial organism is found in non-naturally occurring environments. Therefore, an isolated microbial organism is partly or completely separated from other substances as it is found in nature or as it is grown, stored or subsisted in non-naturally occurring environments. Specific examples of isolated microbial organisms include partially pure microbes, substantially pure microbes and microbes cultured in a medium that is non-naturally occurring.

As used herein, the terms "microbial," "microbial organism" or "microorganism" are intended to mean any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. The term also includes cell cultures of any species that can be cultured for the production of a biochemical.

As used herein, the term "CoA" or "coenzyme A" is intended to mean an organic cofactor or prosthetic group (nonprotein portion of an enzyme) whose presence is required for the activity of many enzymes (the apoenzyme) to form an active enzyme system. Coenzyme A functions in certain condensing enzymes, acts in acetyl or other acyl group transfer and in fatty acid synthesis and oxidation, pyruvate oxidation and in other acetylation.

As used herein, the term "substantially anaerobic" when used in reference to a culture or growth condition is intended to mean that the amount of oxygen is less than about 10% of saturation for dissolved oxygen in liquid media. The term also is intended to include sealed chambers of liquid or solid medium maintained with an atmosphere of less than about 1% oxygen.

"Exogenous" as it is used herein is intended to mean that the referenced molecule or the referenced activity is introduced into the host microbial organism. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the microbial organism. When used in reference to a biosynthetic activity, the term refers to an activity that is introduced into the host reference organism. The source can be, for example, a homologous or heterologous encoding nucleic acid that expresses the referenced activity following introduction into the host microbial organism. Therefore, the term "endogenous" refers to a referenced molecule or activity that is present in the host. Similarly, the term when used in reference to expression of an encoding nucleic acid refers to expression of an encoding nucleic acid contained within the microbial organism. The term "heterologous" refers to a molecule or activity derived from a source other than the referenced species whereas "homologous" refers to a molecule or activity derived from the host microbial organism. Accordingly, exogenous expression of an encoding nucleic acid of the invention can utilize either or both a heterologous or homologous encoding nucleic acid.

It is understood that when more than one exogenous nucleic acid is included in a microbial organism that the more than one exogenous nucleic acids refers to the referenced encoding nucleic acid or biosynthetic activity, as discussed above. It is further understood, as disclosed herein, that such more than one exogenous nucleic acids can be introduced into the host microbial organism on separate nucleic acid molecules, on polycistronic nucleic acid molecules, or a combination thereof, and still be considered as more than one exogenous nucleic acid. For example, as disclosed herein a microbial organism can be engineered to express two or more exogenous nucleic acids encoding a desired pathway enzyme or protein. In the case where two exogenous nucleic acids encoding a desired activity are introduced into a host microbial organism, it is understood that the two exogenous nucleic acids can be introduced as a single nucleic acid, for example, on a single plasmid, on separate plasmids, can be integrated into the host chromosome at a single site or multiple sites, and still be considered as two exogenous nucleic acids. Similarly, it is understood that more than two exogenous nucleic acids can be introduced into a host organism in any desired combination, for example, on a single plasmid, on separate plasmids, can be integrated into the host chromosome at a single site or multiple sites, and still be considered as two or more exogenous nucleic acids, for example three exogenous nucleic acids. Thus, the number of referenced exogenous nucleic acids or biosynthetic activities refers to the number of encoding nucleic acids or the number of biosynthetic activities, not the number of separate nucleic acids introduced into the host organism.

As used herein, the phrase "enhance carbon flux" is intended to mean to intensify, increase, or further improve the extent or flow of metabolic carbon through or to a desired pathway, pathway product, intermediate, or bioderived compound. The intensity, increase or improvement can be relative to a predetermined baseline of a pathway product, intermediate or bioderived compound. For example, an increased yield of acetyl-CoA can be achieved per mole of methanol with a phosphoketolase enzyme described herein (see, e.g., FIG. 1) than in the absence of a phosphoketolase enzyme. Similarly, an increased yield of acetyl-CoA can be achieved per mole of methanol with the formate assimilation enzymes (see, e.g., FIG. 1) than in the absence of the enzymes. Since an increased yield of acetyl-CoA can be achieved, a higher yield of acetyl-CoA derived compounds, such as 1,3-butanediol, crotyl alcohol, butadiene, 3-buten-2-ol, 1,4-butanediol, adipate, 6-aminocaproate, caprolactam, hexamethylenediamine, methacylic acid and 2-hydroxyisobutyric acid the invention, can also be achieved.

As used herein, the term "gene disruption," or grammatical equivalents thereof, is intended to mean a genetic alteration that renders the encoded gene product inactive or attenuated. The genetic alteration can be, for example, deletion of the entire gene, deletion of a regulatory sequence required for transcription or translation, deletion of a portion of the gene which results in a truncated gene product, or by any of various mutation strategies that inactivate or attenuate the encoded gene product, for example, replacement of a gene's promoter with a weaker promoter, replacement or insertion of one or more amino acid of the encoded protein to reduce its activity, stability or concentration, or inactivation of a gene's transactivating factor such as a regulatory protein. One particularly useful method of gene disruption is complete gene deletion because it reduces or eliminates the occurrence of genetic reversions in the non-naturally occurring microorganisms of the invention. A gene disruption also includes a null mutation, which refers to a mutation within a gene or a region containing a gene that results in the gene not being transcribed into RNA and/or translated into a functional gene product. Such a null mutation can arise from many types of mutations including, for example, inactivating point mutations, deletion of a portion of a gene, entire gene deletions, or deletion of chromosomal segments.

As used herein, the term "growth-coupled" when used in reference to the production of a biochemical product is intended to mean that the biosynthesis of the referenced biochemical product is produced during the growth phase of a microorganism. In a particular embodiment, the growth-coupled production can be obligatory, meaning that the biosynthesis of the referenced biochemical is an obligatory product produced during the growth phase of a microorganism.

As used herein, the term "attenuate," or grammatical equivalents thereof, is intended to mean to weaken, reduce or diminish the activity or amount of an enzyme or protein. Attenuation of the activity or amount of an enzyme or protein can mimic complete disruption if the attenuation causes the activity or amount to fall below a critical level required for a given pathway to function. However, the attenuation of the activity or amount of an enzyme or protein that mimics complete disruption for one pathway, can still be sufficient for a separate pathway to continue to function. For example, attenuation of an endogenous enzyme or protein can be sufficient to mimic the complete disruption of the same enzyme or protein for production of acetyl-CoA or a bioderived compound of the invention, but the remaining activity or amount of enzyme or protein can still be sufficient to maintain other pathways, such as a pathway that is critical for the host microbial organism to survive, reproduce or grow. Attenuation of an enzyme or protein can also be weakening, reducing or diminishing the activity or amount of the enzyme or protein in an amount that is sufficient to increase yield of acetyl-CoA or a bioderived compound of the invention, but does not necessarily mimic complete disruption of the enzyme or protein.

As used herein, the term "bioderived" means derived from or synthesized by a biological organism and can be considered a renewable resource since it can be generated by a biological organism. Such a biological organism, in particular the microbial organisms of the invention, can utilize a variety of carbon sources described herein including feedstock or biomass, such as, sugars and carbohydrates obtained from an agricultural, plant, bacterial, or animal source. Alternatively, the biological organism can utilize, for example, atmospheric carbon and/or methanol as a carbon source.

As used herein, the term "biobased" means a product as described herein that is composed, in whole or in part, of a bioderived compound of the invention. A biobased product is in contrast to a petroleum based product, wherein such a product is derived from or synthesized from petroleum or a petrochemical feedstock.

A "bioderived compound," as used herein, refers to a target molecule or chemical that is derived from or synthesized by a biological organism. In the context of the present invention, engineered microbial organisms are used to produce a bioderived compound or intermediate thereof via acetyl-CoA, including optionally further through acetoacetyl-CoA, malonyl-CoA and/or succinyl-CoA. Bioderived compounds of the invention include, but are not limited to, alcohols, glycols, organic acids, alkenes, dienes, organic amines, organic aldehydes, vitamins, nutraceuticals and pharmaceuticals.

Alcohols of the invention, including biofuel alcohols, include primary alcohols, secondary alcohols, diols and triols, preferably having C3 to C10 carbon atoms. Alcohols include n-propanol and isopropanol. Biofuel alcohols are preferably C3-C10 and include 1-Propanol, Isopropanol, 1-Butanol, Isobutanol, 1-Pentanol, Isopentenol, 2-Methyl-1-butanol, 3-Methyl-1-butanol, 1-Hexanol, 3-Methyl-1-pentanol, 1-Heptanol, 4-Methyl-1-hexanol, and 5-Methyl-1-hexanol. Diols include propanediols and butanediols, including 1,4 butanediol, 1,3-butanediol and 2,3-butanediol. Fatty alcohols include C4-C27 fatty alcohols, including C12-C18, especially C12-C14, including saturate or unsaturated linear fatty alcohols.

Further exemplary bioderived compounds of the invention include: (a) 1,4-butanediol and intermediates thereto, such as 4-hydroxybutanoic acid (4-hydroxybutanoate, 4-hydroxybutyrate (4-HB); (b) butadiene (1,3-butadiene) and intermediates thereto, such as 1,4-butanediol, 1,3-butanediol, 2,3-butanediol, crotyl alcohol, 3-buten-2-ol (methyl vinyl carbinol) and 3-buten-1-ol; (c) 1,3-butanediol and intermediates thereto, such as 3-hydroxybutyrate (3-HB), 2,4-pentadienoate, crotyl alcohol or 3-buten-1-ol; (d) adipate, 6-aminocaproic acid (6-ACA), caprolactam, hexamethylenediamine (HMDA) and levulinic acid and their intermediates, e.g. adipyl-CoA, 4-aminobutyryl-CoA; (e) methacrylic acid (2-methyl-2-propenoic acid) and its esters, such as methyl methacrylate and methyl methacrylate (known collectively as methacrylates), 3-hydroxyisobutyrate and/or 2-hydroxyisobutyrate and their intermediates; (f) glycols, including 1,2-propanediol (propylene glycol), 1,3-propanediol, glycerol, ethylene glycol, diethylene glycol, triethylene glycol, dipropylene glycol, tripropylene glycol, neopentyl glycol and bisphenol A and their intermediates; (g) succinic acid and intermediates thereto; and (h) fatty alcohols, which are aliphatic compounds containing one or more hydroxyl groups and a chain of 4 or more carbon atoms, or fatty acids and fatty aldehydes thereof, which are preferably C4-C27 carbon atoms. Fatty alcohols include saturated fatty alcohols, unsaturated fatty alcohols and linear saturated fatty alcohols. Examples fatty alcohols include butyl, pentyl, hexyl, heptyl, octyl, nonyl, decyl, undecyl and dodecyl alcohols, and their corresponding oxidized derivatives, i.e. fatty aldehydes or fatty acids having the same number of carbon atoms. Preferred fatty alcohols, fatty aldehydes and fatty acids have C8 to C18 carbon atoms, especially C12-C18, C12-C14, and C16-C18, including C12, C13, C14, C15, C16, C17, and C18 carbon atoms. Preferred fatty alcohols include linear unsaturated fatty alcohols, such as dodecanol (C12; lauryl alcohol), tridecyl alcohol (C13; 1-tridecanol, tridecanol, isotridecanol), myristyl alcohol (C14; 1-tetradecanol), pentadecyl alcohol (C15; 1-pentadecanol, pentadecanol), cetyl alcohol (C16; 1-hexadecanol), heptadecyl alcohol (C17; 1-n-heptadecanol, heptadecanol) and stearyl alcohol (C18; 1-octadecanol) and unsaturated counterparts including palmitoleyl alcohol (C16 unsaturated; cis-9-hexadecen-1-ol), or their corresponding fatty aldehydes or fatty acids.

1,4-Butanediol and intermediates thereto, such as 4-hydroxybutanoic acid (4-hydroxybutanoate, 4-hydroxybutyrate, 4-HB), are bioderived compounds that can be made via enzymatic pathways described herein and in the following publications. Suitable bioderived compound pathways and enzymes, methods for screening and methods for isolating are found in: WO2008115840A2 published 25 Sep. 2008 entitled Compositions and Methods for the Biosynthesis of 1,4-Butanediol and Its Precursors; WO2010141780A1 published 9 Dec. 2010 entitled Process of Separating Components of A Fermentation Broth; WO2010141920A2 published 9 Dec. 2010 entitled Microorganisms for the Production of 1,4-Butanediol and Related Methods; WO2010030711A2 published 18 Mar. 2010 entitled Microorganisms for the Production of 1,4-Butanediol; WO2010071697A1 published 24 Jun. 2010 Microorganisms and Methods for Conversion of Syngas and Other Carbon Sources to Useful Products; WO2009094485A1 published 30 Jul. 2009 Methods and Organisms for Utilizing Synthesis Gas or Other Gaseous Carbon Sources and Methanol; WO2009023493A1 published 19 Feb. 2009 entitled Methods and Organisms for the Growth-Coupled Production of 1,4-Butanediol; and WO2008115840A2 published 25 Sep. 2008 entitled Compositions and Methods for the Biosynthesis of 1,4-Butanediol and Its Precursors, which are all incorporated herein by reference.

Butadiene and intermediates thereto, such as 1,4-butanediol, 2,3-butanediol, 1,3-butanediol, crotyl alcohol, 3-buten-2-ol (methyl vinyl carbinol) and 3-buten-1-ol, are bioderived compounds that can be made via enzymatic pathways described herein and in the following publications. In addition to direct fermentation to produce butadiene, 1,3-butanediol, 1,4-butanediol, crotyl alcohol, 3-buten-2-ol (methyl vinyl carbinol) or 3-buten-1-ol can be separated, purified (for any use), and then chemically dehydrated to butadiene by metal-based catalysis. Suitable bioderived compound pathways and enzymes, methods for screening and methods for isolating are found in: WO2011140171A2 published 10 Nov. 2011 entitled Microorganisms and Methods for the Biosynthesis of Butadiene; WO2012018624A2 published 9 Feb. 2012 entitled Microorganisms and Methods for the Biosynthesis of Aromatics, 2,4-Pentadienoate and 1,3-Butadiene; WO2011140171A2 published 10 Nov. 2011 entitled Microorganisms and Methods for the Biosynthesis of Butadiene; WO2013040383A1 published 21 Mar. 2013 entitled Microorganisms and Methods for Producing Alkenes; WO2012177710A1 published 27 Dec. 2012 entitled Microorganisms for Producing Butadiene and Methods Related thereto; WO2012106516A1 published 9 Aug. 2012 entitled Microorganisms and Methods for the Biosynthesis of Butadiene; and WO2013028519A1 published 28 Feb. 2013 entitled Microorganisms and Methods for Producing 2,4-Pentadienoate, Butadiene, Propylene, 1,3-Butanediol and Related Alcohols, which are all incorporated herein by reference.

1,3-Butanediol and intermediates thereto, such as 2,4-pentadienoate, crotyl alcohol or 3-buten-1-ol, are bioderived compounds that can be made via enzymatic pathways described herein and in the following publications. Suitable bioderived compound pathways and enzymes, methods for screening and methods for isolating are found in: WO2011071682A1 published 16 Jun. 2011 entitled Methods and Organisms for Converting Synthesis Gas or Other Gaseous Carbon Sources and Methanol to 1,3-Butanediol; WO2011031897A published 17 Mar. 2011 entitled Microorganisms and Methods for the Co-Production of Isopropanol with Primary Alcohols, Diols and Acids; WO2010127319A2 published 4 Nov. 2010 entitled Organisms for the Production of 1,3-Butanediol; WO2013071226A1 published 16 May 2013 entitled Eukaryotic Organisms and Methods for Increasing the Availability of Cytosolic Acetyl-CoA, and for Producing 1,3-Butanediol; WO2013028519A1 published 28 Feb. 2013 entitled Microorganisms and Methods for Producing 2,4-Pentadienoate, Butadiene, Propylene, 1,3-Butanediol and Related Alcohols; WO2013036764A1 published 14 Mar. 2013 entitled Eukaryotic Organisms and Methods for Producing 1,3-Butanediol; WO2013012975A1 published 24 Jan. 2013 entitled Methods for Increasing Product Yields; and WO2012177619A2 published 27 Dec. 2012 entitled Microorganisms for Producing 1,3-Butanediol and Methods Related Thereto, which are all incorporated herein by reference.

Adipate, 6-aminocaproic acid, caprolactam, hexamethylenediamine and levulinic acid, and their intermediates, e.g. 4-aminobutyryl-CoA, are bioderived compounds that can be made via enzymatic pathways described herein and in the following publications. Suitable bioderived compound pathways and enzymes, methods for screening and methods for isolating are found in: WO2010129936A1 published 11 Nov. 2010 entitled Microorganisms and Methods for the Biosynthesis of Adipate, Hexamethylenediamine and 6-Aminocaproic Acid; WO2013012975A1 published 24 Jan. 2013 entitled Methods for Increasing Product Yields; WO2012177721A1 published 27 Dec. 2012 entitled Microorganisms for Producing 6-Aminocaproic Acid; WO2012099621A1 published 26 Jul. 2012 entitled Methods for Increasing Product Yields; and WO2009151728 published 17 Dec. 2009 entitled Microorganisms for the production of adipic acid and other compounds, which are all incorporated herein by reference.

Methacrylic acid (2-methyl-2-propenoic acid) is used in the preparation of its esters, known collectively as methacrylates (e.g. methyl methacrylate, which is used most notably in the manufacture of polymers). Methacrylate esters such as methyl methacrylate, 3-hydroxyisobutyrate and/or 2-hydroxyisobutyrate and their intermediates are bioderived compounds that can be made via enzymatic pathways described herein and in the following publications. Suitable bioderived compound pathways and enzymes, methods for screening and methods for isolating are found in: WO2012135789A2 published 4 Oct. 2012 entitled Microorganisms for Producing Methacrylic Acid and Methacrylate Esters and Methods Related Thereto; and WO2009135074A2 published 5 Nov. 2009 entitled Microorganisms for the Production of Methacrylic Acid, which are all incorporated herein by reference.

1,2-Propanediol (propylene glycol), n-propanol, 1,3-propanediol and glycerol, and their intermediates are bioderived compounds that can be made via enzymatic pathways described herein and in the following publications. Suitable bioderived compound pathways and enzymes, methods for screening and methods for isolating are found in: WO2009111672A1 published 9 Nov. 2009 entitled Primary Alcohol Producing Organisms; WO2011031897A1 17 Mar. 2011 entitled Microorganisms and Methods for the Co-Production of Isopropanol with Primary Alcohols, Diols and Acids; WO2012177599A2 published 27 Dec. 2012 entitled Microorganisms for Producing N-Propanol 1,3-Propanediol, 1,2-Propanediol or Glycerol and Methods Related Thereto, which are all incorporated herein by referenced.

Succinic acid and intermediates thereto, which are useful to produce products including polymers (e.g. PBS), 1,4-butanediol, tetrahydrofuran, pyrrolidone, solvents, paints, deicers, plastics, fuel additives, fabrics, carpets, pigments, and detergents, are bioderived compounds that can be made via enzymatic pathways described herein and in the following publication. Suitable bioderived compound pathways and enzymes, methods for screening and methods for isolating are found in: EP1937821A2 published 2 Jul. 2008 entitled Methods and Organisms for the Growth-Coupled Production of Succinate, which is incorporated herein by reference.

Primary alcohols and fatty alcohols (also known as long chain alcohols), including fatty acids and fatty aldehydes thereof, and intermediates thereto, are bioderived compounds that can be made via enzymatic pathways in the following publications. Suitable bioderived compound pathways and enzymes, methods for screening and methods for isolating are found in: WO2009111672 published 11 Sep.

2009 entitled Primary Alcohol Producing Organisms; WO2012177726 published 27 Dec. 2012 entitled Microorganism for Producing Primary Alcohols and Related Compounds and Methods Related Thereto, which are all incorporated herein by reference.

Further suitable bioderived compounds that the microbial organisms of the invention can be used to produce via acetyl-CoA, including optionally further through acetoacetyl-CoA and/or succinyl-CoA, are included in the invention. Exemplary well known bioderived compounds, their pathways and enzymes for production, methods for screening and methods for isolating are found in the following patents and publications: succinate (U.S. publication 2007/0111294, WO 2007/030830, WO 2013/003432), 3-hydroxypropionic acid (3-hydroxypropionate) (U.S. publication 2008/0199926, WO 2008/091627, U.S. publication 2010/0021978), 1,4-butanediol (U.S. Pat. No. 8,067,214, WO 2008/115840, U.S. Pat. No. 7,947,483, WO 2009/023493, U.S. Pat. No. 7,858,350, WO 2010/030711, U.S. publication 2011/0003355, WO 2010/141780, U.S. Pat. No. 8,129,169, WO 2010/141920, U.S. publication 2011/0201068, WO 2011/031897, U.S. Pat. No. 8,377,666, WO 2011/047101, U.S. publication 2011/0217742, WO 2011/066076, U.S. publication 2013/0034884, WO 2012/177943), 4-hydroxybutanoic acid (4-hydroxybutanoate, 4-hydroxybutyrate, 4-hydroxybutyrate) (U.S. Pat. No. 8,067,214, WO 2008/115840, U.S. Pat. No. 7,947,483, WO 2009/023493, U.S. Pat. No. 7,858,350, WO 2010/030711, U.S. publication 2011/0003355, WO 2010/141780, U.S. Pat. No. 8,129,155, WO 2010/071697), γ-butyrolactone (U.S. Pat. No. 8,067,214, WO 2008/115840, U.S. Pat. No. 7,947,483, WO 2009/023493, U.S. Pat. No. 7,858,350, WO 2010/030711, U.S. publication 2011/0003355, WO 2010/141780, U.S. publication 2011/0217742, WO 2011/066076), 4-hydroxybutyryl-CoA (U.S. publication 2011/0003355, WO 2010/141780, U.S. publication 2013/0034884, WO 2012/177943), 4-hydroxybutanal (U.S. publication 2011/0003355, WO 2010/141780, U.S. publication 2013/0034884, WO 2012/177943), putrescine (U.S. publication 2011/0003355, WO 2010/141780, U.S. publication 2013/0034884, WO 2012/177943), Olefins (such as acrylic acid and acrylate ester) (U.S. Pat. No. 8,026,386, WO 2009/045637), acetyl-CoA (U.S. Pat. No. 8,323,950, WO 2009/094485), methyl tetrahydrofolate (U.S. Pat. No. 8,323,950, WO 2009/094485), ethanol (U.S. Pat. No. 8,129,155, WO 2010/071697), isopropanol (U.S. Pat. No. 8,129,155, WO 2010/071697, U.S. publication 2010/0323418, WO 2010/127303, U.S. publication 2011/0201068, WO 2011/031897), n-butanol (U.S. Pat. No. 8,129,155, WO 2010/071697), isobutanol (U.S. Pat. No. 8,129,155, WO 2010/071697), n-propanol (U.S. publication 2011/0201068, WO 2011/031897), methylacrylic acid (methylacrylate) (U.S. publication 2011/0201068, WO 2011/031897), primary alcohol (U.S. Pat. No. 7,977,084, WO 2009/111672, WO 2012/177726), long chain alcohol (U.S. Pat. No. 7,977,084, WO 2009/111672, WO 2012/177726), adipate (adipic acid) (U.S. Pat. No. 8,062,871, WO 2009/151728, U.S. Pat. No. 8,377,680, WO 2010/129936, WO 2012/177721), 6-aminocaproate (6-aminocaproic acid) (U.S. Pat. No. 8,062,871, WO 2009/151728, U.S. Pat. No. 8,377,680, WO 2010/129936, WO 2012/177721), caprolactam (U.S. Pat. No. 8,062,871, WO 2009/151728, U.S. Pat. No. 8,377,680, WO 2010/129936, WO 2012/177721), hexamethylenediamine (U.S. Pat. No. 8,377,680, WO 2010/129936, WO 2012/177721), levulinic acid (U.S. Pat. No. 8,377,680, WO 2010/129936), 2-hydroxyisobutyric acid (2-hydroxyisobutyrate) (U.S. Pat. No. 8,241,877, WO 2009/135074, U.S. publication 2013/0065279, WO 2012/135789), 3-hydroxyisobutyric acid (3-hydroxyisobutyrate) (U.S. Pat. No. 8,241,877, WO 2009/135074, U.S. publication 2013/0065279, WO 2012/135789), methacrylic acid (methacrylate) (U.S. Pat. No. 8,241,877, WO 2009/135074, U.S. publication 2013/0065279, WO 2012/135789), methacrylate ester (U.S. publication 2013/0065279, WO 2012/135789), fumarate (fumaric acid) (U.S. Pat. No. 8,129,154, WO 2009/155382), malate (malic acid) (U.S. Pat. No. 8,129,154, WO 2009/155382), acrylate (carboxylic acid) (U.S. Pat. No. 8,129,154, WO 2009/155382), methyl ethyl ketone (U.S. publication 2010/0184173, WO 2010/057022, U.S. Pat. No. 8,420,375, WO 2010/144746), 2-butanol (U.S. publication 2010/0184173, WO 2010/057022, U.S. Pat. No. 8,420,375, WO 2010/144746), 1,3-butanediol (U.S. publication 2010/0330635, WO 2010/127319, U.S. publication 2011/0201068, WO 2011/031897, U.S. Pat. No. 8,268,607, WO 2011/071682, U.S. publication 2013/0109064, WO 2013/028519, U.S. publication 2013/0066035, WO 2013/036764), cyclohexanone (U.S. publication 2011/0014668, WO 2010/132845), terephthalate (terephthalic acid) (U.S. publication 2011/0124911, WO 2011/017560, U.S. publication 2011/0207185, WO 2011/094131, U.S. publication 2012/0021478, WO 2012/018624), muconate (muconic acid) (U.S. publication 2011/0124911, WO 2011/017560), aniline (U.S. publication 2011/0097767, WO 2011/050326), p-toluate (p-toluic acid) (U.S. publication 2011/0207185, WO 2011/094131, U.S. publication 2012/0021478, WO 2012/018624), (2-hydroxy-3-methyl-4-oxobutoxy)phosphonate (U.S. publication 2011/0207185, WO 2011/094131, U.S. publication 2012/0021478, WO 2012/018624), ethylene glycol (U.S. publication 2011/0312049, WO 2011/130378, WO 2012/177983), propylene (U.S. publication 2011/0269204, WO 2011/137198, U.S. publication 2012/0329119, U.S. publication 2013/0109064, WO 2013/028519), butadiene (1,3-butadiene) (U.S. publication 2011/0300597, WO 2011/140171, U.S. publication 2012/0021478, WO 2012/018624, U.S. publication 2012/0225466, WO 2012/106516, U.S. publication 2013/0011891, WO 2012/177710, U.S. publication 2013/0109064, WO 2013/028519), toluene (U.S. publication 2012/0021478, WO 2012/018624), benzene (U.S. publication 2012/0021478, WO 2012/018624), (2-hydroxy-4-oxobutoxy)phosphonate (U.S. publication 2012/0021478, WO 2012/018624), benzoate (benzoic acid) (U.S. publication 2012/0021478, WO 2012/018624), styrene (U.S. publication 2012/0021478, WO 2012/018624), 2,4-pentadienoate (U.S. publication 2012/0021478, WO 2012/018624, U.S. publication 2013/0109064, WO 2013/028519), 3-butene-1-ol (U.S. publication 2012/0021478, WO 2012/018624, U.S. publication 2013/0109064, WO 2013/028519), 3-buten-2-ol (U.S. publication 2013/0109064, WO 2013/028519), 1,4-cyclohexanedimethanol (U.S. publication 2012/0156740, WO 2012/082978), crotyl alcohol (U.S. publication 2013/0011891, WO 2012/177710, U.S. publication 2013/0109064, WO 2013/028519), alkene (U.S. publication 2013/0122563, WO 2013/040383, US 2011/0196180), hydroxyacid (WO 2012/109176), ketoacid (WO 2012/109176), wax esters (WO 2007/136762) or caprolactone (U.S. publication 2013/0144029, WO 2013/067432) pathway. The patents and patent application publications listed above that disclose bioderived compound pathways are herein incorporated by reference.

Acetyl-CoA is the immediate precursor for the synthesis of bioderived compounds as shown in FIGS. 5-10. Phosphoketolase pathways make possible synthesis of acetyl-CoA without requiring decarboxylation of pyruvate (Bogorad et al, *Nature*, 2013, published online 29 Sep. 2013; United States Publication 2006-0040365), which thereby provides higher yields of bioderived compounds of the invention from carbohydrates and methanol than the yields attainable without phosphoketolase enzymes.

For example, synthesis of an exemplary fatty alcohol, dodecanol, from methanol using methanol dehydrogenase (step A of FIG. 1), a formaldehyde assimilation pathway (steps B, C, D of FIG. 1), the pentose phosphate pathway, and glycolysis can provide a maximum theoretical yield of 0.0556 mole dodecanol/mole methanol.

$$18CH_4O+9O_2 \rightarrow C_{12}H_{26}O+23H_2O+6CO_2$$

However, if these pathways are combined with a phosphoketolase pathway (steps T, U, V, W, X of FIG. 1), a maximum theoretical yield of 0.0833 mole dodecanol/mole methanol can be obtained if we assume that the pathway is not required to provide net generation of ATP for cell growth and maintenance requirements.

$$12CH_4O \rightarrow C_{12}H_{26}O+11H_2O$$

Figure 2:
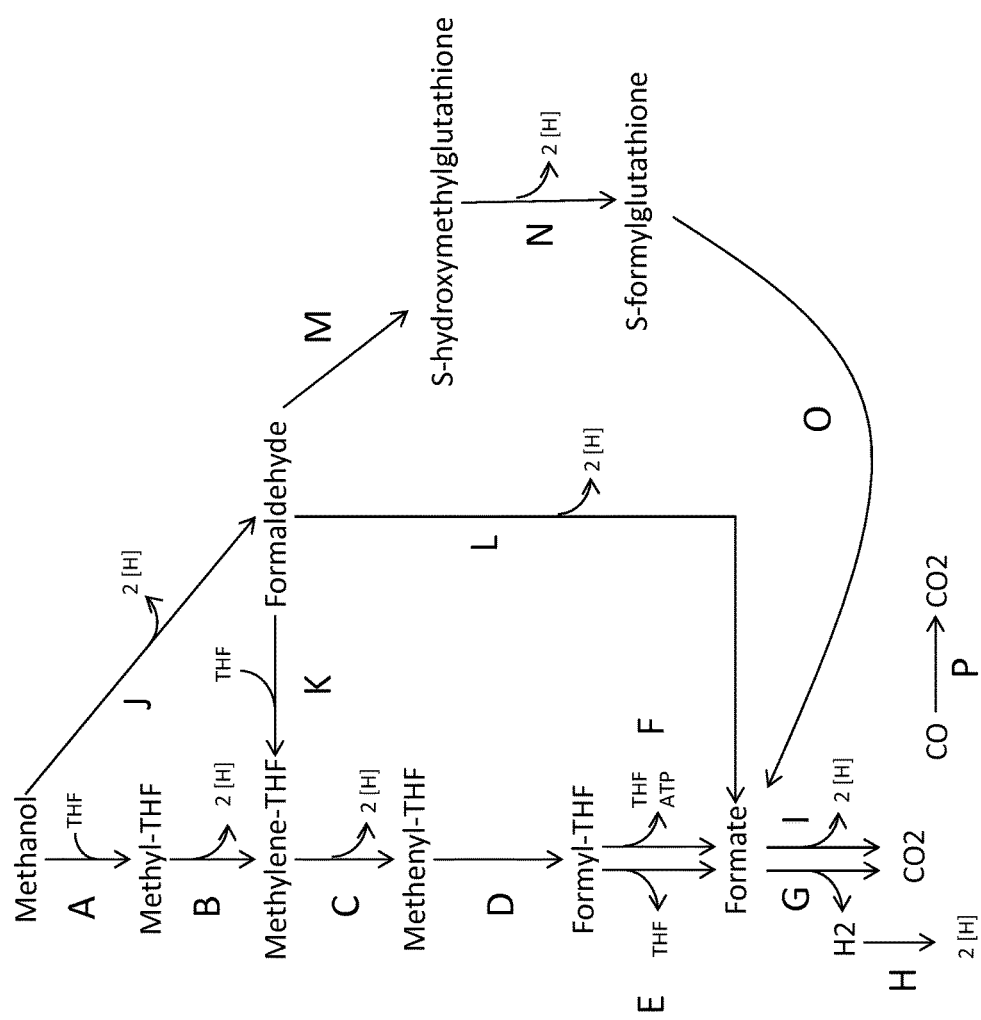
FIG. 2 shows exemplary metabolic pathways that provide the extraction of reducing equivalents from methanol, hydrogen, or carbon monoxide. Enzymes are: A) methanol methyltransferase, B) methylenetetrahydrofolate reductase, C) methylenetetrahydrofolate dehydrogenase, D) methenyltetrahydrofolate cyclohydrolase, E) formyltetrahydrofolate deformylase, F) formyltetrahydrofolate synthetase, G) formate hydrogen lyase, H) hydrogenase, I) formate dehydrogenase, J) methanol dehydrogenase, K) spontaneous or formaldehyde activating enzyme, L) formaldehyde dehydrogenase, M) spontaneous or S-(hydroxymethyl)glutathione synthase, N) Glutathione-Dependent Formaldehyde Dehydrogenase, O) S-formylglutathione hydrolase, P) carbon monoxide dehydrogenase. See abbreviation list below for compound names.

ATP for energetic requirements can be synthesized, at the expense of lowering the maximum theoretical product yield, by oxidizing methanol to $CO_2$ using several combinations of enzymes depicted in FIG. 2, glycolysis, the TCA cycle, the pentose phosphate pathway, and oxidative phosphorylation.

Similarly, synthesis of isopropanol from methanol using methanol dehydrogenase (step A of FIG. 1), a formaldehyde assimilation pathway (steps B, C, D of FIG. 1), the pentose phosphate pathway and glycolysis can provide a maximum theoretical yield of 0.1667 mole isopropanol/mole methanol.

$$6CH_4O+4.5O_2 \rightarrow C_3H_8O+8H_2O+3CO_2$$

However, if these pathways are applied in combination with a phosphoketolase pathway (steps T, U, V, W, X of FIG. 1), a maximum theoretical yield of 0.250 mole isopropanol/mole methanol can be obtained.

$$4CH_4O+1.5O_2 \rightarrow C_3H_8O+4H_2O+CO_2$$

The overall pathway is ATP and redox positive enabling synthesis of both ATP and NAD(P)H from conversion of MeOH to isopropanol. Additional ATP can be synthesized, at the expense of lowering the maximum theoretical product yield, by oxidizing methanol to $CO_2$ using several combinations of enzymes depicted in FIG. 2, glycolysis, the TCA cycle, the pentose phosphate pathway, and oxidative phosphorylation.

Synthesis of several other products from methanol using methanol dehydrogenase (step A of FIG. 1), a formaldehyde assimilation pathway (steps B, C, D of FIG. 1), the pentose phosphate pathway and glycolysis can provide the following maximum theoretical yield stoichiometries:

| Product | CH4O | O2 | NH3 | Product | H2O | CO2 |
|---|---|---|---|---|---|---|
| 1,3-Butanediol | 6.000 | 3.500 | 0.000 | --> 1.000 | 7.000 | 2.000 |
| Crotyl Alcohol | 6.000 | 3.500 | 0.000 | --> 1.000 | 8.000 | 2.000 |
| 3-Buten-2-ol | 6.000 | 3.500 | 0.000 | --> 1.000 | 8.000 | 2.000 |
| Butadiene | 6.000 | 3.500 | 0.000 | --> 1.000 | 9.000 | 2.000 |
| 2-Hydroxyisobutyrate | 6.000 | 4.500 | 0.000 | --> 1.000 | 8.000 | 2.000 |
| Methacrylate (via 2-hydroxyisobutyrate) | 6.000 | 4.500 | 0.000 | --> 1.000 | 9.000 | 2.000 |
| 3-Hydroxyisobutyrate (oxidative TCA cycle) | 6.000 | 4.500 | 0.000 | --> 1.000 | 8.000 | 2.000 |
| Methacrylate (via 3-hydroxyisobutyrate) | 6.000 | 4.500 | 0.000 | --> 1.000 | 9.000 | 2.000 |
| 1,4-Butanediol (oxidative TCA cycle) | 6.000 | 3.500 | 0.000 | --> 1.000 | 9.000 | 2.000 |
| Adipate (oxidative TCA cycle) | 9.000 | 7.000 | 0.000 | --> 1.000 | 13.000 | 3.000 |
| 6-Aminocaproate (oxidative TCA cycle) | 9.000 | 6.000 | 1.000 | --> 1.000 | 13.000 | 3.000 |
| Caprolactam (via 6-aminocaproate) | 9.000 | 6.000 | 1.000 | --> 1.000 | 14.000 | 3.000 |
| Hexamethylene-diamine (oxidative TCA cycle) | 9.000 | 5.000 | 2.000 | --> 1.000 | 13.000 | 3.000 |

In the products marked "oxidative TCA cycle", the maximum yield stoichiometries assume that the reductive TCA cycle enzymes (e.g., malate dehydrogenase, fumarase, fumarate reductase, and succinyl-CoA ligase) are not utilized for product formation. Exclusive use of the oxidative TCA cycle for product formation can be advantageous for succinyl-CoA derived products such as 3-hydroxyisobutyrate, 1,4-butanediol, adipate, 6-aminocaproate, and hexamethylenediamine because it enables all of the product pathway flux to originate from alpha-ketoglutarate dehydrogenase—an irreversible enzyme in vivo.

However, if these pathways are applied in combination with a phosphoketolase pathway (steps T, U, V, W, X of FIG. 1), an increased maximum theoretical yield can be obtained as shown below:

| Product | CH4O | O2 | NH3 | Product | H2O | CO2 |
|---|---|---|---|---|---|---|
| 1,3-Butanediol | 4.000 | 0.500 | 0.000 | --> 1.000 | 3.000 | 0.000 |
| Crotyl Alcohol | 4.000 | 0.500 | 0.000 | --> 1.000 | 4.000 | 0.000 |
| 3-Buten-2-ol | 4.000 | 0.500 | 0.000 | --> 1.000 | 4.000 | 0.000 |
| Butadiene | 4.000 | 0.500 | 0.000 | --> 1.000 | 5.000 | 0.000 |
| 2-Hydroxyisobutyrate | 4.000 | 1.500 | 0.000 | --> 1.000 | 4.000 | 0.000 |
| Methacrylate (via 2-hydroxyisobutyrate) | 4.000 | 1.500 | 0.000 | --> 1.000 | 5.000 | 0.000 |
| 3-Hydroxyisobutyrate (oxidative TCA cycle) | 5.000 | 3.000 | 0.000 | --> 1.000 | 6.000 | 1.000 |
| Methacrylate (via 3-hydroxyisobutyrate) | 5.000 | 3.000 | 0.000 | --> 1.000 | 7.000 | 1.000 |
| 1,4-Butanediol (oxidative TCA cycle) | 5.000 | 2.000 | 0.000 | --> 1.000 | 5.000 | 1.000 |
| Adipate (oxidative TCA cycle) | 7.000 | 4.000 | 0.000 | --> 1.000 | 9.000 | 1.000 |
| 6-Aminocaproate (oxidative TCA cycle) | 7.000 | 3.000 | 1.000 | --> 1.000 | 9.000 | 1.000 |
| Caprolactam (via 6-aminocaproate) | 7.000 | 3.000 | 1.000 | --> 1.000 | 10.000 | 1.000 |

| Product | CH4O | O2 | NH3 | Product | H2O | CO2 |
|---|---|---|---|---|---|---|
| Hexamethylene-diamine (oxidative TCA cycle) | 7.000 | 2.000 | 2.000 | --> 1.000 | 9.000 | 1.000 |

The theoretical yield of bioderived compounds of the invention from carbohydrates including but not limited to glucose, glycerol, sucrose, fructose, xylose, arabinose, and galactose, can also be enhanced by phosphoketolase enzymes, particularly when reducing equivalents are provided by an exogenous source such as hydrogen or methanol. This is because phosphoketolase enzymes provide acetyl-CoA synthesis with 100% carbon conversion efficiency (e.g., 3 acetyl-CoA's per glucose, 2.5 acetyl-CoA's per xylose, 1.5 acetyl-CoA's per glycerol).

For example, synthesis of an exemplary fatty alcohol, dodecanol, from glucose in the absence of phosphoketolase enzymes can reach a maximum theoretical dodecanol yield of 0.3333 mole dodecanol/mole glucose.

$$3C_6H_{12}O_6 \rightarrow C_{12}H_{26}O + 5H_2O + 6CO_2$$

However, if enzyme steps T, U, V, W, X of FIG. 1 are applied in combination with glycolysis, the pentose phosphate pathway, and an external redox source (e.g., methanol, hydrogen) using the pathways shown in FIG. 2, the maximum theoretical yield can be increased to 0.5000 mole dodecanol/mole glucose.

$$2C_6H_{12}O_6 + 4CH_4O \rightarrow C_{12}H_{26}O + 7H_2O + 4CO_2$$

This assumes that the pathway is not required to provide net generation of ATP for cell growth and maintenance requirements. ATP for energetic requirements can be synthesized by oxidizing additional methanol to $CO_2$ using several combinations of enzymes depicted in FIG. 2.

Similarly, synthesis of isopropanol from glucose in the absence of phosphoketolase enzymes can achieve a maximum theoretical isopropanol yield of 1.000 mole isopropanol/mole glucose.

$$C_6H_{12}O_6 + 1.5O_2 \rightarrow C_3H_8O + 2H_2O + 3CO_2$$

However, if enzyme steps T, U, V, W, X of FIG. 1 are applied in combination with glycolysis and the pentose phosphate pathway, the maximum theoretical yield can be increased to 1.333 mole isopropanol/mole glucose.

$$C_6H_{12}O_6 \rightarrow 1.333C_3H_8O + 0.667H_2O + 2CO_2$$

If enzyme steps T, U, V, W, X of FIG. 1 are applied in combination with glycolysis, the pentose phosphate pathway, and external redox source (e.g., methanol, hydrogen) using the pathways shown in FIG. 2, the maximum theoretical yield can be increased to 1.500 mole isopropanol/mole glucose.

$$C_6H_{12}O_6 + 0.5CH_4O + 1.5C_3H_8O + H_2O + 2CO_2$$

In the absence of phosphoketolase activity, synthesis of several other products from a carbohydrate source (e.g., glucose) can provide the following maximum theoretical yield stoichiometries using glycolysis, pentose phosphate pathway, and TCA cycle reactions to build the pathway precursors.

| Product | C6H12O6 | O2 | NH3 | Product | H2O | CO2 |
|---|---|---|---|---|---|---|
| 1,3-Butanediol | 1.000 | 0.500 | 0.000 | → 1.000 | 1.000 | 2.000 |
| Crotyl Alcohol | 1.000 | 0.500 | 0.000 | → 1.000 | 2.000 | 2.000 |
| 3-Buten-2-ol | 1.000 | 0.500 | 0.000 | → 1.000 | 2.000 | 2.000 |
| Butadiene | 1.000 | 0.500 | 0.000 | → 1.000 | 3.000 | 2.000 |
| 2-Hydroxyisobutyrate | 1.000 | 1.500 | 0.000 | → 1.000 | 2.000 | 2.000 |
| Methacrylate (via 2-hydroxyisobutyrate) | 1.000 | 1.500 | 0.000 | → 1.000 | 3.000 | 2.000 |
| 3-Hydroxyisobutyrate (oxidative TCA cycle) | 1.000 | 1.500 | 0.000 | → 1.000 | 2.000 | 2.000 |
| Methacrylate (via 3-hydroxyisobutyrate) | 1.000 | 1.500 | 0.000 | → 1.000 | 3.000 | 2.000 |
| 1,4-Butanediol (oxidative TCA cycle) | 1.000 | 0.500 | 0.000 | → 1.000 | 1.000 | 2.000 |
| Adipate (oxidative TCA cycle) | 1.000 | 1.667 | 0.000 | → 0.667 | 2.667 | 2.000 |
| 6-Aminocaproate (oxidative TCA cycle) | 1.000 | 1.000 | 0.667 | → 0.667 | 2.667 | 2.000 |
| Caprolactam (via 6-aminocaproate) | 1.000 | 1.000 | 0.667 | → 0.667 | 3.333 | 2.000 |
| Hexamethylene-diamine (oxidative TCA cycle) | 1.000 | 0.333 | 1.333 | → 0.667 | 2.667 | 2.000 |

In the products marked "oxidative TCA cycle", the maximum yield stoichiometries assume that the TCA cycle enzymes (e.g., malate dehydrogenase, fumarase, fumarate reductase, and succinyl-CoA ligase) are not utilized for product formation in the reductive direction. Exclusive use of the oxidative TCA cycle for product formation can be advantageous for succinyl-CoA derived products such as 3-hydroxyisobutyrate, 1,4-butanediol, adipate, 6-aminocaproate, and hexamethylenediamine because it enables all of the product pathway flux to originate from alpha-ketoglutarate dehydrogenase—an irreversible enzyme in vivo.

Notably, when these product pathways are applied in combination with a phosphoketolase pathway (steps T, U, V, W, X of FIG. 1), an increased maximum theoretical yield can be obtained as shown below:

| Product | C6H12O6 | O2 | NH3 | Product | H2O | CO2 |
|---|---|---|---|---|---|---|
| 1,3-Butanediol | 1.000 | 0.000 | 0.000 | → 1.091 | 0.545 | 1.636 |
| Crotyl Alcohol | 1.000 | 0.000 | 0.000 | → 1.091 | 1.636 | 1.636 |
| 3-Buten-2-ol | 1.000 | 0.000 | 0.000 | → 1.091 | 1.636 | 1.636 |
| Butadiene | 1.000 | 0.107 | 0.000 | → 1.071 | 2.786 | 1.714 |
| 2-Hydroxyisobutyrate | 1.000 | 0.014 | 0.000 | → 1.330 | 0.679 | 0.679 |
| Methacrylate (via 2-hydroxyisobutyrate) | 1.000 | 0.014 | 0.000 | → 1.330 | 2.009 | 0.679 |
| 3-Hydroxyisobutyrate (oxidative TCA cycle) | 1.000 | 0.600 | 0.000 | → 1.200 | 1.200 | 1.200 |
| Methacrylate (via 3-hydroxyisobutyrate) | 1.000 | 0.600 | 0.000 | → 1.200 | 2.400 | 1.200 |
| 1,4-Butanediol (oxidative TCA cycle) | 1.000 | 0.124 | 0.000 | → 1.068 | 0.658 | 1.727 |

| Product | C6H12O6 | O2 | NH3 | Product | H2O | CO2 |
|---|---|---|---|---|---|---|
| Adipate (oxidative TCA cycle) | 1.000 | 0.429 | 0.000 | → 0.857 | 1.714 | 0.857 |
| 6-Aminocaproate (oxidative TCA cycle) | 1.000 | 0.000 | 0.800 | → 0.800 | 2.000 | 1.200 |
| Caprolactam (via 6-aminocaproate) | 1.000 | 0.000 | 0.800 | → 0.800 | 2.800 | 1.200 |
| Hexamethylene-diamine (oxidative TCA cycle) | 1.000 | 0.064 | 1.397 | → 0.698 | 2.508 | 1.810 |

As with glucose, a similar yield increase can occur with use of a phosphoketolase enzyme on other carbohydrates such as glycerol, sucrose, fructose, xylose, arabinose and galactose.

Also provided herein are methanol metabolic pathways and a methanol oxidation pathway to improve that availability of reducing equivalents and/or substrates for production of a compound of the invention. Because methanol is a relatively inexpensive organic feedstock that can be used as a redox, energy, and carbon source for the production of bioderived compounds of the invention, and their intermediates, it is a desirable substrate for the non-naturally occurring microbial organisms of the invention. Employing one or more methanol metabolic enzymes as described herein, for example as shown in FIGS. 1 and 2, methanol can enter central metabolism in most production hosts by employing methanol dehydrogenase (FIG. 1, step A) along with a pathway for formaldehyde assimilation. One exemplary formaldehyde assimilation pathway that can utilize formaldehyde produced from the oxidation of methanol is shown in FIG. 1, which involves condensation of formaldehyde and D-ribulose-5-phosphate to form hexulose-6-phosphate (H6P) by hexulose-6-phosphate synthase (FIG. 1, step B). The enzyme can use $Mg^{2+}$ or $Mn^{2+}$ for maximal activity, although other metal ions are useful, and even non-metal-ion-dependent mechanisms are contemplated. H6P is converted into fructose-6-phosphate by 6-phospho-3-hexuloisomerase (FIG. 1, step C). Another exemplary pathway that involves the detoxification and assimilation of formaldehyde produced from the oxidation of methanol proceeds through dihydroxyacetone. Dihydroxyacetone synthase (FIG. 1, step D) is a transketolase that first transfers a glycolaldehyde group from xylulose-5-phosphate to formaldehyde, resulting in the formation of dihydroxyacetone (DHA) and glyceraldehyde-3-phosphate (G3P), which is an intermediate in glycolysis. The DHA obtained from DHA synthase can be then further phosphorylated to form DHA phosphate by a DHA kinase. DHAP can be assimilated into glycolysis, e.g. via isomerization to G3P, and several other pathways. Alternatively, DHA and G3P can be converted by fructose-6-phosphate aldolase to form fructose-6-phosphate (F6P) (FIG. 1, step Z).

By combining the pathways for methanol oxidation (FIG. 1, step A) and formaldehyde fixation (FIG. 1, Steps B and C or Step D), molar yields of 0.333 mol acetyl-CoA/mol methanol can be achieved for production of a bioderived compound and their intermediates. The following maximum theoretical yield stoichiometries for a fatty alcohol (e.g., a C12), a fatty acid (e.g., a C12), a fatty aldehyde (e.g., a C12), isopropanol, 1,3-butanediol, crotyl alcohol, butadiene, 3-buten-2-ol, 1,4-butanediol, adipate, 6-aminocaproate, caprolactam, hexamethylenediamine, methacylic acid and 2-hydroxyisobutyric acid are thus made possible by combining the steps for methanol oxidation, formaldehyde fixation, and product synthesis.

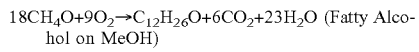
$18CH_4O+9O_2 \rightarrow C_{12}H_{26}O+6CO_2+23H_2O$ (Fatty Alcohol on MeOH)

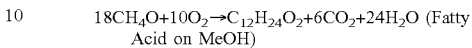
$18CH_4O+10O_2 \rightarrow C_{12}H_{24}O_2+6CO_2+24H_2O$ (Fatty Acid on MeOH)

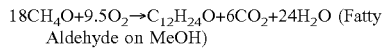
$18CH_4O+9.5O_2 \rightarrow C_{12}H_{24}O+6CO_2+24H_2O$ (Fatty Aldehyde on MeOH)

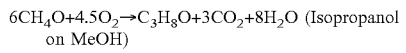
$6CH_4O+4.5O_2 \rightarrow C_3H_8O+3CO_2+8H_2O$ (Isopropanol on MeOH)

Additional stoichiometries are shown in the table below:

| Product | CH4O | O2 | NH3 | Product | H2O | CO2 |
|---|---|---|---|---|---|---|
| 1,3-Butanediol | 6.000 | 3.500 | 0.000 | --> 1.000 | 7.000 | 2.000 |
| Crotyl Alcohol | 6.000 | 3.500 | 0.000 | --> 1.000 | 8.000 | 2.000 |
| 3-Buten-2-ol | 6.000 | 3.500 | 0.000 | --> 1.000 | 8.000 | 2.000 |
| Butadiene | 6.000 | 3.500 | 0.000 | --> 1.000 | 9.000 | 2.000 |
| 2-Hydroxyisobutyrate | 6.000 | 4.500 | 0.000 | --> 1.000 | 8.000 | 2.000 |
| Methacrylate (via 2-hydroxyisobutyrate) | 6.000 | 4.500 | 0.000 | --> 1.000 | 9.000 | 2.000 |
| 3-Hydroxyisobutyrate (oxidative TCA cycle) | 6.000 | 4.500 | 0.000 | --> 1.000 | 8.000 | 2.000 |
| Methacrylate (via 3-hydroxyisobutyrate) | 6.000 | 4.500 | 0.000 | --> 1.000 | 9.000 | 2.000 |
| 1,4-Butanediol (oxidative TCA cycle) | 6.000 | 3.500 | 0.000 | --> 1.000 | 9.000 | 2.000 |
| Adipate (oxidative TCA cycle) | 9.000 | 7.000 | 0.000 | --> 1.000 | 13.000 | 3.000 |
| 6-Aminocaproate (oxidative TCA cycle) | 9.000 | 6.000 | 1.000 | --> 1.000 | 13.000 | 3.000 |
| Caprolactam (via 6-aminocaproate) | 9.000 | 6.000 | 1.000 | --> 1.000 | 14.000 | 3.000 |
| Hexamethylene-diamine (oxidative TCA cycle) | 9.000 | 5.000 | 2.000 | --> 1.000 | 13.000 | 3.000 |

In the products marked "oxidative TCA cycle", the maximum yield stoichiometries assume that the reductive TCA cycle enzymes (e.g., malate dehydrogenase, fumarase, fumarate reductase, and succinyl-CoA ligase) are not utilized for product formation. Exclusive use of the oxidative TCA cycle for product formation can be advantageous for succinyl-CoA derived products such as 3-hydroxyisobutyrate, 1,4-butanediol, adipate, 6-aminocaproate, and hexamethylenediamine because it enables all of the product pathway flux to originate from alpha-ketoglutarate dehydrogenase—an irreversible enzyme in vivo.

The yield on several substrates, including methanol, can be further increased by capturing some of the carbon lost from the conversion of pathway intermediates, e.g. pyruvate to acetyl-CoA, using one of the formate reutilization pathways shown in FIG. 1. For example, the $CO_2$ generated by conversion of pyruvate to acetyl-CoA (FIG. 1, step R) can be converted to formate via formate dehydrogenase (FIG. 1, step S). Alternatively, pyruvate formate lyase, which forms formate directly instead of $CO_2$, can be used to convert pyruvate to acetyl-CoA (FIG. 1, step Q). Formate can be converted to formaldehyde by using: 1) formate reductase (FIG. 1, step E), 2) a formyl-CoA synthetase, transferase, or ligase along with formyl-CoA reductase (FIG. 1, steps F-G), or 3) formyltetrahydrofolate synthetase, methenyltetrahydrofolate cyclohydrolase, methylenetetrahydrofolate dehydrogenase, and formaldehyde-forming enzyme (FIG. 1, steps H-I-J-K). Conversion of methylene-THF to formaldehyde alternatively will occur spontaneously. Alternatively, formate can be reutilized by converting it to pyruvate or acetyl-CoA using FIG. 1, steps H-I-J-L-M-N or FIG. 1, steps H-I-J-O-P, respectively. Formate reutilization is also useful when formate is an external carbon source. For example, formate can be obtained from organocatalytic, electrochemical, or photoelectrochemical conversion of CO2 to formate. An alternative source of methanol for use in the present methods is organocatalytic, electrochemical, or photoelectrochemical conversion of $CO_2$ to methanol.

By combining the pathways for methanol oxidation (FIG. 1, step A), formaldehyde fixation (FIG. 1, Steps B and C or Step D), and formate reutilization, molar yields as high as 0.500 mol acetyl-CoA/mol methanol can be achieved for production of a bioderived compound and their intermediates. Thus, for example, the following maximum theoretical yield stoichiometries for a fatty alcohol (e.g., a C12), a fatty acid (e.g., a C12), a fatty aldehyde (e.g., a C12), isopropanol, 1,3-butanediol, crotyl alcohol, butadiene, 3-buten-2-ol, 1,4-butanediol, adipate, 6-aminocaproate, caprolactam, hexamethylenediamine, methacylic acid and 2-hydroxyisobutyric acid are thus made possible by combining the steps for methanol oxidation, formaldehyde fixation, formate reutilization, and product synthesis.

$$12CH_4O \rightarrow C_{12}H_{26}O + 11H_2O \text{ (Fatty Alcohol on MeOH)}$$

$$12CH_4O + O_2 \rightarrow C_{12}H_{24}O_2 + 12H_2O \text{ (Fatty Acid on MeOH)}$$

$$12CH_4O + 0.5O_2 \rightarrow C_{12}H_{24}O + 12H_2O \text{ (Fatty Aldehyde on MeOH)}$$

$$4\ CH_4O + 1.5O_2 \rightarrow C_3H_8O + 4H_2O + CO_2 \text{ (Isopropanol on MeOH)}$$

Additional enhanced maximum yield stoichiometries can be found in the table below. These stoichiometries assume that the carbon generated from converting pyruvate to acetyl-CoA is recycled back into product and not emitted as CO2.

| Product | CH4O | O2 | NH3 | Product | H2O | CO2 |
|---|---|---|---|---|---|---|
| 1,3-Butanediol | 4.000 | 0.500 | 0.000 | --> 1.000 | 3.000 | 0.000 |
| Crotyl Alcohol | 4.000 | 0.500 | 0.000 | --> 1.000 | 4.000 | 0.000 |
| 3-Buten-2-ol | 4.000 | 0.500 | 0.000 | --> 1.000 | 4.000 | 0.000 |
| Butadiene | 4.000 | 0.500 | 0.000 | --> 1.000 | 5.000 | 0.000 |
| 2-Hydroxyisobutyrate | 4.000 | 1.500 | 0.000 | --> 1.000 | 4.000 | 0.000 |
| Methacrylate (via 2-hydroxyisobutyrate) | 4.000 | 1.500 | 0.000 | --> 1.000 | 5.000 | 0.000 |
| 3-Hydroxyisobutyrate (oxidative TCA cycle) | 5.000 | 3.000 | 0.000 | --> 1.000 | 6.000 | 1.000 |
| Methacrylate (via 3-hydroxyisobutyrate) | 5.000 | 3.000 | 0.000 | --> 1.000 | 7.000 | 1.000 |
| 1,4-Butanediol (oxidative TCA cycle) | 5.000 | 2.000 | 0.000 | --> 1.000 | 5.000 | 1.000 |
| Adipate (oxidative TCA cycle) | 7.000 | 4.000 | 0.000 | --> 1.000 | 9.000 | 1.000 |
| 6-Aminocaproate (oxidative TCA cycle) | 7.000 | 3.000 | 1.000 | --> 1.000 | 9.000 | 1.000 |
| Caprolactam (via 6-aminocaproate) | 7.000 | 3.000 | 1.000 | --> 1.000 | 10.000 | 1.000 |
| Hexamethylenediamine (oxidative TCA cycle) | 7.000 | 2.000 | 2.000 | --> 1.000 | 9.000 | 1.000 |

By combining pathways for formaldehyde fixation and formate reutilization, yield increases on additional substrates are also available including but not limited to glucose, glycerol, sucrose, fructose, xylose, arabinose and galactose. For example, the following maximum theoretical yield stoichiometries for a fatty alcohol (e.g., a C12), a fatty acid (e.g., a C12), a fatty aldehyde (e.g., a C12) and isopropanol on glucose are made possible by combining the steps for formaldehyde fixation, formate reutilization, and compound synthesis.

$$3C_6H_{12}O_6 \rightarrow C_{12}H_{26}O + 5H_2O + 6CO_2 \text{ (Fatty Alcohol on glucose)}$$

$$3C_6H_{12}O_6 \rightarrow 1.0588\ C_{12}H_{24}O_2 + 5.2941\ H_2O + 5.2941\ CO_2 \text{ (Fatty Acid on glucose)}$$

$$3C_6H_{12}O_6 \rightarrow 1.0286\ C_{12}H_{24}O + 5.6571\ H_2O + 5.6571\ CO_2 \text{ (Fatty Aldehyde on glucose)}$$

$$C_6H_{12}O_6 \rightarrow 1.3333\ C_3H_8O + 0.6667\ H_2O + 2\ CO_2 \text{ (Isopropanol on glucose)}$$

Similar yield increases are observed for 1,3-butanediol, crotyl alcohol, butadiene, 3-buten-2-ol, 1,4-butanediol, adipate, 6-aminocaproate, caprolactam, hexamethylenediamine, methacylic acid, 3-hydroxyisobutric acid and 2-hydroxyisobutyric acid when formaldehyde fixation and formate reutilization pathways are used in conjunction with glycolysis, the TCA cycle, and the pentose phosphate pathway.

| Product | C6H12O6 | O2 | NH3 | Product | H2O | CO2 |
|---|---|---|---|---|---|---|
| 1,3-Butanediol | 1.000 | 0.000 | 0.000 | → 1.091 | 0.545 | 1.636 |
| Crotyl Alcohol | 1.000 | 0.000 | 0.000 | → 1.091 | 1.636 | 1.636 |
| 3-Buten-2-ol | 1.000 | 0.000 | 0.000 | → 1.091 | 1.636 | 1.636 |
| Butadiene | 1.000 | 0.107 | 0.000 | → 1.071 | 2.786 | 1.714 |
| 2-Hydroxyisobutyrate | 1.000 | 0.000 | 0.000 | → 1.333 | 0.667 | 0.667 |
| Methacrylate (via 2-hydroxyisobutyrate) | 1.000 | 0.000 | 0.000 | → 1.333 | 2.000 | 0.667 |
| 3-Hydroxyisobutyrate (oxidative TCA cycle) | 1.000 | 0.214 | 0.000 | → 1.286 | 0.857 | 0.857 |

-continued

| Product | C6H12O6 | O2 | NH3 | | Product | H2O | CO2 |
|---|---|---|---|---|---|---|---|
| Methacrylate (via 3-hydroxyisobutyrate) | 1.000 | 0.214 | 0.000 | → | 1.286 | 2.143 | 0.857 |
| 1,4-Butanediol (oxidative TCA cycle) | 1.000 | 0.107 | 0.000 | → | 1.071 | 0.643 | 1.714 |
| Adipate (oxidative TCA cycle) | 1.000 | 0.168 | 0.000 | → | 0.897 | 1.514 | 0.617 |
| 6-Aminocaproate (oxidative TCA cycle) | 1.000 | 0.000 | 0.800 | → | 0.800 | 2.000 | 1.200 |
| Caprolactam (via 6-aminocaproate) | 1.000 | 0.000 | 0.800 | → | 0.800 | 2.800 | 1.200 |
| Hexamethylene-diamine (oxidative TCA cycle) | 1.000 | 0.050 | 1.400 | → | 0.700 | 2.500 | 1.800 |

Similarly, the maximum theoretical yield of a bioderived compound from glycerol can be increased by enabling fixation of formaldehyde from generation and utilization of formate. The following maximum theoretical yield stoichiometries for a fatty alcohol (e.g., a C12), a fatty acid (e.g., a C12), a fatty aldehyde (e.g., a C12) and isopropanol on glycerol are thus made possible by combining the steps for formaldehyde fixation, formate reutilization, and product synthesis.

$$6\ C_3H_8O_3 \rightarrow 1.1667\ C_{12}H_{26}O + 8.8333\ H_2O + 4\ CO_2$$
(Fatty Alcohol on glycerol)

$$6\ C_3H_8O_3 \rightarrow 1.2353\ C_{12}H_{24}O_2 + 9.1765\ H_2O + 3.1765\ CO_2$$ (Fatty Acid on glycerol)

$$6\ C_3H_8O_3 \rightarrow 1.2000\ C_{12}H_{24}O + 9.6000\ H_2O + 3.6000\ CO_2$$ (Fatty Aldehyde on glycerol)

$$C_3H_8O_3 \rightarrow 0.7778\ C_3H_8O + 0.8889\ H_2O + 0.6667\ CO_2$$
(Isopropanol on glycerol)

In numerous engineered pathways, product yields based on carbohydrate feedstock are hampered by insufficient reducing equivalents or by loss of reducing equivalents to byproducts. Methanol is a relatively inexpensive organic feedstock that can be used to generate reducing equivalents by employing one or more methanol metabolic enzymes as shown in FIG. 2. Reducing equivalents can also be extracted from hydrogen and carbon monoxide by employing hydrogenase and carbon monoxide dehydrogenase enzymes, respectively, as shown in FIG. 2. The reducing equivalents are then passed to acceptors such as oxidized ferredoxins, oxidized quinones, oxidized cytochromes, NAD(P)+, water, or hydrogen peroxide to form reduced ferredoxin, reduced quinones, reduced cytochromes, NAD(P)H, H$_2$, or water, respectively. Reduced ferredoxin, reduced quinones and NAD(P)H are particularly useful as they can serve as redox carriers for various Wood-Ljungdahl pathway, reductive TCA cycle, or product pathway enzymes.

The reducing equivalents produced by the metabolism of methanol, hydrogen, and carbon monoxide can be used to power several bioderived compound production pathways. For example, the maximum theoretical yield of a fatty alcohol, a fatty acid, a fatty aldehyde, isopropanol, 1,3-butanediol, crotyl alcohol, butadiene, 3-buten-2-ol, 1,4-butanediol, adipate, 6-aminocaproate, caprolactam, hexamethylenediamine, methacylic acid or 2-hydroxyisobutyric acid from glucose and glycerol can be increased by enabling fixation of formaldehyde, formate reutilization, and extraction of reducing equivalents from an external source such as hydrogen. In fact, by combining pathways for formaldehyde fixation, formate reutilization, reducing equivalent extraction, and product synthesis, the following maximum theoretical yield stoichiometries for fatty alcohol, a fatty acid, a fatty aldehyde, and isopropanol on glucose and glycerol are made possible.

$$2C_6H_{12}O_6 + 12H_2 \rightarrow C_{12}H_{26}O + 11H_2O$$ (Fatty Alcohol on glucose+external redox)

$$2C_6H_{12}O_6 + 10H_2 \rightarrow C_{12}H_{24}O_2 + 10H_2O$$ (Fatty Acid on glucose+external redox)

$$2C_6H_{12}O_6 + 11H_2 \rightarrow C_{12}H_{24}O + 11H_2O$$ (Fatty Aldehyde on glucose+external redox)

$$C_6H_{12}O_6 + 6\ H_2 \rightarrow 2\ C_3H_8O + 4H_2O$$ (Isopropanol on glucose+external redox)

$$4C_3H_8O_3 + 8H_2 \rightarrow C_{12}H_{26}O + 11H_2O$$ (Fatty Alcohol on glycerol+external redox)

$$4C_3H_8O_3 + 6H_2 \rightarrow C_{12}H_{24}O_2 + 10H_2O$$ (Fatty Acid on glycerol+external redox)

$$4C_3H_8O_3 + 7H_2 \rightarrow C_{12}H_{24}O + 11H_2O$$ (Fatty Aldehyde on glycerol+external redox)

$$C_3H_8O_3 + 2H_2 \rightarrow C_3H_8O + 2H_2O$$ (Isopropanol on glycerol+external redox)

In most instances, achieving such maximum yield stoichiometries may require some oxidation of reducing equivalents (e.g., $H_2 + \frac{1}{2}\ O_2 \rightarrow H_2O$, $CO + \frac{1}{2}\ O_2 \rightarrow CO_2$, $CH_4O + 1.5\ O_2 \rightarrow CO_2 + 2\ H_2O$, $C_6H_{12}O_6 + 6\ O_2 \rightarrow 6\ CO_2 + 6\ H_2O$) to provide sufficient energy for the substrate to product pathways to operate. Nevertheless, if sufficient reducing equivalents are available, enabling pathways for fixation of formaldehyde, formate reutilization, extraction of reducing equivalents, and product synthesis can even lead to production of a fatty alcohol, a fatty acid, a fatty aldehyde, isopropanol, and their intermediates, directly from $CO_2$.

Pathways identified herein, and particularly pathways exemplified in specific combinations presented herein, are superior over other pathways based in part on the applicant's ranking of pathways based on attributes including maximum theoretical compound yield, maximal carbon flux, maximal production of reducing equivalents, minimal production of $CO_2$, pathway length, number of non-native steps, thermodynamic feasibility, number of enzymes active on pathway substrates or structurally similar substrates, and having steps with currently characterized enzymes, and furthermore, the latter pathways are even more favored by having in addition at least the fewest number of non-native steps required, the most enzymes known active on pathway substrates or structurally similar substrates, and the fewest total number of steps from central metabolism.

The non-naturally occurring microbial organisms of the invention can contain stable genetic alterations, which refers to microorganisms that can be cultured for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely.

In the case of gene disruptions, a particularly useful stable genetic alteration is a gene deletion. The use of a gene deletion to introduce a stable genetic alteration is particularly useful to reduce the likelihood of a reversion to a phenotype prior to the genetic alteration. For example, stable growth-coupled production of a biochemical can be achieved, for example, by deletion of a gene encoding an enzyme catalyzing one or more reactions within a set of metabolic modifications. The stability of growth-coupled production of a biochemical can be further enhanced through multiple deletions, significantly reducing the likelihood of multiple compensatory reversions occurring for each disrupted activity.

Those skilled in the art will understand that the genetic alterations, including metabolic modifications exemplified herein, are described with reference to a suitable host organism such as E. coli and their corresponding metabolic reactions or a suitable source organism for desired genetic material such as genes for a desired metabolic pathway. However, given the complete genome sequencing of a wide variety of organisms and the high level of skill in the area of genomics, those skilled in the art will readily be able to apply the teachings and guidance provided herein to essentially all other organisms. For example, the E. coli metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

An ortholog is a gene or genes that are related by vertical descent and are responsible for substantially the same or identical functions in different organisms. For example, mouse epoxide hydrolase and human epoxide hydrolase can be considered orthologs for the biological function of hydrolysis of epoxides. Genes are related by vertical descent when, for example, they share sequence similarity of sufficient amount to indicate they are homologous, or related by evolution from a common ancestor. Genes can also be considered orthologs if they share three-dimensional structure but not necessarily sequence similarity, of a sufficient amount to indicate that they have evolved from a common ancestor to the extent that the primary sequence similarity is not identifiable. Genes that are orthologous can encode proteins with sequence similarity of about 25% to 100% amino acid sequence identity. Genes encoding proteins sharing an amino acid similarity less that 25% can also be considered to have arisen by vertical descent if their three-dimensional structure also shows similarities. Members of the serine protease family of enzymes, including tissue plasminogen activator and elastase, are considered to have arisen by vertical descent from a common ancestor.

Orthologs include genes or their encoded gene products that through, for example, evolution, have diverged in structure or overall activity. For example, where one species encodes a gene product exhibiting two functions and where such functions have been separated into distinct genes in a second species, the three genes and their corresponding products are considered to be orthologs. For the production of a biochemical product, those skilled in the art will understand that the orthologous gene harboring the metabolic activity to be introduced or disrupted is to be chosen for construction of the non-naturally occurring microorganism. An example of orthologs exhibiting separable activities is where distinct activities have been separated into distinct gene products between two or more species or within a single species. A specific example is the separation of elastase proteolysis and plasminogen proteolysis, two types of serine protease activity, into distinct molecules as plasminogen activator and elastase. A second example is the separation of mycoplasma 5'-3' exonuclease and Drosophila DNA polymerase III activity. The DNA polymerase from the first species can be considered an ortholog to either or both of the exonuclease or the polymerase from the second species and vice versa.

In contrast, paralogs are homologs related by, for example, duplication followed by evolutionary divergence and have similar or common, but not identical functions. Paralogs can originate or derive from, for example, the same species or from a different species. For example, microsomal epoxide hydrolase (epoxide hydrolase I) and soluble epoxide hydrolase (epoxide hydrolase II) can be considered paralogs because they represent two distinct enzymes, co-evolved from a common ancestor, that catalyze distinct reactions and have distinct functions in the same species. Paralogs are proteins from the same species with significant sequence similarity to each other suggesting that they are homologous, or related through co-evolution from a common ancestor. Groups of paralogous protein families include HipA homologs, luciferase genes, peptidases, and others.

A nonorthologous gene displacement is a nonorthologous gene from one species that can substitute for a referenced gene function in a different species. Substitution includes, for example, being able to perform substantially the same or a similar function in the species of origin compared to the referenced function in the different species. Although generally, a nonorthologous gene displacement will be identifiable as structurally related to a known gene encoding the referenced function, less structurally related but functionally similar genes and their corresponding gene products nevertheless will still fall within the meaning of the term as it is used herein. Functional similarity requires, for example, at least some structural similarity in the active site or binding region of a nonorthologous gene product compared to a gene encoding the function sought to be substituted. Therefore, a nonorthologous gene includes, for example, a paralog or an unrelated gene.

Therefore, in identifying and constructing the non-naturally occurring microbial organisms of the invention having acetyl-CoA or a bioderived compound biosynthetic capability, those skilled in the art will understand with applying the teaching and guidance provided herein to a particular species that the identification of metabolic modifications can include identification and inclusion or inactivation of orthologs. To the extent that paralogs and/or nonorthologous gene displacements are present in the referenced microorganism that encode an enzyme catalyzing a similar or substantially similar metabolic reaction, those skilled in the art also can utilize these evolutionarily related genes. Similarly for a gene disruption, evolutionarily related genes can also be disrupted or deleted in a host microbial organism to reduce or eliminate functional redundancy of enzymatic activities targeted for disruption.

Orthologs, paralogs and nonorthologous gene displacements can be determined by methods well known to those skilled in the art. For example, inspection of nucleic acid or amino acid sequences for two polypeptides will reveal sequence identity and similarities between the compared sequences. Based on such similarities, one skilled in the art can determine if the similarity is sufficiently high to indicate the proteins are related through evolution from a common ancestor. Algorithms well known to those skilled in the art, such as Align, BLAST, Clustal W and others compare and determine a raw sequence similarity or identity, and also determine the presence or significance of gaps in the sequence which can be assigned a weight or score. Such algorithms also are known in the art and are similarly applicable for determining nucleotide sequence similarity or identity. Parameters for sufficient similarity to determine relatedness are computed based on well known methods for calculating statistical similarity, or the chance of finding a similar match in a random polypeptide, and the significance of the match determined. A computer comparison of two or more sequences can, if desired, also be optimized visually by those skilled in the art. Related gene products or proteins can be expected to have a high similarity, for example, 25% to 100% sequence identity. Proteins that are unrelated can have an identity which is essentially the same as would be expected to occur by chance, if a database of sufficient size is scanned (about 5%). Sequences between 5% and 24% may or may not represent sufficient homology to conclude that the compared sequences are related. Additional statistical analysis to determine the significance of such matches given the size of the data set can be carried out to determine the relevance of these sequences.

Exemplary parameters for determining relatedness of two or more sequences using the BLAST algorithm, for example, can be as set forth below. Briefly, amino acid sequence alignments can be performed using BLASTP version 2.0.8 (Jan. 5, 1999) and the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN version 2.0.6 (Sep. 16, 1998) and the following parameters: Match: 1; mismatch: −2; gap open: 5; gap extension: 2; x_dropoff: 50; expect: 10.0; wordsize: 11; filter: off. Those skilled in the art will know what modifications can be made to the above parameters to either increase or decrease the stringency of the comparison, for example, and determine the relatedness of two or more sequences.

In some embodiments, the invention provides a non-naturally occurring microbial organism having a methanol metabolic pathway and an acetyl-CoA pathway as depicted in FIGS. 1 and 2. In some embodiments, the methanol metabolic pathway comprises 2A or 2J, wherein 2A is a methanol methyltransferase and 2J is a methanol dehydrogenase. In some embodiments, the methanol metabolic pathway comprises 2A. In some embodiments, the methanol metabolic pathway comprises 2J. In some embodiments, the acetyl-CoA pathway comprises a pathway selected from: (1) 1T and 1V; (2) 1T, 1W, and 1X; (3) 1U and 1V; (4) 1U, 1W, and 1X; wherein 1T is a fructose-6-phosphate phosphoketolase, wherein 1U is a xylulose-5-phosphate phosphoketolase, wherein 1V is a phosphotransacetylase, wherein 1W is an acetate kinase, wherein 1X is an acetyl-CoA transferase, an acetyl-CoA synthetase, or an acetyl-CoA ligase. In some embodiments, the acetyl-CoA pathway comprises (1) 1T and 1V. In some embodiments, the acetyl-CoA pathway comprises (2) 1T, 1W, and 1X. In some embodiments, the acetyl-CoA pathway comprises (3) 1U and 1V. In some embodiments, the acetyl-CoA pathway comprises (4) 1U, 1W, and 1X. In some embodiments, an enzyme of the methanol metabolic pathway or the acetyl-CoA pathway is encoded by at least one exogenous nucleic acid and is expressed in a sufficient amount to enhance carbon flux through acetyl-CoA.

In some embodiments, the invention provides a non-naturally occurring microbial organism as described herein further comprising a formaldehyde fixation pathway as depicted in FIG. 1. In some embodiments, the formaldehyde fixation pathway comprises: (1) 1D and 1Z; (2) 1D; or (3) 1B and 1C, wherein 1B is a 3-hexulose-6-phosphate synthase, wherein 1C is a 6-phospho-3-hexuloisomerase, wherein 1D is a dihydroxyacetone synthase, wherein 1Z is a fructose-6-phosphate aldolase. In some embodiments, the formaldehyde fixation pathway comprises (1) 1D and 1Z. In some embodiments, the formaldehyde fixation pathway comprises (2) 1D. In some embodiments, the formaldehyde fixation pathway comprises (3) 1B and 1C. In some embodiments, an enzyme of the formaldehyde fixation pathway is encoded by at least one exogenous nucleic acid and is expressed in a sufficient amount to enhance carbon flux through acetyl-CoA.

In some embodiments, the invention provides a non-naturally occurring microbial organism as described herein further comprising a methanol metabolic pathway selected from: (1) 2A and 2B; (2) 2A, 2B and 2C; (3) 2J, 2K and 2C; (4) 2J, 2M, and 2N; (5) 2J and 2L; (6) 2J, 2L, and 2G; (7) 2J, 2L, and 2I; (8) 2A, 2B, 2C, 2D, and 2E; (9) 2A, 2B, 2C, 2D, and 2F; (10) 2J, 2K, 2C, 2D, and 2E; (11) 2J, 2K, 2C, 2D, and 2F; (12) 2J, 2M, 2N, and 2O; (13) 2A, 2B, 2C, 2D, 2E, and 2G; (14) 2A, 2B, 2C, 2D, 2F, and 2G; (15) 2J, 2K, 2C, 2D, 2E, and 2G; (16) 2J, 2K, 2C, 2D, 2F, and 2G; (17) 2J, 2M, 2N, 2O, and 2G; (18) 2A, 2B, 2C, 2D, 2E, and 2I; (19) 2A, 2B, 2C, 2D, 2F, and 2I; (20) 2J, 2K, 2C, 2D, 2E, and 2I; (21) 2J, 2K, 2C, 2D, 2F, and 2I; and (22) 2J, 2M, 2N, 2O, and 2I, wherein 2A is a methanol methyltransferase, wherein 2B is a methylenetetrahydrofolate reductase, wherein 2C is a methylenetetrahydrofolate dehydrogenase, wherein 2D is a methenyltetrahydrofolate cyclohydrolase, wherein 2E is a formyltetrahydrofolate deformylase, wherein 2F is a formyltetrahydrofolate synthetase, wherein 2G is a formate hydrogen lyase, wherein 2I is a formate dehydrogenase, wherein 2J is a methanol dehydrogenase, wherein 2K is a formaldehyde activating enzyme or spontaneous, wherein 2L is a formaldehyde dehydrogenase, wherein 2M is a S-(hydroxymethyl)glutathione synthase or spontaneous, wherein 2N is a glutathione-dependent formaldehyde dehydrogenase, and wherein 2O is a S-formylglutathione hydrolase. In some embodiments, the methanol metabolic pathway comprises (1) 2A and 2B. In some embodiments, the methanol metabolic pathway comprises (2) 2A, 2B and 2C. In some embodiments, the methanol metabolic pathway comprises (3) 2J, 2K and 2C. In some embodiments, the methanol metabolic pathway comprises (4) 2J, 2M, and 2N. In some embodiments, the methanol metabolic pathway comprises (5) 2J and 2L. In some embodiments, the methanol metabolic pathway comprises (6) 2J, 2L, and 2G. In some embodiments, the methanol metabolic pathway comprises (7) 2J, 2L, and 2I. In some embodiments, the methanol metabolic pathway comprises (8) 2A, 2B, 2C, 2D, and 2E. In some embodiments, the methanol metabolic pathway comprises (9) 2A, 2B, 2C, 2D, and 2F. In some embodiments, the methanol metabolic pathway comprises (10) 2J, 2K, 2C, 2D, and 2E. In some embodiments, the methanol metabolic pathway comprises (11) 2J, 2K, 2C, 2D, and 2F. In some embodiments, the methanol metabolic pathway comprises (12) 2J, 2M, 2N, and 2O. In some embodiments, the methanol metabolic pathway comprises (13) 2A, 2B, 2C, 2D, 2E, and 2G; (14) 2A, 2B, 2C, 2D, 2F, and 2G. In some embodiments, the methanol metabolic pathway comprises (15) 2J, 2K, 2C, 2D, 2E, and 2G. In some embodiments, the methanol metabolic pathway comprises (16) 2J, 2K, 2C, 2D, 2F, and 2G. In some embodiments, the methanol metabolic pathway comprises (17) 2J, 2M, 2N, 2O, and 2G. In some embodiments, the methanol metabolic pathway comprises (18) 2A, 2B, 2C, 2D, 2E, and 2I. In some embodiments, the methanol metabolic pathway comprises (19) 2A, 2B, 2C, 2D, 2F, and 2I. In some embodiments, the methanol metabolic pathway comprises (20) 2J, 2K, 2C, 2D, 2E, and 2I. In some embodiments, the methanol metabolic pathway comprises (21) 2J, 2K, 2C, 2D, 2F, and 2I. In some embodiments, the methanol metabolic pathway comprises (22) 2J, 2M, 2N, 2O, and 2I.

In some embodiments, the non-naturally occurring microbial organism described herein comprises one, two, three, four, five, or six exogenous nucleic acids each encoding a methanol metabolic pathway enzyme. In some embodiments, the non-naturally occurring microbial organism described herein comprises exogenous nucleic acids encoding each of the enzymes of at least one of the pathways selected from (1)-(22) as describe above. In some embodiments, the non-naturally occurring microbial organism described herein comprises one, two, or three exogenous nucleic acids each encoding an acetyl-CoA pathway enzyme. In some embodiments, the non-naturally occurring microbial organism described herein comprises exogenous nucleic acids encoding each of the enzymes of at least one of the acetyl-CoA pathway selected from (1)-(4) described above.

In some embodiments, the invention provides a non-naturally occurring microbial organism as described herein further comprising a formate assimilation pathway as depicted in FIG. 1. In some embodiments, the formate assimilation pathway comprises a pathway selected from: (1) 1E; (2) 1F, and 1G; (3) 1H, 1I, 1J, and 1K; (4) 1H, 1I, 1J, 1L, 1M, and 1N; (5) 1E, 1H, 1I, 1J, 1L, 1M, and 1N; (6) 1F, 1G, 1H, 1I, 1J, 1L, 1M, and 1N; (7) 1K, 1H, 1I, 1J, 1L, 1M, and 1N; and (8) 1H, 1I, 1J, 1O, and 1P, wherein 1E is a formate reductase, IF is a formate ligase, a formate transferase, or a formate synthetase, wherein 1G is a formyl-CoA reductase, wherein 1H is a formyltetrahydrofolate synthetase, wherein 1I is a methenyltetrahydrofolate cyclohydrolase, wherein 1J is a methylenetetrahydrofolate dehydrogenase, wherein 1K is a formaldehyde-forming enzyme or spontaneous, wherein 1L is a glycine cleavage system, wherein 1M is a serine hydroxymethyltransferase, wherein 1N is a serine deaminase, wherein 1O is a methylenetetrahydrofolate reductase, and wherein 1P is an acetyl-CoA synthase. In some embodiments, the formate assimilation pathway comprises (1) 1E. In some embodiments, the formate assimilation pathway comprises (2) 1F, and 1G. In some embodiments, the formate assimilation pathway comprises (3) 1H, 1I, 1J, and 1K. In some embodiments, the formate assimilation pathway comprises (4) 1H, 1I, 1J, 1L, 1M, and 1N. In some embodiments, the formate assimilation pathway comprises (5) 1E, 1H, 1I, 1J, 1L, 1M, and 1N. In some embodiments, the formate assimilation pathway comprises (6) 1F, 1G, 1H, 1I, 1J, 1L, 1M, and 1N. In some embodiments, the formate assimilation pathway comprises (7) 1K, 1H, 1I, 1J, 1L, 1M, and 1N. In some embodiments, the formate assimilation pathway comprises (8) 1H, 1I, 1J, 1O, and 1P. In some embodiments, an enzyme of the formate assimilation pathway is encoded by at least one exogenous nucleic acid and is expressed in a sufficient amount to enhance carbon flux through acetyl-CoA.

Figures 2, 3:
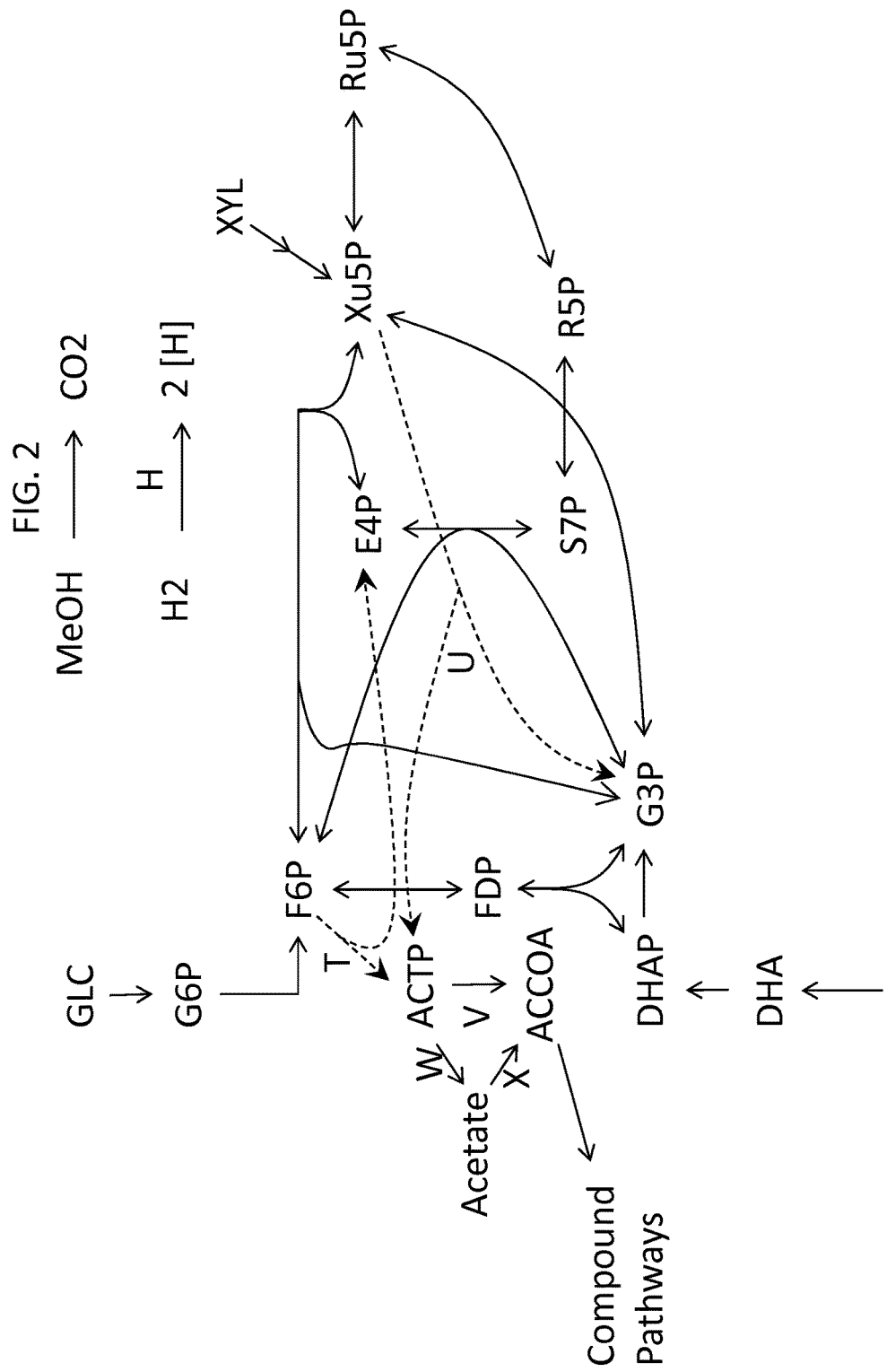
FIG. 3 shows exemplary pathways which can be used to increase carbon flux through acetyl-CoA from carbohydrates when reducing equivalents produced by a methanol or hydrogen oxidation pathway provided herein are available. The enzymatic transformations shown are carried out by the following enzymes: T) fructose-6-phosphate phosphoketolase, U) xylulose-5-phosphate phosphoketolase, V) phosphotransacetylase, W) acetate kinase, X) acetyl-CoA transferase, synthetase, or ligase, and H) hydrogenase. See abbreviation list below for compound names.

In some embodiments, the invention provides a non-naturally occurring microbial organism having a formaldehyde fixation pathway, a formate assimilation pathway and/or an acetyl-CoA pathway as described here. Accordingly, in some embodiments, the non-naturally occurring microbial organism of the invention can have an acetyl-CoA pathway as depicted in FIG. 3. In some embodiments, the non-naturally occurring microbial organism of the invention can have a formaldehyde fixation pathway and an acetyl-CoA pathway as depicted in FIG. 1. In some embodiments, the non-naturally occurring microbial organism of the invention can have a formate assimilation pathway and an acetyl-CoA pathway as depicted in FIG. 1. In some embodiments, the non-naturally occurring microbial organism of the invention can have a formaldehyde fixation pathway, a formate assimilation pathway and an acetyl-CoA pathway as depicted in FIG. 1. In some embodiments, the formaldehyde fixation pathway comprises. (1) 1D and 1Z; (2) 1D; or (3)1B and 1C, wherein 1B is a 3-hexulose-6-phosphate synthase, wherein 1C is a 6-phospho-3-hexuloisomerase, wherein 1D is a dihydroxyacetone synthase, wherein 1Z is a fructose-6-phosphate aldolase. In some embodiments, the formaldehyde fixation pathway comprises (1) 1D and 1Z. In some embodiments, the formaldehyde fixation pathway comprises (2) 1D. In some embodiments, the formaldehyde fixation pathway comprises (3)1B and 1C. In some embodiment, the formate assimilation pathway comprises a pathway selected from: (4) 1E; (5) 1F, and 1G; (6) 1H, 1I, 1J, and 1K; (7) 1H, 1I, 1J, 1L, 1M, and 1N; (8) 1E, 1H, 1I, 1J, 1L, 1M, and 1N; (9) 1F, 1G, 1H, 1I, 1J, 1L, 1M, and 1N; (10) 1K, 1H, 1I, 1J, 1L, 1M, and 1N; and (11) 1H, 1I, 1J, 1O, and 1P, wherein 1E is a formate reductase, 1F is a formate ligase, a formate transferase, or a formate synthetase, wherein 1G is a formyl-CoA reductase, wherein 1H is a formyltetrahydrofolate synthetase, wherein 1I is a methenyltetrahydrofolate cyclohydrolase, wherein 1J is a methylenetetrahydrofolate dehydrogenase, wherein 1K is a formaldehyde-forming enzyme or spontaneous, wherein 1L is a glycine cleavage system, wherein 1M is a serine hydroxymethyltransferase, wherein 1N is a serine deaminase, wherein 1O is a methylenetetrahydrofolate reductase, and wherein 1P is an acetyl-CoA synthase. In some embodiments, the formate assimilation pathway comprises (4) 1E. In some embodiments, the formate assimilation pathway comprises (5) 1F, and 1G. In some embodiments, the formate assimilation pathway comprises (6) 1H, 1I, 1J, and 1K. In some embodiments, the formate assimilation pathway comprises (7) 1H, 1I, 1J, 1L, 1M, and 1N. In some embodiments, the formate assimilation pathway comprises (8) 1E, 1H, 1I, 1J, 1L, 1M, and 1N. In some embodiments, the formate assimilation pathway comprises (9) 1F, 1G, 1H, 1I, 1J, 1L, 1M, and 1N. In some embodiments, the formate assimilation pathway comprises (10) 1K, 1H, 1I, 1J, 1L, 1M, and 1N. In some embodiments, the formate assimilation pathway comprises (11) 1H, 1I, 1J, 1O, and 1P. In some embodiments, acetyl-CoA pathway comprises a pathway selected from: (12) 1T and 1V; (13) 1T, 1W, and 1X; (14) 1U and 1V; and (15) 1U, 1W, and 1X, wherein 1T is a fructose-6-phosphate phosphoketolase, wherein 1U is a xylulose-5-phosphate phosphoketolase, wherein 1V is a phosphotransacetylase, wherein 1W is an acetate kinase, wherein 1X is an acetyl-CoA transferase, an acetyl-CoA synthetase, or an acetyl-CoA ligase. In some embodiments, acetyl-CoA pathway comprises (12) 1T and 1V. In some embodiments, acetyl-CoA pathway comprises (13) 1T, 1W, and 1X. In some embodiments, acetyl-CoA pathway comprises (14) 1U and 1V. In some embodiments, acetyl-CoA pathway comprises (15) 1U, 1W, and 1X. In some embodiments, the non-naturally occurring microbial organism described herein comprises an acetyl-CoA pathway that comprises 1T and 1V and a formaldehyde fixation pathway that comprises 1D and 1Z. In some embodiments, the non-naturally occurring microbial organism described herein comprises an acetyl-CoA pathway that comprises 1T and 1V and a formaldehyde fixation pathway comprises 1B and 1C. In some embodiments, an enzyme of the formaldehyde fixation pathway, the formate assimilation pathway, and/or the acetyl-CoA pathway is encoded by at least one exogenous nucleic acid and is expressed in a sufficient amount to enhance carbon flux through acetyl-CoA.

In some embodiments, the non-naturally occurring microbial organism described herein comprises one or two exogenous nucleic acids each encoding an formaldehyde fixation pathway enzyme. In some embodiments, the non-naturally occurring microbial organism described herein comprises one, two, three, four, five, six, seven or eight exogenous nucleic acids each encoding a formate assimilation pathway enzyme. In some embodiments, the non-naturally occurring microbial organism described herein comprises one, two, or three exogenous nucleic acids each encoding an acetyl-CoA pathway enzyme. In some embodiments, the non-naturally occurring microbial organism described herein comprises exogenous nucleic acids encoding each of the enzymes of at least one of the pathways selected from (1)-(15) as described above.

In some embodiments, the invention further provides a non-naturally occurring microbial organism described herein that has a formate assimilation pathway further comprises. (1) 1Q; (2) 1R and 1S, (3) 1Y and 1Q; or (4) 1Y, 1R, and 1S, as depicted in FIG. 1, wherein 1Q is a pyruvate formate lyase, wherein 1R is a pyruvate dehydrogenase, a pyruvate ferredoxin oxidoreductase, or a pyruvate:NADP+ oxidoreductase, wherein 1S is a formate dehydrogenase, wherein 1Y is a glyceraldehyde-3-phosphate dehydrogenase or an enzyme of lower glycolysis. In some embodiments, the formate assimilation pathway further comprises (1) 1Q. In some embodiments, the formate assimilation pathway further comprises (2) 1R and 1S. In some embodiments, the formate assimilation pathway further comprises (3) 1Y and 1. In some embodiments, the formate assimilation pathway further comprises (4) 1Y, 1R, and 1S.

In some embodiments, a non-naturally occurring microbial organism of the invention includes a methanol oxidation pathway. Such a pathway can include at least one exogenous nucleic acid encoding a methanol oxidation pathway enzyme expressed in a sufficient amount to produce formaldehyde in the presence of methanol. An exemplary methanol oxidation pathway enzyme is a methanol dehydrogenase. Accordingly, in some embodiments, a non-naturally occurring microbial organism of the invention includes at least one exogenous nucleic acid encoding a methanol dehydrogenase expressed in a sufficient amount to produce formaldehyde in the presence of methanol.

In some embodiments, the exogenous nucleic acid encoding an methanol dehydrogenase is expressed in a sufficient amount to produce an amount of formaldehyde greater than or equal to 1 µM, 10 µM, 20 µM, or 50 µM, or a range thereof, in culture medium or intracellularly. In other embodiments, the exogenous nucleic acid encoding an methanol dehydrogenase is capable of producing an amount of formaldehyde greater than or equal to 1 µM, 10 µM, 20 µM, or 50 µM, or a range thereof, in culture medium or intracellularly. In some embodiments, the range is from 1 µM to 50 µM or greater. In other embodiments, the range is from 10 µM to 50 µM or greater. In other embodiments, the range is from 20 µM to 50 µM or greater. In other embodiments, the amount of formaldehyde production is 50 µM or greater. In specific embodiments, the amount of formaldehyde production is in excess of, or as compared to, that of a negative control, e.g., the same species of organism that does not comprise the exogenous nucleic acid, such as a wild-type microbial organism or a control microbial organism thereof. In certain embodiments, the methanol dehydrogenase is selected from those provided herein, e.g., as exemplified in Example II (see FIG. 1, Step A, or FIG. 10, Step J). In certain embodiments, the amount of formaldehyde production is determined by a whole cell assay, such as that provided in Example II (see FIG. 1, Step A, or FIG. 10, Step J), or by another assay provided herein or otherwise known in the art. In certain embodiments, formaldehyde utilization activity is absent in the whole cell.

In certain embodiments, the exogenous nucleic acid encoding an methanol dehydrogenase is expressed in a sufficient amount to produce at least 1×, 2×, 3×, 4×, 5×, 6×, 7×, 8×, 9×, 10×, 15×, 20×, 30×, 40×, 50×, 100× or more formaldehyde in culture medium or intracellularly. In other embodiments, the exogenous nucleic acid encoding an methanol dehydrogenase is capable of producing an amount of formaldehyde at least 1×, 2×, 3×, 4×, 5×, 6×, 7×, 8×, 9×, 10×, 15×, 20×, 30×, 40×, 50×, 100×, or a range thereof, in culture medium or intracellularly. In some embodiments, the range is from 1× to 100×. In other embodiments, the range is from 2× to 100×. In other embodiments, the range is from 5× to 100×. In other embodiments, the range is from 10× to 100×. In other embodiments, the range is from 50× to 100×. In some embodiments, the amount of formaldehyde production is at least 20×. In other embodiments, the amount of formaldehyde production is at least 50×. In specific embodiments, the amount of formaldehyde production is in excess of, or as compared to, that of a negative control, e.g., the same species of organism that does not comprise the exogenous nucleic acid, such as a wild-type microbial organism or a control microbial organism thereof. In certain embodiments, the methanol dehydrogenase is selected from those provided herein, e.g., as exemplified herein (see FIG. 1, Step A, or FIG. 2, Step J). In certain embodiments, the amount of formaldehyde production is determined by a whole cell assay, such as that provided herein (see FIG. 1, Step A, or FIG. 2, Step J), or by another assay provided herein or otherwise known in the art. In certain embodiments, formaldehyde utilization activity is absent in the whole cell.

In some embodiments, a non-naturally occurring microbial organism of the invention includes one or more enzymes for generating reducing equivalents. For example, the microbial organism can further include a hydrogenase and/or a carbon monoxide dehydrogenase. In some aspects, the organism comprises an exogenous nucleic acid encoding the hydrogenase or the carbon monoxide dehydrogenase.

A reducing equivalent can also be readily obtained from a glycolysis intermediate by any of several central metabolic reactions including glyceraldehyde-3-phosphate dehydrogenase, pyruvate dehydrogenase, pyruvate formate lyase and NAD(P)-dependent formate dehydrogenase, isocitrate dehydrogenase, alpha-ketoglutarate dehydrogenase, succinate dehydrogenase, and malate dehydrogenase. Additionally, reducing equivalents can be generated from glucose 6-phosphate-1-dehydrogenase and 6-phosphogluconate dehydrogenase of the pentose phosphate pathway. Overall, at most twelve reducing equivalents can be obtained from a C6 glycolysis intermediate (e.g., glucose-6-phosphate, fructose-6-phosphate, fructose-1,6-diphosphate) and at most six reducing equivalents can be generated from a C3 glycolysis intermediate (e.g., dihydroxyacetone phosphate, glyceraldehyde-3-phosphate).

In some embodiments, the at least one exogenous nucleic acid included in the non-naturally occurring microbial organism of the invention is a heterologous nucleic acid. Accordingly, in some embodiments, the at least one exogenous nucleic acid encoding a formaldehyde fixation pathway enzyme described herein is a heterologous nucleic acid. In some embodiments, the at least one exogenous nucleic acid encoding a formate assimilation pathway enzyme described herein is a heterologous nucleic acid. In some embodiments, the at least one exogenous nucleic acid encoding a methanol metabolic pathway enzyme described herein is a heterologous nucleic acid. In some embodiments, the at least one exogenous nucleic acid encoding a methanol oxidation pathway enzyme described herein is a heterologous nucleic acid. In some embodiments, the at least one exogenous nucleic acid encoding a hydrogenase or a carbon monoxide dehydrogenase is a heterologous nucleic acid.

In some embodiments, the non-naturally occurring microbial organism of the invention is in a substantially anaerobic culture medium.

In some embodiments, a non-naturally occurring microbial organism described herein further includes a pathway capable of producing succinyl-CoA, malonyl-CoA, and/or acetoacetyl-CoA, wherein the pathway converts acetyl-CoA to succinyl-CoA, malonyl-CoA, and/or acetoacetyl-CoA by one or more enzymes. Accordingly, in some embodiments the micoribal organism includes a succinyl-CoA pathway, wherein the pathway converts acetyl-CoA to the succinyl-CoA by one or more enzymes. In some embodiments, the microbial organism includes a malonyl-CoA pathway, wherein the pathway converts acetyl-CoA to malonyl-CoA by one or more enzymes. In some embodiments, the microbial organism includes an acetoacetyl-CoA pathway, wherein the pathway converts acetyl-CoA to acetoacetyl-CoA by one or more enzymes.

In some embodiments, the invention provides that a non-naturally occurring microbial organism as described herein further includes a pathway capable of producing a bioderived compound as described herein. In some aspects, the bioderived compound is an alcohol, a glycol, an organic acid, an alkene, a diene, an organic amine, an organic aldehyde, a vitamin, a nutraceutical or a pharmaceutical.

In some embodiments, the non-naturally occurring microbial organism of the invention includes a pathway for production of an alcohol as described herein. Accordingly, in some embodiments, the alcohol is selected from: (i) a biofuel alcohol, wherein said biofuel is a primary alcohol, a secondary alcohol, a diol or triol comprising C3 to C10 carbon atoms; (ii) n-propanol or isopropanol; and (iii) a fatty alcohol, wherein said fatty alcohol comprises C4 to C27 carbon atoms, C8 to C18 carbon atoms, C12 to C18 carbon atoms, or C12 to C14 carbon atoms. In some aspects, the biofuel alcohol is selected from 1-propanol, isopropanol, 1-butanol, isobutanol, 1-pentanol, isopentenol, 2-methyl-1-butanol, 3-methyl-1-butanol, 1-hexanol, 3-methyl-1-pentanol, 1-heptanol, 4-methyl-1-hexanol, and 5-methyl-1-hexanol.

In some embodiments, the non-naturally occurring microbial organism of the invention includes a pathway for production of an diol. Accordingly, in some embodiments, the diol is a propanediol or a butanediol. In some aspects, the butanediol is 1,4 butanediol, 1,3-butanediol or 2,3-butanediol.

In some embodiments, the non-naturally occurring microbial organism of the invention includes a pathway for production of a bioderived compound selected from: (i) 1,4-butanediol or an intermediate thereto, wherein said intermediate is optionally 4-hydroxybutanoic acid (4-1-1B); butadiene (1,3-butadiene) or an intermediate thereto, wherein said intermediate is optionally 1,4-butanediol, 1,3-butanediol, 2,3-butanediol, crotyl alcohol, 3-buten-2-ol (methyl vinyl carbinol) or 3-buten-1-ol; 1,3-butanediol or an intermediate thereto, wherein said intermediate is optionally 3-hydroxybutyrate (3-HB), 2,4-pentadienoate, crotyl alcohol or 3-buten-1-ol; (iv) adipate, 6-aminocaproic acid, caprolactam, hexamethylenediamine, levulinic acid or an intermediate thereto, wherein said intermediate is optionally adipyl-CoA or 4-aminobutyryl-CoA; (v) methacrylic acid or an ester thereof, 3-hydroxyisobutyrate, 2-hydroxyisobutyrate, or an intermediate thereto, wherein said ester is optionally methyl methacrylate or poly(methyl methacrylate); (vi) 1,2-propanediol (propylene glycol), 1,3-propanediol, glycerol, ethylene glycol, diethylene glycol, triethylene glycol, dipropylene glycol, tripropylene glycol, neopentyl glycol, bisphenol A or an intermediate thereto; (vii) succinic acid or an intermediate thereto; and (viii) a fatty alcohol, a fatty aldehyde or a fatty acid comprising C4 to C27 carbon atoms, C8 to C18 carbon atoms, C12 to C18 carbon atoms, or C12 to C14 carbon atoms, wherein said fatty alcohol is optionally dodecanol (C12; lauryl alcohol), tridecyl alcohol (C13; 1-tridecanol, tridecanol, isotridecanol), myristyl alcohol (C14; 1-tetradecanol), pentadecyl alcohol (C15; 1-pentadecanol, pentadecanol), cetyl alcohol (C16; 1-hexadecanol), heptadecyl alcohol (C17; 1-n-heptadecanol, heptadecanol) and stearyl alcohol (C18; 1-octadecanol) or palmitoleyl alcohol (C16 unsaturated; cis-9-hexadecen-1-ol). Accordingly, in some embodiments, the non-naturally occurring microbial organism of the invention includes a pathway for production of 1,4-butanediol or an intermediate thereto, wherein said intermediate is optionally 4-hydroxybutanoic acid (4-HB). In some embodiments, the non-naturally occurring microbial organism of the invention includes a pathway for production of butadiene (1,3-butadiene) or an intermediate thereto, wherein said intermediate is optionally 1,4-butanediol, 1,3-butanediol, 2,3-butanediol, crotyl alcohol, 3-buten-2-ol (methyl vinyl carbinol) or 3-buten-1-ol. In some embodiments, the non-naturally occurring microbial organism of the invention includes a pathway for production of 1,3-butanediol or an intermediate thereto, wherein said intermediate is optionally 3-hydroxybutyrate (3-1-1B), 2,4-pentadienoate, crotyl alcohol or 3-buten-1-ol. In some embodiments, the non-naturally occurring microbial organism of the invention includes a pathway for production of adipate, 6-aminocaproic acid, caprolactam, hexamethylenediamine, levulinic acid or an intermediate thereto, wherein said intermediate is optionally adipyl-CoA or 4-aminobutyryl-CoA. In some embodiments, the non-naturally occurring microbial organism of the invention includes a pathway for production of methacrylic acid or an ester thereof, 3-hydroxyisobutyrate, 2-hydroxyisobutyrate, or an intermediate thereto, wherein said ester is optionally methyl methacrylate or poly(methyl methacrylate). In some embodiments, the non-naturally occurring microbial organism of the invention includes a pathway for production of 1,2-propanediol (propylene glycol), 1,3-propanediol, glycerol, ethylene glycol, diethylene glycol, triethylene glycol, dipropylene glycol, tripropylene glycol, neopentyl glycol, bisphenol A or an intermediate thereto. In some embodiments, the non-naturally occurring microbial organism of the invention includes a pathway for production of succinic acid or an intermediate thereto. In some embodiments, the non-naturally occurring microbial organism of the invention includes a pathway for production of a fatty alcohol, a fatty aldehyde or a fatty acid comprising C4 to C27 carbon atoms, C8 to C18 carbon atoms, C12 to C18 carbon atoms, or C12 to C14 carbon atoms, wherein said fatty alcohol is optionally dodecanol (C12; lauryl alcohol), tridecyl alcohol (C13; 1-tridecanol, tridecanol, isotridecanol), myristyl alcohol (C14; 1-tetradecanol), pentadecyl alcohol (C15; 1-pentadecanol, pentadecanol), cetyl alcohol (C16; 1-hexadecanol), heptadecyl alcohol (C17; 1-n-heptadecanol, heptadecanol) and stearyl alcohol (C18; 1-octadecanol) or palmitoleyl alcohol (C16 unsaturated; cis-9-hexadecen-1-ol).

Figure 5:
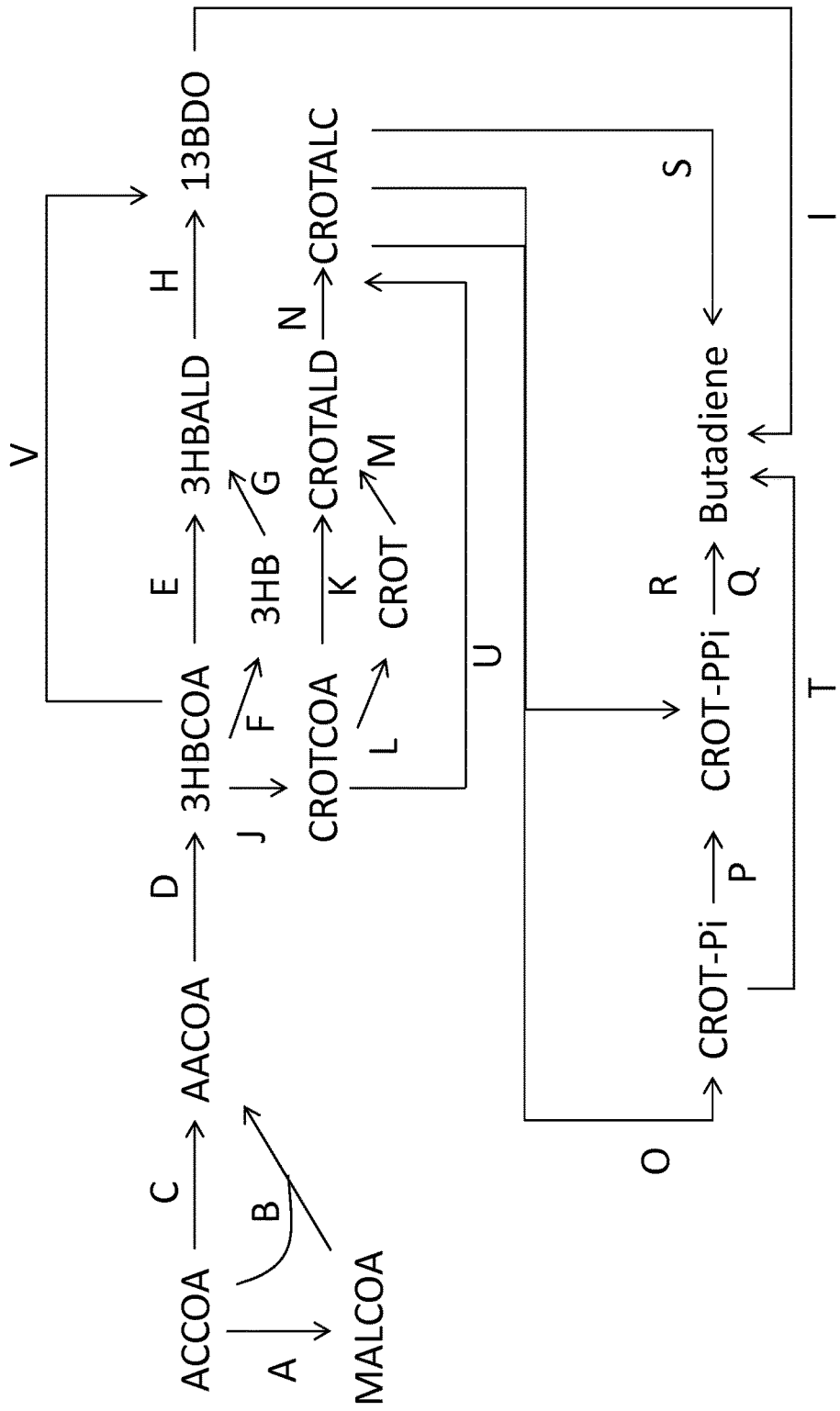
FIG. 5 shows exemplary pathways enabling production of 1,3-butanediol, crotyl alcohol, and butadiene from acetyl-CoA. 1,3-butanediol, crotyl alcohol, and butadiene production is carried out by the following enzymes: A) acetyl-CoA carboxylase, B) an acetoacetyl-CoA synthase, C) an acetyl-CoA:acetyl-CoA acyltransferase, D) an acetoacetyl-CoA reductase (ketone reducing), E) a 3-hydroxybutyryl-CoA reductase (aldehyde forming), F) a 3-hydroxybutyryl-CoA hydrolase, transferase or synthetase, G) a 3-hydroxybutyrate reductase, H) a 3-hydroxybutyraldehyde reductase, I) chemical dehydration or FIG. 6, J) a 3-hydroxybutyryl-CoA dehydratase, K) a crotonyl-CoA reductase (aldehyde forming), L) a crotonyl-CoA hydrolase, transferase or synthetase, M) a crotonate reductase, N) a crotonaldehyde reductase, O) a crotyl alcohol kinase, P) a 2-butenyl-4-phosphate kinase, Q) a butadiene synthase, R) a crotyl alcohol diphosphokinase, S) chemical dehydration or a crotyl alcohol dehydratase, T) a butadiene synthase (monophosphate), T) a butadiene synthase (monophosphate), U) a crotonyl-CoA reductase (alcohol forming), and V) a 3-hydroxybutyryl-CoA reductase (alcohol forming). See abbreviation list below for compound names.

In some embodiments, a non-naturally occurring microbial organism of the invention further comprises a 1,3-butanediol pathway and an exogenous nucleic acid encoding a 1,3-butanediol pathway enzyme expressed in a sufficient amount to produce 1,3-butanediol as depicted in FIG. 5. Accordingly, in some embodiments, the 1,3-butanediol pathway comprises a pathway selected from: (1) 5A, 5B, 5D, 5E, and 5H; (2) 5A, 5B, 5D, 5F, 5G, and 5H; (3) 5C, 5D, 5E, and 5H; (4) 5C, 5D, 5F, 5G, and 5H; (5) 5A, 5B, 5D and 5V; and (6) 5C, 5D and 5V wherein 5A is an acetyl-CoA carboxylase, wherein 5B is an acetoacetyl-CoA synthase, wherein 5C is an acetyl-CoA:acetyl-CoA acyltransferase, wherein 5D is an acetoacetyl-CoA reductase (ketone reducing), wherein 5E is a 3-hydroxybutyryl-CoA reductase (aldehyde forming), wherein 5F is a 3-hydroxybutyryl-CoA hydrolase, transferase or synthetase, wherein 5G is a 3-hydroxybutyrate reductase, wherein 5H is a 3-hydroxybutyraldehyde reductase, wherein 5V is a 3-hydroxybutyryl-CoA reductase (alcohol forming).

In some embodiments, a non-naturally occurring microbial organism of the invention further comprises a crotyl alcohol pathway and an exogenous nucleic acid encoding a crotyl alcohol pathway enzyme expressed in a sufficient amount to produce crotyl alcohol as depicted in FIG. 5. Accordingly, in some embodiments, the crotyl alcohol pathway comprises a pathway selected from: (1) 5A, 5B, 5D, 5J, 5K, and 5N; (2) 5A, 5B, 5D, 5J, 5L, 5M, and 5N; (3) 5C, 5D, 5J, 5K, and 5N; (4) 5C, 5D, 5J, 5L, 5M, and 5N; (5) 5A, 5B, 5D, 5J and 5U; and (6) 5C, 5D, 5J and 5U, wherein 5A is an acetyl-CoA carboxylase, wherein 5B is an acetoacetyl-CoA synthase, wherein 5C is an acetyl-CoA:acetyl-CoA acyltransferase, wherein 5D is an acetoacetyl-CoA reductase (ketone reducing), wherein 5J is a 3-hydroxybutyryl-CoA dehydratase, wherein 5K is a crotonyl-CoA reductase (aldehyde forming), wherein 5L is a crotonyl-CoA hydrolase, crotonyl-CoA transferase or crotonyl-CoA synthetase, wherein 5M is a crotonate reductase, wherein 5N is a crotonaldehyde reductase, wherein 5U is a crotonyl-CoA reductase (alcohol forming).

Figure 6:
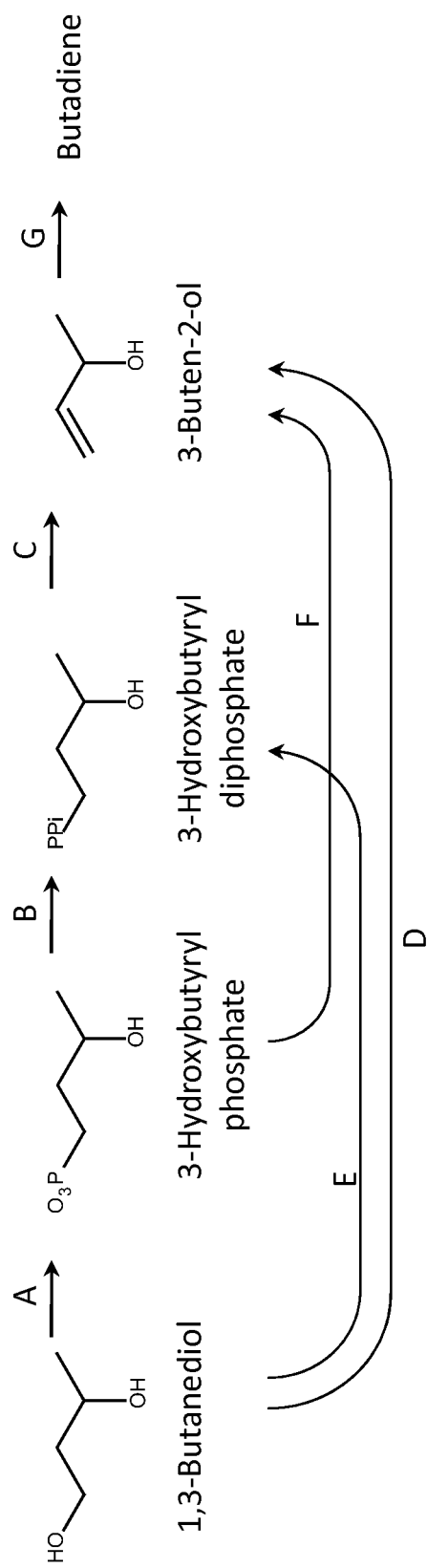
FIG. 6 shows exemplary pathways for converting 1,3-butanediol to 3-buten-2-ol and/or butadiene. 3-Buten-2-ol and butadiene production is carried out by the following enzymes: A. 1,3-butanediol kinase, B. 3-hydroxybutyrylphosphate kinase, C. 3-hydroxybutyryldiphosphate lyase, D. 1,3-butanediol diphosphokinase, E. 1,3-butanediol dehydratase, F. 3-hydroxybutyrylphosphate lyase, G. 3-buten-2-ol dehydratase or chemical dehydration.

In some embodiments, a non-naturally occurring microbial organism of the invention further comprises a butadiene pathway and an exogenous nucleic acid encoding a butadiene pathway enzyme expressed in a sufficient amount to produce butadiene as depicted in FIGS. 5 and 6. Accordingly, in some embodiments, the butadiene pathway comprises a pathway selected from: (1) 5A, 5B, 5D, 5E, 5H, 6A, 6B, 6C, and 6G; (2) 5A, 5B, 5D, 5F, 5G, 5H, 6A, 6B, 6C, and 6G; (3) 5C, 5D, 5E, 5H, 6A, 6B, 6C, and 6G; (4) 5C, 5D, 5F, 5G, 5H, 6A, 6B, 6C, and 6G; (5) 5A, 5B, 5D, 5E, 5H, 6A, 6F, and 6G; (6) 5A, 5B, 5D, 5F, 5G, 5H, 6A, 6F, and 6G; (7) 5C, 5D, 5E, 5H, 6A, 6F, and 6G; (8) 5C, 5D, 5F, 5G, 5H, 6A, 6F, and 6G; (9) 5A, 5B, 5D, 5E, 5H, 6E, 6C, and 6G; (10) 5A, 5B, 5D, 5F, 5G, 5H, 6E, 6C, and 6G; (11) 5C, 5D, 5E, 5H, 6E, 6C, and 6G; (12) 5C, 5D, 5F, 5G, 5H, 6E, 6C, and 6G; (13) 5A, 5B, 5D, 5E, 5H, 6D, and 6G; (14) 5A, 5B, 5D, 5F, 5G, 5H, 6D, and 6G; (15) 5C, 5D, 5E, 5H, 6D, and 6G; (16) 5C, 5D, 5F, 5G, 5H, 6D, and 6G; (17) 5A, 5B, 5D, 5J, 5K, 5N, and 5S; (18) 5A, 5B, 5D, 5J, 5L, 5M, 5N, and 5S; (19) 5C, 5D, 5J, 5K, 5N, and 5S; (20) 5C, 5D, 5J, 5L, 5M, 518I, and 5S; (21) 5A, 5B, 5D, 5J, 5K, 5N, 5R, and 5Q; (22) 5A, 5B, 5D, 5J, 5L, 5M, 5N, 5R, and 5Q; (23) 5C, 5D, 5J, 5K, 518I, 5R, and 5Q; (24) 5C, 5D, 5J, 5L, 5M, 518I, 5R, and 5Q; (25) 5A, 5B, 5D, 5J, 5K, 5N, 5O, 5P, and 5Q; (26) 5A, 5B, 5D, 5J, 5L, 5M, 5N, 5O, 5P, and 5Q; (27) 5C, 5D, 5J, 5K, 5N, 5O, 5P, and 5Q; (28) 5C, 5D, 5J, 5L, 5M, 5N, 5O, 5P, and 5Q; (29) 5A, 5B, 5D, 5J, 5K, 5N, 5O, and 5T; (30) 5A, 5B, 5D, 5J, 5L, 5M, 5N, 5O, and 5T; (31) 5C, 5D, 5J, 5K, 5N, 5O, and 5T; (32) 5C, 5D, 5J, 5L, 5M, 5N, 5O, and 5T, (33) 5A, 5B, 5D, 5V, 6A, 6B, 6C, and 6G; (34) 5C, 5D, 5V, 6A, 6B, 6C, and 6G; (35) 5A, 5B, 5D, 5J, 5U, and 5S; (36) 5C, 5D, 5J, 5U, and 5S; (37) 5A, 5B, 5D, 5J, 5U, 5R, and 5Q; (38) 5C, 5D, 5J, 5U, 5R, and 5Q; (39) 5A, 5B, 5D, 5J, 5U, 5O, 5P, and 5Q; (40) 5C, 5D, 5J, 5U, 5O, 5P, and 5Q; (41) 5A, 5B, 5D, 5J, 5U, 5O, and 5T; and (42) 5C, 5D, 5J, 5U, 5O, and 5T, wherein 5A is an acetyl-CoA carboxylase, wherein 5B is an acetoacetyl-CoA synthase, wherein 5C is an acetyl-CoA:acetyl-CoA acyltransferase, wherein 5D is an acetoacetyl-CoA reductase (ketone reducing), wherein 5E is a 3-hydroxybutyryl-CoA reductase (aldehyde forming), wherein 5F is a 3-hydroxybutyryl-CoA hydrolase, 3-hydroxybutyryl-CoA transferase or 3-hydroxybutyryl-CoA synthetase, wherein 5G is a 3-hydroxybutyrate reductase, wherein 5H is a 3-hydroxybutyraldehyde reductase, wherein 5J is a 3-hydroxybutyryl-CoA dehydratase, wherein 5K is a crotonyl-CoA reductase (aldehyde forming), wherein 5L is a crotonyl-CoA hydrolase, crotonyl-CoA transferase or crotonyl-CoA synthetase, wherein 5M is a crotonate reductase, wherein 518I is a crotonaldehyde reductase, wherein 5O is a crotyl alcohol kinase, wherein 5P is a 2-butenyl-4-phosphate kinase, wherein 5Q is a butadiene synthase, wherein 5R is a crotyl alcohol diphosphokinase, wherein 5S is chemical dehydration or a crotyl alcohol dehydratase, wherein 5T is a butadiene synthase (monophosphate), wherein 5T is a butadiene synthase (monophosphate), wherein 5U is a crotonyl-CoA reductase (alcohol forming), wherein 5V is a 3-hydroxybutyryl-CoA reductase (alcohol forming), wherein 6A is a 1,3-butanediol kinase, wherein 6B is a 3-hydroxybutyrylphosphate kinase, wherein 6C is a 3-hydroxybutyryldiphosphate lyase, wherein 6D is a 1,3-butanediol diphosphokinase, wherein 6E is a 1,3-butanediol dehydratase, wherein 6F is a 3-hydroxybutyrylphosphate lyase, wherein 6G is a 3-buten-2-ol dehydratase or chemical dehydration.

In some embodiments, a non-naturally occurring microbial organism of the invention further comprises a 3-buten-2-ol pathway and an exogenous nucleic acid encoding a 3-buten-2-ol pathway enzyme expressed in a sufficient amount to produce 3-buten-2-ol as depicted in FIGS. 5 and 6. Accordingly, in some embodiments, the 3-buten-2-ol pathway comprises a pathway selected from: (1) 5A, 5B, 5D, 5E, 5H, 6A, 6B, and 6C; (2) 5A, 5B, 5D, 5F, 5G, 5H, 6A, 6B, and 6C; (3) 5C, 5D, 5E, 5H, 6A, 6B, and 6C; (4) 5C, 5D, 5F, 5G, 5H, 6A, 6B, and 6C; (5) 5A, 5B, 5D, 5E, 5H, 6A, and 6F; (6) 5A, 5B, 5D, 5F, 5G, 5H, 6A, and 6F; (7) 5C, 5D, 5E, 5H, 6A, and 6F; (8) 5C, 5D, 5F, 5G, 5H, 6A, and 6F; (9) 5A, 5B, 5D, 5E, 5H, 6E, and 6C; (10) 5A, 5B, 5D, 5F, 5G, 5H, 6E, and 6C; (11) 5C, 5D, 5E, 5H, 6E, and 6C; (12) 5C, 5D, 5F, 5G, 5H, 6E, and 6C; (13) 5A, 5B, 5D, 5E, 5H, and 6D; (14) 5A, 5B, 5D, 5F, 5G, 5H, and 6D; (15) 5C, 5D, 5E, 5H, and 6D; (16) 5C, 5D, 5F, 5G, 5H, and 6D; (17) 5A, 5B, 5D, 5V, 6A, 6B, and 6C; (18) 5C, 5D, 5V, 6A, 6B, and 6C; (19) 5A, 5B, 5D, 5V, 6A, and 6F; (20) 5C, 5D, 5V, 6A, and 6F; (21) 5A, 5B, 5D, 5V, 6E, and 6C; (22) 5C, 5D, 5V, 6E, and 6C; (23) 5A, 5B, 5D, 5V and 6D; and (24) 5C, 5D, 5V and 6D, wherein 5A is an acetyl-CoA carboxylase, wherein 5B is an acetoacetyl-CoA synthase, wherein 5C is an acetyl-CoA:acetyl-CoA acyltransferase, wherein 5D is an acetoacetyl-CoA reductase (ketone reducing), wherein 5E is a 3-hydroxybutyryl-CoA reductase (aldehyde forming), wherein 5F is a 3-hydroxybutyryl-CoA hydrolase, 3-hydroxybutyryl-CoA transferase or 3-hydroxybutyryl-CoA synthetase, wherein 5G is a 3-hydroxybutyrate reductase, wherein 5H is a 3-hydroxybutyraldehyde reductase, wherein 5V is a 3-hydroxybutyryl-CoA reductase (alcohol forming), wherein 6A is a 1,3-butanediol kinase, wherein 6B is a 3-hydroxybutyrylphosphate kinase, wherein 6C is a 3-hydroxybutyryldiphosphate lyase, wherein 6D is a 1,3-butanediol diphosphokinase, wherein 6E is a 1,3-butanediol dehydratase, wherein 6F is a 3-hydroxybutyrylphosphate lyase.

Figure 7:
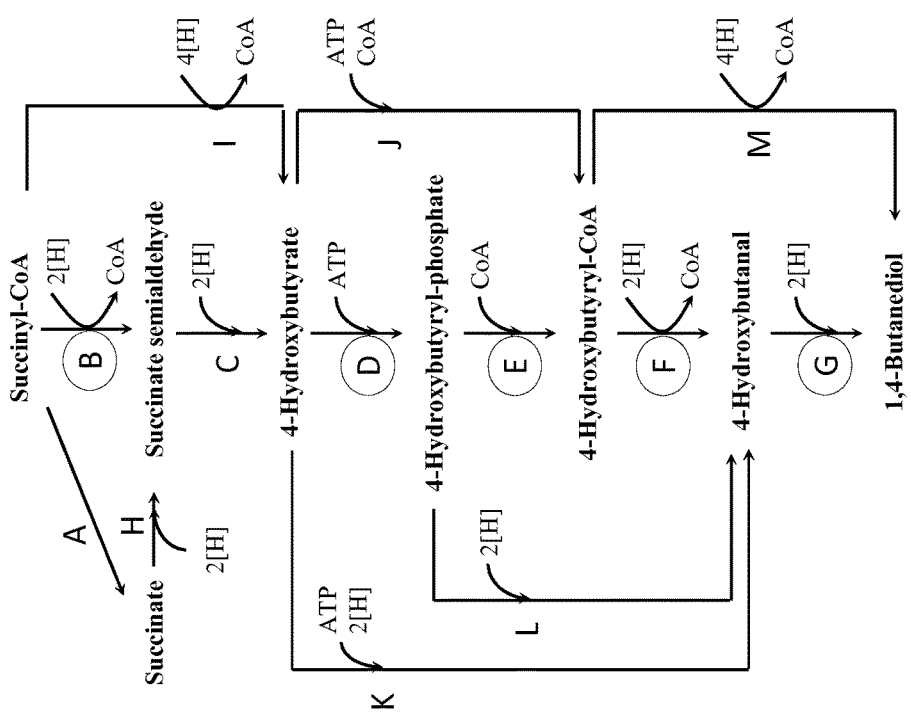
FIG. 7 shows exemplary pathways enabling production of 1,4-butanediol from succinyl-CoA. 1,4-Butanediol production is carried out by the following enzymes: A) a succinyl-CoA transferase or a succinyl-CoA synthetase, B) a succinyl-CoA reductase (aldehyde forming), C) a 4-HB dehydrogenase, D) a 4-HB kinase, E) a phosphotrans-4-hydroxybutyrylase, F) a 4-hydroxybutyryl-CoA reductase (aldehyde forming), G) a 1,4-butanediol dehydrogenase, H) a succinate reductase, I) a succinyl-CoA reductase (alcohol forming), J) a 4-hydroxybutyryl-CoA transferase or 4-hydroxybutyryl-CoA synthetase, K) a 4-HB reductase, L) a 4-hydroxybutyryl-phosphate reductase, and M) a 4-hydroxybutyryl-CoA reductase (alcohol forming).

In some embodiments, a non-naturally occurring microbial organism of the invention further comprises a 1,4-butanediol pathway and an exogenous nucleic acid encoding a 1,4-butanediol pathway enzyme expressed in a sufficient amount to produce 1,4-butanediol as depicted in FIG. 7. Accordingly, in some embodiments, the 1,4-butanediol pathway comprises a pathway selected from: (1) 7B, 7C, 7D, 7E, 7F, and 7G; (2) 7A, 7H, 7C, 7D, 7E, 7F, and 7G; (3) 7I, 7D, 7E, 7F, and 7G; (4) 7B, 7C, 7K, and 7G; (5) 7A, 7H, 7C, 7K, and 7G; (6) 7I, 7K, and 7G; (7) 7B, 7C, 7D, 7L, and 7G; (8) 7A, 7H, 7C, 7D, 7L, and 7G; (9) 7I, 7D, 7L, and 7G; (10) 7B, 7C, 7J, 7F, and 7G; (11) 7A, 7H, 7C, 7J, 7F, and 7G; (12) 7I, 7J, 7F, and 7G; (13) 7B, 7C, 7D, 7E, and 7M; (14) 7A, 7H, 7C, 7D, 7E, and 7M; and (15) 7I, 7D, 7E, and 7M, wherein 7A is a succinyl-CoA transferase or a succinyl-CoA synthetase, wherein 7B is a succinyl-CoA reductase (aldehyde forming), wherein 7C is a 4-HB dehydrogenase, wherein 7D is a 4-HB kinase, wherein 7E is a phosphotrans-4-hydroxybutyrylase, wherein 7F is a 4-hydroxybutyryl-CoA reductase (aldehyde forming), wherein 7G is a 1,4-butanediol dehydrogenase, wherein 7H is a succinate reductase, wherein 7I is a succinyl-CoA reductase (alcohol forming), wherein 7J is a 4-hydroxybutyryl-CoA transferase or 4-hydroxybutyryl-CoA synthetase, wherein 7K is a 4-HB reductase, wherein 7L is a 4-hydroxybutyryl-phosphate reductase, wherein 7M is a 4-hydroxybutyryl-CoA reductase (alcohol forming).

Figure 8:
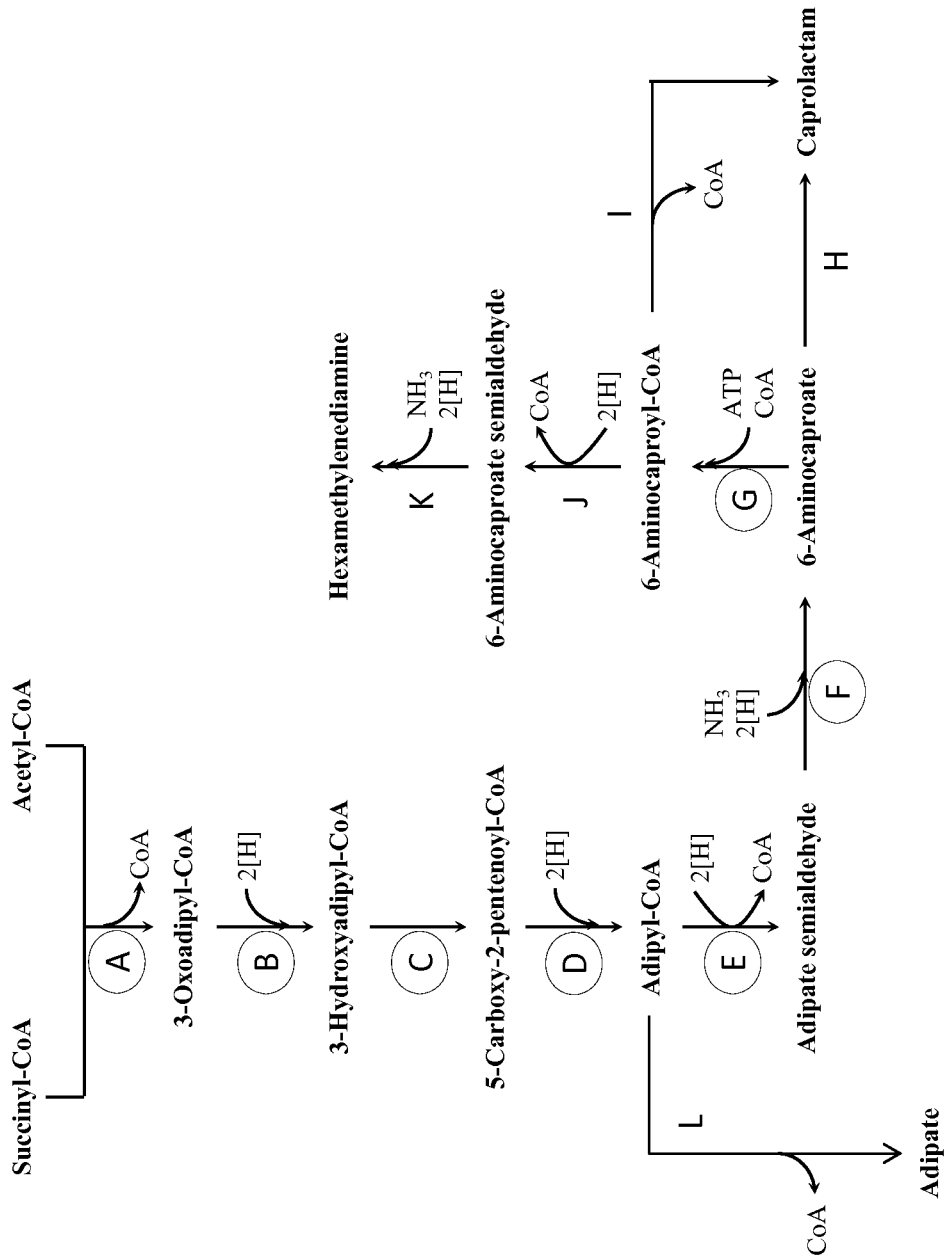
FIG. 8 shows exemplary pathways enabling production of adipate, 6-aminocaproic acid, caprolactam, and hexamethylenediamine from succinyl-CoA and acetyl-CoA. Adipate, 6-aminocaproic acid, caprolactam, and hexamethylenediamine production is carried out by the following enzymes: A) 3-oxoadipyl-CoA thiolase, B) 3-oxoadipyl-CoA reductase, C) 3-hydroxyadipyl-CoA dehydratase, D) 5-carboxy-2-pentenoyl-CoA reductase, E) adipyl-CoA reductase (aldehyde forming), F) 6-aminocaproate transaminase or 6-aminocaproate dehydrogenase, G) 6-aminocaproyl-CoA/acyl-CoA transferase or 6-aminocaproyl-CoA synthase, H) amidohydrolase, I) spontaneous cyclization, J) 6-aminocaproyl-CoA reductase (aldehyde forming), K) HMDA transaminase or HMDA dehydrogenase, L) Adipyl-CoA hydrolase, adipyl-CoA ligase, adipyl-CoA transferase, or phosphotransadipylase/adipate kinase.

In some embodiments, a non-naturally occurring microbial organism of the invention further comprises an adipate pathway and an exogenous nucleic acid encoding an adipate pathway enzyme expressed in a sufficient amount to produce adipate as depicted in FIG. 8. Accordingly, in some embodiments, the adipate pathway comprises 8A, 8B, 8C, 8D and 8L, wherein 8A is a 3-oxoadipyl-CoA thiolase, wherein 8B is a 3-oxoadipyl-CoA reductase, wherein 8C is a 3-hydroxyadipyl-CoA dehydratase, wherein 8D is a 5-carboxy-2-pentenoyl-CoA reductase, wherein 8L is an adipyl-CoA hydrolase, adipyl-CoA ligase, adipyl-CoA transferase, or phosphotransadipylase/adipate kinase.

In some embodiments, a non-naturally occurring microbial organism of the invention further comprises a 6-aminocaproate pathway and an exogenous nucleic acid encoding a 6-aminocaproate pathway enzyme expressed in a sufficient amount to produce 6-aminocaproate as depicted in FIG. 8. Accordingly, in some embodiments, the 6-aminocaproate pathway comprises 8A, 8B, 8C, 8D, 8E, and 8F, wherein 8A is a 3-oxoadipyl-CoA thiolase, wherein 8B is a 3-oxoadipyl-CoA reductase, wherein 8C is a 3-hydroxyadipyl-CoA dehydratase, wherein 8D is a 5-carboxy-2-pentenoyl-CoA reductase, wherein 8E is an adipyl-CoA reductase (aldehyde forming), wherein 8F is a 6-aminocaproate transaminase or 6-aminocaproate dehydrogenase.

In some embodiments, a non-naturally occurring microbial organism of the invention further includes a caprolactam pathway and an exogenous nucleic acid encoding a caprolactam pathway enzyme expressed in a sufficient amount to produce caprolactam as depicted in FIG. 8. Accordingly, in some embodiments, the caprolactam pathway comprises: (1) 8A, 8B, 8C, 8D, 8E, 8F, and 8H; or (2) 8A, 8B, 8C, 8D, 8E, 8F, 8G, and 8I, wherein 8A is a 3-oxoadipyl-CoA thiolase, wherein 8B is a 3-oxoadipyl-CoA reductase, wherein 8C is a 3-hydroxyadipyl-CoA dehydratase, wherein 8D is a 5-carboxy-2-pentenoyl-CoA reductase, wherein 8E is an adipyl-CoA reductase (aldehyde forming), wherein 8F is a 6-aminocaproate transaminase or 6-aminocaproate dehydrogenase, wherein 8G is a 6-aminocaproyl-CoA/acyl-CoA transferase or 6-aminocaproyl-CoA synthase, wherein 8H is an amidohydrolase, wherein 8I is spontaneous cyclization.

In some embodiments, a non-naturally occurring microbial organism of the invention further comprises a hexamethylenediamine pathway and an exogenous nucleic acid encoding a hexamethylenediamine pathway enzyme expressed in a sufficient amount to produce hexamethylenediamine as depicted in FIG. 8. Accordingly, in some embodiments, the hexamethylenediamine pathway comprises 8A, 8B, 8C, 8D, 8E, 8F, 8G, 8J, 8K, wherein 8A is a 3-oxoadipyl-CoA thiolase, wherein 8B is a 3-oxoadipyl-CoA reductase, wherein 8C is a 3-hydroxyadipyl-CoA dehydratase, wherein 8D is a 5-carboxy-2-pentenoyl-CoA reductase, wherein 8E is an adipyl-CoA reductase (aldehyde forming), wherein 8F is a 6-aminocaproate transaminase or 6-aminocaproate dehydrogenase, wherein 8G is a 6-aminocaproyl-CoA/acyl-CoA transferase or 6-aminocaproyl-CoA synthase, wherein 8J is a 6-aminocaproyl-CoA reductase (aldehyde forming), wherein 8K is a hexamethylenediamine transaminase or hexamethylenediamine dehydrogenase.

Figure 9:
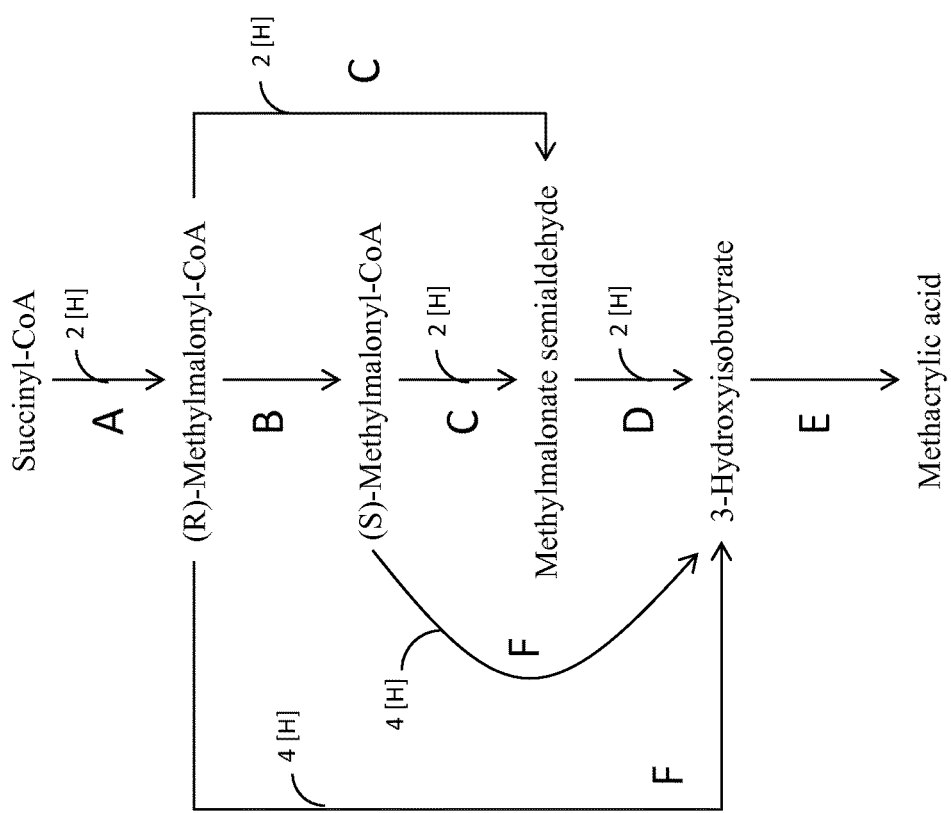
FIG. 9 shows exemplary pathways enabling production of 3-hydroxyisobutyrate and methacrylic acid from succinyl-CoA. 3-Hydroxyisobutyrate and methacrylic acid production are carried out by the following enzymes: A) Methylmalonyl-CoA mutase, B) Methylmalonyl-CoA epimerase, C) Methylmalonyl-CoA reductase (aldehyde forming), D) Methylmalonate semialdehyde reductase, E) 3-hydroxyisobutyrate dehydratase, F) Methylmalonyl-CoA reductase (alcohol forming).
Figure 10:
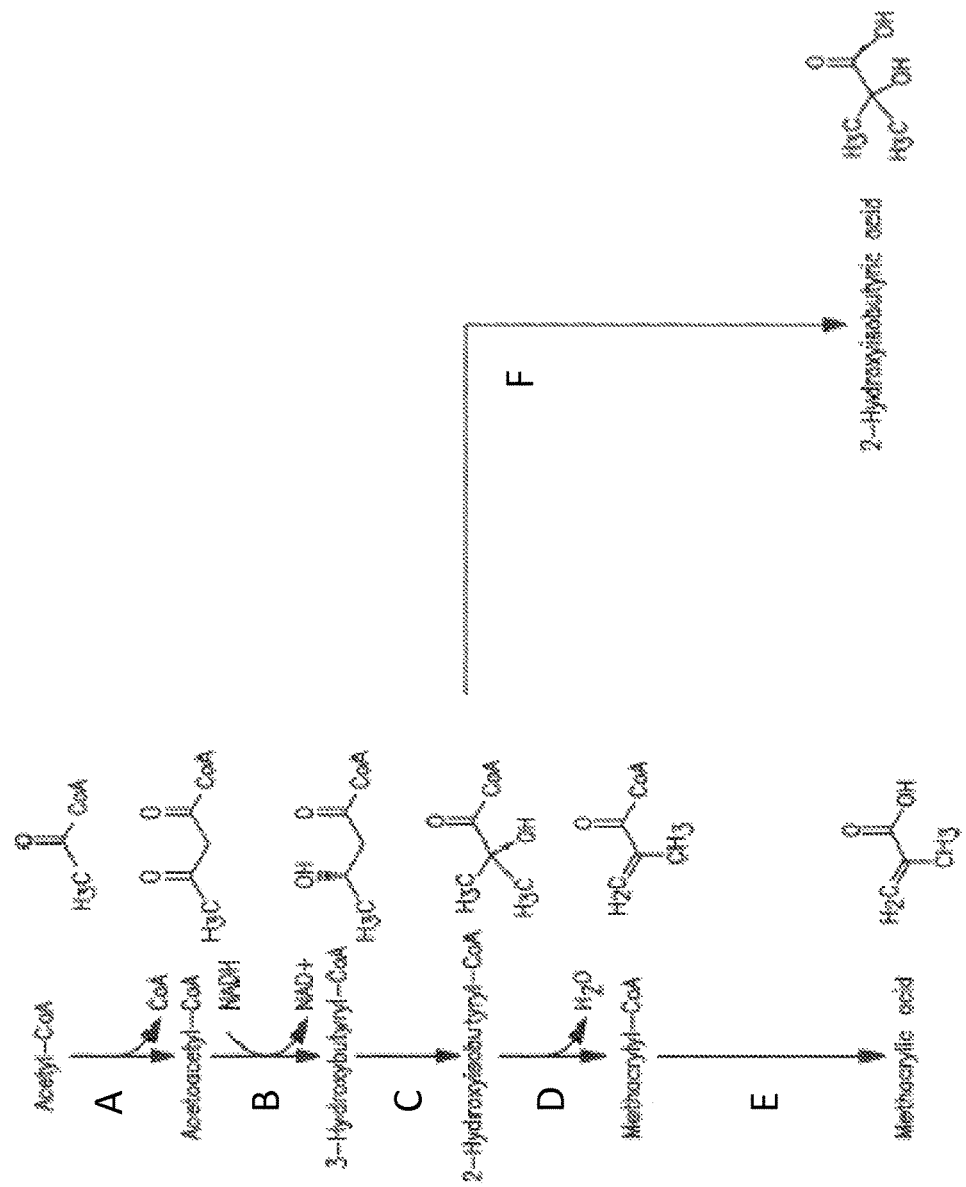
FIG. 10 shows exemplary pathways enabling production of 2-hydroxyisobutyrate and methacrylic acid from acetyl-CoA. 2-Hydroxyisobutyrate and methacrylic acid production are carried out by the following enzymes: A) acetyl-CoA:acetyl-CoA acyltransferase, B) acetoacetyl-CoA reductase (ketone reducing), C) 3-hydroxybutyryl-CoA mutase, D) 2-hydroxyisobutyryl-CoA dehydratase, E) methacrylyl-CoA synthetase, hydrolase, or transferase, F) 2-hydroxyisobutyryl-CoA synthetase, hydrolase, or transferase.

In some embodiments, a non-naturally occurring microbial organism of the invention further comprises a methacrylic acid pathway and an exogenous nucleic acid encoding a methacrylic acid pathway enzyme expressed in a sufficient amount to produce methacrylic acid as depicted in FIGS. 9 and 10. Accordingly, in some embodiments, the methacrylic acid pathway comprises a pathway selected from: (1) 9A, 9B, 9C, 9D, and 9E; (2) 9A, 9F, and 9E; (3) 9A, 9B, 9F, and 9E; (4) 9A, 9C, 9D, and 9E; and (5) 10A, 10B, 10C, 10D, and 10E, wherein 9A is a methylmalonyl-CoA mutase, wherein 9B is a methylmalonyl-CoA epimerase, wherein 9C is a methylmalonyl-CoA reductase (aldehyde forming), wherein 9D is a methylmalonate semialdehyde reductase, wherein 9E is a 3-hydroxyisobutyrate dehydratase, wherein 9F is a methylmalonyl-CoA reductase (alcohol forming), wherein 10A is an acetyl-CoA:acetyl-CoA acyltransferase, wherein 10B is an acetoacetyl-CoA reductase (ketone reducing), wherein 10C is a 3-hydroxybutyrl-CoA mutase, wherein 10D is a 2-hydroxyisobutyryl-CoA dehydratase, wherein 10E is a methacrylyl-CoA synthetase, methacrylyl-CoA hydrolase, or methacrylyl-CoA transferase.

In some embodiments, a non-naturally occurring microbial organism of the invention further comprises a 2-hydroxyisobutyric acid pathway and an exogenous nucleic acid encoding a 2-hydroxyisobutyric acid pathway enzyme expressed in a sufficient amount to produce 2-hydroxyisobutyric acid as depicted in FIG. 10. Accordingly, in some embodiments, the 2-hydroxyisobutyric acid pathway comprises 10A, 10B, 10C, and 10F, wherein 10A is an acetyl-CoA:acetyl-CoA acyltransferase, wherein 10B is an acetoacetyl-CoA reductase (ketone reducing), wherein 10C is a 3-hydroxybutyrl-CoA mutase, wherein 10F is a 2-hydroxyisobutyryl-CoA synthetase, 2-hydroxyisobutyryl-CoA hydrolase, or 2-hydroxyisobutyryl-CoA transferase.

Figure 4:
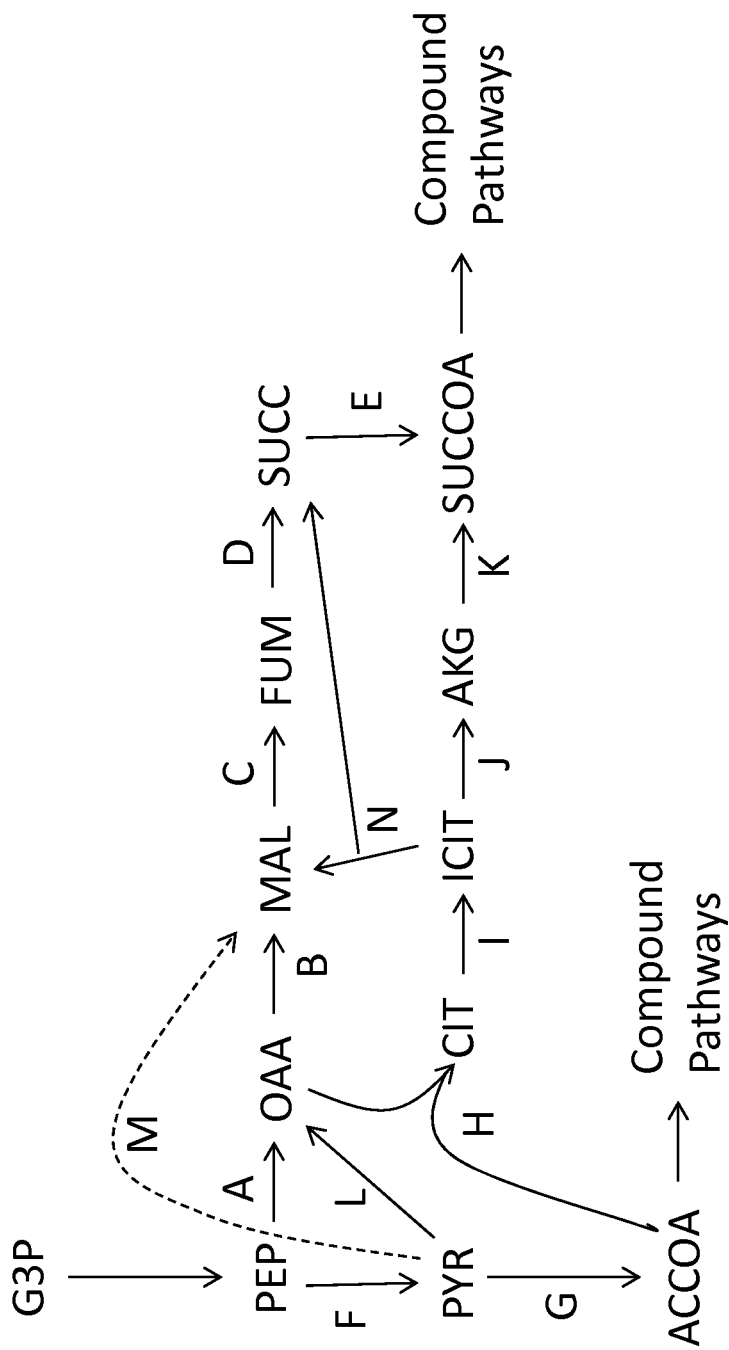
FIG. 4 shows exemplary metabolic pathways enabling the conversion of the glycolysis intermediate glyceraldehye-3-phosphate (G3P) to acetyl-CoA (ACCOA) and/or succinyl-CoA (SUCCOA). The enzymatic transformations shown are carried out by the following enzymes: A) PEP carboxylase or PEP carboxykinase, B) malate dehydrogenase, C) fumarase, D) fumarate reductase, E) succinyl-CoA synthetase or transferase, F) pyruvate kinase or PTS-dependent substrate import, G) pyruvate dehydrogenase, pyruvate formate lyase, or pyruvate:ferredoxin oxidoreductase, H) citrate synthase, I) aconitase, J) isocitrate dehydrogenase, K) alpha-ketoglutarate dehydrogenase, L) pyruvate carboxylase, M) malic enzyme, N) isocitrate lyase and malate synthase. See abbreviation list below for compound names.

In some embodiments, a non-naturally occurring microbial organism of the invention further comprises a succinyl-CoA pathway and an exogenous nucleic acid encoding a succinyl-CoA pathway enzyme expressed in a sufficient amount to produce succinyl-CoA as depicted in FIG. 4. Accordingly, in some embodiments, the succinyl-CoA pathway comprises a pathway selected from: (1) 4H, 4I, 4J, and 4K; (2) 4H, 4I, 4N, and 4E; (3) 4H, 4I, 4N, 4C, 4D, and 4E; (4) 4L, 4H, 4I, 4J, and 4K; (5) 4L, 4H, 4I, 4N, and 4E; (6) 4L, 4H, 4I, 4J, 4N, 4C, 4D, and 4E; (7) 4A, 4H, 4I, 4J, and 4K; (8) 4A, 4H, 4I, 4N, and 4E; (9) 4A, 4H, 4I, 4N, 4C, 4D, and 4E; (10) 4M, 4C, 4D, and 4E; (11) 4F, 4L, 4H, 4I, 4J, and 4K; (12) 4F, 4L, 4H, 4I, 4N, and 4E; (13) 4F, 4L, 4H, 4I, 4N, 4C, 4D, and 4E; (14) 4F, 4M, 4C, 4D, and 4E; (15) 4F, 4G, 4H, 4I, 4J, and 4K; (16) 4F, 4G, 4H, 4I, 4N, and 4E; and (17) 4F, 4G, 4H, 4I, 4N, 4C, 4D, and 4E, wherein 4A is a PEP carboxylase or PEP carboxykinase, wherein 4B is a malate dehydrogenase, wherein 4C is a fumarase, wherein 4D is a fumarate reductase, wherein 4E is a succinyl-CoA synthetase or succinyl-CoA transferase, wherein 4F is a pyruvate kinase or PTS-dependent substrate import, wherein 4G is a pyruvate dehydrogenase, pyruvate formate lyase, or pyruvate:ferredoxin oxidoreductase, wherein 4H is a citrate synthase, wherein 4I is an aconitase, wherein 4J is an isocitrate dehydrogenase, wherein 4K is an alpha-ketoglutarate dehydrogenase, wherein 4L is a pyruvate carboxylase, wherein 4M is a malic enzyme, wherein 4N is an isocitrate lyase and malate synthase.

In an additional embodiment, the invention provides a non-naturally occurring microbial organism having an acetyl-CoA or bioderived compound pathway, wherein the non-naturally occurring microbial organism comprises at least one exogenous nucleic acid encoding an enzyme or protein that converts a substrate to a product selected from the group consisting of MeOH to Fald, Fald to H6P, H6P to F6P, Fald to DHA and G3P, DHA and G3P to F6P, F6P to ACTP and E4P, ACTP to ACCOA, ACTP to acetate, acetate to ACCOA, Xu5P to ACTP and G3P, G3P to PYR, PYR to formate and ACCOA, PYR to CO2 and ACCOA, CO2 to formate, formate to Fald, formate to Formyl-CoA, Formyl-CoA to Fald, Formate to FTHF, FTHF to methenyl-THF, methenyl-THF to methylene-THF, methylene-THF to Fald, methylene-THF to glycine, glycine to serine, serine to PYR, methylene-THF to methyl-THF, methyl-THF to ACCOA, G3P to PEP, PEP to PYR, PYR to ACCOA, PEP to OAA, OAA to MAL, MAL to FUM, FUM to SUCC, SUCC to SUCCOA, ACCOA and OAA to CIT, CIT to ICIT, ICIT to AKG, AKG to SUCCOA, PYR to OAA, PYR to MAL, ICIT to MAL and SUCC, ACCOA to MALCOA, MALCOA and ACCOA to AACOA, ACCOA to AACOA, ACCOA to 3HBCOA, 3HBCOA to 3HBALD, 3HBALD to 13BDO; 13BDO to Butadiene, 3HBCOA to CROTCOA, CROTCOA to CROTALD, CROTCOA to CROT, CROT to CROTALD, CROTALD to CROTALC, CROTALD to CROT-Pi, CROT-Pi to CROT-PPi, CROT-Ppi to butadiene, CROTALD to CROT-PPi, CROT-Pi to butadiene, 1,3-butanediol to 3-hydroxybutyryl phosphate, 3-hydroxybutyryl phosphate to 3-hydroxybutyryl diphosphate; 3-hydroxybutyryl diphosphate to 3-buten-2-ol, 3-buten-2-ol to butadiene, 1,3-butandediol to 3-buten-2-ol, 1,3-butanediol to 3-hydroxybutyryl diphosphate, 3-hydroxybutyryl phosphate to 3-buten-2-ol, succinyl-CoA to succinate, succinyl-CoA to succinate semialdehyde, succinate semialdehyde to 4-hydroxybutyrate, 4-hydroxybutyrate to 4-hydroxybutyryl-phosphate, 4-hydroxybutyryl-phosphate to 4-hydroxybutyryl-CoA, 4-hydroxybutyryl-CoA to 4-hydroxybutanal, 4-hydroxybutanal to 1,4-butanediol, succinate to succinate semialdehyde, succinyl-CoA to 4-hydroxybutyrate, 4-hydroxybutyrate to 4-hydroxybutyryl-CoA, 4-hydroxybutyrate to 4-hydroxybutanal, 4-hydroxybutyryl-phosphate to 4-hydroxybutanal, 4-hydroxybutyryl-CoA to 1,4-butanediol, succinyl-CoA and acetyl-CoA to 3-oxoadipyl-CoA, 3-oxoadipyl-CoA to 3-hydroxyadiply-CoA, 3-hydroxyadiply-CoA to 5-carboxy-2-pentenoyl-CoA, 5-carboxy-2-pentenoyl-CoA to adipyl-CoA, adipyl-CoA to adipate, adipyl-CoA to adipate semialdehyde, adipate semialdehyde to 6-aminocaproate, 6-aminocaproate to caprolactam, 6-aminocaproate to 6-aminocaproyl-CoA, 6-aminocaproyl-CoA to 6-aminocaproate semialdehyde, 6-aminocaproate semialdehyde to hexamethylenediamine, succinyl-CoA to (R)-methylmalonyl-CoA, (R)-methylmalonyl-CoA to methylmalonate semialdehyde, (R)-methylmalonyl-CoA to (S)-methylmalonyl-CoA, (S)-methylmalonyl-CoA to methylmalonate semialdehyde, (R)-methylmalonyl-CoA to 3-hydroxyisobutyrate, (S)-methylmalonyl-CoA to 3-hydroxyisobutyrate, 3-hydroxyisobutyrate to methacrylic acid, 3-hydroxybutyryl-CoA to 2-hydroxyisobutyryl-CoA, 2-hydroxyisobutyryl-CoA to 2-hydroxyisobutyric acid, 2-hydroxyisobutyryl-CoA to methacrylyl-CoA, methacrylyl-CoA to methacrylic acid. One skilled in the art will understand that these are merely exemplary and that any of the substrate-product pairs disclosed herein suitable to produce a desired product and for which an appropriate activity is available for the conversion of the substrate to the product can be readily determined by one skilled in the art based on the teachings herein. Thus, the invention provides a non-naturally occurring microbial organism containing at least one exogenous nucleic acid encoding an enzyme or protein, where the enzyme or protein converts the substrates and products of an acetyl-CoA or a bioderived compound pathway, such as that shown in FIG. 1-10.

While generally described herein as a microbial organism that contains an acetyl-CoA or a bioderived compound pathway, it is understood that the invention additionally provides a non-naturally occurring microbial organism comprising at least one exogenous nucleic acid encoding an acetyl-CoA or a bioderived compound pathway enzyme expressed in a sufficient amount to produce an intermediate of an acetyl-CoA or a bioderived compound pathway. For example, as disclosed herein, an acetyl-CoA or a bioderived compound pathway is exemplified in FIGS. 1-10. Therefore, in addition to a microbial organism containing an acetyl-CoA or a bioderived compound pathway that produces acetyl-CoA or a bioderived compound, the invention additionally provides a non-naturally occurring microbial organism comprising at least one exogenous nucleic acid encoding an acetyl-CoA or a bioderived compound pathway enzyme, where the microbial organism produces an acetyl-CoA or a bioderived compound pathway intermediate, for example, acetate, ACTP, G3P, PYR, Formate, Fald, formyl-CoA, FTHF, Methenyl-THF, Methylene-THF, Glycine, Serine, Methyl-THF, H6P, F6P, DHA, S-hydroxymethyglutathione, S-formylglutathione, OAA, CIT, ICIT, MAL, FUM, AKG, SUCC, SUCCOA, MALCOA, AACOA, 3HBCOA, 3HBALD, 3HB, CROTCOA, CROT, CROALD, CROT-Pi, CROT-PPi, 3-hydroxybutyryl phosphate, 3-hydroxybutyryl diphosphate, succinate semialdehyde, 4-hydroxybutyrate, 4-hydroxybutyryl-phosphate, 4-hydroxybutyryl-CoA, 4-hydroxybutanal, 3-oxoadipyl-CoA, 3-hydroxyadipyl-CoA, 5-hydroxy-2-pentenoyl-CoA, adipate semialdehyde, 6-aminocaproyl-CoA, 6-aminocaproate semialdehyde, (R)-methylmalonyl-CoA, (S)-methylmalonyl-CoA, methylmalonate semialdehyde, 3-hydrdoxyisobutyrate, 2-hydroxyisobutyryl-CoA, and methacrylyl-CoA.

It is understood that any of the pathways disclosed herein, as described in the Examples and exemplified in the Figures, including the pathways of FIGS. 1-10, can be utilized to generate a non-naturally occurring microbial organism that produces any pathway intermediate or product, as desired. As disclosed herein, such a microbial organism that produces an intermediate can be used in combination with another microbial organism expressing downstream pathway enzymes to produce a desired product. However, it is understood that a non-naturally occurring microbial organism that produces an acetyl-CoA or a bioderived compound pathway intermediate can be utilized to produce the intermediate as a desired product.

In one embodiment, the invention provides a non-naturally occurring microbial organism having an acetyl-CoA pathway, wherein said acetyl-CoA pathway comprises a pathway selected from: (1) 1T and 1V; (2) 1T, 1W, and 1X; (3) 1U and 1V; (4) 1U, 1W, and 1X; wherein 1T is a fructose-6-phosphate phosphoketolase, wherein 1U is a xylulose-5-phosphate phosphoketolase, wherein 1V is a phosphotransacetylase, wherein 1W is an acetate kinase, wherein 1X is an acetyl-CoA transferase, an acetyl-CoA synthetase, or an acetyl-CoA ligase; wherein said non-naturally occurring microbial organism further comprises a pathway capable of producing a bioderived compound, wherein said bioderived compounds is selected from the group consisting of: (i) 1,4-butanediol or an intermediate thereto, wherein said intermediate is optionally 4-hydroxybutanoic acid (4-HB); butadiene (1,3-butadiene) or an intermediate thereto, wherein said intermediate is optionally 1,4-butanediol, 1,3-butanediol, 2,3-butanediol, crotyl alcohol, 3-buten-2-ol (methyl vinyl carbinol) or 3-buten-1-ol; 1,3-butanediol or an intermediate thereto, wherein said intermediate is optionally 3-hydroxybutyrate (3-HB), 2,4-pentadienoate, crotyl alcohol or 3-buten-1-ol; (iv) adipate, 6-aminocaproic acid, caprolactam, hexamethylenediamine, levulinic acid or an intermediate thereto, wherein said intermediate is optionally adipyl-CoA or 4-aminobutyryl-CoA; (v) methacrylic acid or an ester thereof, 3-hydroxyisobutyrate, 2-hydroxyisobutyrate, or an intermediate thereto, wherein said ester is optionally methyl methacrylate or poly(methyl methacrylate); (vi) 1,2-propanediol (propylene glycol), 1,3-propanediol, glycerol, ethylene glycol, diethylene glycol, triethylene glycol, dipropylene glycol, tripropylene glycol, neopentyl glycol, bisphenol A or an intermediate thereto; (vii) succinic acid or an intermediate thereto; and (viii) a fatty alcohol, a fatty aldehyde or a fatty acid comprising C4 to C27 carbon atoms, C8 to C18 carbon atoms, C12 to C18 carbon atoms, or C12 to C14 carbon atoms, wherein said fatty alcohol is optionally dodecanol (C12; lauryl alcohol), tridecyl alcohol (C13; 1-tridecanol, tridecanol, isotridecanol), myristyl alcohol (C14; 1-tetradecanol), pentadecyl alcohol (C15; 1-pentadecanol, pentadecanol), cetyl alcohol (C16; 1-hexadecanol), heptadecyl alcohol (C17; 1-n-heptadecanol, heptadecanol) and stearyl alcohol (C18; 1-octadecanol) or palmitoleyl alcohol (C16 unsaturated; cis-9-hexadecen-1-ol).

In some aspects, the non-naturally occurring microbial organism having an acetyl-CoA pathway can further comprise a 1,3-butanediol pathway and an exogenous nucleic acid encoding a 1,3-butanediol pathway enzyme expressed in a sufficient amount to produce 1,3-butanediol, wherein said 1,3-butanediol pathway comprises a pathway selected from: (1) 5A, 5B, 5D, 5E, and 5H; (2) 5A, 5B, 5D, 5F, 5G, and 5H; (3) 5C, 5D, 5E, and 5H; (4) 5C, 5D, 5F, 5G, and 5H; (5) 5A, 5B, 5D and 5V; and (6) 5C, 5D and 5V, wherein 5A is an acetyl-CoA carboxylase, wherein 5B is an acetoacetyl-CoA synthase, wherein 5C is an acetyl-CoA:acetyl-CoA acyltransferase, wherein 5D is an acetoacetyl-CoA reductase (ketone reducing), wherein 5E is a 3-hydroxybutyryl-CoA reductase (aldehyde forming), wherein 5F is a 3-hydroxybutyryl-CoA hydrolase, transferase or synthetase, wherein 5G is a 3-hydroxybutyrate reductase, wherein 5H is a 3-hydroxybutyraldehyde reductase, wherein 5V is a 3-hydroxybutyryl-CoA reductase (alcohol forming).

In some aspects, the non-naturally occurring microbial organism having an acetyl-CoA pathway can further comprise a crotyl alcohol pathway and an exogenous nucleic acid encoding a crotyl alcohol pathway enzyme expressed in a sufficient amount to produce crotyl alcohol, wherein said crotyl alcohol pathway comprises a pathway selected from: (1) 5A, 5B, 5D, 5J, 5K, and 5N; (2) 5A, 5B, 5D, 5J, 5L, 5M, and 5N; (3) 5C, 5D, 5J, 5K, and 5N; (4) 5C, 5D, 5J, 5L, 5M, and 5N; (5) 5A, 5B, 5D, 5J and 5U; and (6) 5C, 5D, 5J and 5U, wherein 5A is an acetyl-CoA carboxylase, wherein 5B is an acetoacetyl-CoA synthase, wherein 5C is an acetyl-CoA:acetyl-CoA acyltransferase, wherein 5D is an acetoacetyl-CoA reductase (ketone reducing), wherein 5J is a 3-hydroxybutyryl-CoA dehydratase, wherein 5K is a crotonyl-CoA reductase (aldehyde forming), wherein 5L is a crotonyl-CoA hydrolase, crotonyl-CoA transferase or crotonyl-CoA synthetase, wherein 5M is a crotonate reductase, wherein 5N is a crotonaldehyde reductase, wherein 5U is a crotonyl-CoA reductase (alcohol forming).

In some aspects, the non-naturally occurring microbial organism having an acetyl-CoA pathway can further comprise a butadiene pathway and an exogenous nucleic acid encoding a butadiene pathway enzyme expressed in a sufficient amount to produce butadiene, wherein said butadiene pathway comprises a pathway selected from: (1) 5A, 5B, 5D, 5E, 5H, 6A, 6B, 6C, and 6G; (2) 5A, 5B, 5D, 5F, 5G, 5H, 6A, 6B, 6C, and 6G; (3) 5C, 5D, 5E, 5H, 6A, 6B, 6C, and 6G; (4) 5C, 5D, 5F, 5G, 5H, 6A, 6B, 6C, and 6G; (5) 5A, 5B, 5D, 5E, 5H, 6A, 6F, and 6G; (6) 5A, 5B, 5D, 5F, 5G, 5H, 6A, 6F, and 6G; (7) 5C, 5D, 5E, 5H, 6A, 6F, and 6G; (8) 5C, 5D, 5F, 5G, 5H, 6A, 6F, and 6G; (9) 5A, 5B, 5D, 5E, 5H, 6E, 6C, and 6G; (10) 5A, 5B, 5D, 5F, 5G, 5H, 6E, 6C, and 6G; (11) 5C, 5D, 5E, 5H, 6E, 6C, and 6G; (12) 5C, 5D, 5F, 5G, 5H, 6E, 6C, and 6G; (13) 5A, 5B, 5D, 5E, 5H, 6D, and 6G; (14) 5A, 5B, 5D, 5F, 5G, 5H, 6D, and 6G; (15) 5C, 5D, 5E, 5H, 6D, and 6G; (16) 5C, 5D, 5F, 5G, 5H, 6D, and 6G; (17) 5A, 5B, 5D, 5J, 5K, 5N, and 5S; (18) 5A, 5B, 5D, 5J, 5L, 5M, 5N, and 5S; (19) 5C, 5D, 5J, 5K, 5N, and 5S; (20) 5C, 5D, 5J, 5L, 5M, 5N, and 5S; (21) 5A, 5B, 5D, 5J, 5K, 5N, 5R, and 5Q; (22) 5A, 5B, 5D, 5J, 5L, 5M, 5N, 5R, and 5Q; (23) 5C, 5D, 5J, 5K, 5N, 5R, and 5Q; (24) 5C, 5D, 5J, 5L, 5M, 5N, 5R, and 5Q; (25) 5A, 5B, 5D, 5J, 5K, 5N, 5O, 5P, and 5Q; (26) 5A, 5B, 5D, 5J, 5L, 5M, 5N, 5O, 5P, and 5Q; (27) 5C, 5D, 5J, 5K, 5N, 5O, 5P, and 5Q; (28) 5C, 5D, 5J, 5L, 5M, 5N, 5O, 5P, and 5Q; (29) 5A, 5B, 5D, 5J, 5K, 5N, 5O, and 5T; (30) 5A, 5B, 5D, 5J, 5L, 5M, 5N, 5O, and 5T; (31) 5C, 5D, 5J, 5K, 5N, 5O, and 5T; (32) 5C, 5D, 5J, 5L, 5M, 5N, 5O, and 5T; (33) 5A, 5B, 5D, 5V, 6A, 6B, 6C, and 6G; (34) 5C, 5D, 5V, 6A, 6B, 6C, and 6G; (35) 5A, 5B, 5D, 5J, 5U, and 5S; (36) 5C, 5D, 5J, 5U, and 5S; (37) 5A, 5B, 5D, 5J, 5U, 5R, and 5Q; (38) 5C, 5D, 5J, 5U, 5R, and 5Q; (39) 5A, 5B, 5D, 5J, 5U, 5O, 5P, and 5Q; (40) 5C, 5D, 5J, 5U, 5O, 5P, and 5Q; (41) 5A, 5B, 5D, 5J, 5U, 5O, and 5T; and (42) 5C, 5D, 5J, 5U, 5O, and 5T, wherein 5A is an acetyl-CoA carboxylase, wherein 5B is an acetoacetyl-CoA synthase, wherein 5C is an acetyl-CoA:acetyl-CoA acyltransferase, wherein 5D is an acetoacetyl-CoA reductase (ketone reducing), wherein 5E is a 3-hydroxybutyryl-CoA reductase (aldehyde forming), wherein 5F is a 3-hydroxybutyryl-CoA hydrolase, 3-hydroxybutyryl-CoA transferase or 3-hydroxybutyryl-CoA synthetase, wherein 5G is a 3-hydroxybutyrate reductase, wherein 5H is a 3-hydroxybutyraldehyde reductase, wherein 5J is a 3-hydroxybutyryl-CoA dehydratase, wherein 5K is a crotonyl-CoA reductase (aldehyde forming), wherein 5L is a crotonyl-CoA hydrolase, crotonyl-CoA transferase or crotonyl-CoA synthetase, wherein 5M is a crotonate reductase, wherein 5N is a crotonaldehyde reductase, wherein 5O is a crotyl alcohol kinase, wherein 5P is a 2-butenyl-4-phosphate kinase, wherein 5Q is a butadiene synthase, wherein 5R is a crotyl alcohol diphosphokinase, wherein 5S is chemical dehydration or a crotyl alcohol dehydratase, wherein 5T is a butadiene synthase (monophosphate), wherein 5U is a crotonyl-CoA reductase (alcohol forming), wherein 5V is a 3-hydroxybutyryl-CoA reductase (alcohol forming), wherein 6A is a 1,3-butanediol kinase, wherein 6B is a 3-hydroxybutyrylphosphate kinase, wherein 6C is a 3-hydroxybutyryldiphosphate lyase, wherein 6D is a 1,3-butanediol diphosphokinase, wherein 6E is a 1,3-butanediol dehydratase, wherein 6F is a 3-hydroxybutyrylphosphate lyase, wherein 6G is a 3-buten-2-ol dehydratase or chemical dehydration.

In some aspects, the non-naturally occurring microbial organism having an acetyl-CoA pathway can further comprise a 3-buten-2-ol pathway and an exogenous nucleic acid encoding a 3-buten-2-ol pathway enzyme expressed in a sufficient amount to produce 3-buten-2-ol, wherein said 3-buten-2-ol pathway comprises a pathway selected from: (1) 5A, 5B, 5D, 5E, 5H, 6A, 6B, and 6C; (2) 5A, 5B, 5D, 5F, 5G, 5H, 6A, 6B, and 6C; (3) 5C, 5D, 5E, 5H, 6A, 6B, and 6C; (4) 5C, 5D, 5F, 5G, 5H, 6A, 6B, and 6C; (5) 5A, 5B, 5D, 5E, 5H, 6A, and 6F; (6) 5A, 5B, 5D, 5F, 5G, 5H, 6A, and 6F; (7) 5C, 5D, 5E, 5H, 6A, and 6F; (8) 5C, 5D, 5F, 5G, 5H, 6A, and 6F; (9) 5A, 5B, 5D, 5E, 5H, 6E, and 6C; (10) 5A, 5B, 5D, 5F, 5G, 5H, 6E, and 6C; (11) 5C, 5D, 5E, 5H, 6E, and 6C; (12) 5C, 5D, 5F, 5G, 5H, 6E, and 6C; (13) 5A, 5B, 5D, 5E, 5H, and 6D; (14) 5A, 5B, 5D, 5F, 5G, 5H, and 6D; (15) 5C, 5D, 5E, 5H, and 6D; (16) 5C, 5D, 5F, 5G, 5H, and 6D; (17) 5A, 5B, 5D, 5V, 6A, 6B, and 6C; (18) 5C, 5D, 5V, 6A, 6B, and 6C; (19) 5A, 5B, 5D, 5V, 6A, and 6F; (20) 5C, 5D, 5V, 6A, and 6F; (21) 5A, 5B, 5D, 5V, 6E, and 6C; (22) 5C, 5D, 5V, 6E, and 6C; (23) 5A, 5B, 5D, 5V and 6D; and (24) 5C, 5D, 5V and 6D, wherein 5A is an acetyl-CoA carboxylase, wherein 5B is an acetoacetyl-CoA synthase, wherein 5C is an acetyl-CoA:acetyl-CoA acyltransferase, wherein 5D is an acetoacetyl-CoA reductase (ketone reducing), wherein 5E is a 3-hydroxybutyryl-CoA reductase (aldehyde forming), wherein 5F is a 3-hydroxybutyryl-CoA hydrolase, 3-hydroxybutyryl-CoA transferase or 3-hydroxybutyryl-CoA synthetase, wherein 5G is a 3-hydroxybutyrate reductase, wherein 5H is a 3-hydroxybutyraldehyde reductase, wherein 5V is a 3-hydroxybutyryl-CoA reductase (alcohol forming), wherein 6A is a 1,3-butanediol kinase, wherein 6B is a 3-hydroxybutyrylphosphate kinase, wherein 6C is a 3-hydroxybutyryldiphosphate lyase, wherein 6D is a 1,3-butanediol diphosphokinase, wherein 6E is a 1,3-butanediol dehydratase, wherein 6F is a 3-hydroxybutyrylphosphate lyase.

In some aspects the non-naturally occurring microbial organism having an acetyl-CoA pathway can further comprise a 1,4-butanediol pathway and an exogenous nucleic acid encoding a 1,4-butanediol pathway enzyme expressed in a sufficient amount to produce 1,4-butanediol, wherein said 1,4-butanediol pathway comprises a pathway selected from: (1) 7B, 7C, 7D, 7E, 7F, and 7G; (2) 7A, 7H, 7C, 7D, 7E, 7F, and 7G; (3) 7I, 7D, 7E, 7F, and 7G; (4) 7B, 7C, 7K, and 7G; (5) 7A, 7H, 7C, 7K, and 7G; (6) 7I, 7K, and 7G; (7) 7B, 7C, 7D, 7L, and 7G; (8) 7A, 7H, 7C, 7D, 7L, and 7G; (9) 7I, 7D, 7L, and 7G; (10) 7B, 7C, 7J, 7F, and 7G; (11) 7A, 7H, 7C, 7J, 7F, and 7G; (12) 7I, 7J, 7F, and 7G; (13) 7B, 7C, 7D, 7E, and 7M; (14) 7A, 7H, 7C, 7D, 7E, and 7M; and (15) 7I, 7D, 7E, and 7M, wherein 7A is a succinyl-CoA transferase or a succinyl-CoA synthetase, wherein 7B is a succinyl-CoA reductase (aldehyde forming), wherein 7C is a 4-HB dehydrogenase, wherein 7D is a 4-HB kinase, wherein 7E is a phosphotrans-4-hydroxybutyrylase, wherein 7F is a 4-hydroxybutyryl-CoA reductase (aldehyde forming), wherein 7G is a 1,4-butanediol dehydrogenase, wherein 7H is a succinate reductase, wherein 7I is a succinyl-CoA reductase (alcohol forming), wherein 7J is a 4-hydroxybutyryl-CoA transferase or 4-hydroxybutyryl-CoA synthetase, wherein 7K is a 4-HB reductase, wherein 7L is a 4-hydroxybutyryl-phosphate reductase, wherein 7M is a 4-hydroxybutyryl-CoA reductase (alcohol forming).

In some aspects, the non-naturally occurring microbial organism having an acetyl-CoA pathway can further comprise an adipate pathway and an exogenous nucleic acid encoding an adipate pathway enzyme expressed in a sufficient amount to produce adipate, wherein said adipate pathway comprises 8A, 8B, 8C, 8D and 8L, wherein 8A is a 3-oxoadipyl-CoA thiolase, wherein 8B is a 3-oxoadipyl-CoA reductase, wherein 8C is a 3-hydroxyadipyl-CoA dehydratase, wherein 8D is a 5-carboxy-2-pentenoyl-CoA reductase, wherein 8L is an adipyl-CoA hydrolase, adipyl-CoA ligase, adipyl-CoA transferase, or phosphotransadipylase/adipate kinase.

In some aspects, the non-naturally occurring microbial organism having an acetyl-CoA pathway can further comprise a 6-aminocaproate pathway and an exogenous nucleic acid encoding a 6-aminocaproate pathway enzyme expressed in a sufficient amount to produce 6-aminocaproate, wherein said 6-aminocaproate pathway comprises 8A, 8B, 8C, 8D, 8E, and 8F, wherein 8A is a 3-oxoadipyl-CoA thiolase, wherein 8B is a 3-oxoadipyl-CoA reductase, wherein 8C is a 3-hydroxyadipyl-CoA dehydratase, wherein 8D is a 5-carboxy-2-pentenoyl-CoA reductase, wherein 8E is an adipyl-CoA reductase (aldehyde forming), wherein 8F is a 6-aminocaproate transaminase or 6-aminocaproate dehydrogenase.

In some aspects, the non-naturally occurring microbial organism having an acetyl-CoA pathway can further comprise a caprolactam pathway and an exogenous nucleic acid encoding a caprolactam pathway enzyme expressed in a sufficient amount to produce caprolactam, wherein said caprolactam pathway comprises: (1) 8A, 8B, 8C, 8D, 8E, 8F, and 8H; or (2) 8A, 8B, 8C, 8D, 8E, 8F, 8G, and 8I, wherein 8A is a 3-oxoadipyl-CoA thiolase, wherein 8B is a 3-oxoadipyl-CoA reductase, wherein 8C is a 3-hydroxyadipyl-CoA dehydratase, wherein 8D is a 5-carboxy-2-pentenoyl-CoA reductase, wherein 8E is an adipyl-CoA reductase (aldehyde forming), wherein 8F is a 6-aminocaproate transaminase or 6-aminocaproate dehydrogenase, wherein 8G is a 6-aminocaproyl-CoA/acyl-CoA transferase or 6-aminocaproyl-CoA synthase, wherein 8H is an amidohydrolase, wherein 8I is spontaneous cyclization.

In some aspects, the non-naturally occurring microbial organism having an acetyl-CoA pathway can further comprise a hexamethylenediamine pathway and an exogenous nucleic acid encoding a hexamethylenediamine pathway enzyme expressed in a sufficient amount to produce hexamethylenediamine, wherein said hexamethylenediamine pathway comprises 8A, 8B, 8C, 8D, 8E, 8F, 8G, 8J, 8K, wherein 8A is a 3-oxoadipyl-CoA thiolase, wherein 8B is a 3-oxoadipyl-CoA reductase, wherein 8C is a 3-hydroxyadipyl-CoA dehydratase, wherein 8D is a 5-carboxy-2-pentenoyl-CoA reductase, wherein 8E is an adipyl-CoA reductase (aldehyde forming), wherein 8F is a 6-aminocaproate transaminase or 6-aminocaproate dehydrogenase, wherein 8G is a 6-aminocaproyl-CoA/acyl-CoA transferase or 6-aminocaproyl-CoA synthase, wherein 8J is a 6-aminocaproyl-CoA reductase (aldehyde forming), wherein 8K is a hexamethylenediamine transaminase or hexamethylenediamine dehydrogenase.

In some aspects, the non-naturally occurring microbial organism having an acetyl-CoA pathway can further comprise a methacrylic acid pathway and an exogenous nucleic acid encoding a methacrylic acid pathway enzyme expressed in a sufficient amount to produce methacrylic acid, wherein said methacrylic acid pathway comprises a pathway selected from: (1) 9A, 9B, 9C, 9D, and 9E; (2) 9A, 9F, and 9E; (3) 9A, 9B, 9F, and 9E; (4) 9A, 9C, 9D, and 9E; and (5) 10A, 10B, 10C, 10D, and 10E, wherein 9A is a methylmalonyl-CoA mutase, wherein 9B is a methylmalonyl-CoA epimerase, wherein 9C is a methylmalonyl-CoA reductase (aldehyde forming), wherein 9D is a methylmalonate semialdehyde reductase, wherein 9E is a 3-hydroxyisobutyrate dehydratase, wherein 9F is a methylmalonyl-CoA reductase (alcohol forming), wherein 10A is an acetyl-CoA:acetyl-CoA acyltransferase, wherein 10B is an acetoacetyl-CoA reductase (ketone reducing), wherein 10C is a 3-hydroxybutyrl-CoA mutase, wherein 10D is a 2-hydroxyisobutyryl-CoA dehydratase, wherein 10E is a methacrylyl-CoA synthetase, methacrylyl-CoA hydrolase, or methacrylyl-CoA transferase.

In some aspects, the non-naturally occurring microbial organism having an acetyl-CoA pathway can further comprise a 2-hydroxyisobutyric acid pathway and an exogenous nucleic acid encoding a 2-hydroxyisobutyric acid pathway enzyme expressed in a sufficient amount to produce 2-hydroxyisobutyric acid, wherein said 2-hydroxyisobutyric acid pathway comprises 10A, 10B, 10C, and 10F, wherein 10A is an acetyl-CoA:acetyl-CoA acyltransferase, wherein 10B is an acetoacetyl-CoA reductase (ketone reducing), wherein 10C is a 3-hydroxybutyrl-CoA mutase, wherein 10F is a 2-hydroxyisobutyryl-CoA synthetase, 2-hydroxyisobutyryl-CoA hydrolase, or 2-hydroxyisobutyryl-CoA transferase.

In certain embodiments, such as the above non-naturally occurring microbial organisms having an acetyl-CoA pathway and 1,4-butanediol pathway, an adipate pathway, a 6-aminocaproate pathway, a caprolactam pathway, a hexamethylenediamine pathway or a methacrylic acid pathway, the non-naturally occurring microbial organism can further comprise a succinyl-CoA pathway and an exogenous nucleic acid encoding a succinyl-CoA pathway enzyme expressed in a sufficient amount to produce succinyl-CoA, wherein said succinyl-CoA pathway comprises a pathway selected from: (1) 4H, 4I, 4J, and 4K; (2) 4H, 4I, 4N, and 4E; (3) 4H, 4I, 4N, 4C, 4D, and 4E; (4) 4L, 4H, 4I, 4J, and 4K; (5) 4L, 4H, 4I, 4N, and 4E; (6) 4L, 4H, 4I, 4N, 4C, 4D, and 4E; (7) 4A, 4H, 4I, 4J, and 4K; (8) 4A, 4H, 4I, 4N, and 4E; (9) 4A, 4H, 4I, 4N, 4C, 4D, and 4E; (10) 4M, 4C, 4D, and 4E; (11) 4F, 4L, 4H, 4I, 4J, and 4K; (12) 4F, 4L, 4H, 4I, 4N, and 4E; (13) 4F, 4L, 4H, 4I, 4N, 4C, 4D, and 4E; (14) 4F, 4M, 4C, 4D, and 4E; (15) 4F, 4G, 4H, 4I, 4J, and 4K; (16) 4F, 4G, 4H, 4I, 4N, and 4E; and (17) 4F, 4G, 4H, 4I, 4N, 4C, 4D, and 4E, wherein 4A is a PEP carboxylase or PEP carboxykinase, wherein 4B is a malate dehydrogenase, wherein 4C is a fumarase, wherein 4D is a fumarate reductase, wherein 4E is a succinyl-CoA synthetase or succinyl-CoA transferase, wherein 4F is a pyruvate kinase or PTS-dependent substrate import, wherein 4G is a pyruvate dehydrogenase, pyruvate formate lyase, or pyruvate: ferredoxin oxidoreductase, wherein 4H is a citrate synthase, wherein 4I is an aconitase, wherein 4J is an isocitrate dehydrogenase, wherein 4K is an alpha-ketoglutarate dehydrogenase, wherein 4L is a pyruvate carboxylase, wherein 4M is a malic enzyme, wherein 4N is an isocitrate lyase and malate synthase.

In certain aspects, the non-naturally occurring microbial organism having an acetyl-CoA pathway can be a microbial organism species selected from a bacteria, yeast, or fungus.

The invention further provides non-naturally occurring microbial organisms that have elevated or enhanced synthesis or yields of acetyl-CoA or a bioderived compound and methods of using those non-naturally occurring organisms to produce such biosynthetic products, the bioderived compound including alcohols, diols, fatty acids, glycols, organic acids, alkenes, dienes, organic amines, organic aldehydes, vitamins, nutraceuticals and pharmaceuticals. The enhanced synthesis of intracellular acetyl-CoA enables enhanced production of bioderived compounds for which acetyl-CoA is an intermediate and further, may have been rate-limiting.

The non-naturally occurring microbial organisms having enhanced yields of a biosynthetic product include one or more of the various pathway configurations employing a methanol dehydrogenase for methanol oxidation, a formaldehyde fixation pathway and/or an acetyl-CoA enhancing pathway, e.g. phosphoketolase, for directing the carbon from methanol into acetyl-CoA and other desired products via formaldehyde fixation. The various different methanol oxidation and formaldehyde fixation configurations exemplified below can be engineered in conjunction with any or each of the various methanol oxidation, formaldehyde fixation, formate reutilization, acetyl-CoA or bioderived compound pathways exemplified previously and herein. The metabolic modifications exemplified below increase biosynthetic product yields over, for example, endogenous methanol utilization pathways because they further focus methanol derived carbon into the assimilation pathways described herein, decrease inefficient use of methanol carbon through competing methanol utilization and/or formaldehyde fixation pathways and/or increase the production of reducing equivalents.

In this regard, methylotrophs microbial organisms utilize methanol as the sole source of carbon and energy. In such methylotrophic organisms, the oxidation of methanol to formaldehyde is catalyzed by one of three different enzymes: NADH dependent methanol dehydrogenase (MeDH), PQQ-dependent methanol dehydrogenase (MeDH-PQQ) and alcohol oxidase (AOX). Methanol oxidase is a specific type of AOX with activity on methanol. Gram positive bacterial methylotrophs such as *Bacillus methanolicus* utilize a cytosolic MeDH which generates reducing equivalents in the form of NADH. Gram negative bacterial methylotrophs utilize periplasmic PQQ-containing methanol dehydrogenase enzymes which transfer electrons from methanol to specialized cytochromes CL, and subsequently to a cytochrome oxidase (Afolabi et al, *Biochem* 40:9799-9809 (2001)). Eukaryotic methylotrophs employ a peroxisomal oxygen-consuming and hydrogen-peroxide producing alcohol oxidase.

Bacterial methylotrophs are found in the genera *Bacillus, Methylobacterium, Methyloversatilis, Methylococcus, Methylocystis* and *Hyphomicrobium*. These organisms utilize either the serine cycle (type II) or the RuMP cycle (type I) to further assimilate formaldehyde into central metabolism (Hanson and Hanson, *Microbiol Rev* 60:439-471 (1996)). As described previously, the RuMP pathway combines formaldehyde with ribulose monophosphate to form hexulose-6-phosphate, which is further converted to fructose-6-phosphate (see FIG. 1, step C). In the serine cycle formaldehyde is initially converted to 5,10-methylene-THF, which is combined with glycine to form serine. Overall, the reactions of the serine cycle produce one equivalent of acetyl-CoA from three equivalents of methanol (Anthony, *Science Prog* 94:109-37 (2011)). The RuMP cycle also yields one equivalent of acetyl-CoA from three equivalents methanol in the absence of phosphoketolase activity or a formate assimilation pathway. Genetic tools are available for numerous prokaryotic methylotrophs and methanotrophs.

Eukaryotic methylotrophs are found in the genera *Candida, Pichia, Ogataea, Kuraishia* and *Komagataella*. Particularly useful methylotrophic host organisms are those with well-characterized genetic tools and gene expression systems such as *Hansenula polymorpha, Pichia pastoris, Candida boidinii* and *Pichia methanolica* (for review see Yurimoto et al, *Int J Microbiol* (2011)). The initial step of methanol assimilation in eukaryotic methylotrophs occurs in the peroxisomes, where methanol and oxygen are oxidized to formaldehyde and hydrogen peroxide by alcohol oxidase (AOX). Formaldehyde assimilation with xylulose-5-phosphate via DHA synthase also occurs in the peroxisomes. During growth on methanol, the two enzymes DHA synthase and AOX together comprise 80% of the total cell protein (Horiguchi et al, *J Bacteriol* 183:6372-83 (2001)). DHA synthase products, DHA and glyceraldehyde-3-phosphate, are secreted into the cytosol where they undergo a series of rearrangements catalyzed by pentose phosphate pathway enzymes, and are ultimately converted to cellular constituents and xylulose-5-phosphate, which is transported back into the peroxisomes. The initial step of formaldehyde dissimilation, catalyzed by S-(hydroxymethyl)-glutathione synthase, also occurs in the peroxisomes. Like the bacterial methylotrophic pathways described above, eukaryotic methylotrophic pathways convert three equivalents of methanol to at most one equivalent of acetyl-CoA because they lack phosphoketolase activity or a formate assimilation pathway.

As exemplified further below, the various configurations of metabolic modifications disclosed herein for enhancing product yields via methanol derived carbon include enhancing methanol oxidation and production of reducing equivalents using either and an endogenous NADH dependent methanol dehydrogenase, an exogenous NADH dependent methanol dehydrogenase, both an endogenous NADH dependent methanol dehydrogenase and exogenous NADH dependent methanol dehydrogenase alone or in combination with one or more metabolic modifications that attenuate, for example, DHA synthase and/or AOX. In addition, other metabolic modifications as exemplified below that reduce carbon flux away from methanol oxidation and formaldehyde fixation also can be included, alone or in combination, with the methanol oxidation and formaldehyde fixation pathway configurations disclosed herein that enhance carbon flux into product precursors such as acetyl-CoA and, therefore, enhance product yields.

Accordingly, the microbial organism of the invention having one or more of any of the above and/or below metabolic modifications to a methanol utilization pathway and/or formaldehyde assimilation pathway configurations for enhancing product yields can be combined with any one or more, including all of the previously described methanol oxidation, formaldehyde fixation, formate reutilization, and/or acetyl-CoA pathways to enhance the yield and/or production of a product such as any of the bioderived compounds described herein.

Given the teachings and guidance provided herein, the methanol oxidation and formaldehyde fixation pathway configurations can be equally engineered into both prokaryotic and eukaryotic organisms. In prokaryotic microbial organisms, for example, one skilled in the art will understand that utilization of an endogenous methanol oxidation pathway enzyme or expression of an exogenous nucleic acid encoding a methanol oxidation pathway enzyme will naturally occur cytosolically because prokaryotic organisms lack peroxisomes. In eukaryotic microbial organisms one skilled in the art will understand that certain methanol oxidation pathways occur in the peroxisome as described above and that cytosolic expression of the methanol oxidation pathway or pathways described herein to enhance product yields can be beneficial. The peroxisome located pathways and competing pathways remain or, alternatively, attenuated as described below to further enhance methanol oxidation and formaldehyde fixation.

With respect to eukaryotic microbial host organisms, those skilled in the art will know that yeasts and other eukaryotic microorganisms exhibit certain characteristics distinct from prokaryotic microbial organisms. When such characteristics are desirable, one skilled in the art can choose to use such eukaryotic microbial organisms as a host for engineering the various different methanol oxidation and formaldehyde fixation configurations exemplified herein for enhancing product yields. For example, yeast are robust organisms, able to grow over a wide pH range and able to tolerate more impurities in the feedstock. Yeast also ferment under low growth conditions and are not susceptible to infection by phage. Less stringent aseptic design requirements can also reduce production costs. Cell removal, disposal and propagation are also cheaper, with the added potential for by-product value for animal feed applications. The potential for cell recycle and semi-continuous fermentation offers benefits in increased overall yields and rates. Other benefits include: potential for extended fermentation times under low growth conditions, lower viscosity broth (vs *E. coli*) with insoluble hydrophobic products, the ability to employ large fermenters with external loop heat exchangers.

Eukaryotic host microbial organisms suitable for engineering carbon efficient methanol utilization capability can be selected from, and the non-naturally occurring microbial organisms generated in, for example, yeast, fungus or any of a variety of other microorganisms applicable to fermentation processes. As described previously, exemplary yeasts or fungi include species selected from the genera *Saccharomyces, Schizosaccharomyces, Schizochytrium, Rhodotorula, Thraustochytrium, Aspergillus, Kluyveromyces, Issatchenkia, Yarrowia, Candida, Pichia, Ogataea, Kuraishia, Hansenula* and *Komagataella*. Useful host organisms include *Saccharomyces cerevisiae, Schizosaccharomyces pombe, Hansenula polymorpha, Pichia methanolica, Candida boidinii, Kluyveromyces lactis, Kluyveromyces marxianus, Aspergillus terreus, Aspergillus niger, Pichia pastoris, Rhizopus arrhizus, Rhizobus oryzae, Yarrowia lipolytica, Issatchenkia orientalis* and the like.

The methanol oxidation and/or formaldehyde assimilation pathway configurations described herein for enhancing product yields include, for example, a NADH-dependent methanol dehydrogenase (MeDH), one or more formaldehyde assimilation pathways and/or one or more phosphoketolases. Such engineered pathways provide a yield advantage over endogenous pathways found in methylotrophic organisms. For example, methanol assimilation via methanol dehydrogenase provides reducing equivalents in the useful form of NADH, whereas alcohol oxidase and PQQ-dependent methanol dehydrogenase do not. Several product pathways described herein have several NADH-dependant enzymatic steps. In addition, deletion of redox-inefficient methanol oxidation enzymes as described further below, combined with increased cytosolic or peroxisomal expression of an NADH-dependent methanol dehydrogenase, improves the ability of the organism to extract useful reducing equivalents from methanol. In some aspects, if NADH-dependent methanol dehydrogenase is engineered into the peroxisome, an efficient means of shuttling redox in the form of NADH out of the peroxisome and into the cytosol can be included. Further employment of a formaldehyde assimilation pathway in combination with a phosphoketolase or formate assimilation pathway enables high yield conversion of methanol to acetyl-CoA, and subsequently to acetyl-CoA derived products.

For example, in a eukaryotic organism such as *Pichia pastoris*, deleting the endogenous alcohol oxidase and peroxisomal formaldehyde assimilation and dissimilation pathways, and expressing redox and carbon-efficient cytosolic methanol utilization pathways significantly improves the yield of dodecanol, an acetyl-CoA derived product. The maximum docidecanol yield of *Pichia pastoris* from methanol using endogenous methanol oxidase and formaldehyde assimilation enzymes is 0.256 g dodecanol/g methanol. Adding one or more heterologous cytosolic phosphoketolase enzymes, in combination with a formaldehyde assimilation pathway such as the DHA pathway or the RUMP pathway, boosts the dodecanol yield to 0.306 g dodecanol/g methanol. Deletion of peroxisomal methanol oxidase and formaldehyde assimilation pathway enzymes (alcohol oxidase, DHA synthase), and replacement with cytosolic methanol dehydrogenase (NADH dependent) and formaldehyde assimilation pathways, together with a phosphoketolase, provides a significant boost of yield to 0.422 g/g.

| Strain design (assumes DHA pathway) | Max FA yield (g dodecanol/g MeOH) |
| --- | --- |
| Pichia + AOX + fatty acid pathway | 0.256 |
| Pichia + AOX + PK | 0.306 |
| Pichia + MeDH + PK | 0.422 |

The combination of NADH-dependent methanol dehydrogenase and phosphoketolase together results in a significant boost in yield for other acetyl-CoA derived products. For 13-BDO production as shown via the pathway in FIG. 5, methanol dehydrogenase in combination with phosphoketolase improves the yield from 0.469 to 0.703 g 13-BDO/g methanol.

| Strain design (assumes RuMP pathway) | MeOH per 1,3-BDO (mol/mol) | 13-BDO per MeOH (g/g) |
| --- | --- | --- |
| 13-BDO + AOX | 6 | .469 |
| 13-BDO + AOX + PK | 5.778 | .487 |
| 13-BDO + MeDH + PK | 4 | .703 |

Metabolic modifications for enabling redox- and carbon-efficient cytosolic methanol utilization in a eukaryotic or prokaryotic organism are exemplified in further detail below.

In one embodiment, the invention provides cytosolic expression of one or more methanol oxidation and/or formaldehyde assimilation pathways. Engineering into a host microbial organism carbon- and redox-efficient cytosolic formaldehyde assimilation can be achieved by expression of one or more endogenous or exogenous methanol oxidation pathways and/or one or more endogenous or exogenous formaldehyde assimilation pathway enzymes in the cytosol.

An exemplary pathway for methanol oxidation includes NADH dependent methanol dehydrogenase as shown in FIG. 1. Exemplary pathways for converting cytosolic formaldehyde into glycolytic intermediates also are shown in FIG. 1. Such pathways include methanol oxidation via expression of an cytosolic NADH dependent methanol dehydrogenase, formaldehyde fixation via expression of cytosolic DHA synthase, both methanol oxidation via expression of an cytosolic NADH dependent methanol dehydrogenase and formaldehyde fixation via expression of cytosolic DHA synthase alone or together with the metabolic modifications exemplified below that attenuate less beneficial methanol oxidation and/or formaldehyde fixation pathways. Such attenuating metabolic modifications include, for example, attenuation of alcohol oxidase, attenuation of DHA kinase and/or when utilization of ribulose-5-phosphate (Ru5P) pathway for formaldehyde fixation attenuation of DHA synthase.

For example, in the carbon-efficient DHA pathway of formaldehyde assimilation shown in FIG. 1, step D, formaldehyde is converted to dihydroxyacetone (DHA) and glyceraldehyde-3-phosphate (GAP) by DHA synthase (FIG. 1D). DHA and G3P are then converted to fructose-6-phosphate in one step by F6P aldolase (FIG. 1C) or in three steps by DHA kinase, FBP aldolase and fructose-1,6-bisphosphatase (not shown). Formation of F6P from DHA and G3P by F6P aldolase is more ATP efficient than using DHA kinase, FBP aldolase, and fructose-1,6-bisphosphatase. Rearrangement of F6P and E4P by enzymes of the pentose phosphate pathway (transaldolase, transketolase, R5P epimerase and Ru5P epimerase) regenerates xylulose-5-phosphate, the DHA synthase substrate. Conversion of F6P to acetyl-phosphate and E4P (FIG. 1T), or Xu5P to G3P and acetyl-phosphate (FIGS. 1T and 1U) by one or more phosphoketolase enzymes results in the carbon-efficient generation of cytosolic acetyl-CoA. Exemplary enzymes catalyzing each step of the carbon efficient DHA pathway are described elsewhere herein.

An alternate carbon efficient pathway for formaldehyde assimilation proceeding through ribulose-5-phosphate (Ru5P) is shown in FIG. 1, step B. The formaldehyde assimilation enzyme of this pathway is 3-hexulose-6-phosphate synthase, which combines ru5p and formaldehyde to form hexulose-6-phosphate (FIG. 1B). 6-Phospho-3-hexuloisomerase converts H6P to F6P (FIG. 1C). Regeneration of Ru5P from F6P proceeds by pentose phosphate pathway enzymes. Carbon-efficient phosphoketolase enzymes catalyze the conversion of F6P and/or Xu5P to acetyl-phosphate and pentose phosphate intermediates. Exemplary enzymes catalyzing each step of the carbon efficient RUMP pathway are described elsewhere herein. Yet another approach is to combine the RUMP and DHA pathways together (FIG. 1).

Thus, in this embodiment, conversion of cytosolic formaldehyde into glycolytic intermediates can occur via expression of a cytosolic 3-hexulose-6-phosphate (3-Hu6P) synthase and 6-phospho-3-hexuloisomerase. Thus, exemplary pathways that can be engineered into a microbial organism of the invention can include methanol oxidation via expression of a cytosolic NADH dependent methanol dehydrogenase, formaldehyde fixation via expression of cytosolic 3-Hu6P synthase and 6-phospho-3-hexuloisomerase, both methanol oxidation via expression of an cytosolic NADH dependent methanol dehydrogenase and formaldehyde fixation via expression of cytosolic 3-Hu6P synthase and 6-phospho-3-hexuloisomerase alone or together with the metabolic modifications exemplified below that attenuate less beneficial methanol oxidation and/or formaldehyde fixation pathways. Such attenuating metabolic modifications include, for example, attenuation of alcohol oxidase, attenuation of DHA kinase and/or attenuation of DHA kinase and/or attenuation of DHA synthase (e.g. when ribulose-5-phosphate (Ru5P) pathway for formaldehyde fixation is utilized).

In yet another embodiment increased product yields can be accomplished by engineering into the host microbial organism of the invention both the RuMP and DHA pathways as shown in FIG. 1. In this embodiment, the microbial organisms can have cytosolic expression of one or more methanol oxidation and/or formaldehyde assimilation pathways. The formaldehyde assimilation pathways can include both assimilation through cytosolic DHA synthase and 3-Hu6P synthase. Such pathways include methanol oxidation via expression of a cytosolic NADH dependent methanol dehydrogenase, formaldehyde fixation via expression of cytosolic DHA synthase and 3-Hu6P synthase, both methanol oxidation via expression of an cytosolic NADH dependent methanol dehydrogenase and formaldehyde fixation via expression of cytosolic DHA synthase and 3-Hu6P synthase alone or together with the metabolic modifications exemplified previously and also below that attenuate less beneficial methanol oxidation and/or formaldehyde fixation pathways. Such attenuating metabolic modifications include, for example, attenuation of alcohol oxidase, attenuation of DHA kinase and/or attenuation of DHA kinase and/or attenuation of DHA synthase (e.g. when ribulose-5-phosphate (Ru5P) pathway for formaldehyde fixation is utilized).

Increasing the expression and/or activity of one or more formaldehyde assimilation pathway enzymes in the cytosol can be utilized to assimilate formaldehyde at a high rate. Increased activity can be achieved by increased expression, altering the ribosome binding site, altering the enzyme activity, or altering the sequence of the gene to ensure, for example, that codon usage is balanced with the needs of the host organism, or that the enzyme is targeted to the cytosol as disclosed herein.

In some embodiments, the invention provides a non-naturally occurring microbial organism as described herein, wherein the microbial organism further includes attenuation of one or more endogenous enzymes, which enhances carbon flux through acetyl-CoA. For example, in some aspects, the endogenous enzyme can be selected from DHA kinase, methanol oxidase, PQQ-dependent methanol dehydrogenase, DHA synthase or any combination thereof. Accordingly, in some aspects, the attenuation is of the endogenous enzyme DHA kinase. In some aspects, the attenuation is of the endogenous enzyme methanol oxidase. In some aspects, the attenuation is of the endogenous enzyme PQQ-dependent methanol dehydrogenase. In some aspects, the attenuation is of the endogenous enzyme DHA synthase. The invention also provides a microbial organism wherein attenuation is of any combination of two or three endogenous enzymes described herein. For example, a microbial organism of the invention can include attenuation of DHA kinase and DHA synthase, or alternatively methanol oxidase and PQQ-dependent methanol dehydrogenase, or alternatively DHA kinase, methanol oxidase, and PQQ-dependent methanol dehydrogenase, or alternatively DHA kinase, methanol oxidase, and DHA synthase. The invention also provides a microbial organism wherein attenuation is of all endogenous enzymes described herein. For example, in some aspects, a microbial organism described herein includes attenuation of DHA kinase, methanol oxidase, PQQ-dependent methanol dehydrogenase and DHA synthase.

In some embodiments, the invention provides a non-naturally occurring microbial organism as described herein, wherein the microbial organism further includes attenuation of one or more endogenous enzymes of a competing formaldehyde assimilation or dissimilation pathway. Examples of these endogenous enzymes are disclosed in FIG. 1 and described in Example XIII. It is understood that a person skilled in the art would be able to readily identify enzymes of such competing pathways. Competing pathways can be dependent upon the host microbial organism and/or the exogenous nucleic acid introduced into the microbial organism as described herein. Accordingly, in some aspects of the invention, the microbial organism includes attenuation of one, two, three, four, five, six, seven, eight, nine, ten or more endogenous enzymes of a competing formaldehyde assimilation or dissimilation pathway.

In some embodiments, the invention provides a non-naturally occurring microbial organism as described herein, wherein the microbial organism further includes a gene disruption of one or more endogenous nucleic acids encoding enzymes, which enhances carbon flux through acetyl-CoA. For example, in some aspects, the endogenous enzyme can be selected from DHA kinase, methanol oxidase, PQQ-dependent methanol dehydrogenase, DHA synthase or any combination thereof. According, in some aspects, the gene disruptiondisruption is of an endogenous nucleic acid encoding the enzyme DHA kinase. In some aspects, the gene disruptiondisruption is of an endogenous nucleic acid encoding the enzyme methanol oxidase. In some aspects, the gene disruptiondisruption is of an endogenous nucleic acid encoding the enzyme PQQ-dependent methanol dehydrogenase. In some aspects, the gene disruption is of an endogenous nucleic acid encoding the enzyme DHA synthase. The invention also provides a microbial organism wherein the gene disruption is of any combination of two or three nucleic acids encoding endogenous enzymes described herein. For example, a microbial organism of the invention can include a gene disruption of DHA kinase and DHA synthase, or alternatively methanol oxidase and PQQ-dependent methanol dehydrogenase, or alternatively DHA kinase, methanol oxidase, and PQQ-dependent methanol dehydrogenase, or alternatively DHA kinase, methanol oxidase, and DHA synthase. The invention also provides a microbial organism wherein all endogenous nucleic acids encoding enzymes described herein are disrupted. For example, in some aspects, a microbial organism described herein includes disruption of DHA kinase, methanol oxidase, PQQ-dependent methanol dehydrogenase and DHA synthase.

In some embodiments, the invention provides a non-naturally occurring microbial organism as described herein, wherein the microbial organism further includes a gene disruption of one or more enzymes of a competing formaldehyde assimilation or dissimilation pathway. Examples of these endogenous enzymes are disclosed in FIG. 1 and described in Example XIII. It is understood that a person skilled in the art would be able to readily identify enzymes of such competing pathways. Competing pathways can be dependent upon the host microbial organism and/or the exogenous nucleic acid introduced into the microbial organism as described herein. Accordingly, in some aspects of the invention, the microbial organism includes a gene disruption of one, two, three, four, five, six, seven, eight, nine, ten or more endogenous nucleic acids encoding enzymes of a competing formaldehyde assimilation or dissimilation pathway.

In the case of gene disruptions, a particularly useful stable genetic alteration is a gene deletion. The use of a gene deletion to introduce a stable genetic alteration is particularly useful to reduce the likelihood of a reversion to a phenotype prior to the genetic alteration. For example, stable growth-coupled production of a biochemical can be achieved, for example, by deletion of a gene encoding an enzyme catalyzing one or more reactions within a set of metabolic modifications. The stability of growth-coupled production of a biochemical can be further enhanced through multiple deletions, significantly reducing the likelihood of multiple compensatory reversions occurring for each disrupted activity.

Also provided is a method of producing a non-naturally occurring microbial organisms having stable growth-coupled production of acetyl-CoA or a bioderived compound. The method can include identifying in silico a set of metabolic modifications that increase production of acetyl-CoA or a bioderived compound, for example, increase production during exponential growth; genetically modifying an organism to contain the set of metabolic modifications that increase production of acetyl-CoA or a bioderived compound, and culturing the genetically modified organism. If desired, culturing can include adaptively evolving the genetically modified organism under conditions requiring production of acetyl-CoA or a bioderived compound. The methods of the invention are applicable to bacterium, yeast and fungus as well as a variety of other cells and microorganism, as disclosed herein.

Thus, the invention provides a non-naturally occurring microbial organism comprising one or more gene disruptions that confer increased synthesis or production of acetyl-CoA or a bioderived compound. In one embodiment, the one or more gene disruptions confer growth-coupled production of acetyl-CoA or a bioderived compound, and can, for example, confer stable growth-coupled production of acetyl-CoA or a bioderived compound. In another embodiment, the one or more gene disruptions can confer obligatory coupling of acetyl-CoA or a bioderived compound production to growth of the microbial organism. Such one or more gene disruptions reduce the activity of the respective one or more encoded enzymes.

The non-naturally occurring microbial organism can have one or more gene disruptions included in a gene encoding a enzyme or protein disclosed herein. As disclosed herein, the one or more gene disruptions can be a deletion. Such non-naturally occurring microbial organisms of the invention include bacteria, yeast, fungus, or any of a variety of other microorganisms applicable to fermentation processes, as disclosed herein.

Thus, the invention provides a non-naturally occurring microbial organism, comprising one or more gene disruptions, where the one or more gene disruptions occur in genes encoding proteins or enzymes where the one or more gene disruptions confer increased production of acetyl-CoA or a bioderived compound. The production of acetyl-CoA or a bioderived compound can be growth-coupled or not growth-coupled. In a particular embodiment, the production of acetyl-CoA or a bioderived compound can be obligatorily coupled to growth of the organism, as disclosed herein.

The invention provides non naturally occurring microbial organisms having genetic alterations such as gene disruptions that increase production of acetyl-CoA or a bioderived compound, for example, growth-coupled production of acetyl-CoA or a bioderived compound. Product production can be, for example, obligatorily linked to the exponential growth phase of the microorganism by genetically altering the metabolic pathways of the cell, as disclosed herein. The genetic alterations can increase the production of the desired product or even make the desired product an obligatory product during the growth phase. Metabolic alterations or transformations that result in increased production and elevated levels of acetyl-CoA or a bioderived compound biosynthesis are exemplified herein. Each alteration corresponds to the requisite metabolic reaction that should be functionally disrupted. Functional disruption of all reactions within one or more of the pathways can result in the increased production of acetyl-CoA or a bioderived compound by the engineered strain during the growth phase.

Each of these non-naturally occurring alterations result in increased production and an enhanced level of acetyl-CoA or a bioderived compound, for example, during the exponential growth phase of the microbial organism, compared to a strain that does not contain such metabolic alterations, under appropriate culture conditions. Appropriate conditions include, for example, those disclosed herein, including conditions such as particular carbon sources or reactant availabilities and/or adaptive evolution.

Given the teachings and guidance provided herein, those skilled in the art will understand that to introduce a metabolic alteration such as attenuation of an enzyme, it can be necessary to disrupt the catalytic activity of the one or more enzymes involved in the reaction. Alternatively, a metabolic alteration can include disrupting expression of a regulatory protein or cofactor necessary for enzyme activity or maximal activity. Furthermore, genetic loss of a cofactor necessary for an enzymatic reaction can also have the same effect as a disruption of the gene encoding the enzyme. Disruption can occur by a variety of methods including, for example, deletion of an encoding gene or incorporation of a genetic alteration in one or more of the encoding gene sequences. The encoding genes targeted for disruption can be one, some, or all of the genes encoding enzymes involved in the catalytic activity. For example, where a single enzyme is involved in a targeted catalytic activity, disruption can occur by a genetic alteration that reduces or eliminates the catalytic activity of the encoded gene product. Similarly, where the single enzyme is multimeric, including heteromeric, disruption can occur by a genetic alteration that reduces or destroys the function of one or all subunits of the encoded gene products. Destruction of activity can be accomplished by loss of the binding activity of one or more subunits required to form an active complex, by destruction of the catalytic subunit of the multimeric complex or by both. Other functions of multimeric protein association and activity also can be targeted in order to disrupt a metabolic reaction of the invention. Such other functions are well known to those skilled in the art. Similarly, a target enzyme activity can be reduced or eliminated by disrupting expression of a protein or enzyme that modifies and/or activates the target enzyme, for example, a molecule required to convert an apoenzyme to a holoenzyme. Further, some or all of the functions of a single polypeptide or multimeric complex can be disrupted according to the invention in order to reduce or abolish the catalytic activity of one or more enzymes involved in a reaction or metabolic modification of the invention. Similarly, some or all of enzymes involved in a reaction or metabolic modification of the invention can be disrupted so long as the targeted reaction is reduced or eliminated.

Given the teachings and guidance provided herein, those skilled in the art also will understand that an enzymatic reaction can be disrupted by reducing or eliminating reactions encoded by a common gene and/or by one or more orthologs of that gene exhibiting similar or substantially the same activity. Reduction of both the common gene and all orthologs can lead to complete abolishment of any catalytic activity of a targeted reaction. However, disruption of either the common gene or one or more orthologs can lead to a reduction in the catalytic activity of the targeted reaction sufficient to promote coupling of growth to product biosynthesis. Exemplified herein are both the common genes encoding catalytic activities for a variety of metabolic modifications as well as their orthologs. Those skilled in the art will understand that disruption of some or all of the genes encoding a enzyme of a targeted metabolic reaction can be practiced in the methods of the invention and incorporated into the non-naturally occurring microbial organisms of the invention in order to achieve the increased production of acetyl-CoA or a bioderived compound or growth-coupled product production.

Given the teachings and guidance provided herein, those skilled in the art also will understand that enzymatic activity or expression can be attenuated using well known methods. Reduction of the activity or amount of an enzyme can mimic complete disruption of a gene if the reduction causes activity of the enzyme to fall below a critical level that is normally required for a pathway to function. Reduction of enzymatic activity by various techniques rather than use of a gene disruption can be important for an organism's viability. Methods of reducing enzymatic activity that result in similar or identical effects of a gene disruption include, but are not limited to: reducing gene transcription or translation; destabilizing mRNA, protein or catalytic RNA; and mutating a gene that affects enzyme activity or kinetics (See, Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999). Natural or imposed regulatory controls can also accomplish enzyme attenuation including: promoter replacement (See, Wang et al., *Mol. Biotechnol.* 52(2):300-308 (2012)); loss or alteration of transcription factors (Dietrick et al., *Annu. Rev. Biochem.* 79:563-590 (2010); and Simicevic et al., *Mol. Biosyst.* 6(3):462-468 (2010)); introduction of inhibitory RNAs or peptides such as siRNA, antisense RNA, RNA or peptide/small-molecule binding aptamers, ribozymes, aptazymes and riboswitches (Wieland et al., *Methods* 56(3):351-357 (2012); O'Sullivan, *Anal. Bioanal. Chem.* 372(1):44-48 (2002); and Lee et al., *Curr. Opin. Biotechnol.* 14(5):505-511 (2003)); and addition of drugs or other chemicals that reduce or disrupt enzymatic activity such as an enzyme inhibitor, an antibiotic or a target-specific drug.

One skilled in the art will also understand and recognize that attenuation of an enzyme can be done at various levels. For example, at the gene level, a mutation causing a partial or complete null phenotype, such as a gene disruption, or a mutation causing epistatic genetic effects that mask the activity of a gene product (Miko, *Nature Education* 1(1) (2008)), can be used to attenuate an enzyme. At the gene expression level, methods for attenuation include: coupling transcription to an endogenous or exogenous inducer, such as isopropylthio-β-galactoside (IPTG), then adding low amounts of inducer or no inducer during the production phase (Donovan et al., *J. Ind. Microbiol.* 16(3):145-154 (1996); and Hansen et al., *Curr. Microbiol.* 36(6):341-347 (1998)); introducing or modifying a positive or a negative regulator of a gene; modify histone acetylation/deacetylation in a eukaryotic chromosomal region where a gene is integrated (Yang et al., *Curr. Opin. Genet. Dev.* 13(2):143-153 (2003) and Kurdistani et al., *Nat. Rev. Mol. Cell Biol.* 4(4):276-284 (2003)); introducing a transposition to disrupt a promoter or a regulatory gene (Bleykasten-Brosshans et al., *C. R. Biol.* 33(8-9):679-686 (2011); and McCue et al., *PLoS Genet.* 8(2):e1002474 (2012)); flipping the orientation of a transposable element or promoter region so as to modulate gene expression of an adjacent gene (Wang et al., *Genetics* 120(4):875-885 (1988); Hayes, *Anna. Rev. Genet* 37:3-29 (2003); in a diploid organism, deleting one allele resulting in loss of heterozygosity (Daigaku et al., *Mutation Research/Fundamental and Molecular Mechanisms of Mutagenesis* 600(1-2)177-183 (2006)); introducing nucleic acids that increase RNA degradation (Houseley et al., *Cell*, 136(4):763-776 (2009); or in bacteria, for example, introduction of a transfer-messenger RNA (tmRNA) tag, which can lead to RNA degradation and ribosomal stalling (Sunohara et al., *RNA* 10(3):378-386 (2004); and Sunohara et al., *J. Biol. Chem.* 279:15368-15375 (2004)). At the translational level, attenuation can include: introducing rare codons to limit translation (Angov, *Biotechnol. J.* 6(6):650-659 (2011)); introducing RNA interference molecules that block translation (Castel et al., *Nat. Rev. Genet.* 14(2):100-112 (2013); and Kawasaki et al., *Curr. Opin. Mol. Ther.* 7(2):125-131(2005); modifying regions outside the coding sequence, such as introducing secondary structure into an untranslated region (UTR) to block translation or reduce efficiency of translation (Ringnér et al., *PLoS Comput. Biol.* 1(7):e72 (2005)); adding RNAase sites for rapid transcript degradation (Pasquinelli, *Nat. Rev. Genet.* 13(4):271-282 (2012); and Arraiano et al., *FEMS Microbiol. Rev.* 34(5):883-932 (2010); introducing antisense RNA oligomers or antisense transcripts (Nashizawa et al., *Front. Biosci.* 17:938-958 (2012)); introducing RNA or peptide aptamers, ribozymes, aptazymes, riboswitches (Wieland et al., *Methods* 56(3):351-357 (2012); O'Sullivan, *Anal. Bioanal. Chem.* 372(1):44-48 (2002); and Lee et al., *Curr. Opin. Biotechnol.* 14(5):505-511(2003)); or introducing translational regulatory elements involving RNA structure that can prevent or reduce translation that can be controlled by the presence or absence of small molecules (Araujo et al., *Comparative and Functional Genomics*, Article ID 475731, 8 pages (2012)). At the level of enzyme localization and/or longevity, enzyme attenuation can include: adding a degradation tag for faster protein turnover (Hochstrasser, *Annual Rev. Genet.* 30:405-439 (1996); and Yuan et al., *PLoS One* 8(4):e62529 (2013)); or adding a localization tag that results in the enzyme being secreted or localized to a subcellular compartment in a eukaryotic cell, where the enzyme would not be able to react with its normal substrate (Nakai et al. *Genomics* 14(4):897-911(1992); and Russell et al., *J. Bact.* 189(21)7581-7585 (2007)). At the level of post-translational regulation, enzyme attenuation can include: increasing intracellular concentration of known inhibitors; or modifying post-translational modified sites (Mann et al., *Nature Biotech.* 21:255-261(2003)). At the level of enzyme activity, enzyme attenuation can include: adding an endogenous or an exogenous inhibitor, such as an enzyme inhibitor, an antibiotic or a target-specific drug, to reduce enzyme activity; limiting availability of essential cofactors, such as vitamin B12, for an enzyme that requires the cofactor; chelating a metal ion that is required for enzyme activity; or introducing a dominant negative mutation. The applicability of a technique for attenuation described above can depend upon whether a given host microbial organism is prokaryotic or eukaryotic, and it is understand that a determination of what is the appropriate technique for a given host can be readily made by one skilled in the art.

In some embodiments, microaerobic designs can be used based on the growth-coupled formation of the desired product. To examine this, production cones can be constructed for each strategy by first maximizing and, subsequently minimizing the product yields at different rates of biomass formation feasible in the network. If the rightmost boundary of all possible phenotypes of the mutant network is a single point, it implies that there is a unique optimum yield of the product at the maximum biomass formation rate possible in the network. In other cases, the rightmost boundary of the feasible phenotypes is a vertical line, indicating that at the point of maximum biomass the network can make any amount of the product in the calculated range, including the lowest amount at the bottommost point of the vertical line. Such designs are given a low priority.

The acetyl-CoA or a bioderived compound production strategies identified herein can be disrupted to increase production of acetyl-CoA or a bioderived compound. Accordingly, the invention also provides a non-naturally occurring microbial organism having metabolic modifications coupling acetyl-CoA or a bioderived compound production to growth of the organism, where the metabolic modifications includes disruption of one or more genes selected from the genes encoding proteins and/or enzymes shown in the various tables disclosed herein.

Each of the strains can be supplemented with additional deletions if it is determined that the strain designs do not sufficiently increase the production of acetyl-CoA or a bioderived compound and/or couple the formation of the product with biomass formation. Alternatively, some other enzymes not known to possess significant activity under the growth conditions can become active due to adaptive evolution or random mutagenesis. Such activities can also be knocked out. However, the genes disclosed herein allows the construction of strains exhibiting high-yield synthesis or production of acetyl-CoA or a bioderived compound, including growth-coupled production of acetyl-CoA or a bioderived compound.

The invention is described herein with general reference to the metabolic reaction, reactant or product thereof, or with specific reference to one or more nucleic acids or genes encoding an enzyme associated with or catalyzing, or a protein associated with, the referenced metabolic reaction, reactant or product. Unless otherwise expressly stated herein, those skilled in the art will understand that reference to a reaction also constitutes reference to the reactants and products of the reaction. Similarly, unless otherwise expressly stated herein, reference to a reactant or product also references the reaction, and reference to any of these metabolic constituents also references the gene or genes encoding the enzymes that catalyze or proteins involved in the referenced reaction, reactant or product. Likewise, given the well known fields of metabolic biochemistry, enzymology and genomics, reference herein to a gene or encoding nucleic acid also constitutes a reference to the corresponding encoded enzyme and the reaction it catalyzes or a protein associated with the reaction as well as the reactants and products of the reaction.

As disclosed herein, the bioderived compounds adipate, 6-aminocaproate, methacrylic acid, 2-hydroxyisobutyric acid, as well as other intermediates, are carboxylic acids, which can occur in various ionized forms, including fully protonated, partially protonated, and fully deprotonated forms. Accordingly, the suffix "-ate," or the acid form, can be used interchangeably to describe both the free acid form as well as any deprotonated form, in particular since the ionized form is known to depend on the pH in which the compound is found. It is understood that carboxylate products or intermediates includes ester forms of carboxylate products or pathway intermediates, such as O-carboxylate and S-carboxylate esters. O- and S-carboxylates can include lower alkyl, that is C1 to C6, branched or straight chain carboxylates. Some such O- or S-carboxylates include, without limitation, methyl, ethyl, n-propyl, n-butyl, i-propyl, sec-butyl, and tert-butyl, pentyl, hexyl O- or S-carboxylates, any of which can further possess an unsaturation, providing for example, propenyl, butenyl, pentyl, and hexenyl O- or S-carboxylates. O-carboxylates can be the product of a biosynthetic pathway. Exemplary O-carboxylates accessed via biosynthetic pathways can include, without limitation, methyl adipate, ethyl adipate, and n-propyl adipate. Other biosynthetically accessible O-carboxylates can include medium to long chain groups, that is C7-C22, O-carboxylate esters derived from fatty alcohols, such heptyl, octyl, nonyl, decyl, undecyl, lauryl, tridecyl, myristyl, pentadecyl, cetyl, palmitoyl, heptadecyl, stearyl, nonadecyl, arachidyl, heneicosyl, and behenyl alcohols, any one of which can be optionally branched and/or contain unsaturations. O-carboxylate esters can also be accessed via a biochemical or chemical process, such as esterification of a free carboxylic acid product or transesterification of an O- or S-carboxylate. S-carboxylates are exemplified by CoA S-esters, cysteinyl S-esters, alkylthioesters, and various aryl and heteroaryl thioesters.

The non-naturally occurring microbial organisms of the invention can be produced by introducing expressible nucleic acids encoding one or more of the enzymes or proteins participating in one or more acetyl-CoA or a bioderived compound biosynthetic pathways. Depending on the host microbial organism chosen for biosynthesis, nucleic acids for some or all of a particular acetyl-CoA or a bioderived compound biosynthetic pathway can be expressed. For example, if a chosen host is deficient in one or more enzymes or proteins for a desired biosynthetic pathway, then expressible nucleic acids for the deficient enzyme(s) or protein(s) are introduced into the host for subsequent exogenous expression. Alternatively, if the chosen host exhibits endogenous expression of some pathway genes, but is deficient in others, then an encoding nucleic acid is needed for the deficient enzyme(s) or protein(s) to achieve acetyl-CoA or a bioderived compound biosynthesis. Thus, a non-naturally occurring microbial organism of the invention can be produced by introducing exogenous enzyme or protein activities to obtain a desired biosynthetic pathway or a desired biosynthetic pathway can be obtained by introducing one or more exogenous enzyme or protein activities that, together with one or more endogenous enzymes or proteins, produces a desired product such as acetyl-CoA or a bioderived compound.

Host microbial organisms can be selected from, and the non-naturally occurring microbial organisms generated in, for example, bacteria, yeast, fungus or any of a variety of other microorganisms applicable or suitable to fermentation processes. Exemplary bacteria include any species selected from the order Enterobacteriales, family Enterobacteriaceae, including the genera *Escherichia* and *Klebsiella*; the order Aeromonadales, family Succinivibrionaceae, including the genus *Anaerobiospirillum*; the order Pasteurellales, family Pasteurellaceae, including the genera *Actinobacillus* and *Mannheimia*; the order Rhizobiales, family Bradyrhizobiaceae, including the genus *Rhizobium*; the order Bacillales, family Bacillaceae, including the genus *Bacillus*; the order Actinomycetales, families Colynebacteriaceae and Streptomycetaceae, including the genera *Corynebacterium* and the genus *Streptomyces*, respectively; order Rhodospirillales, family Acetobacteraceae, including the genus *Gluconobacter;* the order Sphingomonadales, family Sphingomonadaceae, including the genus *Zymomonas*; the order Lactobacillales, families Lactobacillaceae and Streptococcaceae, including the genus *Lactobacillus* and the genus *Lactococcus*, respectively; the order Clostridiales, family Clostridiaceae, genus *Clostridium*; and the order Pseudomonadales, family Pseudomonadaceae, including the genus *Pseudomonas*. Non-limiting species of host bacteria include *Escherichia coli, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens,* and *Pseudomonas putida*. Exemplary bacterial methylotrophs include, for example, *Bacillus, Methylobacterium, Methyloversatilis, Methylococcus, Methylocystis* and *Hyphomicrobium*.

Similarly, exemplary species of yeast or fungi species include any species selected from the order Saccharomycetales, family Saccaromycetaceae, including the genera *Saccharomyces, Kluyveromyces* and *Pichia*; the order Saccharomycetales, family Dipodascaceae, including the genus *Yarrowia*; the order Schizosaccharomycetales, family Schizosaccaromycetaceae, including the genus *Schizosaccharomyces*; the order Eurotiales, family Trichocomaceae, including the genus *Aspergillus*; and the order Mucorales, family Mucoraceae, including the genus *Rhizopus*. Non-limiting species of host yeast or fungi include *Saccharomyces cerevisiae, Schizosaccharomyces pombe, Kluyveromyces lactis, Kluyveromyces marxianus, Aspergillus terreus, Aspergillus niger, Pichia pastoris, Rhizopus arrhizus, Rhizobus oryzae, Yarrowia lipolytica*, and the like. *E. coli* is a particularly useful host organism since it is a well characterized microbial organism suitable for genetic engineering. Other particularly useful host organisms include yeast such as *Saccharomyces cerevisiae* and yeasts or fungi selected from the genera *Saccharomyces, Schizosaccharomyces, Schizochytrium, Rhodotorula, Thraustochytrium, Aspergillus, Kluyveromyces, Issatchenkia, Yarrowia, Candida, Pichia, Ogataea, Kuraishia, Hansenula* and *Komagataella*. Useful host organisms include *Saccharomyces cerevisiae, Schizosaccharomyces pombe, Hansenula polymorpha, Pichia methanolica, Candida boidinii, Kluyveromyces lactis, Kluyveromyces marxianus, Aspergillus terreus, Aspergillus niger, Pichia pastoris, Rhizopus arrhizus, Rhizobus oryzae, Yarrowia lipolytica, Issatchenkia orientalis* and the like. It is understood that any suitable microbial host organism can be used to introduce metabolic and/or genetic modifications to produce a desired product.

Depending on the acetyl-CoA or the bioderived compound biosynthetic pathway constituents of a selected host microbial organism, the non-naturally occurring microbial organisms of the invention will include at least one exogenously expressed acetyl-CoA or a bioderived compound pathway-encoding nucleic acid and up to all encoding nucleic acids for one or more acetyl-CoA or a bioderived compound biosynthetic pathways. For example, acetyl-CoA or a bioderived compound biosynthesis can be established in a host deficient in a pathway enzyme or protein through exogenous expression of the corresponding encoding nucleic acid. In a host deficient in all enzymes or proteins of an acetyl-CoA or a bioderived compound pathway, exogenous expression of all enzyme or proteins in the pathway can be included, although it is understood that all enzymes or proteins of a pathway can be expressed even if the host contains at least one of the pathway enzymes or proteins. For example, exogenous expression of all enzymes or proteins in a pathway for production of acetyl-CoA or a bioderived compound can be included, such as a fructose-6-phosphate phosphoketolase and a phosphotransacetylase (see, e.g. FIG. 1), or a xylulose-5-phosphate phosphoketolase and a phosphotransacetylase (see, e.g. FIG. 1), or a methanol dehydrogenase, a 3-hexulose-6-phosphate synthase, a 6-phospho-3-hexuloisomerase, a fructose-6-phosphate phosphoketolase and a phosphotransacetylase (see, e.g. FIG. 1), or an acetyl-CoA:acetyl-CoA acyltransferase, an acetoacetyl-CoA reductase (ketone reducing), a 3-hydroxybutyryl-CoA reductase (aldehyde forming), and a 3-hydroxybutyraldehyde reductase (see, e.g. FIG. 5), or a succinyl-CoA reductase (aldehyde forming), a 4-HB dehydrogenase, a 4-HB kinase, a phosphotrans-4-hydroxybutyrylase, a 4-hydroxybutyryl-CoA reductase (aldehyde forming), and a 1,4-butanediol dehydrogenase (see, e.g. FIG. 7), or a 3-oxoadipyl-CoA thiolase, a 3-oxoadipyl-CoA reductase, a 3-hydroxyadipyl-CoA dehydratase, a 5-carboxy-2-pentenoyl-CoA reductase, an adipyl-CoA reductase (aldehyde forming), and 6-aminocaproate transaminase (see, e.g. FIG. 8), or an acetyl-CoA:acetyl-CoA acyltransferase, an acetoacetyl-CoA reductase (ketone reducing), a 3-hydroxybutyrl-CoA mutase, a 2-hydroxyisobutyryl-CoA dehydratase, and a methacrylyl-CoA synthetase (see, e.g. FIG. 10).

Given the teachings and guidance provided herein, those skilled in the art will understand that the number of encoding nucleic acids to introduce in an expressible form will, at least, parallel the acetyl-CoA or the bioderived compound pathway deficiencies of the selected host microbial organism. Therefore, a non-naturally occurring microbial organism of the invention can have one, two, three, four, five, six, seven, eight, nine, ten, eleven, or twelve up to all nucleic acids encoding the enzymes or proteins constituting an acetyl-CoA or a bioderived compound biosynthetic pathway disclosed herein. In some embodiments, the non-naturally occurring microbial organisms also can include other genetic modifications that facilitate or optimize acetyl-CoA or a bioderived compound biosynthesis or that confer other useful functions onto the host microbial organism. One such other functionality can include, for example, augmentation of the synthesis of one or more of the acetyl-CoA or the bioderived compound pathway precursors such as Fald, H6P, DHA, G3P, malonyl-CoA, acetoacetyl-CoA, PEP, PYR and Succinyl-CoA.

Generally, a host microbial organism is selected such that it produces the precursor of an acetyl-CoA or a bioderived compound pathway, either as a naturally produced molecule or as an engineered product that either provides de novo production of a desired precursor or increased production of a precursor naturally produced by the host microbial organism. For example, malonyl-CoA, acetoacetyl-CoA and pyruvate are produced naturally in a host organism such as *E. coli*. A host organism can be engineered to increase production of a precursor, as disclosed herein. In addition, a microbial organism that has been engineered to produce a desired precursor can be used as a host organism and further engineered to express enzymes or proteins of an acetyl-CoA or a bioderived compound pathway.

In some embodiments, a non-naturally occurring microbial organism of the invention is generated from a host that contains the enzymatic capability to synthesize acetyl-CoA or a bioderived compound. In this specific embodiment it can be useful to increase the synthesis or accumulation of an acetyl-CoA or a bioderived compound pathway product to, for example, drive acetyl-CoA or a bioderived compound pathway reactions toward acetyl-CoA or a bioderived compound production. Increased synthesis or accumulation can be accomplished by, for example, overexpression of nucleic acids encoding one or more of the above-described acetyl-CoA or a bioderived compound pathway enzymes or proteins. Overexpression of the enzyme or enzymes and/or protein or proteins of the acetyl-CoA or the bioderived compound pathway can occur, for example, through exogenous expression of the endogenous gene or genes, or through exogenous expression of the heterologous gene or genes. Therefore, naturally occurring organisms can be readily generated to be non-naturally occurring microbial organisms of the invention, for example, producing acetyl-CoA or a bioderived compound, through overexpression of one, two, three, four, five, six, seven, eight, nine, ten, eleven, twelve, that is, up to all nucleic acids encoding acetyl-CoA or a bioderived compound biosynthetic pathway enzymes or proteins. In addition, a non-naturally occurring organism can be generated by mutagenesis of an endogenous gene that results in an increase in activity of an enzyme in the acetyl-CoA or the bioderived compound biosynthetic pathway.

In particularly useful embodiments, exogenous expression of the encoding nucleic acids is employed. Exogenous expression confers the ability to custom tailor the expression and/or regulatory elements to the host and application to achieve a desired expression level that is controlled by the user. However, endogenous expression also can be utilized in other embodiments such as by removing a negative regulatory effector or induction of the gene's promoter when linked to an inducible promoter or other regulatory element. Thus, an endogenous gene having a naturally occurring inducible promoter can be up-regulated by providing the appropriate inducing agent, or the regulatory region of an endogenous gene can be engineered to incorporate an inducible regulatory element, thereby allowing the regulation of increased expression of an endogenous gene at a desired time. Similarly, an inducible promoter can be included as a regulatory element for an exogenous gene introduced into a non-naturally occurring microbial organism.

It is understood that, in methods of the invention, any of the one or more exogenous nucleic acids can be introduced into a microbial organism to produce a non-naturally occurring microbial organism of the invention. The nucleic acids can be introduced so as to confer, for example, an acetyl-CoA or a bioderived compound biosynthetic pathway onto the microbial organism. Alternatively, encoding nucleic acids can be introduced to produce an intermediate microbial organism having the biosynthetic capability to catalyze some of the required reactions to confer acetyl-CoA or a bioderived compound biosynthetic capability. For example, a non-naturally occurring microbial organism having an acetyl-CoA or a bioderived compound biosynthetic pathway can comprise at least two exogenous nucleic acids encoding desired enzymes or proteins, such as the combination of a 3-hexulose-6-phosphate synthase and a fructose-6-phosphate phosphoketolase, or alternatively a xylulose-5-phosphate phosphoketolase and an acetyl-CoA transferase, or alternatively a fructose-6-phosphate phosphoketolase and a formate reductase, or alternatively a xylulose-5-phosphate phosphoketolase and a methanol dehydrogenase, and the like. Thus, it is understood that any combination of two or more enzymes or proteins of a biosynthetic pathway can be included in a non-naturally occurring microbial organism of the invention. Similarly, it is understood that any combination of three or more enzymes or proteins of a biosynthetic pathway can be included in a non-naturally occurring microbial organism of the invention, for example, a methanol dehydrogenase, a fructose-6-phosphate aldolase, and a fructose-6-phosphate phosphoketolase, or alternatively a methanol methyltransferase, fructose-6-phosphate phosphoketolase and a 3-hydroxybutyraldehyde reductase, or alternatively a xylulose-5-phosphate phosphoketolase, a pyruvate formate lyase and a 4-hydroxybutyryl-CoA reductase (alcohol forming), or alternatively a fructose-6-phosphate aldolase, a phosphotransacetylase, and a 3-hydroxyisobutyrate dehydratase, and so forth, as desired, so long as the combination of enzymes and/or proteins of the desired biosynthetic pathway results in production of the corresponding desired product. Similarly, any combination of four, five, six, seven, eight, nine, ten, eleven, twelve or more enzymes or proteins of a biosynthetic pathway as disclosed herein can be included in a non-naturally occurring microbial organism of the invention, as desired, so long as the combination of enzymes and/or proteins of the desired biosynthetic pathway results in production of the corresponding desired product.

In addition to the biosynthesis of acetyl-CoA or a bioderived compound as described herein, the non-naturally occurring microbial organisms and methods of the invention also can be utilized in various combinations with each other and/or with other microbial organisms and methods well known in the art to achieve product biosynthesis by other routes. For example, one alternative to produce acetyl-CoA or a bioderived compound other than use of the acetyl-CoA or the bioderived compound producers is through addition of another microbial organism capable of converting an acetyl-CoA or a bioderived compound pathway intermediate to acetyl-CoA or a bioderived compound. One such procedure includes, for example, the fermentation of a microbial organism that produces an acetyl-CoA or a bioderived compound pathway intermediate. The acetyl-CoA or the bioderived compound pathway intermediate can then be used as a substrate for a second microbial organism that converts the acetyl-CoA or the bioderived compound pathway intermediate to acetyl-CoA or a bioderived compound. The acetyl-CoA or the bioderived compound pathway intermediate can be added directly to another culture of the second organism or the original culture of the acetyl-CoA or the bioderived compound pathway intermediate producers can be depleted of these microbial organisms by, for example, cell separation, and then subsequent addition of the second organism to the fermentation broth can be utilized to produce the final product without intermediate purification steps.

In other embodiments, the non-naturally occurring microbial organisms and methods of the invention can be assembled in a wide variety of subpathways to achieve biosynthesis of, for example, acetyl-CoA or a bioderived compound. In these embodiments, biosynthetic pathways for a desired product of the invention can be segregated into different microbial organisms, and the different microbial organisms can be co-cultured to produce the final product. In such a biosynthetic scheme, the product of one microbial organism is the substrate for a second microbial organism until the final product is synthesized. For example, the biosynthesis of acetyl-CoA or a bioderived compound can be accomplished by constructing a microbial organism that contains biosynthetic pathways for conversion of one pathway intermediate to another pathway intermediate or the product. Alternatively, acetyl-CoA or a bioderived compound also can be biosynthetically produced from microbial organisms through co-culture or co-fermentation using two organisms in the same vessel, where the first microbial organism produces an acetyl-CoA or a bioderived compound intermediate and the second microbial organism converts the intermediate to acetyl-CoA or a bioderived compound.

Given the teachings and guidance provided herein, those skilled in the art will understand that a wide variety of combinations and permutations exist for the non-naturally occurring microbial organisms and methods of the invention together with other microbial organisms, with the co-culture of other non-naturally occurring microbial organisms having subpathways and with combinations of other chemical and/or biochemical procedures well known in the art to produce acetyl-CoA or a bioderived compound.

Similarly, it is understood by those skilled in the art that a host organism can be selected based on desired characteristics for introduction of one or more gene disruptions to increase synthesis or production of acetyl-CoA or a bioderived compound. Thus, it is understood that, if a genetic modification is to be introduced into a host organism to disrupt a gene, any homologs, orthologs or paralogs that catalyze similar, yet non-identical metabolic reactions can similarly be disrupted to ensure that a desired metabolic reaction is sufficiently disrupted. Because certain differences exist among metabolic networks between different organisms, those skilled in the art will understand that the actual genes disrupted in a given organism may differ between organisms. However, given the teachings and guidance provided herein, those skilled in the art also will understand that the methods of the invention can be applied to any suitable host microorganism to identify the cognate metabolic alterations needed to construct an organism in a species of interest that will increase acetyl-CoA or a bioderived compound biosynthesis. In a particular embodiment, the increased production couples biosynthesis of acetyl-CoA or a bioderived compound to growth of the organism, and can obligatorily couple production of acetyl-CoA or a bioderived compound to growth of the organism if desired and as disclosed herein.

Sources of encoding nucleic acids for an acetyl-CoA or a bioderived compound pathway enzyme or protein can include, for example, any species where the encoded gene product is capable of catalyzing the referenced reaction. Such species include both prokaryotic and eukaryotic organisms including, but not limited to, bacteria, including archaea and eubacteria, and eukaryotes, including yeast, plant, insect, animal, and mammal, including human. Exemplary species for such sources include, for example, *Escherichia coli, Abies grandis, Acetobacter aceti, Acetobacter pasteurians, Achromobacter denitqicans, Acidaminococcus fermentans, Acinetobacter baumannii* Naval-82, *Acinetobacter baylyi, Acinetobacter calcoaceticus, Acinetobacter* sp. ADP1, *Acinetobacter* sp. Strain M-1, *Actinobacillus succinogenes, Actinobacillus succinogenes* 130Z, *Aeropyrum pernix, Agrobacterium tumefaciens, Alkaliphilus metalliredigenes* QYF, *Allochromatium vinosum* DSM 180, *Aminomonas aminovorus, Amycolicicoccus subflavus* DQS3-9A1, *Anaerobiospirillum succiniciproducens, Anaerotruncus colihominis, Aquifex aeolicus* VF 5, *Arabidopsis thaliana, Arabidopsis thaliana* col, *Archaeglubus fulgidus, Archaeoglobus fulgidus, Archaeoglobus fulgidus* DSM 4304, *Arthrobacter globiformis, Ascaris suum, Aspergillus fumigatus, Aspergillus nidulans, Aspergillus niger, Aspergillus niger* CBS 513.88, *Aspergillus terreus* 1VIH2624, *Atopobium parvulum* DSM 20469, *Azotobacter vinelandii* DJ, *Bacillus alcalophilus* ATCC 27647, *Bacillus azotofomians* LMG 9581, *Bacillus cereus, Bacillus cereus* ATCC 14579, *Bacillus coagulans* 36D1, *Bacillus megaterium, Bacillus methanolicus* MGA3, *Bacillus methanolicus* PB1, *Bacillus methanolicus* PB-1, *Bacillus selenitireducens* MLS10, *Bacillus smithii, Bacillus sphaericus, Bacillus subtilis, Bacteroides capillosus, Bifidobacterium animalis lactis, Bifidobacterium breve, Bifidobacterium dentium* ATCC 27678, *Bifidobacterium pseudolongum* subsp. *globosum, Bos taurus, Burkholderia cenocepacia, Burkholderia cepacia, Burkholderia multivorans, Burkholderia pyrrocinia, Burkholderia stabilis, Burkholderia thailandensis* E264, *Burkholderia xenovorans*, butyrate producing bacterium L2-50, *Caenorhabditis elegans, Campylobacter curvus* 525.92, *Campylobacter jejuni, Candida albicans, Candida boidinii, Candida methylica, Candida parapsilosis, Candida tropicalis, Candida tropicalis* MYA-3404, *Carboxydothermus hydrogenoformans, Carboxydothermus hydrogenoformans* Z-2901, *Castellaniella defragrans, Caulobacter* sp. AP07, *Chlamydomonas reinhardtii, Chlorobium phaeobacteroides* DSM 266, *Chlorobium limicola, Chlorobium tepidum, Chloroflexus aggregans* DSM 9485, *Chloroflexus aurantiacus, Chloroflexus aurantiacus* J-10-fl, *Citrobacter koseri* ATCC BAA-895, *Citrobacter youngae, Citrobacter youngae* ATCC 29220, *Clostridium acetobutylicum, Clostridium acetobutylicum* ATCC 824, *Clostridium acidurici, Clostridium aminobuOxicum, Clostridium asparagiforme* DSM 15981, *Clostridium beijerinckii, Clostridium beijerinckii* NCIMB 8052, *Clostridium beijerinckii* NRRL B593, *Clostridium beijerinckii, Clostridium bolteae* ATCC BAA-613, *Clostridium botulinum* C str. Eklund, *Clostridium carboxidivorans* P7, *Clostridium cellulolyticum* H10, *Clostridium cellulovorans* 743B, *Clostridium difficile, Clostridium dOicile* 630, *Clostridium hiranonis* DSM 13275, *Clostridium hylemonae* DSM 15053, *Clostridium kluyveri, Clostridium kluyveri* DSM 555, *Clostridium ljungdahli, Clostridium ljungdahlii* DSM, *Clostridium ljungdahlii* DSM 13528, *Clostridium methylpentosum* DSM 5476, *Clostridium novyi* NT, *Clostridium pasteurianum, Clostridium pasteurianum* DSM 525, *Clostridium perfringens, Clostridium perfringens* ATCC 13124, *Clostridium perfringens* str. 13, *Clostridium phytofermentans* ISDg, *Clostridium propionicum, Clostridium saccharobutylicum, Clostridium saccharoperbutylacetonicum, Clostridium saccharoperbutylacetonicum* N1-4, *Clostridium tetani, Comamonas* sp. CNB-1, *Comamonas* sp. CNB-1, *Corynebacterium glutamicum, Corynebacterium glutamicum* ATCC 13032, *Corynebacterium glutamicum* ATCC 14067, *Corynebacterium glutamicum* R, *Corynebacterium* sp., *Corynebacterium* sp. U-96, *Corynebacterium variabile, Cryptosporidium parvum* Iowa II, *Cucumis sativus, Cupriavidus necator* N-1, *Cyanobium* PCC7001, *Deinococcus radiodurans* R1, *Desulfatibacillum alkenivorans* AK-01, *Desulfitobacterium hafinense, Desulfitobacterium metallireducens* DSM 15288, *Desulfbtomaculum reducens* MI-1, *Desulfovibrio africanus, Desulfovibrio africanus* str. Walvis Bay, *DesulfoVibrio desulfuricans* G20, *Desulfovibrio desulfuricans* subsp. *desulfuricans* str. ATCC 27774, *Desulfovibrio fructosovorans* JJ, *Desulfovibrio vulgaris* str. Hildenborough, *Dictyostelium discoideum* AX4, *Elizabethkingia meningoseptica, Enterococcus faecalis, Erythrobacter* sp. NAP1, *Escherichia coli* C, *Escherichia coli* K12, *Escherichia coli* K-12 MG1655, *Escherichia coli* W, *Eubacterium barkeri, Eubacterium hallii* DSM 3353, *Eubacterium rectale* ATCC 33656, *Euglena gracilis, Flavobacterium frigoris, Fusobacterium nucleatum, Fusobacterium nucleatum* subsp. polymorphum ATCC 10953, *Geobacillus* sp. GHH01, *Geobacillus* sp. M10EXG, *Geobacillus* sp. Y4.1MC1, *Geobacillus stearothermophilus, Geobacillus themodenitnficans* NG80-2, *Geobacillus thermoglucosidasius, Geobacter bemidjiensis* Bem, *Geobacter metallireducens* GS-15, *Geobacter sulfurreducens, Geobacter sul-* furreducens PCA, Haemophilus influenza, Haemophilus influenzae, Haloarcula marismortui, Haloarcula marismortui ATCC 43049, Halobacterium salinarum, Hansenula polymorpha DL-1, Helicobacter pylori, Helicobacter pylori 26695, Heliobacter pylori, Homo sapiens, human gut metagenome, Hydrogenobacter thermophilus, Hydrogenobacter thermophilus TK-6, Hyphomicrobium denitnficans ATCC 51888, Hyphomicrobium zavarzinii, Klebsiella pneumoniae, Klebsiella pneumoniae subsp. pneumoniae MGH 78578, Kluyveromyces lactis, Kluyveromyces lactis NRRL Y-1140, Lactobacillus acidophilus, Lactobacillus brevis ATCC 367, Lactobacillus paraplantarum, Lactococcus lactis, Leuconostoc mesenteroides, Lysinibacillus fusifbnnis, Lysinibacillus sphaericus, Malus x domestica, Mannheimia succiniciproducens, marine gamma proteobacterium HTCC2080, Marine metagenome JCVI_SCAF_1096627185304, Mesorhizobium loti MAFF303099, Metallosphaera sedula, Metarhizium acridum CQMa 102, Methanocaldococcus janaschii, Methanocaldococcus jannaschii, Methanosarcina acetivorans, Methanosarcina acetivorans C2A, Methanosarcina barkeri, Methanosarcina mazei, Methanosarcina mazei Tuc01, Methanosarcina thermophila, Methanothermobacter thermautotrophicus, Methylibium petroleiphilum PM1, Methylobacillusf lagellatus, Methylobacillus flagellatus KT, Methylobacter marinus, Methylobacterium extorquens, Methylobacterium extorquens AM1, Methylococcus capsulatas, Methylomicrobium album BG8, Methylomonas aminofaciens, Methylovorus glucosetrophus SIP3-4, Methylovorus sp. MP688, Moorella thermoacetica, Mus musculus, Mycobacter sp. strain JC1 DSM 3803, Mycobacterium avium subsp. paratuberculosis K-10, Mycobacterium bovis BCG, Mycobacterium gastri, Mycobacterium marinum M, Mycobacterium smegmatis, Mycobacterium smegmatis MC2 155, Mycobacterium tuberculosis, Mycoplasma pneumoniae M129, Natranaerobius thermophilus, Nectria haematococca mpVI 77-13-4, Neurospora crassa, Nitrososphaera gargensis Ga9.2, Nocardia brasiliensis, Nocardia farcinica IFM 10152, Nocardia iowensis, Nocardia iowensis (sp. NRRL 5646), Nostoc sp. PCC 7120, Ogataea parapolymorpha DL-1 (Hansenula polymorpha DL-1), Organism, Oryctolagus cuniculus, Oxalobacter fonnigenes, Paenibacillus peoriae KCTC 3763, Paracoccus denitnficans, Pelobacter carbinolicus DSM 2380, Pelotomaculum thermopropionicum, Penicillium chrysogenum, Perkinsus marinus ATCC 50983, Photobacterium profundum 3TCK, Picea abies, Pichia pastoris, Picrophilus torridus DSM9790, Pinus sabiniana, Plasmodium falciparum, Populus alba, Populus tremula x Populus alba, Porphyromonas gingivalis, Porphyromonas gingivalis W83, Propionibacterium acnes, Propionibacterium fredenreichii sp. shermanii, Pseudomonas aeruginosa, Pseudomonas aeruginosa PA01, Pseudomonas chlororaphis, Pseudomonas fluorescens, Pseudomonas knackmussii, Pseudomonas knackmussii (B13), Pseudomonas mendocina, Pseudomonas putida, Pseudomonas sp, Pseudomonas syringae pv. syringae B728a, Psychroflexus torquis ATCC 700755, Pueraria montana, Pyrobaculum aerophilum str. IM2, Pyrobaculum islandicum DSM 4184, Pyrococcus abyssi, Pyrococcus furiosus, Pyrococcus horikoshii OT3, Ralstonia eutropha, Ralstonia eutropha H16, Rattus norvegicus, Rhizobium leguminosarum, Rhodobacter capsulatus, Rhodobacter sphaeroides, Rhodobacter sphaeroides ATCC 17025, Rhodococcus opacus B4, Rhodococcus ruber, Rhodopseudomonas palustris, Rhodopseudomonas palustris CGA009, Rhodospirillum rubrum, Rhodospirillum rubrum ATCC 11170, Roseburia intestinalis L1-82, Roseburia inulinivorans, Roseburia sp. A2-183, Roseiflexus castenholzii, Rubrivivax gelatinosus, Ruminococcus obeum ATCC 29174, Saccharomyces cerevisiae, Saccharomyces cerevisiae s288c, Saccharomyces kluyveri, Saccharomyces serevisiae, Sachharomyces cerevisiae, Salmonella enteric, Salmonella enterica, Salmonella enterica subsp. arizonae serovar, Salmonella enterica subsp. enterica serovar Typhimurium str. LT2, Salmonella enterica Typhimurium, Salmonella typhimurium, Salmonella typhimurium LT2, Schizosaccharomyces pombe, Sebaldella termitidis ATCC 33386, Seffatia proteamaculans, Shewanella oneidensis MR-1, Shigella flexneri, Sinorhizobium meliloti 1021, Solanum lycopersicum, Staphylococcus aureus, Stereum hirsutum FP-91666 SS1, Streptococcus mutans, Streptococcus pneumonia, Streptococcus pneumoniae, Streptococcus pyogenes ATCC 10782, Streptomyces anulatus, Streptomyces avermitilis, Streptomyces cinnamonensis, Streptomyces clavuligerus, Streptomyces coelicolor, Streptomyces coelicolor A3(2), Streptomyces griseus, Streptomyces griseus subsp. griseus 1VBRC 13350, Streptomyces sp CL190, Streptomyces sp. 2065, Streptomyces sp. ACT-1, Streptomyces sp. KO-3988, Sulfolobus acidocalarius, Sulfolobus acidocaldarius, Sulfolobus solfataricus, Sulfolobus solfataricus P-2, Sulfolobus sp. strain 7, Sulfolobus tokodaii, Sulfurimonas denitqicans, Sus scrofa, Synechococcus elongatus PCC 7942, Synechococcus sp. PCC 7002, Synechocystis str. PCC 6803, Syntrophobacter fumaroxidans, Thauera aromatica, Thermoanaerobacter brockii HTD4, Thermoanaerobacter sp. X514, Thermoanaerobacter tengcongensis MB4, Thermococcus kodakaraensis, Thermococcus litoralis, Thermoplasma acidophilum, Thermoproteus neutrophilus, Thermotoga maritima, Thermotoga maritime, Thermotoga maritime MSB8, Thermus thermophilus, Thiocapsa roseopersicina, Tolumonas auensis DSM 9187, Treponema denticola, Trichomonas vaginalis G3, Triticum aestivum, Trypanosoma brucei, Tsukamurella paurometabola DSM 20162, Uncultured bacterium, uncultured organism, Vibrio cholera, Vibrio harveyi ATCC BAA-1116, Xanthobacter autotrophicus Py2, Yarrowia lipolytica, Yersinia frederiksenii, Yersinia intermedia, Yersinia intermedia ATCC 29909, Yersinia pestis, Zea mays, Zoogloea ramigera, Zymomonas mobilus, as well as other exemplary species disclosed herein or available as source organisms for corresponding genes. However, with the complete genome sequence available for now more than 550 species (with more than half of these available on public databases such as the NCBI), including 395 microorganism genomes and a variety of yeast, fungi, plant, and mammalian genomes, the identification of genes encoding the requisite acetyl-CoA or a bioderived compound biosynthetic activity for one or more genes in related or distant species, including for example, homologues, orthologs, paralogs and nonorthologous gene displacements of known genes, and the interchange of genetic alterations between organisms is routine and well known in the art. Accordingly, the metabolic alterations allowing biosynthesis of acetyl-CoA or a bioderived compound described herein with reference to a particular organism such as E. coli can be readily applied to other microorganisms, including prokaryotic and eukaryotic organisms alike. Given the teachings and guidance provided herein, those skilled in the art will know that a metabolic alteration exemplified in one organism can be applied equally to other organisms.

In some instances, such as when an alternative acetyl-CoA or a bioderived compound biosynthetic pathway exists in an unrelated species, acetyl-CoA or a bioderived compound biosynthesis can be conferred onto the host species by, for example, exogenous expression of a paralog or paralogs from the unrelated species that catalyzes a similar, yet non-identical metabolic reaction to replace the referenced reaction. Because certain differences among metabolic networks exist between different organisms, those skilled in the art will understand that the actual gene usage between different organisms may differ. However, given the teachings and guidance provided herein, those skilled in the art also will understand that the teachings and methods of the invention can be applied to all microbial organisms using the cognate metabolic alterations to those exemplified herein to construct a microbial organism in a species of interest that will synthesize acetyl-CoA or a bioderived compound.

A nucleic acid molecule encoding an acetyl-CoA or a bioderived compound pathway enzyme or protein of the invention can also include a nucleic acid molecule that hybridizes to a nucleic acid disclosed herein by SEQ ID NO, GenBank and/or GI number or a nucleic acid molecule that hybridizes to a nucleic acid molecule that encodes an amino acid sequence disclosed herein by SEQ ID NO, GenBank and/or GI number. Hybridization conditions can include highly stringent, moderately stringent, or low stringency hybridization conditions that are well known to one of skill in the art such as those described herein. Similarly, a nucleic acid molecule that can be used in the invention can be described as having a certain percent sequence identity to a nucleic acid disclosed herein by SEQ ID NO, GenBank and/or GI number or a nucleic acid molecule that hybridizes to a nucleic acid molecule that encodes an amino acid sequence disclosed herein by SEQ ID NO, GenBank and/or GI number. For example, the nucleic acid molecule can have at least 65%, 70%, 75%, 80%, 85%, 90%, 91%, 92%, 93%, 94%, 95%, 96%, 97%, 98% or 99% sequence identity to a nucleic acid described herein.

Stringent hybridization refers to conditions under which hybridized polynucleotides are stable. As known to those of skill in the art, the stability of hybridized polynucleotides is reflected in the melting temperature ($T_m$) of the hybrids. In general, the stability of hybridized polynucleotides is a function of the salt concentration, for example, the sodium ion concentration and temperature. A hybridization reaction can be performed under conditions of lower stringency, followed by washes of varying, but higher, stringency. Reference to hybridization stringency relates to such washing conditions. Highly stringent hybridization includes conditions that permit hybridization of only those nucleic acid sequences that form stable hybridized polynucleotides in 0.018M NaCl at 65° C., for example, if a hybrid is not stable in 0.018M NaCl at 65° C., it will not be stable under high stringency conditions, as contemplated herein. High stringency conditions can be provided, for example, by hybridization in 50% formamide, 5× Denhart's solution, 5× SSPE, 0.2% SDS at 42° C., followed by washing in 0.1×SSPE, and 0.1% SDS at 65° C. Hybridization conditions other than highly stringent hybridization conditions can also be used to describe the nucleic acid sequences disclosed herein. For example, the phrase moderately stringent hybridization refers to conditions equivalent to hybridization in 50% formamide, 5× Denhart's solution, 5×SSPE, 0.2% SDS at 42° C., followed by washing in 0.2×SSPE, 0.2% SDS, at 42° C. The phrase low stringency hybridization refers to conditions equivalent to hybridization in 10% formamide, 5× Denhart's solution, 6×SSPE, 0.2% SDS at 22° C., followed by washing in 1×SSPE, 0.2% SDS, at 37° C. Denhart's solution contains 1% Ficoll, 1% polyvinylpyrrolidone, and 1% bovine serum albumin (BSA). 20×SSPE (sodium chloride, sodium phosphate, ethylene diamine tetraacetic acid (EDTA)) contains 3M sodium chloride, 0.2M sodium phosphate, and 0.025 M (EDTA). Other suitable low, moderate and high stringency hybridization buffers and conditions are well known to those of skill in the art and are described, for example, in Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999).

A nucleic acid molecule encoding an acetyl-CoA or a bioderived compound pathway enzyme or protein of the invention can have at least a certain sequence identity to a nucleotide sequence disclosed herein. According, in some aspects of the invention, a nucleic acid molecule encoding an acetyl-CoA or a bioderived compound pathway enzyme or protein has a nucleotide sequence of at least 65% identity, at least 70% identity, at least 75% identity, at least 80% identity, at least 85% identity, at least 90% identity, at least 91% identity, at least 92% identity, at least 93% identity, at least 94% identity, at least 95% identity, at least 96% identity, at least 97% identity, at least 98% identity, or at least 99% identity to a nucleic acid disclosed herein by SEQ ID NO, GenBank and/or GI number or a nucleic acid molecule that hybridizes to a nucleic acid molecule that encodes an amino acid sequence disclosed herein by SEQ ID NO, GenBank and/or GI number.

Sequence identity (also known as homology or similarity) refers to sequence similarity between two nucleic acid molecules or between two polypeptides. Identity can be determined by comparing a position in each sequence, which may be aligned for purposes of comparison. When a position in the compared sequence is occupied by the same base or amino acid, then the molecules are identical at that position. A degree of identity between sequences is a function of the number of matching or homologous positions shared by the sequences. The alignment of two sequences to determine their percent sequence identity can be done using software programs known in the art, such as, for example, those described in Ausubel et al., *Current Protocols in Molecular Biology*, John Wiley and Sons, Baltimore, Md. (1999). Preferably, default parameters are used for the alignment. One alignment program well known in the art that can be used is BLAST set to default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+ EMBL+DDBJ+PDB+GenBank CDS translations+SwissProtein+SPupdate+PIR. Details of these programs can be found at the National Center for Biotechnology Information.

Methods for constructing and testing the expression levels of a non-naturally occurring acetyl-CoA or a bioderived compound-producing host can be performed, for example, by recombinant and detection methods well known in the art. Such methods can be found described in, for example, Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999).

Exogenous nucleic acid sequences involved in a pathway for production of acetyl-CoA or a bioderived compound can be introduced stably or transiently into a host cell using techniques well known in the art including, but not limited to, conjugation, electroporation, chemical transformation, transduction, transfection, and ultrasound transformation. For exogenous expression in *E. coli* or other prokaryotic cells, some nucleic acid sequences in the genes or cDNAs of eukaryotic nucleic acids can encode targeting signals such as an N-terminal mitochondrial or other targeting signal, which can be removed before transformation into prokaryotic host cells, if desired. For example, removal of a mitochondrial leader sequence led to increased expression in *E. coli* (Hoffmeister et al., *J. Biol. Chem.* 280:4329-4338 (2005)). For exogenous expression in yeast or other eukaryotic cells, genes can be expressed in the cytosol without the addition of leader sequence, or can be targeted to mitochondrion or other organelles, or targeted for secretion, by the addition of a suitable targeting sequence such as a mitochondrial targeting or secretion signal suitable for the host cells. Thus, it is understood that appropriate modifications to a nucleic acid sequence to remove or include a targeting sequence can be incorporated into an exogenous nucleic acid sequence to impart desirable properties. Furthermore, genes can be subjected to codon optimization with techniques well known in the art to achieve optimized expression of the proteins.

An expression vector or vectors can be constructed to include one or more acetyl-CoA or a bioderived compound biosynthetic pathway encoding nucleic acids as exemplified herein operably linked to expression control sequences functional in the host organism. Expression vectors applicable for use in the microbial host organisms of the invention include, for example, plasmids, phage vectors, viral vectors, episomes and artificial chromosomes, including vectors and selection sequences or markers operable for stable integration into a host chromosome. Additionally, the expression vectors can include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences involved in a metabolic or synthetic pathway can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

In some embodiments, the invention also provides a method for producing a bioderived compound described herein. Such a method can comprise culturing the non-naturally occurring microbial organism as described herein under conditions and for a sufficient period of time to produce the bioderived compound. In another embodiment, method further includes separating the bioderived compound from other components in the culture. In this aspect, separating can include extraction, continuous liquid-liquid extraction, pervaporation, membrane filtration, membrane separation, reverse osmosis, electrodialysis, distillation, crystallization, centrifugation, extractive filtration, ion exchange chromatography, absorption chromatography, or ultrafiltration.

In some embodiments, depending on the bioderived compound, the method of the invention may further include chemically converting a bioderived compound to the directed final compound. For example, in some embodiments, wherein the bioderived compound is butadiene, the method of the invention can further include chemically dehydrating 1,3-butanediol, crotyl alcohol, or 3-buten-2-ol to produce the butadiene.

Suitable purification and/or assays to test for the production of acetyl-CoA or a bioderived compound can be performed using well known methods. Suitable replicates such as triplicate cultures can be grown for each engineered strain to be tested. For example, product and byproduct formation in the engineered production host can be monitored. The final product and intermediates, and other organic compounds, can be analyzed by methods such as HPLC (High Performance Liquid Chromatography), GC-MS (Gas Chromatography-Mass Spectroscopy) and LC-MS (Liquid Chromatography-Mass Spectroscopy) or other suitable analytical methods using routine procedures well known in the art. The release of product in the fermentation broth can also be tested with the culture supernatant. Byproducts and residual glucose can be quantified by HPLC using, for example, a refractive index detector for glucose and alcohols, and a UV detector for organic acids (Lin et al., *Biotechnol. Bioeng.* 90:775-779 (2005)), or other suitable assay and detection methods well known in the art. The individual enzyme or protein activities from the exogenous DNA sequences can also be assayed using methods well known in the art.

The bioderived compound can be separated from other components in the culture using a variety of methods well known in the art. Such separation methods include, for example, extraction procedures as well as methods that include continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, and ultrafiltration. All of the above methods are well known in the art.

Any of the non-naturally occurring microbial organisms described herein can be cultured to produce and/or secrete the biosynthetic products of the invention. For example, the bioderived compound producers can be cultured for the biosynthetic production of a bioderived compound disclosed herein. Accordingly, in some embodiments, the invention provides culture medium having the bioderived compound or bioderived compound pathway intermediate described herein. In some aspects, the culture medium can also be separated from the non-naturally occurring microbial organisms of the invention that produced the bioderived compound or bioderived compound pathway intermediate. Methods for separating a microbial organism from culture medium are well known in the art. Exemplary methods include filtration, flocculation, precipitation, centrifugation, sedimentation, and the like.

For the production of acetyl-CoA or a bioderived compound, the recombinant strains are cultured in a medium with carbon source and other essential nutrients. It is sometimes desirable and can be highly desirable to maintain anaerobic conditions in the fermenter to reduce the cost of the overall process. Such conditions can be obtained, for example, by first sparging the medium with nitrogen and then sealing the flasks with a septum and crimp-cap. For strains where growth is not observed anaerobically, microaerobic or substantially anaerobic conditions can be applied by perforating the septum with a small hole for limited aeration. Exemplary anaerobic conditions have been described previously and are well-known in the art. Exemplary aerobic and anaerobic conditions are described, for example, in United State publication 2009/0047719, filed Aug. 10, 2007. Fermentations can be performed in a batch, fed-batch or continuous manner, as disclosed herein. Fermentations can also be conducted in two phases, if desired. The first phase can be aerobic to allow for high growth and therefore high productivity, followed by an anaerobic phase of high acetyl-CoA or a bioderived compound yields.

If desired, the pH of the medium can be maintained at a desired pH, in particular neutral pH, such as a pH of around 7 by addition of a base, such as NaOH or other bases, or acid, as needed to maintain the culture medium at a desirable pH. The growth rate can be determined by measuring optical density using a spectrophotometer (600 nm), and the glucose uptake rate by monitoring carbon source depletion over time.

The growth medium, can include, for example, any carbohydrate source which can supply a source of carbon to the non-naturally occurring microbial organism of the invention. Such sources include, for example, sugars such as glucose, xylose, arabinose, galactose, mannose, fructose, sucrose and starch; or glycerol, alone as the sole source of carbon or in combination with other carbon sources described herein or known in the art. In one embodiment, the carbon source is a sugar. In one embodiment, the carbon source is a sugar-containing biomass. In some embodiments, the sugar is glucose. In one embodiment, the sugar is xylose. In another embodiment, the sugar is arabinose. In one embodiment, the sugar is galactose. In another embodiment, the sugar is fructose. In other embodiments, the sugar is sucrose. In one embodiment, the sugar is starch. In certain embodiments, the carbon source is glycerol. In some embodiments, the carbon source is crude glycerol. In one embodiment, the carbon source is crude glycerol without treatment. In other embodiments, the carbon source is glycerol and glucose. In another embodiment, the carbon source is methanol and glycerol. In one embodiment, the carbon source is carbon dioxide. In one embodiment, the carbon source is formate. In one embodiment, the carbon source is methane. In one embodiment, the carbon source is methanol. In certain embodiments, methanol is used alone as the sole source of carbon or in combination with other carbon sources described herein or known in the art. In a specific embodiment, the methanol is the only (sole) carbon source. In one embodiment, the carbon source is chemoelectro-generated carbon (see, e.g., Liao et al. (2012) Science 335:1596). In one embodiment, the chemoelectro-generated carbon is methanol. In one embodiment, the chemoelectro-generated carbon is formate. In one embodiment, the chemo-electro-generated carbon is formate and methanol. In one embodiment, the carbon source is a carbohydrate and methanol. In one embodiment, the carbon source is a sugar and methanol. In another embodiment, the carbon source is a sugar and glycerol. In other embodiments, the carbon source is a sugar and crude glycerol. In yet other embodiments, the carbon source is a sugar and crude glycerol without treatment. In one embodiment, the carbon source is a sugar-containing biomass and methanol. In another embodiment, the carbon source is a sugar-containing biomass and glycerol. In other embodiments, the carbon source is a sugar-containing biomass and crude glycerol. In yet other embodiments, the carbon source is a sugar-containing biomass and crude glycerol without treatment. In some embodiments, the carbon source is a sugar-containing biomass, methanol and a carbohydrate. Other sources of carbohydrate include, for example, renewable feedstocks and biomass. Exemplary types of biomasses that can be used as feedstocks in the methods provided herein include cellulosic biomass, hemi-cellulosic biomass and lignin feedstocks or portions of feedstocks. Such biomass feedstocks contain, for example, carbohydrate substrates useful as carbon sources such as glucose, xylose, arabinose, galactose, mannose, fructose and starch. Given the teachings and guidance provided herein, those skilled in the art will understand that renewable feedstocks and biomass other than those exemplified above also can be used for culturing the microbial organisms provided herein for the production of succinate and other pathway intermediates.

In one embodiment, the carbon source is glycerol. In certain embodiments, the glycerol carbon source is crude glycerol or crude glycerol without further treatment. In a further embodiment, the carbon source comprises glycerol or crude glycerol, and also sugar or a sugar-containing biomass, such as glucose. In a specific embodiment, the concentration of glycerol in the fermentation broth is maintained by feeding crude glycerol, or a mixture of crude glycerol and sugar (e.g., glucose). In certain embodiments, sugar is provided for sufficient strain growth. In some embodiments, the sugar (e.g., glucose) is provided at a molar concentration ratio of glycerol to sugar of from 200:1 to 1:200. In some embodiments, the sugar (e.g., glucose) is provided at a molar concentration ratio of glycerol to sugar of from 100:1 to 1:100. In some embodiments, the sugar (e.g., glucose) is provided at a molar concentration ratio of glycerol to sugar of from 100:1 to 5:1. In some embodiments, the sugar (e.g., glucose) is provided at a molar concentration ratio of glycerol to sugar of from 50:1 to 5:1. In certain embodiments, the sugar (e.g., glucose) is provided at a molar concentration ratio of glycerol to sugar of 100:1. In one embodiment, the sugar (e.g., glucose) is provided at a molar concentration ratio of glycerol to sugar of 90:1. In one embodiment, the sugar (e.g., glucose) is provided at a molar concentration ratio of glycerol to sugar of 80:1. In one embodiment, the sugar (e.g., glucose) is provided at a molar concentration ratio of glycerol to sugar of 70:1. In one embodiment, the sugar (e.g., glucose) is provided at a molar concentration ratio of glycerol to sugar of 60:1. In one embodiment, the sugar (e.g., glucose) is provided at a molar concentration ratio of glycerol to sugar of 50:1. In one embodiment, the sugar (e.g., glucose) is provided at a molar concentration ratio of glycerol to sugar of 40:1. In one embodiment, the sugar (e.g., glucose) is provided at a molar concentration ratio of glycerol to sugar of 30:1. In one embodiment, the sugar (e.g., glucose) is provided at a molar concentration ratio of glycerol to sugar of 20:1. In one embodiment, the sugar (e.g., glucose) is provided at a molar concentration ratio of glycerol to sugar of 10:1. In one embodiment, the sugar (e.g., glucose) is provided at a molar concentration ratio of glycerol to sugar of 5:1. In one embodiment, the sugar (e.g., glucose) is provided at a molar concentration ratio of glycerol to sugar of 2:1. In one embodiment, the sugar (e.g., glucose) is provided at a molar concentration ratio of glycerol to sugar of 1:1. In certain embodiments, the sugar (e.g., glucose) is provided at a molar concentration ratio of glycerol to sugar of 1:100. In one embodiment, the sugar (e.g., glucose) is provided at a molar concentration ratio of glycerol to sugar of 1:90. In one embodiment, the sugar (e.g., glucose) is provided at a molar concentration ratio of glycerol to sugar of 1:80. In one embodiment, the sugar (e.g., glucose) is provided at a molar concentration ratio of glycerol to sugar of 1:70. In one embodiment, the sugar (e.g., glucose) is provided at a molar concentration ratio of glycerol to sugar of 1:60. In one embodiment, the sugar (e.g., glucose) is provided at a molar concentration ratio of glycerol to sugar of 1:50. In one embodiment, the sugar (e.g., glucose) is provided at a molar concentration ratio of glycerol to sugar of 1:40. In one embodiment, the sugar (e.g., glucose) is provided at a molar concentration ratio of glycerol to sugar of 1:30. In one embodiment, the sugar (e.g., glucose) is provided at a molar concentration ratio of glycerol to sugar of 1:20. In one embodiment, the sugar (e.g., glucose) is provided at a molar concentration ratio of glycerol to sugar of 1:10. In one embodiment, the sugar (e.g., glucose) is provided at a molar concentration ratio of glycerol to sugar of 1:5. In one embodiment, the sugar (e.g., glucose) is provided at a molar concentration ratio of glycerol to sugar of 1:2. In certain embodiments of the ratios provided above, the sugar is a sugar-containing biomass. In certain other embodiments of the ratios provided above, the glycerol is a crude glycerol or a crude glycerol without further treatment. In other embodiments of the ratios provided above, the sugar is a sugar-containing biomass, and the glycerol is a crude glycerol or a crude glycerol without further treatment.

Crude glycerol can be a by-product produced in the production of biodiesel, and can be used for fermentation without any further treatment. Biodiesel production methods include (1) a chemical method wherein the glycerol-group of vegetable oils or animal oils is substituted by low-carbon alcohols such as methanol or ethanol to produce a corresponding fatty acid methyl esters or fatty acid ethyl esters by transesterification in the presence of acidic or basic catalysts; (2) a biological method where biological enzymes or cells are used to catalyze transesterification reaction and the corresponding fatty acid methyl esters or fatty acid ethyl esters are produced; and (3) a supercritical method, wherein transesterification reaction is carried out in a supercritical solvent system without any catalysts. The chemical composition of crude glycerol can vary with the process used to produce biodiesel, the transesterification efficiency, recovery efficiency of the biodiesel, other impurities in the feedstock, and whether methanol and catalysts were recovered. For example, the chemical compositions of eleven crude glycerol collected from seven Australian biodiesel producers reported that glycerol content ranged between 38% and 96%, with some samples including more than 14% methanol and 29% ash. In certain embodiments, the crude glycerol comprises from 5% to 99% glycerol. In some embodiments, the crude glycerol comprises from 10% to 90% glycerol. In some embodiments, the crude glycerol comprises from 10% to 80% glycerol. In some embodiments, the crude glycerol comprises from 10% to 70% glycerol. In some embodiments, the crude glycerol comprises from 10% to 60% glycerol. In some embodiments, the crude glycerol comprises from 10% to 50% glycerol. In some embodiments, the crude glycerol comprises from 10% to 40% glycerol. In some embodiments, the crude glycerol comprises from 10% to 30% glycerol. In some embodiments, the crude glycerol comprises from 10% to 20% glycerol. In some embodiments, the crude glycerol comprises from 80% to 90% glycerol. In some embodiments, the crude glycerol comprises from 70% to 90% glycerol. In some embodiments, the crude glycerol comprises from 60% to 90% glycerol. In some embodiments, the crude glycerol comprises from 50% to 90% glycerol. In some embodiments, the crude glycerol comprises from 40% to 90% glycerol.

In some embodiments, the crude glycerol comprises from 30% to 90% glycerol. In some embodiments, the crude glycerol comprises from 20% to 90% glycerol. In some embodiments, the crude glycerol comprises from 20% to 40% glycerol. In some embodiments, the crude glycerol comprises from 40% to 60% glycerol. In some embodiments, the crude glycerol comprises from 60% to 80% glycerol. In some embodiments, the crude glycerol comprises from 50% to 70% glycerol. In one embodiment, the glycerol comprises 5% glycerol. In one embodiment, the glycerol comprises 10% glycerol. In one embodiment, the glycerol comprises 15% glycerol. In one embodiment, the glycerol comprises 20% glycerol. In one embodiment, the glycerol comprises 25% glycerol. In one embodiment, the glycerol comprises 30% glycerol. In one embodiment, the glycerol comprises 35% glycerol. In one embodiment, the glycerol comprises 40% glycerol. In one embodiment, the glycerol comprises 45% glycerol. In one embodiment, the glycerol comprises 50% glycerol. In one embodiment, the glycerol comprises 55% glycerol. In one embodiment, the glycerol comprises 60% glycerol. In one embodiment, the glycerol comprises 65% glycerol. In one embodiment, the glycerol comprises 70% glycerol. In one embodiment, the glycerol comprises 75% glycerol. In one embodiment, the glycerol comprises 80% glycerol. In one embodiment, the glycerol comprises 85% glycerol. In one embodiment, the glycerol comprises 90% glycerol. In one embodiment, the glycerol comprises 95% glycerol. In one embodiment, the glycerol comprises 99% glycerol.

In one embodiment, the carbon source is methanol or formate. In certain embodiments, methanol is used as a carbon source in a formaldehyde fixation pathway provided herein. In one embodiment, the carbon source is methanol or formate. In other embodiments, formate is used as a carbon source in a formaldehyde fixation pathway provided herein. In specific embodiments, methanol is used as a carbon source in a methanol oxidation pathway provided herein, either alone or in combination with the fatty alcohol, fatty aldehyde, fatty acid or isopropanol pathways provided herein. In one embodiment, the carbon source is methanol. In another embodiment, the carbon source is formate.

In one embodiment, the carbon source comprises methanol, and sugar (e.g., glucose) or a sugar-containing biomass. In another embodiment, the carbon source comprises formate, and sugar (e.g., glucose) or a sugar-containing biomass. In one embodiment, the carbon source comprises methanol, formate, and sugar (e.g., glucose) or a sugar-containing biomass. In specific embodiments, the methanol or formate, or both, in the fermentation feed is provided as a mixture with sugar (e.g., glucose) or sugar-comprising biomass. In certain embodiments, sugar is provided for sufficient strain growth.

In certain embodiments, the carbon source comprises methanol and a sugar (e.g., glucose). In some embodiments, the sugar (e.g., glucose) is provided at a molar concentration ratio of methanol to sugar of from 200:1 to 1:200. In some embodiments, the sugar (e.g., glucose) is provided at a molar concentration ratio of methanol to sugar of from 100:1 to 1:100. In some embodiments, the sugar (e.g., glucose) is provided at a molar concentration ratio of methanol to sugar of from 100:1 to 5:1. In some embodiments, the sugar (e.g., glucose) is provided at a molar concentration ratio of methanol to sugar of from 50:1 to 5:1. In certain embodiments, the sugar (e.g., glucose) is provided at a molar concentration ratio of methanol to sugar of 100:1. In one embodiment, the sugar (e.g., glucose) is provided at a molar concentration ratio of methanol to sugar of 90:1. In one embodiment, the sugar (e.g., glucose) is provided at a molar concentration ratio of methanol to sugar of 80:1. In one embodiment, the sugar (e.g., glucose) is provided at a molar concentration ratio of methanol to sugar of 70:1. In one embodiment, the sugar (e.g., glucose) is provided at a molar concentration ratio of methanol to sugar of 60:1. In one embodiment, the sugar (e.g., glucose) is provided at a molar concentration ratio of methanol to sugar of 50:1. In one embodiment, the sugar (e.g., glucose) is provided at a molar concentration ratio of methanol to sugar of 40:1. In one embodiment, the sugar (e.g., glucose) is provided at a molar concentration ratio of methanol to sugar of 30:1. In one embodiment, the sugar (e.g., glucose) is provided at a molar concentration ratio of methanol to sugar of 20:1. In one embodiment, the sugar (e.g., glucose) is provided at a molar concentration ratio of methanol to sugar of 10:1. In one embodiment, the sugar (e.g., glucose) is provided at a molar concentration ratio of methanol to sugar of 5:1. In one embodiment, the sugar (e.g., glucose) is provided at a molar concentration ratio of methanol to sugar of 2:1. In one embodiment, the sugar (e.g., glucose) is provided at a molar concentration ratio of methanol to sugar of 1:1. In certain embodiments, the sugar (e.g., glucose) is provided at a molar concentration ratio of methanol to sugar of 1:100. In one embodiment, the sugar (e.g., glucose) is provided at a molar concentration ratio of methanol to sugar of 1:90. In one embodiment, the sugar (e.g., glucose) is provided at a molar concentration ratio of methanol to sugar of 1:80. In one embodiment, the sugar (e.g., glucose) is provided at a molar concentration ratio of methanol to sugar of 1:70. In one embodiment, the sugar (e.g., glucose) is provided at a molar concentration ratio of methanol to sugar of 1:60. In one embodiment, the sugar (e.g., glucose) is provided at a molar concentration ratio of methanol to sugar of 1:50. In one embodiment, the sugar (e.g., glucose) is provided at a molar concentration ratio of methanol to sugar of 1:40. In one embodiment, the sugar (e.g., glucose) is provided at a molar concentration ratio of methanol to sugar of 1:30. In one embodiment, the sugar (e.g., glucose) is provided at a molar concentration ratio of methanol to sugar of 1:20. In one embodiment, the sugar (e.g., glucose) is provided at a molar concentration ratio of methanol to sugar of 1:10. In one embodiment, the sugar (e.g., glucose) is provided at a molar concentration ratio of methanol to sugar of 1:5. In one embodiment, the sugar (e.g., glucose) is provided at a molar concentration ratio of methanol to sugar of 1:2. In certain embodiments of the ratios provided above, the sugar is a sugar-containing biomass.

In certain embodiments, the carbon source comprises formate and a sugar (e.g., glucose). In some embodiments, the sugar (e.g., glucose) is provided at a molar concentration ratio of formate to sugar of from 200:1 to 1:200. In some embodiments, the sugar (e.g., glucose) is provided at a molar concentration ratio of formate to sugar of from 100:1 to 1:100. In some embodiments, the sugar (e.g., glucose) is provided at a molar concentration ratio of formate to sugar of from 100:1 to 5:1. In some embodiments, the sugar (e.g., glucose) is provided at a molar concentration ratio of formate to sugar of from 50:1 to 5:1. In certain embodiments, the sugar (e.g., glucose) is provided at a molar concentration ratio of formate to sugar of 100:1. In one embodiment, the sugar (e.g., glucose) is provided at a molar concentration ratio of formate to sugar of 90:1. In one embodiment, the sugar (e.g., glucose) is provided at a molar concentration ratio of formate to sugar of 80:1. In one embodiment, the sugar (e.g., glucose) is provided at a molar concentration ratio of formate to sugar of 70:1. In one embodiment, the sugar (e.g., glucose) is provided at a molar concentration ratio of formate to sugar of 60:1. In one embodiment, the sugar (e.g., glucose) is provided at a molar concentration ratio of formate to sugar of 50:1. In one embodiment, the sugar (e.g., glucose) is provided at a molar concentration ratio of formate to sugar of 40:1. In one embodiment, the sugar (e.g., glucose) is provided at a molar concentration ratio of formate to sugar of 30:1. In one embodiment, the sugar (e.g., glucose) is provided at a molar concentration ratio of formate to sugar of 20:1. In one embodiment, the sugar (e.g., glucose) is provided at a molar concentration ratio of formate to sugar of 10:1. In one embodiment, the sugar (e.g., glucose) is provided at a molar concentration ratio of formate to sugar of 5:1. In one embodiment, the sugar (e.g., glucose) is provided at a molar concentration ratio of formate to sugar of 2:1. In one embodiment, the sugar (e.g., glucose) is provided at a molar concentration ratio of formate to sugar of 1:1. In certain embodiments, the sugar (e.g., glucose) is provided at a molar concentration ratio of formate to sugar of 1:100. In one embodiment, the sugar (e.g., glucose) is provided at a molar concentration ratio of formate to sugar of 1:90. In one embodiment, the sugar (e.g., glucose) is provided at a molar concentration ratio of formate to sugar of 1:80. In one embodiment, the sugar (e.g., glucose) is provided at a molar concentration ratio of formate to sugar of 1:70. In one embodiment, the sugar (e.g., glucose) is provided at a molar concentration ratio of formate to sugar of 1:60. In one embodiment, the sugar (e.g., glucose) is provided at a molar concentration ratio of formate to sugar of 1:50. In one embodiment, the sugar (e.g., glucose) is provided at a molar concentration ratio of formate to sugar of 1:40. In one embodiment, the sugar (e.g., glucose) is provided at a molar concentration ratio of formate to sugar of 1:30. In one embodiment, the sugar (e.g., glucose) is provided at a molar concentration ratio of formate to sugar of 1:20. In one embodiment, the sugar (e.g., glucose) is provided at a molar concentration ratio of formate to sugar of 1:10. In one embodiment, the sugar (e.g., glucose) is provided at a molar concentration ratio of formate to sugar of 1:5. In one embodiment, the sugar (e.g., glucose) is provided at a molar concentration ratio of formate to sugar of 1:2. In certain embodiments of the ratios provided above, the sugar is a sugar-containing biomass.

In certain embodiments, the carbon source comprises a mixture of methanol and formate, and a sugar (e.g., glucose). In certain embodiments, sugar is provided for sufficient strain growth. In some embodiments, the sugar (e.g., glucose) is provided at a molar concentration ratio of methanol and formate to sugar of from 200:1 to 1:200. In some embodiments, the sugar (e.g., glucose) is provided at a molar concentration ratio of methanol and formate to sugar of from 100:1 to 1:100. In some embodiments, the sugar (e.g., glucose) is provided at a molar concentration ratio of methanol and formate to sugar of from 100:1 to 5:1. In some embodiments, the sugar (e.g., glucose) is provided at a molar concentration ratio of methanol and formate to sugar of from 50:1 to 5:1. In certain embodiments, the sugar (e.g., glucose) is provided at a molar concentration ratio of methanol and formate to sugar of 100:1. In one embodiment, the sugar (e.g., glucose) is provided at a molar concentration ratio of methanol and formate to sugar of 90:1. In one embodiment, the sugar (e.g., glucose) is provided at a molar concentration ratio of methanol and formate to sugar of 80:1. In one embodiment, the sugar (e.g., glucose) is provided at a molar concentration ratio of methanol and formate to sugar of 70:1. In one embodiment, the sugar (e.g., glucose) is provided at a molar concentration ratio of methanol and formate to sugar of 60:1. In one embodiment, the sugar (e.g., glucose) is provided at a molar concentration ratio of methanol and formate to sugar of 50:1. In one embodiment, the sugar (e.g., glucose) is provided at a molar concentration ratio of methanol and formate to sugar of 40:1. In one embodiment, the sugar (e.g., glucose) is provided at a molar concentration ratio of methanol and formate to sugar of 30:1. In one embodiment, the sugar (e.g., glucose) is provided at a molar concentration ratio of methanol and formate to sugar of 20:1. In one embodiment, the sugar (e.g., glucose) is provided at a molar concentration ratio of methanol and formate to sugar of 10:1. In one embodiment, the sugar (e.g., glucose) is provided at a molar concentration ratio of methanol and formate to sugar of 5:1. In one embodiment, the sugar (e.g., glucose) is provided at a molar concentration ratio of methanol and formate to sugar of 2:1. In one embodiment, the sugar (e.g., glucose) is provided at a molar concentration ratio of methanol and formate to sugar of 1:1. In certain embodiments, the sugar (e.g., glucose) is provided at a molar concentration ratio of methanol and formate to sugar of 1:100. In one embodiment, the sugar (e.g., glucose) is provided at a molar concentration ratio of methanol and formate to sugar of 1:90. In one embodiment, the sugar (e.g., glucose) is provided at a molar concentration ratio of methanol and formate to sugar of 1:80. In one embodiment, the sugar (e.g., glucose) is provided at a molar concentration ratio of methanol and formate to sugar of 1:70. In one embodiment, the sugar (e.g., glucose) is provided at a molar concentration ratio of methanol and formate to sugar of 1:60. In one embodiment, the sugar (e.g., glucose) is provided at a molar concentration ratio of methanol and formate to sugar of 1:50. In one embodiment, the sugar (e.g., glucose) is provided at a molar concentration ratio of methanol and formate to sugar of 1:40. In one embodiment, the sugar (e.g., glucose) is provided at a molar concentration ratio of methanol and formate to sugar of 1:30. In one embodiment, the sugar (e.g., glucose) is provided at a molar concentration ratio of methanol and formate to sugar of 1:20. In one embodiment, the sugar (e.g., glucose) is provided at a molar concentration ratio of methanol and formate to sugar of 1:10. In one embodiment, the sugar (e.g., glucose) is provided at a molar concentration ratio of methanol and formate to sugar of 1:5. In one embodiment, the sugar (e.g., glucose) is provided at a molar concentration ratio of methanol and formate to sugar of 1:2. In certain embodiments of the ratios provided above, the sugar is a sugar-containing biomass.

In addition to renewable feedstocks such as those exemplified above, the acetyl-CoA or the bioderived compound producing microbial organisms of the invention also can be modified for growth on syngas as its source of carbon. In this specific embodiment, one or more proteins or enzymes are expressed in the acetyl-CoA or the bioderived compound producing organisms to provide a metabolic pathway for utilization of syngas or other gaseous carbon source.

Synthesis gas, also known as syngas or producer gas, is the major product of gasification of coal and of carbonaceous materials such as biomass materials, including agricultural crops and residues. Syngas is a mixture primarily of $H_2$ and CO and can be obtained from the gasification of any organic feedstock, including but not limited to coal, coal oil, natural gas, biomass, and waste organic matter. Gasification is generally carried out under a high fuel to oxygen ratio. Although largely $H_2$ and CO, syngas can also include $CO_2$ and other gases in smaller quantities. Thus, synthesis gas provides a cost effective source of gaseous carbon such as CO and, additionally, $CO_2$.

Accordingly, given the teachings and guidance provided herein, those skilled in the art will understand that a non-naturally occurring microbial organism can be produced that secretes the biosynthesized compounds of the invention when grown on a carbon source such as a carbohydrate. Such compounds include, for example, acetyl-CoA or a bioderived compound and any of the intermediate metabolites in the acetyl-CoA or the bioderived compound pathway. All that is required is to engineer in one or more of the required enzyme or protein activities to achieve biosynthesis of the desired compound or intermediate including, for example, inclusion of some or all of the acetyl-CoA or the bioderived compound biosynthetic pathways. Accordingly, the invention provides a non-naturally occurring microbial organism that produces and/or secretes acetyl-CoA or a bioderived compound when grown on a carbohydrate or other carbon source and produces and/or secretes any of the intermediate metabolites shown in the acetyl-CoA or the bioderived compound pathway when grown on a carbohydrate or other carbon source. The acetyl-CoA or the bioderived compound producing microbial organisms of the invention can initiate synthesis from an intermediate, for example, F6P, E4P, formate, formyl-CoA, G3P, PYR, DHA, H6P, 3HBCOA, 3HB, 3-hydroxybutyryl phosphate, 4-hydroxybutyrate, 4-hydroxybutyryl-CoA, adipyl-CoA, adipate semialdehyde, 3-hydroxyisobutyrate, or 2-hydroxyisobutyryl-CoA.

The non-naturally occurring microbial organisms of the invention are constructed using methods well known in the art as exemplified herein to exogenously express at least one nucleic acid encoding an acetyl-CoA or a bioderived compound pathway enzyme or protein in sufficient amounts to produce acetyl-CoA or a bioderived compound. It is understood that the microbial organisms of the invention are cultured under conditions sufficient to produce acetyl-CoA or a bioderived compound. Following the teachings and guidance provided herein, the non-naturally occurring microbial organisms of the invention can achieve biosynthesis of a bioderived compound resulting in intracellular concentrations between about 0.1-200 mM or more. Generally, the intracellular concentration of a bioderived compound is between about 3-150 mM, particularly between about 5-125 mM and more particularly between about 8-100 mM, including about 10 mM, 20 mM, 50 mM, 80 mM, or more. Intracellular concentrations between and above each of these exemplary ranges also can be achieved from the non-naturally occurring microbial organisms of the invention.

In some embodiments, culture conditions include anaerobic or substantially anaerobic growth or maintenance conditions. Exemplary anaerobic conditions have been described previously and are well known in the art. Exemplary anaerobic conditions for fermentation processes are described herein and are described, for example, in U.S. publication 2009/0047719, filed Aug. 10, 2007. Any of these conditions can be employed with the non-naturally occurring microbial organisms as well as other anaerobic conditions well known in the art. Under such anaerobic or substantially anaerobic conditions, the acetyl-CoA or the bioderived compound producers can synthesize a bioderived compound at intracellular concentrations of 5-10 mM or more as well as all other concentrations exemplified herein. It is understood that, even though the above description refers to intracellular concentrations, acetyl-CoA or a bioderived compound producing microbial organisms can produce a bioderived compound intracellularly and/or secrete the product into the culture medium.

Exemplary fermentation processes include, but are not limited to, fed-batch fermentation and batch separation; fed-batch fermentation and continuous separation; and continuous fermentation and continuous separation. In an exemplary batch fermentation protocol, the production organism is grown in a suitably sized bioreactor sparged with an appropriate gas. Under anaerobic conditions, the culture is sparged with an inert gas or combination of gases, for example, nitrogen, $N_2/CO_2$ mixture, argon, helium, and the like. As the cells grow and utilize the carbon source, additional carbon source(s) and/or other nutrients are fed into the bioreactor at a rate approximately balancing consumption of the carbon source and/or nutrients. The temperature of the bioreactor is maintained at a desired temperature, generally in the range of 22-37 degrees C., but the temperature can be maintained at a higher or lower temperature depending on the growth characteristics of the production organism and/or desired conditions for the fermentation process. Growth continues for a desired period of time to achieve desired characteristics of the culture in the fermenter, for example, cell density, product concentration, and the like. In a batch fermentation process, the time period for the fermentation is generally in the range of several hours to several days, for example, 8 to 24 hours, or 1, 2, 3, 4 or 5 days, or up to a week, depending on the desired culture conditions. The pH can be controlled or not, as desired, in which case a culture in which pH is not controlled will typically decrease to pH 3-6 by the end of the run. Upon completion of the cultivation period, the fermenter contents can be passed through a cell separation unit, for example, a centrifuge, filtration unit, and the like, to remove cells and cell debris. In the case where the desired product is expressed intracellularly, the cells can be lysed or disrupted enzymatically or chemically prior to or after separation of cells from the fermentation broth, as desired, in order to release additional product. The fermentation broth can be transferred to a product separations unit. Isolation of product occurs by standard separations procedures employed in the art to separate a desired product from dilute aqueous solutions. Such methods include, but are not limited to, liquid-liquid extraction using a water immiscible organic solvent (e.g., toluene or other suitable solvents, including but not limited to diethyl ether, ethyl acetate, tetrahydrofuran (THF), methylene chloride, chloroform, benzene, pentane, hexane, heptane, petroleum ether, methyl tertiary butyl ether (MTBE), dioxane, dimethylformamide (DMF), dimethyl sulfoxide (DMSO), and the like) to provide an organic solution of the product, if appropriate, standard distillation methods, and the like, depending on the chemical characteristics of the product of the fermentation process.

In an exemplary fully continuous fermentation protocol, the production organism is generally first grown up in batch mode in order to achieve a desired cell density. When the carbon source and/or other nutrients are exhausted, feed medium of the same composition is supplied continuously at a desired rate, and fermentation liquid is withdrawn at the same rate. Under such conditions, the product concentration in the bioreactor generally remains constant, as well as the cell density. The temperature of the fermenter is maintained at a desired temperature, as discussed above. During the continuous fermentation phase, it is generally desirable to maintain a suitable pH range for optimized production. The pH can be monitored and maintained using routine methods, including the addition of suitable acids or bases to maintain a desired pH range. The bioreactor is operated continuously for extended periods of time, generally at least one week to several weeks and up to one month, or longer, as appropriate and desired. The fermentation liquid and/or culture is monitored periodically, including sampling up to every day, as desired, to assure consistency of product concentration and/or cell density. In continuous mode, fermenter contents are constantly removed as new feed medium is supplied. The exit stream, containing cells, medium, and product, are generally subjected to a continuous product separations procedure, with or without removing cells and cell debris, as desired. Continuous separations methods employed in the art can be used to separate the product from dilute aqueous solutions, including but not limited to continuous liquid-liquid extraction using a water immiscible organic solvent (e.g., toluene or other suitable solvents, including but not limited to diethyl ether, ethyl acetate, tetrahydrofuran (THF), methylene chloride, chloroform, benzene, pentane, hexane, heptane, petroleum ether, methyl tertiary butyl ether (MTBE), dioxane, dimethylformamide (DMF), dimethyl sulfoxide (DMSO), and the like), standard continuous distillation methods, and the like, or other methods well known in the art.

In addition to the culturing and fermentation conditions disclosed herein, growth condition for achieving biosynthesis of acetyl-CoA or a bioderived compound can include the addition of an osmoprotectant to the culturing conditions. In certain embodiments, the non-naturally occurring microbial organisms of the invention can be sustained, cultured or fermented as described herein in the presence of an osmoprotectant. Briefly, an osmoprotectant refers to a compound that acts as an osmolyte and helps a microbial organism as described herein survive osmotic stress. Osmoprotectants include, but are not limited to, betaines, amino acids, and the sugar trehalose. Non-limiting examples of such are glycine betaine, praline betaine, dimethylthetin, dimethylslfoniopropionate, 3-dimethylsulfonio-2-methylpropionate, pipecolic acid, dimethylsulfonioacetate, choline, L-carnitine and ectoine. In one aspect, the osmoprotectant is glycine betaine. It is understood to one of ordinary skill in the art that the amount and type of osmoprotectant suitable for protecting a microbial organism described herein from osmotic stress will depend on the microbial organism used. The amount of osmoprotectant in the culturing conditions can be, for example, no more than about 0.1 mM, no more than about 0.5 mM, no more than about 1.0 mM, no more than about 1.5 mM, no more than about 2.0 mM, no more than about 2.5 mM, no more than about 3.0 mM, no more than about 5.0 mM, no more than about 7.0 mM, no more than about 10 mM, no more than about 50 mM, no more than about 100 mM or no more than about 500 mM.

In some embodiments, the carbon feedstock and other cellular uptake sources such as phosphate, ammonia, sulfate, chloride and other halogens can be chosen to alter the isotopic distribution of the atoms present in acetyl-CoA or a bioderived compound or any acetyl-CoA or a bioderived compound pathway intermediate. The various carbon feedstock and other uptake sources enumerated above will be referred to herein, collectively, as "uptake sources." Uptake sources can provide isotopic enrichment for any atom present in the acetyl-CoA, bioderived compound or pathway intermediate, or for side products generated in reactions diverging away from an acetyl-CoA or a bioderived compound pathway. Isotopic enrichment can be achieved for any target atom including, for example, carbon, hydrogen, oxygen, nitrogen, sulfur, phosphorus, chloride or other halogens.

In some embodiments, the uptake sources can be selected to alter the carbon-12, carbon-13, and carbon-14 ratios. In some embodiments, the uptake sources can be selected to alter the oxygen-16, oxygen-17, and oxygen-18 ratios. In some embodiments, the uptake sources can be selected to alter the hydrogen, deuterium, and tritium ratios. In some embodiments, the uptake sources can be selected to alter the nitrogen-14 and nitrogen-15 ratios. In some embodiments, the uptake sources can be selected to alter the sulfur-32, sulfur-33, sulfur-34, and sulfur-35 ratios. In some embodiments, the uptake sources can be selected to alter the phosphorus-31, phosphorus-32, and phosphorus-33 ratios. In some embodiments, the uptake sources can be selected to alter the chlorine-35, chlorine-36, and chlorine-37 ratios.

In some embodiments, the isotopic ratio of a target atom can be varied to a desired ratio by selecting one or more uptake sources. An uptake source can be derived from a natural source, as found in nature, or from a man-made source, and one skilled in the art can select a natural source, a man-made source, or a combination thereof, to achieve a desired isotopic ratio of a target atom. An example of a man-made uptake source includes, for example, an uptake source that is at least partially derived from a chemical synthetic reaction. Such isotopically enriched uptake sources can be purchased commercially or prepared in the laboratory and/or optionally mixed with a natural source of the uptake source to achieve a desired isotopic ratio. In some embodiments, a target atom isotopic ratio of an uptake source can be achieved by selecting a desired origin of the uptake source as found in nature. For example, as discussed herein, a natural source can be a biobased derived from or synthesized by a biological organism or a source such as petroleum-based products or the atmosphere. In some such embodiments, a source of carbon, for example, can be selected from a fossil fuel-derived carbon source, which can be relatively depleted of carbon-14, or an environmental or atmospheric carbon source, such as $CO_2$, which can possess a larger amount of carbon-14 than its petroleum-derived counterpart.

The unstable carbon isotope carbon-14 or radiocarbon makes up for roughly 1 in $10^{12}$ carbon atoms in the earth's atmosphere and has a half-life of about 5700 years. The stock of carbon is replenished in the upper atmosphere by a nuclear reaction involving cosmic rays and ordinary nitrogen ($^{14}N$). Fossil fuels contain no carbon-14, as it decayed long ago. Burning of fossil fuels lowers the atmospheric carbon-14 fraction, the so-called "Suess effect".

Methods of determining the isotopic ratios of atoms in a compound are well known to those skilled in the art. Isotopic enrichment is readily assessed by mass spectrometry using techniques known in the art such as accelerated mass spectrometry (AMS), Stable Isotope Ratio Mass Spectrometry (SIRMS) and Site-Specific Natural Isotopic Fractionation by Nuclear Magnetic Resonance (SNIF-NMR). Such mass spectral techniques can be integrated with separation techniques such as liquid chromatography (LC), high performance liquid chromatography (HPLC) and/or gas chromatography, and the like.

In the case of carbon, ASTM D6866 was developed in the United States as a standardized analytical method for determining the biobased content of solid, liquid, and gaseous samples using radiocarbon dating by the American Society for Testing and Materials (ASTM) International. The standard is based on the use of radiocarbon dating for the determination of a product's biobased content ASTM D6866 was first published in 2004, and the current active version of the standard is ASTM D6866-11 (effective Apr. 1, 2011). Radiocarbon dating techniques are well known to those skilled in the art, including those described herein.

The biobased content of a compound is estimated by the ratio of carbon-14 ($^{14}C$) to carbon-12 ($^{12}C$). Specifically, the Fraction Modern (Fm) is computed from the expression: Fm=(S−B)/(M−B), where B, S and M represent the $^{14}C/^{12}C$ ratios of the blank, the sample and the modern reference, respectively. Fraction Modern is a measurement of the deviation of the $^{14}C/^{12}C$ ratio of a sample from "Modern." Modern is defined as 95% of the radiocarbon concentration (in AD 1950) of National Bureau of Standards (NBS) Oxalic Acid I (i.e., standard reference materials (SRM) 4990b) normalized to $\delta^{13}C_{VPDB}$=19 per mil (Olsson, *The use of Oxalic acid as a Standard*. in, *Radiocarbon Variations and Absolute Chronology*, Nobel Symposium, 12th Proc., John Wiley & Sons, New York (1970)). Mass spectrometry results, for example, measured by ASM, are calculated using the internationally agreed upon definition of 0.95 times the specific activity of NBS Oxalic Acid I (SRM 4990b) normalized to $\delta^{13}C_{VPDB}$=19 per mil. This is equivalent to an absolute (AD 1950) $^{14}C/^{12}C$ ratio of 1.176±0.010×10$^{-12}$ (Karlen et al., *Arkiv Geofisik*, 4:465-471 (1968)). The standard calculations take into account the differential uptake of one isotope with respect to another, for example, the preferential uptake in biological systems of $C^{12}$ over $C^{13}$ over $C^{14}$, and these corrections are reflected as a Fm corrected for $\delta^{13}$.

An oxalic acid standard (SRM 4990b or HOx 1) was made from a crop of 1955 sugar beet. Although there were 1000 lbs made, this oxalic acid standard is no longer commercially available. The Oxalic Acid II standard (HOx 2; N.I.S.T designation SRM 4990 C) was made from a crop of 1977 French beet molasses. In the early 1980's, a group of 12 laboratories measured the ratios of the two standards. The ratio of the activity of Oxalic acid II to 1 is 1.2933±0.001 (the weighted mean). The isotopic ratio of HOx II is −17.8 per mil. ASTM D6866-11 suggests use of the available Oxalic Acid II standard SRM 4990 C (Hox2) for the modern standard (see discussion of original vs. currently available oxalic acid standards in Mann, *Radiocarbon*, 25(2):519-527 (1983)). A Fm=0% represents the entire lack of carbon-14 atoms in a material, thus indicating a fossil (for example, petroleum based) carbon source. A Fm=100%, after correction for the post-1950 injection of carbon-14 into the atmosphere from nuclear bomb testing, indicates an entirely modern carbon source. As described herein, such a "modern" source includes biobased sources.

As described in ASTM D6866, the percent modern carbon (pMC) can be greater than 100% because of the continuing but diminishing effects of the 1950s nuclear testing programs, which resulted in a considerable enrichment of carbon-14 in the atmosphere as described in ASTM D6866-11. Because all sample carbon-14 activities are referenced to a "pre-bomb" standard, and because nearly all new biobased products are produced in a post-bomb environment, all pMC values (after correction for isotopic fraction) must be multiplied by 0.95 (as of 2010) to better reflect the true biobased content of the sample. A biobased content that is greater than 103% suggests that either an analytical error has occurred, or that the source of biobased carbon is more than several years old.

ASTM D6866 quantifies the biobased content relative to the material's total organic content and does not consider the inorganic carbon and other non-carbon containing substances present. For example, a product that is 50% starch-based material and 50% water would be considered to have a Biobased Content=100% (50% organic content that is 100% biobased) based on ASTM D6866. In another example, a product that is 50% starch-based material, 25% petroleum-based, and 25% water would have a Biobased Content=66.7% (75% organic content but only 50% of the product is biobased). In another example, a product that is 50% organic carbon and is a petroleum-based product would be considered to have a Biobased Content=0% (50% organic carbon but from fossil sources). Thus, based on the well known methods and known standards for determining the biobased content of a compound or material, one skilled in the art can readily determine the biobased content and/or prepared downstream products that utilize of the invention having a desired biobased content.

Applications of carbon-14 dating techniques to quantify bio-based content of materials are known in the art (Currie et al., *Nuclear Instruments and Methods in Physics Research B*, 172:281-287 (2000)). For example, carbon-14 dating has been used to quantify bio-based content in terephthalate-containing materials (Colonna et al., *Green Chemistry*, 13:2543-2548 (2011)). Notably, polypropylene terephthalate (PPT) polymers derived from renewable 1,3-propanediol and petroleum-derived terephthalic acid resulted in Fm values near 30% (i.e., since 3/11 of the polymeric carbon derives from renewable 1,3-propanediol and 8/11 from the fossil end member terephthalic acid) (Currie et al., supra, 2000). In contrast, polybutylene terephthalate polymer derived from both renewable 1,4-butanediol and renewable terephthalic acid resulted in bio-based content exceeding 90% (Colonna et al., supra, 2011).

Accordingly, in some embodiments, the present invention provides acetyl-CoA or a bioderived compound or an acetyl-CoA or a bioderived compound pathway intermediate that has a carbon-12, carbon-13, and carbon-14 ratio that reflects an atmospheric carbon, also referred to as environmental carbon, uptake source. For example, in some aspects the acetyl-CoA or the bioderived compound or an acetyl-CoA or a bioderived compound pathway intermediate can have an Fm value of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98% or as much as 100%. In some such embodiments, the uptake source is $CO_2$. In some embodiments, the present invention provides acetyl-CoA or a bioderived compound or an acetyl-CoA or a bioderived compound pathway intermediate that has a carbon-12, carbon-13, and carbon-14 ratio that reflects petroleum-based carbon uptake source. In this aspect, the acetyl-CoA or the bioderived compound or an acetyl-CoA or a bioderived compound pathway intermediate can have an Fm value of less than 95%, less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, less than 5%, less than 2% or less than 1%. In some embodiments, the present invention provides acetyl-CoA or a bioderived compound or an acetyl-CoA or a bioderived compound pathway intermediate that has a carbon-12, carbon-13, and carbon-14 ratio that is obtained by a combination of an atmospheric carbon uptake source with a petroleum-based uptake source. Using such a combination of uptake sources is one way by which the carbon-12, carbon-13, and carbon-14 ratio can be varied, and the respective ratios would reflect the proportions of the uptake sources.

Further, the present invention relates to the biologically produced acetyl-CoA, a bioderived compound or pathway intermediate as disclosed herein, and to the products derived therefrom, wherein the acetyl-CoA or the bioderived compound or an acetyl-CoA or a bioderived compound pathway intermediate has a carbon-12, carbon-13, and carbon-14 isotope ratio of about the same value as the $CO_2$ that occurs in the environment. For example, in some aspects the invention provides bioderived acetyl-CoA or a bioderived compound or a bioderived acetyl-CoA or a bioderived compound intermediate having a carbon-12 versus carbon-13 versus carbon-14 isotope ratio of about the same value as the $CO_2$ that occurs in the environment, or any of the other ratios disclosed herein. It is understood, as disclosed herein, that a product can have a carbon-12 versus carbon-13 versus carbon-14 isotope ratio of about the same value as the $CO_2$ that occurs in the environment, or any of the ratios disclosed herein, wherein the product is generated from a bioderived compound or a bioderived compound pathway intermediate as disclosed herein, wherein the bioderived product is chemically modified to generate a final product. Methods of chemically modifying a bioderived product of a bioderived compound, or an intermediate thereof, to generate a desired product are well known to those skilled in the art, as described herein. The invention further provides biobased products having a carbon-12 versus carbon-13 versus carbon-14 isotope ratio of about the same value as the $CO_2$ that occurs in the environment, wherein the biobased products are generated directly from or in combination with bioderived compound or a bioderived compound pathway intermediate as disclosed herein.

Fatty alcohol, fatty aldehyde or fatty acid is a chemical used in commercial and industrial applications. Non-limiting examples of such applications include production of biofuels, chemicals, polymers, surfactants, soaps, detergents, shampoos, lubricating oil additives, fragrances, flavor materials and acrylates. Accordingly, in some embodiments, the invention provides biobased biofuels, chemicals, polymers, surfactants, soaps, detergents, shampoos, lubricating oil additives, fragrances, flavor materials and acrylates comprising one or more bioderived fatty alcohol, fatty aldehyde or fatty acid or bioderived fatty alcohol, fatty aldehyde or fatty acid pathway intermediate produced by a non-naturally occurring microorganism of the invention or produced using a method disclosed herein.

In some embodiments, the invention provides a biofuel, chemical, polymer, surfactant, soap, detergent, shampoo, lubricating oil additive, fragrance, flavor material or acrylate comprising bioderived fatty alcohol, fatty aldehyde or fatty acid or bioderived fatty alcohol, fatty aldehyde or fatty acid pathway intermediate, wherein the bioderived fatty alcohol, fatty aldehyde or fatty acid or bioderived fatty alcohol, fatty aldehyde or fatty acid pathway intermediate includes all or part of the fatty alcohol, fatty aldehyde or fatty acid or fatty alcohol, fatty aldehyde or fatty acid pathway intermediate used in the production of a biofuel, chemical, polymer, surfactant, soap, detergent, shampoo, lubricating oil additive, fragrance, flavor material or acrylate. For example, the final biofuel, chemical, polymer, surfactant, soap, detergent, shampoo, lubricating oil additive, fragrance, flavor material or acrylate can contain the bioderived fatty alcohol, fatty aldehyde or fatty acid, fatty alcohol, fatty aldehyde or fatty acid pathway intermediate, or a portion thereof that is the result of the manufacturing of the biofuel, chemical, polymer, surfactant, soap, detergent, shampoo, lubricating oil additive, fragrance, flavor material or acrylate. Such manufacturing can include chemically reacting the bioderived fatty alcohol, fatty aldehyde or fatty acid, or bioderived fatty alcohol, fatty aldehyde or fatty acid pathway intermediate (e.g. chemical conversion, chemical functionalization, chemical coupling, oxidation, reduction, polymerization, copolymerization and the like) with itself or another compound in a reaction that produces the final biofuel, chemical, polymer, surfactant, soap, detergent, shampoo, lubricating oil additive, fragrance, flavor material or acrylate. Thus, in some aspects, the invention provides a biobased biofuel, chemical, polymer, surfactant, soap, detergent, shampoo, lubricating oil additive, fragrance, flavor material or acrylate comprising at least 2%, at least 3%, at least 5%, at least 10%, at least 15%, at least 20%, at least 25%, at least 30%, at least 35%, at least 40%, at least 50%, at least 60%, at least 70%, at least 80%, at least 90%, at least 95%, at least 98% or 100% bioderived fatty alcohol, fatty aldehyde or fatty acid or bioderived fatty alcohol, fatty aldehyde or fatty acid pathway intermediate as disclosed herein. In some aspects, when the product is a biobased polymer that includes or is obtained from a bioderived fatty alcohol, fatty aldehyde or fatty acid, or fatty alcohol, fatty aldehyde or fatty acid pathway intermediate described herein, the biobased polymer can be molded using methods well known in the art. Accordingly, in some embodiments, provided herein is a molded product comprising the biobased polymer described herein.

Butadiene is a chemical commonly used in many commercial and industrial applications. Provided herein are a bioderived butadiene and biobased products comprising one or more bioderived butadiene or bioderived butadiene intermediate produced by a non-naturally occurring microorganism of the invention or produced using a method disclosed herein. Also provided herein are uses for bioderived butadiene and the biobased products. Non-limiting examples are described herein and include the following. Biobased products comprising all or a portion of bioderived butadiene include polymers, including synthetic rubbers and ABS resins, and chemicals, including hexamethylenediamine (HMDA), 1,4-butanediol, tetrahydrofuran (THF), adiponitrile, lauryl lactam, caprolactam, chloroprene, sulfalone, n-octanol and octene-1. The biobased polymers, including co-polymers, and resins include those where butadiene is reacted with one or more other chemicals, such as other alkenes, e.g. styrene, to manufacture numerous copolymers, including acrylonitrile 1,3-butadiene styrene (ABS), styrene-1,3-butadiene rubber (styrene butadiene rubber; SBR), styrene-1,3-butadiene latex. Products comprising biobased butadiene in the form of polymer synthetic rubber (SBR) include synthetic rubber articles, including tires, adhesives, seals, sealants, coatings, hose and shoe soles, and in the form of synthetic ruber polybutadiene (polybutadiene rubber, PBR or BR) which is used in synthetic rubber articles including tires, seals, gaskets and adhesives and as an intermediate in production of thermoplastic resin including acrylonitrile-butadiene-styrene (ABS) and in production of high impact modifier of polymers such as high impact polystyrene (HIPS). ABS is used in molded articles, including pipe, telephone, computer casings, mobile phones, radios, and appliances. Other biobased BD polymers include a latex, including styrene-butadiene latex (SB), used for example in paper coatings, carpet backing, adhesives, and foam mattresses; nitrile rubber, used in for example hoses, fuel lines, gasket seals, gloves and footwear; and styrene-butadiene block copolymers, used for example in asphalt modifiers (for road and roofing construction applications), adhesives, footwear and toys. Chemical intermediates made from butadiene include adiponitrile, HMDA, lauryl lactam, and caprolactam, used for example in production of nylon, including nylon-6,6 and other nylon-6,X, and chloroprene used for example in production of polychloroprene (neoprene). Butanediol produced from butadiene is used for example in production of specialty polymer resins including thermoplastic including polybutylene terephthalate (PBT), used in molded articles including parts for automotive, electrical, water systems and small appliances. Butadiene is also a co-monomer for polyurethane and polyurethane-polyurea copolymers. Butadiene is a co-monomer for biodegradable polymers, including PBAT (poly(butylene adipate-co-terephthalate)) and PBS (poly(butylene succinate)). Tetrahydrofuran produced from butadiene finds use as a solvent and in production of elastic fibers. Conversion of butadiene to THF, and subsequently to polytetramethylene ether glycol (PTMEG) (also referred to as PTMO, polytetramethylene oxide and PTHF, poly(tetrahydrofuran)), provides an intermediate used to manufacture elastic fibers, e.g. spandex fiber, used in products such as LYCRA® fibers or elastane, for example when combined with polyurethane-polyurea copolymers. THF also finds use as an industrial solvent and in pharmaceutical production. PTMEG is also combined with in the production of specialty thermoplastic elastomers (1PE), including thermoplastic elastomer polyester (TPE-E or TPEE) and copolyester ethers (COPE). COPES are high modulus elastomers with excellent mechanical properties and oil/environmental resistance, allowing them to operate at high and low temperature extremes. PTMEG and butadiene also make thermoplastic polyurethanes (e.g. TPE-U or TPEU) processed on standard thermoplastic extrusion, calendaring, and molding equipment, and are characterized by their outstanding toughness and abrasion resistance. Other biobased products of bioderived BD include styrene block copolymers used for example in bitumen modification, footwear, packaging, and molded extruded products; methylmethacrylate butadiene styrene and methacrylate butadiene styrene (MBS) resins—clear resins—used as impact modifier for transparent thermoplastics including polycarbonate (PC), polyvinyl carbonate (PVC) and poly)methyl methacrylate (PMMA); sulfalone used as a solvent or chemical; n-octanol and octene-1. Accordingly, in some embodiments, the invention provides a biobased product comprising one or more bioderived butadiene or bioderived butadiene intermediate produced by a non-naturally occurring microorganism of the invention or produced using a method disclosed herein.

Crotyl alcohol, also referred to as 2-buten-1-ol, is a valuable chemical intermediate. Crotyl alcohol is a chemical commonly used in many commercial and industrial applications. Non-limiting examples of such applications include production of crotyl halides, esters, and ethers, which in turn are chemical are chemical intermediates in the production of monomers, fine chemicals, such as sorbic acid, trimethylhydroquinone, crotonic acid and 3-methoxybutanol, agricultural chemicals, and pharmaceuticals. Exemplary fine chemical products include sorbic acid, trimethylhydroquinone, crotonic acid and 3-methoxybutanol. Crotyl alcohol is also a precursor to 1,3-butadiene. Crotyl alcohol is currently produced exclusively from petroleum feedstocks. For example Japanese Patent 47-013009 and U.S. Pat Nos. 3,090,815, 3,090,816, and 3,542,883 describe a method of producing crotyl alcohol by isomerization of 1,2-epoxybutane. The ability to manufacture crotyl alcohol from alternative and/or renewable feedstocks would represent a major advance in the quest for more sustainable chemical production processes. Accordingly, in some embodiments, the invention provides a biobased monomer, fine chemical, agricultural chemical, or pharmaceutical comprising one or more bioderived crotyl alcohol or bioderived crotyl alcohol intermediate produced by a non-naturally occurring microorganism of the invention or produced using a method disclosed herein.

1,3-Butanediol is a chemical commonly used in many commercial and industrial applications. Non-limiting examples of such applications include its use as an organic solvent for food flavoring agents or as a hypoglycemic agent and its use in the production of polyurethane and polyester resins. Moreover, optically active 1,3-butanediol is also used in the synthesis of biologically active compounds and liquid crystals. Still further, 1,3-butanediol can be used in commercial production of 1,3-butadiene, a compound used in the manufacture of synthetic rubbers (e.g., tires), latex, and resins. 1,3-butanediol can also be sued to synthesize (R)-3-hydroxybutyryl-(R)-1,3-butanediol monoester or (R)-3-ketobutyryl-(R)-1,3-butanediol. Accordingly, in some embodiments, the invention provides a biobased organic solvent, hypoglycemic agent, polyurethane, polyester resin, synthetic rubber, latex, or resin comprising one or more bioderived 1,3-butanediol or bioderived 1,3-butanediol intermediate produced by a non-naturally occurring microorganism of the invention or produced using a method disclosed herein.

3-Buten-2-ol is a chemical commonly used in many commercial and industrial applications. Non-limiting examples of such applications include it use as a solvent, e.g. as a viscosity adjustor, a monomer for polymer production, or a precursor to a fine chemical such as in production of contrast agents for imaging (see US20110091374) or production of glycerol (see US20120302800A1). 3-Buten-2-ol can also be used as a precursor in the production of 1,3-butadiene. Accordingly, in some embodiments, the invention provides a biobased solvent, polymer (or plastic or resin made from that polymer), or fine chemical comprising one or more bioderived 3-buten-2-ol or bioderived 3-buten-2-ol intermediate produced by a non-naturally occurring microorganism of the invention or produced using a method disclosed herein.

In some embodiments, the invention provides polymer, synthetic rubber, resin, or chemical comprising bioderived butadiene or bioderived butadiene pathway intermediate, wherein the bioderived butadiene or bioderived butadiene pathway intermediate includes all or part of the butadiene or butadiene pathway intermediate used in the production of polymer, synthetic rubber, resin, or chemical, or other biobased products described herein (for example hexamethylenediamine (HMDA), 1,4-butanediol, tetrahydrofuran (THF), adiponitrile, lauryl lactam, caprolactam, chloroprene, sulfalone, n-octanol, octene-1, ABS, SBR, PBR, PTMEG, COPE). Thus, in some aspects, the invention provides a biobased polymer, synthetic rubber, resin, or chemical or other biobased product described herein comprising at least 2%, at least 3%, at least 5%, at least 10%, at least 15%, at least 20%, at least 25%, at least 30%, at least 35%, at least 40%, at least 50%, at least 60%, at least 70%, at least 80%, at least 90%, at least 95%, at least 98% or 100% bioderived butadiene or bioderived butadiene pathway intermediate as disclosed herein. Additionally, in some aspects, the invention provides a biobased polymer, synthetic rubber, resin, or chemical or other biobased product described herein (for example hexamethylenediamine (HMDA), 1,4-butanediol, tetrahydrofuran (THF), adiponitrile, lauryl lactam, caprolactam, sulfalone, n-octanol, octene-1, ABS, SBR, PBR, PTMEG, COPE), wherein the butadiene or butadiene pathway intermediate used in its production is a combination of bioderived and petroleum derived butadiene or butadiene pathway intermediate. For example, a biobased polymer, synthetic rubber, resin, or chemical or other biobased product described herein (for example hexamethylenediamine (HMDA), 1,4-butanediol, tetrahydrofuran (THF), adiponitrile, lauryl lactam, caprolactam, chloroprene, sulfalone, n-octanol, octene-1, ABS, SBR, PBR, PTMEG, COPE) can be produced using 50% bioderived butadiene and 50% petroleum derived butadiene or other desired ratios such as 60%/40%, 70%/30%, 80%/20%, 90%/10%, 95%/5%, 100%/0%, 40%/60%, 30%/70%, 20%/80%, 10%/90% of bioderived/petroleum derived precursors, so long as at least a portion of the product comprises a bioderived product produced by the microbial organisms disclosed herein. It is understood that methods for producing polymer, synthetic rubber, resin, or chemical or other biobased product described herein (for example hexamethylenediamine (HMDA), 1,4-butanediol, tetrahydrofuran (THF), adiponitrile, lauryl lactam, caprolactam, chloroprene, sulfalone, n-octanol, octene-1, ABS, SBR, PBR, PTMEG, COPE) using the bioderived butadiene or bioderived butadiene pathway intermediate of the invention are well known in the art.

In some embodiments, the invention provides organic solvent, hypoglycemic agent, polyurethane, polyester resin, synthetic rubber, latex, or resin comprising bioderived 1,3-butanediol or bioderived 1,3-butanediol pathway intermediate, wherein the bioderived 1,3-butanediol or bioderived 1,3-butanediol pathway intermediate includes all or part of the 1,3-butanediol or 1,3-butanediol pathway intermediate used in the production of organic solvent, hypoglycemic agent, polyurethane, polyester resin, synthetic rubber, latex, or resin. Thus, in some aspects, the invention provides a biobased organic solvent, hypoglycemic agent, polyurethane, polyester resin, synthetic rubber, latex, or resin comprising at least 2%, at least 3%, at least 5%, at least 10%, at least 15%, at least 20%, at least 25%, at least 30%, at least 35%, at least 40%, at least 50%, at least 60%, at least 70%, at least 80%, at least 90%, at least 95%, at least 98% or 100% bioderived 1,3-butanediol or bioderived 1,3-butanediol pathway intermediate as disclosed herein. Additionally, in some aspects, the invention provides a biobased organic solvent, hypoglycemic agent, polyurethane, polyester resin, synthetic rubber, latex, or resin wherein the 1,3-butanediol or 1,3-butanediol pathway intermediate used in its production is a combination of bioderived and petroleum derived 1,3-butanediol or 1,3-butanediol pathway intermediate. For example, a biobased organic solvent, hypoglycemic agent, polyurethane, polyester resin, synthetic rubber, latex, or resin can be produced using 50% bioderived 1,3-butanediol and 50% petroleum derived 1,3-butanediol or other desired ratios such as 60%/40%, 70%/30%, 80%/20%, 90%/10%, 95%/5%, 100%/0%, 40%/60%, 30%/70%, 20%/80%, 10%/90% of bioderived/petroleum derived precursors, so long as at least a portion of the product comprises a bioderived product produced by the microbial organisms disclosed herein. It is understood that methods for producing organic solvent, hypoglycemic agent, polyurethane, polyester resin, synthetic rubber, latex, or resin using the bioderived 1,3-butanediol or bioderived 1,3-butanediol pathway intermediate of the invention are well known in the art.

In some embodiments, the invention provides monomer, fine chemical, agricultural chemical, or pharmaceutical comprising bioderived crotyl alcohol or bioderived crotyl alcohol pathway intermediate, wherein the bioderived crotyl alcohol or bioderived crotyl alcohol pathway intermediate includes all or part of the crotyl alcohol or crotyl alcohol pathway intermediate used in the production of monomer, fine chemical, agricultural chemical, or pharmaceutical.

Thus, in some aspects, the invention provides a biobased monomer, fine chemical, agricultural chemical, or pharmaceutical comprising at least 2%, at least 3%, at least 5%, at least 10%, at least 15%, at least 20%, at least 25%, at least 30%, at least 35%, at least 40%, at least 50%, at least 60%, at least 70%, at least 80%, at least 90%, at least 95%, at least 98% or 100% bioderived crotyl alcohol or bioderived crotyl alcohol pathway intermediate as disclosed herein. Additionally, in some aspects, the invention provides a biobased monomer, fine chemical, agricultural chemical, or pharmaceutical wherein the crotyl alcohol or crotyl alcohol pathway intermediate used in its production is a combination of bioderived and petroleum derived crotyl alcohol or crotyl alcohol pathway intermediate. For example, a biobased monomer, fine chemical, agricultural chemical, or pharmaceutical can be produced using 50% bioderived crotyl alcohol and 50% petroleum derived crotyl alcohol or other desired ratios such as 60%/40%, 70%/30%, 80%/20%, 90%/10%, 95%/5%, 100%/0%, 40%/60%, 30%/70%, 20%/80%, 10%/90% of bioderived/petroleum derived precursors, so long as at least a portion of the product comprises a bioderived product produced by the microbial organisms disclosed herein. It is understood that methods for producing monomer, fine chemical, agricultural chemical, or pharmaceutical using the bioderived crotyl alcohol or bioderived crotyl alcohol pathway intermediate of the invention are well known in the art.

In some embodiments, the invention provides solvent (or solvent-containing composition), polymer (or plastic or resin made from that polymer), or a fine chemical, comprising bioderived 3-buten-2-ol or bioderived 3-buten-2-ol pathway intermediate, wherein the bioderived 3-buten-2-ol or bioderived 3-buten-2-ol pathway intermediate includes all or part of the 3-buten-2-ol or 3-buten-2-ol pathway intermediate used in the production of the solvent (or composition containing the solvent), polymer (or plastic or resin made from that polymer) or fine chemical. Thus, in some aspects, the invention provides a biobased solvent (or composition containing the solvent), polymer (or plastic or resin made from that polymer) or fine chemical comprising at least 2%, at least 3%, at least 5%, at least 10%, at least 15%, at least 20%, at least 25%, at least 30%, at least 35%, at least 40%, at least 50%, at least 60%, at least 70%, at least 80%, at least 90%, at least 95%, at least 98% or 100% bioderived 3-buten-2-ol or bioderived 3-buten-2-ol pathway intermediate as disclosed herein. Additionally, in some aspects, the invention provides the biobased solvent (or composition containing the solvent), polymer (or plastic or resin made from that polymer) or fine chemical wherein the 3-buten-2-ol or 3-buten-2-ol pathway intermediate used in its production is a combination of bioderived and petroleum derived 3-buten-2-ol or 3-buten-2-ol pathway intermediate. For example, the biobased the solvent (or composition containing the solvent), polymer (or plastic or resin made from that polymer) or fine chemical can be produced using 50% bioderived 3-buten-2-ol and 50% petroleum derived 3-buten-2-ol or other desired ratios such as 60%/40%, 70%/30%, 80%/20%, 90%/10%, 95%/5%, 100%/0%, 40%/60%, 30%/70%, 20%/80%, 10%/90% of bioderived/petroleum derived precursors, so long as at least a portion of the product comprises a bioderived product produced by the microbial organisms disclosed herein. It is understood that methods for producing the solvent (or composition containing the solvent), polymer (or plastic or resin made from that polymer) or fine chemical using the bioderived 3-buten-2-ol or bioderived 3-buten-2-ol pathway intermediate of the invention are well known in the art.

1,4-Butanediol and/or 4-HB are chemicals used in commercial and industrial applications. Non-limiting examples of such applications include production of plastics, elastic fibers, polyurethanes, polyesters, including polyhydroxyalkanoates such as P4HB or co-polymers thereof, PTMEG and polyurethane-polyurea copolymers, referred to as spandex, elastane or Lycra™, nylons, and the like. Moreover, 1,4-butanediol and/or 4-HB are also used as a raw material in the production of a wide range of products including plastics, elastic fibers, polyurethanes, polyesters, including polyhydroxyalkanoates such as P4HB or co-polymers thereof, PTMEG and polyurethane-polyurea copolymers, referred to as spandex, elastane or Lycra™, nylons, and the like. Accordingly, in some embodiments, provided are biobased plastics, elastic fibers, polyurethanes, polyesters, including polyhydroxyalkanoates such as P4HB or co-polymers thereof, PTMEG and polyurethane-polyurea copolymers, referred to as spandex, elastane or Lycra™, nylons, and the like, comprising one or more bioderived 1,4-butanediol and/or 4-HB or bioderived 1,4-butanediol and/or 4-HB intermediate thereof produced by a non-naturally occurring microbial organism provided herein or produced using a method disclosed herein.

In some embodiments, the invention provides plastics, elastic fibers, polyurethanes, polyesters, including polyhydroxyalkanoates such as P4HB or co-polymers thereof, PTMEG and polyurethane-polyurea copolymers, referred to as spandex, elastane or Lycra™, nylons, and the like, comprising bioderived 1,4-butanediol and/or 4-HB or bioderived 1,4-butanediol and/or 4-HB intermediate thereof, wherein the bioderived 1,4-butanediol and/or 4-HB or bioderived 1,4-butanediol and/or 4-HB intermediate thereof includes all or part of the 1,4-butanediol and/or 4-HB or 1,4-butanediol and/or 4-HB intermediate thereof used in the production of plastics, elastic fibers, polyurethanes, polyesters, including polyhydroxyalkanoates such as P4HB or co-polymers thereof, PTMEG and polyurethane-polyurea copolymers, referred to as spandex, elastane or Lycra™, nylons, and the like. Thus, in some aspects, the invention provides a biobased plastics, elastic fibers, polyurethanes, polyesters, including polyhydroxyalkanoates such as P4HB or co-polymers thereof, PTMEG and polyurethane-polyurea copolymers, referred to as spandex, elastane or Lycra™, nylons, and the like, comprising at least 2%, at least 3%, at least 5%, at least 10%, at least 15%, at least 20%, at least 25%, at least 30%, at least 35%, at least 40%, at least 50%, at least 60%, at least 70%, at least 80%, at least 90%, at least 95%, at least 98% or 100% bioderived 1,4-butanediol and/or 4-HB or bioderived 1,4-butanediol and/or 4-HB intermediate thereof as disclosed herein.

In one embodiment, the product is a plastic. In one embodiment, the product is an elastic fiber. In one embodiment, the product is a polyurethane. In one embodiment, the product is a polyester. In one embodiment, the product is a polyhydroxyalkanoate. In one embodiment, the product is a poly-4-HB. In one embodiment, the product is a co-polymer of poly-4-HB. In one embodiment, the product is a poly (tetramethylene ether) glycol. In one embodiment, the product is a polyurethane-polyurea copolymer. In one embodiment, the product is a spandex. In one embodiment, the product is an elastane. In one embodiment, the product is a Lycra™. In one embodiment, the product is a nylon.

Adipate, 6-aminocaproate, hexamethylenediamine and caprolactam, as well as intermediates thereof, are chemicals used in commercial and industrial applications. Non-limiting examples of such applications include production of polymers, plastics, epoxy resins, nylons (e.g., nylon-6 or nylon 6-6), textiles, polyurethanes, plasticizers, unsaturated polyesters, fibers, polyester polyols, polyurethane, lubricant components, PVC, food additives, food ingredients, flavorants, gelling aids, food and oral medicinal coatings/products, and the like. Moreover, adipate, 6-aminocaproate, hexamethylenediamine and caprolactam are also used as a raw material in the production of a wide range of products including polymers, plastics, epoxy resins, nylons (e.g., nylon-6 or nylon 6-6), textiles, polyurethanes, plasticizers, unsaturated polyesters, fibers, polyester polyols, polyurethane, lubricant components, PVC, food additives, food ingredients, flavorants, gelling aids, food and oral medicinal coatings/products, and the like. Accordingly, in some embodiments, provided is biobased polymers, plastics, epoxy resins, nylons (e.g., nylon-6 or nylon 6-6), textiles, polyurethanes, plasticizers, unsaturated polyesters, fibers, polyester polyols, polyurethane, lubricant components, PVC, food additives, food ingredients, flavorants, gelling aids, food and oral medicinal coatings/products, and the like, comprising one or more of bioderived adipate, 6-aminocaproate, hexamethylenediamine or caprolactam, or a bioderived intermediate thereof, produced by a non-naturally occurring microbial organism provided herein or produced using a method disclosed herein.

In one embodiment, the product is a polymer. In one embodiment, the product is a plastic. In one embodiment, the product is an epoxy resin. In one embodiment, the product is a nylons (e.g., nylon-6 or nylon 6-6). In one embodiment, the product is a textile. In one embodiment, the product is a polyurethane. In one embodiment, the product is a plasticizer. In one embodiment, the product is an unsaturated polyester. In one embodiment, the product is a fiber. In one embodiment, the product is a polyester polyol. In one embodiment, the product is a polyurethane. In one embodiment, the product is a lubricant component. In one embodiment, the product is a PVC. In one embodiment, the product is a food additive. In one embodiment, the product is a food ingredient. In one embodiment, the product is a flavorant. In one embodiment, the product is a gelling aid. In one embodiment, the product is a food coating. In one embodiment, the product is a food product. In one embodiment, the product is an oral medicinal coatings. In one embodiment, the product is an oral product.

In some embodiments, provided is polymers, plastics, epoxy resins, nylons (e.g., nylon-6 or nylon 6-6), textiles, polyurethanes, plasticizers, unsaturated polyesters, fibers, polyester polyols, polyurethane, lubricant components, PVC, food additives, food ingredients, flavorants, gelling aids, food and oral medicinal coatings/products, and the like, comprising bioderived adipate, 6-aminocaproate, hexamethylenediamine or caprolactam, or a bioderived intermediate thereof, wherein the bioderived adipate, 6-aminocaproate, hexamethylenediamine or caprolactam, or bioderived intermediate thereof, includes all or part of an adipate, 6-aminocaproate, hexamethylenediamine or caprolactam, or an intermediate thereof, used in the production of polymers, plastics, epoxy resins, nylons (e.g., nylon-6 or nylon 6-6), textiles, polyurethanes, plasticizers, unsaturated polyesters, fibers, polyester polyols, polyurethane, lubricant components, PVC, food additives, food ingredients, flavorants, gelling aids, food and oral medicinal coatings/products, and the like, comprising at least 2%, at least 3%, at least 5%, at least 10%, at least 15%, at least 20%, at least 25%, at least 30%, at least 35%, at least 40%, at least 50%, at least 60%, at least 70%, at least 80%, at least 90%, at least 95%, at least 98% or 100% bioderived adipate, 6-aminocaproate, hexamethylenediamine or caprolactam, or a bioderived adipate, 6-aminocaproate, hexamethylenediamine or caprolactam intermediate, as disclosed herein.

Methacylic acid, as well as intermediates thereof such as 3-hydroxyisobutyrate, and 2-hydroxyisobutyric acid is a chemical used in commercial and industrial applications. Non-limiting examples of such applications include production of polymers, co-polymers, plastics, methacrylates (e.g., a methyl methacrylate or a butyl methacrylate), glacial methacylic acid, and the like. 2-Hydroxyisobutyric acid can be dehydrated to form methacrylic acid as described, for example, in U.S. Pat. No. 7,186,856. Moreover, 3-hydroxyisobutyrate and methacylic acid are also used as a raw material in the production of a wide range of products including polymers, co-polymers, plastics, methacrylates (e.g., a methyl methacrylate or a butyl methacrylate), glacial methacylic acid, and the like. Accordingly, in some embodiments, the invention provides biobased polymers, co-polymers, plastics, methacrylates (e.g., a methyl methacrylate or a butyl methacrylate), glacial methacylic acid, and the like, comprising one or more of bioderived methacylic acid, 3-hydroxyisobutyrate or 2-hydroxyisobutyric acid, or a bioderived intermediate thereof, produced by a non-naturally occurring microorganism of the invention or produced using a method disclosed herein.

In some embodiments, the invention provides polymers, co-polymers, plastics, methacrylates (e.g., a methyl methacrylate or a butyl methacrylate), glacial methacylic acid, and the like, comprising bioderived methacylic acid, 3-hydroxyisobutyrate or 2-hydroxyisobutyric acid, or a bioderived intermediate thereof, wherein the bioderived methacylic acid, 3-hydroxyisobutyrate or 2-hydroxyisobutyric acid, or bioderived intermediate thereof, includes all or part of the a methacylic acid, 3-hydroxyisobutyrate or 2-hydroxyisobutyric acid, or an intermediate thereof, used in the production of polymers, co-polymers, plastics, methacrylates (e.g., a methyl methacrylate or a butyl methacrylate), glacial methacylic acid, and the like. Thus, in some aspects, the invention provides a biobased polymers, co-polymers, plastics, methacrylates (e.g., a methyl methacrylate or a butyl methacrylate), glacial methacylic acid, and the like, comprising at least 2%, at least 3%, at least 5%, at least 10%, at least 15%, at least 20%, at least 25%, at least 30%, at least 35%, at least 40%, at least 50%, at least 60%, at least 70%, at least 80%, at least 90%, at least 95%, at least 98% or 100% bioderived methacylic acid, 3-hydroxyisobutyrate or 2-hydroxyisobutyric acid, or a bioderived methacylic acid, 3-hydroxyisobutyrate or 2-hydroxyisobutyric acid intermediate, as disclosed herein.

Additionally, in some embodiments, the invention provides a composition having a bioderived compound or pathway intermediate disclosed herein and a compound other than the bioderived compound or pathway intermediate. For example, in some aspects, the invention provides a biobased product as described herein wherein the bioderived compound or bioderived compound pathway intermediate used in its production is a combination of bioderived and petroleum derived compound or compound pathway intermediate. For example, a biobased product described herein can be produced using 50% bioderived compound and 50% petroleum derived compound or other desired ratios such as 60%/40%, 70%/30%, 80%/20%, 90%/10%, 95%/5%, 100%/0%, 40%/60%, 30%/70%, 20%/80%, 10%/90% of bioderived/petroleum derived precursors, so long as at least a portion of the product comprises a bioderived product produced by the microbial organisms disclosed herein. It is understood that methods for producing a biobased product as described herein using the bioderived compound or bioderived compound pathway intermediate of the invention are well known in the art.

The invention further provides a composition comprising bioderived compound described herein and a compound other than the bioderived bioderived. The compound other than the bioderived product can be a cellular portion, for example, a trace amount of a cellular portion of, or can be fermentation broth or culture medium, or a purified or partially purified fraction thereof produced in the presence of, a non-naturally occurring microbial organism of the invention. The composition can comprise, for example, a reduced level of a byproduct when produced by an organism having reduced byproduct formation, as disclosed herein. The composition can comprise, for example, bioderived compound, or a cell lysate or culture supernatant of a microbial organism of the invention.

In certain embodiments, provided herein is a composition comprising a bioderived compound provided herein produced by culturing a non-naturally occurring microbial organism described herein. In some embodiments, the composition further comprises a compound other than said bioderived compound. In certain embodiments, the compound other than said bioderived compound is a trace amount of a cellular portion of a non-naturally occurring microbial organism described herein.

The culture conditions can include, for example, liquid culture procedures as well as fermentation and other large scale culture procedures. As described herein, particularly useful yields of the biosynthetic products of the invention can be obtained under anaerobic or substantially anaerobic culture conditions.

As described herein, one exemplary growth condition for achieving biosynthesis of acetyl-CoA or a bioderived compound includes anaerobic culture or fermentation conditions. In certain embodiments, the non-naturally occurring microbial organisms of the invention can be sustained, cultured or fermented under anaerobic or substantially anaerobic conditions. Briefly, an anaerobic condition refers to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also includes growing or resting cells in liquid medium or on solid agar inside a sealed chamber maintained with an atmosphere of less than 1% oxygen. The percent of oxygen can be maintained by, for example, sparging the culture with an $N_2/CO_2$ mixture or other suitable non-oxygen gas or gases.

The culture conditions described herein can be scaled up and grown continuously for manufacturing of acetyl-CoA or a bioderived compound. Exemplary growth procedures include, for example, fed-batch fermentation and batch separation; fed-batch fermentation and continuous separation, or continuous fermentation and continuous separation. All of these processes are well known in the art. Fermentation procedures are particularly useful for the biosynthetic production of commercial quantities of acetyl-CoA or a bioderived compound. Generally, and as with non-continuous culture procedures, the continuous and/or near-continuous production of acetyl-CoA or a bioderived compound will include culturing a non-naturally occurring acetyl-CoA or a bioderived compound producing organism of the invention in sufficient nutrients and medium to sustain and/or nearly sustain growth in an exponential phase. Continuous culture under such conditions can include, for example, growth or culturing for 1 day, 2, 3, 4, 5, 6 or 7 days or more. Additionally, continuous culture can include longer time periods of 1 week, 2, 3, 4 or 5 or more weeks and up to several months. Alternatively, organisms of the invention can be cultured for hours, if suitable for a particular application. It is to be understood that the continuous and/or near-continuous culture conditions also can include all time intervals in between these exemplary periods. It is further understood that the time of culturing the microbial organism of the invention is for a sufficient period of time to produce a sufficient amount of product for a desired purpose.

Fermentation procedures are well known in the art. Briefly, fermentation for the biosynthetic production of acetyl-CoA or a bioderived compound can be utilized in, for example, fed-batch fermentation and batch separation; fed-batch fermentation and continuous separation, or continuous fermentation and continuous separation. Examples of batch and continuous fermentation procedures are well known in the art.

In addition to the above fermentation procedures using the acetyl-CoA or the bioderived compound producers of the invention for continuous production of substantial quantities of acetyl-CoA or a bioderived compound, the acetyl-CoA or the bioderived compound producers also can be, for example, simultaneously subjected to chemical synthesis and/or enzymatic procedures to convert the product to other compounds or the product can be separated from the fermentation culture and sequentially subjected to chemical and/or enzymatic conversion to convert the product to other compounds, if desired.

To generate better producers, metabolic modeling can be utilized to optimize growth conditions. Modeling can also be used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of acetyl-CoA or a bioderived compound.

One computational method for identifying and designing metabolic alterations favoring biosynthesis of a desired product is the OptKnock computational framework (Burgard et al., *Biotechnol. Bioeng.* 84:647-657 (2003)). OptKnock is a metabolic modeling and simulation program that suggests gene deletion or disruption strategies that result in genetically stable microorganisms which overproduce the target product. Specifically, the framework examines the complete metabolic and/or biochemical network of a microorganism in order to suggest genetic manipulations that force the desired biochemical to become an obligatory byproduct of cell growth. By coupling biochemical production with cell growth through strategically placed gene deletions or other functional gene disruption, the growth selection pressures imposed on the engineered strains after long periods of time in a bioreactor lead to improvements in performance as a result of the compulsory growth-coupled biochemical production. Lastly, when gene deletions are constructed there is a negligible possibility of the designed strains reverting to their wild-type states because the genes selected by OptKnock are to be completely removed from the genome. Therefore, this computational methodology can be used to either identify alternative pathways that lead to biosynthesis of a desired product or used in connection with the non-naturally occurring microbial organisms for further optimization of biosynthesis of a desired product.

Briefly, OptKnock is a term used herein to refer to a computational method and system for modeling cellular metabolism. The OptKnock program relates to a framework of models and methods that incorporate particular constraints into flux balance analysis (FBA) models. These constraints include, for example, qualitative kinetic information, qualitative regulatory information, and/or DNA microarray experimental data. OptKnock also computes solutions to various metabolic problems by, for example, tightening the flux boundaries derived through flux balance models and subsequently probing the performance limits of metabolic networks in the presence of gene additions or deletions. OptKnock computational framework allows the construction of model formulations that allow an effective query of the performance limits of metabolic networks and provides methods for solving the resulting mixed-integer linear programming problems. The metabolic modeling and simulation methods referred to herein as OptKnock are described in, for example, U.S. publication 2002/0168654, filed Jan. 10, 2002, in International Patent No. PCT/US02/00660, filed Jan. 10, 2002, and U.S. publication 2009/0047719, filed Aug. 10, 2007.

Another computational method for identifying and designing metabolic alterations favoring biosynthetic production of a product is a metabolic modeling and simulation system termed SimPheny®. This computational method and system is described in, for example, U.S. publication 2003/0233218, filed Jun. 14, 2002, and in International Patent Application No. PCT/US03/18838, filed Jun. 13, 2003. SimPheny® is a computational system that can be used to produce a network model in silico and to simulate the flux of mass, energy or charge through the chemical reactions of a biological system to define a solution space that contains any and all possible functionalities of the chemical reactions in the system, thereby determining a range of allowed activities for the biological system. This approach is referred to as constraints-based modeling because the solution space is defined by constraints such as the known stoichiometry of the included reactions as well as reaction thermodynamic and capacity constraints associated with maximum fluxes through reactions. The space defined by these constraints can be interrogated to determine the phenotypic capabilities and behavior of the biological system or of its biochemical components.

These computational approaches are consistent with biological realities because biological systems are flexible and can reach the same result in many different ways. Biological systems are designed through evolutionary mechanisms that have been restricted by fundamental constraints that all living systems must face. Therefore, constraints-based modeling strategy embraces these general realities. Further, the ability to continuously impose further restrictions on a network model via the tightening of constraints results in a reduction in the size of the solution space, thereby enhancing the precision with which physiological performance or phenotype can be predicted.

Given the teachings and guidance provided herein, those skilled in the art will be able to apply various computational frameworks for metabolic modeling and simulation to design and implement biosynthesis of a desired compound in host microbial organisms. Such metabolic modeling and simulation methods include, for example, the computational systems exemplified above as SimPheny® and OptKnock. For illustration of the invention, some methods are described herein with reference to the OptKnock computation framework for modeling and simulation. Those skilled in the art will know how to apply the identification, design and implementation of the metabolic alterations using OptKnock to any of such other metabolic modeling and simulation computational frameworks and methods well known in the art.

The methods described above will provide one set of metabolic reactions to disrupt. Elimination of each reaction within the set or metabolic modification can result in a desired product as an obligatory product during the growth phase of the organism. Because the reactions are known, a solution to the bilevel OptKnock problem also will provide the associated gene or genes encoding one or more enzymes that catalyze each reaction within the set of reactions. Identification of a set of reactions and their corresponding genes encoding the enzymes participating in each reaction is generally an automated process, accomplished through correlation of the reactions with a reaction database having a relationship between enzymes and encoding genes.

Once identified, the set of reactions that are to be disrupted in order to achieve production of a desired product are implemented in the target cell or organism by functional disruption of at least one gene encoding each metabolic reaction within the set. One particularly useful means to achieve functional disruption of the reaction set is by deletion of each encoding gene. However, in some instances, it can be beneficial to disrupt the reaction by other genetic aberrations including, for example, mutation, deletion of regulatory regions such as promoters or cis binding sites for regulatory factors, or by truncation of the coding sequence at any of a number of locations. These latter aberrations, resulting in less than total deletion of the gene set can be useful, for example, when rapid assessments of the coupling of a product are desired or when genetic reversion is less likely to occur.

To identify additional productive solutions to the above described bilevel OptKnock problem which lead to further sets of reactions to disrupt or metabolic modifications that can result in the biosynthesis, including growth-coupled biosynthesis of a desired product, an optimization method, termed integer cuts, can be implemented. This method proceeds by iteratively solving the OptKnock problem exemplified above with the incorporation of an additional constraint referred to as an integer cut at each iteration. Integer cut constraints effectively prevent the solution procedure from choosing the exact same set of reactions identified in any previous iteration that obligatorily couples product biosynthesis to growth. For example, if a previously identified growth-coupled metabolic modification specifies reactions 1, 2, and 3 for disruption, then the following constraint prevents the same reactions from being simultaneously considered in subsequent solutions. The integer cut method is well known in the art and can be found described in, for example, Burgard et al., *Biotechnol. Prog.* 17:791-797 (2001). As with all methods described herein with reference to their use in combination with the OptKnock computational framework for metabolic modeling and simulation, the integer cut method of reducing redundancy in iterative computational analysis also can be applied with other computational frameworks well known in the art including, for example, SimPheny®.

The methods exemplified herein allow the construction of cells and organisms that biosynthetically produce a desired product, including the obligatory coupling of production of a target biochemical product to growth of the cell or organism engineered to harbor the identified genetic alterations. Therefore, the computational methods described herein allow the identification and implementation of metabolic modifications that are identified by an in silico method selected from OptKnock or SimPheny®. The set of metabolic modifications can include, for example, addition of one or more biosynthetic pathway enzymes and/or functional disruption of one or more metabolic reactions including, for example, disruption by gene deletion.

As discussed above, the OptKnock methodology was developed on the premise that mutant microbial networks can be evolved towards their computationally predicted maximum-growth phenotypes when subjected to long periods of growth selection. In other words, the approach leverages an organism's ability to self-optimize under selective pressures. The OptKnock framework allows for the exhaustive enumeration of gene deletion combinations that force a coupling between biochemical production and cell growth based on network stoichiometry. The identification of optimal gene/reaction knockouts requires the solution of a bilevel optimization problem that chooses the set of active reactions such that an optimal growth solution for the resulting network overproduces the biochemical of interest (Burgard et al., *Biotechnol. Bioeng.* 84:647-657 (2003)).

An in silico stoichiometric model of *E. coli* metabolism can be employed to identify essential genes for metabolic pathways as exemplified previously and described in, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379. As disclosed herein, the OptKnock mathematical framework can be applied to pinpoint gene deletions leading to the growth-coupled production of a desired product. Further, the solution of the bilevel OptKnock problem provides only one set of deletions. To enumerate all meaningful solutions, that is, all sets of knockouts leading to growth-coupled production formation, an optimization technique, termed integer cuts, can be implemented. This entails iteratively solving the OptKnock problem with the incorporation of an additional constraint referred to as an integer cut at each iteration, as discussed above.

As disclosed herein, a nucleic acid encoding a desired activity of an acetyl-CoA or a bioderived compound pathway can be introduced into a host organism. In some cases, it can be desirable to modify an activity of an acetyl-CoA or a bioderived compound pathway enzyme or protein to increase production of acetyl-CoA or a bioderived compound. For example, known mutations that increase the activity of a protein or enzyme can be introduced into an encoding nucleic acid molecule. Additionally, optimization methods can be applied to increase the activity of an enzyme or protein and/or decrease an inhibitory activity, for example, decrease the activity of a negative regulator.

One such optimization method is directed evolution. Directed evolution is a powerful approach that involves the introduction of mutations targeted to a specific gene in order to improve and/or alter the properties of an enzyme. Improved and/or altered enzymes can be identified through the development and implementation of sensitive high-throughput screening assays that allow the automated screening of many enzyme variants (for example, >$10^4$). Iterative rounds of mutagenesis and screening typically are performed to afford an enzyme with optimized properties. Computational algorithms that can help to identify areas of the gene for mutagenesis also have been developed and can significantly reduce the number of enzyme variants that need to be generated and screened. Numerous directed evolution technologies have been developed (for reviews, see Hibbert et al., *Biomol. Eng* 22:11-19 (2005); Huisman and Lalonde, In Biocatalysis in the pharmaceutical and biotechnology industries pgs. 717-742 (2007), Patel (ed.), CRC Press; Often and Quax. *Biomol. Eng* 22:1-9 (2005)$_4$ and Sen et al., *Appl Biochem. Biotechnol* 143:212-223 (2007)) to be effective at creating diverse variant libraries, and these methods have been successfully applied to the improvement of a wide range of properties across many enzyme classes. Enzyme characteristics that have been improved and/or altered by directed evolution technologies include, for example: selectivity/specificity, for conversion of non-natural substrates; temperature stability, for robust high temperature processing; pH stability, for bioprocessing under lower or higher pH conditions; substrate or product tolerance, so that high product titers can be achieved; binding ($K_m$), including broadening substrate binding to include non-natural substrates; inhibition ($K_i$), to remove inhibition by products, substrates, or key intermediates; activity (kcat), to increases enzymatic reaction rates to achieve desired flux; expression levels, to increase protein yields and overall pathway flux; oxygen stability, for operation of air sensitive enzymes under aerobic conditions; and anaerobic activity, for operation of an aerobic enzyme in the absence of oxygen.

A number of exemplary methods have been developed for the mutagenesis and diversification of genes to target desired properties of specific enzymes. Such methods are well known to those skilled in the art. Any of these can be used to alter and/or optimize the activity of an acetyl-CoA or a bioderived compound pathway enzyme or protein. Such methods include, but are not limited to EpPCR, which introduces random point mutations by reducing the fidelity of DNA polymerase in PCR reactions (Pritchard et al., *J Theor. Biol.* 234:497-509 (2005)); Error-prone Rolling Circle Amplification (epRCA), which is similar to epPCR except a whole circular plasmid is used as the template and random 6-mers with exonuclease resistant thiophosphate linkages on the last 2 nucleotides are used to amplify the plasmid followed by transformation into cells in which the plasmid is re-circularized at tandem repeats (Fujii et al., *Nucleic Acids Res.* 32:e145 (2004); and Fujii et al., *Nat. Protoc.* 1:2493-2497 (2006)); DNA or Family Shuffling, which typically involves digestion of two or more variant genes with nucleases such as Dnase I or EndoV to generate a pool of random fragments that are reassembled by cycles of annealing and extension in the presence of DNA polymerase to create a library of chimeric genes (Stemmer, *Proc Natl Acad Sci USA* 91:10747-10751 (1994); and Stemmer, *Nature* 370:389-391 (1994)); Staggered Extension (StEP), which entails template priming followed by repeated cycles of 2 step PCR with denaturation and very short duration of annealing/extension (as short as 5 sec) (Zhao et al., *Nat. Biotechnol.* 16:258-261 (1998)); Random Priming Recombination (RPR), in which random sequence primers are used to generate many short DNA fragments complementary to different segments of the template (Shao et al., *Nucleic Acids Res* 26:681-683 (1998)).

Additional methods include Heteroduplex Recombination, in which linearized plasmid DNA is used to form heteroduplexes that are repaired by mismatch repair (Volkov et al, *Nucleic Acids Res.* 27:e18 (1999); and Volkov et al., *Methods Enzymol.* 328:456-463 (2000)); Random Chimeragenesis on Transient Templates (RACHITT), which employs Dnase I fragmentation and size fractionation of single stranded DNA (ssDNA) (Coco et al., *Nat. Biotechnol.*

19:354-359 (2001)); Recombined Extension on Truncated templates (RETT), which entails template switching of unidirectionally growing strands from primers in the presence of unidirectional ssDNA fragments used as a pool of templates (Lee et al., *J. Molec. Catalysis* 26:119-129 (2003)); Degenerate Oligonucleotide Gene Shuffling (DOGS), in which degenerate primers are used to control recombination between molecules; (Bergquist and Gibbs, *Methods Mol. Biol* 352:191-204 (2007); Bergquist et al., *Biomol. Eng* 22:63-72 (2005); Gibbs et al., *Gene* 271:13-20 (2001)); Incremental Truncation for the Creation of Hybrid Enzymes (ITCHY), which creates a combinatorial library with 1 base pair deletions of a gene or gene fragment of interest (Ostermeier et al., *Proc. Natl. Acad. Sci. USA* 96:3562-3567 (1999); and Ostermeier et al., *Nat. Biotechnol.* 17:1205-1209 (1999)); Thio-Incremental Truncation for the Creation of Hybrid Enzymes (THIO-ITCHY), which is similar to ITCHY except that phosphothioate dNTPs are used to generate truncations (Lutz et al., *Nucleic Acids Res* 29:E16 (2001)); SCRATCHY, which combines two methods for recombining genes, ITCHY and DNA shuffling (Lutz et al., *Proc. Natl. Acad. Sci. USA* 98:11248-11253 (2001)); Random Drift Mutagenesis (RNDM), in which mutations made via epPCR are followed by screening/selection for those retaining usable activity (Bergquist et al., *Biomol. Eng.* 22:63-72 (2005)); Sequence Saturation Mutagenesis (SeSaM), a random mutagenesis method that generates a pool of random length fragments using random incorporation of a phosphothioate nucleotide and cleavage, which is used as a template to extend in the presence of "universal" bases such as inosine, and replication of an inosine-containing complement gives random base incorporation and, consequently, mutagenesis (Wong et al., *Biotechnol. J.* 3:74-82 (2008); Wong et al., *Nucleic Acids Res.* 32:e26 (2004); and Wong et al., *Anal. Biochem.* 341:187-189 (2005)); Synthetic Shuffling, which uses overlapping oligonucleotides designed to encode "all genetic diversity in targets" and allows a very high diversity for the shuffled progeny (Ness et al., *Nat. Biotechnol.* 20:1251-1255 (2002)); Nucleotide Exchange and Excision Technology NexT, which exploits a combination of dUTP incorporation followed by treatment with uracil DNA glycosylase and then piperidine to perform endpoint DNA fragmentation (Muller et al., *Nucleic Acids Res.* 33:e117 (2005)).

Further methods include Sequence Homology-Independent Protein Recombination (SHIPREC), in which a linker is used to facilitate fusion between two distantly related or unrelated genes, and a range of chimeras is generated between the two genes, resulting in libraries of single-crossover hybrids (Sieber et al., *Nat. Biotechnol.* 19:456-460 (2001)); Gene Site Saturation Mutagenesis™ (GSSM™), in which the starting materials include a supercoiled double stranded DNA (dsDNA) plasmid containing an insert and two primers which are degenerate at the desired site of mutations (Kretz et al., *Methods Enzymol.* 388:3-11 (2004)); Combinatorial Cassette Mutagenesis (CCM), which involves the use of short oligonucleotide cassettes to replace limited regions with a large number of possible amino acid sequence alterations (Reidhaar-Olson et al. *Methods Enzymol.* 208:564-586 (1991); and Reidhaar-Olson et al. *Science* 241:53-57 (1988)); Combinatorial Multiple Cassette Mutagenesis (CMCM), which is essentially similar to CCM and uses epPCR at high mutation rate to identify hot spots and hot regions and then extension by CMCM to cover a defined region of protein sequence space (Reetz et al., *Angew. Chem. Int. Ed Engl.* 40:3589-3591 (2001)); the Mutator Strains technique, in which conditional is mutator plasmids, utilizing the mutD5 gene, which encodes a mutant subunit of DNA polymerase III, to allow increases of 20 to 4000-X in random and natural mutation frequency during selection and block accumulation of deleterious mutations when selection is not required (Selifonova et al., *Appl. Environ. Microbiol.* 67:3645-3649 (2001)); Low et al., *J. Mol. Biol.* 260:359-3680 (1996)).

Additional exemplary methods include Look-Through Mutagenesis (LTM), which is a multidimensional mutagenesis method that assesses and optimizes combinatorial mutations of selected amino acids (Rajpal et al., *Proc. Natl. Acad. Sci. USA* 102:8466-8471(2005)); Gene Reassembly, which is a DNA shuffling method that can be applied to multiple genes at one time or to create a large library of chimeras (multiple mutations) of a single gene (Tunable GeneReassembly™ (TGR™) Technology supplied by Verenium Corporation), in Silico Protein Design Automation (PDA), which is an optimization algorithm that anchors the structurally defined protein backbone possessing a particular fold, and searches sequence space for amino acid substitutions that can stabilize the fold and overall protein energetics, and generally works most effectively on proteins with known three-dimensional structures (Hayes et al., *Proc. Natl. Acad. Sci. USA* 99:15926-15931(2002)); and Iterative Saturation Mutagenesis (ISM), which involves using knowledge of structure/function to choose a likely site for enzyme improvement, performing saturation mutagenesis at chosen site using a mutagenesis method such as Stratagene QuikChange (Stratagene; San Diego Calif.), screening/selecting for desired properties, and, using improved clone(s), starting over at another site and continue repeating until a desired activity is achieved (Reetz et al., *Nat. Protoc.* 2:891-903 (2007); and Reetz et al., *Angew. Chem. Int. Ed Engl.* 45:7745-7751(2006)).

Any of the aforementioned methods for mutagenesis can be used alone or in any combination. Additionally, any one or combination of the directed evolution methods can be used in conjunction with adaptive evolution techniques, as described herein.

It is understood that modifications which do not substantially affect the activity of the various embodiments of this invention are also provided within the definition of the invention provided herein. Accordingly, the following examples are intended to illustrate but not limit the present invention.

Example I

Formate Assimilation Pathways

This example describes enzymatic pathways for converting pyruvate to formaldehyde, and optionally in combination with producing acetyl-CoA and/or reproducing pyruvate.

Step E, FIG. 1: Formate Reductase

The conversion of formate to formaldehyde can be carried out by a formate reductase (step E, FIG. 1). A suitable enzyme for these transformations is the aryl-aldehyde dehydrogenase, or equivalently a carboxylic acid reductase, from *Nocardia iowensis*. Expression of the npt gene product improved activity of the enzyme via post-transcriptional modification. The npt gene encodes a specific phosphopantetheine transferase (PPTase) that converts the inactive apo-enzyme to the active holo-enzyme. Information related to these proteins and genes is shown below.

| Protein | GenBank ID | GI number | Organism |
|---|---|---|---|
| Car | AAR91681.1 | 40796035 | Nocardia iowensis (sp. NRRL 5646) |
| Npt | ABI83656.1 | 114848891 | Nocardia iowensis (sp. NRRL 5646) |

Additional car and npt genes can be identified based on sequence homology.

| Protein | GenBank ID | GI number | Organism |
|---|---|---|---|
| fadD9 | YP_978699.1 | 121638475 | Mycobacterium bovis BCG |
| BCG_2812c | YP_978898.1 | 121638674 | Mycobacterium bovis BCG |
| nfa20150 | YP_118225.1 | 54023983 | Nocardia farcinica IFM 10152 |
| nfa40540 | YP_120266.1 | 54026024 | Nocardia farcinica IFM 10152 |
| SGR_6790 | YP_001828302.1 | 182440583 | Streptomyces griseus subsp. griseus NBRC 13350 |
| SGR_665 | YP_001822177.1 | 182434458 | Streptomyces griseus subsp. griseus NBRC 13350 |
| MSMEG_2956 | YP_887275.1 | 118473501 | Mycobacterium smegmatis MC2 155 |
| MSMEG_5739 | YP_889972.1 | 118469671 | Mycobacterium smegmatis MC2 155 |
| MSMEG_2648 | YP_886985.1 | 118471293 | Mycobacterium smegmatis MC2 155 |
| MAP1040c | NP_959974.1 | 41407138 | Mycobacterium avium subsp. paratuberculosis K-10 |
| MAP2899c | NP_961833.1 | 41408997 | Mycobacterium avium subsp. paratuberculosis K-10 |
| MMAR_2117 | YP_001850422.1 | 183982131 | Mycobacterium marinum M |
| MMAR_2936 | YP_001851230.1 | 183982939 | Mycobacterium marinum M |
| MMAR_1916 | YP_001850220.1 | 183981929 | Mycobacterium marinum M |
| TpauDRAFT_33060 | ZP_04027864.1 | 227980601 | Tsukamurella paurometabola DSM 20162 |
| TpauDRAFT_20920 | ZP_04026660.1 | 227979396 | Tsukamurella paurometabola DSM 20162 |
| CPCC7001_1320 | ZP_05045132.1 | 254431429 | Cyanobium PCC7001 |
| DDBDRAFT_0187729 | XP_636931.1 | 66806417 | Dictyostelium discoideum AX4 |

An additional enzyme candidate found in Streptomyces griseus is encoded by the griC and griD genes. This enzyme is believed to convert 3-amino-4-hydroxybenzoic acid to 3-amino-4-hydroxybenzaldehyde. Co-expression of griC and griD with SGR_665, an enzyme similar in sequence to the Nocardia iowensis npt, can be beneficial. Information related to these proteins and genes is shown below.

| Protein | GenBank ID | GI number | Organism |
|---|---|---|---|
| griC | YP_001825755.1 | 182438036 | Streptomyces griseus subsp. griseus NBRC 13350 |
| griD | YP_001825756.1 | 182438037 | Streptomyces griseus subsp. griseus NBRC 13350 |

An enzyme with similar characteristics, alpha-aminoadipate reductase (AAR, EC 1.2.1.31), participates in lysine biosynthesis pathways in some fungal species. This enzyme naturally reduces alpha-aminoadipate to alpha-aminoadipate semialdehyde. The carboxyl group is first activated through the ATP-dependent formation of an adenylate that is then reduced by NAD(P)H to yield the aldehyde and AMP. Like CAR, this enzyme utilizes magnesium and requires activation by a PPTase. Enzyme candidates for AAR and its corresponding PPTase are shown below.

| Protein | GenBank ID | GI number | Organism |
|---|---|---|---|
| LYS2 | AAA34747.1 | 171867 | Saccharomyces cerevisiae |
| LYS5 | P50113.1 | 1708896 | Saccharomyces cerevisiae |
| LYS2 | AAC02241.1 | 2853226 | Candida albicans |
| LYS5 | AAO26020.1 | 28136195 | Candida albicans |

| Protein | GenBank ID | GI number | Organism |
|---|---|---|---|
| Lys1p | P40976.3 | 13124791 | Schizosaccharomyces pombe |
| Lys7p | Q10474.1 | 1723561 | Schizosaccharomyces pombe |
| Lys2 | CAA74300.1 | 3282044 | Penicillium chrysogenum |

Tani et al (Agric Biol Chem, 1978, 42: 63-68; Agric Biol Chem, 1974, 38: 2057-2058) showed that purified enzymes from Escherichia coli strain B could reduce the sodium salts of different organic acids (e.g. formate, glycolate, acetate, etc.) to their respective aldehydes (e.g. formaldehyde, glycoaldehyde, acetaldehyde, etc.). Of three purified enzymes examined by Tani et al (1978), only the "A" isozyme was shown to reduce formate to formaldehyde. Collectively, this group of enzymes was originally termed glycoaldehyde dehydrogenase; however, their novel reductase activity led the authors to propose the name glycolate reductase as being more appropriate (Morita et al, Agric Biol Chem, 1979, 43: 185-186). Morita et al (Agric Biol Chem, 1979, 43: 185-186) subsequently showed that glycolate reductase activity is relatively widespread among microorganisms, being found for example in: Pseudomonas, Agrobacterium, Escherichia, Flavobacterium, Micrococcus, Staphylococcus, Bacillus, and others. Without wishing to be bound by any particular theory, it is believed that some of these glycolate reductase enzymes are able to reduce formate to formaldehyde.

Any of these CAR or CAR-like enzymes can exhibit formate reductase activity or can be engineered to do so.

Step F, FIG. 1 Formate Ligase, Formate Transferase, Formate Synthetase

The acylation of formate to formyl-CoA is catalyzed by enzymes with formate transferase, synthetase, or ligase activity (Step F, FIG. 1). Formate transferase enzymes have been identified in several organisms including Escherichia coli, acalobacter formigenes, and Lactobacillus acidophilus. Homologs exist in several other organisms. Enzymes acting on the CoA-donor for formate transferase may also be expressed to ensure efficient regeneration of the CoA-donor.

For example, if oxalyl-CoA is the CoA donor substrate for formate transferase, an additional transferase, synthetase, or ligase may be required to enable efficient regeneration of oxalyl-CoA from oxalate. Similarly, if succinyl- or acetyl-CoA is the CoA donor substrate for formate transferase, an additional transferase, synthetase, or ligase may be required to enable efficient regeneration of succinyl-CoA from succinate or acetyl-CoA from acetate, respectively.

| Protein | GenBank ID | GI number | Organism |
|---|---|---|---|
| YfdW | NP_416875.1 | 16130306 | Escherichia coli |
| frc | O06644.3 | 21542067 | Oxalobacter formigenes |
| frc | ZP_04021099.1 | 227903294 | Lactobacillus acidophilus |

Suitable CoA-donor regeneration or formate transferase enzymes are encoded by the gene products of cat1, cat2, and cat3 of *Clostridium kluyveri*. These enzymes have been shown to exhibit succinyl-CoA, 4-hydroxybutyryl-CoA, and butyryl-CoA acetyltransferase activity, respectively. Similar CoA transferase activities are also present in *Trichomonas vaginalis* and *Trypanosoma brucei*. Yet another transferase capable of the desired conversions is butyryl-CoA:acetoacetate CoA-transferase. Exemplary enzymes are shown below. Genes FN0272 and FN0273 have been annotated as a butyrate-acetoacetate CoA-transferase

| Protein | GenBank ID | GI number | Organism |
|---|---|---|---|
| Cat1 | P38946.1 | 729048 | Clostridium kluyveri |
| Cat2 | P38942.2 | 1705614 | Clostridium kluyveri |
| Cat3 | EDK35586.1 | 146349050 | Clostridium kluyveri |
| TVAG_395550 | XP_001330176 | 123975034 | Trichomonas vaginalis G3 |
| Tb11.02.0290 | XP_828352 | 71754875 | Trypanosoma brucei |
| FN0272 | NP_603179.1 | 19703617 | Fusobacterium nucleatum |
| FN0273 | NP_603180.1 | 19703618 | Fusobacterium nucleatum |
| FN1857 | NP_602657.1 | 19705162 | Fusobacterium nucleatum |
| FN1856 | NP_602656.1 | 19705161 | Fusobacterium nucleatum |
| PG1066 | NP_905281.1 | 34540802 | Porphyromonas gingivalis W83 |
| PG1075 | NP_905290.1 | 34540811 | Porphyromonas gingivalis W83 |
| TTE0720 | NP_622378.1 | 20807207 | Thermoanaerobacter tengcongensis MB4 |
| TTE0721 | NP_622379.1 | 20807208 | Thermoanaerobacter tengcongensis MB4 |

Additional transferase enzymes of interest include proteins and genes shown below.

| Protein | GenBank ID | GI number | Organism |
|---|---|---|---|
| AtoA | P76459.1 | 2492994 | Escherichia coli |
| AtoD | P76458.1 | 2492990 | Escherichia coli |
| CtfA | NP_149326.1 | 15004866 | Clostridium acetobutylicum |
| CtfB | NP_149327.1 | 15004867 | Clostridium acetobutylicum |
| CtfA | AAP42564.1 | 31075384 | Clostridium saccharoperbutylacetonicum |
| CtfB | AAP42565.1 | 31075385 | Clostridium saccharoperbutylacetonicum |

Succinyl-CoA:3-ketoacid-CoA transferase naturally converts succinate to succinyl-CoA while converting a 3-ketoacyl-CoA to a 3-ketoacid. Exemplary succinyl-CoA:3-ketoacid-CoA transferases proteins and genes are shown below.

| Protein | GenBank ID | GI number | Organism |
|---|---|---|---|
| HPAG1_0676 | YP_627417 | 108563101 | Helicobacter pylori |
| HPAG1_0677 | YP_627418 | 108563102 | Helicobacter pylori |
| ScoA | NP_391778 | 16080950 | Bacillus subtilis |
| ScoB | NP_391777 | 16080949 | Bacillus subtilis |
| OXCT1 | NP_000427 | 4557817 | Homo sapiens |
| OXCT2 | NP_071403 | 11545841 | Homo sapiens |

Two additional enzymes that catalyze the activation of formate to formyl-CoA reaction are AMP-forming formyl-CoA synthetase and ADP-forming formyl-CoA synthetase. Exemplary enzymes, known to function on acetate, are shown below. Such enzymes may also acylate formate naturally or can be engineered to do so.

| Protein | GenBank ID | GI Number | Organism |
|---|---|---|---|
| acs | AAC77039.1 | 1790505 | Escherichia coli |
| acoE | AAA21945.1 | 141890 | Ralstonia eutropha |
| acs1 | ABC87079.1 | 86169671 | Methanothermobacter thermautotrophicus |
| acs1 | AAL23099.1 | 16422835 | Salmonella enterica |
| ACS1 | Q01574.2 | 257050994 | Saccharomyces cerevisiae |

ADP-forming acetyl-CoA synthetase (ACD, EC 6.2.1.13) is another candidate enzyme that couples the conversion of acyl-CoA esters to their corresponding acids with the concurrent synthesis of ATP. Several enzymes with broad substrate specificities have been described in the literature. Such enzymes may also acylate formate naturally or can be engineered to do so. Information related to these proteins and genes is shown below.

| Protein | GenBank ID | GI number | Organism |
|---|---|---|---|
| AF1211 | NP_070039.1 | 11498810 | Archaeoglobus fulgidus DSM 4304 |
| AF1983 | NP_070807.1 | 11499565 | Archaeoglobus fulgidus DSM 4304 |
| scs | YP_135572.1 | 55377722 | Haloarcula marismortui ATCC 43049 |
| PAE3250 | NP_560604.1 | 18313937 | Pyrobaculum aerophilum str. IM2 |
| sucC | NP_415256.1 | 16128703 | Escherichia coli |
| sucD | AAC73823.1 | 1786949 | Escherichia coli |
| paaF | AAC24333.2 | 22711873 | Pseudomonas putida |

An alternative method for adding the CoA moiety to formate is to apply a pair of enzymes such as a phosphate-transferring acyltransferase and a kinase. These activities enable the net formation of formyl-CoA with the simultaneous consumption of ATP. An exemplary phosphate-transferring acyltransferase is phosphotransacetylase, encoded by pta. Exemplary enzymes are shown below. Such enzymes may also phosphorylate formate naturally or can be engineered to do so.

| Protein | GenBank ID | GI number | Organism |
|---|---|---|---|
| Pta | NP_416800.1 | 16130232 | Escherichia coli |
| Pta | NP_461280.1 | 16765665 | Salmonella enterica subsp. enterica serovar Typhimurium str. LT2 |
| PAT2 | XP_001694504.1 | 159472743 | Chlamydomonas reinhardtii |
| PAT1 | XP_001691787.1 | 159467202 | Chlamydomonas reinhardtii |

An exemplary acetate kinase is the E. coli acetate kinase, encoded by ackA (Skarstedt and Silverstein J. Biol. Chem. 251:6775-6783 (1976)). Homologs exist in several other organisms including Salmonella enterica and Chlamydomonas reinhardtii. It is likely that such enzymes naturally possess formate kinase activity or can be engineered to have this activity. Information related to these proteins and genes is shown below:

| Protein | GenBank ID | GI number | Organism |
|---|---|---|---|
| AckA | NP_416799.1 | 16130231 | Escherichia coli |
| AckA | NP_461279.1 | 16765664 | Salmonella enterica subsp. enterica serovar Typhimurium str. LT2 |
| ACK1 | XP_001694505.1 | 159472745 | Chlamydomonas reinhardtii |
| ACK2 | XP_001691682.1 | 159466992 | Chlamydomonas reinhardtii |

The acylation of formate to formyl-CoA can also be carried out by a formate ligase. Such enzymes may also acylate formate naturally or can be engineered to do so. Information related to these proteins and genes is shown below.

| Protein | GenBank ID | GI number | Organism |
|---|---|---|---|
| SucC | NP_415256.1 | 16128703 | Escherichia coli |
| SucD | AAC73823.1 | 1786949 | Escherichia coli |
| LSC1 | NP_014785 | 6324716 | Saccharomyces cerevisiae |
| LSC2 | NP_011760 | 6321683 | Saccharomyces cerevisiae |

Additional exemplary CoA-ligases include the rat dicarboxylate-CoA ligase for which the sequence is yet uncharacterized (Vamecq et al., Biochemical J. 230:683-693 (1985)), and exemplary enzymes shown below. Such enzymes may also acylate formate naturally or can be engineered to do so. Information related to these proteins and genes is shown below.

| Protein | GenBank ID | GI number | Organism |
|---|---|---|---|
| Phl | CAJ15517.1 | 77019264 | Penicillium chrysogenum |
| PhlB | ABS19624.1 | 152002983 | Penicillium chrysogenum |
| PaaF | AAC24333.2 | 22711873 | Pseudomonas putida |
| BioW | NP_390902.2 | 50812281 | Bacillus subtilis |
| AACS | NP_084486.1 | 21313520 | Mus musculus |
| AACS | NP_076417.2 | 31982927 | Homo sapiens |
| Msed_1422 | YP_001191504 | 146304188 | Metallosphaera sedula |

Step G, FIG. 1: Formyl-CoA Reductase

Several acyl-CoA dehydrogenases are capable of reducing an acyl-CoA (e.g., formyl-CoA) to its corresponding aldehyde (e.g., formaldehyde) (Steps F, FIG. 1). Exemplary genes that encode such enzymes include those below. Such enzymes may be capable of naturally converting formyl-CoA to formaldehyde or can be engineered to do so.

| Protein | GenBank ID | GI number | Organism |
|---|---|---|---|
| acr1 | YP_047869.1 | 50086355 | Acinetobacter calcoaceticus |
| acr1 | AAC45217 | 1684886 | Acinetobacter baylyi |
| acr1 | BAB85476.1 | 18857901 | Acinetobacter sp. Strain M-1 |
| sucD | P38947.1 | 172046062 | Clostridium kluyveri |
| sucD | NP_904963.1 | 34540484 | Porphyromonas gingivalis |
| bphG | BAA03892.1 | 425213 | Pseudomonas sp |
| adhE | AAV66076.1 | 55818563 | Leuconostoc mesenteroides |
| Bld | AAP42563.1 | 31075383 | Clostridium saccharoperbutylacetonicum |
| Ald | ACL06658.1 | 218764192 | Desulfatibacillum alkenivorans AK-01 |
| Ald | YP_001452373 | 157145054 | Citrobacter koseri ATCC BAA-895 |
| pduP | NP_460996.1 | 16765381 | Salmonella enterica Typhimurium |
| pduP | ABJ64680.1 | 116099531 | Lactobacillus brevis ATCC 367 |
| BselDRAFT_1651 | ZP_02169447 | 163762382 | Bacillus selenitireducens MLS10 |

An additional enzyme type that converts an acyl-CoA to its corresponding aldehyde is malonyl-CoA reductase which transforms malonyl-CoA to malonic semialdehyde. Malonyl-CoA reductase is a key enzyme in autotrophic carbon fixation via the 3-hydroxypropionate cycle in thermoacidophilic archaeal bacteria (Berg et al., Science 318:1782-1786 (2007); Thauer, Science 318:1732-1733 (2007)). The enzyme utilizes NADPH as a cofactor. Although the aldehyde dehydrogenase functionality of these enzymes is similar to the bifunctional dehydrogenase from Chloroflexus aurantiacus, there is little sequence similarity. Both malonyl-CoA reductase enzyme candidates have high sequence similarity to aspartate-semialdehyde dehydrogenase, an enzyme catalyzing the reduction and concurrent dephosphorylation of aspartyl-4-phosphate to aspartate semialdehyde. Additional gene candidates can be found by sequence homology to proteins in other organisms including Sulfolobus solfataricus and Sulfolobus acidocaldarius and have been listed below. Such enzymes may be capable of naturally converting formyl-CoA to formaldehyde or can be engineered to do so.

| Protein | GenBank ID | GI number | Organism |
|---|---|---|---|
| Msed_0709 | YP_001190808.1 | 146303492 | Metallosphaera sedula |
| Mcr | NP_378167.1 | 15922498 | Sulfolobus tokodaii |
| asd-2 | NP_343563.1 | 15898958 | Sulfolobus solfataricus |
| Saci_2370 | YP_256941.1 | 70608071 | Sulfolobus acidocaldarius |
| Ald | AAT66436 | 9473535 | Clostridium beijerinckii |
| eutE | AAA80209 | 687645 | Salmonella typhimurium |
| eutE | P77445 | 2498347 | Escherichia coli |

Step H, FIG. 1: Formyltetrahydrofolate Synthetase

Formyltetrahydrofolate synthetase ligates formate to tetrahydrofolate at the expense of one ATP. This enzyme is found in several other organisms as listed below.

| Protein | GenBank ID | GI number | Organism |
|---|---|---|---|
| Moth_0109 | YP_428991.1 | 83588982 | Moorella thermoacetica |
| CHY_2385 | YP_361182.1 | 78045024 | Carboxydothermus hydrogenoformans |
| FHS | P13419.1 | 120562 | Clostridium acidurici |
| CcarbDRAFT_1913 | ZP_05391913.1 | 255524966 | Clostridium carboxidivorans P7 |
| CcarbDRAFT_2946 | ZP_05392946.1 | 255526022 | Clostridium carboxidivorans P7 |
| Dhaf_0555 | ACL18622.1 | 219536883 | Desulfitobacterium hafniense |
| fhs | YP_001393842.1 | 153953077 | Clostridium kluyveri DSM 555 |
| fhs | YP_003781893.1 | 300856909 | Clostridium ljungdahlii DSM 13528 |
| MGA3_08300 | EIJ83208.1 | 387590889 | Bacillus methanolicus MGA3 |
| PB1_13509 | ZP_10132113.1 | 387929436 | Bacillus methanolicus PB1 |

Steps I and J, FIG. 1: Formyltetrahydrofolate Synthetase and Methylenetetrahydrofolate Dehydrogenase In *M. thermoacetica*, *E. coli*, and *C. hydrogenoformans*, methenyltetrahydrofolate cyclohydrolase and methylenetetrahydrofolate dehydrogenase are carried out by the bi-functional gene products. Several other organisms also encode for this bifunctional protein as tabulated below.

| Protein | GenBank ID | GI number | Organism |
|---|---|---|---|
| Moth_1516 | YP_430368.1 | 83590359 | Moorella thermoacetica |
| folD | NP_415062.1 | 16128513 | Escherichia coli |
| CHY_1878 | YP_360698.1 | 78044829 | Carboxydothermus hydrogenoformans |
| CcarbDRAFT_2948 | ZP_05392948.1 | 255526024 | Clostridium carboxidivorans P7 |
| folD | ADK16789.1 | 300437022 | Clostridium ljungdahlii DSM 13528 |
| folD-2 | NP_951919.1 | 39995968 | Geobacter sulfurreducens PCA |
| folD | YP_725874.1 | 113867385 | Ralstonia eutropha H16 |
| folD | NP_348702.1 | 15895353 | Clostridium acetobutylicum ATCC 824 |
| folD | YP_696506.1 | 110800457 | Clostridium perfringens |
| MGA3_09460 | EIJ83438.1 | 387591119 | Bacillus methanolicus MGA3 |
| PB1_14689 | ZP_10132349.1 | 387929672 | Bacillus methanolicus PB1 |

Steps K, FIG. 1: Formaldehyde-Forming Enzyme or Spontaneous

Methylene-THF, or active formaldehyde, will spontaneously decompose to formaldehyde and THF. To achieve higher rates, a formaldehyde-forming enzyme can be applied. Such an activity can be obtained by engineering an enzyme that reversibly forms methylene-THF from THF and a formaldehyde donor, to release free formaldehyde. Such enzymes include glycine cleavage system enzymes which naturally transfer a formaldehyde group from methylene-THF to glycine (see Step L, FIG. 1 for candidate enzymes). Additional enzymes include serine hydroxymethyltransferase (see Step M, FIG. 1 for candidate enzymes), dimethylglycine dehydrogenase (Porter, et al., *Arch Biochem Biophys*. 1985, 243(2) 396-407; Brizio et al., 2004, (37) 2, 434-442), sarcosine dehydrogenase (Porter, et al., *Arch Biochem Biophys*. 1985, 243(2) 396-407), and dimethylglycine oxidase (Leys, et al., 2003, *The EMBO Journal* 22(16) 4038-40481.

| Protein | GenBank ID | GI number | Organism |
|---|---|---|---|
| dmgo | ZP_09278452.1 | 359775109 | Arthrobacter globiformis |
| dmgo | YP_002778684.1 | 226360906 | Rhodococcus opacus B4 |
| dmgo | EFY87157.1 | 322695347 | Metarhizium acridum CQMa 102 |

-continued

| Protein | GenBank ID | GI number | Organism |
|---|---|---|---|
| shd | AAD53398.2 | 5902974 | Homo sapiens |
| shd | NP_446116.1 | GI: 25742657 | Rattus norvegicus |

-continued

| Protein | GenBank ID | GI number | Organism |
|---|---|---|---|
| dmgdh | NP_037523.2 | 24797151 | Homo sapiens |
| dmgdh | Q63342.1 | 2498527 | Rattus norvegicus |

Step L, FIG. 1: Glycine Cleavage System

The reversible NAD(P)H-dependent conversion of 5,10-methylenetetrahydrofolate and $CO_2$ to glycine is catalyzed by the glycine cleavage complex, also called glycine cleavage system, composed of four protein components; P, H, T and L. The glycine cleavage complex is involved in glycine catabolism in organisms such as *E. coli* and glycine biosynthesis in eukaryotes (Kikuchi et al, *Proc Jpn Acad Ser* 84:246 (2008)). The glycine cleavage system of *E. coli* is encoded by four genes: gcvPHT and lpdA (Okamura et al, *Eur J Biochem* 216:539-48 (1993); Heil et al, *Microbiol* 148:2203-14 (2002)). Activity of the glycine cleavage system in the direction of glycine biosynthesis has been demonstrated in vivo in *Saccharomyces cerevisiae* (Maaheimo et al, *Eur J Biochem* 268:2464-79 (2001)). The yeast GCV is encoded by GCV1, GCV2, GCV3 and LPD1.

| Protein | GenBank ID | GI Number | Organism |
|---|---|---|---|
| gcvP | AAC75941.1 | 1789269 | Escherichia coli |
| gcvT | AAC75943.1 | 1789272 | Escherichia coli |
| gcvH | AAC75942.1 | 1789271 | Escherichia coli |
| lpdA | AAC73227.1 | 1786307 | Escherichia coli |

-continued

| Protein | GenBank ID | GI Number | Organism |
|---|---|---|---|
| GCV1 | NP_010302.1 | 6320222 | Saccharomyces cerevisiae |
| GCV2 | NP_013914.1 | 6323843 | Saccharomyces cerevisiae |
| GCV3 | NP_009355.3 | 269970294 | Saccharomyces cerevisiae |
| LPD1 | NP_116635.1 | 14318501 | Saccharomyces cerevisiae |

Step M, FIG. 1: Serine Hydroxymethyltransferase

Conversion of glycine to serine is catalyzed by serine hydroxymethyltransferase, also called glycine hydroxymethyltranferase. This enzyme reversibly converts glycine and 5,10-methylenetetrahydrofolate to serine and THF. Serine methyltransferase has several side reactions including the reversible cleavage of 3-hydroxyacids to glycine and an aldehyde, and the hydrolysis of 5,10-methenyl-THF to 5-formyl-THF. Exemplary enzymes are listed below.

| Protein | GenBank ID | GI Number | Organism |
|---|---|---|---|
| glyA | AAC75604.1 | 1788902 | Escherichia coli |
| SHM1 | NP_009822.2 | 37362622 | Saccharomyces cerevisiae |
| SHM2 | NP_013159.1 | 6323087 | Saccharomyces cerevisiae |
| glyA | AAA64456.1 | 496116 | Methylobacterium extorquens |
| glyA | AAK60516.1 | 14334055 | Corynebacterium glutamicum |

Step N, FIG. 1: Serine Deaminase

Serine can be deaminated to pyruvate by serine deaminase. Exemplary enzymes are listed below.

| Protein | GenBank ID | GI Number | Organism |
|---|---|---|---|
| sdaA | YP_490075.1 | 388477887 | Escherichia coli |
| sdaB | YP_491005.1 | 388478813 | Escherichia coli |
| tdcG | YP_491301.1 | 388479109 | Escherichia coli |
| tdcB | YP_491307.1 | 388479115 | Escherichia coli |
| sdaA | YP_225930.1 | 62390528 | Corynebacterium sp. |

Step O, FIG. 1: Methylenetetrahydrofolate Reductase

In *M. thermoacetica*, this enzyme is oxygen-sensitive and contains an iron-sulfur cluster (Clark and Ljungdahl, *J. Biol. Chem.* 259:10845-10849 (1984). This enzyme is encoded by metF in *E. coli* (Sheppard et al., *J. Bacteriol.* 181:718-725 (1999) and CHY_1233 in *C. hydrogenoformans* (Wu et al., *PLoS Genet.* 1:e65 (2005). The *M thermoacetica* genes, and its *C. hydrogenoformans* counterpart, are located near the CODH/ACS gene cluster, separated by putative hydrogenase and heterodisulfide reductase genes. Some additional gene candidates found bioinformatically are listed below. In *Acetobacterium woodii* metF is coupled to the Rnf complex through RnfC2 (Poehlein et al, PLoS One. 7:e33439). Homologs of RnfC are found in other organisms by blast search. The Rnf complex is known to be a reversible complex (Fuchs (2011) Annu. Rev. Microbiol. 65:631-658).

| Protein | GenBank ID | GI number | Organism |
|---|---|---|---|
| Moth_1191 | YP_430048.1 | 83590039 | Moorella thermoacetica |
| Moth_1192 | YP_430049.1 | 83590040 | Moorella thermoacetica |
| metF | NP_418376.1 | 16131779 | Escherichia coli |
| CHY_1233 | YP_360071.1 | 78044792 | Carboxydothermus hydrogenoformans |
| CLJU_c37610 | YP_003781889.1 | 300856905 | Clostridium ljungdahlii DSM 13528 |
| DesfrDRAFT_3717 | ZP_07335241.1 | 303248996 | Desulfovibrio fructosovorans JJ |
| CcarbDRAFT_2950 | ZP_05392950.1 | 255526026 | Clostridium carboxidivorans P7 |
| Ccel74_010100023124 | ZP_07633513.1 | 307691067 | Clostridium cellulovorans 743B |
| Cphy_3110 | YP_001560205.1 | 160881237 | Clostridium phytofermentans ISDg |

Step P, FIG. 1: Acetyl-CoA Synthase

Acetyl-CoA synthase is the central enzyme of the carbonyl branch of the Wood-Ljungdahl pathway. It catalyzes the synthesis of acetyl-CoA from carbon monoxide, coenzyme A, and the methyl group from a methylated corrinoid-iron-sulfur protein. The corrinoid-iron-sulfur-protein is methylated by methyltetrahydrofolate via a methyltransferase. Expression in a foreign host entails introducing one or more of the following proteins and their corresponding activities: Methyltetrahydrofolate:corrinoid protein methyltransferase (AcsE), Corrinoid iron-sulfur protein (AcsD), Nickel-protein assembly protein (AcsF), Ferredoxin (Orf7), Acetyl-CoA synthase (AcsB and AcsC), Carbon monoxide dehydrogenase (AcsA), and Nickel-protein assembly protein (CooC).

The genes used for carbon-monoxide dehydrogenase/acetyl-CoA synthase activity typically reside in a limited region of the native genome that can be an extended operon (Ragsdale, S. W., *Crit. Rev. Biochem. Mol. Biol.* 39:165-195 (2004); Morton et al., *J. Biol. Chem.* 266:23824-23828 (1991); Roberts et al., *Proc. Natl. Acad. Sci. U.S.A.* 86:32-36 (1989). Each of the genes in this operon from the acetogen, *M. thermoacetica*, has already been cloned and expressed actively in *E. coli* (Morton et al. supra; Roberts et al. supra; Lu et al., *J. Biol. Chem.* 268:5605-5614 (1993). The protein sequences of these genes can be identified by the following GenBank accession numbers.

| Protein | GenBank ID | GI number | Organism |
|---|---|---|---|
| AcsE | YP_430054 | 83590045 | Moorella thermoacetica |
| AcsD | YP_430055 | 83590046 | Moorella thermoacetica |
| AcsF | YP_430056 | 83590047 | Moorella thermoacetica |
| Orf7 | YP_430057 | 83590048 | Moorella thermoacetica |
| AcsC | YP_430058 | 83590049 | Moorella thermoacetica |
| AcsB | YP_430059 | 83590050 | Moorella thermoacetica |
| AcsA | YP_430060 | 83590051 | Moorella thermoacetica |
| CooC | YP_430061 | 83590052 | Moorella thermoacetica |

The hydrogenic bacterium, *Carboxydothermus hydrogenoformans*, can utilize carbon monoxide as a growth substrate by means of acetyl-CoA synthase (Wu et al., *PLoS Genet.* 1:e65 (2005)). In strain Z-2901, the acetyl-CoA synthase enzyme complex lacks carbon monoxide dehydrogenase due to a frameshift mutation (Wu et al. supra (2005)), whereas in strain DSM 6008, a functional unframeshifted full-length version of this protein has been purified (Svetlitchnyi et al., *Proc. Natl. Acad. Sci. U.S.A.* 101:446-

451(2004)). The protein sequences of the *C. hydrogenoformans* genes from strain Z-2901 can be identified by the following GenBank accession numbers.

| Protein | GenBank ID | GI number | Organism |
|---|---|---|---|
| AcsE | YP_360065 | 78044202 | *Carboxydothermus hydrogenoformans* |
| AcsD | YP_360064 | 78042962 | *Carboxydothermus hydrogenoformans* |
| AcsF | YP_360063 | 78044060 | *Carboxydothermus hydrogenoformans* |
| Orf7 | YP_360062 | 78044449 | *Carboxydothermus hydrogenoformans* |
| AcsC | YP_360061 | 78043584 | *Carboxydothermus hydrogenoformans* |
| AcsB | YP_360060 | 78042742 | *Carboxydothermus hydrogenoformans* |
| CooC | YP_360059 | 78044249 | *Carboxydothermus hydrogenoformans* |

Homologous ACS/CODH genes can also be found in the draft genome assembly of *Clostridium carboxidivorans* P7.

| Protein | GenBank ID | GI Number | Organism |
|---|---|---|---|
| AcsA | ZP_05392944.1 | 255526020 | *Clostridium carboxidivorans* P7 |
| CooC | ZP_05392945.1 | 255526021 | *Clostridium carboxidivorans* P7 |
| AcsF | ZP_05392952.1 | 255526028 | *Clostridium carboxidivorans* P7 |
| AcsD | ZP_05392953.1 | 255526029 | *Clostridium carboxidivorans* P7 |
| AcsC | ZP_05392954.1 | 255526030 | *Clostridium carboxidivorans* P7 |
| AcsE | ZP_05392955.1 | 255526031 | *Clostridium carboxidivorans* P7 |
| AcsB | ZP_05392956.1 | 255526032 | *Clostridium carboxidivorans* P7 |
| Orf7 | ZP_05392958.1 | 255526034 | *Clostridium carboxidivorans* P7 |

The methanogenic archaeon, *Methanosarcina acetivorans*, can also grow on carbon monoxide, exhibits acetyl-CoA synthase/carbon monoxide dehydrogenase activity, and produces both acetate and formate (Lessner et al., *Proc. Natl. Acad. Sci. U.S.A.* 103:17921-17926 (2006)). This organism contains two sets of genes that encode ACS/CODH activity (Rother and Metcalf, *Proc. Natl. Acad Sci. U.S.A.* 101:16929-16934 (2004)). The protein sequences of both sets of *M. acetivorans* genes are identified by the following GenBank accession numbers.

| Protein | GenBank ID | GI number | Organism |
|---|---|---|---|
| AcsC | NP_618736 | 20092661 | *Methanosarcina acetivorans* |
| AcsD | NP_618735 | 20092660 | *Methanosarcina acetivorans* |
| AcsF, CooC | NP_618734 | 20092659 | *Methanosarcina acetivorans* |
| AcsB | NP_618733 | 20092658 | *Methanosarcina acetivorans* |
| AcsEps | NP_618732 | 20092657 | *Methanosarcina acetivorans* |
| AcsA | NP_618731 | 20092656 | *Methanosarcina acetivorans* |
| AcsC | NP_615961 | 20089886 | *Methanosarcina acetivorans* |
| AcsD | NP_615962 | 20089887 | *Methanosarcina acetivorans* |
| AcsF, CooC | NP_615963 | 20089888 | *Methanosarcina acetivorans* |
| AcsB | NP_615964 | 20089889 | *Methanosarcina acetivorans* |
| AcsEps | NP_615965 | 20089890 | *Methanosarcina acetivorans* |
| AcsA | NP_615966 | 20089891 | *Methanosarcina acetivorans* |

The AcsC, AcsD, AcsB, AcsEps, and AcsA proteins are commonly referred to as the gamma, delta, beta, epsilon, and alpha subunits of the methanogenic CODH/ACS. Homologs to the epsilon encoding genes are not present in acetogens such as *M. thermoacetica* or hydrogenogenic bacteria such as *C. hydrogenoformans*. Hypotheses for the existence of two active CODH/ACS operons in *M. acetivorans* include catalytic properties (i.e., $K_m$, $V_{max}$, $k_{at}$) that favor carboxidotrophic or aceticlastic growth or differential gene regulation enabling various stimuli to induce CODH/ACS expression (Rother et al., Arch. *Microbiol.* 188:463-472 (2007)).

Step Y, FIG. 1: Glyceraldehydes-3-phosphate Dehydrogenase and Enzymes of Lower Glycolysis Enzymes comprising Step Y, G3P to PYR include: Glyceraldehyde-3-phosphate dehydrogenase; Phosphoglycerate kinase; Phosphoglyceromutase; Enolase; Pyruvate kinase or PTS-dependent substrate import.

Glyceraldehyde-3-phosphate dehydrogenase enzymes include:

NADP-denendent glyceraldehyde-3-phosphate dehydrogenase exemplary enzymes are:

| Protein | GenBank ID | GI Number | Organism |
|---|---|---|---|
| gapN | AAA91091.1 | 642667 | *Streptococcus mutans* |
| NP-GAPDH | AEC07555.1 | 330252461 | *Arabidopsis thaliana* |
| GAPN | AAM77679.2 | 82469904 | *Triticum aestivum* |
| gapN | CAI56300.1 | 87298962 | *Clostridium acetobutylicum* |
| NADP-GAPDH | 2D2I_A | 112490271 | *Synechococcus elongatus* PCC 7942 |
| NADP-GAPDH | CAA62619.1 | 4741714 | *Synechococcus elongatus* PCC 7942 |
| GDP1 | XP_455496.1 | 50310947 | *Kluyveromyces lactis* NRRL Y-1140 |
| HP1346 | NP_208138.1 | 15645959 | *Helicobacter pylori* 26695 | and NAD-dependent glyceraldehyde-3-phosphate dehydrogenase, exemplary enzymes are:

| Protein | GenBank ID | GI Number | Organism |
|---|---|---|---|
| TDH1 | NP_012483.1 | 6322409 | *Saccharomyces cerevisiae* s288c |
| TDH2 | NP_012542.1 | 6322468 | *Saccharomyces cerevisiae* s288c |
| TDH3 | NP_011708.1 | 632163 | *Saccharomyces cerevisiae* s288c |
| KLLA0A11858g | XP_451516.1 | 50303157 | *Kluyveromyces lactis* NRRL Y-1140 |
| KLLA0F20988g | XP_456022.1 | 50311981 | *Kluyveromyces lactis* NRRL Y-1140 |
| ANI_1_256144 | XP_001397496.1 | 145251966 | *Aspergillus niger* CBS 513.88 |
| YALI0C06369g | XP_501515.1 | 50548091 | *Yarrowia lipolytica* |
| CTRG_05666 | XP_002551368.1 | 255732890 | *Candida tropicalis* MYA-3404 |
| HPODL_1089 | EFW97311.1 | 320583095 | *Hansenula polymorpha* DL-1 |
| gapA | YP_490040.1 | 388477852 | *Escherichia coli* |

Phosphoglycerate kinase enzymes include:

| Protein | GenBank ID | GI Number | Organism |
|---|---|---|---|
| PGK1 | NP_009938.2 | 10383781 | *Saccharomyces cerevisiae* s288c |
| PGK | BAD83658.1 | 57157302 | *Candida boidinii* |
| PGK | EFW98395.1 | 320584184 | *Hansenula polymorpha* DL-1 |
| pgk | EIJ77825.1 | 387585500 | *Bacillus methanolicus* MGA3 |
| pgk | YP_491126.1 | 388478934 | *Escherichia coli* |

Phosphoglyceromutase (aka phosphoglycerate mutase) enzymes include;

| Protein | GenBank ID | GI Number | Organism |
|---|---|---|---|
| GPM1 | NP_012770.1 | 6322697 | Saccharomyces cerevisiae s288c |
| GPM2 | NP_010263.1 | 6320183 | Saccharomyces cerevisiae s288c |
| GPM3 | NP_014585.1 | 6324516 | Saccharomyces cerevisiae s288c |
| HPODL_1391 | EFW96681.1 | 320582464 | Hansenula polymorpha DL-1 |
| HPODL_0376 | EFW97746.1 | 320583533 | Hansenula polymorpha DL-1 |
| gpmI | EIJ77827.1 | 387585502 | Bacillus methanolicus MGA3 |
| gpmA | YP_489028.1 | 388476840 | Escherichia coli |
| gpmM | AAC76636.1 | 1790041 | Escherichia coli |

Enolase (also known as phosphopyruvate hydratase and 2-phosphoglycerate dehydratase) enzymes include:

| Protein | GenBank ID | GI Number | Organism |
|---|---|---|---|
| ENO1 | NP_011770.3 | 398366315 | Saccharomyces cerevisiae s288c |
| ENO2 | AAB68019.1 | 458897 | Saccharomyces cerevisiae s288c |
| HPODL_2596 | EFW95743.1 | 320581523 | Hansenula polymorpha DL-1 |
| eno | EIJ77828.1 | 387585503 | Bacillus methanolicus MGA3 |
| eno | AAC75821.1 | 1789141 | Escherichia coli |

Pyruvate kinase (also known as phosphoenolpyruvate kinase and phosphoenolpyruvate kinase) or PTS-dependent substrate import enzymes include those below. Pyruvate kinase, also known as phosphoenolpyruvate synthase (EC 2.7.9.2), converts pyruvate and ATP to PEP and AMP. This enzyme is encoded by the PYK1 (Burke et al., J. Biol. Chem. 258:2193-2201 (1983)) and PYK2 (Boles et al., J. Bacteriol. 179:2987-2993 (1997)) genes in S. cerevisiae. In E. coli, this activity is catalyzed by the gene products of pykF and pykA. Note that pykA and pykF are genes encoding separate enzymes potentially capable of carrying out the PYK reaction. Selected homologs of the S. cerevisiae enzymes are also shown in the table below.

| Protein | GenBank ID | GI Number | Organism |
|---|---|---|---|
| PYK1 | NP_009362 | 6319279 | Saccharomyces cerevisiae |
| PYK2 | NP_014992 | 6324923 | Saccharomyces cerevisiae |
| pykF | NP_416191.1 | 16129632 | Escherichia coli |
| pykA | NP_416368.1 | 16129807 | Escherichia coli |
| KLLA0F23397g | XP_456122.1 | 50312181 | Kluyveromyces lactis |
| CaO19.3575 | XP_714934.1 | 68482353 | Candida albicans |
| CaO19.11059 | XP_714997.1 | 68482226 | Candida albicans |
| YALI0F09185p | XP_505195 | 210075987 | Yarrowia lipolytica |
| ANI_1_1126064 | XP_001391973 | 145238652 | Aspergillus niger |
| MGA3_03005 | EIJ84220.1 | 387591903 | Bacillus methanolicus MGA3 |
| HPODL_1539 | EFW96829.1 | 320582612 | Hansenula polymorpha DL-1 |

PTS-dependent substrate uptake systems catalyze a phosphotransfer cascade that couples conversion of PEP to pyruvate with the transport and phosphorylation of carbon substrates. For example, the glucose PTS system transports glucose, releasing glucose-6-phosphate into the cytoplasm and concomitantly converting phosphoenolpyruvate to pyruvate. PTS systems are comprised of substrate-specific and non-substrate-specific components. In E. coli the two non-specific components are encoded by ptsI (Enzyme I) and ptsH (HPr). The sugar-dependent components are encoded by crr and ptsG. Pts systems have been extensively studied and are reviewed, for example in Postma et al, Microbiol Rev 57: 543-94 (1993).

| Protein | GenBank ID | GI Number | Organism |
|---|---|---|---|
| ptsG | AC74185.1 | 1787343 | Escherichia coli |
| ptsI | AAC75469.1 | 1788756 | Escherichia coli |
| ptsH | AAC75468.1 | 1788755 | Escherichia coli |
| crr | AAC75470.1 | 1788757 | Escherichia coli |

The IIA[Glc] component mediates the transfer of the phosphoryl group from histidine protein Hpr (ptsH) to the IIB[Glc] (ptsG) component. A truncated variant of the crr gene was introduced into 1,4-butanediol producing strains.

Alternatively, Phosphoenolpyruvate phosphatase (EC 3.1.3.60) catalyzes the hydrolysis of PEP to pyruvate and phosphate. Numerous phosphatase enzymes catalyze this activity, including alkaline phosphatase (EC 3.1.3.1), acid phosphatase (EC 3.1.3.2), phosphoglycerate phosphatase (EC 3.1.3.20) and PEP phosphatase (EC 3.1.3.60). PEP phosphatase enzymes have been characterized in plants such as Vignia radiate, Bruguiera sexangula and Brassica nigra. Exemplary enzymes are listed below. Enzyme engineering and/or removal of targeting sequences may be required for alkaline phosphatase enzymes to function in the cytoplasm.

| Protein | GenBank ID | GI Number | Organism |
|---|---|---|---|
| phyA | O00092.1 | 41017447 | Aspergillus fumigatus |
| Acp5 | P13686.3 | 56757583 | Homo sapiens |
| phoA | NP_414917.2 | 49176017 | Escherichia coli |
| phoX | ZP_01072054.1 | 86153851 | Campylobacter jejuni |
| PHO8 | AAA34871.1 | 172164 | Saccharomyces cerevisiae |
| SaurJH1_2706 | YP_001317815.1 | 150395140 | Staphylococcus aureus |

Step Q, FIG. 1: Pyruvate Formate Lyase

Pyruvate formate-lyase (PFL, EC 2.3.1.54), encoded by pflB in E. coli, can convert pyruvate into acetyl-CoA and formate. The activity of PFL can be enhanced by an activating enzyme encoded by pflA. Keto-acid formate-lyase (EC 2.3.1.-), also known as 2-ketobutyrate formate-lyase (KFL) and pyruvate formate-lyase 4, is the gene product of tdcE in E. coli. This enzyme catalyzes the conversion of 2-ketobutyrate to propionyl-CoA and formate during anaerobic threonine degradation, and can also substitute for pyruvate formate-lyase in anaerobic catabolism. The enzyme is oxygen-sensitive and, like POB, can require post-translational modification by PFL-AE to activate a glycyl radical in the active site (Hesslinger et al., Mol. Microbiol 27:477-492 (1998)). Exemplary enzymes are listed below.

| Protein | GenBank ID | GI Number | Organism |
|---|---|---|---|
| pflB | NP_415423 | 16128870 | Escherichia coli |
| pflA | NP_415422.1 | 16128869 | Escherichia coli |
| tdcE | AAT48170.1 | 48994926 | Escherichia coli |

| Protein | GenBank ID | GI Number | Organism |
|---|---|---|---|
| pflD | NP_070278.1 | 11499044 | Archaeglubus fulgidus |
| Pfl | CAA03993 | 2407931 | Lactococcus lactis |
| Pfl | BAA09085 | 1129082 | Streptococcus mutans |
| PFL1 | XP_001689719.1 | 159462978 | Chlamydomonas reinhardtii |
| pflA1 | XP_001700657.1 | 159485246 | Chlamydomonas reinhardtii |
| Pfl | Q46266.1 | 2500058 | Clostridium pasteurianum |
| Act | CAA63749.1 | 1072362 | Clostridium pasteurianum |

Step R, FIG. 1: Pyruvate Dehydrogenase, Pyruvate Ferredoxin Oxidoreductase, Pyruvate:NADP+Oxidoreductase The pyruvate dehydrogenase (PDH) complex catalyzes the conversion of pyruvate to acetyl-CoA (FIG. 3H). The E. coli PDH complex is encoded by the genes aceEF and lpdA. Enzyme engineering efforts have improved the E. coli PDH enzyme activity under anaerobic conditions (Kim et al., J. Bacteriol. 190:3851-3858 (2008); Kim et al., Appl. Environ. Microbiol. 73:1766-1771(2007); Zhou et al., Biotechnol. Lett. 30:335-342 (2008)). In contrast to the E. coli PDH, the B. subtilis complex is active and required for growth under anaerobic conditions (Nakano et al., 179:6749-6755 (1997)). The Klebsiella pneumoniae PDH, characterized during growth on glycerol, is also active under anaerobic conditions (Menzel et al., 56:135-142 (1997)). Comparative kinetics of Rattus norvegicus PDH and BCKAD indicate that BCKAD has higher activity on 2-oxobutanoate as a substrate (Paxton et al., Biochem. J. 234:295-303 (1986)). The S. cerevisiae PDH complex can consist of an E2 (LAT1) core that binds E1 (PDA1, PDB1), E3 (LPD1), and Protein X (PDX1) components (Pronk et al., Yeast 12:1607-1633 (1996)). The PDH complex of S. cerevisiae is regulated by phosphorylation of E1 involving PKP1 (PDH kinase I), PTC5 (PDH phosphatase I), PKP2 and PTC6. Modification of these regulators may also enhance PDH activity. Coexpression of lipoyl ligase (LplA of E. coli and AIM22 in S. cerevisiae) with PDH in the cytosol may be necessary for activating the PDH enzyme complex. Increasing the supply of cytosolic lipoate, either by modifying a metabolic pathway or media supplementation with lipoate, may also improve PDH activity.

| Gene | Accession No. | GI Number | Organism |
|---|---|---|---|
| aceE | NP_414656.1 | 16128107 | Escherichia coli |
| aceF | NP_414657.1 | 16128108 | Escherichia coli |
| lpd | NP_414658.1 | 16128109 | Escherichia coli |
| lplA | NP_418803.1 | 16132203 | Escherichia coli |
| pdhA | P21881.1 | 3123238 | Bacillus subtilis |
| pdhB | P21882.1 | 129068 | Bacillus subtilis |
| pdhC | P21883.2 | 129054 | Bacillus subtilis |
| pdhD | P21880.1 | 118672 | Bacillus subtilis |
| aceE | YP_001333808.1 | 152968699 | Klebsiella pneumoniae |
| aceF | YP_001333809.1 | 152968700 | Klebsiella pneumoniae |
| lpdA | YP_001333810.1 | 152968701 | Klebsiella pneumoniae |
| Pdha1 | NP_001004072.2 | 124430510 | Rattus norvegicus |
| Pdha2 | NP_446446.1 | 16758900 | Rattus norvegicus |
| Dlat | NP_112287.1 | 78365255 | Rattus norvegicus |
| Dld | NP_955417.1 | 40786469 | Rattus norvegicus |
| LAT1 | NP_014328 | 6324258 | Saccharomyces cerevisiae |
| PDA1 | NP_011105 | 37362644 | Saccharomyces cerevisiae |
| PDB1 | NP_009780 | 6319698 | Saccharomyces cerevisiae |
| LPD1 | NP_116635 | 14318501 | Saccharomyces cerevisiae |
| PDX1 | NP_011709 | 6321632 | Saccharomyces cerevisiae |
| AIM22 | NP_012489.2 | 83578101 | Saccharomyces cerevisiae |

As an alternative to the large multienzyme PDH complexes described above, some organisms utilize enzymes in the 2-ketoacid oxidoreductase family (OFOR) to catalyze acylating oxidative decarboxylation of 2-keto-acids. Unlike the PDH complexes, PFOR enzymes contain iron-sulfur clusters, utilize different cofactors and use ferredoxin or flavodixin as electron acceptors in lieu of NAD(P)H. Pyruvate ferredoxin oxidoreductase (PFOR) can catalyze the oxidation of pyruvate to form acetyl-CoA (FIG. 3H). Several additional PFOR enzymes are described in Ragsdale, Chem. Rev. 103:2333-2346 (2003). Finally, flavodoxin reductases (e.g., fqrB from Helicobacter pylori or Campylobacter jejuni (St Maurice et al., J. Bacteriol. 189:4764-4773 (2007))) or Rnf-type proteins (Seedorf et al., Proc. Natl. Acad. Sci. U.S.A. 105:2128-2133 (2008); Herrmann et al., J. Bacteriol. 190:784-791(2008)) provide a means to generate NADH or NADPH from the reduced ferredoxin generated by PFOR. These proteins are identified below.

| Protein | GenBank ID | GI Number | Organism |
|---|---|---|---|
| Por | CAA70873.1 | 1770208 | Desulfovibrio africanus |
| Por | YP_428946.1 | 83588937 | Moorella thermoacetica |
| ydbK | NP_415896.1 | 16129339 | Escherichia coli |
| fqrB | NP_207955.1 | 15645778 | Helicobacter pylori |
| fqrB | YP_001482096.1 | 157414840 | Campylobacter jejuni |
| RnfC | EDK33306.1 | 146346770 | Clostridium kluyveri |
| RnfD | EDK33307.1 | 146346771 | Clostridium kluyveri |
| RnfG | EDK33308.1 | 146346772 | Clostridium kluyveri |
| RnfE | EDK33309.1 | 146346773 | Clostridium kluyveri |
| RnfA | EDK33310.1 | 146346774 | Clostridium kluyveri |
| RnfB | EDK33311.1 | 146346775 | Clostridium kluyveri |

Pyruvate:NADP oxidoreductase (PNO) catalyzes the conversion of pyruvate to acetyl-CoA. This enzyme is encoded by a single gene and the active enzyme is a homodimer, in contrast to the multi-subunit PDH enzyme complexes described above. The enzyme from Euglena gracilis is stabilized by its cofactor, thiamin pyrophosphate (Nakazawa et al, Arch Biochem Biophys 411:183-8 (2003)). The mitochondrial targeting sequence of this enzyme should be removed for expression in the cytosol. The PNO protein of E. gracilis and other NADP-dependent pyruvate:NADP+ oxidoreductase enzymes are listed in the table below.

| Protein | GenBank ID | GI Number | Organism |
|---|---|---|---|
| PNO | Q94IN5.1 | 33112418 | Euglena gracilis |
| cgd4_690 | XP_625673.1 | 66356990 | Cryptosporidium parvum Iowa II |
| TPP_PFOR_PNO | XP_002765111.11 | 294867463 | Perkinsus marinus ATCC 50983 |

Step S, FIG. 1: Formate Dehydrogenase

Formate dehydrogenase (FDH) catalyzes the reversible transfer of electrons from formate to an acceptor. Enzymes with FDH activity utilize various electron carriers such as, for example, NADH (EC 1.2.1.2), NADPH (EC 1.2.1.43), quinols (EC 1.1.5.6), cytochromes (EC 1.2.2.3) and hydrogenases (EC 1.1.99.33). The loci, Moth_2312 is responsible for encoding the alpha subunit of formate dehydrogenase while the beta subunit is encoded by Moth_2314. Another set of genes encoding formate dehydrogenase activity with a propensity for $CO_2$ reduction is encoded by Sfum_2703 through Sfum_2706 in *Syntrophobacter fumaroxidans* (de Bok et al., *Eur J Biochem.* 270:2476-2485 (2003)); Reda et al., *PNAS* 105:10654-10658 (2008)). A similar set of genes presumed to carry out the same function are encoded by CHY_0731, CHY_0732, and CHY_0733 in *C. hydrogenoformans* (Wu et al., *PLoS Genet* 1:e65 (2005)).

Several EM8 enzymes have been identified that have higher specificity for NADP as the cofactor as compared to NAD. This enzyme has been deemed as the NADP-dependent formate dehydrogenase and has been reported from 5 species of the *Burkholderia cepacia* complex. More gene candidates can be identified using sequence homology of proteins deposited in Public databases such as NCBI, JGI and the metagenomic databases.

Example II

Production of Reducing Equivalents

This example describes methanol metabolic pathways and other additional enzymes generating reducing equivalents as shown in FIG. 2.

FIG. 2, Step A—Methanol Methyltransferase

A complex of 3-methyltransferase proteins, denoted MtaA, MtaB, and MtaC, perform the desired methanol methyltransferase activity (Ragsdale, S. W., *Crit. Rev. Biochem. Mol. Biol.* 39:165-195 (2004)).

MtaB is a zinc protein that can catalyze the transfer of a methyl group from methanol to MtaC, a corrinoid protein. The protein sequences of various MtaB and MtaC encoding genes in *M. barkeri, M. acetivorans,* and *M. thermoaceticum* can be identified by their following GenBank accession numbers.

| Protein | GenBank ID | GI number | Organism |
| --- | --- | --- | --- |
| MtaB1 | YP_304299 | 73668284 | *Methanosarcina barkeri* |
| MtaC1 | YP_304298 | 73668283 | *Methanosarcina barkeri* |
| MtaB2 | YP_307082 | 73671067 | *Methanosarcina barkeri* |
| MtaC2 | YP_307081 | 73671066 | *Methanosarcina barkeri* |
| MtaB3 | YP_304612 | 73668597 | *Methanosarcina barkeri* |
| MtaC3 | YP_304611 | 73668596 | *Methanosarcina barkeri* |
| MtaB1 | NP_615421 | 20089346 | *Methanosarcina acetivorans* |
| MtaB1 | NP_615422 | 20089347 | *Methanosarcina acetivorans* |
| MtaB2 | NP_619254 | 20093179 | *Methanosarcina acetivorans* |
| MtaC2 | NP_619253 | 20093178 | *Methanosarcina acetivorans* |
| MtaB3 | NP_616549 | 20090474 | *Methanosarcina acetivorans* |

| Protein | GenBank ID | GI Number | Organism |
| --- | --- | --- | --- |
| Moth_2312 | YP_431142 | 148283121 | *Moorella thermoacetica* |
| Moth_2314 | YP_431144 | 83591135 | *Moorella thermoacetica* |
| Sfum_2703 | YP_846816.1 | 116750129 | *Syntrophobacter fumaroxidans* |
| Sfum_2704 | YP_846817.1 | 116750130 | *Syntrophobacter fumaroxidans* |
| Sfum_2705 | YP_846818.1 | 116750131 | *Syntrophobacter fumaroxidans* |
| Sfum_2706 | YP_846819.1 | 116750132 | *Syntrophobacter fumaroxidans* |
| CHY_0731 | YP_359585.1 | 78044572 | *Carboxydothermus hydrogenoformans* |
| CHY_0732 | YP_359586.1 | 78044500 | *Carboxydothermus hydrogenoformans* |
| CHY_0733 | YP_359587.1 | 78044647 | *Carboxydothermus hydrogenoformans* |
| CcarbDRAFT_0901 | ZP_05390901.1 | 255523938 | *Clostridium carboxidivorans* P7 |
| CcarbDRAFT_4380 | ZP_05394380.1 | 255527512 | *Clostridium carboxidivorans* P7 |
| fdhA, MGA3_06625 | EIJ82879.1 | 387590560 | *Bacillus methanolicus* MGA3 |
| fdhA, PB1_11719 | ZP_10131761.1 | 387929084 | *Bacillus methanolicus* PB1 |
| fdhD, MGA3_06630 | EIJ82880.1 | 387590561 | *Bacillus methanolicus* MGA3 |
| fdhD, PB1_11724 | ZP_10131762.1 | 387929085 | *Bacillus methanolicus* PB1 |
| fdh | ACF35003.1 | 194220249 | *Burkholderia stabilis* |
| fdh | ACF35004.1 | 194220251 | *Burkholderia pyrrocinia* |
| fdh | ACF35002.1 | 194220247 | *Burkholderia cenocepacia* |
| fdh | ACF35001.1 | 194220245 | *Burkholderia multivorans* |
| fdh | ACF35000.1 | 194220243 | *Burkholderia cepacia* |
| FDH1 | AAC49766.1 | 2276465 | *Candida boidinii* |
| fdh | CAA57036.1 | 1181204 | *Candida methylica* |
| FDH2 | P0CF35.1 | 294956522 | *Saccharomyces cerevisiae* S288c |
| FDH1 | NP_015033.1 | 6324964 | *Saccharomyces cerevisiae* S288c |
| fdsG | YP_725156.1 | 113866667 | *Ralstonia eutropha* |
| fdsB | YP_725157.1 | 113866668 | *Ralstonia eutropha* |
| fdsA | YP_725158.1 | 113866669 | *Ralstonia eutropha* |
| fdsC | YP_725159.1 | 113866670 | *Ralstonia eutropha* |
| fdsD | YP_725160.1 | 113866671 | *Ralstonia eutropha* |

-continued

| Protein | GenBank ID | GI number | Organism |
|---------|-----------|-----------|----------|
| MtaC3 | NP_616550 | 20090475 | *Methanosarcina acetivorans* |
| MtaB | YP_430066 | 83590057 | *Moorella thermoacetica* |
| MtaC | YP_430065 | 83590056 | *Moorella thermoacetica* |
| MtaA | YP_430064 | 83590056 | *Moorella thermoacetica* |

In general, homology searches are an effective means of identifying methanol methyltransferases because MtaB encoding genes show little or no similarity to methyltransferases that act on alternative substrates such as trimethylamine, dimethylamine, monomethylamine, or dimethylsulfide. Mutant strains lacking two of the sets were able to grow on methanol, whereas a strain lacking all three sets of MtaB and MtaC genes sets could not grow on methanol. This suggests that each set of genes plays a role in methanol utilization.

MtaA is zinc protein that catalyzes the transfer of the methyl group from MtaC to either Coenzyme M in methanogens or methyltetrahydrofolate in acetogens. MtaA can also utilize methylcobalamin as the methyl donor. Exemplary genes encoding MtaA can be found in methanogenic archaea such as *Methanosarcina barkeri* (Maeder et al., *J. Bacteriol.* 188:7922-7931(2006) and *Methanosarcina acetivorans* (Galagan et al., *Genome Res.* 12:532-542 (2002), as well as the acetogen, *Moorella thermoacetica* ((Das et al., *Proteins* 67:167-176 (2007)). In general, MtaA proteins that catalyze the transfer of the methyl group from $CH_3$-MtaC are difficult to identify bioinformatically as they share similarity to other corrinoid protein methyltransferases and are not oriented adjacent to the MtaB and MtaC genes on the chromosomes. Nevertheless, a number of MtaA encoding genes have been characterized. The protein sequences of these genes in *M. barkeri* and *M. acetivorans* can be identified by the following GenBank accession numbers.

| Protein | GenBank ID | GI number | Organism |
|---------|-----------|-----------|----------|
| MtaA | YP_304602 | 73668587 | *Methanosarcina barkeri* |
| MtaA1 | NP_619241 | 20093166 | *Methanosarcina acetivorans* |
| MtaA2 | NP_616548 | 20090473 | *Methanosarcina acetivorans* |

The MtaA gene, YP_304602, from *M. barkeri* was cloned, sequenced, and functionally overexpressed in *E. coli* (Harms and Thauer, *Eur. J. Biochem.* 235:653-659 (1996)).

Putative MtaA encoding genes in *M. thermoacetica* were identified by their sequence similarity to the characterized methanogenic MtaA genes. Specifically, three *M. thermoacetica* genes show high homology (>30% sequence identity) to YP_304602 from *M. barkeri*. The protein sequences of putative MtaA encoding genes from *M. thermoacetica* can be identified by the following GenBank accession numbers.

| Protein | GenBank ID | GI number | Organism |
|---------|-----------|-----------|----------|
| MtaA | YP_430937 | 83590928 | *Moorella thermoacetica* |
| MtaA | YP_431175 | 83591166 | *Moorella thermoacetica* |
| MtaA | YP_430935 | 83590926 | *Moorella thermoacetica* |
| MtaA | YP_430064 | 83590056 | *Moorella thermoacetica* |

FIG. 2, Step B—Methylenetetrahydrofolate Reductase

The conversion of methyl-THF to methylenetetrahydrofolate is catalyzed by methylenetetrahydrofolate reductase. Some additional gene candidates found bioinformatically are listed below. In *Acetobacterium woodii* metF is coupled to the Rnf complex through RnfC2 (Poehlein et al, *PLoS One.* 7:e33439). Homologs of RnfC are found in other organisms by blast search. The Rnf complex is known to be a reversible complex (Fuchs (2011) *Annu. Rev. Microbiol.* 65:631-658).

| Protein | GenBank ID | GI number | Organism |
|---------|-----------|-----------|----------|
| Moth_1191 | YP_430048.1 | 83590039 | *Moorella thermoacetica* |
| Moth_1192 | YP_430049.1 | 83590040 | *Moorella thermoacetica* |
| metF | NP_418376.1 | 16131779 | *Escherichia coli* |
| CHY_1233 | YP_360071.1 | 78044792 | *Carboxydothermus hydrogenoformans* |
| CLJU_c37610 | YP_003781889.1 | 300856905 | *Clostridium ljungdahlii* DSM 13528 |
| DesfrDRAFT_3717 | ZP_07335241.1 | 303248996 | *Desulfovibrio fructosovorans* JJ |
| CcarbDRAFT_2950 | ZP_05392950.1 | 255526026 | *Clostridium carboxidivorans* P7 |
| Ccel74_010100023124 | ZP_07633513.1 | 307691067 | *Clostridium cellulovorans* 743B |
| Cphy_3110 | YP_001560205.1 | 160881237 | *Clostridium phytofermentans* ISDg |

FIG. 2, Steps C and D—Methylenetetrahydrofolate Dehydrogenase, Methenyltetrahydrofolate Cyclohydrolase In *M. thermoacetica*, *E. coli*, and *C. hydrogenoformans*, methenyltetrahydrofolate cyclohydrolase and methylenetetrahydrofolate dehydrogenase are carried out by the bifunctional gene products of Moth_1516, folD, and CHY_1878, respectively (Pierce et al., *Environ. Microbiol.* 10:2550-2573 (2008); Wu et al., *PLoS Genet.* 1:e65 (2005); D'Ari and Rabinowitz, *J. Biol. Chem.* 266:23953-23958 (1991)). A homolog exists in *C. carboxidivorans* P7. Several other organisms also encode for this bifunctional protein as tabulated below.

| Protein | GenBank ID | GI number | Organism |
|---------|-----------|-----------|----------|
| Moth_1516 | YP_430368.1 | 83590359 | *Moorella thermoacetica* |
| folD | NP_415062.1 | 16128513 | *Escherichia coli* |
| CHY_1878 | YP_360698.1 | 78044829 | *Carboxydothermus hydrogenoformans* |
| CcarbDRAFT_2948 | ZP_05392948.1 | 255526024 | *Clostridium carboxidivorans* P7 |
| folD | ADK16789.1 | 300437022 | *Clostridium ljungdahlii* DSM 13528 |
| folD-2 | NP_951919.1 | 39995968 | *Geobacter sulfurreducens* PCA |

| Protein | GenBank ID | GI number | Organism |
|---|---|---|---|
| folD | YP_725874.1 | 113867385 | Ralstonia eutropha H16 |
| folD | NP_348702.1 | 15895353 | Clostridium acetobutylicum ATCC 824 |
| folD | YP_696506.1 | 110800457 | Clostridium perfringens |
| MGA3_09460 | EIJ83438.1 | 387591119 | Bacillus methanolicus MGA3 |
| PB1_14689 | ZP_10132349.1 | 387929672 | Bacillus methanolicus PB1 |

FIG. 2, Step E—Formyltetrahydrofolate Deformylase

This enzyme catalyzes the hydrolysis of 10-formyltetrahydrofolate (formyl-THF) to THF and formate. In *E. coli*, this enzyme is encoded by purU and has been overproduced, purified, and characterized (Nagy, et al., *J. Bacteriol.* 3:1292-1298 (1995)).

| Protein | GenBank ID | GI number | Organism |
|---|---|---|---|
| purU | AAC74314.1 | 1787483 | Escherichia coli K-12 MG1655 |
| purU | BAD97821.1 | 63002616 | Corynebacterium sp. U-96 |
| purU | EHE84645.1 | 354511740 | Corynebacterium glutamicum ATCC 14067 |
| purU | NP_460715.1 | 16765100 | Salmonella enterica subsp. enterica serovar Typhimurium str. LT2 |

FIG. 2, Step F—Formyltetrahydrofolate Synthetase

Formyltetrahydrofolate synthetase ligates formate to tetrahydrofolate at the expense of one ATP. This enzyme is found in several organisms as listed below.

| Protein | GenBank ID | GI number | Organism |
|---|---|---|---|
| Moth_0109 | YP_428991.1 | 83588982 | Moorella thermoacetica |
| CHY_2385 | YP_361182.1 | 78045024 | Carboxydothermus hydrogenoformans |
| FHS | P13419.1 | 120562 | Clostridium acidurici |
| CcarbDRAFT_1913 | ZP_05391913.1 | 255524966 | Clostridium carboxidivorans P7 |
| CcarbDRAFT_2946 | ZP_05392946.1 | 255526022 | Clostridium carboxidivorans P7 |
| Dhaf_0555 | ACL18622.1 | 219536883 | Desulfitobacterium hafniense |
| fhs | YP_001393842.1 | 153953077 | Clostridium kluyveri DSM 555 |
| fhs | YP_003781893.1 | 300856909 | Clostridium ljungdahlii DSM 13528 |
| MGA3_08300 | EIJ83208.1 | 387590889 | Bacillus methanolicus MGA3 |
| PB1_13509 | ZP_10132113.1 | 387929436 | Bacillus methanolicus PB1 |

FIG. 2, Step G—Formate Hydrogen Lyase

A formate hydrogen lyase enzyme can be employed to convert formate to carbon dioxide and hydrogen. An exemplary formate hydrogen lyase enzyme can be found in *Escherichia coli*. The *E. coli* formate hydrogen lyase consists of hydrogenase 3 and formate dehydrogenase-H (Maeda et al., *Appl Microbiol Biotechnol* 77:879-890 (2007)). It is activated by the gene product of fhlA. (Maeda et al., *Appl Microbiol Biotechnol* 77:879-890 (2007)). The addition of the trace elements, selenium, nickel and molybdenum, to a fermentation broth has been shown to enhance formate hydrogen lyase activity (Soini et al., *Microb. Cell Fact.* 7:26 (2008)). Various hydrogenase 3, formate dehydrogenase and transcriptional activator genes are shown below.

| Protein | GenBank ID | GI number | Organism |
|---|---|---|---|
| hycA | NP_417205 | 16130632 | Escherichia coli K-12 MG1655 |
| hycB | NP_417204 | 16130631 | Escherichia coli K-12 MG1655 |
| hycC | NP_417203 | 16130630 | Escherichia coli K-12 MG1655 |
| hycD | NP_417202 | 16130629 | Escherichia coli K-12 MG1655 |
| hycE | NP_417201 | 16130628 | Escherichia coli K-12 MG1655 |
| hycF | NP_417200 | 16130627 | Escherichia coli K-12 MG1655 |
| hycG | NP_417199 | 16130626 | Escherichia coli K-12 MG1655 |
| hycH | NP_417198 | 16130625 | Escherichia coli K-12 MG1655 |
| hycI | NP_417197 | 16130624 | Escherichia coli K-12 MG1655 |
| fdhF | NP_418503 | 16131905 | Escherichia coli K-12 MG1655 |
| fhlA | NP_417211 | 16130638 | Escherichia coli K-12 MG1655 |

A formate hydrogen lyase enzyme also exists in the hyperthermophilic archaeon, *Thermococcus litoralis* (Takacs et al., *BMC. Microbiol* 8:88 (2008)).

| Protein | GenBank ID | GI number | Organism |
|---|---|---|---|
| mhyC | ABW05543 | 157954626 | Thermococcus litoralis |
| mhyD | ABW05544 | 157954627 | Thermococcus litoralis |
| mhyE | ABW05545 | 157954628 | Thermococcus litoralis |
| myhF | ABW05546 | 157954629 | Thermococcus litoralis |
| myhG | ABW05547 | 157954630 | Thermococcus litoralis |
| myhH | ABW05548 | 157954631 | Thermococcus litoralis |
| fdhA | AAB94932 | 2746736 | Thermococcus litoralis |
| fdhB | AAB94931 | 157954625 | Thermococcus litoralis |

Additional formate hydrogen lyase systems have been found in *Salmonella typhimurium, Klebsiella pneumoniae, Rhodospirillum rubrum, Methanobacterium formicicum* (Vardar-Schara et al., Microbial Biotechnology 1:107-125 (2008)).

FIG. 2, Step H—Hydrogenase

Hydrogenase enzymes can convert hydrogen gas to protons and transfer electrons to acceptors such as ferredoxins, NAD+, or NADP+. *Ralstonia eutropha* H16 uses hydrogen as an energy source with oxygen as a terminal electron acceptor. Its membrane-bound uptake [NiFe]-hydrogenase is an "O2-tolerant" hydrogenase (Cracknell, et al. Proc Nat Acad Sci, 106(49) 20681-20686 (2009)) that is periplasmically-oriented and connected to the respiratory chain via a b-type cytochrome (Schink and Schlegel, *Biochim. Biophys. Acta,* 567, 315-324 (1979); Bernhard et al., *Eur. J. Biochem.* 248, 179-186 (1997)). *R. eutropha* also contains an $O_2$-tolerant soluble hydrogenase encoded by the Hox operon which is cytoplasmic and directly reduces NAD+ at the expense of hydrogen (Schneider and Schlegel, *Biochim. Biophys. Acta* 452, 66-80 (1976); Burgdorf, *J. Bact.* 187(9) 3122-3132(2005)). Soluble hydrogenase enzymes are additionally present in several other organisms including *Geobacter sulfurreducens* (Coppi, *Microbiology* 151, 1239-1254 (2005)), *Synechocystis* str. PCC 6803 (Germer, *J. Biol. Chem.,* 284(52), 36462-36472 (2009)), and *Thiocapsa roseopersicina* (Rakhely, *Appl. Environ. Microbiol.* 70(2) 722-728 (2004)). The *Synechocystis* enzyme is capable of generating NADPH from hydrogen. Overexpression of both the Hox operon from *Synechocystis* str. PCC 6803 and the accessory genes encoded by the Hyp operon from Nostoc sp. PCC 7120 led to increased hydrogenase activity compared to expression of the Hox genes alone (Germer, *J. Biol. Chem.* 284(52), 36462-36472 (2009)).

| Protein | GenBank ID | GI number | Organism |
| --- | --- | --- | --- |
| HoxF | NP_942727.1 | 38637753 | *Ralstonia eutropha* H16 |
| HoxU | NP_942728.1 | 38637754 | *Ralstonia eutropha* H16 |
| HoxY | NP_942729.1 | 38637755 | *Ralstonia eutropha* H16 |
| HoxH | NP_942730.1 | 38637756 | *Ralstonia eutropha* H16 |
| HoxW | NP_942731.1 | 38637757 | *Ralstonia eutropha* H16 |
| HoxI | NP_942732.1 | 38637758 | *Ralstonia eutropha* H16 |
| HoxE | NP_953767.1 | 39997816 | *Geobacter sulfurreducens* |
| HoxF | NP_953766.1 | 39997815 | *Geobacter sulfurreducens* |
| HoxU | NP_953765.1 | 39997814 | *Geobacter sulfurreducens* |
| HoxY | NP_953764.1 | 39997813 | *Geobacter sulfurreducens* |
| HoxH | NP_953763.1 | 39997812 | *Geobacter sulfurreducens* |
| GSU2717 | NP_953762.1 | 39997811 | *Geobacter sulfurreducens* |
| HoxE | NP_441418.1 | 16330690 | *Synechocystis* str. PCC 6803 |
| HoxF | NP_441417.1 | 16330689 | *Synechocystis* str. PCC 6803 |
| Unknown function | NP_441416.1 | 16330688 | *Synechocystis* str. PCC 6803 |
| HoxU | NP_441415.1 | 16330687 | *Synechocystis* str. PCC 6803 |
| HoxY | NP_441414.1 | 16330686 | *Synechocystis* str. PCC 6803 |
| Unknown function | NP_441413.1 | 16330685 | *Synechocystis* str. PCC 6803 |
| Unknown function | NP_441412.1 | 16330684 | *Synechocystis* str. PCC 6803 |
| HoxH | NP_441411.1 | 16330683 | *Synechocystis* str. PCC 6803 |
| HypF | NP_484737.1 | 17228189 | *Nostoc* sp. PCC 7120 |
| HypC | NP_484738.1 | 17228190 | *Nostoc* sp. PCC 7120 |
| HypD | NP_484739.1 | 17228191 | *Nostoc* sp. PCC 7120 |
| Unknown function | NP_484740.1 | 17228192 | *Nostoc* sp. PCC 7120 |
| HypE | NP_484741.1 | 17228193 | *Nostoc* sp. PCC 7120 |
| HypA | NP_484742.1 | 17228194 | *Nostoc* sp. PCC 7120 |
| HypB | NP_484743.1 | 17228195 | *Nostoc* sp. PCC 7120 |
| Hox1E | AAP50519.1 | 37787351 | *Thiocapsa roseopersicina* |
| Hox1F | AAP50520.1 | 37787352 | *Thiocapsa roseopersicina* |
| Hox1U | AAP50521.1 | 37787353 | *Thiocapsa roseopersicina* |
| Hox1Y | AAP50522.1 | 37787354 | *Thiocapsa roseopersicina* |
| Hox1H | AAP50523.1 | 37787355 | *Thiocapsa roseopersicina* |

The genomes of *E. coli* and other enteric bacteria encode up to four hydrogenase enzymes (Sawers, G., Antonie Van Leeuwenhoek 66:57-88 (1994); Sawers et al., *J Bacteriol.* 164:1324-1331 (1985); Sawers and Boxer, *Eur. J Biochem.* 156:265-275 (1986); Sawers et al., *J Bacteriol.* 168:398-404 (1986)). Given the multiplicity of enzyme activities *E. coli* or another host organism can provide sufficient hydrogenase activity to split incoming molecular hydrogen and reduce the corresponding acceptor. Endogenous hydrogen-lyase enzymes of *E. coli* include hydrogenase 3, a membrane-bound enzyme complex using ferredoxin as an acceptor, and hydrogenase 4 that also uses a ferredoxin acceptor. Hydrogenase 3 and 4 are encoded by the hyc and hyf gene clusters, respectively. Hydrogenase activity in *E. coli* is also dependent upon the expression of the hyp genes whose corresponding proteins are involved in the assembly of the hydrogenase complexes (Jacobi et al., *Arch. Microbiol* 158: 444-451 (1992); Rangarajan et al., *J Bacteriol.* 190:1447-1458 (2008)). The *M. thermoacetica* and *Clostridium ljungdahli* hydrogenases are suitable for a host that lacks sufficient endogenous hydrogenase activity. *M. thermoacetica* and *C. ljungdahli* can grow with $CO_2$ as the exclusive carbon source indicating that reducing equivalents are extracted from $H_2$ to enable acetyl-CoA synthesis via the Wood-Ljungdahl pathway (Drake, H. L., *J Bacteriol.* 150: 702-709 (1982); Drake and Daniel, *Res Microbiol* 155:869-883 (2004); Kellum and Drake, *J Bacteriol.* 160:466-469 (1984)). *M. thermoacetica* has homologs to several hyp, hyc, and hyf genes from *E. coli*. These protein sequences encoded for by these genes are identified by the following GenBank accession numbers. In addition, several gene clusters encoding hydrogenase functionality are present in *M. thermoacetica* and *C. ljungdahli* (see for example US 2012/0003652).

| Protein | GenBank ID | GI Number | Organism |
| --- | --- | --- | --- |
| HypA | NP_417206 | 16130633 | *Escherichia coli* |
| HypB | NP_417207 | 16130634 | *Escherichia coli* |
| HypC | NP_417208 | 16130635 | *Escherichia coli* |
| HypD | NP_417209 | 16130636 | *Escherichia coli* |
| HypE | NP_417210 | 226524740 | *Escherichia coli* |
| HypF | NP_417192 | 16130619 | *Escherichia coli* |
| HycA | NP_417205 | 16130632 | *Escherichia coli* |
| HycB | NP_417204 | 16130631 | *Escherichia coli* |
| HycC | NP_417203 | 16130630 | *Escherichia coli* |
| HycD | NP_417202 | 16130629 | *Escherichia coli* |
| HycE | NP_417201 | 16130628 | *Escherichia coli* |
| HycF | NP_417200 | 16130627 | *Escherichia coli* |
| HycG | NP_417199 | 16130626 | *Escherichia coli* |
| HycH | NP_417198 | 16130625 | *Escherichia coli* |
| HycI | NP_417197 | 16130624 | *Escherichia coli* |
| HyfA | NP_416976 | 90111444 | *Escherichia coli* |
| HyfB | NP_416977 | 16130407 | *Escherichia coli* |
| HyfC | NP_416978 | 90111445 | *Escherichia coli* |
| HyfD | NP_416979 | 16130409 | *Escherichia coli* |
| HyfE | NP_416980 | 16130410 | *Escherichia coli* |
| HyfF | NP_416981 | 16130411 | *Escherichia coli* |
| HyfG | NP_416982 | 16130412 | *Escherichia coli* |
| HyfH | NP_416983 | 16130413 | *Escherichia coli* |
| HyfI | NP_416984 | 16130414 | *Escherichia coli* |
| HyfJ | NP_416985 | 90111446 | *Escherichia coli* |
| HyfR | NP_416986 | 90111447 | *Escherichia coli* |

Proteins in *M. thermoacetica* whose genes are homologous to the *E. coli* hydrogenase genes are shown below.

| Protein | GenBank ID | GI Number | Organism |
| --- | --- | --- | --- |
| Moth_2175 | YP_431007 | 83590998 | *Moorella thermoacetica* |
| Moth_2176 | YP_431008 | 83590999 | *Moorella thermoacetica* |
| Moth_2177 | YP_431009 | 83591000 | *Moorella thermoacetica* |
| Moth_2178 | YP_431010 | 83591001 | *Moorella thermoacetica* |
| Moth_2179 | YP_431011 | 83591002 | *Moorella thermoacetica* |
| Moth_2180 | YP_431012 | 83591003 | *Moorella thermoacetica* |
| Moth_2181 | YP_431013 | 83591004 | *Moorella thermoacetica* |
| Moth_2182 | YP_431014 | 83591005 | *Moorella thermoacetica* |
| Moth_2183 | YP_431015 | 83591006 | *Moorella thermoacetica* |
| Moth_2184 | YP_431016 | 83591007 | *Moorella thermoacetica* |
| Moth_2185 | YP_431017 | 83591008 | *Moorella thermoacetica* |
| Moth_2186 | YP_431018 | 83591009 | *Moorella thermoacetica* |
| Moth_2187 | YP_431019 | 83591010 | *Moorella thermoacetica* |
| Moth_2188 | YP_431020 | 83591011 | *Moorella thermoacetica* |
| Moth_2189 | YP_431021 | 83591012 | *Moorella thermoacetica* |
| Moth_2190 | YP_431022 | 83591013 | *Moorella thermoacetica* |
| Moth_2191 | YP_431023 | 83591014 | *Moorella thermoacetica* |

| Protein | GenBank ID | GI Number | Organism |
|---|---|---|---|
| Moth_2192 | YP_431024 | 83591015 | Moorella thermoacetica |
| Moth_0439 | YP_429313 | 83589304 | Moorella thermoacetica |
| Moth_0440 | YP_429314 | 83589305 | Moorella thermoacetica |
| Moth_0441 | YP_429315 | 83589306 | Moorella thermoacetica |
| Moth_0442 | YP_429316 | 83589307 | Moorella thermoacetica |
| Moth_0809 | YP_429670 | 83589661 | Moorella thermoacetica |
| Moth_0810 | YP_429671 | 83589662 | Moorella thermoacetica |
| Moth_0811 | YP_429672 | 83589663 | Moorella thermoacetica |
| Moth_0812 | YP_429673 | 83589664 | Moorella thermoacetica |
| Moth_0814 | YP_429674 | 83589665 | Moorella thermoacetica |
| Moth_0815 | YP_429675 | 83589666 | Moorella thermoacetica |
| Moth_0816 | YP_429676 | 83589667 | Moorella thermoacetica |
| Moth_1193 | YP_430050 | 83590041 | Moorella thermoacetica |
| Moth_1194 | YP_430051 | 83590042 | Moorella thermoacetica |
| Moth_1195 | YP_430052 | 83590043 | Moorella thermoacetica |
| Moth_1196 | YP_430053 | 83590044 | Moorella thermoacetica |
| Moth_1717 | YP_430562 | 83590553 | Moorella thermoacetica |
| Moth_1718 | YP_430563 | 83590554 | Moorella thermoacetica |
| Moth_1719 | YP_430564 | 83590555 | Moorella thermoacetica |
| Moth_1883 | YP_430726 | 83590717 | Moorella thermoacetica |
| Moth_1884 | YP_430727 | 83590718 | Moorella thermoacetica |
| Moth_1885 | YP_430728 | 83590719 | Moorella thermoacetica |
| Moth_1886 | YP_430729 | 83590720 | Moorella thermoacetica |
| Moth_1887 | YP_430730 | 83590721 | Moorella thermoacetica |
| Moth_1888 | YP_430731 | 83590722 | Moorella thermoacetica |
| Moth_1452 | YP_430305 | 83590296 | Moorella thermoacetica |
| Moth_1453 | YP_430306 | 83590297 | Moorella thermoacetica |
| Moth_1454 | YP_430307 | 83590298 | Moorella thermoacetica |

Genes encoding hydrogenase enzymes from *C. ljungdahli* are shown below.

| Protein | GenBank ID | GI Number | Organism |
|---|---|---|---|
| CLJU_c20290 | ADK15091.1 | 300435324 | Clostridium ljungdahli |
| CLJU_c07030 | ADK13773.1 | 300434006 | Clostridium ljungdahli |
| CLJU_c07040 | ADK13774.1 | 300434007 | Clostridium ljungdahli |
| CLJU_c07050 | ADK13775.1 | 300434008 | Clostridium ljungdahli |
| CLJU_c07060 | ADK13776.1 | 300434009 | Clostridium ljungdahli |
| CLJU_c07070 | ADK13777.1 | 300434010 | Clostridium ljungdahli |
| CLJU_c07080 | ADK13778.1 | 300434011 | Clostridium ljungdahli |
| CLJU_c14730 | ADK14541.1 | 300434774 | Clostridium ljungdahli |
| CLJU_c14720 | ADK14540.1 | 300434773 | Clostridium ljungdahli |
| CLJU_c14710 | ADK14539.1 | 300434772 | Clostridium ljungdahli |
| CLJU_c14700 | ADK14538.1 | 300434771 | Clostridium ljungdahli |
| CLJU_c28670 | ADK15915.1 | 300436148 | Clostridium ljungdahli |
| CLJU_c28660 | ADK15914.1 | 300436147 | Clostridium ljungdahli |
| CLJU_c28650 | ADK15913.1 | 300436146 | Clostridium ljungdahli |
| CLJU_c28640 | ADK15912.1 | 300436145 | Clostridium ljungdahli |

In some cases, hydrogenase encoding genes are located adjacent to a CODH. In *Rhodospirillum rubrum*, the encoded CODH/hydrogenase proteins form a membrane-bound enzyme complex that has been indicated to be a site where energy, in the form of a proton gradient, is generated from the conversion of CO and $H_2O$ to $CO_2$ and $H_2$ (Fox et al., *J Bacteriol.* 178:6200-6208 (1996)). The CODH-I of *C. hydrogenoformans* and its adjacent genes have been proposed to catalyze a similar functional role based on their similarity to the *R. rubrum* CODH/hydrogenase gene cluster (Wu et al., *PLoS Genet.* 1:e65 (2005)). The *C. hydrogenoformans* CODH-I was also shown to exhibit intense CO oxidation and $CO_2$ reduction activities when linked to an electrode (Parkin et al., *J Am. Chem. Soc.* 129:10328-10329 (2007)).

| Protein | GenBank ID | GI Number | Organism |
|---|---|---|---|
| CooL | AAC45118 | 1515468 | Rhodospirillum rubrum |
| CooX | AAC45119 | 1515469 | Rhodospirillum rubrum |
| CooU | AAC45120 | 1515470 | Rhodospirillum rubrum |
| CooH | AAC45121 | 1498746 | Rhodospirillum rubrum |
| CooF | AAC45122 | 1498747 | Rhodospirillum rubrum |
| CODH (CooS) | AAC45123 | 1498748 | Rhodospirillum rubrum |
| CooC | AAC45124 | 1498749 | Rhodospirillum rubrum |
| CooT | AAC45125 | 1498750 | Rhodospirillum rubrum |
| CooJ | AAC45126 | 1498751 | Rhodospirillum rubrum |
| CODH-I (CooS-I) | YP_360644 | 78043418 | Carboxydothermus hydrogenoformans |
| CooF | YP_360645 | 78044791 | Carboxydothermus hydrogenoformans |
| HypA | YP_360646 | 78044340 | Carboxydothermus hydrogenoformans |
| CooH | YP_360647 | 78043871 | Carboxydothermus hydrogenoformans |
| CooU | YP_360648 | 78044023 | Carboxydothermus hydrogenoformans |
| CooX | YP_360649 | 78043124 | Carboxydothermus hydrogenoformans |
| CooL | YP_360650 | 78043938 | Carboxydothermus hydrogenoformans |
| CooK | YP_360651 | 78044700 | Carboxydothermus hydrogenoformans |
| CooM | YP_360652 | 78043942 | Carboxydothermus hydrogenoformans |
| CooC | YP_360654.1 | 78043296 | Carboxydothermus hydrogenoformans |
| CooA-1 | YP_360655.1 | 78044021 | Carboxydothermus hydrogenoformans |

Some hydrogenase and CODH enzymes transfer electrons to ferredoxins. Ferredoxins are small acidic proteins containing one or more iron-sulfur clusters that function as intracellular electron carriers with a low reduction potential. Reduced ferredoxins donate electrons to Fe-dependent enzymes such as ferredoxin-$NADP^+$ oxidoreductase, pyruvate:ferredoxin oxidoreductase (PFOR) and 2-oxoglutarate: ferredoxin oxidoreductase (OFOR). The *H. thermophilus* gene fdx1 encodes a [4Fe-4S]-type ferredoxin that is required for the reversible carboxylation of 2-oxoglutarate and pyruvate by OFOR and PFOR, respectively (Yamamoto et al., *Extremophiles* 14:79-85 (2010)). The ferredoxin associated with the *Sulfolobus solfataricus* 2-oxoacid:ferredoxin reductase is a monomeric dicluster [3Fe-4S][4Fe-4S] type ferredoxin (Park et al. 2006). While the gene associated with this protein has not been fully sequenced, the N-terminal domain shares 93% homology with the zfx ferredoxin from *S. acidocaldarius*. The *E. coli* genome encodes a soluble ferredoxin of unknown physiological function, fdy. Some evidence indicates that this protein can function in iron-sulfur cluster assembly (Takahashi and Nakamura, 1999).

Additional ferredoxin proteins have been characterized in *Helicobacter pylori* (Mukhopadhyay et al. 2003) and *Campylobacter jejuni* (van Vliet et al. 2001). A 2Fe-2S ferredoxin from *Clostridium pasteurianum* has been cloned and expressed in *E. coli* (Fujinaga and Meyer, Biochemical and Biophysical Research Communications, 192(3): (1993)). Acetogenic bacteria such as *Moorella thelmoacetica*, *Clostridium carboxidivorans* P7, *Clostridium ljungdahli* and *Rhodospirillum rubrum* are predicted to encode several ferredoxins, listed below.

| Protein | GenBank ID | GI Number | Organism |
|---|---|---|---|
| fdx1 | BAE02673.1 | 68163284 | *Hydrogenobacter thermophilus* |
| M11214.1 | AAA83524.1 | 144806 | *Clostridium pasteurianum* |
| Zfx | AAY79867.1 | 68566938 | *Sulfolobus acidocalarius* |
| Fdx | AAC75578.1 | 1788874 | *Escherichia coli* |
| hp_0277 | AAD07340.1 | 2313367 | *Helicobacter pylori* |
| fdxA | CAL34484.1 | 112359698 | *Campylobacter jejuni* |
| Moth_0061 | ABC18400.1 | 83571848 | *Moorella thermoacetica* |
| Moth_1200 | ABC19514.1 | 83572962 | *Moorella thermoacetica* |
| Moth_1888 | ABC20188.1 | 83573636 | *Moorella thermoacetica* |
| Moth_2112 | ABC20404.1 | 83573852 | *Moorella thermoacetica* |
| Moth_1037 | ABC19351.1 | 83572799 | *Moorella thermoacetica* |
| CcarbDRAFT_4383 | ZP_05394383.1 | 255527515 | *Clostridium carboxidivorans* P7 |
| CcarbDRAFT_2958 | ZP_05392958.1 | 255526034 | *Clostridium carboxidivorans* P7 |
| CcarbDRAFT_2281 | ZP_05392281.1 | 255525342 | *Clostridium carboxidivorans* P7 |
| CcarbDRAFT_5296 | ZP_05395295.1 | 255528511 | *Clostridium carboxidivorans* P7 |
| CcarbDRAFT_1615 | ZP_05391615.1 | 255524662 | *Clostridium carboxidivorans* P7 |
| CcarbDRAFT_1304 | ZP_05391304.1 | 255524347 | *Clostridium carboxidivorans* P7 |
| cooF | AAG29808.1 | 11095245 | *Carboxydothermus hydrogenoformans* |
| fdxN | CAA35699.1 | 46143 | *Rhodobacter capsulatus* |
| Rru_A2264 | ABC23064.1 | 83576513 | *Rhodospirillum rubrum* |
| Rru_A1916 | ABC22716.1 | 83576165 | *Rhodospirillum rubrum* |
| Rru_A2026 | ABC22826.1 | 83576275 | *Rhodospirillum rubrum* |
| cooF | AAC45122.1 | 1498747 | *Rhodospirillum rubrum* |
| fdxN | AAA26460.1 | 152605 | *Rhodospirillum rubrum* |
| Alvin_2884 | ADC63789.1 | 288897953 | *Allochromatium vinosum* DSM 180 |
| Fdx | YP_002801146.1 | 226946073 | *Azotobacter vinelandii* DJ |
| CKL_3790 | YP_001397146.1 | 153956381 | *Clostridium kluyveri* DSM 555 |
| fer1 | NP_949965.1 | 39937689 | *Rhodopseudomonas palustris* CGA009 |
| Fdx | CAA12251.1 | 3724172 | *Thauera aromatica* |
| CHY_2405 | YP_361202.1 | 78044690 | *Carboxydothermus hydrogenoformans* |
| Fer | YP_359966.1 | 78045103 | *Carboxydothermus hydrogenoformans* |
| Fer | AAC83945.1 | 1146198 | *Bacillus subtilis* |
| fdx1 | NP_249053.1 | 15595559 | *Pseudomonas aeruginosa* PA01 |
| yfhL | AP_003148.1 | 89109368 | *Escherichia coli* K-12 |
| CLJU_c00930 | ADK13195.1 | 300433428 | *Clostridium ljungdahli* |
| CLJU_c00010 | ADK13115.1 | 300433348 | *Clostridium ljungdahli* |
| CLJU_c01820 | ADK13272.1 | 300433505 | *Clostridium ljungdahli* |
| CLJU_c17980 | ADK14861.1 | 300435094 | *Clostridium ljungdahli* |
| CLJU_c17970 | ADK14860.1 | 300435093 | *Clostridium ljungdahli* |
| CLJU_c22510 | ADK15311.1 | 300435544 | *Clostridium ljungdahli* |
| CLJU_c26680 | ADK15726.1 | 300435959 | *Clostridium ljungdahli* |
| CLJU_c29400 | ADK15988.1 | 300436221 | *Clostridium ljungdahli* |

Ferredoxin oxidoreductase enzymes transfer electrons from ferredoxins or flavodoxins to NAD(P)H. Two enzymes catalyzing the reversible transfer of electrons from reduced ferredoxins to NAD(P)+ are ferredoxin:NAD+ oxidoreductase (EC 1.18.1.3) and ferredoxin:NADP+ oxidoreductase (FNR, EC 1.18.1.2). Ferredoxin:NADP+ oxidoreductase (FNR, EC 1.18.1.2) has a noncovalently bound FAD cofactor that facilitates the reversible transfer of electrons from NADPH to low-potential acceptors such as ferredoxins or flavodoxins.

| Protein | GenBank ID | GI Number | Organism |
|---|---|---|---|
| fqrB | NP_207955.1 | 15645778 | *Helicobacter pylori* |
| fqrB | YP_001482096.1 | 157414840 | *Campylobacter jejuni* |
| RPA3954 | CAE29395.1 | 39650872 | *Rhodopseudomonas palustris* |
| Fpr | BAH29712.1 | 225320633 | *Hydrogenobacter thermophilus* |
| yumC | NP_391091.2 | 255767736 | *Bacillus subtilis* |
| Fpr | P28861.4 | 399486 | *Escherichia coli* |
| hcaD | AAC75595.1 | 1788892 | *Escherichia coli* |
| LOC100282643 | NP_001149023.1 | 226497434 | *Zea mays* |
| NfnA | YP_001393861.1 | 153953096 | *Clostridium kluyveri* |
| NfnB | YP_001393862.1 | 153953097 | *Clostridium kluyveri* |
| CcarbDRAFT_2639 | ZP_05392639.1 | 255525707 | *Clostridium carboxidivorans* P7 |

-continued

| Protein | GenBank ID | GI Number | Organism |
|---|---|---|---|
| CcarbDRAFT_2638 | ZP_05392638.1 | 255525706 | Clostridium carboxidivorans P7 |
| CcarbDRAFT_2636 | ZP_05392636.1 | 255525704 | Clostridium carboxidivorans P7 |
| CcarbDRAFT_5060 | ZP_05395060.1 | 255528241 | Clostridium carboxidivorans P7 |
| CcarbDRAFT_2450 | ZP_05392450.1 | 255525514 | Clostridium carboxidivorans P7 |
| CcarbDRAFT_1084 | ZP_05391084.1 | 255524124 | Clostridium carboxidivorans P7 |
| RnfC | EDK33306.1 | 146346770 | Clostridium kluyveri |
| RnfD | EDK33307.1 | 146346771 | Clostridium kluyveri |
| RnfG | EDK33308.1 | 146346772 | Clostridium kluyveri |
| RnfE | EDK33309.1 | 146346773 | Clostridium kluyveri |
| RnfA | EDK33310.1 | 146346774 | Clostridium kluyveri |
| RnfB | EDK33311.1 | 146346775 | Clostridium kluyveri |
| CLJU_c11410 (RnfB) | ADK14209.1 | 300434442 | Clostridium ljungdahlii |
| CLJU_c11400 (RnfA) | ADK14208.1 | 300434441 | Clostridium ljungdahlii |
| CLJU_c11390 (RnfE) | ADK14207.1 | 300434440 | Clostridium ljungdahlii |
| CLJU_c11380 (RnfG) | ADK14206.1 | 300434439 | Clostridium ljungdahlii |
| CLJU_c11370 (RnfD) | ADK14205.1 | 300434438 | Clostridium ljungdahlii |
| CLJU_c11360 (RnfC) | ADK14204.1 | 300434437 | Clostridium ljungdahlii |
| MOTH_1518 (NfnA) | YP_430370.1 | 83590361 | Moorella thermoacetica |
| MOTH_1517(NfnB) | YP_430369.1 | 83590360 | Moorella thermoacetica |
| CHY_1992 (NfnA) | YP_360811.1 | 78045020 | Carboxydothermus hydrogenoformans |
| CHY_1993 (NfnB) | YP_360812.1 | 78044266 | Carboxydothermus hydrogenoformans |
| CLJU_c37220 (NfnAB) | YP_003781850.1 | 300856866 | Clostridium ljungdahlii |

FIG. 2, Step I—Formate Dehydrogenase

Formate dehydrogenase (FDH) catalyzes the reversible transfer of electrons from formate to an acceptor. Exemplary enzymes include those described in the section for Step S, FIG. 1: Formate dehydrogenase.

FIG. 2, Step J—Methanol Dehydrogenase

NAD+ dependent methanol dehydrogenase enzymes (EC 1.1.1.244) catalyze the conversion of methanol and NAD+ to formaldehyde and NADH. An enzyme with this activity was first characterized in Bacillus methanolicus (Heggeset, et al., Applied and Environmental Microbiology, 78(15): 5170-5181(2012)). This enzyme is zinc and magnesium dependent, and activity of the enzyme is enhanced by the activating enzyme encoded by act (Kloosterman et al, J Biol Chem 277:34785-92 (2002)). The act is a Nudix hydrolase. Several of these candidates have been identified and shown to have activity on methanol. Additional NAD(P)+ dependent enzymes can be identified by sequence homology. Methanol dehydrogenase enzymes utilizing different electron acceptors are also known in the art. Examples include cytochrome dependent enzymes such as mxaIF of the methylotroph Methylobacterium extorquens (Nunn et al, Nucl Acid Res 16:7722 (1988)). Methanol dehydrogenase enzymes of methanotrophs such as Methylococcus capsulatis function in a complex with methane monooxygenase (MMO) (Myronova et al, Biochem 45:11905-14 (2006)). Methanol can also be oxidized to formaldehyde by alcohol oxidase enzymes such as methanol oxidase (EC 1.1.3.13) of Candida boidinii (Sakai et al, Gene 114: 67-73 (1992)).

| Protein | GenBank ID | GI Number | Organism |
|---|---|---|---|
| mdh, MGA3_17392 | EIJ77596.1 | 387585261 | Bacillus methanolicus MGA3 |
| mdh2, MGA3_07340 | EIJ83020.1 | 387590701 | Bacillus methanolicus MGA3 |
| mdh3, MGA3_10725 | EIJ80770.1 | 387588449 | Bacillus methanolicus MGA3 |
| act, MGA3_09170 | EIJ83380.1 | 387591061 | Bacillus methanolicus MGA3 |
| mdh, PB1_17533 | ZP_10132907.1 | 387930234 | Bacillus methanolicus PB1 |
| mdh1, PB1_14569 | ZP_10132325.1 | 387929648 | Bacillus methanolicus PB1 |
| mdh2, PB1_12584 | ZP_10131932.1 | 387929255 | Bacillus methanolicus PB1 |
| act, PB1_14394 | ZP_10132290.1 | 387929613 | Bacillus methanolicus PB1 |
| BFZC1_05383 | ZP_07048751.1 | 299535429 | Lysinibacillus fusiformis |
| BFZC1_20163 | ZP_07051637.1 | 299538354 | Lysinibacillus fusiformis |
| Bsph_4187 | YP_001699778.1 | 169829620 | Lysinibacillus sphaericus |
| Bsph_1706 | YP_001697432.1 | 169827274 | Lysinibacillus sphaericus |
| mdh2 | YP_004681552.1 | 339322658 | Cupriavidus necator N-1 |
| nudF1 | YP_004684845.1 | 339325152 | Cupriavidus necator N-1 |
| BthaA_010200007655 | ZP_05587334.1 | 257139072 | Burkholderia thailandensis E264 |
| BTH_I1076 (MutT/NUDIX NTP pyrophosphatase) | YP_441629.1 | 83721454 | Burkholderia thailandensis E264 |
| BalcAV_11743 | ZP_10819291.1 | 402299711 | Bacillus alcalophilus ATCC 27647 |
| BalcAV_05251 | ZP_10818002.1 | 402298299 | Bacillus alcalophilus ATCC 27647 |
| alcohol dehydrogenase | YP_001447544 | 156976638 | Vibrio harveyi ATCC BAA-1116 |
| P3TCK_27679 | ZP_01220157.1 | 90412151 | Photobacterium profundum 3TCK |
| alcohol dehydrogenase | YP_694908 | 110799824 | Clostridium perfringens ATCC 13124 |
| adhB | NP_717107 | 24373064 | Shewanella oneidensis MR-1 |
| alcohol dehydrogenase | YP_237055 | 66047214 | Pseudomonas syringae pv. syringae B728a |
| alcohol dehydrogenase | YP_359772 | 78043360 | Carboxydothermus hydrogenoformans Z-2901 |
| alcohol dehydrogenase | YP_003990729 | 312112413 | Geobacillus sp. Y4.1MC1 |

-continued

| Protein | GenBank ID | GI Number | Organism |
|---|---|---|---|
| PpeoK3_010100018471 | ZP_10241531.1 | 390456003 | Paenibacillus peoriae KCTC 3763 |
| OBE_12016 | EKC54576 | 406526935 | human gut metagenome |
| alcohol dehydrogenase | YP_001343716 | 152978087 | Actinobacillus succinogenes 130Z |
| dhaT | AAC45651 | 2393887 | Clostridium pasteurianum DSM 525 |
| alcohol dehydrogenase | NP_561852 | 18309918 | Clostridium perfringens str. 13 |
| BAZO_10081 | ZP_11313277.1 | 410459529 | Bacillus azotoformans LMG 9581 |
| alcohol dehydrogenase | YP_007491369 | 452211255 | Methanosarcina mazei Tuc01 |
| alcohol dehydrogenase | YP_004860127 | 347752562 | Bacillus coagulans 36D1 |
| alcohol dehydrogenase | YP_002138168 | 197117741 | Geobacter bemidjiensis Bem |
| DesmeDRAFT_1354 | ZP_08977641.1 | 354558386 | Desulfitobacterium metallireducens DSM 15288 |
| alcohol dehydrogenase | YP_001337153 | 152972007 | Klebsiella pneumoniae subsp. pneumoniae MGH 78578 |
| alcohol dehydrogenase | YP_001113612 | 134300116 | Desulfotomaculum reducens MI-1 |
| alcohol dehydrogenase | YP_001663549 | 167040564 | Thermoanaerobacter sp. X514 |
| ACINNAV82_2382 | ZP_16224338.1 | 421788018 | Acinetobacter baumannii Naval-82 |
| alcohol dehydrogenase | YP_005052855 | 374301216 | Desulfovibrio africanus str. Walvis Bay |
| alcohol dehydrogenase | AGF87161 | 451936849 | uncultured organism |
| DesfrDRAFT_3929 | ZP_07335453.1 | 303249216 | Desulfovibrio fructosovorans JJ |
| alcohol dehydrogenase | NP_617528 | 20091453 | Methanosarcina acetivorans C2A |
| alcohol dehydrogenase | NP_343875.1 | 15899270 | Sulfolobus solfataricus P-2 |
| adh4 | YP_006863258 | 408405275 | Nitrososphaera gargensis Ga9.2 |
| Ta0841 | NP_394301.1 | 16081897 | Thermoplasma acidophilum |
| PTO1151 | YP_023929.1 | 48478223 | Picrophilus torridus DSM9790 |
| alcohol dehydrogenase | ZP_10129817.1 | 387927138 | Bacillus methanolicus PB-1 |
| cgR_2695 | YP_001139613.1 | 145296792 | Corynebacterium glutamicum R |
| alcohol dehydrogenase | YP_004758576.1 | 340793113 | Corynebacterium variabile |
| HMPREF1015_01790 | ZP_09352758.1 | 365156443 | Bacillus smithii |
| ADH1 | NP_014555.1 | 6324486 | Saccharomyces cerevisiae |
| NADH-dependent butanol dehydrogenase A | YP_001126968.1 | 138896515 | Geobacillus themodenitrificans NG80-2 |
| alcohol dehydrogenase | WP_007139094.1 | 494231392 | Flavobacterium frigoris |
| methanol dehydrogenase | WP_003897664.1 | 489994607 | Mycobacterium smegmatis |
| ADH1B | NP_000659.2 | 34577061 | Homo sapiens |
| PMI01_01199 | ZP_10750164.1 | 399072070 | Caulobacter sp. AP07 |
| YiaY | YP_026233.1 | 49176377 | Escherichia coli |
| MCA0299 | YP_112833.1 | 53802410 | Methylococcus capsulatis |
| MCA0782 | YP_113284.1 | 53804880 | Methylococcus capsulatis |
| mxaI | YP_002965443.1 | 240140963 | Methylobacterium extorquens |
| mxaF | YP_002965446.1 | 240140966 | Methylobacterium extorquens |
| AOD1 | AAA34321.1 | 170820 | Candida boidinii |
| hypothetical protein GOS_1920437 | EDA87976.1 | 142827286 | Marine metagenome JCVI_SCAF_1096627185304 |
| alcohol dehydrogenase | CAA80989.1 | 580823 | Geobacillus stearothermophilus |

An in vivo assay was developed to determine the activity of methanol dehydrogenases. This assay relies on the detection of formaldehyde (HCHO), thus measuring the forward activity of the enzyme (oxidation of methanol). To this end, a strain comprising a BDOP and lacking frmA, frmB, frmR was created using Lambda Red recombinase technology (Datsenko and Wanner, Proc. Natl. Acad. Sci. USA, 697(12): 6640-5 (2000). Plasmids expressing methanol dehydrogenases were transformed into the strain, then grown to saturation in LB medium+ antibiotic at 37° C. with shaking. Transformation of the strain with an empty vector served as a negative control. Cultures were adjusted by O.D. and then diluted 1:10 into M9 medium+0.5% glucose+antibiotic and cultured at 37° C. with shaking for 6-8 hours until late log phase. Methanol was added to 2% v/v and the cultures were further incubated for 30 min. with shaking at 37° C. Cultures were spun down and the supernatant was assayed for formaldehyde produced using DETECTX Formaldehyde Detection kit (Arbor Assays; Ann Arbor, Mich.) according to manufacturer's instructions. The frmA, frmB, frmR deletions resulted in the native formaldehyde utilization pathway to be deleted, which enables the formation of formaldehyde that can be used to detect methanol dehydrogenase activity in the non-naturally occurring microbial organism.

The activity of several enzymes was measured using the assay described above. The results of four independent experiments are provided in the below table.

Results of in vivo assays showing formaldehyde (HCHO) production by various non-naturally occurring microbial organism comprising a plasmid expressing a methanol dehydrogenase.

| Accession number Experiment 1 | HCHO (µM) | Accession number Experiment 2 | HCHO (µM) | Accession number Experiment 3 | HCHO (µM) | Accession number Experiment 4 | HCHO (µM) |
|---|---|---|---|---|---|---|---|
| EIJ77596.1 | >50 | EIJ77596.1 | >50 | EIJ77596.1 | >50 | EIJ77596.1 | >20 |
| EIJ83020.1 | >20 | NP_00659.2 | >50 | NP_561852 | >50 | ZP_11313277.1 | >50 |
| EIJ80770.1 | >50 | YP_004758576.1 | >20 | YP_002138168 | >50 | YP_001113612 | >50 |

| Accession number Experiment 1 | HCHO (µM) | Accession number Experiment 2 | HCHO (µM) | Accession number Experiment 3 | HCHO (µM) | Accession number Experiment 4 | HCHO (µM) |
|---|---|---|---|---|---|---|---|
| ZP_10132907.1 | >20 | ZP_09352758.1 | >50 | YP_026233.1 | >50 | YP_001447544 | >20 |
| ZP_10132325.1 | >20 | ZP_10129817.1 | >20 | YP_001447544 | >50 | AGF87161 | >50 |
| ZP_10131932.1 | >50 | YP_001139613.1 | >20 | Metalibrary | >50 | EDA87976.1 | >20 |
| ZP_07048751.1 | >50 | NP_014555.1 | >10 | YP_359772 | >50 | Empty vector | −0.8 |
| YP_001699778.1 | >50 | WP_007139094.1 | >10 | ZP_01220157.1 | >50 | | |
| YP_004681552.1 | >10 | NP_343875.1 | >1 | ZP_07335453.1 | >20 | | |
| ZP_10819291.1 | <1 | YP_006863258 | >1 | YP_001337153 | >20 | | |
| Empty vector | 2.33 | NP_394301.1 | >1 | YP_694908 | >20 | | |
| | | ZP_10750164.1 | >1 | NP_717107 | >20 | | |
| | | YP_023929.1 | >1 | AAC45651 | >10 | | |
| | | ZP_08977641.1 | <1 | ZP_11313277.1 | >10 | | |
| | | ZP_10117398.1 | <1 | ZP_16224338.1 | >10 | | |
| | | YP_004108045.1 | <1 | YP_001113612 | >10 | | |
| | | ZP_09753449.1 | <1 | YP_004860127 | >10 | | |
| | | Empty vector | 0.17 | YP_003310546 | >10 | | |
| | | | | YP_001343716 | >10 | | |
| | | | | NP_717107 | >10 | | |
| | | | | YP_002434746 | >10 | | |
| | | | | Empty vector | 0.11 | | |

FIG. 2, Step K—Spontaneous or Formaldehyde Activating Enzyme

The conversion of formaldehyde and THF to methylenetetrahydrofolate can occur spontaneously. It is also possible that the rate of this reaction can be enhanced by a formaldehyde activating enzyme. A formaldehyde activating enzyme (Fae) has been identified in *Methylobacterium extorquens* AM1 which catalyzes the condensation of formaldehyde and tetrahydromethanopterin to methylene tetrahydromethanopterin (Vorholt, et al., J. Bacteriol., 182(23), 6645-6650 (2000)). It is possible that a similar enzyme exists or can be engineered to catalyze the condensation of formaldehyde and tetrahydrofolate to methylenetetrahydrofolate. Homologs exist in several organisms.

| Protein | GenBank ID | GI Number | Organism |
|---|---|---|---|
| MexAM1_META1p1766 | Q9FA38.3 | 17366061 | *Methylobacterium extorquens* AM1 |
| Xaut_0032 | YP_001414948.1 | 154243990 | *Xanthobacter autotrophicus* Py2 |
| Hden_1474 | YP_003755607.1 | 300022996 | *Hyphomicrobium denitrificans* ATCC 51888 |

FIG. 2, Step L—Formaldehyde Dehydrogenase

Oxidation of formaldehyde to formate is catalyzed by formaldehyde dehydrogenase. An NAD+ dependent formaldehyde dehydrogenase enzyme is encoded by fdhA of *Pseudomonas putida* (Ito et al, *J Bacteriol* 1176: 2483-2491 (1994)). Additional formaldehyde dehydrogenase enzymes include the NAD+ and glutathione independent formaldehyde dehydrogenase from *Hyphomicrobium zavarzinii* (Jerome et al, Appl Microbiol Biotechnol 77:779-88 (2007)), the glutathione dependent formaldehyde dehydrogenase of *Pichia pastoris* (Sunga et al, Gene 330:39-47 (2004)) and the NAD(P)+ dependent formaldehyde dehydrogenase of *Methylobacter marinus* (Speer et al, FEMS Microbiol Lett, 121(3):349-55 (1994)).

| Protein | GenBank ID | GI Number | Organism |
|---|---|---|---|
| fdhA | P46154.3 | 1169603 | *Pseudomonas putida* |
| faoA | CAC85637.1 | 19912992 | *Hyphomicrobium zavarzinii* |
| Fld1 | CCA39112.1 | 328352714 | *Pichia pastoris* |
| fdh | P47734.2 | 221222447 | *Methylobacter marinus* |

In addition to the formaldehyde dehydrogenase enzymes listed above, alternate enzymes and pathways for converting formaldehyde to formate are known in the art. For example, many organisms employ glutathione-dependent formaldehyde oxidation pathways, in which formaldehyde is converted to formate in three steps via the intermediates S-hydroxymethylglutathione and S-formylglutathione (Vorholt et al, *J Bacteriol* 182:6645-50 (2000)). The enzymes of this pathway are S-(hydroxymethyl)glutathione synthase (EC 4.4.1.22), glutathione-dependent formaldehyde dehydrogenase (EC 1.1.1.284) and S-formylglutathione hydrolase (EC 3.1.2.12).

FIG. 2, Step M—Spontaneous or S-(hydroxymethybglutathione Synthase

While conversion of formaldehyde to S-hydroxymethylglutathione can occur spontaneously in the presence of glutathione, it has been shown by Goenrich et al (Goenrich, et al., J Biol Chem 277(5); 3069-72 (2002)) that an enzyme from *Paracoccus denitrificans* can accelerate this spontaneous condensation reaction. The enzyme catalyzing the conversion of formaldehyde and glutathione was purified and named glutathione-dependent formaldehyde-activating enzyme (Gfa). Putative proteins with sequence identity to Gfa from *P. denitnficans* are present also in *Rhodobacter sphaeroides, Sinorhizobium meliloti*, and *Mesorhizobium loti*.

| Protein | GenBank ID | GI Number | Organism |
|---|---|---|---|
| Gfa | Q51669.3 | 38257308 | *Paracoccus denitrificans* |
| Gfa | ABP71667.1 | 145557054 | *Rhodobacter sphaeroides* ATCC 17025 |
| Gfa | Q92WX6.1 | 38257348 | *Sinorhizobium meliloti* 1021 |
| Gfa | Q98LU4.2 | 38257349 | *Mesorhizobium loti* MAFF303099 |

FIG. 2, Step N—Glutathione-Dependent Formaldehyde Dehydrogenase

Glutathione-dependent formaldehyde dehydrogenase (GS-FDH) belongs to the family of class III alcohol dehydrogenases. Glutathione and formaldehyde combine non-enzymatically to form hydroxymethylglutathione, the true substrate of the GS-FDH catalyzed reaction. The product, S-formylglutathione, is further metabolized to formic acid.

| Protein | GenBank ID | GI Number | Organism |
|---|---|---|---|
| frmA | YP_488650.1 | 388476464 | *Escherichia coli* K-12 MG1655 |
| SFA1 | NP_010113.1 | 6320033 | *Saccharomyces cerevisiae* S288c |
| flhA | AAC44551.1 | 1002865 | *Paracoccus denitrificans* |
| adhI | AAB09774.1 | 986949 | *Rhodobacter sphaeroides* |

FIG. 2, Step O—S-formylglutathione Hydrolase

S-formylglutathione hydrolase is a glutathione thiol esterase found in bacteria, plants and animals. It catalyzes conversion of S-formylglutathione to formate and glutathione. Exemplary enzymes are below. YeiG of *E. coli* is a promiscuous serine hydrolase; its highest specific activity is with the substrate S-formylglutathione.

| Protein | GenBank ID | GI Number | Organism |
|---|---|---|---|
| frmB | NP_414889.1 | 16128340 | *Escherichia coli* K-12 MG1655 |
| yeiG | AAC75215.1 | 1788477 | *Escherichia coli* K-12 MG1655 |
| fghA | AAC44554.1 | 1002868 | *Paracoccus denitrificans* |

FIG. 2, Step P—Carbon Monoxide Dehydrogenase (CODH)

CODH is a reversible enzyme that interconverts CO and $CO_2$ at the expense or gain of electrons. The natural physiological role of the CODH in ACS/CODH complexes is to convert $CO_2$ to CO for incorporation into acetyl-CoA by acetyl-CoA synthase. Nevertheless, such CODH enzymes are suitable for the extraction of reducing equivalents from CO due to the reversible nature of such enzymes. Expressing such CODH enzymes in the absence of ACS allows them to operate in the direction opposite to their natural physiological role (i.e., CO oxidation).

In *M. thermoacetica, C. hydrogenoformans, C. carboxidivorans* P7, and several other organisms, additional CODH encoding genes are located outside of the ACS/CODH operons. These enzymes provide a means for extracting electrons (or reducing equivalents) from the conversion of carbon monoxide to carbon dioxide. The *M. thermoacetica* gene (Genbank Accession Number: YP_430813) is expressed by itself in an operon and is believed to transfer electrons from CO to an external mediator like ferredoxin in a "Ping-pong" reaction. The reduced mediator then couples to other reduced nicolinamide adenine dinucleotide phosphate (NAD(P)H) carriers or ferredoxin-dependent cellular processes (Ragsdale, *Annals of the New York Academy of Sciences* 1125: 129-136 (2008)). Similar ACS-free CODH enzymes can be found in a diverse array of organisms.

| Protein | GenBank ID | GI Number | Organism |
|---|---|---|---|
| CODH (putative) | YP_430813 | 83590804 | *Moorella thermoacetica* |
| CODH-II (CooS-II) | YP_358957 | 78044574 | *Carboxydothermus hydrogenoformans* |
| CooF | YP_358958 | 78045112 | *Carboxydothermus hydrogenoformans* |
| CODH (putative) | ZP_05390164.1 | 255523193 | *Clostridium carboxidivorans* P7 |
| CcarbDRAFT_0341 | ZP_05390341.1 | 255523371 | *Clostridium carboxidivorans* P7 |
| CcarbDRAFT_1756 | ZP_05391756.1 | 255524806 | *Clostridium carboxidivorans* P7 |
| CcarbDRAFT_2944 | ZP_05392944.1 | 255526020 | *Clostridium carboxidivorans* P7 |
| CODH | YP_384856.1 | 78223109 | *Geobacter metallireducens* GS-15 |
| Cpha266_0148 (cytochrome c) | YP_910642.1 | 119355998 | *Chlorobium phaeobacteroides* DSM 266 |
| Cpha266_0149 (CODH) | YP_910643.1 | 119355999 | *Chlorobium phaeobacteroides* DSM 266 |
| Ccel_0438 | YP_002504800.1 | 220927891 | *Clostridium cellulolyticum* H10 |
| Ddes_0382 (CODH) | YP_002478973.1 | 220903661 | *Desulfovibrio desulfuricans* subsp. *desulfuricans* str. ATCC 27774 |
| Ddes_0381 (CooC) | YP_002478972.1 | 220903660 | *Desulfovibrio desulfuricans* subsp. *desulfuricans* str. ATCC 27774 |
| Pcar_0057 (CODH) | YP_355490.1 | 7791767 | *Pelobacter carbinolicus* DSM 2380 |
| Pcar_0058 (CooC) | YP_355491.1 | 7791766 | *Pelobacter carbinolicus* DSM 2380 |
| Pcar_0058 (HypA) | YP_355492.1 | 7791765 | *Pelobacter carbinolicus* DSM 2380 |
| CooS (CODH) | YP_001407343.1 | 154175407 | *Campylobacter curvus* 525.92 |
| CLJU_c09110 | ADK13979.1 | 300434212 | *Clostridium ljungdahli* |
| CLJU_c09100 | ADK13978.1 | 300434211 | *Clostridium ljungdahli* |
| CLJU_c09090 | ADK13977.1 | 300434210 | *Clostridium ljungdahli* |

Example III

Methods for Formaldehyde Fixation

Provided herein are exemplary pathways, which utilize formaldehyde produced from the oxidation of methanol (see, e.g., FIG. 1, step A, or FIG. 2, step J) or from formate assimilation pathways described in Example I (see, e.g., FIG. 1) in the formation of intermediates of certain central metabolic pathways that can be used for the production of compounds disclosed herein.

One exemplary pathway that can utilize formaldehyde produced from the oxidation of methanol is shown in FIG. 1, which involves condensation of formaldehyde and D-ribulose-5-phosphate to form hexulose-6-phosphate (h6p) by hexulose-6-phosphate synthase (FIG. 1, step B). The enzyme can use $Mg^{2+}$ or $Mn^{2+}$ for maximal activity, although other metal ions are useful, and even non-metal-ion-dependent mechanisms are contemplated. H6p is converted into fructose-6-phosphate by 6-phospho-3-hexuloisomerase (FIG. 1, step C).

Another exemplary pathway that involves the detoxification and assimilation of formaldehyde produced from the oxidation of methanol is shown in FIG. 1 and proceeds through dihydroxyacetone. Dihydroxyacetone synthase is a special transketolase that first transfers a glycoaldehyde group from xylulose-5-phosphate to formaldehyde, resulting in the formation of dihydroxyacetone (DHA) and glyceraldehyde-3-phosphate (G3P), which is an intermediate in glycolysis (FIG. 1). The DHA obtained from DHA synthase can be further phosphorylated to form DHA phosphate and assimilated into glycolysis and several other pathways (FIG. 1). Alternatively, or in addition, a fructose-6-phosphate aldolase can be used to catalyze the conversion of DHA and G3P to fructose-6-phosphate (FIG. 1, step Z).

FIG. 1, Steps B and C—Hexulose-6-phosphate Synthase (Step B) and 6-phospho-3-hexuloisomerase (Step C)

Both of the hexulose-6-phosphate synthase and 6-phospho-3-hexuloisomerase enzymes are found in several organisms, including methanotrophs and methylotrophs where they have been. In addition, these enzymes have been reported in heterotrophs such as *Bacillus subtilis* also where they are reported to be involved in formaldehyde detoxification. Genes for these two enzymes from the methylotrophic bacterium *Alycobacterium gastri* MB19 have been fused and *E. coli* strains harboring the hps-phi construct showed more efficient utilization of formaldehyde (Orita et al., 2007, Appl Microbiol Biotechnol. 76:439-445). In some organisms, these two enzymes naturally exist as a fused version that is bifunctional.

Exemplary candidate genes for hexulose-6-phosphate synthase are:

| Protein | GenBank ID | GI number | Organism |
| --- | --- | --- | --- |
| Hps | AAR39392.1 | 40074227 | *Bacillus methanolicus* MGA3 |
| Hps | EIJ81375.1 | 387589055 | *Bacillus methanolicus* PB1 |
| RmpA | BAA83096.1 | 5706381 | *Methylomonas aminofaciens* |
| RmpA | BAA90546.1 | 6899861 | *Mycobacterium gastri* |
| YckG | BAA08980.1 | 1805418 | *Bacillus subtilis* |
| Hps | YP_544362.1 | 91774606 | *Methylobacillus flagellatus* |
| Hps | YP_545763.1 | 91776007 | *Methylobacillus flagellatus* |
| Hps | AAG29505.1 | 11093955 | *Aminomonas aminovorus* |
| SgbH | YP_004038706.1 | 313200048 | *Methylovorus* sp. MP688 |
| Hps | YP_003050044.1 | 253997981 | *Methylovorus glucosetrophus* SIP3-4 |
| Hps | YP_003990382.1 | 312112066 | *Geobacillus* sp. Y4.1MC1 |
| Hps | gb|AAR91478.1 | 40795504 | *Geobacillus* sp. M10EXG |
| Hps | YP_007402409.1 | 448238351 | *Geobacillus* sp. GHH01 |

Exemplary gene candidates for 6-phospho-3-hexuloisomerase are:

| Protein | GenBank ID | GI number | Organism |
| --- | --- | --- | --- |
| Phi | AAR39393.1 | 40074228 | *Bacillus methanolicus* MGA3 |
| Phi | EIJ81376.1 | 387589056 | *Bacillus methanolicus* PB1 |
| Phi | BAA83098.1 | 5706383 | *Methylomonas aminofaciens* |
| RmpB | BAA90545.1 | 6899860 | *Mycobacterium gastri* |
| Phi | YP_545762.1 | 91776006 | *Methylobacillus flagellatus* KT |
| Phi | YP_003051269.1 | 253999206 | *Methylovorus glucosetrophus* SIP3-4 |
| Phi | YP_003990383.1 | 312112067 | *Geobacillus* sp. Y4.1MC1 |
| Phi | YP_007402408.1 | 448238350 | *Geobacillus* sp. GHH01 |

Candidates for enzymes where both of these functions have been fused into a single open reading frame include the following.

| Protein | GenBank ID | GI number | Organism |
| --- | --- | --- | --- |
| PH1938 | NP_143767.1 | 14591680 | *Pyrococcus horikoshii* OT3 |
| PF0220 | NP_577949.1 | 18976592 | *Pyrococcus furiosus* |
| TK0475 | YP_182888.1 | 57640410 | *Thermococcus kodakaraensis* |
| PAB1222 | NP_127388.1 | 14521911 | *Pyrococcus abyssi* |
| MCA2738 | YP_115138.1 | 53803128 | *Methylococcus capsulatas* |
| Metal_3152 | EIC30826.1 | 380884949 | *Methylomicrobium album* BG8 |

FIG. 1, Step D—Dihydroxyacetone Synthase

The dihydroxyacetone synthase enzyme in *Candida boidinii* uses thiamine pyrophosphate and $Mg^{2+}$ as cofactors and is localized in the peroxisome. The enzyme from the methanol-growing carboxydobacterium, *Mycobacter* sp. strain JC1 DSM 3803, was also found to have DHA synthase and kinase activities. Several other mycobacteria, excluding only *Mycobacterium tuberculosis*, can use methanol as the sole source of carbon and energy and are reported to use dihydroxyacetone synthase.

| Protein | GenBank ID | GI number | Organism |
| --- | --- | --- | --- |
| DAS1 | AAC83349.1 | 3978466 | *Candida boidinii* |
| HPODL_2613 | EFW95760.1 | 320581540 | *Ogataea parapolymorpha* DL-1 (*Hansenula polymorpha* DL-1) |
| | AAG12171.2 | 18497328 | *Mycobacter* sp. strain JC1 DSM 3803 |

FIG. 1, Step Z—Fructose-6-phosphate Aldolase

Fructose-6-phosphate aldolase (F6P aldolase) can catalyze the combination of dihydroxyacetone (DHA) and glyceraldehyde-3-phosphate (G3P) to form fructose-6-phosphate. This activity was recently discovered in *E. coli* and the corresponding gene candidate has been termed fsa. The enzyme prefers the aldol formation over the cleavage reaction.

The selectivity of the *E. coli* enzyme towards DHA can be improved by introducing point mutations. For example, the mutation A129S improved reactivity towards DHA by over 17 fold in terms of $K_{cat}/K_m$ (Gutierrez et al., Chem Commun (Camb), 2011, 47(20), 5762-5764). Genes similar to fsa have been found in other genomes by sequence homology. Some exemplary gene candidates have been listed below.

| Gene | Protein accession no. | GI number | Organism |
| --- | --- | --- | --- |
| fsa | AAC73912.2 | 87081788 | *Escherichia coli* K12 |
| talC | AAC76928.1 | 1790382 | *Escherichia coli* K12 |
| fsa | WP_017209835.1 | 515777235 | *Clostridium beijerinckii* |
| DR_1337 | AAF10909.1 | 6459090 | *Deinococcus radiodurans* R1 |

-continued

| Gene | Protein accession no. | GI number | Organism |
|---|---|---|---|
| talC | NP_213080.1 | 15605703 | *Aquifex aeolicus* VF5 |
| MJ_0960 | NP_247955.1 | 15669150 | *Methanocaldococcus janaschii* |
| mipB | NP_993370.2 | 161511381 | *Yersinia pestis* |

As described below, there is an energetic advantage to using F6P aldolase in the DHA pathway.

The assimilation of formaldehyde formed by the oxidation of methanol can proceed either via the dihydroxyacetone (DHA) pathway (step D, FIG. 1) or the Ribulose monophosphate (RuMP) pathway (steps B and C, FIG. 1). In the RuMP pathway, formaldehyde combines with ribulose-5-phosphate to form F6P. F6P is then either metabolized via glycolysis or used for regeneration of ribulose-5-phosphate to enable further formaldehyde assimilation. Notably, ATP hydrolysis is not required to form F6P from formaldehyde and ribulose-5-phosphate via the RuMP pathway.

In contrast, in the DHA pathway, formaldehyde combines with xylulose-5-phosphate (X5P) to form dihydroxyacetone (DHA) and glyceraldehyde-3-phosphate (G3P). Some of the DHA and G3P must be metabolized to F6P to enable regeneration of xylulose-5-phosphate. In the standard DHA pathway, DHA and G3P are converted to F6P by three enzymes: DHA kinase, fructose bisphosphate aldolase, and fructose bisphosphatase. The net conversion of DHA and G3P to F6P requires ATP hydrolysis as described below. First, DHA is phosphorylated to form DHA phosphate (DHAP) by DHA kinase at the expense of an ATP. DHAP and G3P are then combined by fructose bisphosphate aldolase to form fructose-1,6-diphosphate (FDP). FDP is converted to F6P by fructose bisphosphatase, thus wasting a high energy phosphate bond.

A more ATP efficient sequence of reactions is enabled if DHA synthase functions in combination with F6P aldolase as opposed to in combination with DHA kinase, fructose bisphosphate aldolase, and fructose bisphosphatase. F6P aldolase enables direct conversion of DHA and G3P to F6P, bypassing the need for ATP hydrolysis. Overall, DHA synthase when combined with F6P aldolase is identical in energy demand to the RuMP pathway. Both of these formaldehyde assimilation options (i.e., RuMP pathway, DHA synthase+F6P aldolase) are superior to DHA synthase combined with DHA kinase, fructose bisphosphate aldolase, and fructose bisphosphatase in terms of ATP demand.

Example IV

In Vivo Labeling Assay for Conversion of Methanol to $CO_2$

This example describes a functional methanol pathway in a microbial organism.

Strains with functional reductive TCA branch and pyruvate formate lyase deletion were grown aerobically in LB medium overnight, followed by inoculation of M9 high-seed media containing IPTG and aerobic growth for 4 hrs. These strains had methanol dehydrogenase/ACT pairs in the presence and absence of formaldehyde dehydrogenase or formate dehydrogenase. ACT is an activator protein (a Nudix hydrolase). At this time, strains were pelleted, resuspended in fresh M9 medium high-seed media containing 2% $^{13}CH_3OH$, and sealed in anaerobic vials. Head space was replaced with nitrogen and strains grown for 40 hours at 37° C. Following growth, headspace was analyzed for $^{13}CO_2$. Media was examined for residual methanol as well as 1,4-butanediol and byproducts. All constructs expressing methanol dehydrogenase (MeDH) mutants and MeDH/ACT pairs grew to slightly lower ODs than strains containing empty vector controls. This is likely due to the high expression of these constructs (Data not shown). One construct (2315/2317) displayed significant accumulation of labeled $CO_2$ relative to controls in the presence of FalDH, FDH or no coexpressed protein. This shows a functional MeOH pathway in *E. coli* and that the endogenous glutathione-dependent formaldehyde detoxification genes (frmAB) are sufficient to carry flux generated by the current MeDH/ACT constructs.

2315 is internal laboratory designation for the MeDH from *Bacillus methanolicus* MGA3 (GenBank Accession number: E1177596.1; GI number: 387585261), and 2317 is internal laboratory designation for the activator protein from the same organism (locus tag: MGA3_09170; GenBank Accession number: EIJ83380; GI number: 387591061).

Sequence analysis of the NADH-dependent MeDH from *Bacillus methanolicus* places the enzyme in the alcohol dehydrogenase family III. It does not contain any tryptophan residues, resulting in a low extinction coefficient (18,500 $M^{-1}$, $cm^{-1}$) and should be detected on SDS gels by Coomassie staining.

The enzyme has been characterized as a multisubunit complex built from 43 kDa subunits containing one Zn and 1-2 Mg atoms per subunit. Electron microscopy and sedimentation studies determined it to be a decamer, in which two rings with five-fold symmetry are stacked on top of each other (Vonck et al., *J. Biol. Chem.* 266:3949-3954, 1991). It is described to contain a tightly but not covalently bound cofactor and requires exogenous $NAD^+$ as e-acceptor to measure activity in vitro. A strong increase (10-40-fold) of in vitro activity was observed in the presence of an activator protein (ACT), which is a homodimer (21 kDa subunits) and contains one Zn and one Mg atom per subunit.

The mechanism of the activation was investigated by Kloosterman et al., *J. Biol. Chem.* 277:34785-34792, 2002, showing that ACT is a Nudix hydrolase and Hektor et al., *J. Biol. Chem.* 277:46966-46973, 2002, demonstrating that mutation of residue S97 to G or T in MeDH changes activation characteristics along with the affinity for the cofactor. While mutation of residues G15 and D88 had no significant impact, a role of residue G13 for stability as well as of residues G95, D100, and K103 for the activity is suggested. Both papers together propose a hypothesis in which ACT cleaves MeDH-bound $NAD^+$. MeDH retains AMP bound and enters an activated cycle with increased turnover.

The stoichiometric ratio between ACT and MeDH is not well defined in the literature. Kloosterman et al., supra determine the ratio of dimeric Act to decameric MeDH for full in vitro activation to be 10:1. In contrast, Arfman et al. *J. Biol. Chem.* 266:3955-3960, 1991 determined a ratio of 3:1 in vitro for maximum and a 1:6 ratio for significant activation, but observe a high sensitivity to dilution. Based on expression of both proteins in *Bacillus*, the authors estimate the ratio in vivo to be around 1:17.5.

However, our in vitro experiments with purified activator protein (2317A) and methanol dehydrogenase (2315A) showed the ratio of ACT to MeDH to be 10:1. This in vitro test was done with 5 M methanol, 2 mM NAD and 10 μM methanol dehydrogenase 2315A at pH 7.4.

Example V

Phosphoketolase-Dependent Acetyl-CoA Synthesis Enzymes

This Example provides genes that can be used for enhancing carbon flux through acetyl-CoA using phosphoketolase enzymes.

FIG. 1, Step T—Fructose-6-phosphate Phosphoketolase

Conversion of fructose-6-phosphate and phosphate to acetyl-phosphate and erythrose-5-phosphate can be carried out by fructose-6-phosphate phosphoketolase (EC 4.1.2.22). Conversion of fructose-6-phosphate and phosphate to acetyl-phosphate and erythrose-5-phosphate is one of the key reactions in the Bifidobacterium shunt. There is evidence for the existence of two distinct phosphoketolase enzymes in bifidobacteria (Sgorbati et al, 1976, Antonie Van Leeuwenhoek, 42(1-2) 49-57; Grill et al, 1995, Curr Microbiol, 31(1); 49-54). The enzyme from Bifidobacterium dentium appeared to be specific solely for fructose-6-phosphate (EC: 4.1.2.22) while the enzyme from Bifidobacterium pseudolongum subsp. globosum is able to utilize both fructose-6-phosphate and D-xylulose 5-phosphate (EC: 4.1.2.9) (Sgorbati et al, 1976, Antonie Van Leeuwenhoek, 42(1-2) 49-57). The enzyme encoded by the xfp gene, originally discovered in Bifidobacterium animalis lactis, is the dual-specificity enzyme (Meile et al., 2001, J Bacteriol, 183, 2929-2936; Yin et al, 2005, FEMS Microbiol Left, 246(2); 251-257). Additional phosphoketolase enzymes can be found in Leuconostoc mesenteroides (Lee et al, Biotechnol Left. 2005 June; 27(12):853-8), Clostridium acetobutylicum ATCC 824 (Servinsky et al, Journal of Industrial Microbiology & Biotechnology, 2012, 39, 1859-1867), Aspergillus nidulans (Kocharin et al, 2013, Biotechnol Bioeng, 110(8), 2216-2224; Papini, 2012, Appl Microbiol Biotechnol, 95 (4), 1001-1010), Bifidobacterium breve (Suziki et al, 2010, Acta Crystallogr Sect F Struct Biol Cryst Commun., 66(Pt 8):941-3), Lactobacillus paraplantarum (Jeong et al, 2007, J Microbiol Biotechnol, 17(5), 822-9).

| Protein | GENBANK ID | GI NUMBER | Organism |
|---|---|---|---|
| xfp | YP_006280131.1 | 386867137 | Bifidobacterium animalis lactis |
| xfp | AAV66077.1 | 55818565 | Leuconostoc mesenteroides |
| CAC1343 | NP_347971.1 | 15894622 | Clostridium acetobutylicum ATCC 824 |
| xpkA | CBF76492.1 | 259482219 | Aspergillus nidulans |
| xfp | WP_003840380.1 | 489937073 | Bifidobacterium dentium ATCC 27678 |
| xfp | AAR98788.1 | 41056827 | Bifidobacterium pseudolongum subsp. globosum |
| xfp | WP_022857642.1 | 551237197 | Bifidobacterium pseudolongum subsp. globosum |
| xfp | ADF97524.1 | 295314695 | Bifidobacterium breve |
| xfp | AAQ64626.1 | 34333987 | Lactobacillus paraplantarum |

FIG. 1, Step U—Xylulose-5-phosphate Phosphoketolase

Conversion of xylulose-5-phosphate and phosphate to acetyl-phosphate and glyceraldehyde-3-phosphate can be carried out by xylulose-5-phosphate phosphoketolase (EC 4.1.2.9). There is evidence for the existence of two distinct phosphoketolase enzymes in bifidobacteria (Sgorbati et al, 1976, Antonie Van Leeuwenhoek, 42(1-2) 49-57; Grill et al, 1995, Curr Microbiol, 31(1);49-54). The enzyme from Bifidobacterium dentium appeared to be specific solely for fructose-6-phosphate (EC: 4.1.2.22) while the enzyme from Bifidobacterium pseudolongum subsp. globosum is able to utilize both fructose-6-phosphate and D-xylulose 5-phosphate (EC: 4.1.2.9) (Sgorbati et al, 1976, Antonie Van Leeuwenhoek, 42(1-2) 49-57). Many characterized enzymes have dual-specificity for xylulose-5-phosphate and fructose-6-phosphate. The enzyme encoded by the xfp gene, originally discovered in Bifidobacterium animalis lactis, is the dual-specificity enzyme (Meile et al., 2001, J Bacteriol, 183, 2929-2936; Yin et al, 2005, FEMS Microbiol Left, 246(2); 251-257). Additional phosphoketolase enzymes can be found in Leuconostoc mesenteroides (Lee et al, Biotechnol Left. 2005 June; 27(12):853-8), Clostridium acetobutylicum ATCC 824 (Servinsky et al, Journal of Industrial Microbiology & Biotechnology, 2012, 39, 1859-1867), Aspergillus nidulans (Kocharin et al, 2013, Biotechnol Bioeng, 110(8), 2216-2224; Papini, 2012, Appl Microbiol Biotechnol, 95 (4), 1001-1010), Bifidobacterium breve (Suziki et al, 2010, Acta Crystallogr Sect F Struct Biol Cryst Commun., 66(Pt 8):941-3), and Lactobacillus paraplantarum (Jeong et al, 2007, J Microbiol Biotechnol, 17(5), 822-9).

| Protein | GENBANK ID | GI NUMBER | Organism |
|---|---|---|---|
| xfp | YP_006280131.1 | 386867137 | Bifidobacterium animalis lactis |
| xfp | AAV66077.1 | 55818565 | Leuconostoc mesenteroides |
| CAC1343 | NP_347971.1 | 15894622 | Clostridium acetobutylicum ATCC 824 |
| xpkA | CBF76492.1 | 259482219 | Aspergillus nidulans |
| xfp | AAR98788.1 | 41056827 | Bifidobacterium pseudolongum subsp. globosum |
| xfp | WP_022857642.1 | 551237197 | Bifidobacterium pseudolongum subsp. globosum |
| xfp | ADF97524.1 | 295314695 | Bifidobacterium breve |
| xfp | AAQ64626.1 | 34333987 | Lactobacillus paraplantarum |

FIG. 1, Step V—Phosphotransacetylase

The formation of acetyl-CoA from acetyl-phosphate can be catalyzed by phosphotransacetylase (EC 2.3.1.8). The pta gene from E. coli encodes an enzyme that reversibly converts acetyl-CoA into acetyl-phosphate (Suzuki, T., Biochim. Biophys. Acta 191:559-569 (969)). Additional acetyltransferase enzymes have been characterized in Bacillus subtilis (Rado and Hoch, Biochim. Biophys. Acta 321:114-125 (1973), Clostridium kluyveri (Stadtman, E., Methods Enzymol. 1:5896-599 (1955), and Thermotoga maritima (Bock et al., J. Bacteriol. 181:1861-1867 (1999)). This reaction can also be catalyzed by some phosphotransbutyrylase enzymes (EC 2.3.1.19), including the ptb gene products from Clostridium acetobutylicum (Wiesenborn et al., App. Environ. Microbiol. 55:317-322 (1989); Walter et al., Gene 134:107-111 (1993)). Additional ptb genes are found in butyrate-producing bacterium L2-50 (Louis et al., J. Bacteriol. 186:2099-2106 (2004) and Bacillus megaterium (Vazquez et al., Curr. Microbiol. 42:345-349 (2001). Homologs to the E. coli pta gene exist in several other organisms including Salmonella enterica and Chlamydomonas reinhardtii.

| Protein | GenBank ID | GI Number | Organism |
| --- | --- | --- | --- |
| Pta | NP_416800.1 | 71152910 | Escherichia coli |
| Pta | P39646 | 730415 | Bacillus subtilis |
| Pta | A5N801 | 146346896 | Clostridium kluyveri |
| Pta | Q9X0L4 | 6685776 | Thermotoga maritime |
| Ptb | NP_349676 | 34540484 | Clostridium acetobutylicum |
| Ptb | AAR19757.1 | 38425288 | butyrate-producing bacterium L2-50 |
| Ptb | CAC07932.1 | 10046659 | Bacillus megaterium |
| Pta | NP_461280.1 | 16765665 | Salmonella enterica subsp. enterica serovar Typhimurium str. LT2 |
| PAT2 | XP_001694504.1 | 159472743 | Chlamydomonas reinhardtii |
| PAT1 | XP_001691787.1 | 159467202 | Chlamydomonas reinhardtii |

FIG. 1, Step W—Acetate Kinase

Acetate kinase (EC 2.7.2.1) can catalyze the reversible ATP-dependent phosphorylation of acetate to acetylphosphate. Exemplary acetate kinase enzymes have been characterized in many organisms including *E. coli, Clostridium acetobutylicum* and *Methanosarcina thermophila* (Ingram-Smith et al., *J. Bacteriol.* 187:2386-2394 (2005); Fox and Roseman, *J. Biol. Chem.* 261:13487-13497 (1986); Winzer et al., *Microbioloy* 143 (Pt 10):3279-3286 (1997)). Acetate kinase activity has also been demonstrated in the gene product of *E. coli* purT (Marolewski et al., *Biochemistry* 33:2531-2537 (1994). Some butyrate kinase enzymes (EC 2.7.2.7), for example buk1 and buk2 from *Clostridium acetobutylicum*, also accept acetate as a substrate (Hartmanis, M. G., *J. Biol. Chem.* 262:617-621 (1987)). Homologs exist in several other organisms including *Salmonella enterica* and *Chlamydomonas reinhardtii*.

| Protein | GenBank ID | GI Number | Organism |
| --- | --- | --- | --- |
| ackA | NP_416799.1 | 16130231 | Escherichia coli |
| Ack | AAB18301.1 | 1491790 | Clostridium acetobutylicum |
| Ack | AAA72042.1 | 349834 | Methanosarcina thermophila |
| purT | AAC74919.1 | 1788155 | Escherichia coli |
| buk1 | NP_349675 | 15896326 | Clostridium acetobutylicum |
| buk2 | Q97II1 | 20137415 | Clostridium acetobutylicum |
| ackA | NP_461279.1 | 16765664 | Salmonella typhimurium |
| ACK1 | XP_001694505.1 | 159472745 | Chlamydomonas reinhardtii |
| ACK2 | XP_001691682.1 | 159466992 | Chlamydomonas reinhardtii |

FIG. 1, Step X—Acetyl-CoA Transferase, Synthetase, or Ligase

The acylation of acetate to acetyl-CoA can be catalyzed by enzymes with acetyl-CoA synthetase, ligase or transferase activity. Two enzymes that can catalyze this reaction are AMP-forming acetyl-CoA synthetase or ligase (EC 6.2.1.1) and ADP-forming acetyl-CoA synthetase (EC 6.2.1.13). AMP-forming acetyl-CoA synthetase (ACS) is the predominant enzyme for activation of acetate to acetyl-CoA. ADP-forming acetyl-CoA synthetases are reversible enzymes with a generally broad substrate range (Musfeldt and Schonheit, *J. Bacteriol.* 184:636-644 (2002)). The aforementioned proteins are shown below.

| Protein | GenBank ID | GI Number | Organism |
| --- | --- | --- | --- |
| Acs | AAC77039.1 | 1790505 | Escherichia coli |
| acoE | AAA21945.1 | 141890 | Ralstonia eutropha |
| acs1 | ABC87079.1 | 86169671 | Methanothermobacter thermautotrophicus |
| acs1 | AAL23099.1 | 16422835 | Salmonella enterica |
| ACS1 | Q01574.2 | 257050994 | Saccharomyces cerevisiae |
| AF1211 | NP_070039.1 | 11498810 | Archaeoglobus fulgidus |
| AF1983 | NP_070807.1 | 11499565 | Archaeoglobus fulgidus |
| Scs | YP_135572.1 | 55377722 | Haloarcula marismortui |
| PAE3250 | NP_560604.1 | 18313937 | Pyrobaculum aerophilum str. IM2 |
| sucC | NP_415256.1 | 16128703 | Escherichia coli |
| sucD | AAC73823.1 | 1786949 | Escherichia coli |
| paaF | AAC24333.2 | 22711873 | Pseudomonas putida |

An acetyl-CoA transferase that can utilize acetate as the CoA acceptor is acetoacetyl-CoA transferase, encoded by the *E. coli* atoA (alpha subunit) and atoD (beta subunit) genes. This and other proteins are identified below.

| Protein | GenBank ID | GI Number | Organism |
| --- | --- | --- | --- |
| atoA | P76459.1 | 2492994 | Escherichia coli K12 |
| atoD | P76458.1 | 2492990 | Escherichia coli K12 |
| actA | YP_226809.1 | 62391407 | Corynebacterium glutamicum ATCC 13032 |
| cg0592 | YP_224801.1 | 62389399 | Corynebacterium glutamicum ATCC 13032 |
| ctfA | NP_149326.1 | 15004866 | Clostridium acetobutylicum |
| ctfB | NP_149327.1 | 15004867 | Clostridium acetobutylicum |
| ctfA | AAP42564.1 | 31075384 | Clostridium saccharoperbutylacetonicum |
| ctfB | AAP42565.1 | 31075385 | Clostridium saccharoperbutylacetonicum |

Additional exemplary acetyl-CoA transferase candidates are catalyzed by the gene products of cat1, cat2, and cat3 of *Clostridium kluyveri* which have been shown to exhibit succinyl-CoA, 4-hydroxybutyryl-CoA, and butyryl-CoA transferase activity, respectively. Similar CoA transferase activities are also present in *Trichomonas vaginalis* (van Grinsven et al., *J. Biol. Chem.* 283:1411-1418 (2008)) and *Trypanosoma brucei* (Riviere et al., *J. Biol. Chem.* 279: 45337-45346 (2004)). These and other proteins are identified below.

| Protein | GenBank ID | GI Number | Organism |
| --- | --- | --- | --- |
| cat1 | P38946.1 | 729048 | Clostridium kluyveri |
| cat2 | P38942.2 | 172046066 | Clostridium kluyveri |
| cat3 | EDK35586.1 | 146349050 | Clostridium kluyveri |
| TVAG 395550 | XP_001330176 | 123975034 | Trichomonas vaginalis G3 |
| Tb11.02.0290 | XP_828352 | 71754875 | Trypanosoma brucei |

Example VI

Acetyl-CoA and Succinyl-CoA Synthesis Enzymes

This Example provides genes that can be used for conversion of glycolysis intermediate glyceraldehyde-3-phosphate (G3P) to acetyl-CoA and/or succinyl-CoA as depicted in the pathways of FIG. 4.

A. PEP Carboxylase or PEP Carboxykinase. Carboxylation of phosphoenolpyruvate to oxaloacetate is catalyzed by phosphoenolpyruvate carboxylase. Exemplary PEP carboxylase enzymes are below.

| Protein | GenBank ID | GI Number | Organism |
|---|---|---|---|
| Ppc | NP_418391 | 16131794 | Escherichia coli |
| ppcA | AAB58883 | 28572162 | Methylobacterium extorquens |
| Ppc | ABB53270 | 80973080 | Corynebacterium glutamicum |

An alternative enzyme for converting phosphoenolpyruvate to oxaloacetate is PEP carboxykinase, which simultaneously forms an ATP while carboxylating PEP. In most organisms PEP carboxykinase serves a gluconeogenic function and converts oxaloacetate to PEP at the expense of one ATP. S. cerevisiae is one such organism whose native PEP carboxykinase, PCK1, serves a gluconeogenic role (Valdes-Hevia et al., FEBS Lett. 258:313-316 (1989). E. coli is another such organism, as the role of PEP carboxykinase in producing oxaloacetate is believed to be minor when compared to PEP carboxylase, which does not form ATP, possibly due to the higher $K_m$ for bicarbonate of PEP carboxykinase (Kim et al., Appl. Environ. Microbiol. 70:1238-1241 (2004)). Nevertheless, activity of the native E. coli PEP carboxykinase from PEP towards oxaloacetate has been recently demonstrated in ppc mutants of E. coli K-12 (Kwon et al., J. Microbiol. Biotechnol. 16:1448-1452 (2006)). These strains exhibited no growth defects and had increased succinate production at high NaHCO3 concentrations. Mutant strains of E. coli can adopt Pck as the dominant CO2-fixing enzyme following adaptive evolution (Zhang et al. 2009). In some organisms, particularly rumen bacteria, PEP carboxykinase is quite efficient in producing oxaloacetate from PEP and generating ATP. Examples of PEP carboxykinase genes are shown below.

| Protein | GenBank ID | GI Number | Organism |
|---|---|---|---|
| PCK1 | NP_013023 | 6322950 | Saccharomyces cerevisiae |
| pck | NP_417862.1 | 16131280 | Escherichia coli |
| pckA | YP_089485.1 | 52426348 | Mannheimia succiniciproducens |
| pckA | O09460.1 | 3122621 | Anaerobiospirillum succiniciproducens |
| pckA | Q6W6X5 | 75440571 | Actinobacillus succinogenes |
| pckA | P43923.1 | 1172573 | Haemophilus influenza |

B. Malate Dehydrogenase. Oxaloacetate is converted into malate by malate dehydrogenase (EC 1.1.1.37), an enzyme which functions in both the forward and reverse direction. Exemplary enzymes are show below.

| Protein | GenBank ID | GI Number | Organism |
|---|---|---|---|
| MDH1 | NP_012838 | 6322765 | Saccharomyces cerevisiae |
| MDH2 | NP_014515 | 116006499 | Saccharomyces cerevisiae |
| MDH3 | NP_010205 | 6320125 | Saccharomyces cerevisiae |
| Mdh | NP_417703.1 | 16131126 | Escherichia coli |

C. Fumarase. Fumarate hydratase (EC 4.2.1.2) catalyzes the reversible hydration of fumarate to malate. The three fumarases of E. coli, encoded by fumA, fumB and fumC, are regulated under different conditions of oxygen availability. FumB is oxygen sensitive and is active under anaerobic conditions. FumA is active under microanaerobic conditions, and FumC is active under aerobic growth conditions (Tseng et al., J. Bacteriol. 183:461-467 (2001); Woods et al., Biochim. Biophys. Acta 954:14-26 (1988); Guest et al., J. Gen. Microbiol. 131:2971-2984 (1985)). Additional fumarase enzymes are shown below.

| Protein | GenBank ID | GI Number | Organism |
|---|---|---|---|
| fumA | NP_416129.1 | 16129570 | Escherichia coli |
| fumB | NP_418546.1 | 16131948 | Escherichia coli |
| fumC | NP_416128.1 | 16129569 | Escherichia coli |
| FUM1 | NP_015061 | 6324993 | Saccharomyces cerevisiae |
| fumC | Q8NRN8.1 | 39931596 | Corynebacterium glutamicum |
| fumC | O69294.1 | 9789756 | Campylobacter jejuni |
| fumC | P84127 | 75427690 | Thermus thermophilus |
| fumH | P14408.1 | 120605 | Rattus norvegicus |
| MmcB | YP_001211906 | 147677691 | Pelotomaculum thermopropionicum |
| MmcC | YP_001211907 | 147677692 | Pelotomaculum thermopropionicum |

D. Fumarate Reductase. Fumarate reductase catalyzes the reduction of fumarate to succinate. The fumarate reductase of E. coli, composed of four subunits encoded by frdABCD, is membrane-bound and active under anaerobic conditions. The electron donor for this reaction is menaquinone and the two protons produced in this reaction do not contribute to the proton gradient (Iverson et al., Science 284:1961-1966 (1999)). The yeast genome encodes two soluble fumarate reductase isozymes encoded by FRDS1 and FRDS2.

| Protein | GenBank ID | GI Number | Organism |
|---|---|---|---|
| FRDS1 | P32614 | 418423 | Saccharomyces cerevisiae |
| FRDS2 | NP_012585 | 6322511 | Saccharomyces cerevisiae |
| frdA | NP_418578.1 | 16131979 | Escherichia coli |
| frdB | NP_418577.1 | 16131978 | Escherichia coli |
| frdC | NP_418576.1 | 16131977 | Escherichia coli |
| frdD | NP_418475.1 | 16131877 | Escherichia coli |

E. Succinyl-CoA Synthetase or Transferase. The ATP-dependent acylation of succinate to succinyl-CoA is catalyzed by succinyl-CoA synthetase (EC 6.2.1.5). The product of the LSC1 and LSC2 genes of S. cerevisiae and the sucC and sucD genes of E. coli naturally form a succinyl-CoA synthetase complex that catalyzes the formation of succinyl-CoA from succinate with the concomitant consumption of one ATP, a reaction which is reversible in vivo. These proteins are identified below:

| Protein | GenBank ID | GI Number | Organism |
|---|---|---|---|
| LSC1 | NP_014785 | 6324716 | Saccharomyces cerevisiae |
| LSC2 | NP_011760 | 6321683 | Saccharomyces cerevisiae |
| sucC | NP_415256.1 | 16128703 | Escherichia coli |
| sucD | AAC73823.1 | 1786949 | Escherichia coli |

Succinyl-CoA transferase converts succinate and an acyl-CoA donor to succinyl-CoA and an acid. Succinyl-CoA transferase enzymes include ygfH of E. coli, cat1 of Clostridium kluyveri, and other exemplary enzymes shown below. Additional CoA transferases, described herein, are also suitable candidates.

| Gene | GI # | Accession No. | Organism |
|---|---|---|---|
| ygfH | AAC75957.1 | 1789287 | Escherichia coli |
| cat1 | P38946.1 | 729048 | Clostridium kluyveri |
| CIT292_04485 | ZP_03838384.1 | 227334728 | Citrobacter youngae |
| SARI_04582 | YP_001573497.1 | 161506385 | Salmonella enterica |

| Gene | GI # | Accession No. | Organism |
|---|---|---|---|
| yinte0001_14430 | ZP_04635364.1 | 238791727 | Yersinia intermedia |
| pcaI | 24985644 | AAN69545.1 | Pseudomonas putida |
| pcaJ | 26990657 | NP_746082.1 | Pseudomonas putida |
| pcaI | 50084858 | YP_046368.1 | Acinetobacter sp. ADP1 |
| pcaJ | 141776 | AAC37147.1 | Acinetobacter sp. ADP1 |
| pcaI | 21224997 | NP_630776.1 | Streptomyces coelicolor |
| pcaJ | 21224996 | NP_630775.1 | Streptomyces coelicolor |
| catI | 75404583 | Q8VPF3 | Pseudomonas knackmussii |
| catJ | 75404582 | Q8VPF2 | Pseudomonas knackmussii |
| HPAG1_0676 | 108563101 | YP_627417 | Helicobacter pylori |
| HPAG1_0677 | 108563102 | YP_627418 | Helicobacter pylori |
| ScoA | 16080950 | NP_391778 | Bacillus subtilis |
| ScoB | 16080949 | NP_391777 | Bacillus subtilis |
| OXCT1 | NP_000427 | 4557817 | Homo sapiens |
| OXCT2 | NP_071403 | 11545841 | Homo sapiens |

F. Pyruvate Kinase or PTS-dependent substrate import. See elsewhere herein.

G. Pyruvate Dehydrogenase, Pyruvate Formate Lyase or Pyruvate:ferredoxin oxidoreductase. Pyruvate:ferredoxin oxidoreductase (PFOR) catalyzes the reversible oxidation of pyruvate to form acetyl-CoA. Exemplary PFOR enzymes are found in *Desulfovibrio africanus* (Pieulle et al., *J. Bacteriol.* 179:5684-5692 (1997)) and other *Desulfovibrio* species (Vita et al., Biochemistry, 47: 957-64 (2008)). The *M. thermoacetica* PFOR is also well characterized (Henn and Ragsdale, *Biochemistry* 36:8484-8494 (1997)) and was shown to have high activity in the direction of pyruvate synthesis during autotrophic growth (Furdui and Ragsdale, *J. Biol. Chem.* 275:28494-28499 (2000)). Further, *E. coli* possesses an uncharacterized open reading frame, ydbK, encoding a protein that is 51% identical to the *M. thermoacetica* PFOR. Evidence for pyruvate oxidoreductase activity in *E. coli* has been described (Blaschkowski et al., *Eur. J. Biochem.* 123:563-569 (1982)). Finally, flavodoxin reductases (e.g., fqrB from *Helicobacter pylori* or *Campylobacter jejuni*) (St Maurice et al., *J. Bacteriol.* 189:4764-4773 (2007)) or Rnf-type proteins (Seedorf et al., *Proc. Natl. Acad. Sci. U.S.A.* 105:2128-2133 (2008); and Herrmann, *J. Bacteriol* 190:784-791 (2008)) provide a means to generate NADH or NADPH from the reduced ferredoxin generated by PFOR.

| Protein | GenBank ID | GI Number | Organism |
|---|---|---|---|
| DesfrDRAFT_0121 | ZP_07331646.1 | 303245362 | Desulfovibrio fructosovorans JJ |
| Por | CAA70873.1 | 1770208 | Desulfovibrio africanus |
| por | YP_012236.1 | 46581428 | Desulfovibrio vulgaris str. Hildenborough |
| Dde_3237 | ABB40031.1 | 78220682 | DesulfoVibrio desulfuricans G20 |
| Ddes_0298 | YP_002478891.1 | 220903579 | Desulfovibrio desulfuricans subsp. desulfuricans str. ATCC 27774 |
| Por | YP_428946.1 | 83588937 | Moorella thermoacetica |
| YdbK | NP_415896.1 | 16129339 | Escherichia coli |

The conversion of pyruvate into acetyl-CoA can be catalyzed by several other enzymes or their combinations thereof. For example, pyruvate dehydrogenase can transform pyruvate into acetyl-CoA with the concomitant reduction of a molecule of NAD into NADH. It is a multi-enzyme complex that catalyzes a series of partial reactions which results in acylating oxidative decarboxylation of pyruvate. The enzyme comprises of three subunits: pyruvate decarboxylase (E1), dihydrolipoamide acyltransferase (E2) and dihydrolipoamide dehydrogenase (E3). This enzyme is naturally present in several organisms, including *E. coli* and *S. cerevisiae*. Enzyme engineering efforts have improved the *E. coli* PDH enzyme activity under anaerobic conditions.

| Gene | Accession No. | GI # | Organism |
|---|---|---|---|
| aceE | NP_414656.1 | 16128107 | Escherichia coli |
| aceF | NP_414657.1 | 16128108 | Escherichia coli |
| lpd | NP_414658.1 | 16128109 | Escherichia coli |
| pdhA | P21881.1 | 3123238 | Bacillus subtilis |
| pdhB | P21882.1 | 129068 | Bacillus subtilis |
| pdhC | P21883.2 | 129054 | Bacillus subtilis |
| pdhD | P21880.1 | 118672 | Bacillus subtilis |
| LAT1 | NP_014328 | 6324258 | Saccharomyces cerevisiae |
| PDA1 | NP_011105 | 37362644 | Saccharomyces cerevisiae |
| PDB1 | NP_009780 | 6319698 | Saccharomyces cerevisiae |
| LPD1 | NP_116635 | 14318501 | Saccharomyces cerevisiae |
| PDX1 | NP_011709 | 6321632 | Saccharomyces cerevisiae |

Yet another enzyme that can catalyze this conversion is pyruvate formate lyase. This enzyme catalyzes the conversion of pyruvate and CoA into acetyl-CoA and formate. Pyruvate formate lyase is a common enzyme in prokaryotic organisms that is used to help modulate anaerobic redox balance. Exemplary enzymes are below. Both pflB and tdcE from *E. coli* require the presence of pyruvate formate lyase activating enzyme, encoded by pflA. Further, a short protein encoded by yfiD in *E. coli* can associate with and restore activity to oxygen-cleaved pyruvate formate lyase.

| Protein | GenBank ID | GI Number | Organism |
|---|---|---|---|
| pflB | NP_415423 | 16128870 | Escherichia coli |
| pflA | NP_415422.1 | 16128869 | Escherichia coli |
| tdcE | AAT48170.1 | 48994926 | Escherichia coli |
| yfiD | AAC75632.1 | 1788933 | Escherichia coli |
| pfl | Q46266.1 | 2500058 | Clostridium pasteurianum |
| act | CAA63749.1 | 1072362 | Clostridium pasteurianum |

Further, different enzymes can be used in combination to convert pyruvate into acetyl-CoA in multiple steps. For example, in *S. cerevisiae*, acetyl-CoA is obtained in the cytosol by first decarboxylating pyruvate to form acetaldehyde; the latter is oxidized to acetate by acetaldehyde dehydrogenase and subsequently activated to form acetyl-CoA by acetyl-CoA synthetase. Acetyl-CoA synthetase is a native enzyme in several other organisms including *E. coli*

(Kumari et al., J. Bacteriol. 177:2878-2886 (1995)), *Salmonella enterica* (Starai et al., Microbiology 151:3793-3801 (2005); Starai et al., J. Biol. Chem. 280:26200-26205 (2005)), and *Moorella thermoacetica* (described already). Alternatively, acetate can be activated to form acetyl-CoA by acetate kinase and phosphotransacetylase. Acetate kinase first converts acetate into acetyl-phosphate with the accompanying use of an ATP molecule. Acetyl-phosphate and CoA are next converted into acetyl-CoA with the release of one phosphate by phosphotransacetylase. Exemplary enzymes encoding acetate kinase, acetyl-CoA synthetase and phosphotransacetlyase are described above.

Yet another way of converting pyruvate to acetyl-CoA is via pyruvate oxidase. Pyruvate oxidase converts pyruvate into acetate, using ubiquinone as the electron acceptor. In *E. coli*, this activity is encoded by poxB. PoxB has similarity to pyruvate decarboxylase of *S. cerevisiae* and *Zymomonas mobilis*. The enzyme has a thiamin pyrophosphate cofactor (Koland and Gennis, Biochemistry 21:4438-4442 (1982)); O'Brien et al., Biochemistry 16:3105-3109 (1977); O'Brien and Gennis, J. Biol. Chem. 255:3302-3307 (1980)) and a flavin adenine dinucleotide (FAD) cofactor. Acetate can then be converted into acetyl-CoA by either acetyl-CoA synthetase or by acetate kinase and phosphotransacetylase, as described earlier. Some of these enzymes can also catalyze the reverse reaction from acetyl-CoA to pyruvate.

H. Citrate Synthase. Citrate synthases are well known in the art. For example, the gltA gene of *E. coli* encodes for a citrate synthase. It was previously shown that this gene is inhibited allosterically by NADH, and the amino acids involved in this inhibition have been identified (Pereira et al., *J. Biol. Chem.* 269(1):412-417 (1994); Stokell et al., *J. Biol. Chem.* 278(37):35435-35443 (2003)). An NADH insensitive citrate synthase can be encoded by gltA, such as an R163L mutant of gltA. Other citrate synthase enzymes are less sensitive to NADH, including the aarA enzyme of *Acetobacter aceti* (Francois et al, Biochem 45:13487-99 (2006)).

| Protein | GenBank ID | GI number | Organism |
|---|---|---|---|
| gltA | NP_415248.1 | 16128695 | *Escherichia coli* |
| AarA | P20901.1 | 116462 | *Acetobacter aceti* |
| CIT1 | NP_014398.1 | 6324328 | *Saccharomyces cerevisiae* |
| CS | NP_999441.1 | 47523618 | *Sus scrofa* |

I. Aconitase. Aconitase (EC 4.2.1.3) is an iron-sulfur-containing protein catalyzing the reversible isomerization of citrate and iso-citrate via the intermediate cis-aconitase. Two aconitase enzymes of *E. coli* are encoded by acnA and acnB. AcnB is the main catabolic enzyme, while AcnA is more stable and appears to be active under conditions of oxidative or acid stress. Exemplary enzymes are below.

| Protein | GenBank ID | GI Number | Organism |
|---|---|---|---|
| acnA | AAC7438.1 | 1787531 | *Escherichia coli* |
| acnB | AAC73229.1 | 2367097 | *Escherichia coli* |
| HP0779 | NP_207572.1 | 15645398 | *Helicobacter pylori* 26695 |
| H16_B0568 | CAJ95365.1 | 113529018 | *Ralstonia eutropha* |
| DesfrDRAFT_3783 | ZP_07335307.1 | 303249064 | *Desulfovibrio fructosovorans* JJ |
| Suden_1040 (acnB) | ABB44318.1 | 78497778 | *Sulfurimonas denitrificans* |
| Hydth_0755 | ADO45152.1 | 308751669 | *Hydrogenobacter thermophilus* |
| CT0543 (acn) | AAM71785.1 | 21646475 | *Chlorobium tepidum* |
| Clim_2436 | YP_001944436.1 | 189347907 | *Chlorobium limicola* |
| Clim_0515 | ACD89607.1 | 189340204 | *Chlorobium limicola* |
| acnA | NP_460671.1 | 16765056 | *Salmonella typhimurium* |
| acnB | NP_459163.1 | 16763548 | *Salmonella typhimurium* |
| ACO1 | AAA34389.1 | 170982 | *Saccharomyces cerevisiae* |

J. Isocitrate Dehydrogenase. Isocitrate dehydrogenase catalyzes the decarboxylation of isocitrate to 2-oxoglutarate coupled to the reduction of NAD(P)$^+$. Exemplary enzymes are listed below.

| Protein | GenBank ID | GI Number | Organism |
|---|---|---|---|
| Icd | ACI84720.1 | 209772816 | *Escherichia coli* |
| IDP1 | AAA34703.1 | 171749 | *Saccharomyces cerevisiae* |
| Idh | BAC00856.1 | 21396513 | *Chlorobium limicola* |
| Icd | AAM71597.1 | 21646271 | *Chlorobium tepidum* |
| icd | NP_952516.1 | 39996565 | *Geobacter sulfurreducens* |
| icd | YP_393560. | 78777245 | *Sulfurimonas denitrificans* |

K. AKG Dehydrogenase. Alpha-ketoglutarate dehydrogenase (AKGD) converts alpha-ketoglutarate to succinyl-CoA and is the primary site of control of metabolic flux through the TCA cycle (Hansford, *Curr. Top. Bioenerg.* 10:217-278 (1980)). Exemplary AKGDH enzymes are listed below.

| Gene | GI # | Accession No. | Organism |
|---|---|---|---|
| sucA | 16128701 | NP_415254.1 | *Escherichia coli* |
| sucB | 16128702 | NP_415255.1 | *Escherichia coli* |
| lpd | 16128109 | NP_414658.1 | *Escherichia coli* |
| odhA | 51704265 | P23129.2 | *Bacillus subtilis* |
| odhB | 129041 | P16263.1 | *Bacillus subtilis* |
| pdhD | 118672 | P21880.1 | *Bacillus subtilis* |
| KGD1 | 6322066 | NP_012141.1 | *Saccharomyces cerevisiae* |
| KGD2 | 6320352 | NP_010432.1 | *Saccharomyces cerevisiae* |
| LPD1 | 14318501 | NP_116635.1 | *Saccharomyces cerevisiae* |

The conversion of alpha-ketoglutarate to succinyl-CoA can also be catalyzed by alpha-ketoglutarate:ferredoxin oxidoreductase (EC 1.2.7.3), also known as 2-oxoglutarate synthase or 2-oxoglutarate:ferredoxin oxidoreductase (OFOR). OFOR and pyruvate:ferredoxin oxidoreductase (PFOR) are members of a diverse family of 2-oxoacid:ferredoxin (flavodoxin) oxidoreductases which utilize thiamine pyrophosphate, CoA and iron-sulfur clusters as cofactors and ferredoxin, flavodoxin and FAD as electron carriers (Adams et al., *Archaea. Adv. Protein Chem.* 48.101-180 (1996)). Exemplary OFOR enzymes are found in organisms such as *Hydrogenobacter thermophilus*, *Desulfobacter hydrogenophilus* and *Chlorobium species* (Shiba et al. 1985; Evans et al., *Proc. Natl. Acad. Sci. U.S.A.* 55:92934 (1966); Buchanan, 1971). The two-subunit enzyme from *H. thermophilus*, encoded by korAB, has been cloned and expressed in E. coli. A five subunit OFOR from the same organism with strict substrate specificity for succinyl-CoA, encoded by for DABGE, was recently identified and expressed in E. coli. Exemplary OFOR are below.

| Protein | GenBank ID | GI Number | Organism |
|---|---|---|---|
| korA | BAB21494 | 12583691 | Hydrogenobacter thermophilus |
| korB | BAB21495 | 12583692 | Hydrogenobacter thermophilus |
| forD | BAB62132.1 | 14970994 | Hydrogenobacter thermophilus |
| forA | BAB62133.1 | 14970995 | Hydrogenobacter thermophilus |
| forB | BAB62134.1 | 14970996 | Hydrogenobacter thermophilus |
| forG | BAB62135.1 | 14970997 | Hydrogenobacter thermophilus |
| forE | BAB62136.1 | 14970998 | Hydrogenobacter thermophilus |
| Clim_0204 | ACD89303.1 | 189339900 | Chlorobium limicola |
| Clim_0205 | ACD89302.1 | 189339899 | Chlorobium limicola |
| Clim_1123 | ACD90192.1 | 189340789 | Chlorobium limicola |
| Clim_1124 | ACD90193.1 | 189340790 | Chlorobium limicola |
| korA | CAA12243.2 | 19571179 | Thauera aromatica |
| korB | CAD27440.1 | 19571178 | Thauera aromatica |

L. Pyruvate Carboxylase. Pyruvate carboxylase (EC 6.4.1.1) directly converts pyruvate to oxaloacetate at the cost of one ATP. Pyruvate carboxylase enzymes are below.

| Protein | GenBank ID | GI Number | Organism |
|---|---|---|---|
| PYC1 | NP_011453 | 6321376 | Saccharomyces cerevisiae |
| PYC2 | NP_009777 | 6319695 | Saccharomyces cerevisiae |
| Pyc | YP_890857.1 | 118470447 | Mycobacterium smegmatis |

M. Malic Enzyme. Malic enzyme can be applied to convert $CO_2$ and pyruvate to malate at the expense of one reducing equivalent. Malic enzymes for this purpose can include, without limitation, malic enzyme (NAD-dependent) and malic enzyme (NADP-dependent). For example, one of the E. coli malic enzymes (Takeo, J. Biochem. 66:379-387 (1969)) or a similar enzyme with higher activity can be expressed to enable the conversion of pyruvate and $CO_2$ to malate. By fixing carbon to pyruvate as opposed to PEP, malic enzyme allows the high-energy phosphate bond from PEP to be conserved by pyruvate kinase whereby ATP is generated in the formation of pyruvate or by the phosphotransferase system for glucose transport.

| Protein | GenBank ID | GI Number | Organism |
|---|---|---|---|
| maeA | NP_415996 | 90111281 | Escherichia coli |
| maeB | NP_416958 | 16130388 | Escherichia coli |
| NAD-ME | P27443 | 126732 | Ascaris suum |

Example VII 1,3-Butanediol, Crotyl Alcohol, 3-Buten-2-ol, and Butadiene Synthesis Enzymes This Example provides genes that can be used for conversion of acetyl-CoA to 1,3-butanediol, crotyl alcohol, 3-buten-2-ol, butadiene as depicted in the pathways of FIGS. 5 and 6.

FIG. 5. Pathways for converting 1,3-butanediol to 3-buten-2-ol and/or butadiene. A) acetyl-CoA carboxylase, B) an acetoacetyl-CoA synthase, C) an acetyl-CoA:acetyl-CoA acyltransferase, D) an acetoacetyl-CoA reductase (ketone reducing), E) a 3-hydroxybutyryl-CoA reductase (aldehyde forming), F) a 3-hydroxybutyryl-CoA hydrolase, transferase or synthetase, G) a 3-hydroxybutyrate reductase, H) a 3-hydroxybutyraldehyde reductase, I) chemical dehydration or corresponding step in FIG. 6, J) a 3-hydroxybutyryl-CoA dehydratase, K) a crotonyl-CoA reductase (aldehyde forming), L) a crotonyl-CoA hydrolase, transferase or synthetase, M) a crotonate reductase, N) a crotonaldehyde reductase, O) a crotyl alcohol kinase, P) a 2-butenyl-4-phosphate kinase, Q) a butadiene synthase, R) a crotyl alcohol diphosphokinase, S) chemical dehydration or a crotyl alcohol dehydratase, T) a butadiene synthase (monophosphate), T) a butadiene synthase (monophosphate), U) a crotonyl-CoA reductase (alcohol forming), and V) a 3-hydroxybutyryl-CoA reductase (alcohol forming).

A. Acetyl-CoA Carboxylase. Acetyl-CoA carboxylase (EC 6.4.1.2) catalyzes the ATP-dependent carboxylation of acetyl-CoA to malonyl-CoA. This enzyme is biotin dependent and is the first reaction of fatty acid biosynthesis initiation in several organisms. Exemplary enzymes are below.

| Protein | GenBank ID | GI Number | Organism |
|---|---|---|---|
| ACC1 | CAA96294.1 | 1302498 | Saccharomyces cerevisiae |
| KLLA0F06072g | XP_455355.1 | 50310667 | Kluyveromyces lactis |
| ACC1 | XP_718624.1 | 68474502 | Candida albicans |
| YALI0C11407p | XP_501721.1 | 50548503 | Yarrowia lipolytica |
| ANI_1_1724104 | XP_001395476.1 | 145246454 | Aspergillus niger |
| accA | AAC73296.1 | 1786382 | Escherichia coli |
| accB | AAC76287.1 | 1789653 | Escherichia coli |
| accC | AAC76288.1 | 1789654 | Escherichia coli |
| accD | AAC75376.1 | 1788655 | Escherichia coli |

B. Acetoacetyl-CoA Synthase. The conversion of malonyl-CoA and acetyl-CoA substrates to acetoacetyl-CoA can be catalyzed by a CoA synthetase in the 2.3.1 family of enzymes. Several enzymes catalyzing the CoA synthetase activities have been described in the literature and represent suitable candidates.

3-Oxoacyl-CoA products such as acetoacetyl-CoA, 3-oxopentanoyl-CoA, 3-oxo-5-hydroxypentanoyl-CoA can be synthesized from acyl-CoA and malonyl-CoA substrates by 3-oxoacyl-CoA synthases. As enzymes in this class catalyze an essentially irreversible reaction, they are particularly useful for metabolic engineering applications for overproducing metabolites, fuels or chemicals derived from 3-oxoacyl-CoA intermediates such as acetoacetyl-CoA. Acetoacetyl-CoA synthase, for example, has been heterologously expressed in organisms that biosynthesize butanol (Lan et al, PNAS USA (2012)) and poly-(3-hydroxybutyrate) (Matsumoto et al, Biosci Biotech Biochem, 75:364-366 (2011). Other acetoacetyl-CoA synthase genes can be identified by sequence homology to fhsA.

| Protein | GenBank ID | GI Number | Organism |
|---|---|---|---|
| fhsA | BAJ83474.1 | 325302227 | Streptomyces sp CL190 |
| AB183750.1:11991 . . . 12971 | BAD86806.1 | 57753876 | Streptomyces sp. KO-3988 |
| epzT | ADO43379.1 | 312190954 | Streptomyces cinnamonensis |
| ppzT | CAX48662.1 | 238623523 | Streptomyces anulatus |
| O3I 22085 | ZP 09840373.1 | 378817444 | Nocardia brasiliensis |

C. Acetyl-CoA:acetyl-CoA Acyltransferase (Acetoacetyl-CoA thiolase). Acetoacetyl-CoA thiolase (also known as acetyl-CoA acetyltransferase) converts two molecules of acetyl-CoA into one molecule each of acetoacetyl-CoA and CoA. Exemplary acetoacetyl-CoA thiolase enzymes include genes/proteins identified in the Table below.

| Gene | GenBank ID | GI Number | Organism |
|---|---|---|---|
| AtoB | NP_416728 | 16130161 | Escherichia coli |
| ThlA | NP_349476.1 | 15896127 | Clostridium acetobutylicum |
| ThlB | NP_149242.1 | 15004782 | Clostridium acetobutylicum |
| ERG10 | NP_015297 | 6325229 | Saccharomyces cerevisiae |
| phbA | P07097.4 | 135759 | Zoogloea ramigera |

D. Acetoacetyl-CoA reductase. A suitable enzyme activity is 1.1.1.a Oxidoreductase (oxo to alcohol). See herein. In addition, Acetoacetyl-CoA reductase (EC 1.1.1.36) catalyzes the reduction of acetoacetyl-CoA to 3-hydroxybutyryl-CoA. This enzyme participates in the acetyl-CoA fermentation pathway to butyrate in several species of Clostridia and has been studied in detail (Jones et al., Microbiol Rev. 50:484-524 (1986)). Acetoacetyl-CoA reductase also participates in polyhydroxybutyrate biosynthesis in many organisms, and has also been used in metabolic engineering applications for overproducing PHB and 3-hydroxyisobutyrate. Additional exemplary genes include those below. The Z. ramigera gene is NADPH-dependent and the gene has been expressed in E. coli (Peoples et al., Mol. Microbiol 3:349-357 (1989)). Substrate specificity studies on the gene led to the conclusion that it could accept 3-oxopropionyl-CoA as a substrate besides acetoacetyl-CoA (Ploux et al., Eur. J Biochem. 174:177-182 (1988)). The enzyme from Candida tropicalis is a component of the peroxisomal fatty acid beta-oxidation multifunctional enzyme type 2 (MFE-2). The dehydrogenase B domain of this protein is catalytically active on acetoacetyl-CoA.

| Protein | Genbank ID | GI Number | Organism |
|---|---|---|---|
| fadB | P21177.2 | 119811 | Escherichia coli |
| fadJ | P77399.1 | 3334437 | Escherichia coli |
| paaH | NP_415913.1 | 16129356 | Escherichia coli |
| Hbd2 | EDK34807.1 | 146348271 | Clostridium kluyveri |
| Hbd1 | EDK32512.1 | 146345976 | Clostridium kluyveri |
| phaC | NP_745425.1 | 26990000 | Pseudomonas putida |
| paaC | ABF82235.1 | 106636095 | Pseudomonas fluorescens |

-continued

| Protein | Genbank ID | GI Number | Organism |
|---|---|---|---|
| HSD17B10 | O02691.3 | 3183024 | Bos taurus |
| phbB | P23238.1 | 130017 | Zoogloea ramigera |
| phaB | YP_353825.1 | 77464321 | Rhodobacter sphaeroides |
| phaB | BAA08358 | 675524 | Paracoccus denitrificans |
| Hbd | NP_349314.1 | 15895965 | Clostridium acetobutylicum |
| Hbd | AAM14586.1 | 20162442 | Clostridium beijerinckii |
| Msed_1423 | YP_001191505 | 146304189 | Metallosphaera sedula |
| Msed_0399 | YP_001190500 | 146303184 | Metallosphaera sedula |
| Msed_0389 | YP_001190490 | 146303174 | Metallosphaera sedula |
| Msed_1993 | YP_001192057 | 146304741 | Metallosphaera sedula |
| Fox2 | Q02207 | 399508 | Candida tropicalis |

E. 3-Hydroxybutyryl-CoA Reductase (aldehyde forming). An EC 1.2.1.b Oxidoreductase (acyl-CoA to aldehyde) provides suitable enzyme activity. Acyl-CoA reductases or acylating aldehyde dehydrogenases reduce an acyl-CoA to its corresponding aldehyde. Exemplary enzymes include fatty acyl-CoA reductase, succinyl-CoA reductase (EC 1.2.1.76), acetyl-CoA reductase, butyryl-CoA reductase, propionyl-CoA reductase (EC 1.2.1.3) and others shown in the table below.

| EC Number | Enzyme name |
|---|---|
| 1.2.1.10 | Acetaldehyde dehydrogenase (acetylating) |
| 1.2.1.42 | (Fatty) acyl-CoA reductase |
| 1.2.1.44 | Cinnamoyl-CoA reductase |
| 1.2.1.50 | Long chain fatty acyl-CoA reductase |
| 1.2.1.57 | Butanal dehydrogenase |
| 1.2.1.75 | Malonate semialdehyde dehydrogenase |
| 1.2.1.76 | Succinate semialdehyde dehydrogenase |
| 1.2.1.81 | Sulfoacetaldehyde dehydrogenase |
| 1.2.1.— | Propanal dehydrogenase |
| 1.2.1.— | Hexanal dehydrogenase |
| 1.2.1.— | 4-Hydroxybutyraldehyde dehydrogenase |

Exemplary fatty acyl-CoA reductases enzymes are encoded by acr1 of Acinetobacter calcoaceticus (Reiser, Journal of Bacteriology 179:2969-2975 (1997)) and Acinetobacter sp. M-1 (Ishige et al., Appl. Environ. Microbiol. 68:1192-1195 (2002)). Enzymes with succinyl-CoA reductase activity are encoded by sucD of Clostridium kluyveri (Sohling, J. Bacteriol. 178:871-880 (1996)) and sucD of P. gingivalis (Takahashi, J. Bacteriol 182:4704-4710 (2000)). Additional succinyl-CoA reductase enzymes are exemplified below.

| Protein | GenBank ID | GI Number | Organism |
|---|---|---|---|
| acr1 | YP_047869.1 | 50086359 | Acinetobacter calcoaceticus |
| acr1 | AAC45217 | 1684886 | Acinetobacter baylyi |
| acr | BAB85476.1 | 18857901 | Acinetobacter sp. Strain M-1 |
| MSED_0709 | YP_001190808.1 | 146303492 | Metallosphaera sedula |
| Tneu_0421 | ACB39369.1 | 170934108 | Thermoproteus neutrophilus |
| sucD | P38947.1 | 172046062 | Clostridium kluyveri |
| sucD | NP_904963.1 | 34540484 | Porphyromonas gingivalis |
| bphG | BAA03892.1 | 425213 | Pseudomonas sp |

-continued

| Protein | GenBank ID | GI Number | Organism |
|---|---|---|---|
| adhE | AAV66076.1 | 55818563 | *Leuconostoc mesenteroides* |
| bld | AAP42563.1 | 31075383 | *Clostridium saccharoperbutylacetonicum* |
| pduP | NP_460996 | 16765381 | *Salmonella typhimurium* LT2 |
| eutE | NP_416950 | 16130380 | *Escherichia coli* |

An additional enzyme that converts an acyl-CoA to its corresponding aldehyde is malonyl-CoA reductase which transforms malonyl-CoA to malonic semialdehyde. Although the aldehyde dehydrogenase functionality of these enzymes is similar to the bifunctional dehydrogenase from *Chloroflexus aurantiacus*, there is little sequence similarity. Both malonyl-CoA reductase enzyme candidates have high sequence similarity to aspartate-semialdehyde dehydrogenase, an enzyme catalyzing the reduction and concurrent dephosphorylation of aspartyl-4-phosphate to aspartate semialdehyde. Additional gene candidates can be found by sequence homology to proteins in other organisms including *Sulfolobus solfataricus* and *Sulfolobus acidocaldarius* and have been listed below. Yet another candidate for CoA-acylating aldehyde dehydrogenase is the ald gene from *Clostridium beijerinckii* reported to reduce acetyl-CoA and butyryl-CoA to their corresponding aldehydes.

| Protein | GenBank ID | GI Number | Organism |
|---|---|---|---|
| Msed_0709 | YP_001190808.1 | 146303492 | *Metallosphaera sedula* |
| Mcr | NP_378167.1 | 15922498 | *Sulfolobus tokodaii* |
| asd-2 | NP_343563.1 | 15898958 | *Sulfolobus solfataricus* |
| Saci_2370 | YP_256941.1 | 70608071 | *Sulfolobus acidocaldarius* |
| Ald | AAT66436 | 49473535 | *Clostridium beijerinckii* |
| eutE | AAA80209 | 687645 | *Salmonella typhimurium* |

4-Hydroxybutyryl-CoA reductase catalyzes the reduction of 4-hydroxybutyryl-CoA to its corresponding aldehyde. Several acyl-CoA dehydrogenases are capable of catalyzing this activity. The succinate semialdehyde dehydrogenases (SucD) of *Clostridium kluyveri* and *P. gingivalis* were shown in ref (WO/2008/115840) to convert 4-hydroxybutyryl-CoA to 4-hydroxybutanal as part of a pathway to produce 1,4-butanediol. Many butyraldehyde dehydrogenases are also active on 4-hydroxybutyraldehyde, including bld of *Clostridium saccharoperbutylacetonicum* and bphG of *Pseudomonas* sp (Powlowski et al., *J. Bacteriol.* 175:377-385 (1993)). These and additional proteins with 4-hydroxybutyryl-CoA reductase activity are identified below.

| Protein | GenBank ID | GI Number | Organism |
|---|---|---|---|
| bphG | BAA03892.1 | 425213 | *Pseudomonas* sp |
| ald | YP_001310903.1 | 150018649 | *Clostridium beijerinckii* NCIMB 8052 |
| Ald | ZP_03778292.1 | 225569267 | *Clostridium hylemonae* DSM 15053 |
| Ald | ZP_03705305.1 | 225016072 | *Clostridium methylpentosum* DSM 5476 |
| Ald | ZP_03715465.1 | 225026273 | *Eubacterium hallii* DSM 3353 |
| Ald | ZP_01962381.1 | 153809713 | *Ruminococcus obeum* ATCC 29174 |
| Ald | YP_003701164.1 | 297585384 | *Bacillus selenitireducens* MLS 10 |
| Ald | AAP42563.1 | 31075383 | *Clostridium saccharoperbutylacetonicum* N1-4 |
| Ald | YP_795711.1 | 116334184 | *Lactobacillus brevis* ATCC 367 |
| Ald | YP_002434126.1 | 218782808 | *Desulfatibacillum alkenivorans* AK-01 |
| Ald | YP_001558295.1 | 160879327 | *Clostridium phytofermentans* ISDg |
| Ald | ZP_02089671.1 | 160942363 | *Clostridium bolteae* ATCC BAA-613 |
| Ald | ZP_01222600.1 | 90414628 | *Photobacterium profundum* 3TCK |
| Ald | YP_001452373.1 | 157145054 | *Citrobacter koseri* ATCC BAA-895 |
| Ald | NP_460996.1 | 16765381 | *Salmonella enterica typhimurium* |
| Ald | YP_003307836.1 | 269119659 | *Sebaldella termitidis* ATCC 33386 |
| Ald | ZP_04969437.1 | 254302079 | *Fusobacterium nucleatum* subsp. *polymorphum* ATCC 10953 |
| Ald | YP_002892893.1 | 237808453 | *Tolumonas auensis* DSM 9187 |
| Ald | YP_426002.1 | 83592250 | *Rhodospirillum rubrum* ATCC 11170 |

F. 3-Hydroxybutyryl-CoA Hydrolase, Transferase or Synthetase. An EC 3.1.2.a CoA hydrolase, EC 2.8.3.a CoA transferase, and/or an EC 6.2.1.a CoA synthetase provide suitable enzyme activity. See herein.

G. 3-Hydroxybutyrate Reductase. An EC 1.2.1.e Oxidoreductase (acid to aldehyde) provides suitable activity. See herein.

H. 3-Hydroxybutyraldehyde Reductase. An EC 1.1.1.a Oxidoreductase (oxo to alcohol) provides suitable activity. See herein.

I. Chemical dehydration or alternatively see corresponding enzymatic pathway in FIG. 6.

J. 3-Hydroxybutyryl-CoA Dehydratase. An EC 4.2.1. Hydro-lyase provides suitable enzyme activity, and are described below and herein. The enoyl-CoA hydratase of *Pseudomonas putida*, encoded by ech, catalyzes the conversion of 3-hydroxybutyryl-CoA to crotonyl-CoA (Roberts et al., *Arch. Microbiol* 117:99-108 (1978)). This transformation is also catalyzed by the crt gene product of *Clostridium acetobutylicum*, the crt1 gene product of *C. kluyveri*, and other clostridial organisms Atsumi et al., *Metab Eng* 10:305-311(2008); Boynton et al., *J Bacteriol.* 178:3015-3024 (1996); Hillmer et al., *FEBS Lett.* 21:351-354 (1972)). Additional enoyl-CoA hydratase candidates are described below.

| Protein | GenBank No. | GI No. | Organism |
|---|---|---|---|
| ech | NP_745498.1 | 26990073 | *Pseudomonas putida* |
| crt | NP_349318.1 | 15895969 | *Clostridium acetobutylicum* |
| crt1 | YP_001393856 | 153953091 | *Clostridium kluyveri* |

| Protein | GenBank No. | GI No. | Organism |
|---|---|---|---|
| phaA | ABF82233.1 | 26990002 | Pseudomonas putida |
| phaB | ABF82234.1 | 26990001 | Pseudomonas putida |
| paaA | NP_745427.1 | 106636093 | Pseudomonas fluorescens |
| paaB | NP_745426.1 | 106636094 | Pseudomonas fluorescens |
| maoC | NP_415905.1 | 16129348 | Escherichia coli |
| paaF | NP_415911.1 | 16129354 | Escherichia coli |
| paaG | NP_415912.1 | 16129355 | Escherichia coli |

K. Crotonyl-CoA Reductase (aldehyde forming). An EC 1.2.1.b Oxidoreductase (acyl-CoA to aldehyde) provides suitable enzyme activity. Acyl-CoA reductases in the 1.2.1 family reduce an acyl-CoA to its corresponding aldehyde. Several acyl-CoA reductase enzymes have been described in the open literature and represent suitable candidates for this step. These are described above.

L. Crotonyl-CoA Hydrolase, Transferase or Synthetase. An EC 3.1.2.a CoA hydrolase, EC 2.8.3.a CoA transferase, and/or an EC 6.2.1.a CoA synthetase provide suitable enzyme activity, and are described in the following sections.

EC 3.1.2.a CoA Hydrolase. Enzymes in the 3.1.2 family hydrolyze acyl-CoA molecules to their corresponding acids. Several such enzymes have been described in the literature and represent suitable candidates for these steps.

For example, the enzyme encoded by acot12 from *Rattus norvegicus* brain (Robinson et al., *Biochem. Biophys. Res. Commun.* 71:959-965 (1976)) can react with butyryl-CoA, hexanoyl-CoA and malonyl-CoA. Exemplary enzymes are shown below.

| Protein | GenBank Accession No. | GI Number | Organism |
|---|---|---|---|
| acot12 | NP_570103.1 | 18543355 | Rattus norvegicus |
| tesB | NP_414986 | 16128437 | Escherichia coli |
| acot8 | CAA15502 | 3191970 | Homo sapiens |
| acot8 | NP_570112 | 51036669 | Rattus norvegicus |
| tesA | NP_415027 | 16128478 | Escherichia coli |
| ybgC | NP_415264 | 16128711 | Escherichia coli |
| paaI | NP_415914 | 16129357 | Escherichia coli |
| ybdB | NP_415129 | 16128580 | Escherichia coli |
| ACH1 | NP_009538 | 6319456 | Saccharomyces cerevisiae |

Additional hydrolase enzymes include 3-hydroxyisobutyryl-CoA hydrolase which has been described to efficiently catalyze the conversion of 3-hydroxyisobutyryl-CoA to 3-hydroxyisobutyrate during valine degradation (Shimomura et al., *J Biol Chem.* 269:14248-14253 (1994)). Genes encoding this enzyme include those below.

| Protein | GenBank No. | GI Number | Organism |
|---|---|---|---|
| hibch | Q5XIE6.2 | 146324906 | Rattus norvegicus |
| hibch | Q6NVY1.2 | 146324905 | Homo sapiens |
| hibch | P28817.2 | 2506374 | Saccharomyces cerevisiae |
| BC_2292 | AP09256 | 29895975 | Bacillus cereus |

EC 2.83.a CoA transferase. Enzymes in the 2.8.3 family catalyze the reversible transfer of a CoA moiety from one molecule to another. Several CoA transferase enzymes have been described in the open literature and represent suitable candidates for these steps. These are described below.

Many transferases have broad specificity and thus can utilize CoA acceptors as diverse as acetate, succinate, propionate, butyrate, 2-methylacetoacetate, 3-ketohexanoate, 3-ketopentanoate, valerate, crotonate, 3-mercaptopropionate, propionate, vinylacetate, butyrate, among others.

| Protein | GenBank ID | GI Number | Organism |
|---|---|---|---|
| Ach1 | AAX19660.1 | 60396828 | Roseburia sp. A2-183 |
| ROSINTL182_07121 | ZP_04743841.2 | 257413684 | Roseburia intestinalis L1-82 |
| ROSEINA2194_03642 | ZP_03755203.1 | 225377982 | Roseburia inulinivorans |
| EUBREC_3075 | YP_002938937.1 | 238925420 | Eubacterium rectale ATCC 33656 |
| Pct | CAB77207.1 | 7242549 | Clostridium propionicum |
| NT01CX_2372 | YP_878445.1 | 118444712 | Clostridium novyi NT |
| Cbei_4543 | YP_001311608.1 | 150019354 | Clostridium beijerinckii |
| CBC_A0889 | ZP_02621218.1 | 168186583 | Clostridium botulinum C str. Eklund |
| ygfH | NP_417395.1 | 16130821 | Escherichia coli |
| CIT292_04485 | ZP_03838384.1 | 227334728 | Citrobacter youngae ATCC 29220 |
| SARI_04582 | YP_001573497.1 | 161506385 | Salmonella enterica subsp. arizonae serovar |
| yinte0001_14430 | ZP_04635364.1 | 238791727 | Yersinia intermedia ATCC 29909 |

| Protein | GenBank ID | GI Number | Organism |
|---|---|---|---|
| pcaI | AAN69545.1 | 24985644 | Pseudomonas putida |
| pcaJ | NP_746082.1 | 26990657 | Pseudomonas putida |
| pcaI | YP_046368.1 | 50084858 | Acinetobacter sp. ADP1 |
| pcaJ | AAC37147.1 | 141776 | Acinetobacter sp. ADP1 |
| pcaI | NP_630776.1 | 21224997 | Streptomyces coelicolor |
| pcaJ | NP_630775.1 | 21224996 | Streptomyces coelicolor |
| HPAG1_0676 | YP_627417 | 108563101 | Helicobacter pylori |
| HPAG1_0677 | YP_627418 | 108563102 | Helicobacter pylori |
| ScoA | NP_391778 | 16080950 | Bacillus subtilis |
| ScoB | NP_391777 | 16080949 | Bacillus subtilis |

A CoA transferase that can utilize acetate as the CoA acceptor is acetoacetyl-CoA transferase, encoded by the *E. coli* atoA (alpha subunit) and atoD (beta subunit) genes. Similar enzymes are identified below.

| Protein | GenBank ID | GI Number | Organism |
|---|---|---|---|
| atoA | P76459.1 | 2492994 | Escherichia coli K12 |
| atoD | P76458.1 | 2492990 | Escherichia coli K12 |
| actA | YP_226809.1 | 62391407 | Corynebacterium glutamicum ATCC 13032 |
| cg0592 | YP_224801.1 | 62389399 | Corynebacterium glutamicum ATCC 13032 |
| ctfA | NP_149326.1 | 15004866 | Clostridium acetobutylicum |
| ctfB | NP_149327.1 | 15004867 | Clostridium acetobutylicum |
| ctfA | AAP42564.1 | 31075384 | Clostridium saccharoperbutylacetonicum |
| ctfB | AAP42565.1 | 31075385 | Clostridium saccharoperbutylacetonicum |

Additional exemplary transferase candidates are catalyzed by the gene products of cat1, cat2, and cat3 of *Clostridium kluyveri* which have been shown to exhibit succinyl-CoA, 4-hydroxybutyryl-CoA, and butyryl-CoA transferase activity, respectively. Similar CoA transferase activities are identified below.

| Protein | GenBank ID | GI Number | Organism |
|---|---|---|---|
| cat1 | P38946.1 | 729048 | Clostridium kluyveri |
| cat2 | P38942.2 | 172046066 | Clostridium kluyveri |
| cat3 | EDK35586.1 | 146349050 | Clostridium kluyveri |
| TVAG_395550 | XP_001330176 | 123975034 | Trichomonas vaginalis G3 |
| Tb11.02.0290 | XP_828352 | 71754875 | Trypanosoma brucei |

The glutaconate-CoA-transferase (EC 2.8.3.12) enzyme from anaerobic bacterium Acidaminococcus fermentans reacts with diacid glutaconyl-CoA and 3-butenoyl-CoA (Mack et al., FEBS Lett. 405:209-212 (1997)). The genes encoding this enzyme are gctA and gctB. These proteins are identified below.

| Protein | GenBank ID | GI Number | Organism |
|---|---|---|---|
| gctA | CAA57199.1 | 559392 | Acidaminococcus fermentans |
| gctB | CAA57200.1 | 559393 | Acidaminococcus fermentans |

EC 6.2.1.a CoA synthase (Acid-thiol ligase). The conversion of acyl-CoA substrates to their acid products can be catalyzed by a CoA acid-thiol ligase or CoA synthetase in the 6.2.1 family of enzymes, several of which are reversible. Several enzymes catalyzing CoA acid-thiol ligase or CoA synthetase activities have been described in the literature and represent suitable candidates for these steps.

For example, ADP-forming acetyl-CoA synthetase (ACD, EC 6.2.1.13) is an enzyme that couples the conversion of acyl-CoA esters to their corresponding acids with the concomitant synthesis of ATP. The enzymes from A. fulgidus, H marismortui and P. aerophilum have all been cloned, functionally expressed, and characterized in E. coli (Brasen and Schonheit, supra; Musfeldt and Schonheit, J Bacteriol. 184:636-644 (2002)). An additional candidate is succinyl-CoA synthetase, encoded by sucCD of E. coli and LSC1 and LSC2 genes of Saccharomyces cerevisiae. These enzymes catalyze the formation of succinyl-CoA from succinate with the concomitant consumption of one ATP in a reaction which is reversible in vivo (Buck et al., Biochemistry 24:6245-6252 (1985)). Exemplary enzyme are below.

| Protein | GenBank ID | GI Number | Organism |
|---|---|---|---|
| AF1211 | NP_070039.1 | 11498810 | Archaeoglobus fulgidus |
| AF1983 | NP_070807.1 | 11499565 | Archaeoglobus fulgidus |
| Scs | YP_135572.1 | 55377722 | Haloarcula marismortui |
| PAE3250 | NP_560604.1 | 18313937 | Pyrobaculum aerophilum str. IM2 |
| sucC | NP_415256.1 | 16128703 | Escherichia coli |
| sucD | AAC73823.1 | 1786949 | Escherichia coli |
| LSC1 | NP_014785 | 6324716 | Saccharomyces cerevisiae |
| LSC2 | NP_011760 | 6321683 | Saccharomyces cerevisiae |
| paaF | AAC24333.2 | 22711873 | Pseudomonas putida |
| matB | AAC83455.1 | 3982573 | Rhizobium leguminosarum |

Another candidate enzyme for these steps is 6-carboxy-hexanoate-CoA ligase, also known as pimeloyl-CoA ligase (EC 6.2.1.14), which naturally activates pimelate to pimeloyl-CoA during biotin biosynthesis in gram-positive bacteria. Exemplary enzymes are below.

| Protein | GenBank ID | GI Number | Organism |
|---|---|---|---|
| bioW | NP_390902.2 | 50812281 | Bacillus subtilis |
| bioW | CAA10043.1 | 3850837 | Pseudomonas mendocina |
| bioW | P22822.1 | 115012 | Bacillus sphaericus |

Additional CoA-ligases are listed below.

| Protein | Accession No. | GI No. | Organism |
|---|---|---|---|
| phI | CAJ15517.1 | 77019264 | Penicillium chrysogenum |
| phIB | ABS19624.1 | 152002983 | Penicillium chrysogenum |
| paaF | AAC24333.2 | 22711873 | Pseudomonas putida |
| bioW | NP_390902.2 | 50812281 | Bacillus subtilis |
| AACS | NP_084486.1 | 21313520 | Mus musculus |
| AACS | NP_076417.2 | 31982927 | Homo sapiens |

Like enzymes in other classes, certain enzymes in the EC class 6.2.1 have been determined to have broad substrate specificity. The acyl CoA ligase from Pseudomonas putida has been demonstrated to work on several aliphatic substrates including acetic, propionic, butyric, valeric, hexanoic, heptanoic, and octanoic acids and on aromatic compounds such as phenylacetic and phenoxyacetic acids (Fernandez-Valverde et al., Applied and Environmental Microbiology 59:1149-1154 (1993)). A related enzyme, malonyl CoA synthetase (6.3.4.9) from Rhizobium trifolii could convert several diacids, namely, ethyl-, propyl-, allyl-, isopropyl-, dimethyl-, cyclopropyl-, cyclopropylmethylene-, cyclobutyl-, and benzyl-malonate into their corresponding monothioesteis (Pohl et al., J. Am. Chem. Soc. 123:5822-5823 (2001)).

M. Crotonate Reductase. A suitable enzyme activity is an 1.2.1.e Oxidoreductase (acid to aldehyde), which include the following.

The conversion of an acid to an aldehyde is thermodynamically unfavorable and typically requires energy-rich cofactors and multiple enzymatic steps. Direct conversion of the acid to aldehyde by a single enzyme is catalyzed by an acid reductase enzyme in the 1.2.1 family. Exemplary acid reductase enzymes include carboxylic acid reductase, alpha-aminoadipate reductase and retinoic acid reductase. Carboxylic acid reductase (CAR), found in Nocardia iowensis, catalyzes the magnesium, ATP and NADPH-dependent reduction of carboxylic acids to their corresponding aldehydes. CAR requires post-translational activation by a phosphopantetheine transferase (PPTase) that converts the inactive apo-enzyme to the active holo-enzyme (Hansen et al., Appl. Environ. Microbiol 75:2765-2774 (2009)). Expression of the npt gene, encoding a specific PPTase, product improved activity of the enzyme. Exemplary enzymes include those below.

| Gene | GenBank Accession No. | GI No. | Organism |
|---|---|---|---|
| car | AAR91681.1 | 40796035 | Nocardia iowensis |
| npt | ABI83656.1 | 114848891 | Nocardia iowensis |
| griC | YP_001825755.1 | 182438036 | Streptomyces griseus |
| griD | YP_001825756.1 | 182438037 | Streptomyces griseus |

Additional car and npt genes can be identified based on sequence homology.

| Gene name | GI No. | GenBank Accession No. | Organism |
|---|---|---|---|
| fadD9 | 121638475 | YP_978699.1 | *Mycobacterium bovis* BCG |
| BCG_2812c | 121638674 | YP_978898.1 | *Mycobacterium bovis* BCG |
| nfa20150 | 54023983 | YP_118225.1 | *Nocardia farcinica* IFM 10152 |
| nfa40540 | 54026024 | YP_120266.1 | *Nocardia farcinica* IFM 10152 |
| SGR_6790 | 182440583 | YP_001828302.1 | *Streptomyces griseus* subsp. *griseus* NBRC 13350 |
| SGR_665 | 182434458 | YP_001822177.1 | *Streptomyces griseus* subsp. *griseus* NBRC 13350 |
| MSMEG_2956 | YP_887275.1 | YP_887275.1 | *Mycobacterium smegmatis* MC2 155 |
| MSMEG_5739 | YP_889972.1 | 118469671 | *Mycobacterium smegmatis* MC2 155 |
| MSMEG_2648 | YP_886985.1 | 118471293 | *Mycobacterium smegmatis* MC2 155 |
| MAP1040c | NP_959974.1 | 41407138 | *Mycobacterium avium* subsp. *paratuberculosis* K-10 |
| MAP2899c | NP_961833.1 | 41408997 | *Mycobacterium avium* subsp. *paratuberculosis* K-10 |
| MMAR_2117 | YP_001850422.1 | 183982131 | *Mycobacterium marinum* M |
| MMAR_2936 | YP_001851230.1 | 183982939 | *Mycobacterium marinum* M |
| MMAR_1916 | YP_001850220.1 | 183981929 | *Mycobacterium marinum* M |
| TpauDRAFT_33060 | ZP_04027864.1 | 227980601 | *Tsukamurella paurometabola* DSM 20162 |
| TpauDRAFT_20920 | ZP_04026660.1 | ZP_04026660.1 | *Tsukamurella paurometabola* DSM 20162 |
| CPCC7001_1320 | ZP_05045132.1 | 254431429 | *Cyanobium* PCC7001 |
| DDBDRAFT_0187729 | XP_636931.1 | 66806417 | *Dictyostelium discoideum* AX4 |

An enzyme with similar characteristics, alpha-aminoadipate reductase (AAR, EC 1.2.1.31), participates in lysine biosynthesis pathways in some fungal species. Like CAR, this enzyme utilizes magnesium and requires activation by a PPTase. Enzyme candidates for AAR and its corresponding PPTase are below.

| Gene | GenBank Accession No. | GI No. | Organism |
|---|---|---|---|
| LYS2 | AAA34747.1 | 171867 | *Saccharomyces cerevisiae* |
| LYS5 | P50113.1 | 1708896 | *Saccharomyces cerevisiae* |
| LYS2 | AAC02241.1 | 2853226 | *Candida albicans* |
| LYS5 | AAO26020.1 | 28136195 | *Candida albicans* |
| Lys1p | P40976.3 | 13124791 | *Schizosaccharomyces pombe* |
| Lys7p | Q10474.1 | 1723561 | *Schizosaccharomyces pombe* |
| Lys2 | CAA74300.1 | 3282044 | *Penicillium chrysogenum* |

N. Crotonaldehyde Reductase. A suitable enzyme activity is provided by an EC 1.1.1.a Oxidoreductase (oxo to alcohol). EC 1.1.1.a Oxidoreductase (oxo to alcohol) includes the following:

The reduction of glutarate semialdehyde to 5-hydroxyvalerate by glutarate semialdehyde reductase entails reduction of an aldehyde to its corresponding alcohol. Enzymes with glutarate semialdehyde reductase activity include those below.

| PROTEIN | GENBANK ID | GI NUMBER | ORGANISM |
|---|---|---|---|
| ATEG_00539 | XP_001210625.1 | 115491995 | *Aspergillus terreus* NIH2624 |
| 4hbd | AAK94781.1 | 15375068 | *Arabidopsis thaliana* |

Additional genes encoding enzymes that catalyze the reduction of an aldehyde to alcohol (i.e., alcohol dehydrogenase or equivalently aldehyde reductase) include those below. The enzyme candidates described previously for catalyzing the reduction of methylglyoxal to acetol or lactaldehyde are also suitable lactaldehyde reductase enzyme candidates.

| Protein | GENBANK ID | GI NUMBER | ORGANISM |
|---|---|---|---|
| alrA | BAB12273.1 | 9967138 | *Acinetobacter* sp. strain M-1 |
| ADH2 | NP_014032.1 | 6323961 | *Saccharomyces cerevisiae* |
| yqhD | NP_417484.1 | 16130909 | *Escherichia coli* |
| fucO | NP_417279.1 | 16130706 | *Escherichia coli* |
| bdh I | NP_349892.1 | 15896543 | *Clostridium acetobutylicum* |
| bdh II | NP_349891.1 | 15896542 | *Clostridium acetobutylicum* |
| adhA | YP_162971.1 | 56552132 | *Zymomonas mobilis* |
| bdh | BAF45463.1 | 124221917 | *Clostridium saccharoperbutylacetonicum* |
| Cbei_1722 | YP_001308850 | 150016596 | *Clostridium beijerinckii* |
| Cbei_2181 | YP_001309304 | 150017050 | *Clostridium beijerinckii* |
| Cbei_2421 | YP_001309535 | 150017281 | *Clostridium beijerinckii* |
| GRE3 | P38715.1 | 731691 | *Saccharomyces cerevisiae* |
| ALD2 | CAA89806.1 | 825575 | *Saccharomyces cerevisiae* |
| ALD3 | NP_013892.1 | 6323821 | *Saccharomyces cerevisiae* |
| ALD4 | NP_015019.1 | 6324950 | *Saccharomyces cerevisiae* |
| ALD5 | NP_010996.2 | 330443526 | *Saccharomyces cerevisiae* |
| ALD6 | ABX39841.1 | 160415767 | *Saccharomyces cerevisiae* |
| HFD1 | Q04458.1 | 2494079 | *Saccharomyces cerevisiae* |
| GOR1 | NP_014125.1 | 6324055 | *Saccharomyces cerevisiae* |

| Protein | GENBANK ID | GI NUMBER | ORGANISM |
| --- | --- | --- | --- |
| YPL113C | AAB68248.1 | 1163100 | *Saccharomyces cerevisiae* |
| GCY1 | CAA99318.1 | 1420317 | *Saccharomyces cerevisiae* |

Enzymes exhibiting 4-hydroxybutyrate dehydrogenase activity (EC 1.1.1.61) also fall into this category and exemplary enzymes are below.

| PROTEIN | GENBANK ID | GI NUMBER | ORGANISM |
| --- | --- | --- | --- |
| 4hbd | YP_726053.1 | 113867564 | *Ralstonia eutropha* H16 |
| 4hbd | L21902.1 | 146348486 | *Clostridium kluyveri* DSM 555 |
| adhI | AAR91477.1 | 40795502 | *Geobacillus thermoglucosidasius* |

Another exemplary aldehyde reductase is methylmalonate semialdehyde reductase, also known as 3-hydroxyisobutyrate dehydrogenase (EC 1.1.1.31). This enzyme participates in valine, leucine and isoleucine degradation and has been identified in bacteria, eukaryotes, and mammals. Exemplary enzymes include those below.

| PROTEIN | GENBANK ID | GI NUMBER | ORGANISM |
| --- | --- | --- | --- |
| P84067 | P84067 | 75345323 | *Thermus thermophilus* |
| 3hidh | P31937.2 | 12643395 | *Homo sapiens* |
| 3hidh | P32185.1 | 416872 | *Oryctolagus cuniculus* |
| mmsB | NP_746775.1 | 26991350 | *Pseudomonas putida* |
| mmsB | P28811.1 | 127211 | *Pseudomonas aeruginosa* |
| dhat | Q59477.1 | 2842618 | *Pseudomonas putida* |

There exist several exemplary alcohol dehydrogenases that convert a ketone to a hydroxyl functional group. Two such enzymes from *E. coli* are encoded by malate dehydrogenase (mdh) and lactate dehydrogenase (ldhA). Exemplary enzymes include those below.

| Protein | Genbank ID | GI Number | Organism |
| --- | --- | --- | --- |
| mdh | AAC76268.1 | 1789632 | *Escherichia coli* |
| ldhA | NP_415898.1 | 16129341 | *Escherichia coli* |
| ldh | YP_725182.1 | 113866693 | *Ralstonia eutropha* |
| bdh | AAA58352.1 | 177198 | *Homo sapiens* |
| adh | AAA23199.2 | 60592974 | *Clostridium beijerinckii* NRRL B593 |
| adh | P14941.1 | 113443 | *Thermoanaerobacter brockii* HTD4 |
| sadh | CAD36475 | 21615553 | *Rhodococcus ruber* |
| adhA | AAC25556 | 3288810 | *Pyrococcus furiosus* |

A number of organisms encode genes that catalyze the reduction of 3-oxobutanol to 1,3-butanediol, including those belonging to the genus *Bacillus*, *Brevibacterium*, *Candida*, and *Klebsiella* among others, as described by Matsuyama et al. *J Mol Cat B Enz*, 11:513-521(2001). One of these enzymes, SADH from *Candida parapsilosis*, was cloned and characterized in *E. coli*. A mutated *Rhodococcus* phenylacetaldehyde reductase (Sar268) and a *Leifonia* alcohol dehydrogenase have also been shown to catalyze this transformation at high yields (Itoh et al., *Appl. Microbiol Biotechnol.* 75:1249-1256 (2007)).

| Protein | Genbank ID | GI Number | Organism |
| --- | --- | --- | --- |
| sadh | BAA24528.1 | 2815409 | *Candida parapsilosis* |

O. Crotyl Alcohol Kinase. Crotyl alcohol kinase enzymes catalyze the transfer of a phosphate group to the hydroxyl group of crotyl alcohol. The enzymes described below naturally possess such activity or can be engineered to exhibit this activity. Kinases that catalyze transfer of a phosphate group to an alcohol group are members of the EC 2.7.1 enzyme class. The table below lists several useful kinase enzymes in the EC 2.7.1 enzyme class.

| Enzyme Commission Number | Enzyme Name |
| --- | --- |
| 2.7.1.1 | hexokinase |
| 2.7.1.2 | glucokinase |
| 2.7.1.3 | ketohexokinase |
| 2.7.1.4 | fructokinase |
| 2.7.1.5 | rhamnulokinase |
| 2.7.1.6 | galactokinase |
| 2.7.1.7 | mannokinase |
| 2.7.1.8 | glucosamine kinase |
| 2.7.1.10 | phosphoglucokinase |
| 2.7.1.11 | 6-phosphofructokinase |
| 2.7.1.12 | gluconokinase |
| 2.7.1.13 | dehydrogluconokinase |
| 2.7.1.14 | sedoheptulokinase |
| 2.7.1.15 | ribokinase |
| 2.7.1.16 | ribulokinase |
| 2.7.1.17 | xylulokinase |
| 2.7.1.18 | phosphoribokinase |
| 2.7.1.19 | phosphoribulokinase |
| 2.7.1.20 | adenosine kinase |
| 2.7.1.21 | thymidine kinase |
| 2.7.1.22 | ribosylnicotinamide kinase |
| 2.7.1.23 | NAD+ kinase |
| 2.7.1.24 | dephospho-CoA kinase |
| 2.7.1.25 | adenylyl-sulfate kinase |
| 2.7.1.26 | riboflavin kinase |
| 2.7.1.27 | erythritol kinase |
| 2.7.1.28 | triokinase |
| 2.7.1.29 | glycerone kinase |
| 2.7.1.30 | glycerol kinase |
| 2.7.1.31 | glycerate kinase |
| 2.7.1.32 | choline kinase |
| 2.7.1.33 | pantothenate kinase |
| 2.7.1.34 | pantetheine kinase |
| 2.7.1.35 | pyridoxal kinase |
| 2.7.1.36 | mevalonate kinase |
| 2.7.1.39 | homoserine kinase |
| 2.7.1.40 | pyruvate kinase |
| 2.7.1.41 | glucose-1-phosphate phosphodismutase |
| 2.7.1.42 | riboflavin phosphotransferase |
| 2.7.1.43 | glucuronokinase |
| 2.7.1.44 | galacturonokinase |
| 2.7.1.45 | 2-dehydro-3-deoxygluconokinase |
| 2.7.1.46 | L-arabinokinase |
| 2.7.1.47 | D-ribulokinase |
| 2.7.1.48 | uridine kinase |
| 2.7.1.49 | hydroxymethylpyrimidine kinase |
| 2.7.1.50 | hydroxyethylthiazole kinase |
| 2.7.1.51 | L-fuculokinase |

| Enzyme Commission Number | Enzyme Name |
| --- | --- |
| 2.7.1.52 | fucokinase |
| 2.7.1.53 | L-xylulokinase |
| 2.7.1.54 | D-arabinokinase |
| 2.7.1.55 | allose kinase |
| 2.7.1.56 | 1-phosphofructokinase |
| 2.7.1.58 | 2-dehydro-3-deoxygalactonokinase |
| 2.7.1.59 | N-acetylglucosamine kinase |
| 2.7.1.60 | N-acylmannosamine kinase |
| 2.7.1.61 | acyl-phosphate-hexose phosphotransferase |
| 2.7.1.62 | phosphoramidate-hexose phosphotransferase |
| 2.7.1.63 | polyphosphate-glucose phosphotransferase |
| 2.7.1.64 | inositol 3-kinase |
| 2.7.1.65 | scyllo-inosamine 4-kinase |
| 2.7.1.66 | undecaprenol kinase |
| 2.7.1.67 | 1-phosphatidylinositol 4-kinase |
| 2.7.1.68 | 1-phosphatidylinositol-4-phosphate 5-kinase |
| 2.7.1.69 | protein-Np-phosphohistidine-sugar phosphotransferase |
| 2.7.1.70 | identical to EC 2.7.1.37. |
| 2.7.1.71 | shikimate kinase |
| 2.7.1.72 | streptomycin 6-kinase |
| 2.7.1.73 | inosine kinase |
| 2.7.1.74 | deoxycytidine kinase |
| 2.7.1.76 | deoxyadenosine kinase |
| 2.7.1.77 | nucleoside phosphotransferase |
| 2.7.1.78 | polynucleotide 5'-hydroxyl-kinase |
| 2.7.1.79 | diphosphate-glycerol phosphotransferase |
| 2.7.1.80 | diphosphate-serine phosphotransferase |
| 2.7.1.81 | hydroxylysine kinase |
| 2.7.1.82 | ethanolamine kinase |
| 2.7.1.83 | pseudouridine kinase |
| 2.7.1.84 | alkylglycerone kinase |
| 2.7.1.85 | β-glucoside kinase |
| 2.7.1.86 | NADH kinase |
| 2.7.1.87 | streptomycin 3''-kinase |
| 2.7.1.88 | dihydrostreptomycin-6-phosphate 3'a-kinase |
| 2.7.1.89 | thiamine kinase |
| 2.7.1.90 | diphosphate-fructose-6-phosphate1-phosphotransferase |
| 2.7.1.91 | sphinganine kinase |
| 2.7.1.92 | 5-dehydro-2-deoxygluconokinase |
| 2.7.1.93 | alkylglycerol kinase |
| 2.7.1.94 | acylglycerol kinase |
| 2.7.1.95 | kanamycin kinase |
| 2.7.1.100 | S-methyl-5-thioribose kinase |
| 2.7.1.101 | tagatose kinase |
| 2.7.1.102 | hamamelose kinase |
| 2.7.1.103 | viomycin kinase |
| 2.7.1.105 | 6-phosphofructo-2-kinase |
| 2.7.1.106 | glucose-1,6-bisphosphate synthase |
| 2.7.1.107 | diacylglycerol kinase |
| 2.7.1.108 | dolichol kinase |
| 2.7.1.113 | deoxyguanosine kinase |
| 2.7.1.114 | AMP-thymidine kinase |
| 2.7.1.118 | ADP-thymidine kinase |
| 2.7.1.119 | hygromycin-B 7''-O-kinase |
| 2.7.1.121 | phosphoenolpyruvate-glycerone phosphotransferase |
| 2.7.1.122 | xylitol kinase |
| 2.7.1.127 | inositol-trisphosphate 3-kinase |
| 2.7.1.130 | tetraacyldisaccharide 4'-kinase |
| 2.7.1.134 | inositol-tetrakisphosphate 1-kinase |
| 2.7.1.136 | macrolide 2'-kinase |
| 2.7.1.137 | phosphatidylinositol 3-kinase |
| 2.7.1.138 | ceramide kinase |
| 2.7.1.140 | inositol-tetrakisphosphate 5-kinase |
| 2.7.1.142 | glycerol-3-phosphate-glucose phosphotransferase |
| 2.7.1.143 | diphosphate-purine nucleoside kinase |
| 2.7.1.144 | tagatose-6-phosphate kinase |
| 2.7.1.145 | deoxynucleoside kinase |
| 2.7.1.146 | ADP-dependent phosphofructokinase |
| 2.7.1.147 | ADP-dependent glucokinase |
| 2.7.1.148 | 4-(cytidine 5'-diphospho)-2-C-methyl-D-erythritol kinase |
| 2.7.1.149 | 1-phosphatidylinositol-5-phosphate 4-kinase |
| 2.7.1.150 | 1-phosphatidylinositol-3-phosphate 5-kinase |
| 2.7.1.151 | inositol-polyphosphate multikinase |
| 2.7.1.153 | phosphatidylinositol-4,5-bisphosphate 3-kinase |
| 2.7.1.154 | phosphatidylinositol-4-phosphate 3-kinase |
| 2.7.1.156 | adenosylcobinamide kinase |
| 2.7.1.157 | N-acetylgalactosamine kinase |
| 2.7.1.158 | inositol-pentakisphosphate 2-kinase |
| 2.7.1.159 | inositol-1,3,4-trisphosphate 5/6-kinase |
| 2.7.1.160 | 2'-phosphotransferase |
| 2.7.1.161 | CTP-dependent riboflavin kinase |
| 2.7.1.162 | N-acetylhexosamine 1-kinase |
| 2.7.1.163 | hygromycin B 4-O-kinase |
| 2.7.1.164 | O-phosphoseryl-tRNASec kinase |

Mevalonate kinase (EC 2.7.1.36) phosphorylates the terminal hydroxyl group of mevalonate. Gene candidates for this step include erg12 from *S. cerevisiae*, mvk from *Methanocaldococcus jannaschi*, MVK from *Homo sapiens*, and mvk from *Arabidopsis thaliana* col. Additional mevalonate kinase candidates include the feedback-resistant mevalonate kinase from the archeon *Methanosarcina mazei* (Primak et al, *AEM*, in press (2011)) and the Mvk protein from *Streptococcus pneumoniae* (Andreassi et al, Protein Sci, 16:983-9 (2007)). Exemplary Mvk proteins are below.

| Protein | GenBank ID | GI Number | Organism |
| --- | --- | --- | --- |
| erg12 | CAA39359.1 | 3684 | *Sachharomyces cerevisiae* |
| mvk | Q58487.1 | 2497517 | *Methanocaldococcus jannaschii* |
| mvk | AAH16140.1 | 16359371 | *Homo sapiens* |
| mvk | NP_851084.1 | 30690651 | *Arabidopsis thaliana* |
| mvk | NP_633786.1 | 21227864 | *Methanosarcina mazei* |
| mvk | NP_357932.1 | 15902382 | *Streptococcus pneumoniae* |

Glycerol kinase also phosphorylates the terminal hydroxyl group in glycerol to form glycerol-3-phosphate. This reaction occurs in several species, including *Escherichia coli, Saccharomyces cerevisiae*, and *Thermotoga maritima*. Glycerol kinases have been shown to have a wide range of substrate specificity. Crans and Whiteside studied glycerol kinases from four different organisms (*Escherichia coli, S. cerevisiae, Bacillus stearothermophilus*, and *Candida mycoderma*) (Crafts et al., *J. Am. Chem. Soc.* 107:7008-7018 (2010); Nelson et al., supra, (1999)). They studied 66 different analogs of glycerol and concluded that the enzyme could accept a range of substituents in place of one terminal hydroxyl group and that the hydrogen atom at C2 could be replaced by a methyl group. Interestingly, the kinetic constants of the enzyme from all four organisms were very similar.

| Protein | GenBank ID | GI Number | Organism |
|---|---|---|---|
| glpK | AP_003883.1 | 89110103 | Escherichia coli K12 |
| glpK1 | NP_228760.1 | 15642775 | Thermotoga maritime MSB8 |
| glpK2 | NP_229230.1 | 15642775 | Thermotoga maritime MSB8 |
| Gut1 | NP_011831.1 | 82795252 | Saccharomyces cerevisiae |

Homoserine kinase is another possible candidate. This enzyme is also present in a number of organisms including *E. coli, Streptomyces* sp, and *S. cerevisiae*. The gene candidates are:

| Protein | GenBank ID | GI Number | Organism |
|---|---|---|---|
| thrB | BAB96580.2 | 85674277 | Escherichia coli K12 |
| SACT1DRAFT_4809 | ZP_06280784.1 | 282871792 | Streptomyces sp. ACT-1 |
| Thr1 | AAA35154.1 | 172978 | Saccharomyces serevisiae |

P. 2-Butenyl-4-phosphate Kinase. 2-Butenyl-4-phosphate kinase enzymes catalyze the transfer of a phosphate group to the phosphate group of 2-butenyl-4-phosphate. The enzymes described below naturally possess such activity or can be engineered to exhibit this activity. Kinases that catalyze transfer of a phosphate group to another phosphate group are members of the EC 2.7.4 enzyme class. The table below lists several useful kinase enzymes in the EC 2.7.4 enzyme class.

| Enzyme Commission Number | Enzyme Name |
|---|---|
| 2.7.4.1 | polyphosphate kinase |
| 2.7.4.2 | phosphomevalonate kinase |
| 2.7.4.3 | adenylate kinase |
| 2.7.4.4 | nucleoside-phosphate kinase |
| 2.7.4.6 | nucleoside-diphosphate kinase |
| 2.7.4.7 | phosphomethylpyrimidine kinase |
| 2.7.4.8 | guanylate kinase |
| 2.7.4.9 | dTMP kinase |
| 2.7.4.10 | nucleoside-triphosphate-adenylate kinase |
| 2.7.4.11 | (deoxy)adenylate kinase |
| 2.7.4.12 | T2-induced deoxynucleotide kinase |
| 2.7.4.13 | (deoxy)nucleoside-phosphate kinase |
| 2.7.4.14 | cytidylate kinase |
| 2.7.4.15 | thiamine-diphosphate kinase |
| 2.7.4.16 | thiamine-phosphate kinase |
| 2.7.4.17 | 3-phosphoglyceroyl-phosphate-polyphosphate phosphotransferase |
| 2.7.4.18 | farnesyl-diphosphate kinase |
| 2.7.4.19 | 5-methyldeoxycytidine-5'-phosphate kinase |
| 2.7.4.20 | dolichyl-diphosphate-polyphosphate phosphotransferase |
| 2.7.4.21 | inositol-hexakisphosphate kinase |
| 2.7.4.22 | UMP kinase |
| 2.7.4.23 | ribose 1,5-bisphosphate phosphokinase |
| 2.7.4.24 | diphosphoinositol-pentakisphosphate kinase |
| 2.7.4.— | Farnesyl monophosphate kinase |
| 2.7.4.— | Geranyl-geranyl monophosphate kinase |
| 2.7.4.— | Phytyl-phosphate kinase |

Phosphomevalonate kinase enzymes are of particular interest Phosphomevalonate kinase (EC 2.7.4.2) catalyzes the analogous transformation to 2-butenyl-4-phosphate kinase. Exemplary enzymes include those below.

| Protein | GenBank ID | GI Number | Organism |
|---|---|---|---|
| Erg8 | AAA34596.1 | 171479 | Saccharomyces cerevisiae |
| mvaK2 | AAG02426.1 | 9937366 | Staphylococcus aureus |
| mvaK2 | AAG02457.1 | 9937409 | Streptococcus pneumoniae |
| mvaK2 | AAG02442.1 | 9937388 | Enterococcus faecalis |

Farnesyl monophosphate kinase enzymes catalyze the CTP dependent phosphorylation of farnesyl monophosphate to farnesyl diphosphate. Similarly, geranylgeranyl phosphate kinase catalyzes CTP dependent phosphorylation. Enzymes with these activities were identified in the microsomal fraction of cultured *Nicotiana tabacum* (Thai et al, *PNAS* 96:13080-5 (1999)). However, the associated genes have not been identified to date.

Q. Butadiene Synthase. Butadiene synthase catalyzes the conversion of 2-butenyl-4-diphosphate to 1,3-butadiene. The enzymes described below naturally possess such activity or can be engineered to exhibit this activity. Carbon-oxygen lyases that operate on phosphates are found in the EC 4.2.3 enzyme class. The table below lists several useful enzymes in EC class 4.2.3.

| Enzyme Commission Number | Enzyme Name |
|---|---|
| 4.2.3.15 | Myrcene synthase |
| 4.2.3.26 | Linalool synthase |
| 4.2.3.27 | Isoprene synthase |
| 4.2.3.36 | Terpentriene sythase |
| 4.2.3.46 | (E,E)-alpha-Farnesene synthase |
| 4.2.3.47 | Beta-Farnesene synthase |
| 4.2.3.49 | Nerolidol synthase |

Particularly useful enzymes include isoprene synthase, myrcene synthase and farnesene synthase. Enzyme candidates are described below.

Isoprene synthase naturally catalyzes the conversion of dimethylallyl diphosphate to isoprene, but can also catalyze the synthesis of 1,3-butadiene from 2-butenyl-4-diphosphate. Isoprene synthases can be found in several organisms including *Populus alba* (Sasaki et al., FEBS Letters, 2005, 579 (11), 2514-2518), *Pueraria montana* (Lindberg et al., *Metabolic Eng*, 12(1):70-79 (2010); Sharkey et al., *Plant Physiol.*, 137(2):700-712 (2005)), and *Populus tremula* x *Populus alba*, also called *Populus canescens* (Miller et al., Planta, 2001, 213 (3), 483-487). The crystal structure of the *Populus canescens* isoprene synthase was determined (Koksal et al, J Mol Biol 402:363-373 (2010)). Additional isoprene synthase enzymes are described in (Chotani et al., WO/2010/031079, Systems Using Cell Culture for Production of Isoprene; Cervin et al., US Patent Application 20100003716, Isoprene Synthase Variants for Improved Microbial Production of Isoprene).

| Protein | GenBank ID | GI Number | Organism |
|---|---|---|---|
| ispS | BAD98243.1 | 63108310 | Populus alba |
| ispS | AAQ84170.1 | 35187004 | Pueraria montana |
| ispS | CAC35696.1 | 13539551 | Populus tremula x Populus alba |

Myrcene synthase enzymes catalyze the dephosphorylation of geranyl diphosphate to beta-myrcene (EC 4.2.3.15). Exemplary myrcene synthases are below. These enzymes were heterologously expressed in *E. coli*.

| Protein | GenBank ID | GI Number | Organism |
|---|---|---|---|
| MST2 | ACN58229.1 | 224579303 | *Solanum lycopersicum* |
| TPS-Myr | AAS47690.2 | 77546864 | *Picea abies* |
| G-myr | O24474.1 | 17367921 | *Abies grandis* |
| TPS10 | EC07543.1 | 330252449 | *Arabidopsis thaliana* |

Farnesyl diphosphate is converted to alpha-farnesene and beta-farnesene by alpha-farnesene synthase and beta-farnesene synthase, respectively. Exemplary alpha-farnesene synthase enzymes include those below.

| Protein | GenBank ID | GI Number | Organism |
|---|---|---|---|
| TPS03 | A4FVP2.1 | 205829248 | *Arabidopsis thaliana* |
| TPS02 | P0CJ43.1 | 317411866 | *Arabidopsis thaliana* |
| TPS-Far | AAS47697.1 | 44804601 | *Picea abies* |
| afs | AAU05951.1 | 51537953 | *Cucumis sativus* |
| eafar | Q84LB2.2 | 75241161 | *Malus x domestica* |
| TPS1 | Q84ZW8.1 | 75149279 | *Zea mays* |

R Crotyl Alcohol Diphosphokinase. Crotyl alcohol diphosphokinase enzymes catalyze the transfer of a diphosphate group to the hydroxyl group of crotyl alcohol. The enzymes described below naturally possess such activity or can be engineered to exhibit this activity. Kinases that catalyze transfer of a diphosphate group are members of the EC 2.7.6 enzyme class. The table below lists several useful kinase enzymes in the EC 2.7.6 enzyme class.

| Enzyme Commission Number | Enzyme Name |
|---|---|
| 2.7.6.1 | ribose-phosphate diphosphokinase |
| 2.7.6.2 | thiamine diphosphokinase |
| 2.7.6.3 | 2-amino-4-hydroxy-6-hydroxymethyldihydropteridine diphosphokinase |
| 2.7.6.4 | nucleotide diphosphokinase |
| 2.7.6.5 | GTP diphosphokinase |

Of particular interest are ribose-phosphate diphosphokinase enzymes; exemplary enzymes are below.

| Protein | GenBank ID | GI Number | Organism |
|---|---|---|---|
| prs | NP_415725.1 | 16129170 | *Escherichia coli* |
| prsA | NP_109761.1 | 13507812 | *Mycoplasma pneumoniae* M129 |
| TPK1 | BAH19964.1 | 222424006 | *Arabidopsis thaliona col* |
| TPK2 | BAH57065.1 | 227204427 | *Arabidopsis thaliana col* |

S. Chemical Dehydration or Crotyl Alcohol Dehydratase. Converting crotyl alcohol to butadiene using a crotyl alcohol dehydratase can include combining the activities of the enzymatic isomerization of crotyl alcohol to 3-buten-2-ol then dehydration of 3-buten-2-ol to butadiene. An exemplary bifunctional enzyme with isomerase and dehydratase activities is the linalool dehydratase/isomerase of *Castellaniella defragrans*. This enzyme catalyzes the isomerization of geraniol to linalool and the dehydration of linalool to myrcene, reactants similar in structure to crotyl alcohol, 3-buten-2-ol and butadiene (Brodkorb et al, *J Biol Chem* 285:30436-42 (2010)). Enzyme accession numbers and homologs are listed in the table below.

| Protein | GenBank ID | GI Number | Organism |
|---|---|---|---|
| Ldi | E1XUJ2.1 | 403399445 | *Castellaniella defragrans* |
| STEHIDRAFT_68678 | EIM80109.1 | 389738914 | *Stereum hirsutum* FP-91666 SS1 |
| NECHADRAFT_82460 | XP_003040778.1 | 302883759 | *Nectria haematococca* mpVI 77-13-4 |
| AS9A_2751 | YP_004493998.1 | 333920417 | *Amycolicicoccus subflavus* DQS3-9A1 |

Alternatively, a fusion protein or protein conjugate can be generated using well know methods in the art to generate a bi-functional (dual-functional) enzyme having both the isomerase and dehydratase activities. The fusion protein or protein conjugate can include at least the active domains of the enzymes (or respective genes) of the isomerase and dehydratase reactions. For the first step, the conversion of crotyl alcohol to 3-buten-2-ol, enzymatic conversion can be catalyzed by a crotyl alcohol isomerase (classified as EC 5.4.4). A similar isomerization, the conversion of 2-methyl-3-buten-2-ol to 3-methyl-2-buten-1-ol, is catalyzed by cell extracts of *Pseudomonas putida* MB-1 (Malone et al, AEM 65 (6): 2622-30 (1999)). The extract may be used in vitro, or the protein or gene(s) associated with the isomerase activity can be isolated and used, even though they have not been identified to date.

Alternatively, either or both steps can be done by chemical conversion, or by enzymatic conversion (in vivo or in vitro), or any combination. Enzymes having the desired activity for the conversion of 3-buten-2-ol to butadiene are provided elsewhere herein.

T. Butadiene Synthase (monophosphate). Butadiene synthase (monophosphate) catalyzes the conversion of 2-butenyl-4-phosphate to 1,3-butadiene. Butadiene synthase enzymes are of the EC 4.2.3 enzyme class as described herein that possess such activity or can be engineered to exhibit this activity. Diphosphate lyase enzymes catalyze the conversion of alkyl diphosphates to alkenes. Carbon-oxygen lyases that operate on phosphates are found in the EC 4.2.3 enzyme class. The table below lists several useful enzymes in EC class 4.2.3. Exemplary enzyme candidates are also phosphate lyases.

| Enzyme Commission No. | Enzyme Name |
|---|---|
| 4.2.3.5 | Chorismate synthase |
| 4.2.3.15 | Myrcene synthase |
| 4.2.3.27 | Isoprene synthase |
| 4.2.3.36 | Terpentriene sythase |
| 4.2.3.46 | (E,E)-alpha-Farnesene synthase |
| 4.2.3.47 | Beta-Farnesene synthase |

Phosphate lyase enzymes catalyze the conversion of alkyl phosphates to alkenes. Carbon-oxygen lyases that operate on phosphates are found in the EC 4.2.3 enzyme class. The table below lists several relevant enzymes in EC class 4.2.3.

| Enzyme Commission Number | Enzyme Name |
|---|---|
| 4.2.3.5 | Chorismate synthase |
| 4.2.3.15 | Myrcene synthase |
| 4.2.3.26 | Linalool synthase |
| 4.2.3.27 | Isoprene synthase |
| 4.2.3.36 | Terpentriene sythase |
| 4.2.3.46 | (E,E)-alpha-Farnesene synthase |
| 4.2.3.47 | Beta-Farnesene synthase |
| 4.2.3.49 | Nerolidol synthase |
| 4.2.3.— | Methylbutenol synthase |

Isoprene synthase enzymes catalyzes the conversion of dimethylallyl diphosphate to isoprene. Additional isoprene synthase enzymes are below and are described in (Chotani et al., WO/2010/031079, Systems Using Cell Culture for Production of Isoprene; Cervin et al., US Patent Application 20100003716, Isoprene Synthase Variants for Improved Microbial Production of Isoprene).

| Protein | GenBank ID | GI Number | Organism |
|---|---|---|---|
| ispS | BAD98243.1 | 63108310 | *Populus alba* |
| ispS | AAQ84170.1 | 35187004 | *Pueraria montana* |
| ispS | CAC35696.1 | 13539551 | *Populus tremula* x *Populus alba* |
| Tps-MBO1 | AEB53064.1 | 328834891 | *Pinus sabiniana* |

Chorismate synthase (EC 4.2.3.5) participates in the shikimate pathway, catalyzing the dephosphorylation of 5-enolpyruvylshikimate-3-phosphate to chorismate. The enzyme requires reduced flavin mononucleotide (FMN) as a cofactor, although the net reaction of the enzyme does not involve a redox change. In contrast to the enzyme found in plants and bacteria, the chorismate synthase in fungi is also able to reduce FMN at the expense of NADPH (Macheroux et al., Planta 207:325-334 (1999)). Representative monofunctional enzymes and bifunctional fungal enzymes are below.

| Gene | GenBank Accession No. | GI No. | Organism |
|---|---|---|---|
| aroC | NP_416832.1 | 16130264 | *Escherichia coli* |
| aroC | ACH47980.1 | 197205483 | *Streptococcus pneumoniae* |
| U25818.1: 19 . . . 1317 | AAC49056.1 | 976375 | *Neurospora crassa* |
| ARO2 | CAA42745.1 | 3387 | *Saccharomyces cerevisiae* |

Myrcene synthase enzymes catalyze the dephosphorylation of geranyl diphosphate to beta-myrcene (EC 4.2.3.15). Exemplary myrcene synthases are below. These enzymes were heterologously expressed in *E. coli*.

| Protein | GenBank ID | GI Number | Organism |
|---|---|---|---|
| MST2 | ACN58229.1 | 224579303 | *Solanum lycopersicum* |
| TPS-Myr | AAS47690.2 | 77546864 | *Picea abies* |
| G-myr | O24474.1 | 17367921 | *Abies grandis* |
| TPS10 | EC07543.1 | 330252449 | *Arabidopsis thaliana* |

Farnesyl diphosphate is converted to alpha-farnesene and beta-farnesene by alpha-farnesene synthase and beta-farnesene synthase, respectively. Exemplary alpha-farnesene synthase enzymes are below.

| Protein | GenBank ID | GI Number | Organism |
|---|---|---|---|
| TPS03 | A4FVP2.1 | 205829248 | *Arabidopsis thaliana* |
| TPS02 | P0CJ43.1 | 317411866 | *Arabidopsis thaliana* |
| TPS-Far | AAS47697.1 | 44804601 | *Picea abies* |
| afs | AAU05951.1 | 51537953 | *Cucumis sativus* |
| eafar | Q84LB2.2 | 75241161 | *Malus x domestica* |
| TPS1 | Q84ZW8.1 | 75149279 | *Zea mays* |

U. Crotonyl-CoA reductase (alcohol forming) and V) 3-Hydroxybutyryl-CoA reductase (alcohol forming). The direct conversion of crotonyl-CoA and 3-hydroxybutyryl-CoA substrates to their corresponding alcohols is catalyzed by bifunctional enzymes with acyl-CoA reductase (aldehyde forming) activity and aldehyde reductase or alcohol dehydrogenase activities. Exemplary bifunctional oxidoreductases that convert an acyl-CoA to alcohol are described elsewhere herein.

FIG. 6 shows pathways for converting 1,3-butanediol to 3-buten-2-ol and/or butadiene. Enzymes in FIG. 6 are A. 1,3-butanediol kinase, B. 3-hydroxybutyrylphosphate kinase, C. 3-hydroxybutyryldiphosphate lyase, D. 1,3-butanediol diphosphokinase, E. 1,3-butanediol dehydratase, F. 3-hydroxybutyrylphosphate lyase, G. 3-buten-2-ol dehydratase or chemical reaction.

A. 1,3-Butanediol Kinase. Phosphorylation of 1,3-butanediol to 3-hydroxybutyrylphosphate is catalyzed by an alcohol kinase enzyme. Alcohol kinase enzymes catalyze the transfer of a phosphate group to a hydroxyl group. Kinases that catalyze transfer of a phosphate group to an alcohol group are members of the EC 2.7.1 enzyme class. The table herein in the section on Crotyl Alcohol Kinase lists several useful kinase enzymes in the EC 2.7.1 enzyme class.

Mevalonate kinase (EC 2.7.1.36) phosphorylates the terminal hydroxyl group of mevalonate. Gene candidates for this step include erg12 from *S. cerevisiae*, mvk from *Methanocaldococcus jannaschi*, MVK from *Homo sapiens*, and mvk from *Arabidopsis thaliana* col. Additional mevalonate kinase candidates include those described herein in the section on Crotyl Alcohol Kinase.

Glycerol kinase also phosphorylates the terminal hydroxyl group in glycerol to form glycerol-3-phosphate. Additional glycerol kinase candidates include those described herein in the section on Crotyl Alcohol Kinase.

Homoserine kinase is another similar enzyme candidate. Additional homoserine kinase candidates include those described herein in the section on Crotyl Alcohol Kinase.

B. 3-Hydroxybutyrylphosphate Kinase. Alkyl phosphate kinase enzymes catalyze the transfer of a phosphate group to the phosphate group of an alkyl phosphate. The enzymes described herein and in the section for 2-Butenyl-4-phosphate Kinase naturally possess such activity or can be engineered to exhibit this activity, and include several useful kinase enzymes in the EC 2.7.4 enzyme class.

Phosphomevalonate kinase enzymes are of particular interest. Phosphomevalonate kinase (EC 2.7.4.2) catalyzes the phosphorylation of phosphomevalonate. Exemplary candidates include those listed herein in the section 2-Butenyl-4-phosphate Kinase.

Farnesyl monophosphate kinase enzymes catalyze the CTP dependent phosphorylation of farnesyl monophosphate to farnesyl diphosphate. Similarly, geranylgeranyl phosphate kinase catalyzes CTP dependent phosphorylation. Enzymes with these activities were identified in the microsomal fraction of cultured *Nicotiana tabacum* (Thai et al, PNAS 96:13080-5 (1999)). However, the associated genes have not been identified to date.

C. 3-Hydroxybutyryldiphosphate Lyase. Diphosphate lyase enzymes catalyze the conversion of alkyl diphosphates to alkenes. Carbon-oxygen lyases that operate on phosphates are found in the EC 4.2.3 enzyme class. The table below lists several useful enzymes in EC class 4.2.3. described herein. Exemplary enzyme candidates also include phosphate lyases described herein.

| Enzyme Commission No. | Enzyme Name |
|---|---|
| 4.2.3.5 | Chorismate synthase |
| 4.2.3.15 | Myrcene synthase |
| 4.2.3.27 | Isoprene synthase |
| 4.2.3.36 | Terpentriene sythase |
| 4.2.3.46 | (E,E)-alpha-Farnesene synthase |
| 4.2.3.47 | Beta-Farnesene synthase |

D. 1,3-Butanediol dehydratase. Exemplary dehydratase enzymes suitable for dehydrating 1,3-butanediol to 3-buten-2-ol include oleate hydratases, acyclic 1,2-hydratases and linalool dehydratase. Exemplary enzyme candidates are described above.

E. 1,3-Butanediol Diphosphokinase. Diphosphokinase enzymes catalyze the transfer of a diphosphate group to an alcohol group. The enzymes described in the section on Crotyl Alcohol Diphosphokinase naturally possess such activity. Kinases that catalyze transfer of a diphosphate group are members of the EC 2.7.6 enzyme class.

Of particular interest are ribose-phosphate diphosphokinase enzymes, also described in the section on Crotyl Alcohol Diphosphokinase.

F. 3-Hydroxybutyrylphosphate Lyase. Phosphate lyase enzymes catalyze the conversion of alkyl phosphates to alkenes. Carbon-oxygen lyases that operate on phosphates are found in the EC 4.2.3 enzyme class. The section herein on Butadiene Synthase (monophosphate) enzymes describes relevant enzymes in EC class 4.2.3.

Isoprene synthase enzymes catalyzes the conversion of dimethylallyl diphosphate to isoprene and suitable enzymes are described in the section on Butadiene Synthase (monophosphate).

Chorismate synthase (EC 4.2.3.5) participates in the shikimate pathway, catalyzing the dephosphorylation of 5-enolpyruvylshikimate-3-phosphate to chorismate and suitable enzymes are described in the section on Butadiene Synthase (monophosphate).

Myrcene synthase enzymes catalyze the dephosphorylation of geranyl diphosphate to beta-myrcene (EC 4.2.3.15). Exemplary myrcene synthases are described in the section on Butadiene Synthase (monophosphate).

Farnesyl diphosphate is converted to alpha-farnesene and beta-farnesene by alpha-farnesene synthase and beta-farnesene synthase, respectively. Exemplary alpha-farnesene synthase enzymes include those described in the section on Butadiene Synthase (monophosphate).

G. G. 3-Buten-2-ol Dehydratase. Dehydration of 3-buten-2-ol to butadiene is catalyzed by a 3-buten-2-ol dehydratase enzyme or by chemical dehydration. Exemplary dehydratase enzymes suitable for dehydrating 3-buten-2-ol include oleate hydratase, acyclic 1,2-hydratase and linalool dehydratase enzymes. Exemplary enzymes are described above.

Example VIII 1,4-Butanediol Synthesis Enzymes

This Example provides genes that can be used for conversion of succinyl-CoA to 1,4-butanediol as depicted in the pathways of FIG. 7.

A) Succinyl-CoA Transferase (designated as EB1) or Succinyl-CoA Synthetase (designated as EB2A). The conversion of succinate to succinyl-CoA is catalyzed by EB1 or EB2A (synthetase or ligase). Exemplary EB1 and EB2A enzymes are described above.

B) Succinyl-CoA Reductase (aldehyde forming). Enzymes with succinyl-CoA reductase activity are encoded by sucD of *Clostridium kluyveri* (Sohling, J. Bacteriol. 178:871-880 (1996)) and sucD of *Porphyromonas gingivalis* (Takahashi, *J. Bacteriol* 182:4704-4710 (2000)). Additional succinyl-CoA reductase enzymes participate in the 3-hydroxypropionate/4-HB cycle of thermophilic archaea such as *Metallosphaera sedula* (Berg et al., Science 318:1782-1786 (2007)) and *Thermoproteus neutrophilus* (Ramos-Vera et al., J Bacteriol, 191:4286-4297 (2009)). These and other exemplary succinyl-CoA reductase enzymes are described above.

C) 4-HB Dehydrogenase (designated as EB4). Enzymes exhibiting EB4 activity (EC 1.1.1.61) have been characterized in *Ralstonia eutropha* (Bravo et al., J. Forensic Sci. 49:379-387 (2004), *Clostridium kluyveri* (Wolff and Kenealy, Protein Expr. Purif. 6:206-212 (1995)) and *Arabidopsis thaliana* (Breitkreuz et al., J. Biol. Chem. 278:41552-41556 (2003)). Other EB4 enzymes are found in *Potphyromonas gingivalis* and gbd of an uncultured bacterium. Accession numbers of these genes are listed in the table below.

| Protein | GenBank ID | GI Number | Organism |
|---|---|---|---|
| 4hbd | YP_726053.1 | 113867564 | Ralstonia eutropha H16 |
| 4hbd | L21902.1 | 146348486 | Clostridium kluyveri DSM 555 |
| 4hbd | Q94B07 | 75249805 | Arabidopsis thaliana |
| 4-hBd | NP_904964.1 | 34540485 | Porphyromonas gingivalis W83 |
| gbd | AF148264.1 | 5916168 | Uncultured bacterium |

D) 4-HB Kinase (designated as EB5). Activation of 4-HB to 4-hydroxybutyryl-phosphate is catalyzed by EB5. Phosphotransferase enzymes in the EC class 2.7.2 transform carboxylic acids to phosphonic acids with concurrent hydrolysis of one ATP. Enzymes suitable for catalyzing this reaction include butyrate kinase, acetate kinase, aspartokinase and gamma-glutamyl kinase. Other butyrate kinase enzymes are found in *C. butyricum, C. beijerinckii* and *C. tetanomorphum* (Twarog and Wolfe, *J. Bacteriol.* 86:112-117 (1963)). Aspartokinase catalyzes the ATP-dependent phosphorylation of aspartate and participates in the synthesis of several amino acids. The aspartokinase III enzyme in *E. coli*, encoded by lysC, has a broad substrate range, and the catalytic residues involved in substrate specificity have been elucidated. Exemplary enzymes are below.

| Gene | Accession No. | GI No. | Organism |
|---|---|---|---|
| buk1 | NP_349675 | 15896326 | Clostridium acetobutylicum |
| buk2 | Q97II1 | 20137415 | Clostridium acetobutylicum |
| buk2 | Q9X278.1 | 6685256 | Thermotogo maritima |
| lysC | NP_418448.1 | 16131850 | Escherichia coli |
| ackA | NP_416799.1 | 16130231 | Escherichia coli |
| proB | NP_414777.1 | 16128228 | Escherichia coli |
| buk | YP_001307350.1 | 150015096 | Clostridium beijerinckii |
| buk2 | YP_001311072.1 | 150018818 | Clostridium beijerinckii |

E) Phosphotrans-4-Hydroxybutyrylase (designated as EB6). EB6 catalyzes the transfer of the 4-hydroxybutyryl group from phosphate to CoA. Acyltransferases suitable for catalyzing this reaction include phosphotransacetylase and phosphotransbutyrylase. The pta gene from *E. coli* encodes an enzyme that can convert acetyl-phosphate into acetyl-CoA (Suzuki, *Biochim. Biophys. Acta* 191:559-569 (1969)). This enzyme can also utilize propionyl-CoA instead of acetyl-CoA (Hesslinger et al., *Mol. Microbiol.* 27:477-492 (1998)). Similarly, the ptb gene from *C. acetobutylicum* encodes an enzyme that can convert butyryl-CoA into butyryl-phosphate (Walter et al., *Gene* 134:107-111 (1993)); Huang et al., *J Mol. Microbiol. Biotechnol.* 2:33-38 (2000). Additional ptb genes can be found in Clostridial organisms, butyrate-producing bacterium L2-50 (Louis et al., *J. Bacteriol.* 186:2099-2106 (2004)) and *Bacillus megaterium* (Vazquez et al., *Curr. Microbial.* 42:345-349 (2001)).

| Gene | Accession No. | GI No. | Organism |
| --- | --- | --- | --- |
| pta | NP_416800.1 | 16130232 | *Escherichia coli* |
| ptb | NP_349676 | 15896327 | *Clostridium acetobutylicum* |
| ptb | YP_001307349.1 | 150015095 | *Clostridium beijerinckii* |
| ptb | AAR19757.1 | 38425288 | butyrate-producing bacterium L2-50 |
| ptb | CAC07932.1 | 10046659 | *Bacillus megaterium* |

F) 4-Hydroxybutyryl-CoA Reductase (aldehyde forming). Enzymes with this activity are described above.

G) 1,4-Butanediol Dehydrogenase (designated as EB8). EB8 catalyzes the reduction of 4-hydroxybutyraldehyde to 1,4-butanediol. Enzymes with 1,4-butanediol activity are listed in the table below.

| Protein | GenBank ID | GI Number | Organism |
| --- | --- | --- | --- |
| alrA | BAB12273.1 | 9967138 | *Acinetobacter* sp. strain M-1 |
| ADH2 | NP_014032.1 | 6323961 | *Saccharomyces cerevisiae* |
| fucO | NP_417279.1 | 16130706 | *Escherichia coli* |
| yqhD | NP_417484.1 | 16130909 | *Escherichia coli* |
| bdh I | NP_349892.1 | 15896543 | *Clostridium acetobutylicum* |
| bdh II | NP_349891.1 | 15896542 | *Clostridium acetobutylicum* |
| bdh | BAF45463.1 | 124221917 | *Clostridium saccharoperbutylacetonicum* |
| Cbei_1722 | YP_001308850 | 150016596 | *Clostridium beijerinckii* |
| Cbei_2181 | YP_001309304 | 150017050 | *Clostridium beijerinckii* |
| Cbei_2421 | YP_001309535 | 150017281 | *Clostridium beijerinckii* |
| 14bdh | AAC76047.1 | 1789386 | *Escherichia coli* K-12 MG1655 |
| 14bdh | YP_001309304.1 | 150017050 | *Clostridium beijerinckii* NCIMB 8052 |
| 14bdh | P13604.1 | 113352 | *Clostridium saccharobutylicum* |
| 14bdh | ZP_03760651.1 | 225405462 | *Clostridium asparagiforme* DSM 15981 |
| 14bdh | ZP_02083621.1 | 160936248 | *Clostridium bolteae* ATCC BAA-613 |
| 14bdh | YP_003845251.1 | 302876618 | *Clostridium cellulovorans* 743B |
| 14bdh | ZP_03294286.1 | 210624270 | *Clostridium hiranonis* DSM 13275 |
| 14bdh | ZP_03705769.1 | 225016577 | *Clostridium methylpentosum* DSM 5476 |
| 14bdh | YP_003179160.1 | 257783943 | *Atopobium parvulum* DSM 20469 |
| 14bdh | YP_002893476.1 | 237809036 | *Tolumonas auensis* DSM 9187 |
| 14bdh | ZP_05394983.1 | 255528157 | *Clostridium carboxidivorans* P7 |

H) Succinate Reductase. Direct reduction of succinate to succinate semialdehyde is catalyzed by a carboxylic acid reductase. Exemplary enzymes for catalyzing this transformation are also those described below and herein for K) 4-Hydroxybutyrate reductase.

I) Succinyl-CoA Reductase (alcohol forming) (designated as EB10). EB10 enzymes are bifunctional oxidoreductases that convert succinyl-CoA to 4-HB. Enzyme candidates described below and herein for M) 4-hydroxybutyryl-CoA reductase (alcohol forming) are also suitable for catalyzing the reduction of succinyl-CoA.

J) 4-Hydroxybutyryl-CoA Transferase or 4-Hydroxybutyryl-CoA Synthetase (designated as EB11). Conversion of 4-HB to 4-hydroxybutyryl-CoA is catalyzed by a CoA transferase or synthetase. EB11 enzymes include those listed below.

| Protein | GenBank ID | GI Number | Organism |
| --- | --- | --- | --- |
| cat1 | P38946.1 | 729048 | *Clostridium kluyveri* |
| cat2 | P38942.2 | 172046066 | *Clostridium kluyveri* |
| cat3 | EDK35586.1 | 146349050 | *Clostridium kluyveri* |
| TVAG_395550 | XP_001330176 | 123975034 | *Trichomonas vaginalis* G3 |
| Tb11.02.0290 | XP_828352 | 71754875 | *Trypanosoma brucei* |
| cat2 | CAB60036.1 | 6249316 | *Clostridium aminobutyricum* |
| cat2 | NP_906037.1 | 34541558 | *Porphyromonas gingivalis* W83 |

4HB-CoA synthetase catalyzes the ATP-dependent conversion of 4-HB to 4-hydroxybutyryl-CoA. AMP-forming 4-HB-CoA synthetase enzymes are found in organisms that assimilate carbon via the dicarboxylate/hydroxybutyrate cycle or the 3-hydroxypropionate/4-HB cycle. Enzymes with this activity have been characterized in *Thermoproteus neutrophilus* and *Metallosphaera sedula*. Others can be inferred by sequence homology. ADP forming CoA synthetases, such EB2A, are also suitable candidates.

| Protein | GenBank ID | GI Number | Organism |
| --- | --- | --- | --- |
| Tneu_0420 | ACB39368.1 | 170934107 | *Thermoproteus neutrophilus* |
| Caur_0002 | YP_001633649.1 | 163845605 | *Chloroflexus aurantiacus* J-10-fl |
| Cagg_3790 | YP_002465062 | 219850629 | *Chloroflexus aggregans* DSM 9485 |
| acs | YP_003431745 | 288817398 | *Hydrogenobacter thermophilus* TK-6 |
| Pisl_0250 | YP_929773.1 | 119871766 | *Pyrobaculum islandicum* DSM 4184 |
| Msed_1422 | ABP95580.1 | 145702438 | *Metallosphaera sedula* |

K) 4-11B Reductase. Reduction of 4-HB to 4-hydroxybutanal is catalyzed by a carboxylic acid reductase (CAR) such as the Car enzyme found in *Nocardia iowensis*. This enzyme and other carboxylic acid reductases are described above (see EC 1.2.1.e).

L) 4-Hydroxybutyryl-phosphate Reductase (designated as EB14). EB14 catalyzes the reduction of 4-hydroxybutyryl-phosphate to 4-hydroxybutyraldehyde. An enzyme catalyzing this transformation has not been identified to date. However, similar enzymes include phosphate reductases in the EC class 1.2.1. Exemplary phosphonate reductase enzymes include G3P dehydrogenase (EC 1.2.1.12), aspartate-semialdehyde dehydrogenase (EC 1.2.1.11) acetylglutamylphosphate reductase (EC 1.2.1.38) and glutamate-5-semialdehyde dehydrogenase (EC 1.2.1.-). Aspartate semialdehyde dehydrogenase (ASD, EC 1.2.1.11) catalyzes the NADPH-dependent reduction of 4-aspartyl phosphate to aspartate-4-semialdehyde. The *E. coli* ASD enzyme has been shown to accept the alternate substrate beta-3-methyl-aspartyl phosphate (Shames et al., *J Biol. Chem.* 259:15331-15339 (1984)). A related enzyme candidate is acetylglutamylphosphate reductase (EC 1.2.1.38), an enzyme that naturally reduces acetylglutamylphosphate to acetylglutamate-5-semialdehyde, found in *S. cerevisiae* (Pauwels et al., *Eur. J Biochem.* 270:1014-1024 (2003)), *B. subtilis* (O'Reilly et al., *Microbiology* 140 (Pt 5):1023-1025 (1994)), *E. coli* (Parsot et al., *Gene.* 68:275-283 (1988)), and other organisms. Additional phosphate reductase enzymes of *E. coli* include glyceraldehyde 3-phosphate dehydrogenase (gapA (Branlant et al., *Eur. J. Biochem.* 150:61-66 (1985))) and glutamate-5-semialdehyde dehydrogenase (proA (Smith et al., *J. Bacteriol* 157:545-551 (1984))). Genes encoding glutamate-5-semialdehyde dehydrogenase enzymes from *Salmonella typhimurium* (Mahan et al., *J Bacteriol* 156: 1249-1262 (1983)) and *Campylobacter jejuni* (Louie et al., *Mol. Gen. Genet.* 240:29-35 (1993)) were cloned and expressed in *E. coli*.

| Protein | GenBank ID | GI Number | Organism |
|---|---|---|---|
| asd | NP_417891.1 | 16131307 | *Escherichia coli* |
| asd | YP_248335.1 | 68249223 | *Haemophilus influenzae* |
| asd | AAB49996 | 1899206 | *Mycobacterium tuberculosis* |
| VC2036 | NP_231670 | 15642038 | *Vibrio cholera* |
| asd | YP_002301787.1 | 210135348 | *Heliobacter pylori* |
| ARG5,6 | NP_010992.1 | 6320913 | *Saccharomyces cerevisiae* |
| argC | NP_389001.1 | 16078184 | *Bacillus subtilis* |
| argC | NP_418393.1 | 16131796 | *Escherichia coli* |
| gapA | P0A9B2.2 | 71159358 | *Escherichia coli* |
| proA | NP_414778.1 | 16128229 | *Escherichia coli* |
| proA | NP_459319.1 | 16763704 | *Salmonella typhimurium* |
| proA | P53000.2 | 9087222 | *Campylobacter jejuni* |

M) 4-Hydroxybutyryl-CoA Reductase (alcohol forming) (designated as EB15). EB15 enzymes are bifunctional oxidoreductases that convert an 4-hydroxybutyryl-CoA to 1,4-butanediol. Enzymes with this activity include those below.

| Protein | GenBank ID | GI Number | Organism |
|---|---|---|---|
| adhE | NP_415757.1 | 16129202 | *Escherichia coli* |
| adhE2 | AAK09379.1 | 12958626 | *Clostridium acetobutylicum* |
| bdh I | NP_349892.1 | 15896543 | *Clostridium acetobutylicum* |
| bdh II | NP_349891.1 | 15896542 | *Clostridium acetobutylicum* |
| adhE | AAV66076.1 | 55818563 | *Leuconostoc mesenteroides* |
| adhE | NP_781989.1 | 28211045 | *Clostridium tetani* |
| adhE | NP_563447.1 | 18311513 | *Clostridium perfringens* |
| adhE | YP_001089483.1 | 126700586 | *Clostridium difficile* |

Example IX

Adipate, 6-Aminocaproate, Caprolactam and Hexamethylenediamine Synthesis Enzymes This Example provides genes that can be used for conversion of succinyl-CoA and acetyl-CoA to adipate, 6-aminocaproate, caprolactam and hexamethylenediamine as depicted in the pathways of FIG. 8.

FIG. 8. depicts enzymes: A) 3-oxoadipyl-CoA thiolase, B) 3-oxoadipyl-CoA reductase, C) 3-hydroxyadipyl-CoA dehydratase, D) 5-carboxy-2-pentenoyl-CoA reductase, E) adipyl-CoA reductase (aldehyde forming), F) 6-aminocaproate transaminase, or 6-aminocaproate dehydrogenase, G) 6-aminocaproyl-CoA/acyl-CoA transferase, or 6-aminocaproyl-CoA synthase, H) amidohydrolase, I) spontaneous cyclization, 6-aminocaproyl-CoA reductase (aldehyde forming), K) HMDA transaminase or HMDA dehydrogenase, L) Adipyl-CoA hydrolase, adipyl-CoA ligase, adipyl-CoA transferase, or phosphotransadipylase/adipate kinase.

Transformations depicted in FIG. 8 fall into at least 10 general categories of transformations shown in the Table below. The first three digits of each label correspond to the first three Enzyme Commission number digits which denote the general type of transformation independent of substrate specificity. Below is described a number of biochemically characterized candidate genes in each category. Specifically listed are exemplary genes that can be applied to catalyze the appropriate transformations in FIG. 8 when cloned and expressed.

| Step | Label | Function |
|---|---|---|
| FIG. 8, step B | 1.1.1.a | Oxidoreductase (ketone to hydroxyl or aldehyde to alcohol) |
| FIG. 8, steps E and J | 1.2.1.b | Oxidoreductase (acyl-CoA to aldehyde) |
| FIG. 8, step D | 1.3.1.a | Oxidoreductase operating on CH-CH donors |
| FIG. 8, steps F and K | 1.4.1.a | Oxidoreductase operating on amino acids |
| FIG. 8, step A | 2.3.1.b | Acyltransferase |
| FIG. 8, steps F and K | 2.6.1.a | Aminotransferase |
| FIG. 8, steps G and L | 2.8.3.a | Coenzyme-A transferase |
| FIG. 8, steps G and L | 6.2.1.a | Acid-thiol ligase |
| FIG. 8, Step H | 6.3.1.a/6.3.2.a | Amide synthases/peptide synthases |
| FIG. 8, step I | No enzyme required | Spontaneous cyclization |

FIG. 8, Step A—3-Oxoadipyl-CoA Thiolase.

EC 2.3.1.b Acyl transferase. The first step in the pathway combines acetyl-CoA and succinyl-CoA to form 3-oxoadipyl-CoA. Step A can involve a 3-oxoadipyl-CoA thiolase, or equivalently, succinyl CoA:acetyl CoA acyl transferase (β-ketothiolase). Since beta-ketothiolase enzymes catalyze reversible transformations, these enzymes can be employed for the synthesis of 3-oxoadipyl-CoA. For example, the ketothiolase phaA from *R. eutropha* combines two molecules of acetyl-CoA to form acetoacetyl-CoA (Sato et al., *J Biosci Bioeng* 103:38-44 (2007)). Similarly, a β-keto thiolase (bktB) has been reported to catalyze the condensation of acetyl-CoA and propionyl-CoA to form β-ketovaleryl-CoA (Slater et al., *J. Bacteriol.* 180:1979-1987 (1998)) in *R. eutropha*. The protein sequences for the above-mentioned gene products are well known in the art and can be accessed in the public databases such as GenBank using the following accession numbers.

| Gene name | GI Number | GenBank ID | Organism |
|---|---|---|---|
| PaaJ | 16129358 | NP_415915.1 | Escherichia coli |
| pcaF | 17736947 | AAL02407 | Pseudomonas knackmussii (B13) |
| phaD | 3253200 | AAC24332.1 | Pseudomonas putida |
| paaE | 106636097 | ABF82237.1 | Pseudomonas fluorescens |

These exemplary sequences can be used to identify homologue proteins in GenBank or other databases through sequence similarity searches (for example, BLASTp). The resulting homologue proteins and their corresponding gene sequences provide additional exogenous DNA sequences for transformation into E. coli or other suitable host microorganisms to generate production hosts.

For example, orthologs of paaJ from Escherichia coli K12 can be found using the following GenBank accession numbers:

| GI Number | GenBank ID | Organism |
|---|---|---|
| 152970031 | YP_001335140.1 | Klebsiella pneumoniae |
| 157371321 | YP_001479310.1 | Serratia proteamaculans |
| 3253200 | AAC24332.1 | Pseudomonas putida |

Example orthologs of pcaF from Pseudomonas knackmussii can be found using the following GenBank accession numbers:

| GI Number | GenBank ID | Organism |
|---|---|---|
| 4530443 | AAD22035.1 | Streptomyces sp. 2065 |
| 24982839 | AAN67000.1 | Pseudomonas putida |
| 115589162 | ABJ15177.1 | Pseudomonas aeruginosa |

Additional native candidate genes for the ketothiolase step include atoB, which can catalyze the reversible condensation of 2 acetyl-CoA molecules (Sato et al., J Biosci. Bioengineer. 103:38-44 (2007)), and its homology yqeF. Non-native gene candidates include those in the table below. The protein sequences for each of these exemplary gene products can be found using the following GenBank accession numbers:

| Gene Name | GenBank ID | Organism |
|---|---|---|
| atoB | NP_416728.1 | Escherichia coli |
| yqeF | NP_417321.2 | Escherichia coli |
| phaA | YP_725941 | Ralstonia eutropha |
| bktB | AAC38322.1 | Ralstonia eutropha |

| Gene Name | GenBank ID | Organism |
|---|---|---|
| thiA | NP_349476.1 | Clostridium acetobutylicum |
| thiB | NP_149242.1 | Clostridium acetobutylicum |

2-Amino-4-oxopentanoate (AKP) thiolase or AKP thiolase (AKPT) enzymes present additional candidates for performing step A. AKPT is a pyridoxal phosphate-dependent enzyme participating in ornithine degradation in Clostridium sticklandii (Jeng et al., Biochemistry 13:2898-2903 (1974); Kenklies et al., Microbiology 145:819-826 (1999)). A gene cluster encoding the alpha and beta subunits of AKPT (or-2 (ortA) and or-3 (ortB)) was recently identified and the biochemical properties of the enzyme were characterized (Fonknechten et al., J. Bacteriol. In Press (2009)). The enzyme is capable of operating in both directions and naturally reacts with the D-isomer of alanine. AKPT from Clostridium sticklandii has been characterized but its protein sequence has not yet been published. Enzymes with high sequence homology are found in Clostridium difficile, Alkaliphilus metalliredigenes QYF, Thermoanaerobacter sp. X514, and Thermoanaerobacter tengcongensis MB4 (Fonknechten et al., supra).

| Gene name | GI Number | GenBank ID | Organism |
|---|---|---|---|
| ortA (α) | 126698017 | YP_001086914.1 | Clostridium difficile 630 |
| ortB (β) | 126698018 | YP_001086915.1 | Clostridium difficile 630 |
| Amet_2368 (α) | 150390132 | YP_001320181.1 | Alkaliphilus metalliredigenes QYF |
| Amet_2369 (β) | 150390133 | YP_001320182.1 | Alkaliphilus metalliredigenes QYF |
| Teth514_1478 (α) | 167040116 | YP_001663101.1 | Thermoanaerobacter sp. X514 |
| Teth514_1479 (β) | 167040117 | YP_001663102.1 | Thermoanaerobacter sp. X514 |
| TTE1235 (α) | 20807687 | NP_622858.1 | Thermoanaerobacter tengcongensis MB4 |
| thrC (β) | 20807688 | NP_622859.1 | Thermoanaerobacter tengcongensis MB4 |

Step B—3-Oxoadipyl-CoA Reductase.

EC 1.1.1.a Oxidoreductases. Certain transformations depicted in FIG. 8 involve oxidoreductases that convert a ketone functionality to a hydroxyl group. For example, FIG. 8, step B involves the reduction of a 3-oxoacyl-CoA to a 3-hydroxyacyl-CoA.

Exemplary enzymes that can convert 3-oxoacyl-CoA molecules, such as 3-oxoadipyl-CoA, into 3-hydroxyacyl-CoA molecules, such as 3-hydroxyadipyl-CoA, include enzymes whose natural physiological roles are in fatty acid beta-oxidation or phenylacetate catabolism. For example, subunits of two fatty acid oxidation complexes in E. coli, encoded by fadB and fadJ, function as 3-hydroxyacyl-CoA dehydrogenases (Binstock et al., Methods Enzymol. 71:403-411 (1981)). Furthermore, the gene products encoded by phaC in Pseudomonas putida U (Olivera et al., Proc. Natl. Acad. Sci. USA 95:6419-6424 (1998)) and paaC in Pseudomonas fluorescens ST (Di Gennaro et al., Arch. Microbiol. 188:117-125 (2007)) catalyze the reverse reaction of step B in FIG. 8, that is, the oxidation of 3-hydroxyadipyl-CoA to form 3-oxoadipyl-CoA, during the catabolism of phenylacetate or styrene. Note that the reactions catalyzed by such enzymes are reversible. A similar transformation is also carried out by the gene product of hbd in Clostridium acetobutylicum (Atsumi et al., Metab. Eng. (epub Sep. 14, 2007); Boynton et al., J. Bacteriol. 178:3015-3024 (1996)). This enzyme converts acetoacetyl-CoA to 3-hydroxybutyryl-CoA. In addition, given the proximity in E. coli of paaH to other genes in the phenylacetate degradation operon (Nogales et al., Microbiology 153:357-365 (2007)) and the fact that paaH mutants cannot grow on phenylacetate (Ismail et al., Eur. J Biochem. 270:3047-3054 (2003)), it is expected that the E. coli paaH gene encodes a 3-hydroxyacyl-CoA dehydrogenase.

| Gene name | GI Number | GenBank ID | Organism |
|---|---|---|---|
| fadB | 119811 | P21177.2 | Escherichia coli |
| fadJ | 3334437 | P77399.1 | Escherichia coli |
| paaH | 16129356 | NP_415913.1 | Escherichia coli |
| phaC | 26990000 | NP_745425.1 | Pseudomonas putida |
| paaC | 106636095 | ABF82235.1 | Pseudomonas fluorescens |

Additional exemplary oxidoreductases capable of converting 3-oxoacyl-CoA molecules to their corresponding 3-hydroxyacyl-CoA molecules include 3-hydroxybutyryl-CoA dehydrogenases. Exemplary enzymes are shown below.

| Gene name | GI Number | GenBank ID | Organism |
|---|---|---|---|
| hbd | 18266893 | P52041.2 | Clostridium acetobutylicum |
| Hbd2 | 146348271 | EDK34807.1 | Clostridium kluyveri |
| Hbd1 | 146345976 | EDK32512.1 | Clostridium kluyveri |
| HSD17B10 | 3183024 | O02691.3 | Bos taurus |
| phbB | 130017 | P23238.1 | Zoogloea ramigera |
| phaB | 146278501 | YP_001168660.1 | Rhodobacter sphaeroides |

A number of similar enzymes have been found in other species of *Clostridia* and in *Metallosphaera sedula* (Berg et al., *Science* 318:1782-1786 (2007)).

| Gene name | GI Number | GenBank ID | Organism |
|---|---|---|---|
| hbd | 15895965 | NP_349314.1 | Clostridium acetobutylicum |
| hbd | 20162442 | AAM14586.1 | Clostridium beijerinckii |
| Msed_1423 | 146304189 | YP_001191505 | Metallosphaera sedula |
| Msed_0399 | 146303184 | YP_001190500 | Metallosphaera sedula |
| Msed_0389 | 146303174 | YP_001190490 | Metallosphaera sedula |
| Msed_1993 | 146304741 | YP_001192057 | Metallosphaera sedula |

Step C—3-Hydroxyadipyl-CoA Dehydratase. Step C can involve a 3-hydroxyadipyl-CoA dehydratase. The gene product of crt from *C. acetobutylicum* catalyzes the dehydration of 3-hydroxybutyryl-CoA to crotonyl-CoA (Atsumi et al., *Metab. Eng.* (epub Sep. 14, 2007); Boynton et al., *J. Bacteriol.* 178:3015-3024 (1996)). Homologs of this gene are strong candidates for carrying out the third step (step C) in the synthesis pathways exemplified in FIG. 8. In addition, genes known to catalyze the hydroxylation of double bonds in enoyl-CoA compounds represent additional candidates given the reversibility of such enzymatic transformations. For example, the enoyl-CoA hydratases, phaA and phaB, of *P. putida* are believed to carry out the hydroxylation of double bonds during phenylacetate catabolism (Olivera et al., *Proc. Natl. Acad. Sci. USA* 95:6419-6424 (1998)) and thus represent additional candidates for incorporation into *E. coli*. Lastly, a number of *Escherichia coli* genes have been shown to demonstrate enoyl-CoA hydratase functionality including maoC (Park and Lee, *J. Bacteriol.* 185:5391-5397 (2003)), paaF (Ismail et al., *Eur. J. Biochem.* 270:3047-3054 (2003); Park and Lee, *Biotechnol. Bioeng.* 86:681-686 (2004); Park and Lee, *Appl. Biochem. Biotechnol.* 113-116: 335-346 (2004)), and paaG (Ismail et al., supra, 2003; Park and Lee, supra, 2003; Park and Lee, supra, 2004). The protein sequences for each of these exemplary gene products can be found using the following GenBank accession numbers:

| Gene Name | GenBank ID | Organism |
|---|---|---|
| maoC | NP_415905.1 | Escherichia coli |
| paaF | NP_415911.1 | Escherichia coli |
| paaG | NP_415912.1 | Escherichia coli |
| crt | NP_349318.1 | Clostridium acetobutylicum |
| paaA | NP_745427.1 | Pseudomonas putida |
| paaB | NP_745426.1 | Pseudomonas putida |
| phaA | ABF82233.1 | Pseudomonas fluorescens |
| phaB | ABF82234.1 | Pseudomonas fluorescens |

Alternatively, beta-oxidation genes are candidates for the first three steps in adipate synthesis. Candidate genes for the proposed adipate synthesis pathway also include the native fatty acid oxidation genes of *E. coli* and their homologs in other organisms. The *E. coli* genes fadA and fadB encode a multienzyme complex that exhibits ketoacyl-CoA thiolase, 3-hydroxyacyl-CoA dehydrogenase, and enoyl-CoA hydratase activities (Yang et al., Biochem. 30:6788-6795 (1991); Yang et al., *J. Biol. Chem.* 265:10424-10429 (1990); Yang et al., J. Biol. Chem. 266:16255 (1991); Nakahigashi and Inokuchi, *Nucl. Acids Res.* 18: 4937 (1990)). These activities are mechanistically similar to the first three transformations shown in FIG. 8. The fadI and fadJ genes encode similar functions and are naturally expressed only anaerobically (Campbell et al., *Mol. Microbiol.* 47:793-805 (2003)). These gene products naturally operate to degrade short, medium, and long chain fatty-acyl-CoA compounds to acetyl-CoA, rather than to convert succinyl-CoA and acetyl-CoA into 5-carboxy-2-pentenoyl-CoA as proposed in FIG. 8. However, it is well known that the ketoacyl-CoA thiolase, 3-hydroxyacyl-CoA dehydrogenase, and enoyl-CoA hydratase enzymes catalyze reversible transformations. Furthermore, directed evolution and related approaches can be applied to tailor the substrate specificities of the native beta-oxidation machinery of *E. coli*. Thus these enzymes or homologues thereof can be applied for adipate production. If the native genes operate to degrade adipate or its precursors in vivo, the appropriate genetic modifications are made to attenuate or eliminate these functions. However, it may not be necessary since a method for producing poly[(R)-3-hydroxybutyrate] in *E. coli* that involves activating fadB, by knocking out a negative regulator, fadR, and co-expressing a non-native ketothiolase, phaA from *Ralstonia eutropha*, has been described (Sato et al., J. Biosci. Bioeng. 103:38-44 (2007)). This work clearly demonstrated that a beta-oxidation enzyme, in particular the gene product of fadB which encodes both 3-hydroxyacyl-CoA dehydrogenase and enoyl-CoA hydratase activities, can function as part of a pathway to produce longer chain molecules from acetyl-CoA precursors. The protein sequences for each of these exemplary gene products can be found using the following GenBank accession numbers:

| Gene Name | GenBank ID | Organism |
|---|---|---|
| fadA | YP_026272.1 | Escherichia coli |
| fadB | NP_418288.1 | Escherichia coli |
| fadI | NP_416844.1 | Escherichia coli |
| fadJ | NP_416843.1 | Escherichia coli |
| fadR | NP_415705.1 | Escherichia coli |

Step D—5-Carboxy-2-Pentenoyl-CoA Reductase. EC 1.3.1.a Oxidoreductase operating on CH—CH donors. Step D involves the conversion of 5-carboxy-2-pentenoyl-CoA to adipyl-CoA by 5-carboxy-2-pentenoyl-CoA reductase. Enoyl-CoA reductase enzymes are suitable enzymes for this transformation.

Whereas the ketothiolase, dehydrogenase, and enoyl-CoA hydratase steps are generally reversible, the enoyl-CoA reductase step is almost always oxidative and irreversible under physiological conditions (Hoffmeister et al., *J. Biol. Chem.* 280:4329-4338 (2005)). FadE catalyzes this likely irreversible transformation in *E. coli* (Campbell and Cronan, *J. Bacteriol.* 184:3759-3764 (2002)). The pathway can involve an enzyme that reduces a 2-enoyl-CoA intermediate, not one such as FadE that will only oxidize an acyl-CoA to a 2-enoyl-CoA compound. Furthermore, although it has been suggested that *E. coli* naturally possesses enzymes for enoyl-CoA reduction (Mizugaki et al., *J. Biochem.* 92:1649-1654 (1982); Nishimaki et al., *J. Biochem.* 95:1315-1321 (1984)), no *E. coli* gene possessing this function has been biochemically characterized.

One exemplary enoyl-CoA reductase is the gene product of bcd from *C. acetobutylicum* (Boynton et al., *J Bacteriol.* 178:3015-3024 (1996); Atsumi et al., *Metab. Eng.* 2008 10(6):305-311 (2008)(Epub Sep. 14, 2007), which naturally catalyzes the reduction of crotonyl-CoA to butyryl-CoA. Activity of this enzyme can be enhanced by expressing bcd in conjunction with expression of the *C. acetobutylicum* etfAB genes, which encode an electron transfer flavoprotein. An additional candidate for the enoyl-CoA reductase step is the mitochondrial enoyl-CoA reductase from *E. gracilis* (Hoffmeister et al., *J. Biol. Chem.* 280:4329-4338 (2005)). A construct derived from this sequence following the removal of its mitochondrial targeting leader sequence was cloned in *E. coli* resulting in an active enzyme (Hoffmeister et al., supra). This approach is well known to those skilled in the art of expressing eukaryotic genes, particularly those with leader sequences that may target the gene product to a specific intracellular compartment, in prokaryotic organisms. A close homolog of this gene, TDE0597, from the prokaryote *Treponema denticola* represents a third enoyl-CoA reductase which has been cloned and expressed in *E. coli* (Tucci et al., *FEBS Letters* 581:1561-1566 (2007)).

| Gene name | GI Number | GenBank ID | Organism |
| --- | --- | --- | --- |
| bcd | 15895968 | NP_349317.1 | *Clostridium acetobutylicum* |
| etfA | 15895966 | NP_349315.1 | *Clostridium acetobutylicum* |
| etfB | 15895967 | NP_349316.1 | *Clostridium acetobutylicum* |
| TER | 62287512 | Q5EU90.1 | *Euglena gracilis* |
| TDE0597 | 42526113 | NP_971211.1 | *Treponema denticola* |

Step E—Adipyl-CoA Reductase (Aldehyde Forming). EC 1.2.1.b Oxidoreductase (acyl-CoA to aldehyde). The transformation of adipyl-CoA to adipate semialdehyde in step E can involve an acyl-CoA dehydrogenases capable of reducing an acyl-CoA to its corresponding aldehyde. An EC 1.2.1.b oxidoreductase (acyl-CoA to aldehyde) provides suitable enzyme activity. Exemplary enzymes in this class are described above.

Step F—6-Aminocaproate Transaminase or 6-Aminocaproate Dehydrogenase. EC 1.4.1.a Oxidoreductase operating on amino acids. Step F depicts a reductive amination involving the conversion of adipate semialdehyde to 6-aminocaproate.

Most oxidoreductases operating on amino acids catalyze the oxidative deamination of alpha-amino acids with NAD+ or NADP+ as acceptor, though the reactions are typically reversible. Exemplary oxidoreductases operating on amino acids include glutamate dehydrogenase (deaminating), encoded by gdhA, leucine dehydrogenase (deaminating), encoded by ldh, and aspartate dehydrogenase (deaminating), encoded by nadX. The gdhA gene product from *Escherichia coli* (McPherson et al., *Nucleic. Acids Res.* 11:5257-5266 (1983); Korber et al., *J. Mol. Biol.* 234:1270-1273 (1993)), gdh from *Thermotoga maritima* (Kort et al., *Extremophiles* 1:52-60 (1997); Lebbink et al., *J. Mol. Biol.* 280:287-296 (1998); Lebbink et al., *J. Mol. Biol.* 289:357-369 (1999)), and gdhA1 from *Halobacterium salinarum* (Ingoldsby et al., *Gene.* 349:237-244 (2005)) catalyze the reversible interconversion of glutamate to 2-oxoglutarate and ammonia, while favoring NADP(H), NAD(H), or both, respectively. Exemplary enzymes are described in the table below.

| Gene name | GI Number | GenBank ID | Organism |
| --- | --- | --- | --- |
| gdhA | 118547 | P00370 | *Escherichia coli* |
| gdh | 6226595 | P96110.4 | *Thermotoga maritima* |
| gdhA1 | 15789827 | NP_279651.1 | *Halobacterium salinarum* |
| ldh | 61222614 | P0A393 | *Bacillus cereus* |
| nadX | 15644391 | NP_229443.1 | *Thermotoga maritima* |

The lysine 6-dehydrogenase (deaminating), encoded by the lysDH genes, catalyze the oxidative deamination of the epsilon-amino group of L-lysine to form 2-aminoadipate-6-semialdehyde, which in turn nonenzymatically cyclizes to form $\Delta^1$-piperideine-6-carboxylate (Misono et al., *J. Bacteriol.* 150:398-401(1982)). Exemplary enzymes are shown in the table below. Such enzymes are particularly good candidates for converting adipate semialdehyde to 6-aminocaproate given the structural similarity between adipate semialdehyde and 2-aminoadipate-6-semialdehyde.

| Gene name | GI Number | GenBank ID | Organism |
| --- | --- | --- | --- |
| lysDH | 13429872 | BAB39707 | *Geobacillus stearothermophilus* |
| lysDH | 15888285 | NP_353966 | *Agrobacterium tumefaciens* |
| lysDH | 74026644 | AAZ94428 | *Achromobacter denitrificans* |

EC 2.6.1.a Aminotransferase. Step F of FIG. 8 can also, in certain embodiments, involve the transamination of a 6-aldehyde to an amine. This transformation can be catalyzed by gamma-aminobutyrate transaminase (GABA transaminase). Exemplary enzymes are shown in the table below.

| Gene name | GI Number | GenBank ID | Organism |
| --- | --- | --- | --- |
| gabT | 16130576 | NP_417148.1 | *Escherichia coli* |
| puuE | 16129263 | NP_415818.1 | *Escherichia coli* |
| abat | 37202121 | NP_766549.2 | *Mus musculus* |
| gabT | 70733692 | YP_257332.1 | *Pseudomonas fluorescens* |
| abat | 47523600 | NP_999428.1 | *Sus scrofa* |

Additional enzyme candidates include putrescine aminotransferases or other diamine aminotransferases. Such enzymes are particularly well suited for carrying out the conversion of 6-aminocaproate semialdehyde to hexamethylenediamine. The *E. coli* putrescine aminotransferase is encoded by the ygjG gene and the purified enzyme also was able to transaminate cadaverine and spermidine (Samsonova et al., *BMC Microbiol* 3:2 (2003)). In addition, activity of this enzyme on 1,7-diaminoheptane and with amino acceptors other than 2-oxoglutarate (e.g., pyruvate, 2-oxobutanoate) has been reported (Samsonova et al., supra; Kim, K. H., *J Biol Chem* 239:783-786 (1964)). A putrescine aminotransferase with higher activity with pyruvate as the amino acceptor than alpha-ketoglutarate is the spuC gene of *Pseudomonas aeruginosa* (Lu et al., *J Bacteriol* 184:3765-3773 (2002)).

| Gene name | GI Number | GenBank ID | Organism |
|---|---|---|---|
| ygjG | 145698310 | NP_417544 | *Escherichia coli* |
| spuC | 9946143 | AAG03688 | *Pseudomonas aeruginosa* |

Yet additional candidate enzymes include beta-alanine/alpha-ketoglutarate aminotransferases which produce malonate semialdehyde from beta-alanine (WO08027742). Exemplary enzymes are shown in the table below.

| Gene name | GI Number | GenBank ID | Organism |
|---|---|---|---|
| SkyPYD4 | 98626772 | ABF58893.1 | *Saccharomyces kluyveri* |
| SkUGA1 | 98626792 | ABF58894.1 | *Saccharomyces kluyveri* |
| UGA1 | 6321456 | NP_011533.1 | *Saccharomyces cerevisiae* |
| Abat | 122065191 | P50554.3 | *Rattus norvegicus* |
| Abat | 120968 | P80147.2 | *Sus scrofa* |

Step G—6-Aminocaproyl-CoA/Acyl-CoA Transferase or 6-Aminocaproyl-CoA Synthase.

2.8.3.a Coenzyme-A transferase. CoA transferases catalyze reversible reactions that involve the transfer of a CoA moiety from one molecule to another. For example, step G can be catalyzed by a 6-aminocaproyl-CoA/Acyl CoA transferase. One candidate enzyme for these steps is the two-unit enzyme encoded by pcaI and pcaJ in *Pseudomonas*, which has been shown to have 3-oxoadipyl-CoA/succinate transferase activity ((Kaschabek and Reineke, *J. Bacteriol.* 177: 320-325 (1995); and Kaschabek. and Reineke, *J. Bacteriol.* 175:6075-6081(1993)). Similar enzymes based on homology exist in *Acinetobacter* sp. ADP1 (Kowalchuk et al., *Gene* 146:23-30 (1994)) and *Streptomyces coelicolor*. Exemplary enzymes are shown in the table below.

| Gene name | GI Number | GenBank ID | Organism |
|---|---|---|---|
| pcaI | 24985644 | AAN69545.1 | *Pseudomonas putida* |
| pcaJ | 26990657 | NP_746082.1 | *Pseudomonas putida* |
| pcaI | 50084858 | YP_046368.1 | *Acinetobacter* sp. ADP1 |
| pcaJ | 141776 | AAC37147.1 | *Acinetobacter* sp. ADP1 |
| pcaI | 21224997 | NP_630776.1 | *Streptomyces coelicolor* |
| pcaJ | 21224996 | NP_630775.1 | *Streptomyces coelicolor* |
| HPAG1_0676 | 108563101 | YP_627417 | *Helicobacter pylori* |
| HPAG1_0677 | 108563102 | YP_627418 | *Helicobacter pylori* |
| ScoA | 16080950 | NP_391778 | *Bacillus subtilis* |
| ScoB | 16080949 | NP_391777 | *Bacillus subtilis* |

A 3-oxoacyl-CoA transferase that can utilize acetate as the CoA acceptor is acetoacetyl-CoA transferase, encoded by the *E. coli* atoA (alpha subunit) and atoD (beta subunit) genes (Vanderwinkel et al., *Biochem. Biophys. Res Commun.* 33:902-908 (1968); Korolev et al., *Acta Crystallogr. D Biol Crystallogr.* 58:2116-2121(2002)). This enzyme has also been shown to transfer the CoA moiety to acetate from a variety of branched and linear acyl-CoA substrates, including isobutyrate (Matthies et al., *Appl Environ Microbiol* 58:1435-1439 (1992)), valerate (Vanderwinkel et al., supra) and butanoate (Vanderwinkel et al., supra). Exemplary enzymes are shown in the table below.

| Gene name | GI Number | GenBank ID | Organism |
|---|---|---|---|
| atoA | 2492994 | P76459.1 | *Escherichia coli* K12 |
| atoD | 2492990 | P76458.1 | *Escherichia coli* K12 |
| actA | 62391407 | YP_226809.1 | *Corynebacterium glutamicum* ATCC 13032 |
| cg0592 | 62389399 | YP_224801.1 | *Corynebacterium glutamicum* ATCC 13032 |
| ctfA | 15004866 | NP_149326.1 | *Clostridium acetobutylicum* |
| ctfB | 15004867 | NP_149327.1 | *Clostridium acetobutylicum* |
| ctfA | 31075384 | AAP42564.1 | *Clostridium saccharoperbutylacetonicum* |
| ctfB | 31075385 | AAP42565.1 | *Clostridium saccharoperbutylacetonicum* |

The above enzymes may also exhibit the desired activities on 6-aminocaproate and 6-aminocaproyl-CoA, as in step G. Nevertheless, additional exemplary transferase candidates are catalyzed by the gene products of cat1, cat2, and cat3 of *Clostridium kluyveri* which have been shown to exhibit succinyl-CoA, 4-hydroxybutyryl-CoA, and butyryl-CoA transferase activity, respectively (Seedorf et al., supra; Sohling et al., *Eur. J Biochem.* 212:121-127 (1993); Sohling et al., *J Bacteriol.* 178:871-880 (1996)).

| Gene name | GI Number | GenBank ID | Organism |
|---|---|---|---|
| cat1 | 729048 | P38946.1 | *Clostridium kluyveri* |
| cat2 | 172046066 | P38942.2 | *Clostridium kluyveri* |
| cat3 | 146349050 | EDK35586.1 | *Clostridium kluyveri* |

The glutaconate-CoA-transferase (EC 2.8.3.12) enzyme from anaerobic bacterium *Acidaminococcus fermentans* reacts with diacid glutaconyl-CoA and 3-butenoyl-CoA (Mack et al., *FEBS Lett.* 405:209-212 (1997)). The genes encoding this enzyme are gctA and gctB. This enzyme has reduced but detectable activity with other CoA derivatives including glutaryl-CoA, 2-hydroxyglutaryl-CoA, adipyl-CoA and acrylyl-CoA (Buckel et al., *Eur. J. Biochem.* 118:315-321 (1981)). The enzyme has been cloned and expressed in *E. coli* (Mack et al., *Eur. J. Biochem.* 226:41-51 (1994)).

| Gene name | GI Number | GenBank ID | Organism |
|---|---|---|---|
| gctA | 559392 | CAA57199.1 | *Acidaminococcus fermentans* |
| gctB | 559393 | CAA57200.1 | *Acidaminococcus fermentans* |

EC 6.2.1.a Acid-thiol ligase. Step G can also involve an acid-thiol ligase or synthetase functionality (the terms ligase, synthetase, and synthase are used herein interchangeably and refer to the same enzyme class). Exemplary genes encoding enzymes to carry out these transformations include the sucCD genes of *E. coli* which naturally form a succinyl-CoA synthetase complex. This enzyme complex naturally catalyzes the formation of succinyl-CoA from succinate with the contaminant consumption of one ATP, a reaction which is reversible in vivo (Buck et al., *Biochem.* 24:6245-6252 (1985)). Given the structural similarity between succinate and adipate, that is, both are straight chain dicarboxylic acids, it is reasonable to expect some activity of the sucCD enzyme on adipyl-CoA.

| Gene name | GI Number | GenBank ID | Organism |
|---|---|---|---|
| sucC | 16128703 | NP_415256.1 | Escherichia coli |
| sucD | 1786949 | AAC73823.1 | Escherichia coli |

Additional exemplary CoA-ligases include the rat dicarboxylate-CoA ligase for which the sequence is yet uncharacterized (Vamecq et al., *Biochemical Journal* 230:683-693 (1985)), either of the two characterized phenylacetate-CoA ligases from *P. chrysogenum* (Lamas-Maceiras et al., *Biochem. J.* 395:147-155 (2005); Wang et al., *Biochem Biophy Res Commun* 360(2):453-458 (2007)), the phenylacetate-CoA ligase from *Pseudomonas putida* (Martinez-Blanco et al., *J. Biol. Chem.* 265:7084-7090 (1990)), and the 6-carboxyhexanoate-CoA ligase from *Bacillus subtilis* (Bower et al., *J. Bacteriol.* 178(14):4122-4130 (1996)). Exemplary enzymes are shown in the table below

| Gene name | GI Number | GenBank ID | Organism |
|---|---|---|---|
| phl | 77019264 | CAJ15517.1 | Penicillium chrysogenum |
| phlB | 152002983 | ABS19624.1 | Penicillium chrysogenum |
| paaF | 22711873 | AAC24333.2 | Pseudomonas putida |
| bioW | 50812281 | NP_390902.2 | Bacillus subtilis |
| AACS | 21313520 | NP_084486.1 | Mus musculus |
| AACS | 31982927 | NP_076417.2 | Homo sapiens |

ADP-forming acetyl-CoA synthetase (ACD, EC 6.2.1.13) is another candidate enzyme that couples the conversion of acyl-CoA esters to their corresponding acids with the concurrent synthesis of ATP. Several enzymes with broad substrate specificities have been described in the literature. ACD I from *Archaeoglobus fulgidus*, encoded by AF1211, was shown to operate on a variety of linear and branched-chain substrates including acetyl-CoA, propionyl-CoA, butyryl-CoA, acetate, propionate, butyrate, isobutyrate, isovalerate, succinate, fumarate, phenylacetate, indoleacetate (Musfeldt et al., *J Bacteriol* 184:636-644 (2002)). The enzyme from *Haloarcula marismortui* (annotated as a succinyl-CoA synthetase) accepts propionate, butyrate, and branched-chain acids (isovalerate and isobutyrate) as substrates, and was shown to operate in the forward and reverse directions (Brasen et al., *Arch Microbiol* 182:277-287 (2004)). The ACD encoded by PAE3250 from hyperthermophilic crenarchaeon *Pyrobaculum aerophilum* showed the broadest substrate range of all characterized ACDs, reacting with acetyl-CoA, isobutyryl-CoA (preferred substrate) and phenylacetyl-CoA (Brasen et al., supra). The enzymes from *A. fulgidus, H. marismortui* and *P. aerophilum* have all been cloned, functionally expressed, and characterized in *E. coli* (Musfeldt et al., supra; Brasen et al., supra).

| Gene name | GI Number | GenBank ID | Organism |
|---|---|---|---|
| AF1211 | 11498810 | NP_070039.1 | Archaeoglobus fulgidus DSM 4304 |
| Scs | 55377722 | YP_135572.1 | Haloarcula marismortui ATCC 43049 |
| PAE3250 | 18313937 | NP_560604.1 | Pyrobaculum aerophilum str. IM2 |

Yet another option is to employ a set of enzymes with net ligase or synthetase activity. For example, phosphotransadipylase and adipate kinase enzymes are catalyzed by the gene products of buk1, buk2, and ptb from *C. acetobutylicum* (Walter et al., *Gene* 134:107-111 (1993); Huang et al., *J. Mol. Microbiol. Biotechnol.* 2:33-38 (2000)). The ptb gene encodes an enzyme that can convert butyryl-CoA into butyryl-phosphate, which is then converted to butyrate via either of the buk gene products with the concomitant generation of ATP.

| Gene name | GI Number | GenBank ID | Organism |
|---|---|---|---|
| ptb | 15896327 | NP_349676 | Clostridium acetobutylicum |
| buk1 | 15896326 | NP_349675 | Clostridium acetobutylicum |
| buk2 | 20137415 | Q97II1 | Clostridium acetobutylicum |

Step H—Amidohydrolase. EC 6.3.1.a/6.3.2.a Amide synthases/peptide synthases. The direct conversion of 6-aminocaproate to caprolactam as in step H can involve the formation of an intramolecular peptide bond. Ribosomes, which assemble amino acids into proteins during translation, are nature's most abundant peptide bond-forming catalysts. Nonribosomal peptide synthetases are peptide bond forming catalysts that do not involve messenger mRNA (Schwarzer et al., *Nat Prod. Rep.* 20:275-287 (2003)). Additional enzymes capable of forming peptide bonds are shown in the table below.

| Gene name | GI Number | GenBank ID | Organism |
|---|---|---|---|
| acsA | 60650089 | BAD90933 | Pseudomonas chlororaphis |
| puuA | 87081870 | AAC74379 | Escherichia coli |
| bls | 41016784 | Q9R8E3 | Streptomyces clavuligerus |

Step I—Spontaneous Cyclization. The conversion of 6-aminocaproyl-CoA to caprolactam can occur by spontaneous cyclization. Because 6-aminocaproyl-CoA can cyclize spontaneously to caprolactam, it eliminates the need for a dedicated enzyme for this step. A similar spontaneous cyclization is observed with 4-aminobutyryl-CoA which forms pyrrolidinone (Ohsugi et al., *J Biol Chem* 256:7642-7651 (1981)).

Step J—6-Aminocaproyl-CoA Reductase (Aldehyde Forming). The transformation of 6-aminocaproyl-CoA to 6-aminocaproate semialdehyde as in step J can involve an acyl-CoA dehydrogenases capable of reducing an acyl-CoA to its corresponding aldehyde. An EC 1.2.1.b oxidoreductase (acyl-CoA to aldehyde) provides suitable enzyme activity. Exemplary enzymes in this class are described above.

Step K—HMDA Transaminase or HMDA dehydrogenase.

EC 1.4.1.a Oxidoreductase operating on amino acids. Step K depicts a reductive animation and entails the conversion of 6-aminocaproate semialdehyde to hexamethylenediamine Most oxidoreductases operating on amino acids catalyze the oxidative deamination of alpha-amino acids with NAD+ or NADP+ as acceptor, though the reactions are typically reversible. Exemplary oxidoreductases operating on amino acids of the EC 1.4.1. class are described elsewhere herein, for example those for Step F acting on 6-aminocaproate transaminase or 6-aminocaproate dehydrogenase. The lysine 6-dehydrogenase (deaminating), encoded by the lysDH genes, catalyze the oxidative deamination of the epsilon-amino group of L-lysine to form 2-aminoadipate-6-semialdehyde, which in turn nonenzymatically cyclizes to form $\Delta^1$-piperideine-6-carboxylate (Misono et al., *J. Bacteriol.* 150:398-401 (1982)). Exemplary enzymes can be found in *Geobacillus stearothermophilus* (Heydari et al., *Appl Environ. Microbiol* 70:937-942 (2004)), *Agrobacterium tumefaciens* (Hashimoto et al., *J Biochem* 106:76-80 (1989);

Misono et al., supra), and *Achromobacter denitrificans* (Ruldeekulthamrong et al., *BMB. Rep.* 41:790-795 (2008)). Such enzymes are particularly good candidates for converting adipate semialdehyde to 6-aminocaproate given the structural similarity between adipate semialdehyde and 2-aminoadipate-6-semialdehyde.

| Gene name | GI Number | GenBank ID | Organism |
| --- | --- | --- | --- |
| lysDH | 13429872 | BAB39707 | *Geobacillus stearothermophilus* |
| lysDH | 15888285 | NP_353966 | *Agrobacterium tumefaciens* |
| lysDH | 74026644 | AAZ94428 | *Achromobacter denitrificans* |

EC 2.6.1.a Aminotransferase. Step K, in certain embodiments, can involve the transamination of a 6-aldehyde to an amine. This transformation can be catalyzed by gamma-aminobutyrate transaminase (GABA transaminase). Examples are below.

| Gene name | GI Number | GenBank ID | Organism |
| --- | --- | --- | --- |
| gabT | 16130576 | NP_417148.1 | *Escherichia coli* |
| puuE | 16129263 | NP_415818.1 | *Escherichia coli* |
| abat | 37202121 | NP_766549.2 | *Mus musculus* |
| gabT | 70733692 | YP_257332.1 | *Pseudomonas fluorescens* |
| abat | 47523600 | NP_999428.1 | *Sus scrofa* |

Additional enzyme candidates include putrescine aminotransferases or other diamine aminotransferases. Such enzymes are particularly well suited for carrying out the conversion of 6-aminocaproate semialdehyde to hexamethylenediamine Examples are described below and elsewhere herein.

| Gene name | GI Number | GenBank ID | Organism |
| --- | --- | --- | --- |
| ygjG | 145698310 | NP_417544 | *Escherichia coli* |
| spuC | 9946143 | AAG03688 | *Pseudomonas aeruginosa* |

Yet additional candidate enzymes include beta-alanine/alpha-ketoglutarate aminotransferases which produce malonate semialdehyde from beta-alanine (WO08027742). Exemplary candidates are described elsewhere herein, such as for Step F. Step L—Adipyl-CoA Hydrolase, Adipyl-CoA Ligase, Adipyl-CoA Transferase or Phosphotransadipylase/Adipate Kinase. Step L can involve adipyl-CoA synthetase (also referred to as adipate-CoA ligase), phosphotransadipylase/adipate kinase, adipyl-CoA:acetyl-CoA transferase, or adipyl-CoA hydrolase. From an energetic standpoint, it is desirable for the final step in the adipate synthesis pathway to be catalyzed by an enzyme or enzyme pair that can conserve the ATP equivalent stored in the thioester bond of adipyl-CoA. The product of the sucC and sucD genes of *E. coli*, or homologs thereof, can potentially catalyze the final transformation shown in FIG. 8 should they exhibit activity on adipyl-CoA. The sucCD genes naturally form a succinyl-CoA synthetase complex that catalyzes the formation of succinyl-CoA from succinate with the contaminant consumption of one ATP, a reaction which is reversible in vivo (Buck et al., *Biochem.* 24:6245-6252 (1985)). Given the structural similarity between succinate and adipate, that is, both are straight chain dicarboxylic acids, it is reasonable to expect some activity of the sucCD enzyme on adipyl-CoA. An enzyme exhibiting adipyl-CoA ligase activity can equivalently carry out the ATP-generating production of adipate from adipyl-CoA, here using AMP and PPi as cofactors, when operating in the opposite physiological. Exemplary CoA-ligases include the rat dicarboxylate-CoA ligase for which the sequence is yet uncharacterized (Vamecq et al., *Biochem. J.* 230:683-693 (1985)), either of the two characterized phenylacetate-CoA ligases from *P. chrysogenum* (Lamas-Maceiras et al., *Biochem. J.* 395, 147-155 (2005); Wang et al., *Biochem. Biophy. Res. Commun.* 360:453-458 (2007)), the phenylacetate-CoA ligase from *Pseudomonas putida* (Martinez-Blanco et al., *J. Biol. Chem.* 265:7084-7090 (1990)), and the 6-carboxyhexanoate-CoA ligase from *Bacillus subtilis* (Bower et al., *J. Bacteriol.* 178:4122-4130 (1996)). The protein sequences for each of these exemplary gene products can be found using the following GI numbers and/or GenBank identifiers:

| Gene name | GI Number | GenBank ID | Organism |
| --- | --- | --- | --- |
| sucC | 16128703 | NP_415256.1 | *Escherichia coli* |
| sucD | 1786949 | AAC73823.1 | *Escherichia coli* |

Another option, using phosphotransadipylase/adipate kinase, is catalyzed by the gene products of buk1, buk2, and ptb from *C. acetobutylicum* (Walter et al., *Gene* 134:107-111 (1993); Huang et al., *J. Mol. Microbiol. Biotechnol.* 2:33-38 (2000)), or homologs thereof. The ptb gene encodes an enzyme that can convert butyryl-CoA into butyryl-phosphate, which is then converted to butyrate via either of the buk gene products with the concomitant generation of ATP. The analogous set of transformations, that is, conversion of adipyl-CoA to adipyl-phosphate followed by conversion of adipyl-phosphate to adipate, can be carried out by the buk1, buk2, and ptb gene products. The protein sequences for each of these exemplary gene products can be found using the following GI numbers and/or GenBank identifiers:

| Gene name | GI Number | GenBank ID | Organism |
| --- | --- | --- | --- |
| ptb | 15896327 | NP_349676 | *Clostridium acetobutylicum* |
| buk1 | 15896326 | NP_349675 | *Clostridium acetobutylicum* |
| buk2 | 20137415 | Q97II1 | *Clostridium acetobutylicum* |

Alternatively, an acetyltransferase capable of transferring the CoA group from adipyl-CoA to acetate can be applied. Similar transformations are catalyzed by the gene products of cat1, cat2, and cat3 of *Clostridium kluyveri* which have been shown to exhibit succinyl-CoA, 4-hydroxybutyryl-CoA, and butyryl-CoA acetyltransferase activity, respectively (Sohling and Gottschalk, *J. Bacteriol.* 178:871-880 (1996); Seedorf et al., *Proc. Natl. Acad. Sci. USA* 105:2128-2133 (2008)). The protein sequences for each of these exemplary gene products can be found using the following GI numbers and/or GenBank identifiers:

| Gene name | GI Number | GenBank ID | Organism |
| --- | --- | --- | --- |
| cat1 | 729048 | P38946.1 | *Clostridium kluyveri* |
| cat2 | 172046066 | P38942.2 | *Clostridium kluyveri* |
| cat3 | 146349050 | EDK35586.1 | *Clostridium kluyveri* |

Finally, though not as desirable from an energetic standpoint, the conversion of adipyl-CoA to adipate can also be carried out by an acyl-CoA hydrolase or equivalently a thioesterase. The top *E. coli* gene candidate is tesB (Naggert et al., *J. Biol. Chem.* 266:11044-11050 (1991)), which shows high similarity to the human acot8, which is a dicarboxylic acid acetyltransferase with activity on adipyl-CoA (Westin et al., *J. Biol. Chem.* 280:38125-38132 (2005)). This activity has also been characterized in the rat liver (Deana, *Biochem. Int.* 26:767-773 (1992)). The protein sequences for each of these exemplary gene products can be found using the following GI numbers and/or GenBank identifiers:

| Gene name | GI Number | GenBank ID | Organism |
|---|---|---|---|
| tesB | 16128437 | NP_414986 | *Escherichia coli* |
| acot8 | 3191970 | CAA15502 | *Homo sapiens* |
| acot8 | 51036669 | NP_570112 | *Rattus norvegicus* |

Other native candidate genes include those in the table below. The protein sequences for each of these exemplary gene products can be found using the following GI numbers and/or GenBank identifiers:

| Gene name | GI Number | GenBank ID | Organism |
|---|---|---|---|
| tesA | 16128478 | NP_415027 | *Escherichia coli* |
| ybgC | 16128711 | NP_415264 | *Escherichia coli* |
| paaI | 16129357 | NP_415914 | *Escherichia coli* |
| ybdB | 16128580 | NP_415129 | *Escherichia coli* |

EC 2.8.3.a Coenzyme-A transferase. CoA transferases catalyze reversible reactions that involve the transfer of a CoA moiety from one molecule to another. For example, step L can be catalyzed by a adipyl-CoA transferase. One candidate enzyme for this step is the two-unit enzyme encoded by pcaI and pcaJ in *Pseudomonas*, which has been shown to have 3-oxoadipyl-CoA/succinate transferase activity (Kaschabek and Reineke, *J. Bacteriol.* 177:320-325 (1995); and Kaschabek. and Reineke, *J. Bacteriol.* 175: 6075-6081 (1993)) Similar enzymes based on homology exist in *Acinetobacter* sp. ADP1 (Kowalchuk et al., *Gene* 146:23-30 (1994)) and *Streptomyces coelicolor*. Additional exemplary succinyl-CoA:3:oxoacid-CoA transferases are present in *Helicobacter pylori* (Corthesy-Theulaz et al., *J. Biol. Chem.* 272:25659-25667 (1997)) and *Bacillus subtilis* (Stols et al., *Protein. Expr. Purif.* 53:396-403 (2007)).

| Gene name | GI Number | GenBank ID | Organism |
|---|---|---|---|
| pcaI | 24985644 | AAN69545.1 | *Pseudomonas putida* |
| pcaJ | 26990657 | NP_746082.1 | *Pseudomonas putida* |
| pcaI | 50084858 | YP_046368.1 | *Acinetobacter* sp. ADP1 |
| pcaJ | 141776 | AAC37147.1 | *Acinetobacter* sp. ADP1 |
| pcaI | 21224997 | NP_630776.1 | *Streptomyces coelicolor* |
| pcaJ | 21224996 | NP_630775.1 | *Streptomyces coelicolor* |
| HPAG1_0676 | 108563101 | YP_627417 | *Helicobacter pylori* |
| HPAG1_0677 | 108563102 | YP_627418 | *Helicobacter pylori* |
| ScoA | 16080950 | NP_391778 | *Bacillus subtilis* |
| ScoB | 16080949 | NP_391777 | *Bacillus subtilis* |

A 3-oxoacyl-CoA transferase that can utilize acetate as the CoA acceptor is acetoacetyl-CoA transferase, encoded by the *E. coli* atoA (alpha subunit) and atoD (beta subunit) genes (Vanderwinkel et al., *Biochem. Biophys. Res Commun.* 33:902-908 (1968); Korolev et al., *Acta Crystallogr. D Biol Crystallogr.* 58:2116-2121(2002)). Exemplary candidates are shown in the table below.

| Gene name | GI Number | GenBank ID | Organism |
|---|---|---|---|
| atoA | 2492994 | P76459.1 | *Escherichia coli* K12 |
| atoD | 2492990 | P76458.1 | *Escherichia coli* K12 |
| actA | 62391407 | YP_226809.1 | *Corynebacterium glutamicum* ATCC 13032 |
| cg0592 | 62389399 | YP_224801.1 | *Corynebacterium glutamicum* ATCC 13032 |
| ctfA | 15004866 | NP_149326.1 | *Clostridium acetobutylicum* |
| ctfB | 15004867 | NP_149327.1 | *Clostridium acetobutylicum* |
| ctfA | 31075384 | AAP42564.1 | *Clostridium saccharoperbutylacetonicum* |
| ctfB | 31075385 | AAP42565.1 | *Clostridium saccharoperbutylacetonicum* |

The above enzymes may also exhibit the desired activities on adipyl-CoA and adipate for step L. Nevertheless, additional exemplary transferase candidates are catalyzed by the gene products of cat1, cat2, and cat3 of *Clostridium kluyveri* which have been shown to exhibit succinyl-CoA, 4-hydroxybutyryl-CoA, and butyryl-CoA transferase activity, respectively (Seedorf et al., *Proc. Natl. Acad. Sci U.S.A* 105:2128-2133 (2008); Sohling et al., *Eur. J Biochem.* 212:121-127 (1993); Sohling et al., *J Bacteriol.* 178:871-880 (1996)).

| Gene name | GI Number | GenBank ID | Organism |
|---|---|---|---|
| cat1 | 729048 | P38946.1 | *Clostridium kluyveri* |
| cat2 | 172046066 | P38942.2 | *Clostridium kluyveri* |
| cat3 | 146349050 | EDK35586.1 | *Clostridium kluyveri* |

The glutaconate-CoA-transferase (EC 2.8.3.12) enzyme from anaerobic bacterium *Acidaminococcus fermentans* reacts with diacid glutaconyl-CoA and 3-butenoyl-CoA (Mack et al., *FEBS Lett.* 405:209-212 (1997)). The genes encoding this enzyme are gctA and gctB. This enzyme has reduced but detectable activity with other CoA derivatives including glutaryl-CoA, 2-hydroxyglutaryl-CoA, adipyl-CoA and acrylyl-CoA (Buckel et al., *Eur. J. Biochem.* 118:315-321 (1981)). The enzyme has been cloned and expressed in *E. coli* (Mack et al., *Eur. J. Biochem.* 226:41-51 (1994)).

| Gene name | GI Number | GenBank ID | Organism |
|---|---|---|---|
| gctA | 559392 | CAA57199.1 | *Acidaminococcus fermentans* |
| gctB | 559393 | CAA57200.1 | *Acidaminococcus fermentans* |

Example X

Methacrylic Acid Synthesis Enzymes

This Example provides genes that can be used for conversion of succinyl-CoA to methacrylic acid as depicted in the pathways of FIG. 9.

FIG. 9. depicts 3-Hydroxyisobutyrate and methacrylic acid production are carried out by the following enzymes: A) Methylmalonyl-CoA mutase, B) Methylmalonyl-CoA epimerase, C) Methylmalonyl-CoA reductase (aldehyde forming), D) Methylmalonate semialdehyde reductase, E) 3-hydroxyisobutyrate dehydratase, F) Methylmalonyl-CoA reductase (alcohol forming).

Step A—Methylmalonyl-CoA mutase (designated as EMA2). Methylmalonyl-CoA mutase (MCM) (EMA2) (EC 5.4.99.2) is a cobalamin-dependent enzyme that converts succinyl-CoA to methylmalonyl-CoA. In *E. coli*, the reversible adenosylcobalamin-dependent mutase participates in a three-step pathway leading to the conversion of succinate to propionate (Haller et al., *Biochemistry* 39:4622-4629 (2000)). Overexpression of the EMA2 gene candidate along with the deletion of YgfG can be used to prevent the decarboxylation of methylmalonyl-CoA to propionyl-CoA and to maximize the methylmalonyl-CoA available for MAA synthesis. EMA2 is encoded by genes scpA in *Escherichia coli* (Bobik and Rasche, *Anal. Bioanal. Chem.* 375:344-349 (2003); Haller et al., *Biochemistry* 39:4622-4629 (2000)) and mutA in *Homo sapiens* (Padovani and Banerjee, *Biochemistry* 45:9300-9306 (2006)). In several other organisms EMA2 contains alpha and beta subunits and is encoded by two genes. Exemplary gene candidates encoding the two-subunit protein are *Propionibacterium fredenreichii* sp. *shermani* mutA and mutB (Korotkova and Lidstrom, *J. Biol. Chem.* 279:13652-13658 (2004)), *Methylobacterium extorquens* mcmA and mcmB (Korotkova and Lidstrom, supra, 2004), and *Ralstonia eutropha* sbm1 and sbm2 (Peplinski et al., *Appl. Microbiol. Biotech.* 88:1145-59 (2010)). Additional enzyme candidates identified based on high homology to the *E. coli* spcA gene product are also listed below.

| Protein | GenBank ID | GI Number | Organism |
|---|---|---|---|
| scpA | NP_417392.1 | 16130818 | *Escherichia coli* K12 |
| mutA | P22033.3 | 67469281 | *Homo sapiens* |
| mutA | P11652.3 | 127549 | *Propionibacterium fredenreichii* sp. *shermanii* |
| mutB | P11653.3 | 127550 | *Propionibacterium fredenreichii* sp. *shermanii* |
| mcmA | Q84FZ1 | 75486201 | *Methylobacterium extorquens* |
| mcmB | Q6TMA2 | 75493131 | *Methylobacterium extorquens* |
| Sbm1 | YP_724799.1 | 113866310 | *Ralstonia eutropha* H16 |
| Sbm2 | YP_726418.1 | 113867929 | *Ralstonia eutropha* H16 |
| sbm | NP_838397.1 | 30064226 | *Shigella flexneri* |
| SARI_04585 | ABX24358.1 | 160867735 | *Salmonella enterica* |
| YfreA_01000861 | ZP_00830776.1 | 77975240 | *Yersinia frederiksenii* |

These sequences can be used to identify homologue proteins in GenBank or other databases through sequence similarity searches (for example, BLASTp). The resulting homologue proteins and their corresponding gene sequences provide additional exogenous DNA sequences for transformation into *E. coli* or other suitable host microorganisms to generate production hosts. Additional gene candidates include the following, which were identified based on high homology to the *E. coli* spcA gene product.

There further exists evidence that genes adjacent to the EMA2 catalytic genes contribute to maximum activity. For example, it has been demonstrated that the meaB gene from *M. extorquens* forms a complex with EMA2, stimulates in vitro mutase activity, and possibly protects it from irreversible inactivation (Korotkova and Lidstrom, *J. Biol. Chem.* 279:13652-13658 (2004)). The *M. extorquens* meaB gene product is highly similar to the product of the *E. coli* argK gene (BLASTp: 45% identity, e-value: 4e-67), which is adjacent to scpA on the chromosome. No sequence for a meaB homolog in *P. freudenreichii* is catalogued in GenBank. However, the *Propionibacterium acnes* KPA171202 gene product, YP_055310.1, is 51% identical to the *M. extorquens* meaB protein and its gene is also adjacent to the EMA2 gene on the chromosome. A similar gene is encoded by H16_B1839 of *Ralstonia eutropha* H16.

| Gene | GenBank ID | GI Number | Organism |
|---|---|---|---|
| argK | AAC75955.1 | 1789285 | *Escherichia coli* K12 |
| PPA0597 | YP_055310.1 | 50842083 | *Propionibacterium acnes* |
| KPA171202 | 2QM8_B | 158430328 | *Methylobacterium extorquens* |
| H16_B1839 | YP_841351.1 | 116695775 | *Ralstonia eutropha* H16 |

*E. coli* can synthesize adenosylcobalamin, a necessary cofactor for this reaction, only when supplied with the intermediates cobinamide or cobalamin (Lawrence and Roth. *J. Bacteriol.* 177:6371-6380 (1995); Lawrence and Roth, *Genetics* 142:11-24 (1996)). Alternatively, the ability to synthesize cobalamins de novo has been conferred upon *E. coli* following the expression of heterologous genes (Raux et al., *J. Bacteriol.* 178:753-767 (1996)).

Alternatively, isobutyryl-CoA mutase (ICM) (EC 5.4.99.13) could catalyze the proposed transformation shown in FIG., step B. ICM is a cobalamin-dependent methylmutase in the EMA2 family that reversibly rearranges the carbon backbone of butyryl-CoA into isobutyryl-CoA (Ratnatilleke et al., *J. Biol. Chem.* 274:31679-31685 (1999)). A recent study of a novel ICM in *Methylibium petroleiphilum*, along with previous work, provides evidence that changing a single amino acid near the active site alters the substrate specificity of the enzyme (Ratnatilleke et al., *J. Biol. Chem.* 274:31679-31685 (1999); Rohwerder et al., *Appl. Environ. Microbiol.* 72:4128-4135. (2006)). This indicates that, if a native enzyme is unable to catalyze or exhibits low activity for the conversion of 4HB-CoA to 3HIB-CoA, the enzyme can be rationally engineered to increase this activity. Exemplary genes/proteins are identified below.

| Gene | GenBank ID | GI Number | Organism |
|---|---|---|---|
| icmA | CAB40912.1 | 4585853 | *Streptomyces coelicolor* A3(2) |
| Mpe_B0541 | YP_001023546.1 | 124263076 | *Methylibium petroleiphilum* PM1 |
| icm | AAC08713.1 | 3002492 | *Streptomyces cinnamonensis* |
| icmB | CAB59633.1 | 6137077 | *Streptomyces cinnamonensis* |
| icmA | NP_824008.1 | 29829374 | *Streptomyces avermitilis* |
| icmB | NP_824637.1 | 29830003 | *Streptomyces avermitilis* |

Step B—Methylmalonyl-CoA epimerase (designated as EMA3). Methylmalonyl-CoA epimerase (MMCE) (EMA3) is the enzyme that interconverts (R)-methylmalonyl-CoA and (S)-methylmalonyl-CoA. EMA3 is an essential enzyme in the breakdown of odd-numbered fatty acids and of the amino acids valine, isoleucine, and methionine. EMA3 activity is not believed to be encoded in the *E. coli* genome (Boynton et al., *J. Bacteriol.* 178:3015-3024 (1996)), but is present in other organisms; gene candidates include those shown below. This enzymatic step may or may not be necessary depending upon the stereospecificity of the enzyme or enzymes used for the conversion of methylmalonyl-CoA to 3-HIB. These genes/proteins are described below.

| Gene | GenBank ID | GI Number | Organism |
|---|---|---|---|
| YqjC | NP_390273 | 255767522 | Bacillus subtilis |
| MCEE | Q96PE7.1 | 50401130 | Homo sapiens |
| Mcee_predicted | NP_001099811.1 | 157821869 | Rattus norvegicus |
| AF454511 | AAL57846.1 | 18042135 | Propionibacterium fredenreichii sp. shermanii |
| Mmce | AAT92095.1 | 51011368 | Caenorhabditis elegans |
| AE016877 | AAP08811.1 | 29895524 | Bacillus cereus ATCC 14579 |

Step C—Methylmalonyl-CoA reductase (aldehyde forming) (designated as EMA4). The reduction of methylmalonyl-CoA to its corresponding aldehyde, methylmalonate semialdehyde, is catalyzed by a CoA-dependent aldehyde dehydrogenase (EC 1.2.1.-). Conversion of methylmalonyl-CoA to methylmalonic semialdehyde, is accomplished by a CoA-dependent aldehyde dehydrogenase. An enzyme encoded by a malonyl-CoA reductase gene from *Sulfolobus tokodaii* (Alber et. al., *J. Bacteriol.* 188(24):8551-8559 (2006)), has been shown to catalyze the conversion of methylmalonyl-CoA to its corresponding aldehyde (WO2007141208). A similar enzyme exists in *Metallosphaera sedula* (Alber et al., *J. Bacteriol.* 188(24):8551-8559 (2006)). Several additional CoA dehydrogenases are capable also of reducing an acyl-CoA to its corresponding aldehyde. The reduction of methylmalonyl-CoA to its corresponding aldehyde, methylmalonate semialdehyde, is catalyzed by a CoA-dependent aldehyde dehydrogenase. Exemplary enzymes include fatty acyl-CoA reductase, succinyl-CoA reductase (EC 1.2.1.76), acetyl-CoA reductase and butyryl-CoA reductase. Exemplary fatty acyl-CoA reductase enzymes are shown below. Also known is a CoA- and NADP-dependent succinate semialdehyde dehydrogenase (also referred to as succinyl-CoA reductase) encoded by the sucD gene in *Clostridium kluyveri* (Sohling and Gottschalk, *J. Bacteriol.* 178:871-880 (1996); Sohling and Gottschalk, *J. Bacteriol.* 178:871-880 (1996)) and sucD of *P. gingivalis* (Takahashi, *J. Bacteriol* 182:4704-4710 (2000)). Additional succinyl-CoA reductase enzymes participate in the 3-hydroxypropionate/4-hydroxybutyrate cycle of thermophilic archaea. Exemplary enzymes are shown in the following table.

| Protein | GenBank ID | GI Number | Organism |
|---|---|---|---|
| acr1 | YP_047869.1 | 50086359 | Acinetobacter calcoaceticus |
| acr1 | AAC45217 | 1684886 | Acinetobacter baylyi |
| acr1 | BAB85476.1 | 18857901 | Acinetobacter sp. Strain M-1 |
| MSED_0709 | YP_001190808.1 | 146303492 | Metallosphaera sedula |
| Tneu_0421 | | | Thermoproteus neutrophilus |
| sucD | P38947.1 | 172046062 | Clostridium kluyveri |
| sucD | NP_904963.1 | 34540484 | Porphyromonas gingivalis |
| bphG | BAA03892.1 | 425213 | Pseudomonas sp |
| adhE | AAV66076.1 | 55818563 | Leuconostoc mesenteroides |
| bld | AAP42563.1 | 31075383 | Clostridium saccharoperbutylacetonicum |

An additional enzyme type that converts an acyl-CoA to its corresponding aldehyde is malonyl-CoA reductase which transforms malonyl-CoA to malonic semialdehyde. Malonyl-CoA reductase is a key enzyme in autotrophic carbon fixation via the 3-hydroxypropionate cycle in thermoacidophilic archaeal bacteria (Berg, Science 318:1782-1786 (2007); and Thauer, *Science* 318:1732-1733 (2007)). The enzyme utilizes NADPH as a cofactor and has been characterized in *Metallosphaera* and *Sulfolobus* sp. (Alber et al., *J. Bacteriol.* 188:8551-8559 (2006); and Bugler, *J. Bacteriol.* 184:2404-2410 (2002)). Exemplary enzymes include those in the following table.

| Gene | GenBank ID | GI Number | Organism |
|---|---|---|---|
| Msed_0709 | YP_001190808.1 | 146303492 | Metallosphaera sedula |
| Mcr | NP_378167.1 | 15922498 | Sulfolobus tokodaii |
| asd-2 | NP_343563.1 | 15898958 | Sulfolobus solfataricus |
| Saci_2370 | YP_256941.1 | 70608071 | Sulfolobus acidocaldarius |
| Ald | AAT66436 | 49473535 | Clostridium beijerinckii |
| eutE | AAA80209 | 687645 | Salmonella typhimurium |
| eutE | P77445 | 2498347 | Escherichia coli |

A bifunctional enzyme with acyl-CoA reductase and alcohol dehydrogenase activity can directly convert methylmalonyl-CoA to 3-HIB. Exemplary bifunctional oxidoreductases that convert an acyl-CoA to alcohol include those that transform substrates such as acetyl-CoA to ethanol (for example, adhE from *E. coli* (Kessler et al., *FEBS. Lett.* 281:59-63 (1991))) and butyryl-CoA to butanol (for example, adhE2 from *C. acetobutylicum* (Fontaine et al., *J. Bacteriol.* 184:821-830 (2002)). Exemplary enzymes are those in the table below.

| Protein | GenBank ID | GI Number | Organism |
|---|---|---|---|
| adhE | NP_415757.1 | 16129202 | Escherichia coli |
| adhE2 | AAK09379.1 | 12958626 | Clostridium acetobutylicum |
| adhE | AAV66076.1 | 55818563 | Leuconostoc mesenteroides |
| bdh I | NP_349892.1 | 15896543 | Clostridium acetobutylicum |
| bdh II | NP_349891.1 | 15896542 | Clostridium acetobutylicum |
| Mcr | AAS20429.1 | 42561982 | Chloroflexus aurantiacus |
| Rcas_2929 | YP_001433009.1 | 156742880 | Roseiflexus castenholzii |

-continued

| Protein | GenBank ID | GI Number | Organism |
|---|---|---|---|
| NAP1_02720 | ZP_01039179.1 | 85708113 | Erythrobacter sp. NAP1 |
| MGP2080_00535 | ZP_01626393.1 | 119504313 | marine gamma proteobacterium HTCC2080 |

Step D—Methylmalonate semialdehyde reductase (designated as EMA5). The reduction of methylmalonate semialdehyde to 3-HIB is catalyzed by EMA5 or 3-HIB dehydrogenase. This enzyme participates in valine, leucine and isoleucine degradation and has been identified in bacteria, eukaryotes, and mammals. Exemplary enzymes are shown below.

| Protein | GenBank ID | GI Number | Organism |
|---|---|---|---|
| P84067 | P84067 | 75345323 | Thermus thermophilus |
| 3hidh | P31937.2 | 12643395 | Homo sapiens |
| 3hidh | P32185.1 | 416872 | Oryctolagus cuniculus |
| mmsB | XNP_746775.1 | 26991350 | Pseudomonas putida |
| mmsB | P28811.1 | 127211 | Pseudomonas aeruginosa |
| dhat | Q59477.1 | 2842618 | Pseudomonas putida |

Step E—3-HIB dehydratase (designated as EMA6).

The dehydration of 3-HIB to MAA is catalyzed by an enzyme with EMA6 activity (EC 4.2.1.-). The final step involves the dehydration of 3-HIB to MAA The dehydration of 3-HIB to MAA is catalyzed by an enzyme with EMA6 activity. Although no direct evidence for this specific enzymatic transformation has been identified, most dehydratases catalyze the alpha,beta-elimination of water, which involves activation of the -hydrogen by an electron-withdrawing carbonyl, carboxylate, or CoA-thiol ester group and removal of the hydroxyl group from the beta-position (Buckel and Barker, J Bacteriol. 117:1248-1260 (1974); Martins et al, Proc. Natl. Acad Sci. USA 101:15645-15649 (2004)). This is the exact type of transformation proposed for the final step in the methacrylate pathway. In addition, the proposed transformation is highly similar to the 2-(hydroxymethyl) glutarate dehydratase of Eubacterium barkeri, which can catalyze the conversion of 2-hydroxymethyl glutarate to 2-methylene glutarate. This enzyme has been studied in the context of nicotinate catabolism and is encoded by hmd (Alhapel et al., Proc. Natl. Acad. Sci. USA 103:12341-12346 (2006)). Similar enzymes with high sequence homology are found in Bacteroides capillosus, Anaerotruncus colihominis, and Natranaerobius thermophilius. Several enzymes are known to catalyze the alpha, beta elimination of hydroxyl groups. Exemplary enzymes include 2-(hydroxymethyl)glutarate dehydratase (EC 4.2.1.-), fumarase (EC 4.2.1.2), 2-keto-4-pentenoate dehydratase (EC 4.2.1.80), citramalate hydrolyase and dimethylmaleate hydratase.

2-(Hydroxymethyl)glutarate dehydratase is a [4Fe-4S]-containing enzyme that dehydrates 2-(hydroxymethyl)glutarate to 2-methylene-glutarate, studied for its role in nicontinate catabolism in Eubacterium barkeri (formerly Clostridium barkeri) (Alhapel et al., Proc Natl Acad Sci USA 103:12341-12346 (2006)) Similar enzymes with high sequence homology are found in Bacteroides capillosus, Anaerotruncus colihominis, and Natranaerobius thermophilius. These enzymes are also homologous to the alpha- and beta-subunits of [4Fe-4S]-containing bacterial serine dehydratases, for example, E. coli enzymes encoded by tdcG, sdhB, and sdaA). An enzyme with similar functionality in E. barkeri is dimethylmaleate hydratase, a reversible Fe2+-dependent and oxygen-sensitive enzyme in the aconitase family that hydrates dimethylmaeate to form (2R,3S)-2,3-dimethylmalate. This enzyme is encoded by dmdAB (Alhapel et al., Proc Natl Acad Sci USA 103:12341-6 (2006); Kollmann-Koch et al., Hoppe Seylers. Z. Physiol Chem. 365:847-857 (1984)).

| Protein | GenBank ID | GI Number | Organism |
|---|---|---|---|
| Hmd | ABC88407.1 | 86278275 | Eubacterium barkeri |
| BACCAP_02294 | ZP_02036683.1 | 154498305 | Bacteroides capillosus |
| ANACOL_02527 | ZP_02443222.1 | 167771169 | Anaerotruncus colihominis |
| NtherDRAFT_2368 | ZP_02852366.1 | 169192667 | Natranaerobius thermophilus |
| dmdA | ABC88408 | 86278276 | Eubacterium barkeri |
| dmdB | ABC88409 | 86278277 | Eubacterium barkeri |

Fumarate hydratase enzymes, which naturally catalyze the reversible hydration of fumarate to malate.

Although the ability of fumarate hydratase to react on branched substrates with 3-oxobutanol as a substrate has not been described, a wealth of structural information is available for this enzyme and other researchers have successfully engineered the enzyme to alter activity, inhibition and localization (Weaver, Acta Crystallogr. D Biol. Crystallogr. 61:1395-1401 (2005)). E. coli has three fumarases: FumA, FumB, and FumC that are regulated by growth conditions. FumB is oxygen sensitive and only active under anaerobic conditions. FumA is active under microanaerobic conditions, and FumC is the only active enzyme in aerobic growth (Tseng et al., J Bacteriol. 183:461-467 (2001); Woods et al., Biochem. Biophys. Acta 954:14-26 (1988); Guest et al., J Gen Microbiol 131:2971-2984 (1985)). Exemplary enzyme candidates include those encoded by fumC from Escherichia coli and include those in the table below.

| Protein | GenBank ID | GI Number | Organism |
|---|---|---|---|
| fumA | NP_416129.1 | 16129570 | Escherichia coli |
| fumB | NP_418546.1 | 16131948 | Escherichia coli |
| fumC | NP_416128.1 | 16129569 | Escherichia coli |
| fumC | O69294 | 9789756 | Campylobacter jejuni |
| fumC | P84127 | 75427690 | Thermus thermophilus |
| fumH | P14408 | 120605 | Rattus norvegicus |
| fum1 | P93033 | 39931311 | Arabidopsis thaliana |
| fumC | Q8NRN8 | 39931596 | Corynebacterium glutamicum |
| MmcB | YP_001211906 | 147677691 | Pelotomaculum thermopropionicum |
| MmcC | YP_001211907 | 147677692 | Pelotomaculum thermopropionicum |

Dehydration of 4-hydroxy-2-oxovalerate to 2-oxopentenoate is catalyzed by 4-hydroxy-2-oxovalerate hydratase (EC 4.2.1.80). This enzyme participates in aromatic degradation pathways and is typically co-transcribed with a gene encoding an enzyme with 4-hydroxy-2-oxovalerate aldolase activity. Exemplary gene products include those in the table below. Sequence comparison reveals homologs in a wide range of bacteria, plants and animals. Enzymes with highly similar sequences are contained in Klebsiella pneumonia (91% identity, eval=2e-138) and Salmonella enterica (91% identity, eval=4e-138), among others.

| Gene | GenBank Accession No. | GI No. | Organism |
|---|---|---|---|
| mhpD | AAC73453.2 | 87081722 | Escherichia coli |
| cmtF | AAB62293.1 | 1263188 | Pseudomonas putida |
| todG | AAA61942.1 | 485738 | Pseudomonas putida |
| cnbE | YP_001967714.1 | 190572008 | Comamonas sp. CNB-1 |
| mhpD | Q13VU0 | 123358582 | Burkholderia xenovorans |
| hpcG | CAA57202.1 | 556840 | Escherichia coli C |
| hpaH | CAA86044.1 | 757830 | Escherichia coli W |
| hpaH | ABR80130.1 | 150958100 | Klebsiella pneumoniae |
| Sari_01896 | ABX21779.1 | 160865156 | Salmonella enterica |

Another enzyme candidate is citramalate hydrolyase (EC 4.2.1.34), an enzyme that naturally dehydrates 2-methylmalate to mesaconate. This enzyme has been studied in *Methanocaldococcus jannaschii* in the context of the pyruvate pathway to 2-oxobutanoate, where it has been shown to have a broad substrate specificity (Drevland et al., *J Bacteriol.* 189:4391-4400 (2007)). This enzyme activity was also detected in *Clostridium tetanomorphum, Morganella morganii, Citrobacter amalonaticus* where it is thought to participate in glutamate degradation (Kato et al., *Arch. Microbiol* 168:457-463 (1997)). The *M. jannaschii* protein sequence does not bear significant homology to genes in these organisms.

| Protein | GenBank ID | GI Number | Organism |
|---|---|---|---|
| leuD | Q58673.1 | 3122345 | Methanocaldococcus jannaschii |

Dimethylmaleate hydratase (EC 4.2.1.85) is a reversible $Fe^{2+}$-dependent and oxygen-sensitive enzyme in the aconitase family that hydrates dimethylmaeate to form (2R,3S)-2,3-dimethylmalate. This enzyme is encoded by dmdAB in *Eubacterium barkeri* (Alhapel et al., supra; Kollmann-Koch et al., *Hoppe Seylers. Z. Physiol Chem.* 365:847-857 (1984)).

| Protein | GenBank ID | GI Number | Organism |
|---|---|---|---|
| dmdA | ABC88408 | 86278276 | Eubacterium barkeri |
| dmdB | ABC88409.1 | 86278277 | Eubacterium barkeri |

Step F—Methylmalonyl-CoA reductase (alcohol forming) (designated as EMA7). Step F can involve a combined Alcohol/Aldehyde dehydrogenase (EC 1.2.1.-). Methylmalonyl-CoA can be reduced to 3-HIB in one step by a multifunctional enzyme with dual acyl-CoA reductase and alcohol dehydrogenase activity. Although the direct conversion of methylmalonyl-CoA to 3-HIB has not been reported, this reaction is similar to the common conversions such as acetyl-CoA to ethanol and butyryl-CoA to butanol, which are catalyzed by CoA-dependent enzymes with both alcohol and aldehyde dehydrogenase activities. Gene candidates include the *E. coli* adhE and exemplary enzymes in the table below.

| Protein | GenBank ID | GI Number | Organism |
|---|---|---|---|
| Mcr | YP_001636209.1 | 163848165 | Chloroflexus aurantiacus |
| adhE | NP_415757.1 | 16129202 | Escherichia coli |
| bdh I | NP_349892.1 | 15896543 | Clostridium acetobutylicum |
| bdh II | NP_349891.1 | 15896542 | Clostridium acetobutylicum |
| adhE | AAV66076.1 | 55818563 | Leuconostoc mesenteroides |

Example XI

Methacrylic Acid and 2-Hydroxyisobutyric Synthesis Enzymes

This Example provides genes that can be used for conversion of acetyl-CoA to methacrylic acid and 2-hydroxyisobutyric as depicted in the pathways of FIG. 10.

FIG. 10. Exemplary pathways enabling production of 2-hydroxyisobutyrate and methacrylic acid from acetyl-CoA. 2-Hydroxyisobutyrate and methacrylic acid production are carried out by the following enzymes: A) acetyl-CoA:acetyl-CoA acyltransferase, B) acetoacetyl-CoA reductase (ketone reducing), C) 3-hydroxybutyrl-CoA mutase, D) 2-hydroxyisobutyryl-CoA dehydratase, E) methacrylyl-CoA synthetase, hydrolase, or transferase, F) 2-hydroxyisobutyryl-CoA synthetase, hydrolase, or transferase.

MAA biosynthesis can proceed from acetyl-CoA in a minimum of five enzymatic steps (see FIG. 10). In this pathway, two molecules of acetyl-CoA are combined to form acetoacetyl-CoA, which is then reduced to 3-hydroxybutyryl-CoA. Alternatively, 4-hydroxybutyryl-CoA can be converted to 3-hydroxybutyryl-CoA by way of 4-hydroxybutyryl-CoA dehydratase and crotonase (Martins et al., Proc. Nat. Acad. Sci. USA 101(44) 15645-15649 (2004); Jones and Woods, *Microbiol. Rev.* 50:484-524 (1986); Berg et al., *Science* 318(5857) 1782-1786 (2007)). A methylmutase then rearranges the carbon backbone of 3-hydroxybutyryl-CoA to 2-hydroxyisobutyryl-CoA, which is then dehydrated to form methacrylyl-CoA. Alternatively, 2-hydroxyisobutyryl-CoA can be converted to 2-hydroxyisobutyrate, secreted, and recovered as product. The final step converting methacrylyl-CoA to MAA can be performed by a single enzyme shown in the figure or a series of enzymes.

A) Acetyl-CoA:acetyl-CoA Acyltransferase. Step A involves acetoacetyl-CoA thiolase (EC 2.3.1.9). The formation of acetoacetyl-CoA from two acetyl-CoA units is catalyzed by acetyl-CoA thiolase. This enzyme is native to *E. coli*, encoded by gene atoB, and typically operates in the acetoacetate-degrading direction during fatty acid oxidation (Duncombe and Frerman, *Arch. Biochem. Biophys.* 176:159-170 (1976); Frerman and Duncombe, *Biochim. Biophys. Acta* 580:289-297 (1979)). Additional exemplary genes include those below.

| Protein | GenBank ID | GI Number | Organism |
|---|---|---|---|
| atoB | NP_416728 | 16130161 | Escherichia coli |
| thlA | NP_349476.1 | 15896127 | Clostridium acetobutylicum |
| thlB | NP_149242.1 | 15004782 | Clostridium acetobutylicum |
| thl | ABA18857.1 | 75315385 | Clostridium pasteurianum |
| ERG10 | NP_015297 | 6325229 | Saccharomyces cerevisiae |

B) Acetoacetyl-CoA Reductase (ketone reducing). Step B involves acetoacetyl-CoA reductase (EC #: 1.1.1.35). This second step entails the reduction of acetoacetyl-CoA to 3-hydroxybutyryl-CoA by acetoacetyl-CoA reductase. This enzyme participates in the acetyl-CoA fermentation pathway to butyrate in several species of *Clostridia* and has been studied in detail (Jones and Woods, *Microbiol. Rev.* 50:484-524 (1986)). The enzyme from *Clostridium acetobutylicum*, encoded by hbd, has been cloned and functionally expressed in *E. coli* (Youngleson et al., *J. Bacteriol.* 171:6800-6807 (1989)). Additionally, subunits of two fatty acid oxidation complexes in *E. coli*, encoded by fadB and fadJ, function as 3-hydroxyacyl-CoA dehydrogenases (Binstock and Schulz, *Methods Enzymol.* 71 Pt C:403-411 (1981)). Exemplary enzymes are in the following table.

| Protein | GENBANK ID | GI NUMBER | Organism |
|---|---|---|---|
| fadB | P21177.2 | 119811 | *Escherichia coli* |
| fadJ | P77399.1 | 3334437 | *Escherichia coli* |
| Hbd2 | EDK34807.1 | 146348271 | *Clostridium kluyveri* |
| Hbd1 | EDK32512.1 | 146345976 | *Clostridium kluyveri* |
| HSD17B10 | O02691.3 | 3183024 | *Bos taurus* |
| phbB | P23238.1 | 130017 | *Zoogloea ramigera* |
| phaB | YP_353825.1 | 77464321 | *Rhodobacter sphaeroides* |
| phaB | BAA08358 | 675524 | *Paracoccus denitrificans* |
| Hbd | NP_349314.1 | 15895965 | *Clostridium acetobutylicum* |
| Hbd | AAM14586.1 | 20162442 | *Clostridium beijerinckii* |
| Msed_1423 | YP_001191505 | 146304189 | *Metallosphaera sedula* |
| Msed_0399 | YP_001190500 | 146303184 | *Metallosphaera sedula* |
| Msed_0389 | YP_001190490 | 146303174 | *Metallosphaera sedula* |
| Msed_1993 | YP_001192057 | 146304741 | *Metallosphaera sedula* |
| Fox2 | Q02207 | 399508 | *Candida tropicalis* |

C) 3-hydroxybutyrl-CoA mutase. Step C involves 3-hydroxybutyryl-CoA mutase (EC 5.4.99.-). In this step, 3-hydroxybutyryl-CoA is rearranged to form 2-hydroxyisobutyryl-CoA (2-HIBCoA) by 3-hydroxybutyryl-CoA mutase. This enzyme is a novel ICM-like methylmutase recently discovered and characterized in *Methylibium petroleiphilum* (Ratnatilleke et al., *J. Biol. Chem.* 274:31679-31685 (1999); Rohwerder et al., *Appl. Environ. Microbiol.* 72:4128-4135 (2006)). This enzyme, encoded by Mpe_B0541 in *Methylibium petroleiphilum* PM1, has high sequence homology to the large subunit of methylmalonyl-CoA mutase in other organisms including Rsph17029_3657 in *Rhodobacter sphaeroides* and Xaut_5021 in *Xanthobacter autotrophicus*. Changes to a single amino acid near the active site alters the substrate specificity of the enzyme (Ratnatilleke et al., supra, 1999; Rohwerder et al., supra, 2006), so directed engineering of similar enzymes at this site, such as methylmalonyl-CoA mutase or isobutryryl-CoA mutase described previously, can be used to achieve the desired reactivity.

| Protein | GenBank ID | GI Number | Organism |
|---|---|---|---|
| Mpe_B0541 | YP_001023546.1 | 124263076 | *Methylibium petroleiphilum* PM1 |
| Rsph17029_3657 | YP_001045519.1 | 126464406 | *Rhodobacter sphaeroides* |
| Xaut_5021 | YP_001409455.1 | 154243882 | *Xanthobacter autotrophicus* Py2 |

D) 2-hydroxyisobutyryl-CoA dehydratase. Step D involves 2-hydroxyisobutyryl-CoA dehydratase. The dehydration of 2-hydroxyacyl-CoA such as 2-hydroxyisobutyryl-CoA can be catalyzed by a special class of oxygen-sensitive enzymes that dehydrate 2-hydroxyacyl-CoA derivatives via a radical-mechanism (Buckel and Golding, *Annu. Rev. Microbiol.* 60:27-49 (2006); Buckel et al., *Curr. Opin. Chem. Biol.* 8:462-467 (2004); Buckel et al., *Biol. Chem.* 386:951-959 (2005); Kim et al., *FEBS J.* 272:550-561 (2005); Kim et al., *FEMS Microbiol Rev.* 28:455-468 (2004); Zhang et al., *Microbiology* 145 (Pt 9): 2323-2334 (1999)). Exemplary enzymes are the following.

| Gene | GenBank Accession No. | GI No. | Organism |
|---|---|---|---|
| hgdA | P11569 | 296439332 | *Acidaminococcus fermentans* |
| hgdB | P11570 | 296439333 | *Acidaminococcus fermentans* |
| hgdC | P11568 | 2506909 | *Acidaminococcus fermentans* |
| hadB | YP_001086863 | 126697966 | *Clostridium difficile* |
| hadC | YP_001086864 | 126697967 | *Clostridium difficile* |
| hadI | YP_001086862 | 126697965 | *Clostridium difficile* |
| lcdB | AJ276553 | 7242547 | *Clostridium propionicum* |

E) methacrylyl-CoA synthetase, hydrolase, or transferase, and F) 2-hydroxyisobutyryl-CoA synthetase, hydrolase, or transferase. Steps E and F involve a transferase (EC 2.8.3.-), hydrolase (EC 3.1.2.-), or synthetase (EC 6.2.1.-) with activity on a methacrylic acid or 2-hydroxyisobutyric acid, respectively. Direct conversion of methacrylyl-CoA to MAA or 2-hydroxyisobutyryl-CoA to 2-hydroxyisobutyrate can be accomplished by a CoA transferase, synthetase or hydrolase. Pathway energetics are most favorable if a CoA transferase or a CoA synthetase is employed to accomplish this transformation. In the transferase family, the enzyme acyl-CoA:acetate-CoA transferase, also known as acetate-CoA transferase, is a suitable candidate to catalyze the desired 2-hydroxyisobutyryl-CoA or methacryl-CoA transferase activity due to its broad substrate specificity that includes branched acyl-CoA substrates (Matthies and Schink, *Appl. Environ. Microbiol.* 58:1435-1439 (1992); Vanderwinkel et al., *Biochem. Biophys. Res. Commun.* 33:902-908 (1968)). ADP-forming acetyl-CoA synthetase (ACD) is a promising enzyme in the CoA synthetase family operating on structurally similar branched chain compounds (Brasen and Schonheit, *Arch. Microbiol.* 182:277-287 (2004); Musfeldt and Schonheit, *J. Bacteriol.* 184:636-644 (2002)). In the CoA-hydrolase family, the enzyme 3-hydroxyisobutyryl-CoA hydrolase has been shown to operate on a variety of branched chain acyl-CoA substrates including 3-hydroxyisobutyryl-CoA, methylmalonyl-CoA, and 3-hydroxy-2-methylbutanoyl-CoA (Hawes et al., *Methods Enzymol.* 324: 218-228 (2000); Hawes et al., *J. Biol. Chem.* 271:26430-26434 (1996); Shimomura et al., *J. Biol. Chem.* 269:14248-14253 (1994)). Additional exemplary gene candidates for CoA transferases, synthetases, and hydrolases are discussed elsewhere above.

Example XII

Attenuation or Disruption of Endogenous Enzymes

This example provides endogenous enzyme targets for attenuation or disruption that can be used for enhancing carbon flux through methanol dehydrogenase and formaldehyde assimilation pathways.

DHA Kinase

Methylotrophic yeasts typically utilize a cytosolic DHA kinase to catalyze the ATP-dependent activation of DHA to DHAP. DHAP together with G3P is combined to form fructose-1,6-bisphosphate (FBP) by FBP aldolase. FBP is then hydrolyzed to F6P by fructose bisphosphatase. The net conversion of DHA and G3P to F6P by this route is energetically costly (1 ATP) in comparison to the F6P aldolase route, described above and shown in FIG. 1. DHA kinase also competes with F6P aldolase for the DHA substrate. Attenuation of endogenous DHA kinase activity will thus improve the energetics of formaldehyde assimilation pathways, and also increase the intracellular availability of DHA for DHA synthase. DHA kinases of *Saccharomyces cerevisiae*, encoded by DAK1 and DAK2, enable the organism to maintain low intracellular levels of DHA (Molin et al, *J Biol Chem* 278:1415-23 (2003)). In methylotrophic yeasts DHA kinase is essential for growth on methanol (Luers et al, *Yeast* 14:759-71 (1998)). The DHA kinase enzymes of *Hansenula polymorpha* and *Pichia pastoris* are encoded by DAK (van der Klei et al, *Curr Genet* 34:1-11 (1998); Luers et al, supra). DAK enzymes in other organisms can be identified by sequence similarity to known enzymes.

| Protein | GenBank ID | GI Number | Organism |
| --- | --- | --- | --- |
| DAK1 | NP_013641.1 | 6323570 | *Saccharomyces cerevisiae* |
| DAK2 | NP_116602.1 | 14318466 | *Saccharomyces cerevisiae* |
| DAK | AAC27705.1 | 3171001 | *Hansenula polymorpha* |
| DAK | AAC39490.1 | 3287486 | *Pichia pastoris* |
| DAK2 | XP_505199.1 | 50555582 | *Yarrowia lipolytica* |

Methanol Oxidase

Attenuation of redox-inefficient endogenous methanol oxidizing enzymes, combined with increased expression of a cytosolic NADH-dependent methanol dehydrogenase, will enable redox-efficient oxidation of methanol to formaldehyde in the cytosol. Methanol oxidase, also called alcohol oxidase (EC 1.1.3.13), catalyzes the oxygen-dependent oxidation of methanol to formaldehyde and hydrogen peroxide. In eukaryotic organisms, alcohol oxidase is localized in the peroxisome. Exemplary methanol oxidase enzymes are encoded by AOD of *Candida boidinii* (Sakai and Tani, *Gene* 114:67-73 (1992)); and AOX of *H. polymorpha*, *P. methanolica* and *P. pastoris* (Ledeboer et al, *Nucl Ac Res* 13:3063-82 (1985); Koutz et al, *Yeast* 5:167-77 (1989); Nakagawa et al, *Yeast* 15:1223-1230 (1999)).

| Protein | GenBank ID | GI Number | Organism |
| --- | --- | --- | --- |
| AOX2 | AAF02495.1 | 6049184 | *Pichia methanolica* |
| AOX1 | AAF02494.1 | 6049182 | *Pichia methanolica* |
| AOX1 | AAB57849.1 | 2104961 | *Pichia pastoris* |
| AOX2 | AAB57850.1 | 2104963 | *Pichia pastoris* |
| AOX | P04841.1 | 113652 | *Hansenula polymorpha* |
| AOD1 | Q00922.1 | 231528 | *Candida boidinii* |
| AOX1 | AAQ99151.1 | 37694459 | *Ogataea pini* |

PQQ-dependent Methanol Dehydrogenase

PQQ-dependent methanol dehydrogenase from *M. extorquens* (mxaIF) uses cytochrome as an electron carrier (Nunn et al, *Nucl Acid Res* 16:7722 (1988)). Methanol dehydrogenase enzymes of methanotrophs such as *Methylococcus capsulatis* function in a complex with methane monooxygenase (MMO) (Myronova et al, *Biochem* 45:11905-14 (2006)). Note that of accessory proteins, cytochrome CL and PQQ biosynthesis enzymes are needed for active methanol dehydrogenase. Attenuation of one or more of these required accessory proteins, or retargeting the enzyme to a different cellular compartment, would also have the effect of attenuating PQQ-dependent methanol dehydrogenase activity.

| Protein | GenBank ID | GI Number | Organism |
| --- | --- | --- | --- |
| MCA0299 | YP_112833.1 | 53802410 | *Methylococcus capsulatis* |
| MCA0782 | YP_113284.1 | 53804880 | *Methylococcus capsulatis* |
| mxaI | YP_002965443.1 | 240140963 | *Methylobacterium extorquens* |
| mxaF | YP_002965446.1 | 240140966 | *Methylobacterium extorquens* |

DHA Synthase and Other Competing Formaldehyde Assimilation and Dissimilation Pathways Carbon-efficient formaldehyde assimilation can be improved by attenuation of competing formaldehyde assimilation and dissimilation pathways. Exemplary competing assimilation pathways in eukaryotic organisms include the peroxisomal dissimilation of formaldehyde by DHA synthase, and the DHA kinase pathway for converting DHA to F6P, both described herein. Exemplary competing endogenous dissimilation pathways include one or more of the enzymes shown in FIG. 1.

Methylotrophic yeasts normally target selected methanol assimilation and dissimilation enzymes to peroxisomes during growth on methanol, including methanol oxidase, DHA synthase and S-(hydroxymethyl)-glutathione synthase (see review by Yurimoto et al, supra). The peroxisomal targeting mechanism comprises an interaction between the peroxisomal targeting sequence and its corresponding peroxisomal receptor (Lametschwandtner et al, *J Biol Chem* 273:33635-43 (1998)). Peroxisomal methanol pathway enzymes in methylotrophic organisms contain a PTS1 targeting sequence which binds to a peroxisomal receptor, such as Pex5p in *Candida boidinii* (Horiguchi et al, *J Bacteriol* 183:6372-83 (2001)). Disruption of the PTS1 targeting sequence, the Pex5p receptor and/or genes involved in peroxisomal biogenesis would enable cytosolic expression of DHA synthase, S-(hydroxymethyl)-glutathione synthase or other methanol-inducible peroxisomal enzymes. PTS1 targeting sequences of methylotrophic yeast are known in the art (Horiguchi et al, supra). Identification of peroxisomal targeting sequences of unknown enzymes can be predicted using bioinformatic methods (eg. Neuberger et al, *J Mol Biol* 328:581-92 (2003))).

Example XIII

Methanol Assimilation via Methanol Dehydrogenase and the Ribulose Monophosphate Pathway This example shows that co-expression of an active methanol dehydrogenase (MeDH) and the enzymes of the Ribulose Monophosphate (RuMP) pathway can effectively assimilate methanol derived carbon.

An experimental system was designed to test the ability of a MeDH in conjunction with the enzymes H6P synthase (HPS) and 6-phospho-3-hexuloisomerase (PHI) of the RuMP pathway to assimilate methanol carbon into the glycolytic pathway and the TCA cycle. *Escherichia coli* strain ECh-7150 (ΔlacIA, ΔpflB, ΔptsI, ΔPpckA(pckA), ΔPglk(glk), glk::glfB, ΔhycE, ΔfrmR, ΔfrmA, ΔfrmB) was constructed to remove the glutathione-dependent formaldehyde detoxification capability encoded by the FrmA and FrmB enzyme. This strain was then transformed with plasmid pZA23S variants that either contained or lacked gene 2616A encoding a fusion of the HPS and PHI enzymes. These two transformed strains were then each transformed with pZS*13S variants that contained gene 2315L (encoding an active MeDH), or gene 2315 RIP2 (encoding a catalytically inactive MeDH), or no gene insertion. Genes 2315 and 2616 are internal nomenclatures for NAD-dependent methanol dehydrogenase from *Bacillus methanolicus* MGA3 and 2616 is a fused phs-hpi constructs as described in Orita et al. (2007) *Appl Microbiol Biotechnol* 76:439-45.

The six resulting strains were aerobically cultured in quadruplicate, in 5 ml minimal medium containing 1% arabinose and 0.6 M 13C-methanol as well as 100 ug/ml carbenicillin and 25 µg/ml kanamycin to maintain selection of the plasmids, and 1 mM IPTG to induce expression of the methanol dehydrogenase and HPS-PHI fusion enzymes. After 18 hours incubation at 37° C., the cell density was measured spectrophotometrically at 600 nM wavelength and a clarified sample of each culture medium was submitted for analysis to detect evidence of incorporation of the labeled methanol carbon into TCA-cycle derived metabolites. The label can be further enriched by deleting the gene araD that competes with ribulose-5-phosphate.

$^{13}$C carbon derived from labeled methanol provided in the experiment was found to be significantly enriched in the metabolites pyruvate, lactate, succinate, fumarate, malate, glutamate and citrate, but only in the strain expressing both catalytically active MeDH 2315L and the HPS-PHI fusion 2616A together (data not shown). Moreover, this strain grew significantly better than the strain expressing catalytically active MeDH but lacking expression of the HPS-PHI fusion (data not shown), suggesting that the HPS-PI-11 enzyme is capable of reducing growth inhibitory levels of formaldehyde that cannot be detoxified by other means in this strain background. These results show that co-expression of an active MeDH and the enzymes of the RuMP pathway can effectively assimilate methanol derived carbon and channel it into TCA-cycle derived products.

Throughout this application various publications have been referenced. The disclosures of these publications in their entireties, including GenBank and GI number publications, are hereby incorporated by reference in this application in order to more fully describe the state of the art to which this invention pertains. Although the invention has been described with reference to the examples provided above, it should be understood that various modifications can be made without departing from the spirit of the invention.

What is claimed is:

1. A non-naturally occurring microbial organism having a methanol metabolic pathway and an acetyl-CoA pathway, wherein said methanol metabolic pathway comprises 2A or 2J, wherein 2A is a methanol methyltransferase, wherein 2J is a methanol dehydrogenase,
wherein said acetyl-CoA pathway comprises a pathway selected from:
(1) 1T and 1V; (2) 1T, 1W, and 1X; (3) 1U and 1V; (4) 1U, 1W, and 1X;
wherein 1T is a fructose-6-phosphate phosphoketolase, wherein 1U is a xylulose-5-phosphate phosphoketolase, wherein 1V is a phosphotransacetylase, wherein 1W is an acetate kinase, wherein 1X is an acetyl-CoA transferase, an acetyl-CoA synthetase, or an acetyl-CoA ligase,
wherein an enzyme of the methanol metabolic pathway or the acetyl-CoA pathway is encoded by at least one exogenous nucleic acid and is expressed in a sufficient amount to enhance carbon flux through acetyl-CoA, wherein said microbial organism is a species of bacteria or yeast.

2. The non-naturally occurring microbial organism of claim 1, wherein said microbial organism further comprises a formaldehyde fixation pathway, wherein said formaldehyde fixation pathway comprises:
(1) 1D and 1Z; (2) 1D; or (3) 1B and 1C,
wherein 1B is a 3-hexulose-6-phosphate synthase, wherein 1C is a 6-phospho-3-hexuloisomerase, wherein 1D is a dihydroxyacetone synthase, wherein 1Z is a fructose-6-phosphate aldolase.

3. The non-naturally occurring microbial organism of claim 2, wherein an enzyme of the formaldehyde fixation pathway is encoded by at least one exogenous nucleic acid and is expressed in a sufficient amount to enhance carbon flux through acetyl-CoA.

4. The non-naturally occurring microbial organism of claim 1, wherein said methanol metabolic pathway comprises a pathway selected from:
(1) 2A and 2B; (2) 2A, 2B and 2C; (3) 2J, 2K and 2C; (4) 2J, 2M, and 2N; (5) 2J and 2L; (6) 2J, 2L, and 2G; (7) 2J, 2L, and 2I; (8) 2A, 2B, 2C, 2D, and 2E; (9) 2A, 2B, 2C, 2D, and 2F; (10) 2J, 2K, 2C, 2D, and 2E; (11) 2J, 2K, 2C, 2D, and 2F; (12) 2J, 2M, 2N, and 2O; (13) 2A, 2B, 2C, 2D, 2E, and 2G; (14) 2A, 2B, 2C, 2D, 2F, and 2G; (15) 2J, 2K, 2C, 2D, 2E, and 2G; (16) 2J, 2K, 2C, 2D, 2F, and 2G; (17) 2J, 2M, 2N, 2O, and 2G; (18) 2A, 2B, 2C, 2D, 2E, and 2I; (19) 2A, 2B, 2C, 2D, 2F, and 2I; (20) 2J, 2K, 2C, 2D, 2E, and 2I; (21) 2J, 2K, 2C, 2D, 2F, and 2I; and (22) 2J, 2M, 2N, 2O, and 2I,
wherein 2A is a methanol methyltransferase, wherein 2B is a methylenetetrahydrofolate reductase, wherein 2C is a methylenetetrahydrofolate dehydrogenase, wherein 2D is a methenyltetrahydrofolate cyclohydrolase, wherein 2E is a formyltetrahydrofolate deformylase, wherein 2F is a formyltetrahydrofolate synthetase, wherein 2G is a formate hydrogen lyase, wherein 2I is a formate dehydrogenase, wherein 2J is a methanol dehydrogenase, wherein 2K is a formaldehyde activating enzyme or spontaneous, wherein 2L is a formaldehyde dehydrogenase, wherein 2M is a S-(hydroxymethyl)glutathione synthase or spontaneous, wherein 2N is a glutathione-dependent formaldehyde dehydrogenase, wherein 2O is a S-formylglutathione hydrolase.

5. The non-naturally occurring microbial organism of claim 4, wherein said microbial organism comprises:
(a) one, two, three, four, five, or six exogenous nucleic acids each encoding a methanol metabolic pathway enzyme; or
(b) exogenous nucleic acids encoding each of the enzymes of at least one of the pathways selected from (1)-(22).

6. The non-naturally occurring microbial organism of claim 1, wherein said microbial organism comprises:
(a) one, two, or three exogenous nucleic acids each encoding an acetyl-CoA pathway enzyme; or
(b) exogenous nucleic acids encoding each of the enzymes of at least one of the pathways selected from the group consisting of the pathway (1) to pathway (4).

7. The non-naturally occurring microbial organism of claim 1, wherein said microbial organism further comprises a formate assimilation pathway, wherein said formate assimilation pathway comprises a pathway selected from:
(1) 1E; (2) 1F, and 1G; (3) 1H, 1I, 1J, and 1K; (4) 1H, 1I, 1J, 1L, 1M, and 1N; (5) 1E, 1H, 1I, 1J, 1L, 1M, and 1N; (6) 1F, 1G, 1H, 1I, 1J, 1L, 1M, and 1N; (7) 1K, 1H, 1I, 1J, 1L, 1M, and 1N; and (8) 1H, 1I, 1J, 1O, and 1P,
wherein 1E is a formate reductase, 1F is a formate ligase, a formate transferase, or a formate synthetase, wherein 1G is a formyl-CoA reductase, wherein 1H is a formyltetrahydrofolate synthetase, wherein 1I is a methenyltetrahydrofolate cyclohydrolase, wherein 1J is a methylenetetrahydrofolate dehydrogenase, wherein 1K is a formaldehyde-forming enzyme or spontaneous, wherein 1L is a glycine cleavage system, wherein 1M is a serine hydroxymethyltransferase, wherein 1N is a serine deaminase, wherein 1O is a methylenetetrahydrofolate reductase, wherein 1P is an acetyl-CoA synthase.

8. The non-naturally occurring microbial organism of claim 7, wherein an enzyme of the formate assimilation pathway is encoded by at least one exogenous nucleic acid and is expressed in a sufficient amount to enhance carbon flux through acetyl-CoA.

9. The non-naturally occurring microbial organism of claim 1, wherein said non-naturally occurring microbial organism further comprises a pathway capable of producing a bioderived compound.

10. The non-naturally occurring microbial organism of claim 9, wherein said bioderived compound is an alcohol, a glycol, an organic acid, an alkene, a diene, an organic amine, an organic aldehyde, a vitamin, a nutraceutical or a pharmaceutical.

11. The non-naturally occurring microbial organism of claim 10, wherein said bioderived compounds is selected from the group consisting of:
(i) 1,4-butanediol or an intermediate thereto, wherein said intermediate is optionally 4-hydroxybutanoic acid (4-HB);
(ii) butadiene (1,3-butadiene) or an intermediate thereto, wherein said intermediate is optionally 1,4-butanediol, 1,3-butanediol, 2,3-butanediol, crotyl alcohol, 3-buten-2-ol (methyl vinyl carbinol) or 3-buten-1-ol;
(iii) 1,3-butanediol or an intermediate thereto, wherein said intermediate is optionally 3-hydroxybutyrate (3-HB), 2,4-pentadienoate, crotyl alcohol or 3-buten-1-ol;
(iv) adipate, 6-aminocaproic acid, caprolactam, hexamethylenediamine, levulinic acid or an intermediate thereto, wherein said intermediate is optionally adipyl-CoA or 4-aminobutyryl-CoA;
(v) methacrylic acid or an ester thereof, 3-hydroxyisobutyrate, 2-hydroxyisobutyrate, or an intermediate thereto, wherein said ester is optionally methyl methacrylate or poly(methyl methacrylate);
(vi) 1,2-propanediol (propylene glycol), 1,3-propanediol, glycerol, ethylene glycol, diethylene glycol, triethylene glycol, dipropylene glycol, tripropylene glycol, neopentyl glycol, bisphenol A or an intermediate thereto;
(vii) succinic acid or an intermediate thereto; and
(viii) a fatty alcohol, a fatty aldehyde or a fatty acid comprising C4 to C27 carbon atoms, C8 to C18 carbon atoms, C12 to C18 carbon atoms, or C12 to C14 carbon atoms, wherein said fatty alcohol is optionally dodecanol (C12; lauryl alcohol), tridecyl alcohol (C13; 1-tridecanol, tridecanol, isotridecanol), myristyl alcohol (C14; 1-tetradecanol), pentadecyl alcohol (C15; 1-pentadecanol, pentadecanol), cetyl alcohol (C16; 1-hexadecanol), heptadecyl alcohol (C17; 1-n-heptadecanol, heptadecanol) and stearyl alcohol (C18; 1-octadecanol) or palmitoleyl alcohol (C16 unsaturated; cis-9-hexadecen-1-ol).

12. The non-naturally occurring microbial organism of claim 1, wherein said acetyl-CoA pathway comprises 1T and 1V.

13. The non-naturally occurring microbial organism of claim 12, wherein said formaldehyde fixation pathway comprises 1D and 1Z.

14. The non-naturally occurring microbial organism of claim 12, wherein said microbial organism further comprises a formaldehyde fixation pathway, wherein said formaldehyde fixation pathway comprises 1B and 1C, wherein 1B is a 3-hexulose-6-phosphate synthase, wherein 1C is a 6-phospho-3-hexuloisomerase.

15. The non-naturally occurring microbial organism of claim 1, wherein said microbial organism further comprises:
(a) attenuation of one or more endogenous enzymes selected from dihydroxyacetone (DHA) kinase, methanol oxidase, pyrroloquinoline quinone (PQQ)-dependent methanol dehydrogenase, DHA synthase or any combination thereof; or
(b) a gene disruption of one or more endogenous nucleic acids encoding enzymes selected from DHA kinase, methanol oxidase, PQQ-dependent methanol dehydrogenase, DHA synthase or any combination thereof.

16. The non-naturally occurring microbial organism of claim 1, wherein said bacteria is selected from the group consisting of *Escherichia coli*, *Klebsiella oxytoca*, *Anaerobiospirillum succiniciproducens*, *Actinobacillus succinogenes*, *Mannheimia succiniciproducens*, *Rhizobium etli*, *Bacillus subtilis*, *Corynebacterium glutamicum*, *Cupriavidus necator*, *Gluconobacter oxydans*, *Zymomonas mobilis*, *Lactococcus lactis*, *Lactobacillus plantarum*, *Streptomyces coelicolor*, *Clostridium acetobutylicum*, *Pseudomonas fluorescens*, and *Pseudomonoas putida*.

17. The non-naturally occurring microbial organism of claim 1, wherein said yeast is selected from the group consisting of *Saccharomyces cerevisiae*, *Schizosaccharomyces pombe*, *Kluyveromyces lactis*, *Kluyveromyces marxianus*, *Pichia pastoris*, *Yarrowia lipolytica*, and *Candida albicans*.

18. A non-naturally occurring microbial organism having a formaldehyde fixation pathway, a formate assimilation pathway and an acetyl-CoA pathway, wherein said formaldehyde fixation pathway comprises:
(1) 1D and 1Z; (2) 1D; or (3) 1B and 1C,
wherein 1B is a 3-hexulose-6-phosphate synthase, wherein 1C is a 6-phospho-3-hexuloisomerase, wherein 1D is a dihydroxyacetone synthase, wherein 1Z is a fructose-6-phosphate aldolase,
wherein said formate assimilation pathway comprises a pathway selected from:
(4) 1E; (5) 1F, and 1G; (6) 1H, 1I, 1J, and 1K; (7) 1H, 1I, 1J, 1L, 1M, and 1N; (8) 1E, 1H, 1I, 1J, 1L, 1M, and 1N; (9) 1F, 1G, 1H, 1I, 1J, 1L, 1M, and 1N; (10) 1K, 1H, 1I, 1J, 1L, 1M, and 1N; and (11) 1H, 1I, 1J, 1O, and 1P,
wherein 1E is a formate reductase, 1F is a formate ligase, a formate transferase, or a formate synthetase, wherein 1G is a formyl-CoA reductase, wherein 1H is a formyltetrahydrofolate synthetase, wherein 1I is a methenyltetrahydrofolate cyclohydrolase, wherein 1J is a methylenetetrahydrofolate dehydrogenase, wherein 1K is a formaldehyde-forming enzyme or spontaneous, wherein 1L is a glycine cleavage system, wherein 1M is a serine hydroxymethyltransferase, wherein 1N is a serine deaminase, wherein 1O is a methylenetetrahydrofolate reductase, wherein 1P is an acetyl-CoA synthase,
wherein said acetyl-CoA pathway comprises a pathway selected from:
(12) 1T and 1V; (13) 1T, 1W, and 1X; (14) 1U and 1V; and (15) 1U, 1W, and 1X, wherein 1T is a fructose-6-phosphate phosphoketolase, wherein 1U is a xylulose-5-phosphate phosphoketolase, wherein 1V is a phosphotransacetylase, wherein 1W is an acetate kinase, wherein 1X is an acetyl-CoA transferase, an acetyl-CoA synthetase, or an acetyl-CoA ligase, wherein an enzyme of the formaldehyde fixation pathway, the formate assimilation pathway, or the acetyl-CoA pathway is encoded by at least one exogenous nucleic acid and is expressed in a sufficient amount to enhance carbon flux through acetyl-CoA, wherein said microbial organism is a species of bacteria or yeast.

19. A method for producing a bioderived compound, comprising culturing the non-naturally occurring microbial organism of any claim 9 under conditions and for a sufficient period of time to produce said bioderived compound.

20. The method of claim 19, wherein said method further comprises separating the bioderived compound from other components in the culture.

21. The method of claim 20, wherein the separating comprises extraction, continuous liquid-liquid extraction, pervaporation, membrane filtration, membrane separation, reverse osmosis, electrodialysis, distillation, crystallization, centrifugation, extractive filtration, ion exchange chromatography, absorption chromatography, or ultrafiltration.

* * * * *